US011975073B2

(12) United States Patent
Bonner et al.

(10) Patent No.: US 11,975,073 B2
(45) Date of Patent: May 7, 2024

(54) LIPID PRODRUGS OF NEUROSTEROIDS

(71) Applicants: PureTech LYT, Inc., Boston, MA (US); Monash University, Clayton (AU)

(72) Inventors: Daniel Kenneth Bonner, Sharon, MA (US); Rishab R. Shyam, Arlington, MA (US); Jamie Simpson, Chestnut Hill, MA (US); Christopher John Porter, South Melbourne (AU); Natalie Trevaskis, Newington (AU); Tim Quach, Boston, MA (US); Sifei Han, Bundoora (AU); Luojuan Hu, Bundoora (AU)

(73) Assignees: PureTech LYT, Inc., Boston, MA (US); Monash University, Clayton (AU)

( * ) Notice: Subject to any disclaimer, the term of this patent is extended or adjusted under 35 U.S.C. 154(b) by 0 days.

(21) Appl. No.: 18/341,519

(22) Filed: Jun. 26, 2023

(65) Prior Publication Data
US 2023/0338552 A1 Oct. 26, 2023

Related U.S. Application Data

(63) Continuation of application No. 17/881,458, filed on Aug. 4, 2022, now abandoned, which is a continuation of application No. PCT/US2021/016955, filed on Feb. 5, 2021.

(60) Provisional application No. 63/070,064, filed on Aug. 25, 2020, provisional application No. 63/009,533, filed on Apr. 14, 2020, provisional application No. 62/970,607, filed on Feb. 5, 2020.

(51) Int. Cl.
A61K 47/55 (2017.01)
A61K 9/00 (2006.01)
A61K 31/573 (2006.01)
A61K 47/54 (2017.01)

(52) U.S. Cl.
CPC ............ *A61K 47/55* (2017.08); *A61K 9/0053* (2013.01); *A61K 31/573* (2013.01); *A61K 47/542* (2017.08)

(58) Field of Classification Search
CPC ..... A61K 47/55; A61K 31/573; A61K 47/542
See application file for complete search history.

(56) References Cited

U.S. PATENT DOCUMENTS

| | | |
|---|---|---|
| 4,958,046 A | 9/1990 | Rosenberg et al. |
| 5,962,440 A | 10/1999 | Sulsky |
| 6,013,665 A | 1/2000 | DeMichele et al. |
| 6,054,591 A | 4/2000 | Aono et al. |
| 6,417,191 B1 | 7/2002 | Barry et al. |
| 6,552,065 B2 | 4/2003 | Remiszewski et al. |
| 7,390,799 B2 | 6/2008 | Bruncko et al. |
| 7,557,210 B2 | 7/2009 | Singh et al. |
| 7,635,690 B2 | 12/2009 | Schinazi et al. |
| 8,138,347 B2 | 3/2012 | Knight et al. |
| 8,338,439 B2 | 12/2012 | Singh et al. |
| 8,455,510 B2 | 6/2013 | Nan et al. |
| 8,535,655 B2 | 9/2013 | O'Shea et al. |
| 2007/0191415 A1 | 8/2007 | Kumar et al. |
| 2009/0023805 A1 | 1/2009 | Marrast et al. |
| 2009/0297533 A1 | 12/2009 | Lichter et al. |
| 2010/0298560 A1 | 11/2010 | Choi et al. |
| 2011/0213028 A1 | 9/2011 | Milne et al. |
| 2011/0243884 A1 | 10/2011 | O'Shea et al. |
| 2013/0012462 A1 | 1/2013 | Ip et al. |
| 2013/0245253 A1 | 9/2013 | Marx et al. |
| 2014/0081016 A1 | 3/2014 | Felzmann et al. |
| 2014/0234418 A1 | 8/2014 | Coulter et al. |
| 2014/0328793 A1 | 11/2014 | Gavegnano et al. |
| 2017/0065615 A1 | 3/2017 | MacNevin et al. |
| 2017/0326103 A1 | 11/2017 | Porter et al. |
| 2018/0243425 A1 | 8/2018 | Porter et al. |
| 2018/0258094 A1 | 9/2018 | Long et al. |
| 2018/0318318 A1 | 11/2018 | Wang et al. |
| 2019/0105299 A1 | 4/2019 | Porter et al. |
| 2021/0300962 A1 | 9/2021 | Bonner et al. |
| 2022/0395513 A1 | 12/2022 | Bonner et al. |

FOREIGN PATENT DOCUMENTS

| | | | |
|---|---|---|---|
| JP | 200312691 A | | 1/2003 |
| JP | 2003012691 A | * | 1/2003 |
| WO | 1994009010 A1 | | 4/1994 |

(Continued)

OTHER PUBLICATIONS

Scriba, Synthesis and in vitro Degradation of Testosterone-Lipid Conjugates, Arch. Pharm, 271-276 (Year: 1995).*
Li et al., "Mycophenolate mofetil or tacrolimus compared with intravenous cyclophosphamide in the induction treatment for active lupus nephritis," Nephrol. Dial. Transplant 2012; 27(4): 1467-72.
Ling and Luster, "Allergen-Specific CD4+ T Cells in Human Asthma," Ann. Am. Thorac. Soc. 2016; 13(Suppl 1): S25-S30.
Ling et al., C1q restrains autoimmunity and viral infection by regulating CD8+ T Cell metabolism; Science. May 4, 2018;360(6388):558-563.
Liénard et al., "Structural basis for the broad-spectrum inhibition of metallo-beta-lactamases by thiols," Org. Biomol. Chem. 2008;6(13):2282-94.
Loiseau et al., "Lymphotropic antifilarial agents derived from closantel and chlorambucil," Int. J. Parasitol. 1997; 27(4):443-7.

(Continued)

*Primary Examiner* — Carlos A Azpuru
(74) *Attorney, Agent, or Firm* — WOMBLE BOND DICKINSON (US) LLP; Danielle L. Herritt; Matthew J. Powers

(57) ABSTRACT

The present invention provides lymphatic system-directing lipid prodrugs, pharmaceutical compositions thereof, methods of producing such prodrugs and compositions, as well as methods of improving the bioavailability or other properties of a therapeutic agent that comprises part of the lipid prodrug. The present invention also provides methods of treating a disease, disorder, or condition such as those disclosed herein, comprising administering to a patient in need thereof a disclosed lipid prodrug or a pharmaceutical composition thereof.

15 Claims, No Drawings

(56) References Cited

FOREIGN PATENT DOCUMENTS

| | | |
|---|---|---|
| WO | 2001042246 A2 | 6/2001 |
| WO | 2002088112 A1 | 11/2002 |
| WO | 2003063794 A2 | 8/2003 |
| WO | 2004019973 A1 | 3/2004 |
| WO | 2004089925 A1 | 10/2004 |
| WO | 2004106328 A1 | 12/2004 |
| WO | 2005007623 A2 | 1/2005 |
| WO | 2005112919 A2 | 12/2005 |
| WO | 2005113554 A2 | 12/2005 |
| WO | 2006078846 A1 | 7/2006 |
| WO | 2006122806 A2 | 11/2006 |
| WO | 2007016176 A2 | 2/2007 |
| WO | 2007044729 A2 | 4/2007 |
| WO | 2007053452 A1 | 5/2007 |
| WO | 2007070514 A1 | 6/2007 |
| WO | 2007084786 A1 | 7/2007 |
| WO | 2007129161 A2 | 11/2007 |
| WO | 2008039218 A2 | 4/2008 |
| WO | 2008048611 A1 | 4/2008 |
| WO | 2008109943 A1 | 9/2008 |
| WO | 2008118802 A1 | 10/2008 |
| WO | 2009114512 A1 | 9/2009 |
| WO | 2009143295 A1 | 11/2009 |
| WO | 2011051967 A2 | 5/2011 |
| WO | 2011090760 A1 | 7/2011 |
| WO | 2011120044 A1 | 9/2011 |
| WO | 2015116904 A1 | 8/2015 |
| WO | 2016023082 A1 | 2/2016 |
| WO | 2017041139 A1 | 3/2017 |
| WO | 2018237282 A1 | 12/2018 |
| WO | 2019046478 A1 | 3/2019 |
| WO | 2019046491 A1 | 3/2019 |
| WO | 2020028787 A1 | 2/2020 |
| WO | 2020176856 A1 | 9/2020 |

OTHER PUBLICATIONS

Lonshakov et al., "Synthesis and properties of 3'-azido-3'-deoxythymidine derivatives of glycerolipids," Pharm. Chem. J. 2011;44(10):557-563.

Lui et al., "Effect of mycophenolate mofetil on severity of nephritis and nitric oxide production in lupus-prone MRL/lpr mice," Lupus. 2022; 11(7):411-8.

Lv et al., "Mycophenolate Mofetil Modulates Differentiation of Th1/Th2 and the Secretion of Cytokines in an Active Crohn's Disease Mouse Model," Int. J. Mol. Sci. 2015; 16(11):26654-66.

Maria and Davidson, "Emerging areas for therapeutic discovery in SLE," Curr. Opin. Immunol. 2018;55:1-8.

Mattarei et al., "Novel lipid-mimetic prodrugs delivering active compounds to adipose tissue," Eur. J. Med. Chem. 2017:135:77-78.

Meliambro et al., "Therapy for Proliferative Lupus Nephritis," Rheum. Dis. Clin. North Am. 2018;44(4):545-560.

Mergen et al., "Antiepileptic activity of 1,3-dihexadecanoylamino-2-valproyl-propan-2-ol, a prodrug of valproi acid endowed with a tropism for the central nervous system," J. Pharm. Pharmacol. 1991;43(11):815-6.

Michel et al., "Mycophenolate moftil in multiple sclerosis: a multicentre retrospective study on 344 patients," J. Neurol. Neurosurg. Psychiatry. 2014;85(3):279-83.

Miller and Karpus, "Experimental autoimmune encephalomyelitis in the mouse," Curr. Protoc. Immunol. 2007; Chapter 15: Unit 15.1.

Minard-Colin et al., "Lymphoma depletion during CD20 immunotherapy in mice is mediated by macrophage FcγRI, FcγRIII, and FcγRIV," Blood. 2008; 112(4): 1205-1213.

Miyamoto et al., "A novel prodrug stategy for extremely hydrophobic agents: conjugation to symmetrically branched glycerol trimer improves pharmacological and pharmacokinetic properties of fenofibrate," Mol. Pharm. 2013; 10 (7):2723-9.

Mok, "Mycophenolate mofetil for lupus nehpritis: an update," Expert Rev. Clin. Immunol. 2015;11(12):1353-64.

Nakajima, et al., "Effectiveness of tacrolimus in comparison with methotrexate or biologics in propensity score-matched patients with rheumatoid arthritis," Mod. Rheumatol. 2016; 26(6):836-843.

Nash et al., "Phase 3 study comparing methotrexate and tacrolimus with methotrexat an cyclosporine for prophylaxis of acute graft-versus-host disease after marrow transplantation from unrelated donors," Blood. 2000;96:2062-2068.

Negi and Das, "CNS: Not an immunopivilaged site anymore but a virtual secondary lymphoid organ," Int. Rev.Immunol. 2018;37(1): 57-68.

Nieschlag et al., "Testosterone replacement therapy: current trends and future directions," Hum. Reprod. Update. 2004; 10(5):409-19.

Ning et al., "Visualizing metabolically labeled glycoconjugates of living cells by copper-free and fast huisgen cycloadditions," Angew. Chem. Int. Ed. Engl. 2008; 47(12): 2253-5.

Okayama et al., "Mast cells are involved in the pathogenesis of indomethacin-induced rat enteritis," J. Gastroenterol. 2009; 44(Suppl 19):35-9.

Osborne et al., "Lower allopregnanolone during pregnancy predicts postpartum depression: An exploratory study," Psyhoneuroendocrinology. 2017;79:116-121.

Pallet et al., "Impact of Immunosuppressive Drugs on the Metabolism of T Cells," Int. Rev. Cell. Mol. Biol. 2018; 341:169-200.

Paris et al., "Glycerides as prodrugs. 1. Synthesis and antiinflammatory activity of 1,3-bis(alkanoyl)-2-(O-acetylsalicyloyl)glycerides (aspirin triglycerides).," J. Med. Chem. 1979; 22(6):683-7.

Paris et al., "Glycerides as prodrugs. 2. 1,3-Dialkanoyl-2-(2-methyl-4-oxo-1,3-benzodioxan-2-yl)glycerides (cyclic aspirin triglycerides) as antiinflammatory agents," J. Med. Chem. 1980;23(1):79-82.

Paris et al., "Glycerides as prodrugs. 3. Synthesis and antiinflammatory activity of [1-(p-chlorobenzoyl)-5-methoxy-2-methylindole-3-acetyl]glycerides (indomethacin glycerides)," J. Med. Chem. 1980;23(1):9-13.

PCT International Search Report and Written Opinion from PCT/AU2016/050845 dated Oct. 27, 2016.

PCT International Search Report and Written Opinion from PCT/US2018/048642 dated Dec. 11, 2018.

PCT International Search Report and Written Opinion from PCT/US2018/066580 dated Apr. 24, 2019.

PCT International Search Report and Written Opinion from PCT/AU2015/050460 dated Oct. 15, 2015.

PCT International Search Report and Written Opinion from PCT/US2018/066585 dated Apr. 30, 2019.

PCT International Search Report and Written Opinion from PCT/US2019/044877 dated Oct. 24, 2019.

PCT International Search Report and Written Opinion from PCT/US2020/020387 dated Jun. 24, 2020.

PCT International Search Report and Written Opinion from PCT/US2020/020398 dated Jul. 20, 2020.

PCT International Search Report and Written Opinion from PCT/US2020/020433 dated Jun. 26, 2020.

PCT International Search Report and Written Opinion from PCT/AU2020/050997 dated Dec. 1, 2020.

Perché et al., "Prenatal testosterone treatment potentiates the aggression-inhibiting effect of the neurosteroid dehydroepiandrosterone in female mice," Agress. Behav. 2001;27(2):130-8.

Pesu et al., "Jak3, severe combined immunodeficiency, and a new class of immunosuppressive drugs," Immunol. Rev. 2005; 203:127-42.

Ple et al., "Natural killer cells accumulate in lung-draining lymph nodes and regulate airway eosinophilia in a murine model of asthma," Scand. J. Immunol. 2010;72(2):118-27.

Pond and Tozer, "First-pass elimination. Basic concepts and clinical consequences," Clin. Pharmacokinet. 1984;9(1):1-25.

Pouton "Formulation of poorly water-soluble drugs for oral administration: Physicochemical and physiological issues and the lipid formulation classification system," Eur. J. Pharm. Sci. 2006; 29(3-4):278-87.

Pouton, "Lipid formulations for oral administration of drugs: non-emulsifying, self-emulsifying and 'self-microemulsifying' drug delivery systems," Eur. J. Pharm. Sci. 2000; 11(Suppl 2):S93-8.

Powell et al., "The immunomodulatory drugs cyclosporin A, mycophenolate mofetil, and sirolimus (rapamycin) inhibit allergen-

(56) References Cited

OTHER PUBLICATIONS induced proliferation and IL-5 production by PBMCs from atopic asthmatic patients," 2001; 108(6):915-7.
Pubmed Compound Summary for CID 132121512, '1-O-[3R,5S,8S,9S,10S,13S,14S,17S)-17-Acetyl-10,13-dimethyl-11-oxo-1,2,3,4,5,6,7,8,9,12,14,15,16,17-tetradecahydrocyclopenta[a]phenanthren-3-yl] 3-O-[1,3-di (hexadecanoyloxy)propan-2-yl]propanedioate', U.S. National Library of Medicine, Jan. 28, 2018 (https://pubchem.ncbi.nlm.nih.gov/compound/132131512.
Renna et al., "Optimization of the treatment with immunosuppressants and biologics in inflammatory bowel disease," World J. Gastroenterol. 2014;20(29):9675-9690.
Rodriguez-Lago et al., "Previous exposure to biologics and C-reactive protein are associated with the response to tacrolimus in inflammatory bowel disease," Rev. Esp. Enferm. Dig. 2016;108(9):550-7.
Rogawski et al., "Neuroactive steroids for the treatment of status epilepticus," Epilepsia. 201;54(Suppl 6):93-8.
Rupprecht, "Neuroactive steroids: mechanisms of action and neuropsychopharmacological properties," Psychoneuroendocrinology. 2003;20(2):139-68.
Turkmen, Sahruh et al., "Tolerance to allopregnanolone with focus on the GABA-A receptor", British Journal of Pharmacology, 162:311-327 (2011).
International Search Report and Written Opinion of corresponding PCT/US2021/016955 dated May 25, 2021, 5 pages.
Alouane et al., "Self-immolative spacers: kinetic aspects, structure-proper Alouane applications," et al., Angew. Self-immChem. Int. Ed. Engl. 2015; 54(26):7492-509.
Alouane et al., "Self-immolative spacers: kinetic aspects, structure-property relationships, and applications," Supporting Information, Angew. Chem. Int. Ed. Engl. 2015; (10 pages).
Amory et al., "Oral testosterone-triglyceride conjugate in rabbits: single-dose pharmacokinetics and comparison with oral testosterone undecanoate," J. Androl. 2003; 24 (5): 716-20.
Amsberry et al., "Amine prodrugs which utilize hydroxy amide lactonization. II. A potential esterase-sensitive amide prodrug," Pharm. Res. 1991; 8(4):455-61.
Andréen et al., "Sex steroid induced negative mood may be explained by the Paraoxical effect mediated by GABAA modulators," Psychoneuroendocrinology. 2009:34(8): 1121-32.
Bitran et al., "Anxiolytic effect of progesterone is mediated by the neurosteroid allopregnanolone at brain GABAA receptors," J. Neuroendocrinol. 1995;7(3): 171-7.
Blencowe et al., "Self-immolative linkers in polymeric delivery systems," Polym. Chem. 2011, 2:773-790.
Bourgeois et al., "Application of thermal analysis to the study of lipidic prodrug incorporation into nanocarriers," J. Therm. Anal. Calorim. 2009; 98: 65-71.
Barile-Fabris et al., "Controlled clinical trial of IV cyclophosphamide versus IV methylprednisolone in severe neurological manifestations in systemic lupus erythematosus," Ann. Rheum. Dis. 2005; 64(4): 620-25.
Brand et al., "Collagen-induced arthritis," Nat. Protoc. 2007; 2(5): 1269-75.
Charette et al., "Practical and Highly Regio- and Stereoselective Synthesis of 2-Substituted Dihydropyridines and Piperidines: Application to the Synthesis of (−)-Coniine," J. Am. Chem. Soc. 2001; 123(47): 11829-11830.
Chowdhury and Ghosh, "Highly Regio- and Enantioselective Organocatalytic Conjugate Addition of Alkyl Methyl Ketones to a ß-Silylmethylene Malonate," Org. Lett. 2009; 11(15):3270-3273.
Coutinho and Chapman, "The anti-inflamatory and iummunosuppressive effects of glucocorticoids, recent developments and mechanistic insights," Mol. Cell. Endrocrinol. 2011; 335(1): 2-13.
Cyr et al., "Recent progress on nuclear receptor RORγ modulators," Bioorg. Med. Chem. Lett. 2016; 26(18):4387-4393.
D'yakova et al., "lymphotropic prodrugs based on 2', 3'-didehydro-3'-deoxythymidine. Synthesis and sensitivity to hydrolysis," Russian Journal of Bioorganic Chemistry. 2011; 47(10): 1588-1593.
Deverre et al., "In-vitro evaluation of fila ricidal activity of GABA and 1,3-dipalmitoyl-2-(4-aminobutyryl)glycerol HCI: a diglyceride prodrug," J. Pharm. Pharmacol. 1989; 41(3): 191-3.
DeWolf and Sykes "Alloimmune T Cells in transplantation," J. Clin. Invest. 2017; 127(7):2473-2481.
Edwards et al., "Animal models for the study of intestinal lymphatic drug transport," Adv. Drug. Deliv. Rev. 2011; 50 (1-2):45-60.
Freitag et al., "Gliadin-primed CD4+C45RBlowCD25- T cells drive gluten-dependent small intestinal damage after adoptive transfer into lymphopenic mice," Gut. 2009;58(12):1597-605.
Frye and Duncan, "Progesterone metabolites, effective at the GABAA receptor complex, attenuate pain sensitivity in rats," Brain Res. 1994:643(1-2):194-203.
Frye and Walf, "Changes in progesterone metabolites in the hippocampus can modulate open field and forced swim test behavior of proestrous rats," Horm. Behav. 2022; 41(3):306-15.
Garzon-Aburbeh et al., "1,3-Dipalmitoylglycerol ester of chlorambucil as a lymphotropic, orally administrable antineoplastic agent," J. Med. Chem. 1983; 26(8):1200-1203.
Garzon-Aburbeh et al., "A lymphotropic prodrug of L-dopa: synthesis, pharmacological properties and pharmacokinetic behavior of 1,3-dihexadecanoyl-2-[(S)-2-amino-3-3(3,4-dihydroxyphenyl)propanoyl]propane-1,2,3-triol," J. Med. Chem. 1986; 28(5):687-691.
Goodin, "Glucocorticoid treatment of multiple sclerosis," Handb. Clin. Neurol. 2014;122:455-64.
Gossauer and Kühne, "Synthesen von Gallenfarbstoffen, V. Stereospezifische Totalsynthesen diastereomerer Mesobilirhodine und Isomesobilirhodine," Justus Liebigs Analender Chemie. 1977;4:664-686.
Grainge et al., "Case series reporting the effectiveness of mycophenolate mofetil in treatment-resistant asthma," Eur. Respir. J. 2013; 42(4):1134-7.
Griffin et al., "Niemann-Pick type C disease involves disrupted neurosteroidogensis and responds to allopregnanolone," Nat. Med. 2004; 10(7):704-11.
Guo et al., "Rheumatoid arthritis: Pathological mechanisms and modern pharmacologic therapies," Bone Res. 2018;6:15.
Gupta et al., "Dexamethasone cyclophosphamide pulse therapy in systemic lupus erythematosus: a case report," J. Dermatolg. Treat. 2009;20(1):55-8.
Han et al., "Lymphatic Transport and Lymphocyte Targeting of a Triglyceride Mimetic Prodrug is Enhanced in a Large Animal Model: Studies in Greyhound Dogs," Mol. Pharm. 2016; 13(10):3351-3361.
Han et al., "Targeted delivery of a model immunomodulator to the lymphatic system: comparison of alkyl ester versus triglyceride mimetic lipid prodrug strategies," J. Control Release. 2014; 177:1-10.
Huvelle et al., "Syntheses and kinetic studies of cyclisation-based self-immolative spacers," Org. Biomol. Chem. 2017; 15(16):3435-3443.
Irwin and Diaz Brinton, "Allopregnanolone as regenerative therapeutic for Alzheimer's disease: translational development and clinical promise," Prog. Neurobio. 2014;113:40-55.
Irwin et al., "Frontiers in therapeutic development of allogregnanolone for Alzheimer's disease and other neurological disorders," Front. Cell. Neurosci. 2014;8:203.
Iwaszkiewicz-Grzes et al., "Synthesis and biological activity of mycophenolic acid-amino acid derivatives," Eur. J. Med. Chem. 2013;69:863-71.
Janossy and Greaves, "Lymphocyte activation: I. Response of T and B lymphocytes to phytomitogens," Clin. Exp. Immunol. 1971;9(4):483-498.
Jeong et al., "Does optimization of tacrolimus for improving survival time of PEGylated islets in a rat-to-mouse xenograft model," Macromolecular Research. 2016; 24(12):1047-1054.
Jew et al., "Asymmetric synthesis of (R)-(+)-etomoxir," Tetrahedron: Asymmetry. 1997; 8(8):1187-1192.

(56) References Cited

OTHER PUBLICATIONS

Kai et al., "Structure-activity relationship study of flowering-inducer FN against Lemna paucicostata," Tetrahedron. 2008; 64(28):6760-6769.
Kanes et al., "Brexanolone (SAGE-547 injection) in post-partum depression: a randomised controlled trial," Lancet. 2017;390(10093):480-489.
El Kihel et al., "Synthesis and evaluation of the anti-inflammatory effects of niflumic acid lipophilic prodrugs in brain edema," Arzneimittelforschung. 1996;46(11):1040-4.
Kim et al., "Convenient Synthesis of Electron Deficient Dienes via Pd(0) Catalyzed Coupling," Synlett. 1998; 1998 (10):1059-1060.
Kim et al., "The Anti-Inflammatory Effects of Oral-Formulated Tacrolimus in Mice with Experimental Autoimmune Encephalomyelitis," J. Korean Med. Sci. 2017;32(9):1502-1507.
Koboziev et al., "Gut-associated lymphoid tissue, T cell trafficking, and chronic intestinal inflammation," Ann. NY. Acad. Sci. 2010;1207(Suppl 1):E86-E93.
Kratz et al., "Prodrug strategies in anticancer chermotherapy," ChemMedChem. 2008; 3(1):20-53.
Lalanne et al., "Metabolism evaluation of biomimetic prodrugs by in vitro models and mass spectrometry," Int. J. Pharm> 2009;379(2):235-43.
Lalanne et al., "Synthesis and biological evaluation of two glycerolipidic prodrugs of didanosine for direct lymphatic delivery against HIV," Bioorg. Med. Chem.Lett. 2007;17(8):2237-40.
Levine and Raines, "Trimethyl lock: a trigger for molecular release in chemistry, biology, and pharmacology," Chem. Sci. 2012; 3(8):2412-2420.
Sagiv-Barfi et al., "Ibrutinib enhances the antitumor immune response induced by intratumoral injection of a TLR9 ligand in mouse lymphoma," Blood. 2015;125(13):2079-86.
Schüle et al., "The role of allopregnanolone in depression and anxiety," Prog. Neurobiol. 2014;113:79-87.
Scriba et al., "Bioavailability of Phenytoin Following Oral Administration of Phenytoin-lipid Conjugates to Rats," J. Pharm. Pharmacol. 1995; 47(11):945-948.
Scriba, "Synthesis and in vitro degradation of testosterone-lipid conjugates," Arch. Pharm. (Weinheim), 1995; 328(3):271-6.
Shastina et al., "Synthesis, Properties, and Anti-HIV activity of new lipophilic 3'-azido-3'-deoxythymidine conjugates containing functional phosphoric linkages," Russian Journal of Bioorganic Chemistry. 2013;39:161-169.
Siebert et al., "New Analogues of Mycophenolic Acid," Mini Rev. Med. Chem. 2017;17(9):734-745.
Silverman, "Chapter 8—Prodrugs and Drug Delivery Systems," in The Organic Chemistry of Drug Design and Drug Action (Second Edition), 2004 ([gs. 497-557, 520-525).
Silverman, "Chapter 9—Prodrugs and Drug Delivery Systems," in The Organic Chemistry of Drug Design and Drug Action (Third Edition), 2014 (pp. 423-486).
Skanji et al., "A new nanomedicine based on didanosine glycerolipidic prodrug enhances the long term accumulation of drug in a HIV sanctuary," Int. J. Pharm. 2011;414(1-2):285-97.
Smith and Cooper, "Mycophenolate mofetil therapy in the management of inflammatory bowel disease—a retrospective case series and review," J. Crohns Colitis. 2014;8(8):890-7.
Smith et al., "Modular assembly of macrocyclic organo-peptide hybrids using synthetic and genetically encoded precursors," Angew. Chem. Int. Ed. Engl. 2011;50(22):5075-80.
Sobczak, "Synthesis and characterization of polyester conjugates of ciprofloxacin," Eur. J. Med. Chem. 2010;45 (9):3844-9.
Stadnyk et al., "Neutrophil migration into indomethacin induced rat small intestinal injury is CD11a/CD18 and CD11b/CD18 co-dependent," Gut. 2002;50(5):629-635.
Stump et al., "Lymphatic Changes in Respiratory Diseases: More than Just Remodeling of the Lung?" Am. J. Respir. Cell Mol. Biol. 2017;57(3):272-279.

Subba Reddy et al., "A Concise and Convergent Total Synthesis of Two Novel Cytotoxic Hydroquinones, Lanneaquinol and (R)-2'-Hydroxylanneaquinol," Helv. Chim. Acta. 2013; 96(10):1983-1990.
Sugihara et al., "Studies on intestinal lymphatic absorption of drugs. I. Lymphatic absorption of alkyl ester derivatives and alpha-monoglyceride derivatives of drugs," J. Pharmacobiodyn. 1988; 11(5):369-76.
Sugihara et al., "Studies on intestinal lymphatic absorption of drugs. II. Glyceride prodrugs for improving lymphatic absorption of naproxen and nicotinic acid," J. Pharmacobiodyn. 1988;11(8):555-62.
Takada et al., "Conversion of a novel 5-fluorouracil (5-FU) derivative to 5-FU in rats," Res. Commun. Chem. Pathol. Pharmacol. 1983;40(1):99-108.
Takagi et al., "The synthesis of enantiomerically pure novel liquid crystal compounds containing the bis(trifluoromethyl) alkanediol moiety," Tetrahedron Asymmetry. 2004;15(17):2591-2594.
Tan and Lawrence, "Use of mycophenolate mofetil in inflammatory bowel disease," World J. Gastroenterol. 2009;15(13):1594-1599.
Tanaka et al., "Structure of FK506, a novel immunosuppressant isolated from Streptomyces," J. Am. Chem. Soc. 1987;109(16):5031-5033.
Taniguchi et al., "A Case of Severe Bronchial Asthma Controlled with Tacrolimus," J. Allergy (Cario). 2011;201:479129.
Taylor and Ryan, "Understanding mechanisms of hypertension in systemic lupus erythematosus," Ther. Adv. Cardiovasc. Dis. 2017;11(1):20-32.
Tohda et al., "Establishment of a novel B-cell lymphoma cell line with suppressed growth by gamma-secretase inhibitors," Leuk. Res. 2006;30(11):1385-90.
Tranoy-Opalinski et al., "Design of self-immolative linkers for tumour-activated prodrug therapy," Anticancer Agents Med. Chem. 2008;8(6):618-37.
Trevaskis et al., "Bile increases intestinal lymphatic drug transport in the fasted rat," Pharm. Res. 2005;22(11):1863-1870.
Trevaskis et al., "From sewer to saviour—targeting the lymphatic system to promote drug exposure and activity," Nature Review Drug Discovery. 2015;14:781-803.
Van Bruggen et al., "Attenuation of murine lupus nephritis by mycophenolate mofetil," J. Am. Soc. Nephrol. 1998;9(8):1407-15.
Van Dieren et al., "Local application of tacrolimus in distal colitis: feasible and safe," Inflamm. Bowel Dis. 2009; 15(2):193-8.
Wagner et al., "Selective epimerization and skeletal resection in the ascomycin framework: A study of the biological consequences of lactam rotamer selection," Tetrahedron. 1996;52(29):9643-9654.
Warren et al., "Evaluation of the Structural Determinants of Polymeric Precipitation Inhibitors Using Solvent Shift Methods and Principle Component Analysis," Mol. Pharmaceutics. 2013;10(8):2823-2848.
Weyand and Goronzy, "Immunometabolism in early and late stages of rheumatoid arthritis," Nat. Rev. Rheumatol. 2017;13(5):291-301.
Wiebe and Kavaliers, "Analgesic effects of the putative FSH-suppressing gonadal steroid, 3 alpha-hydroxy-4-pregnen-20-one: possible modes of action," Brain Res. 1988;461(1):150-7.
Wirtz et al., "Chemically induced mouse models of acute and chroni intestinal inflammation," Nat. Protoc. 2017;12(7):1295-1309.
Wittman et al.,. "Synthesis and antitumor activity of novel paclitaxel-chlorambucil hybrids," Bioorg. Med. Chem. Lett. 2001;11(6):811-814.
Wolbers et al., "Viability study of HL60 cells in contact with commonly used microchip materials," Electrophoresis. 2006;27(24):5073-80.
Young and Kerr, "Total Synthesis of (+)-Nakadomarin A," J. Am. Chem. Soc. 2007; 129(5):1465-1469.
Zgair et al., "Oral administration of cannabis with lipids leads to high levels of cannabinoids in the intestinal lymphatic system and prominent immunomodulation," Scientific Report. 2017;7(14542):1-2.
Belin de Chantemèle et al., "Cyclooxygenase-2 preserves flow-mediated remodelling in old obese Zucker rat Mesenteric arteries," Cardiovas. Res. 2010;86(3):516-25.
Benenato K F: "Preparation of compounds and lipid nanoparticle compositions for intracellular delivery of therapeutic agents," WO2017049245 A2, vol. 166, Mar. 23, 2017, pp. 1-2, XP055786021.

(56) References Cited

OTHER PUBLICATIONS

Hsieh et al., "Selective COX2 inhibition improves whole body and muscular insulin resistance in fructose-fed rats," Eur. J. Clin. Invest. 2008;38(11):812-9.

Nair, Abhijit S., et al., "Allopregnanolone: A neurosteroid for managing acute and chronic pain conditions," Saudi Journal of Anaesthesia; vol. 13(3):264-266 (2019).

Tolmacheva, I. A., et al., "Synthesis and antiviral activity of C-3 (C-28)-substituted 2, 3-seco-triterpenoids", Chemistry of Natural Compounds, Consultants Bureau, New York, NY, US, vol. 49(6): 1050-1058, XP035332611, ISSN: 0009-3130, DOI: 10.1007/S10600-014-0821-3 [retrieved on Jan. 15, 2014] *compound 6a p. 1051* (2014).

Genet, Cedric, et al., "Structure-Activity Relationship Study of Betulinic Acid, A Novel and Selective TGR5 Agonist, and Its Synthetic Derivatives: Potential Impact in Diabetes", Journal of Medicinal Chemistry, vol. 53(1): 178-190, XP055043872, ISSN: 0022-2623, DOI: 10.1021/jm900872z *compound 28 p. 1818* (2010).

Nemoto, H., et al., "Design and Synthesis of Cholestane Derivatives Bearing a Cascade-type Polyol and the Effect of Their Property on a Complement System in Rat Serum", Bioorganic & Medicinal Chemistry Letters, Elsevier, Amsterdam, NL, vol. 9(2): 205-208, XP004152601, ISSN: 0960-894X, DOI: 10.1016/S0960-894X (98) 00723-9 *compound 1b p. 206* (1999).

Extended European Search Report for EP3829590, dated Apr. 14, 2022, 10 pages.

Scriba, Gerhard K.E., "Synthesis and in Vitro Degradation of Testosterone-Lipid Conjugates", Arch. Pharm (Weinheim, Germany), 328(3):271-276 (1995).

Hu, Luojuan, et al., "Glyceride-Mimetic Prodrugs Incorporating Self-Immolative Spacers Promote Lymphatic Transport, Avoid First-Pass Metabolism, and Enhance Oral Bioavailability", Angewandte Chemie, 55(44):13700-13705, International Edition (2016).

Khera, Mohit, "Patients with Testosterone Deficiency Syndrome and Depression", Arch. Esp. Urol., vol. 66 (7):729-739 (2013).

Gholaminejad, Azadeh, et al. "Prelimbic of Medial Prefrontal Cortex GABA Modulation through Testosterone on Spatial Learning and Memory", Iranian Journal of Pharmaceutical Research, vol. 18(3):1429-1444 (2019).

Ghit, Amr., et al., "GABAA receptors: structure, function, pharmacology, and related disorders," Journal of Genetic Engineering and Biotechnology, vol. 19(123):1-15 (2021).

Han, Sifei, et al., "Constitutive Triglyceride Turnover into the Mesenteric Lymph ls Unable to Support Efficient Lymphatic Transport ofa Biomimetic Triglyceride Prodrug," Journal of Pharmaceutical Sciences, vol. 105, pp. 786-796 (2016).

Bullock, Amy, et al., "Zuranolone as an oral adjunct to treatment of Parkinsonian tremor: A phase 2, open-label study," Journal of the Neurological Sciences, vol. 421, pp. 1-5 (2021).

Han, Sifei, et al., "Profiling the Role of Deacylation-Reacylation in the Lymphatic Transport of a Triglyceride-Mimetic Prodrug," Pharm. Res., vol. 32, pp. 1830-1844 (2015).

* cited by examiner

LIPID PRODRUGS OF NEUROSTEROIDS

CROSS-REFERENCE TO RELATED APPLICATIONS

This application is a continuation of International Application No. PCT/US2021/016955, filed Feb. 5, 2021, and claims the benefit of U.S. Provisional Patent Application No. 62/970,607, filed on Feb. 5, 2020; U.S. Provisional Patent Application No. 63/009,533, filed on Apr. 14, 2020; and U.S. Provisional Patent Application No. 63/070,064, filed on Aug. 25, 2020; the entirety of each of which is hereby incorporated by reference.

TECHNICAL FIELD

The present invention relates to compounds in the form of prodrugs, in particular, compounds that promote transport of a pharmaceutical agent to the lymphatic system and subsequently enhance release of the parent drug. The present invention also relates to compositions and methods of using such prodrugs.

BACKGROUND OF THE INVENTION

Neurosteroids are steroids synthesized within the brain and modulate neuronal excitability by rapid non-genomic actions. The term "neurosteroid," originally coined by the French physiologist Etienne Baulieu, is now widely used to refer to steroids that are synthesized in the brain. Circulating steroid hormones serve as precursors for the synthesis of neurosteroids, which are produced locally in the hippocampus and other brain structures. Imbalances in neurosteroid levels are implicated in numerous diseases, disorders, and conditions. They are classified as pregnane neurosteroids (for example, allopregnanolone and allotetrahydrodeoxycorticosterone), and androstane neurosteroids (for example, androstanediol and etiocholanone). Neurosteroids such as allopregnanolone are positive allosteric modulators of GABA-A receptors with powerful antiseizure activity in diverse animal models. Neurosteroids increases both synaptic and tonic inhibition. They are endogenous regulators of seizure susceptibility, anxiety and stress. Sulfated neurosteroids such as pregnenolone sulfate, which are negative GABA-A receptor modulators, are memory-enhancing agents. Sex differences in susceptibility to brain disorders could be due to neurosteroids and sexual dimorphism in specific structures of the human brain. Synthetic neurosteroids that exhibit better bioavailability and efficacy and drugs that enhance neurosteroid synthesis have therapeutic potential in anxiety, epilepsy and other brain disorders.

However, therapeutic use of neurosteroids has been hampered by the challenges of selective delivery to specific tissues of the body, such as the brain, as well as undesired metabolism of neurosteroids when delivered orally.

The lymphatic system consists of a specialized network of vessels, nodes and lymphoid tissues that are distributed throughout the body in close proximity to the vascular system. The lymphatic system plays a number of key roles in immune response, fluid balance, nutrient absorption, lipid homeostasis, and tumor metastasis. Due to the unique anatomical and physiological characteristics of the lymphatic system, targeted drug delivery to and through the lymphatic system has been suggested as a means to improve both pharmacokinetic and pharmacodynamic profiles.

Lymphatic drug transport has the potential to enhance oral bioavailability through avoidance of first pass metabolism, to alter systemic drug disposition, and to enhance efficacy against lymph or lymphocyte mediated pathologies such as lymphoma, leukemia, lymphatic tumor metastasis, autoimmune disease, lymph resident infections and transplant rejection. In order for drugs to access the intestinal lymph, they must first associate with intestinal lymph lipoproteins that are assembled in intestinal absorptive cells (enterocytes) in response to lipid absorption. Association with these lipoproteins subsequently promotes drug transport into the lymph since their size precludes ready diffusion across the vascular endothelium lining the blood capillaries that drain the small intestine. Instead, these large colloidal structures enter the lymphatic capillaries since the lymphatic endothelium is considerably more permeable than that of the vascular endothelium.

Historically, drugs with high lymphatic transport have been highly lipophilic in order to promote physical association with lipoproteins (usually, but not exclusively, log D>5 and solubility in long chain triglyceride of >50 mg/g). Therefore, highly lipophilic analogues of drugs have been envisaged as one way to promote lymphatic drug transport. However, chemical modification of a parent drug can result in a reduction in potency and, in many cases, significant increases in lipophilicity have been correlated with increases in toxicity.

Compounds in the form of lipophilic prodrugs provide a means to temporarily increase lipophilicity and lipoprotein affinity of a pharmaceutical compound, thereby increasing lymphatic targeting. Having been transported via the lymphatic system, the prodrug is cleaved, thereby releasing the parent drug in order to be active at its target site.

Accordingly, there exists a need to develop novel lipid-pharmaceutical agent conjugates that facilitate stable transport of the pharmaceutical agent to the intestinal lymph and that readily revert to the parent agent in order to be active. The present invention addresses this need and provides other related advantages.

SUMMARY OF THE INVENTION

In one aspect, the present invention provides a compound of Formula I:

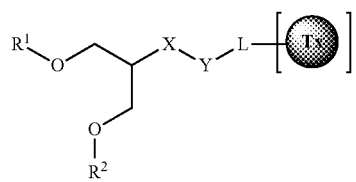

or a pharmaceutically acceptable salt thereof, wherein each variable is as defined herein.

In another aspect, the present invention provides a method of treating a disease, disorder, or condition such as one of those disclosed herein, comprising administering to a patient in need thereof an effective amount of a compound of Formula I, or a pharmaceutically acceptable salt thereof.

DETAILED DESCRIPTION OF THE INVENTION

1. General Description of Certain Aspects of the Invention

Lymphatic System-Directing Prodrugs

Compounds of the present invention, and compositions thereof, are useful in promoting transport of a therapeutic agent to the lymphatic system and in subsequently enhancing release of the parent drug, i.e. the therapeutic agent.

In one aspect, the present invention provides a compound of Formula I:

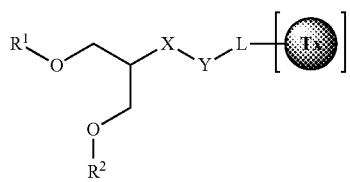

I or a pharmaceutically acceptable salt thereof, wherein:
- $R^1$ and $R^2$ are each independently hydrogen, an acid-labile group, a lipid, or —C(O)$R^3$;
- each $R^3$ independently is a saturated or unsaturated, straight or branched, optionally substituted $C_{1-37}$ hydrocarbon chain;
- X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;
- each R independently is hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
- Y is absent or is —C(O)—, —C(NR)—, or —C(S)—;
- L is a covalent bond or a saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

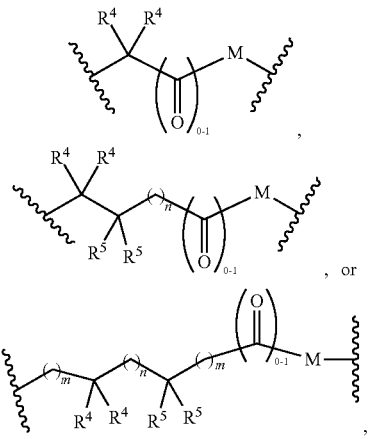

wherein either the right-hand side or left-hand side of L is attached to

;

- each -Cy- independently is an optionally substituted 3-6 membered bivalent saturated, partially unsaturated, or aromatic ring having 0-4 heteroatoms independently selected from nitrogen, oxygen, or sulfur;
- each $R^4$ and $R^5$ independently is hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur;

-M- is a self-immolative group;
n is 0-18;
each m independently is 0-6; and

is a therapeutic agent selected from a naturally-occurring or non naturally-occurring neurosteroid or an analogue or prodrug thereof.

In one aspect, the present invention provides a method of treating a disease, disorder, or condition in a patient in need thereof, comprising administering to the patient an effective amount of a disclosed lipid prodrug, such as a compound of Formula I, or a pharmaceutically acceptable salt thereof.

It is understood that a disclosed lipid prodrug may exist in the form of a pharmaceutically acceptable salt. Thus, a reference to a "lipid prodrug" is also a disclosure of "lipid prodrug or a pharmaceutically acceptable salt thereof." It follows that such a lipid prodrug or pharmaceutically acceptable salt thereof may be used in a pharmaceutical composition and a method of use, such as those disclosed herein.

One approach to directing drugs into the lymphatic transport system is to employ prodrugs that participate in endogenous pathways that control the absorption, transport (including passive transport), and metabolism of dietary lipids. In one aspect, the present invention provides a lipid prodrug comprising a neurosteroid such as a pregnane neurosteroid conjugated to a glycerol-based moiety comprising two fatty acids or other lipids. Without wishing to be bound by theory, it is believed that such a prodrug mimics a dietary triglyercide, such that it participates in triglyceride processing and metabolism in the GI tract.

Dietary lipids, including triglycerides, follow a particular metabolic pathway to gain access to the lymph (and ultimately the systemic circulation) that is entirely distinct from that of other nutrients such as proteins and carbohydrates. After ingestion, dietary triglycerides are hydrolyzed by lipases in the lumen to release one monoglyceride and two fatty acids for each molecule of triglyceride. The monoglyceride and two fatty acids are subsequently absorbed into enterocytes and re-esterified to triglycerides.

Resynthesised triglycerides are assembled into intestinal lipoproteins, primarily chylomicrons. After formation, chylomicrons are exocytosed from enterocytes and subsequently gain preferential access to the intestinal lymphatics. Once within the lymphatic system, chylomicrons containing packaged triglycerides drain through a series of capillaries, nodes and ducts to join the systemic circulation at the junction of the left subclavian vein and internal jugular vein. Following entry into blood circulation, triglycerides in chylomicrons are preferentially and efficiently taken up by tissues with high expression levels of lipoprotein lipases, such as adipose tissue, the liver, and potentially certain types of tumor tissues.

Lipid prodrugs are expected to behave similarly to natural triglycerides and to be transported to and through the lymphatic system to reach the systemic circulation without interacting with the liver. In some embodiments, the lipid prodrugs are cleaved, releasing the neurosteroid such as a pregnane neurosteroid, after the prodrugs have reached the systemic circulation, or after reaching a target tissue. In some embodiments, the lipid prodrugs release the neurosteroid such as a pregnane neurosteroid by destruction of a self-immolative linker that attaches the neurosteroid to the glyercol-derived group, or by enzymatic cleavage of a linker. In this way, the pharmacokinetic and pharmacodynamic profiles of the parent neurosteroid may be manipulated to enhance access to the lymph and lymphoid tissues, thereby promoting oral bioavailability via avoidance of first-pass metabolism (and potentially intestinal efflux). Accordingly, in some embodiments, the disclosed lipid prodrug has improved oral bioavailability, reduced first-pass metabolism, reduced liver toxicity, or improved other pharmacokinetic properties as compared with the parent neurosteroid. In some embodiments, the disclosed lipid prodrug has increased drug targeting (as compared with the parent therapeutic agent) to sites within the lymph, lymph nodes and lymphoid tissues, and to sites of high lipid utilization and lipoprotein lipase expression such as adipose tissue, liver and some tumors. In some embodiments, a disclosed lipid prodrug is delivered to the central nervous system (CNS) or crosses the blood-brain barrier (BBB) via the lymphatic system.

In certain aspects, the present invention provides methods of modulating the delivery, distribution, or other properties of a neurosteroid such as a pregnane neurosteroid. In one aspect, the present invention provides a method of delivering a neurosteroid to the systemic circulation of a patient in need thereof, wherein the neurosteroid partially, substantially, or completely bypasses first-pass liver metabolism in the patient, comprising the step of administering to the patient a disclosed lipid prodrug of the neurosteroid. In another aspect, the present invention provides a method of modifying a neurosteroid to partially, substantially, or completely bypass first-pass liver metabolism in a patient after administration of the neurosteroid, comprising the step of preparing a disclosed lipid prodrug of the neurosteroid. In some embodiments, the lipid prodrug is administered orally. In some embodiments, preparing the lipid prodrug comprises the step of covalently conjugating a neurosteroid to a glycerol-based scaffold comprising two fatty acids or other lipids, thereby providing the lipid prodrug.

In another aspect, the present invention provides a method of improving oral bioavailability of a neurosteroid, enhancing gut absorption of a neurosteroid, or decreasing metabolism, decomposition, or efflux in the gut of a neurosteroid, comprising the step of preparing a disclosed lipid prodrug of the neurosteroid.

In another aspect, the present invention provides a method of modifying, e.g., improving, delivery of a neurosteroid to a target tissue, comprising the step of preparing a disclosed lipid prodrug of the neurosteroid. In some embodiments, the target tissue is the lymph, a lymph node (such as a mesenteric lymph node), adipose tissue, liver, or a tumor, such as a lymph node site of metastasis. In some embodiments, the target tissue is the brain or CNS.

Lipid prodrugs that readily convert to parent therapeutic agent after transport via the systemic circulation have reduced free drug concentrations in the gastrointestinal (GI) tract, which may provide benefits in reducing gastrointestinal irritation or toxicity, and/or in increased drug solubility in intestinal bile salt micelles (due to similarities to endogenous monoglycerides). Disclosed lipid prodrugs may also in certain embodiments have increased passive membrane permeability (due to greater lipophilicity compared with the parent therapeutic agent). In some embodiments, the lipid prodrug has greater solubility in lipid formulations or vehicles comprising either lipids alone or mixtures of lipids with surfactants and/or cosolvents, allowing for the use of lipophilic formulations for otherwise highly hydrophilic therapeutic agents.

Lipid Prodrugs of Neurosteroids

In one aspect, the present invention provides a compound of Formula I:

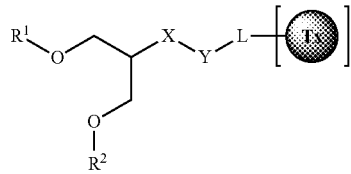

or a pharmaceutically acceptable salt thereof, wherein:
- $R^1$ and $R^2$ are each independently hydrogen, an acid-labile group, a lipid, or —C(O)$R^3$;
- each $R^3$ independently is a saturated or unsaturated, straight or branched, optionally substituted $C_{1-37}$ hydrocarbon chain;
- X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;
- each R independently is hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
- Y is absent or is —C(O)—, —C(NR)—, or —C(S)—;
- L is a covalent bond or a saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or
- L is

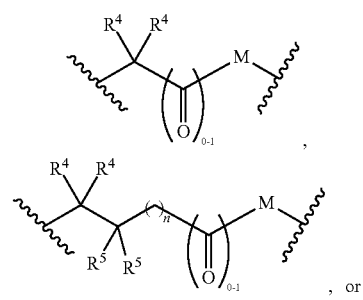

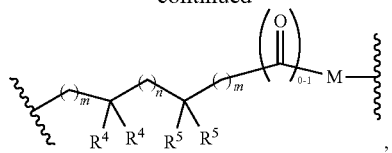

wherein either the right-hand side or left-hand side of L is attached to

;

- each -Cy- independently is an optionally substituted 3-6 membered bivalent saturated, partially unsaturated, or aromatic ring having 0-4 heteroatoms independently selected from nitrogen, oxygen, or sulfur;
- each $R^4$ and $R^5$ independently is hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or
- two instances of $R^4$ or $R^5$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur;
- -M- is a self-immolative group;
- n is 0-18;
- each m independently is 0-6; and

is a therapeutic agent selected from a naturally-occurring or non naturally-occurring neurosteroid or an analogue or prodrug thereof.

As defined above and described herein, $R^1$ and $R^2$ are each independently hydrogen, an acid-labile group, a lipid such as a fatty acid, or —C(O)$R^3$.

In some embodiments, $R^1$ is hydrogen. In some embodiments, $R^1$ is an acid-labile group. In some embodiments, $R^1$ is a lipid. In some embodiments, $R^1$ is a fatty acid. In some embodiments, $R^1$ is —C(O)$R^3$. In some embodiments, $R^1$ is selected from those depicted in Table 1, below.

In some embodiments, $R^2$ is hydrogen. In some embodiments, $R^2$ is an acid-labile group. In some embodiments, $R^2$ is a lipid. In some embodiments, $R^2$ is a fatty acid. In some embodiments, $R^2$ is —C(O)$R^3$. In some embodiments, $R^2$ is selected from those depicted in Table 1, below.

In some embodiments, each of $R^1$ and $R^2$ independently is a fatty acid, phosphatide, phospholipid, or analogue thereof, such as those described in detail below. In some embodiments, each fatty acid independently is a saturated or unsaturated medium-chain or long-chain fatty acid. In some embodiments, each fatty acid independently has an even number of carbon atoms. In some embodiments, each fatty acid independently has an odd number of carbon atoms. In some embodiments, each fatty acid independently has a $C_2$-$C_{40}$ chain. In some embodiments, each fatty acid independently has a $C_6$-$C_{20}$, $C_5$-$C_{20}$, $C_{10}$-$C_{20}$, $C_{10}$-$C_{18}$, $C_{12}$-$C_{18}$, $C_{14}$-$C_{18}$, $C_{16}$-$C_{18}$, $C_{10}$-$C_{16}$, $C_4$-$C_{10}$, or $C_6$-$C_{10}$ chain. In some embodiments, each fatty acid independently is a linear $C_6$-$C_{20}$ fatty acid. In some embodiments, each fatty acid independently is a linear $C_{12}$-$C_{18}$ fatty acid. In some embodiments, each fatty acid independently is a linear saturated $C_6$-$C_{10}$ fatty acid. In some embodiments, each fatty acid independently is selected from oleic acid, palmitic acid, octanoic acid, heptanoic acid, nonanoic acid, EPA, or DHA. In some embodiments, each fatty acid is oleic acid. In some embodiments, each fatty acid is heptanoic acid. In some embodiments, each fatty acid is octanoic acid. In some embodiments, each fatty acid is nonanoic acid.

In some embodiments, $R^1$ and $R^2$ are each independently selected from an acid labile group such as tert-butoxycarbonyl (Boc), an amino acid, PEG group, —C(O)OR, —C(O)$NR_2$, —$CH_2$OR, —C(NR)R, or —P(O)$_2$OR.

For clarity, it is understood that, when $R^1$ or $R^2$ is defined as a fatty acid, $R^1$ or $R^2$ is the acyl residue of the fatty acid. Thus, for example, when $R^1$ is defined as palmitic acid, $R^1$ is the acyl portion of palmitic acid, i.e. —C(O)$C_{15}H_{31}$.

As defined above and described herein, each $R^3$ independently is a saturated or unsaturated, straight or branched, optionally substituted $C_{1-37}$ hydrocarbon chain.

In some embodiments, $R^3$ is a saturated, straight, optionally substituted $C_{1-37}$ hydrocarbon chain. In some embodiments, $R^3$ is an unsaturated, straight, optionally substituted $C_{1-37}$ hydrocarbon chain. In some embodiments, $R^3$ is a saturated, branched, optionally substituted $C_{1-37}$ hydrocarbon chain. In some embodiments, $R^3$ is an unsaturated, branched, optionally substituted $C_{1-37}$ hydrocarbon chain. In some embodiments, $R^3$ is a saturated, straight, optionally substituted $C_{1-20}$ hydrocarbon chain. In some embodiments, $R^3$ is an unsaturated, straight, optionally substituted $C_{1-20}$ hydrocarbon chain. In some embodiments, $R^3$ is a saturated, branched, optionally substituted $C_{1-20}$ hydrocarbon chain. In some embodiments, $R^3$ is an unsaturated, branched, optionally substituted $C_{1-20}$ hydrocarbon chain. In some embodiments, $R^3$ is selected from those depicted in Table 1, below.

As defined above and described herein, X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms.

In some embodiments, X is —O—. In some embodiments, X is —NR—. In some embodiments, X is —S—. In some embodiments, X is —O($C_{1-6}$ aliphatic)-O—. In some embodiments, X is —O($C_{1-6}$ aliphatic)-S—. In some embodiments, X is —O($C_{1-6}$ aliphatic)-NR—. In some embodiments, X is —S($C_{1-6}$ aliphatic)-O—. In some embodiments, X is —S($C_{1-6}$ aliphatic)-S—. In some embodiments, X is —S($C_{1-6}$ aliphatic)-NR—. In some embodiments, X is —NR($C_{1-6}$ aliphatic)-O—. In some embodiments, X is —NR($C_{1-6}$ aliphatic)-S—. In some embodiments, X is —NR($C_{1-6}$ aliphatic)-NR—. In any of the foregoing embodiments, 0-2 methylene units of the bivalent $C_{1-6}$ aliphatic group are independently and optionally replaced with —O—, —NR—, or —S— and the bivalent $C_{1-6}$ aliphatic group is independently and optionally substituted with 1, 2, or 3 deuterium or halogen atoms. In some embodiments, X is selected from those depicted in Table 1, below.

As defined above and described herein, Y is absent or is —C(O)—, —C(NR)—, or —C(S)—.

In some embodiments, Y is absent. In some embodiments, Y is —C(O)—. In some embodiments, Y is —C(NR)—. In some embodiments, Y is —C(S)—. In some embodiments, Y is selected from those depicted in Table 1, below.

As defined above and described herein, L is a covalent bond or a saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

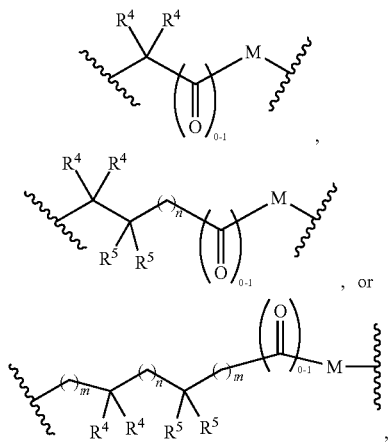

wherein either the right-hand side or left-hand side of L is attached to

In some embodiments, L is a covalent bond. In some embodiments, L is a saturated or unsaturated, straight or branched, optionally substituted bivalent $C_{1-30}$ (e.g., $C_{3-30}$, $C_{5-30}$, $C_{7-30}$, $C_{3-25}$, $C_{5-25}$, $C_{7-25}$, $C_{3-20}$, $C_{5-20}$, or $C_{7-20}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-. In some embodiments, L is

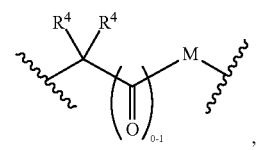

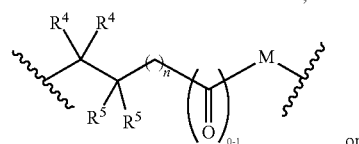

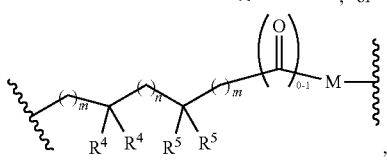, or

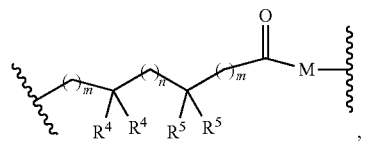, wherein either the right-hand side or left-hand side of L is attached to

.

In some embodiments, L is

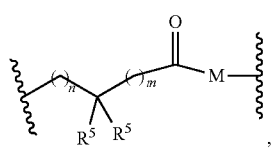, wherein either the right-hand side or left-hand side of L is attached to

.

In some embodiments, L is

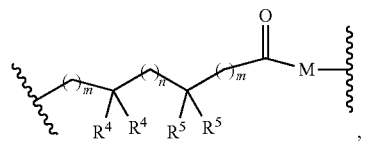, wherein either the right-hand side or left-hand side of L is attached to

.

In some embodiments, L is

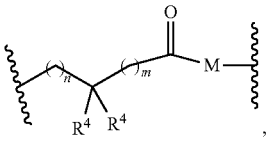, wherein either the right-hand side or left-hand side of L is attached to

.

In some embodiments, L is

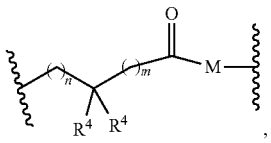, wherein either the right-hand side or left-hand side of L is attached to

.

In some embodiments, L is

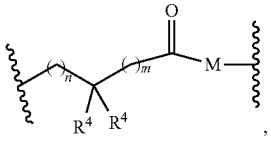, wherein either the right-hand side or left-hand side of L is attached to

.

In some embodiments, L is a covalent bond or a saturated or unsaturated, straight or branched, optionally substituted bivalent $C_{1-30}$ (e.g., $C_{3-30}$, $C_{5-30}$, $C_{7-30}$, $C_{3-25}$, $C_{5-25}$, $C_{7-25}$, $C_{3-20}$, $C_{5-20}$, or $C_{7-20}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid selected from

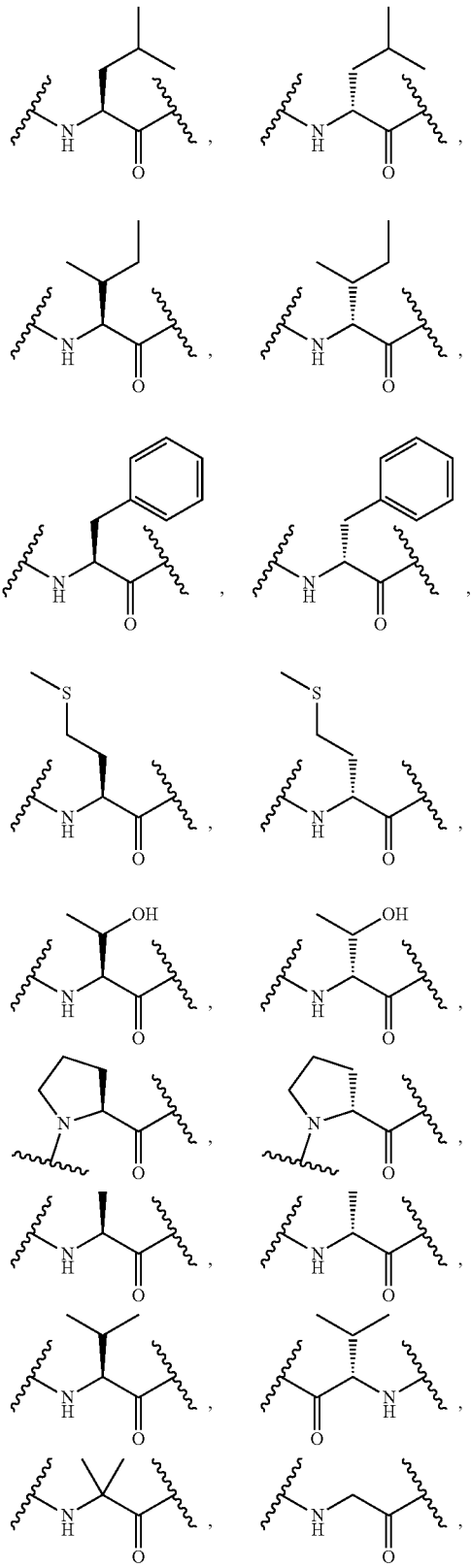

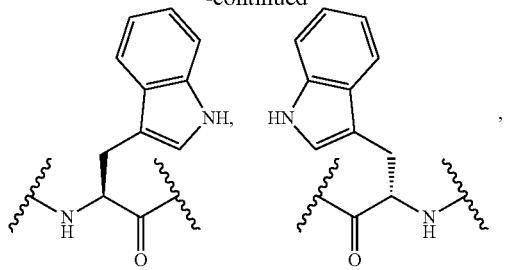

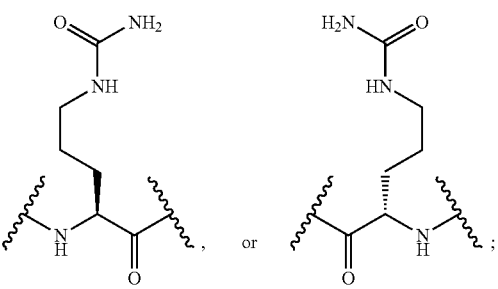

and wherein 1 methylene unit of L is optionally replaced with -M-; or

L is

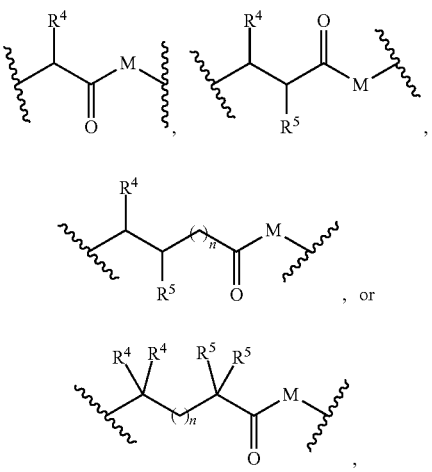

wherein either the right-hand side or left-hand side of L is attached to

In some embodiments, L is a saturated or unsaturated, straight or branched, optionally substituted bivalent $C_{1-20}$ (e.g., $C_{3-20}$, $C_5$-20, or $C_7$-20, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—,

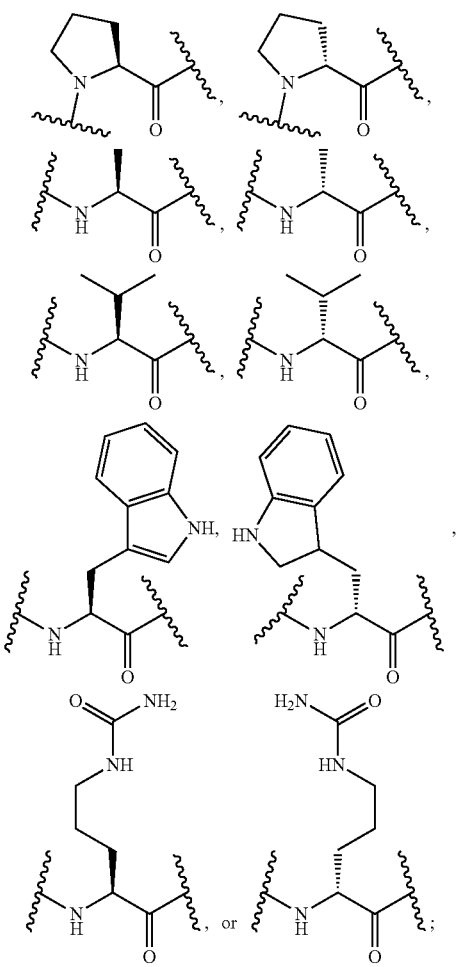

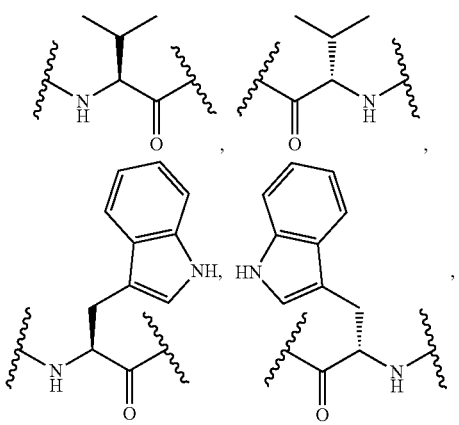

and wherein 1 methylene unit of L is optionally replaced with -M-. In some embodiments, L is a covalent bond or a bivalent, saturated or unsaturated, straight or branched $C_{1-16}$, $C_{1-12}$, $C_{1-10}$ or $C_{6-16}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—,

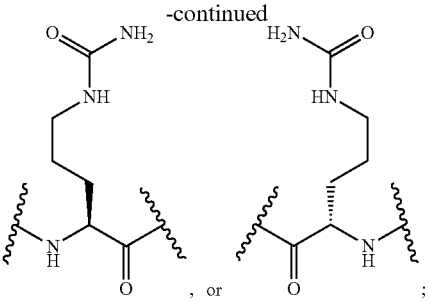

and 1 methylene unit of L is optionally replaced with -M-. In some embodiments, L is a bivalent, saturated, straight $C_{1-20}$, $C_{1-16}$, $C_{1-12}$, $C_{1-10}$ or $C_{1-6}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—; and 1 methylene unit of L is optionally replaced with -M-. In some embodiments, L is a bivalent, saturated, straight $C_{1-20}$, $C_{1-16}$, $C_{1-12}$, $C_{1-10}$ or $C_{1-6}$ hydrocarbon chain, wherein 0-6, 0-4, 0-3, or 0-1 methylene units of L are independently replaced by —O—, —NR—, —S—, —OC(O)—, —C(O)O—, —C(O)—, —S(O)—, —S(O)$_2$—, or —C(S)—; and 1 methylene unit of L is optionally replaced with -M-.

In some embodiments, L is a bivalent, saturated $C_1$–30, $C_{1-25}$, $C_{1-20}$, $C_{3-20}$, $C_5$-20, or $C_{7-20}$ hydrocarbon chain optionally substituted with 1, 2, 3, or 4 $R^4$ groups, wherein 0-4 methylene units of L are independently replaced by —O—, —OC(O)—, —C(O)O—, or —C(O)—; and 1 methylene unit of L is optionally replaced with -M-.

In some embodiments, L is a bivalent, saturated $C_{3-30}$, $C_{3-25}$, $C_{3-20}$, $C_{3-15}$, $C_{5-10}$, $C_{5-15}$, or $C_{7-15}$ hydrocarbon chain optionally substituted with 1, 2, 3, or 4 $R^4$ groups, wherein 0-4 methylene units of L are independently replaced by —O—, —OC(O)—, —C(O)O—, or —C(O)—; and 1 methylene unit of L is optionally replaced with -M-.

In some embodiments, L is a bivalent, saturated $C_{3-30}$, $C_{3-25}$, $C_{3-20}$, $C_{3-15}$, $C_{5-10}$, $C_{5-15}$, or $C_{7-15}$ hydrocarbon chain optionally substituted with 1, 2, 3, or 4 $R^4$ groups, wherein 1-2 methylene units of L are independently replaced by —O—, —OC(O)—, —C(O)O—, or —C(O)—; and 1 methylene unit of L is optionally replaced with -M-.

In some embodiments, L is a bivalent, saturated $C_{3-30}$, $C_{3-25}$, $C_{3-20}$, $C_{3-15}$, $C_{5-10}$, $C_{5-15}$, or $C_{7-15}$ hydrocarbon chain optionally substituted with 1, 2, 3, or 4 groups selected from deuterium, halogen, —CN, or a $C_{1-6}$ aliphatic group optionally substituted with 1, 2, 3, 4, 5, or 6 deuterium or halogen atoms; wherein 0-4 methylene units of L are independently replaced by —O—, —OC(O)—, —C(O)O—, or —C(O)—; and 1 methylene unit of L is optionally replaced with -M-.

In some embodiments, L is a bivalent, saturated $C_{3-30}$, $C_{3-25}$, $C_{3-20}$, $C_{3-15}$, $C_{5-10}$, $C_{5-15}$, or $C_{7-15}$ hydrocarbon chain optionally substituted with 1, 2, 3, or 4 groups selected from deuterium, halogen, —CN, or a $C_{1-6}$ aliphatic group optionally substituted with 1, 2, 3, 4, 5, or 6 deuterium or halogen atoms; wherein 1-2 methylene units of L are independently replaced by —O—, —OC(O)—, —C(O)O—, or —C(O)—; and 1 methylene unit of L is optionally replaced with -M-.

In some embodiments, L is a bivalent, saturated $C_{1-25}$, $C_{5-25}$, $C_{7-25}$, or $C_{1-20}$ hydrocarbon chain optionally substituted with 1, 2, 3, or 4 groups selected from deuterium, halogen, —CN, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with 1, 2, 3, 4, 5, or 6 deuterium or halogen atoms; wherein 0-4 methylene units of L are independently replaced by —O—, —OC(O)—, —C(O)O—, or —C(O)—; and 1 methylene unit of L is optionally replaced with -M-.

In some embodiments, L comprises (—OCH$_2$CH$_2$—)$_{1-8}$ (i.e., 1-8 polyethylene glycol (PEG) units). In some embodiments, L comprises 1, 2, 3, 4, 5, 6, 7, or 8 PEG units.

In some embodiments, 0-6 units of L are independently replaced by —O—, —S—, —OC(O)—, —C(O)O—, —C(O)—, or —C(S)—; and 1 methylene unit of L is optionally replaced with -M-.

In some embodiments, L comprises

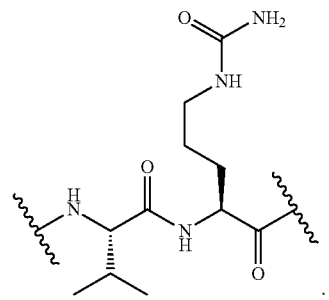 [SMILES: *N[C@H](C(=O)N[C@@H](CCCNC(N)=O)C(*)=O)C(C)C]

In some embodiments, L comprises

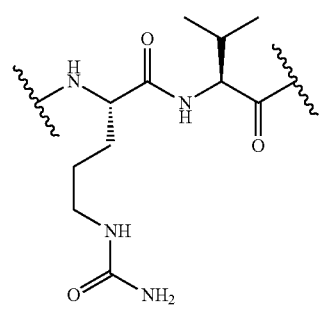

In some embodiments, L comprises

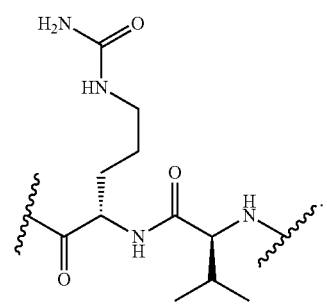 [SMILES: *N[C@H](C(=O)N[C@@H](CCCNC(N)=O)C(*)=O)C(C)C]

In some embodiments, L comprises

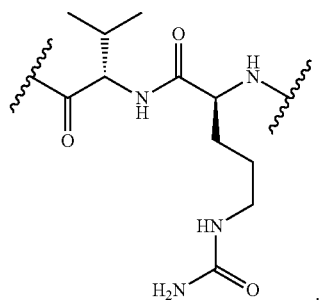 [SMILES: *N[C@@H](CCCNC(N)=O)C(=O)N[C@H](C(*)=O)C(C)C]

In some embodiments, L comprises

In some embodiments, L comprises

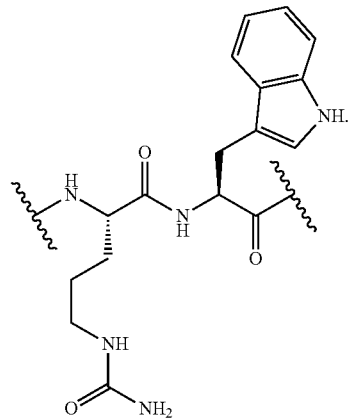 [SMILES: *N[C@@H](CCCNC(N)=O)C(=O)N[C@@H](Cc1c[nH]c2ccccc12)C(*)=O]

In some embodiments, L comprises

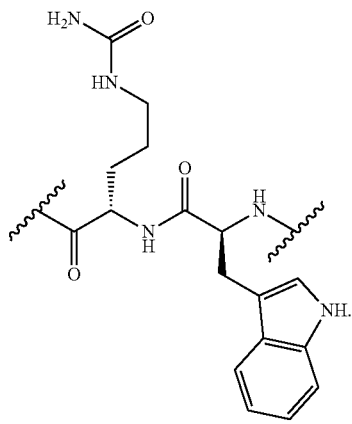 [SMILES: *N[C@@H](Cc1c[nH]c2ccccc12)C(=O)N[C@@H](CCCNC(N)=O)C(*)=O]

In some embodiments, L comprises

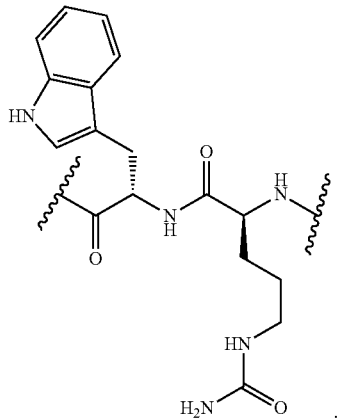 [SMILES: *N[C@@H](CCCNC(N)=O)C(=O)N[C@@H](Cc1c[nH]c2ccccc12)C(*)=O]

In some embodiments, 1 methylene unit of L is replaced with -M-.

In some embodiments, 1, 2, 3, or 4 available hydrogen atoms of L are replaced with an $R^4$ group, i.e., L is optionally substituted with 1, 2, 3, or 4 $R^4$ groups.

In some embodiments, a methylene unit of L is replaced with an amino acid. The amino acid may be naturally-occurring or non-naturally occurring. In some embodiments, the amino acid is selected from a non-polar or branched chain amino acid (BCAA). In some embodiments, the amino acid is selected from valine, isoleucine, leucine, methionine, alanine, proline, glycine, phenylalanine, tyrosine, tryptophan, histidine, asparagine, glutamine, serine threonine, lysine, arginine, histidine, aspartic acid, glutamic acid, cysteine, selenocysteine, or tyrosine. In some embodiments, the amino acid is an L-amino acid. In some embodiments, the amino acid is a D-amino acid.

In some embodiments, L is selected from those depicted in Table 1, below.

As defined above and described herein, each -Cy- independently is an optionally substituted 3-6 membered bivalent saturated, partially unsaturated, or aromatic ring having 0-4 heteroatoms independently selected from nitrogen, oxygen, or sulfur.

In some embodiments, -Cy- is an optionally substituted 3-6 membered bivalent saturated ring having 0-4 heteroatoms independently selected from nitrogen, oxygen, or sulfur. In some embodiments, -Cy- is an optionally substituted 5-membered bivalent saturated, partially unsaturated, or aromatic ring having 0-4 heteroatoms independently selected from nitrogen, oxygen, or sulfur. In some embodiments, -Cy- is an optionally substituted 6-membered bivalent saturated, partially unsaturated, or aromatic ring having 0-4 heteroatoms independently selected from nitrogen, oxygen, or sulfur. In some embodiments, -Cy- is selected from those depicted in Table 1, below.

As defined above and described herein, each $R^4$ and $R^5$ independently is hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur.

In some embodiments, $R^4$ is hydrogen. In some embodiments, $R^4$ is deuterium. In some embodiments, $R^4$ is halogen. In some embodiments, $R^4$ is —CN. In some embodiments, $R^4$ is —OR. In some embodiments, $R^4$ is —NR$_2$. In some embodiments, $R^4$ is —SR. In some embodiments, $R^4$ is a 3-8 membered saturated or partially unsaturated monocyclic carbocyclic ring. In some embodiments, $R^4$ is phenyl. In some embodiments, $R^4$ is an 8-10 membered bicyclic aromatic carbocyclic ring. In some embodiments, $R^4$ is a 4-8 membered saturated or partially unsaturated monocyclic heterocyclic ring having 1-2 heteroatoms independently selected from nitrogen, oxygen, or sulfur. In some embodiments, $R^4$ is a 5-6 membered monocyclic heteroaromatic ring having 1-4 heteroatoms independently selected from nitrogen, oxygen, or sulfur. In some embodiments, $R^4$ is an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with 1, 2, 3, 4, 5, or 6 deuterium or halogen atoms. In some embodiments, two instances of $R^4$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur.

In some embodiments, each $R^4$ independently is hydrogen, deuterium, halogen, —CN, or $C_{1-4}$ aliphatic optionally substituted with 1, 2, 3, 4, 5, or 6 deuterium or halogen atoms; or two instances of $R^4$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur.

In some embodiments, at least one instance of $R^4$ is not hydrogen.

In some embodiments, $R^4$ is $C_{1-4}$ aliphatic optionally substituted with 1, 2, 3, 4, 5, or 6 deuterium or halogen atoms. In some embodiments, $R^4$ is $C_{1-4}$ alkyl optionally substituted with 1, 2, or 3 deuterium or halogen atoms. In some embodiments, $R^4$ is methyl optionally substituted with 1, 2, or 3 deuterium or halogen atoms. In some embodiments, $R^4$ is ethyl. In some embodiments, $R^4$ is n-propyl. In some embodiments, $R^4$ is isopropyl. In some embodiments, $R^4$ is n-butyl. In some embodiments, $R^4$ is isobutyl. In some embodiments, $R^4$ is tert-butyl. In some embodiments, $R^4$ is selected from those depicted in Table 1, below.

In some embodiments, $R^5$ is hydrogen. In some embodiments, $R^5$ is deuterium. In some embodiments, $R^5$ is halogen. In some embodiments, $R^5$ is —CN. In some embodiments, $R^5$ is —OR. In some embodiments, $R^5$ is —NR$_2$. In some embodiments, $R^5$ is —SR. In some embodiments, $R^5$ is a 3-8 membered saturated or partially unsaturated monocyclic carbocyclic ring. In some embodiments, $R^5$ is phenyl. In some embodiments, $R^5$ is an 8-10 membered bicyclic aromatic carbocyclic ring. In some embodiments, $R^5$ is a 4-8 membered saturated or partially unsaturated monocyclic heterocyclic ring having 1-2 heteroatoms independently selected from nitrogen, oxygen, or sulfur. In some embodiments, $R^5$ is a 5-6 membered monocyclic heteroaromatic ring having 1-4 heteroatoms independently selected from nitrogen, oxygen, or sulfur. In some embodiments, $R^5$ is an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with 1, 2, 3, 4, 5, or 6 deuterium or halogen atoms. In some embodiments, two instances of $R^5$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur.

In some embodiments, each $R^5$ independently is hydrogen, deuterium, halogen, —CN, or $C_{1-4}$ aliphatic optionally substituted with 1, 2, 3, 4, 5, or 6 deuterium or halogen atoms; or two instances of $R^5$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur.

In some embodiments, at least one instance of $R^5$ is not hydrogen.

In some embodiments, $R^5$ is $C_{1-4}$ aliphatic optionally substituted with 1, 2, 3, 4, 5, or 6 deuterium or halogen atoms. In some embodiments, $R^5$ is methyl optionally substituted with 1, 2, or 3 deuterium or halogen atoms. In some embodiments, $R^5$ is ethyl. In some embodiments, $R^5$ is n-propyl. In some embodiments, $R^5$ is isopropyl. In some embodiments, $R^5$ is n-butyl. In some embodiments, $R^5$ is isobutyl. In some embodiments, $R^5$ is tert-butyl. In some embodiments, $R^5$ is selected from those depicted in Table 1, below.

As defined above and described herein, -M- is a self-immolative group.

In some embodiments, -M- is an acetal, an o-benzylalcohol, a p-benzylalcohol, a styryl group, a coumarin, or a group that self-immolates via a cyclization reaction. In some embodiments, -M- is selected from a disulfide, hydrazone, acetal self-immolative group, carboxyacetal self-immolative group, carboxy(methylacetal) self-immolative group, para-hydroxybenzyl carbonyl self-immolative groups, flipped ester self-immolative group, trimethyl lock, or 2-hydroxyphenyl carbamate (2-HPC) self-immolative group. In some embodiments, -M- is an acetal. In some embodiments, -M- is a carboxyacetal. In some embodiments, -M- is a carboxy(methylacetal). In some embodiments, -M- is an acetal self-immolative group. In some embodiments, -M- is a carboxyacetal self-immolative group. In some embodiments, -M- is a carboxy(methylacetal) self-immolative group.

In some embodiments, -M- is:

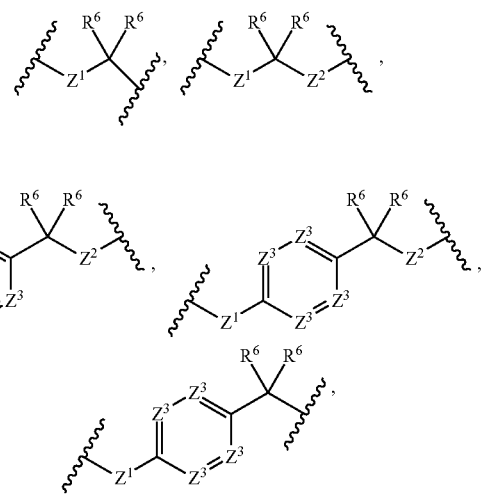

23

-continued

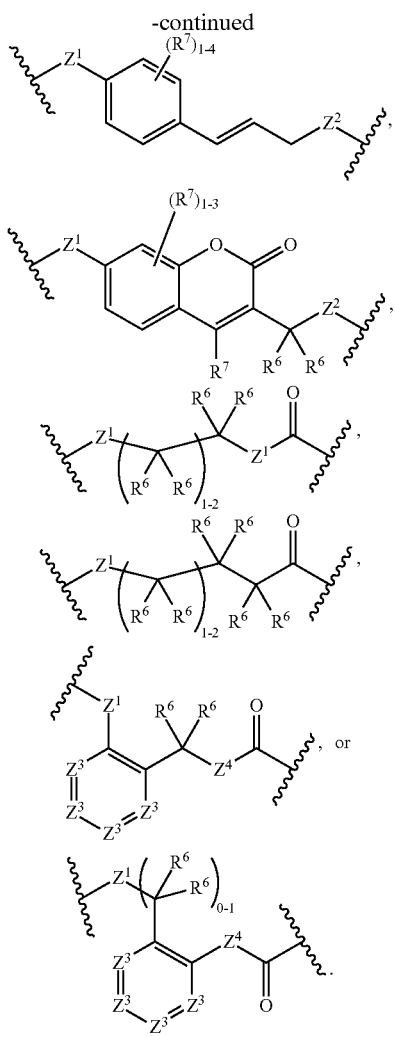

wherein each R independently is selected from hydrogen, deuterium, $C_{1-10}$ aliphatic, halogen, or —CN;
each $R^7$ independently is selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms

24 independently selected from nitrogen, oxygen, or sulfur, or the $C_{1-6}$ aliphatic is optionally substituted with 1, 2, 3, 4, 5, or 6 deuterium or halogen atoms;

each $Z^1$ independently is selected from —O—, —NR—, or —S—;

each $Z^2$ independently is selected from —O—, —NR—, —S—, —OC(O)—, —NRC(O)O—, or —OC(O) NR—;

each $Z^3$ independently is selected from =N— or =C($R^7$)—; and each $Z^4$ independently is selected from —O—, —NR—, —S—, —C($R^6$)$_2$-, or a covalent bond.

In some embodiments, -M- is selected from one of the following:

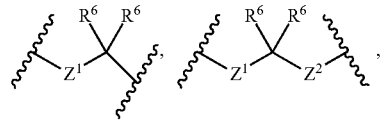

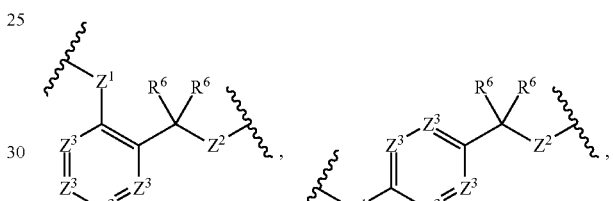

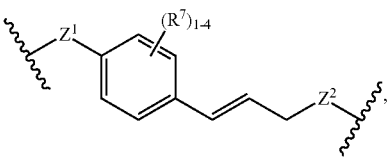

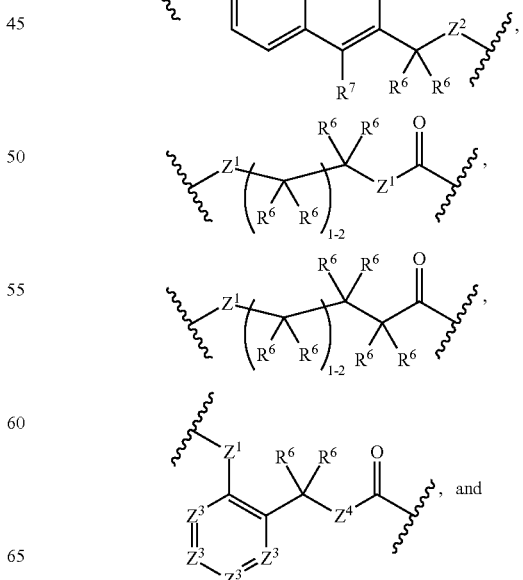

-continued

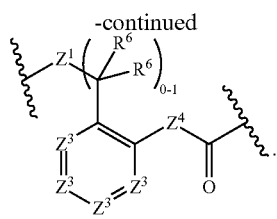

wherein each $R^6$ independently is selected from hydrogen, deuterium, $C_{1-5}$ aliphatic, halogen, or —CN;
each $R^7$ independently is selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;
each $Z^1$ independently is selected from —O—, —NR—, or —S—;
each $Z^2$ independently is selected from —O—, —NR—, —S—, —OC(O)—, —NRC(O)O—, or —OC(O)NR—;
each $Z^3$ independently is selected from =N— or =C(R$^7$)—; and
each $Z^4$ independently is selected from —O—, —NR—, —S—, —C(R$^6$)$_2$-, or a covalent bond.

As defined generally above and described herein, each $R^6$ independently is selected from hydrogen, deuterium, $C_{1-5}$ aliphatic, halogen, or —CN. In some embodiments, $R^6$ is hydrogen. In some embodiments, $R^6$ is deuterium. In some embodiments, $R^6$ is $C_{1-5}$ aliphatic. In some embodiments, $R^6$ is halogen. In some embodiments, $R^6$ is —CN.

In some embodiments, $R^6$ is hydrogen, $C_{1-4}$ alkyl, halogen, or —CN. In some embodiments, $R^6$ is hydrogen or $C_{1-3}$ alkyl. In some embodiments, $R^6$ is hydrogen or methyl.

In some embodiments, each instance of $R^6$ in the above formulae is the same. In some embodiments, each $R^6$ is different. In some embodiments, one $R^6$ is hydrogen. In some embodiments, one $R^6$ is $C_{1-5}$ aliphatic. In some embodiments, each $R^6$ is hydrogen. In some embodiments, each $R^6$ is $C_{1-5}$ aliphatic. In some embodiments, $R^6$ is selected from those depicted in Table 1, below.

As defined generally above and described herein, each $R^7$ independently is selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur, or the $C_{1-6}$ aliphatic group is optionally substituted with 1, 2, 3, 4, 5, or 6 deuterium or halogen atoms.

In some embodiments, $R^7$ is hydrogen. In some embodiments, $R^7$ is deuterium. In some embodiments, $R^7$ is halogen. In some embodiments, $R^7$ is —CN. In some embodiments, $R^7$ is —OR. In some embodiments, $R^7$ is —NR$_2$. In some embodiments, $R^7$ is —NO$_2$. In some embodiments, $R^7$ is —SR. In some embodiments, $R^7$ is a 3-8 membered saturated or partially unsaturated monocyclic carbocyclic ring. In some embodiments, $R^7$ is phenyl. In some embodiments, $R^7$ is an 8-10 membered bicyclic aromatic carbocyclic ring. In some embodiments, $R^7$ is a 4-8 membered saturated or partially unsaturated monocyclic heterocyclic ring having 1-2 heteroatoms independently selected from nitrogen, oxygen, and sulfur. In some embodiments, $R^7$ is a 5-6 membered monocyclic heteroaromatic ring having 1-4 heteroatoms independently selected from nitrogen, oxygen, and sulfur. In some embodiments, $R^7$ is or an 8-10 membered bicyclic heteroaromatic ring having 1-5 heteroatoms independently selected from nitrogen, oxygen, and sulfur. In some embodiments, $R^7$ is or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^7$ is a $C_{1-6}$ aliphatic group optionally substituted with 1, 2, 3, 4, 5, or 6 deuterium or halogen atoms.

In some embodiments, $R^7$ is hydrogen, deuterium, halogen, —CN, —OR, —NR$_2$, —NO$_2$, —SR, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with —CN, —OR, —NR$_2$, —SR, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-6}$ aliphatic group is optionally substituted with 1, 2, 3, 4, 5, or 6 deuterium or halogen atoms. In some embodiments, $R^7$ is hydrogen, deuterium, halogen, —CN, a 3-6 membered saturated or partially unsaturated monocyclic carbocyclic ring, phenyl, a 5-6 membered monocyclic heteroaromatic ring having 1-4 heteroatoms independently selected from nitrogen, oxygen, or sulfur, or a $C_{1-4}$ alkyl group optionally substituted with —CN, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-4}$ alkyl group is optionally substituted with 1, 2, 3, 4, 5, or 6 deuterium or halogen atoms. In some embodiments, $R^7$ is hydrogen, halogen, —CN, —OR, or $C_{1-4}$ alkyl.

In some embodiments, R is hydrogen or $C_{1-4}$ alkyl.

In some embodiments, $R^7$ is selected from those depicted in Table 1, below.

As defined generally above and described herein, each $Z^1$ independently is selected from —O—, —NR—, or —S—. In some embodiments, $Z^1$ is —O—. In some embodiments, $Z^1$ is —NR—. In some embodiments, $Z^1$ is —S. In some embodiments, $Z^1$ is —NH— or —NMe-.

In some embodiments, $Z^1$ is selected from those depicted in Table 1, below.

As defined generally above and described herein, each $Z^2$ independently is selected from —O—, —NR—, —S—, —OC(O)—, —NRC(O)O—, or —OC(O)NR—.

In some embodiments, $Z^2$ is —O—. In some embodiments, $Z^2$ is —NR—. In some embodiments, $Z^2$ is —S—. In some embodiments, $Z^2$ is —OC(O)—. In some embodiments, $Z^2$ is —NRC(O)O—. In some embodiments, $Z^2$ is —OC(O)NR—.

In some embodiments, each $Z^2$ independently is selected from —O—, —NH—, —NMe-, —S—, —OC(O)—, —NHC(O)O—, —NMeC(O)O—, —OC(O)NH—, or —OC(O)NMe-.

In some embodiments, $Z^2$ is covalently bound to

.

In some embodiments, $Z^2$ is —O— or —OC(O)O—.

In some embodiments, $Z^2$ is selected from those depicted in Table 1, below.

In some embodiments, $Z^1$ is —O— and $Z^2$ is —O— or —OC(O)O—.

As defined generally above and described herein, each $Z^3$ independently is selected from =N— or =C($R^7$)—. In some embodiments, $Z^3$ is =N—. In some embodiments, $Z^3$ is =C($R^7$)—.

In some embodiments, $Z^3$ is selected from those depicted in Table 1, below.

As defined generally above and described herein, each $Z^4$ independently is selected from —O—, —NR—, —S—, —C($R^6$)$_2$—, or a covalent bond. In some embodiments, $Z^4$ is —O—. In some embodiments, $Z^4$ is —NR—. In some embodiments, $Z^4$ is —S—. In some embodiments, $Z^4$ is —C($R^6$)$_2$—. In some embodiments, $Z^4$ is a covalent bond.

In some embodiments, $Z^4$ is selected from those depicted in Table 1, below.

In some embodiments, -M- is selected from one of the following:

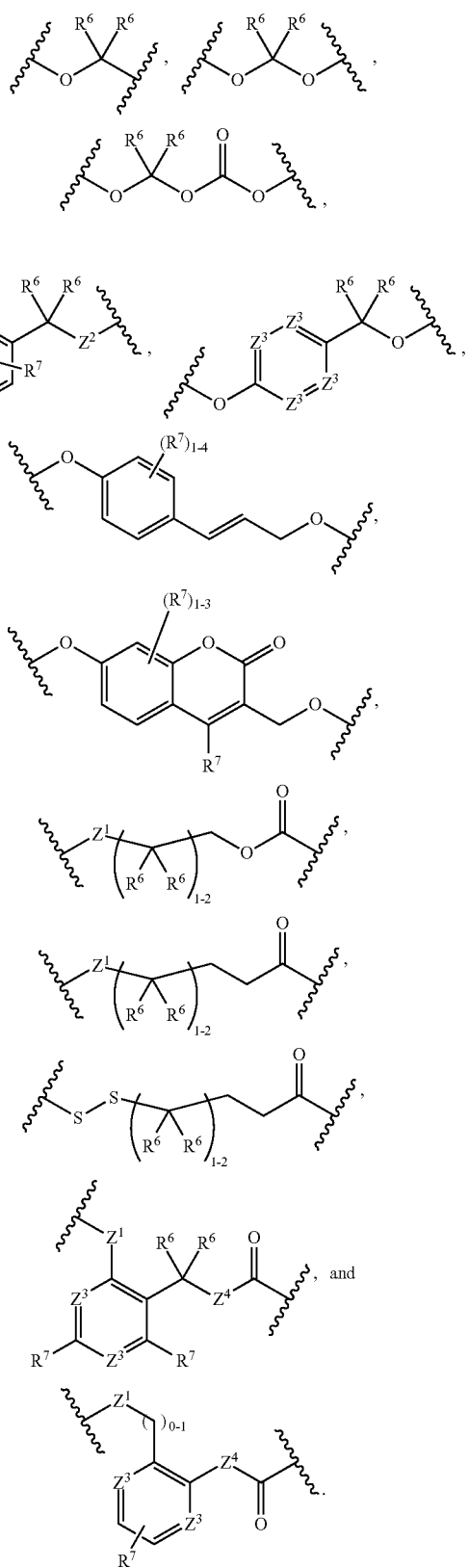

In some embodiments, -M- is
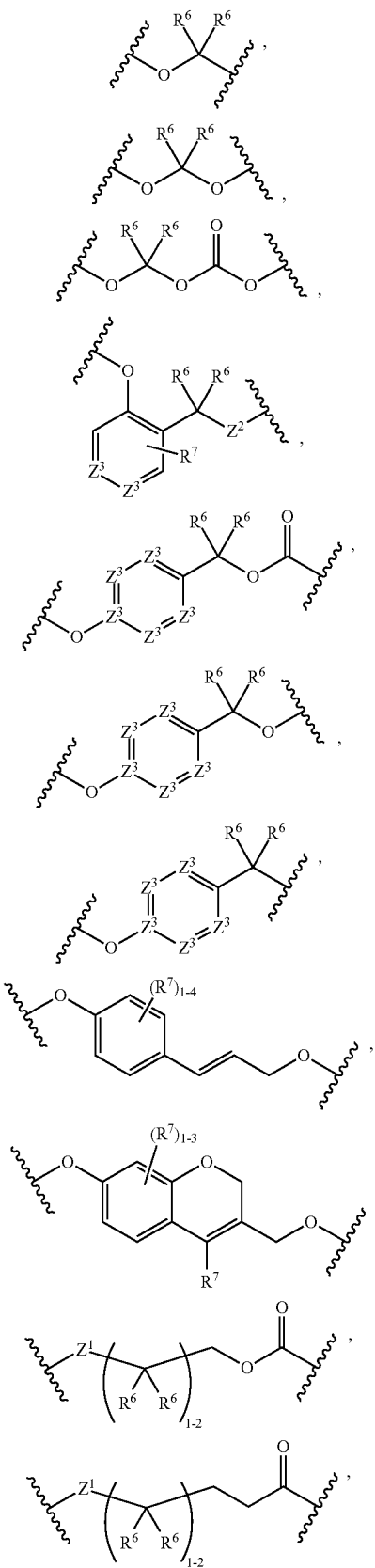
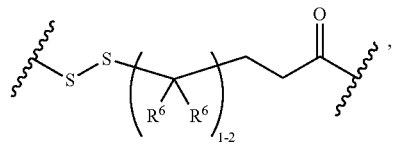
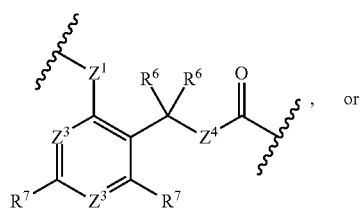
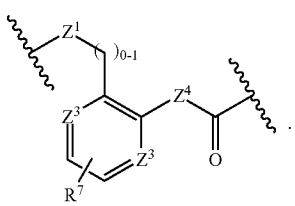
In some embodiments, -M- is
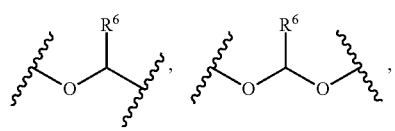
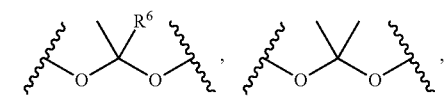
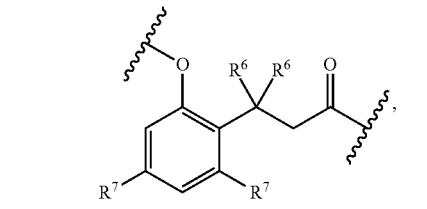
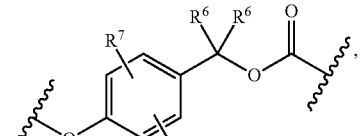
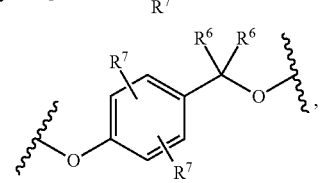

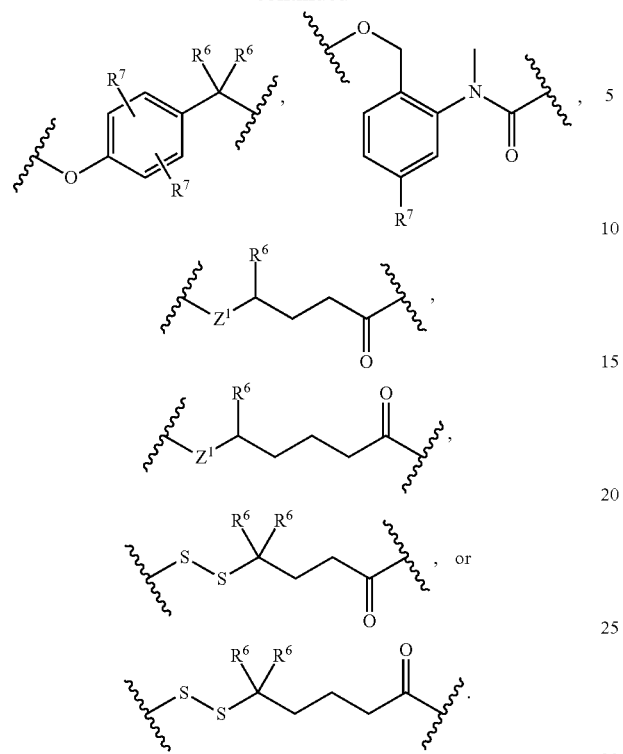
In some embodiments -M- is selected from
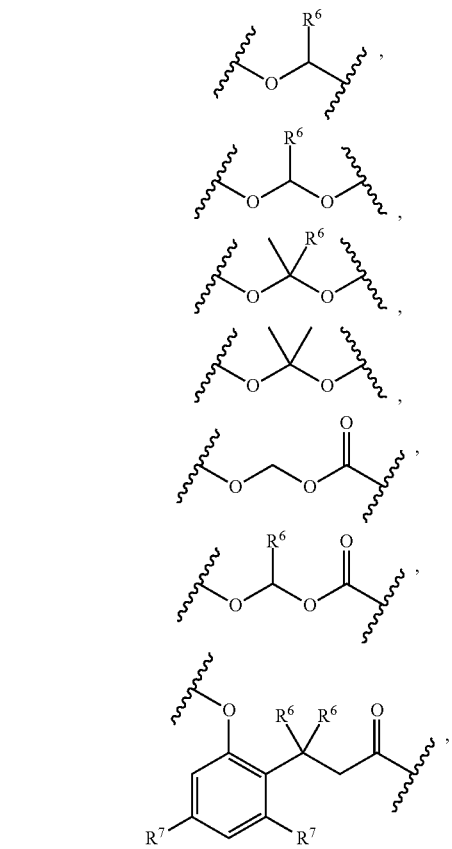
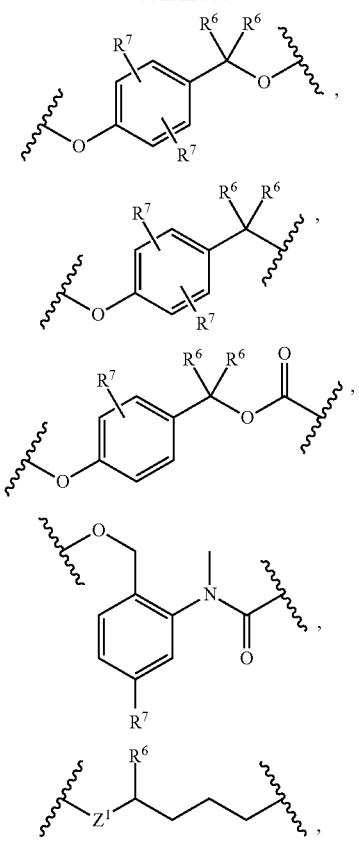
In some embodiments, -M- is selected from
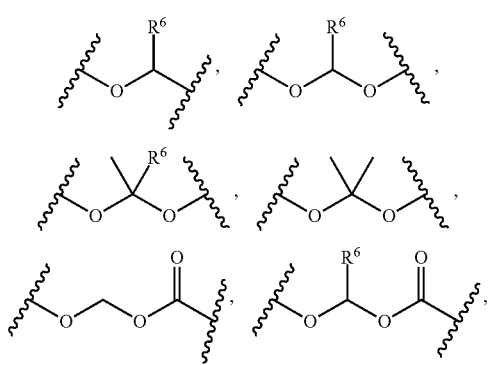

-continued
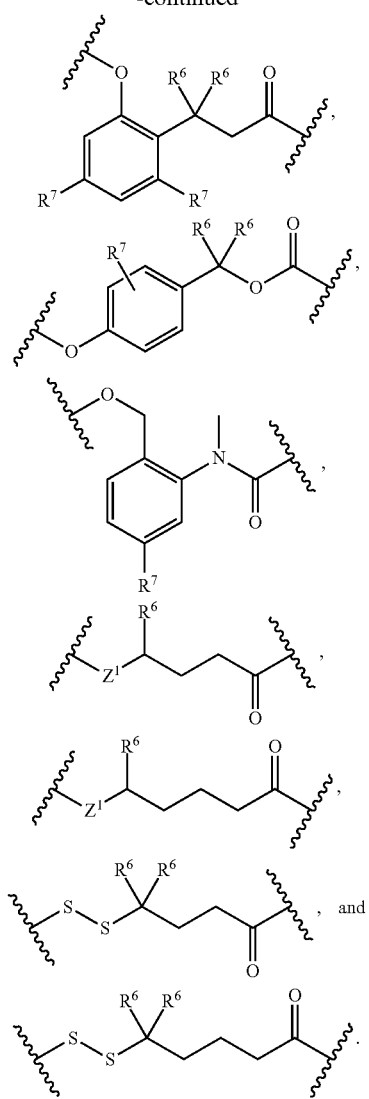
In some embodiments, -M- is selected from
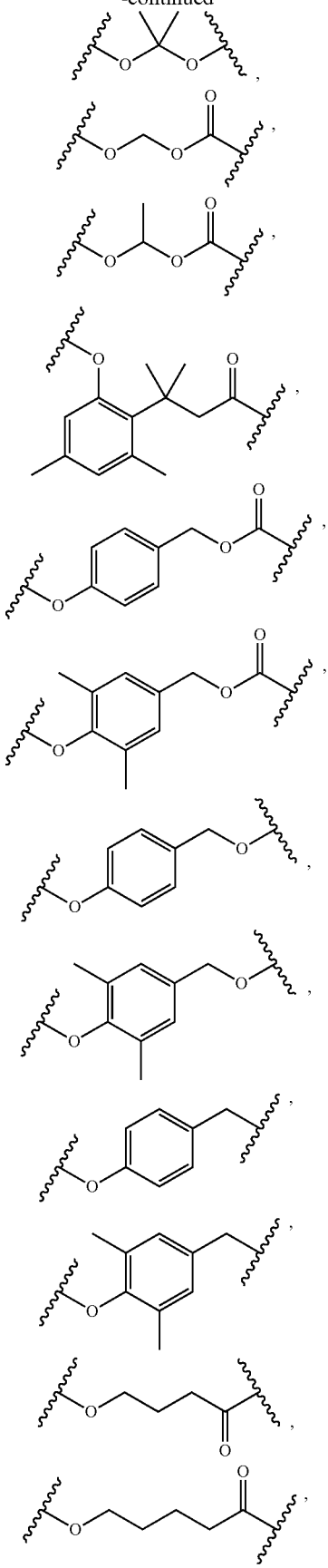

-continued
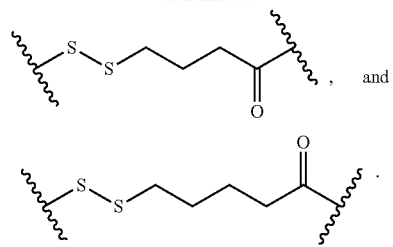
and
In some embodiments -M- is selected from
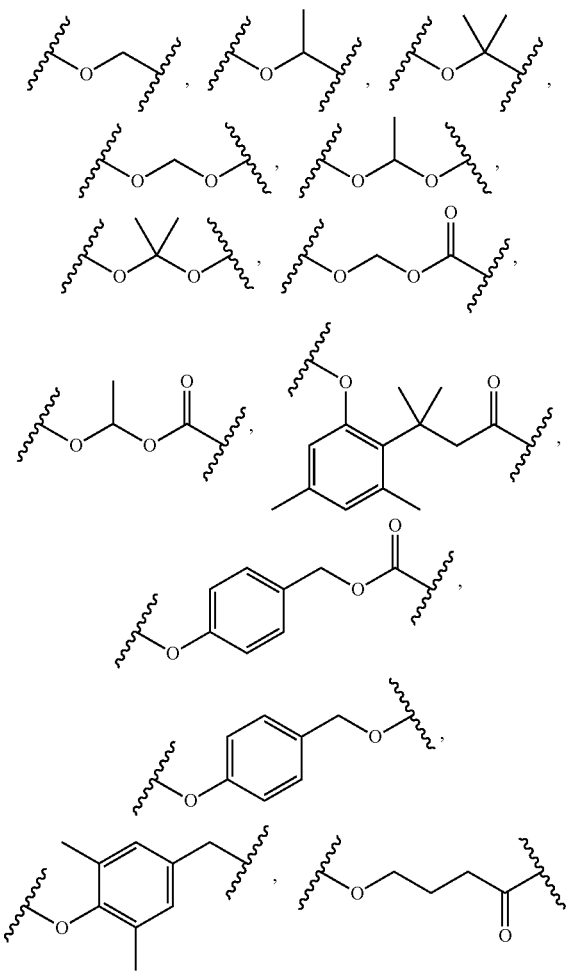
In some embodiments, -M- is selected from
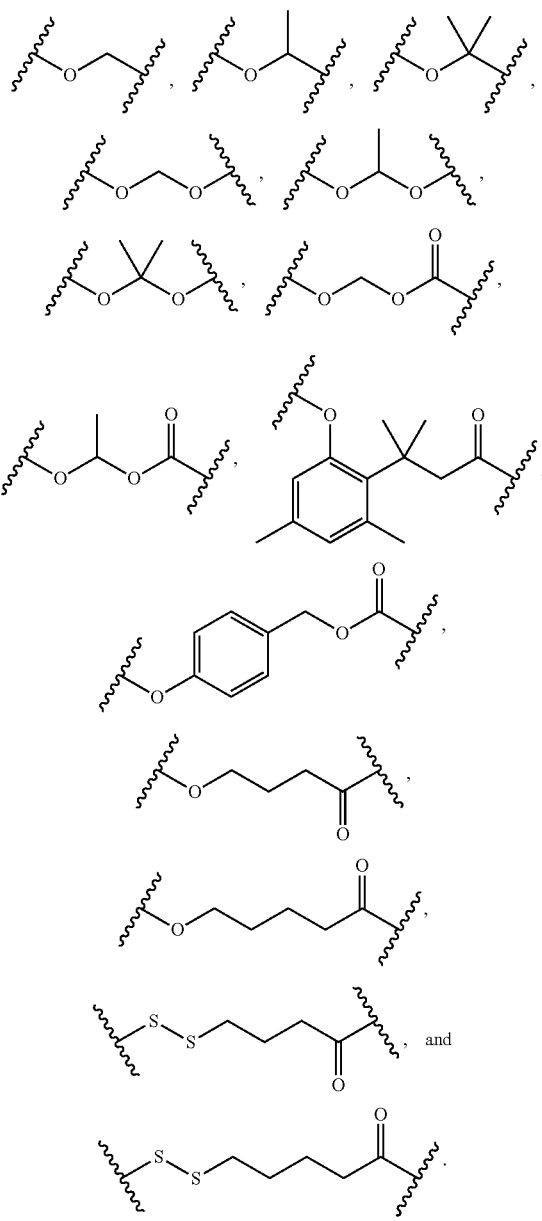
In some embodiments, -M- is selected from
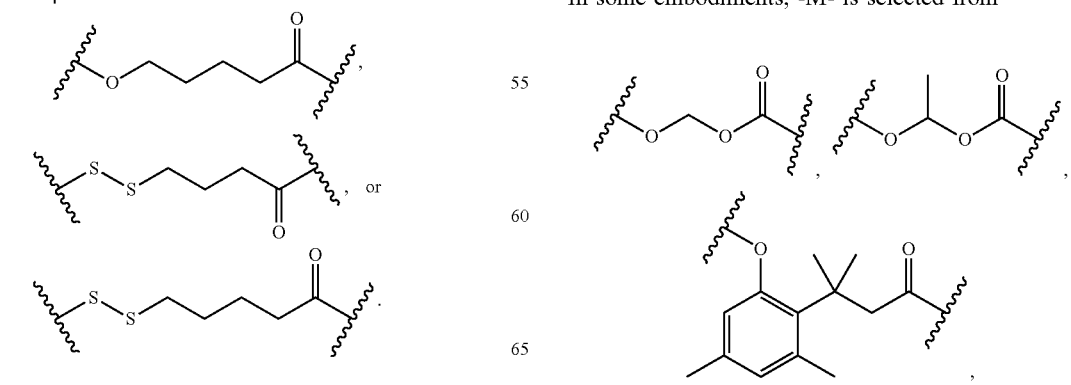

-continued

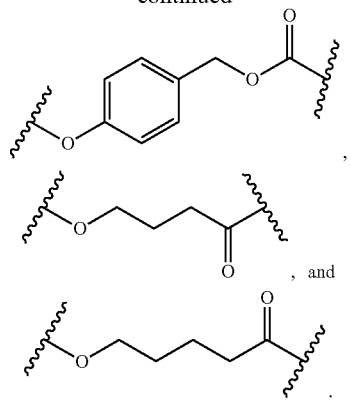

In some embodiments, -M- is selected from

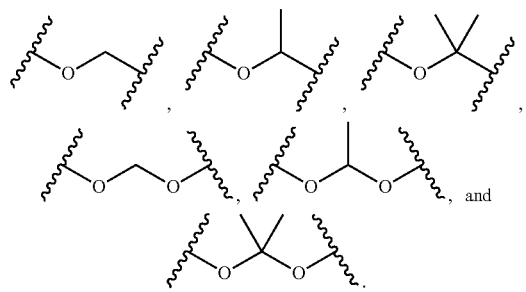

In some embodiments, -M- is

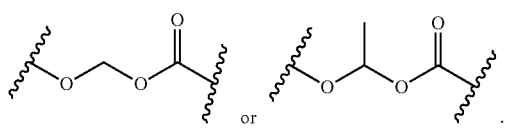

In some embodiments, -M- is

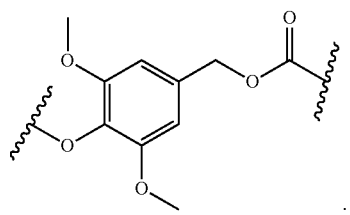 [SMILES: *Oc1c(OC)cc(COC(*)=O)cc1OC]

In some embodiments, -M- is

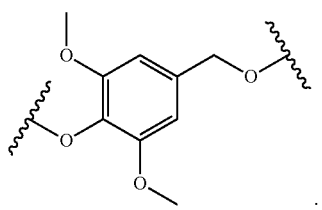 [SMILES: *OCc1cc(OC)c(O*)c(OC)c1]

In some embodiments, -M- is

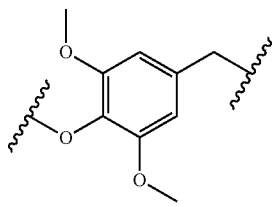

In some embodiments, -M- is selected from those depicted in Table 1, below.

As defined above and described herein, n is 0-18.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 1-16, 1-14, 1-12, 1-10, 1-8, 1-6, 1-3, 2-16, 2-14, 2-12, 2-10, 2-8, 2-6, 3-12, 3-10, 3-8, 3-6, 4-10, 4-8, 4-6, 5-10, 5-8, 5-6, 6-10, 6-8, or 8-12.

As defined above and described herein, each m independently is 0-6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, each m independently is 0, 1, or 2. In some embodiments, each m independently is 1, 2, 3, or 4.

As defined above and described herein, is a therapeutic agent selected from a naturally-occurring or non naturally-occurring neurosteroid, or an analogue or prodrug thereof. Exemplary neurosteroids include those described herein.

Analogues of neurosteroids include deuterated and isotopically-enriched forms of neurosteroids, such as pregnane neurosteroids. In some embodiments, the analogue is a fatty acid ester derivative of the neurosteroid. For example, a neurosteroid bearing two hydroxyl groups may be esterified at one hydroxyl and prepared as a lipid prodrug of Formula I, wherein the lipid prodrug moiety is bound to the other hydroxyl. In some embodiments, the fatty acid ester comprises a carbon chain of 8-20 carbons. In some embodiments, the fatty acid is one of those described herein.

In some embodiments, is allopregnanolone or an analogue or prodrug thereof. In some embodiments,

is allopregnanolone. In some embodiments,

is isopregnanolone or an analogue or prodrug thereof. In some embodiments,

is isopregnanolone.
In some embodiments,

is a pregnane neurosteroid. In some embodiments,

is selected from allopregnanolone (also known as brexanolone, SAGE-547, 5α-pregnan-3α-ol-20-one, 3α-hydroxy-5α-pregnan-20-one, or 3α,5α-tetrahydroprogesterone), 3,5-tetrahydroprogesterone, pregnanolone (5β-pregnan-3α-ol-20-one), isopregnanolone (5α-pregnan-3β-ol-20-one), epipregnanolone (5β-pregnan-3β-ol-20-one), 21-hydroallopregnanolone, or an analogue or prodrug thereof.
In some embodiments,

is selected from alfadolone (3α,21-dihydroxy-5α-pregnane-11,20-dione), alfaxolone (3α-hydroxy-5α-pregnane-11,20-dione), ganaxolone (3α-hydroxy-3β-methyl-5α-pregnan-20-one), hydroxydione (21-hydroxy-5β-pregnane-3,20-dione), minaxolone (11α-(dimethylamino)-20-ethoxy-3α-hydroxy-5α-pregnan-20-one), Org 20599 (21-chloro-3α-hydroxy-20-morpholin-4-yl-5β-pregnan-20-one), Org 21465 (20-(2,2-dimethyl-4-morpholinyl)-3α-hydroxy-11,20-dioxo-5α-pregnan-2l-yl methanesulfonate), renanolone (3α-hydroxy-5β-pregnan-11,20-dione), or SAGE-217 (1-(2-((3R,5R,8R,9R,10S,13S,14S,17S)-3-hydroxy-3,13-dimethylhexadecahydro-1H-cyclopenta[a]phenanthren-17-yl)-2-oxoethyl)-1H-pyrazole-4-carbonitrile).
In some embodiments,

is allopregnanolone, pregnanolone, pregnenolone, ganaxolone, alfaxalone, 3β-dihydroprogesterone, isopregnanolone, epipregnanolone, or 21-hydroxyallopregnanolone.

In some embodiments the present invention provides a compound of formula I, wherein

is

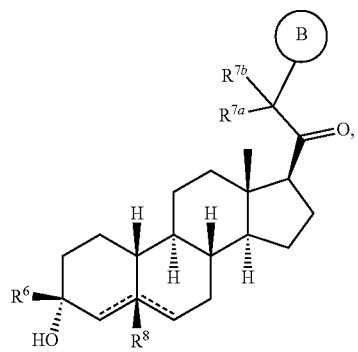

to provide a compound of formula II:

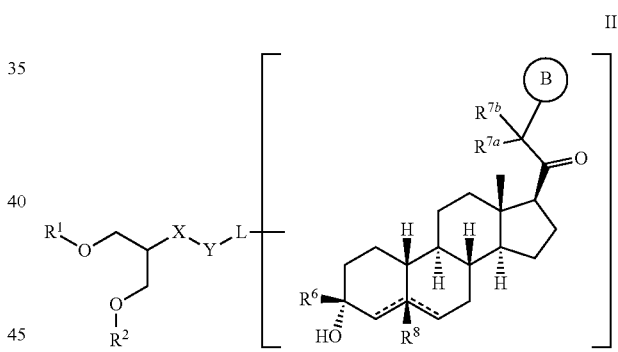

or a pharmaceutically acceptable salt thereof, wherein:

Ring B is selected from phenyl, a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-10 membered monocyclic or bicyclic heteroaryl ring having 1-4 heteroatoms independently selected from nitrogen, oxygen, and sulfur, wherein Ring B is further optionally substituted with 1-2 oxo groups;

$R^6$ is an optionally substituted $C_{1-6}$ aliphatic group;

$R^{7a}$ is an optionally substituted $C_{1-6}$ aliphatic group;

$R^{7b}$ is hydrogen or an optionally substituted $C_{1-6}$ aliphatic group; or $R^{7a}$ and $R^{7b}$ are optionally taken together with their intervening carbon atom to form a 4-7 membered saturated or partially unsaturated spirocyclic carbocyclic or heterocyclic ring, having 0-3 heteroatoms, in addition to the carbon, independently selected from nitrogen, oxygen, and sulfur; or $R^{7a}$ and $R^{7b}$ are optionally taken together to form an oxo group;

$R^8$ is absent or hydrogen;

---- represents a single or double bond, wherein when one of ---- is a double bond, the other ---- is a single bond, and when one of the ---- is a double bond, $R^8$ is absent; and each of $R^1$, $R^2$, X, Y, and L is as defined above and described in embodiments herein, both singly and in combination.

In some embodiments, the present invention provides a compound of formula I, wherein

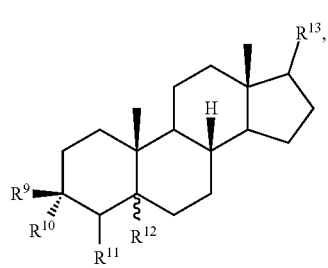

is to provide a compound of formula III:

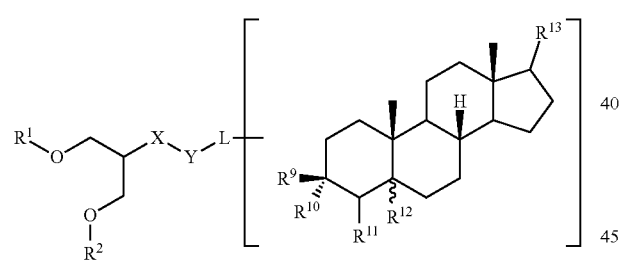

or a pharmaceutically acceptable salt thereof, wherein:

$R^9$ is hydrogen or methyl;

$R^{10}$ is —OC(O)R;

$R^{11}$ is hydrogen or methyl;

$R^{12}$ is alpha or beta hydrogen or methyl;

$R^{13}$ is —C(O)R; and each of R, $R^1$, $R^2$, X, Y, and L is as defined above and described in embodiments herein, both singly and in combination.

In some embodiments, the present invention provides a compound of formula I, wherein

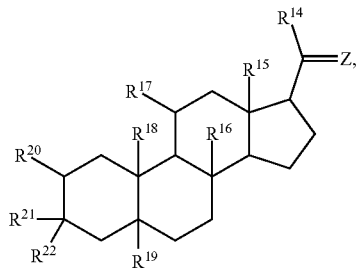

is

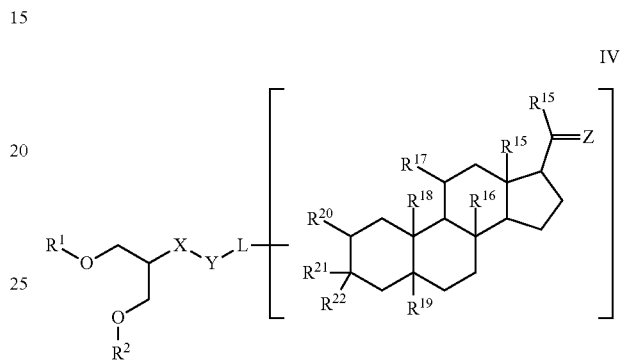

to provide a compound of formula IV:

or a pharmaceutically acceptable salt thereof, wherein:

Z is =O, =S, =NR, =NOR;

$R^{14}$ is hydrogen, hydroxyl, —CHO, —CHS, —CHNR, —CH$_2$OR, —CH$_2$SR, —CH$_2$N(R)$_2$, —CH$_2$N(R)(OR), or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^{17}$ is hydrogen, —OH, oxo, or an optionally substituted group selected from C$_{1-6}$ aliphatic or a 4-8 membered saturated or partially unsaturated monocyclic heterocyclic ring having 1-2 heteroatoms independently selected from nitrogen, oxygen, or sulfur;

$R^{15}$, $R^{16}$, $R^{18}$, $R^{19}$, and $R^{20}$ are independently absent, hydrogen, halogen, —OR, or an optionally substituted group selected from a 5-6 membered monocyclic heteroaromatic ring having 1-4 heteroatoms independently selected from nitrogen, oxygen, or sulfur; or an 8-10 membered bicyclic heteroaromatic ring having 1-5 heteroatoms independently selected from nitrogen, oxygen, or sulfur;

$R^{21}$ and $R^{22}$ are each independently selected from hydrogen, or an optionally substituted C$_{1-6}$ aliphatic group or —OC$_{1-6}$ aliphatic group; or $R^{21}$ and $R^{22}$ are optionally taken together to form an oxo group; and each of R, $R^1$, $R^2$, X, Y, and L is as defined above and described in embodiments herein, both singly and in combination.

In some embodiments, the present invention provides a compound of formula I, wherein

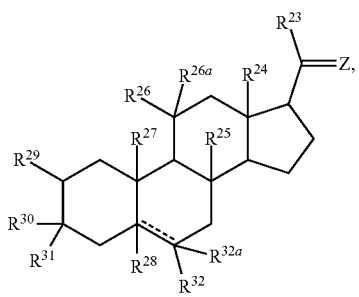

is to provide a compound of formula V:

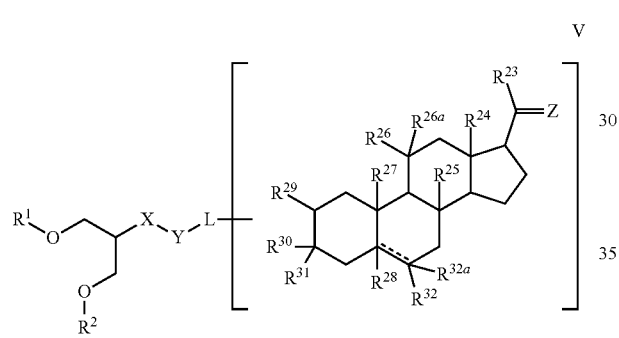

or a pharmaceutically acceptable salt thereof, wherein:
==== is a double or single bond;
Z is =O, =S, =NR, or =NOR;
$R^{23}$ is hydrogen, —OH, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^{26}$ is hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
$R^{26a}$ is hydrogen; or
$R^{26}$ and $R^{26a}$ are optionally taken together to form an oxo group;
$R^{24}$, $R^{25}$, $R^{27}$, and $R^{28}$ are each independently hydrogen, —OH, halogen, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, provided that if ==== is a double bond $R^{28}$ is absent;
$R^{29}$ is hydrogen, halogen, —OR, or an optionally substituted group selected from $C_{1-6}$ aliphatic or a 3-8 membered saturated or partially unsaturated monocyclic carbocyclic ring;
$R^{30}$ is hydrogen or an optionally substituted group selected from $C_{1-6}$ aliphatic or a 3-8 membered saturated or partially unsaturated monocyclic carbocyclic ring;
$R^{31}$ is —OH; or $R^{30}$ and $R^{31}$ are optionally taken together to form an oxo group;
$R^{32}$ is hydrogen, halogen, —OH, or an optionally substituted group selected from $C_{1-6}$ aliphatic or a 3-8 membered saturated or partially unsaturated monocyclic carbocyclic ring;
$R^{32a}$ is hydrogen, halogen, or an optionally substituted $C_{1-6}$ aliphatic group, provided that if ==== is a double bond $R^{32a}$ is absent; and
each of R, $R^1$, $R^2$, X, Y, and L is as defined above and described in embodiments herein, both singly and in combination.

In certain embodiments, the present invention provides a compound of formula I, wherein

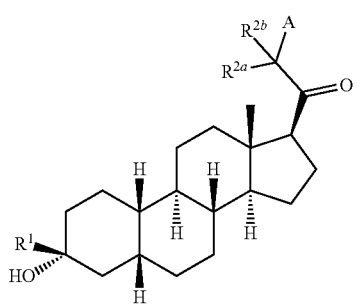

is

-continued
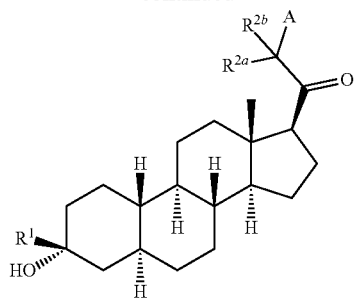
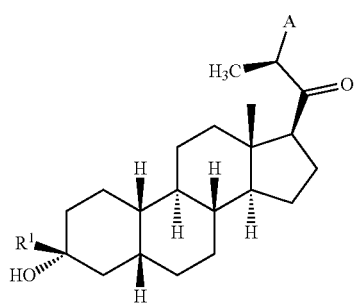
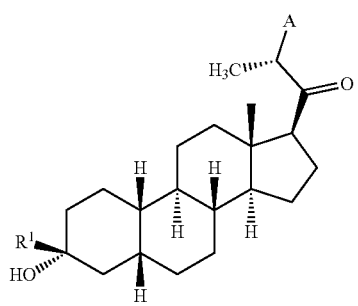
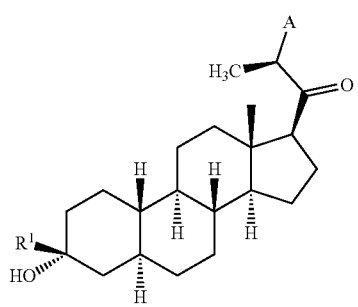
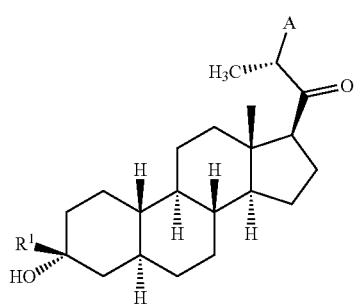
-continued
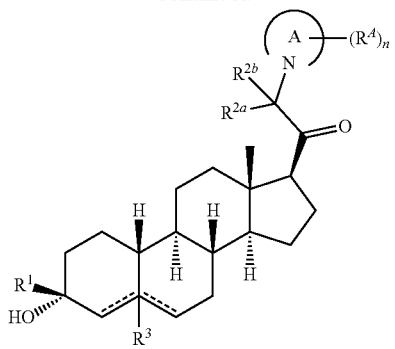
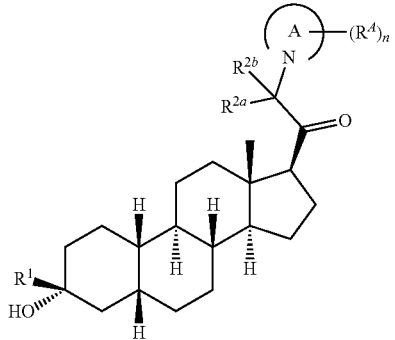
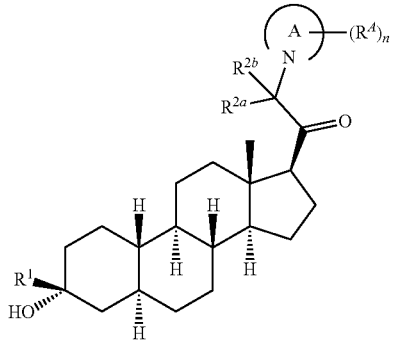
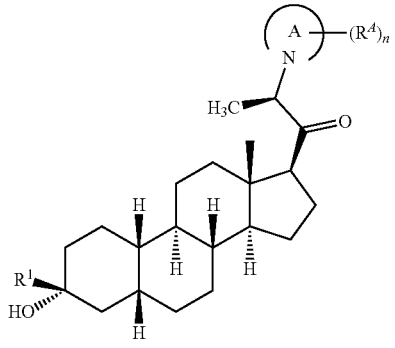
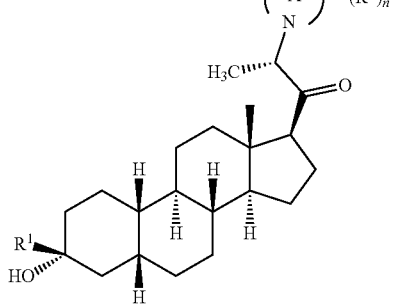

-continued
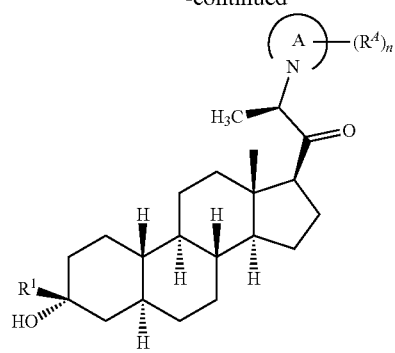
or
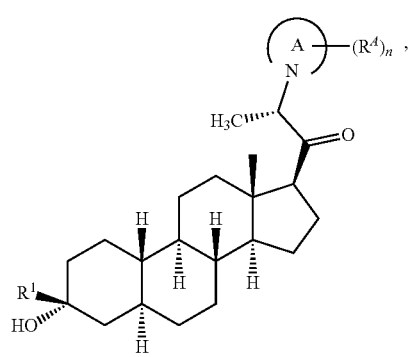
thereby forming a compound of formula VI-a:
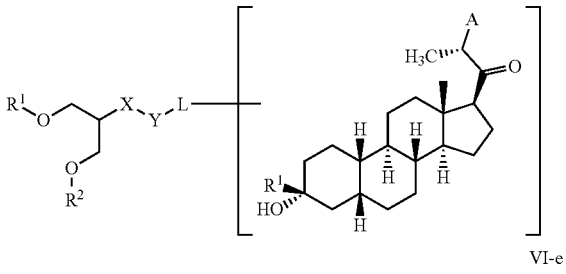
VI-a
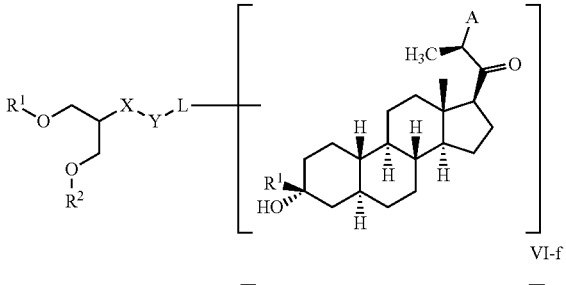
VI-b
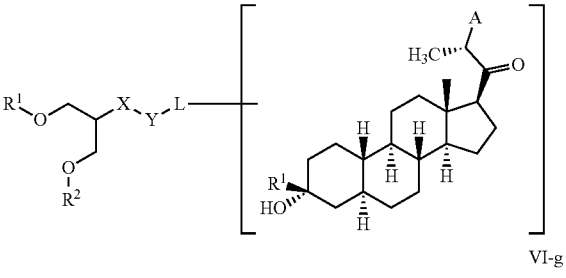
VI-c
-continued
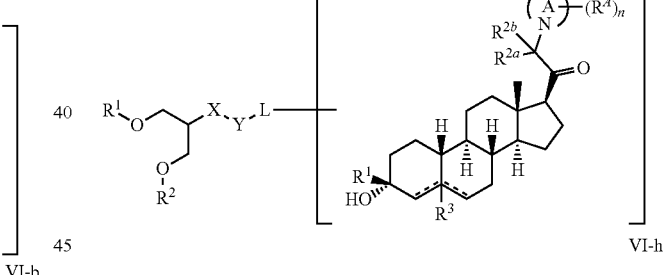
VI-d
VI-e
VI-f
VI-g
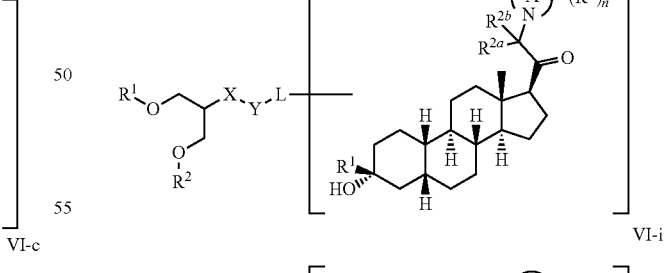
VI-h
VI-i
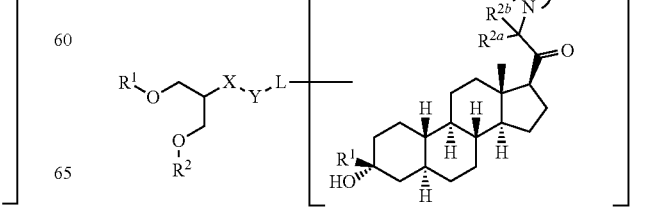

-continued

VI-j

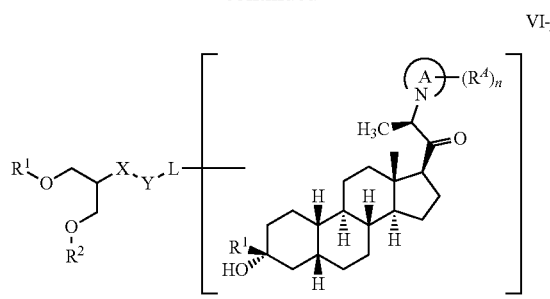

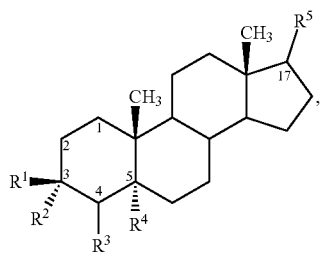

thereby forming a compound of formula VII:

VI-k

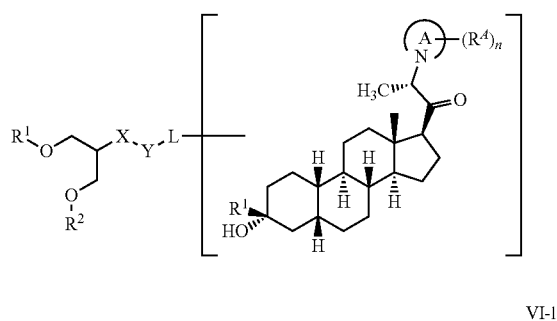

VII

VI-l

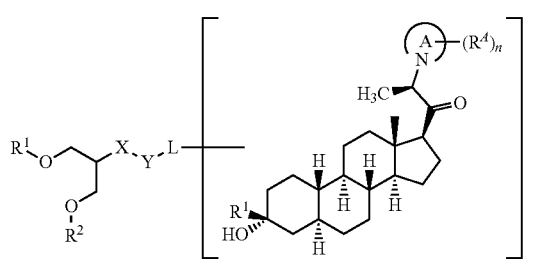

or a pharmaceutically acceptable salt thereof, wherein $R^1$, $R^2$, X, Y, and L are as defined above and described in embodiments herein, and wherein each of the VI-m

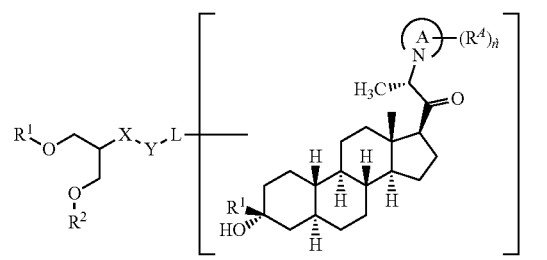

group variables $R^1$, $R^2$, $R^3$, $R^4$, and $R^5$ is as described and defined in US 2019/0337975, the entirety of which is herein incorporated by reference.

In some embodiments,

is not allopregnanolone or an analogue or prodrug thereof.

In some embodiments,

or a pharmaceutically acceptable salt thereof, wherein $R^1$, $R^2$, X, Y, and L are as defined above and described in embodiments herein, and wherein each of the A group variables $R^1$, $R^{2a}$, $R^{2b}$, $R^A$, A (or Ring A) and n is as described and defined in US 2020/0024301, the entirety of which is herein incorporated by reference.

In certain embodiments, the present invention provides a compound of formula I, wherein is is not allopregnanolone.

In some embodiments,

is a not a naturally-occurring pregnane neurosteroid.

In some embodiments,

is not selected from allopregnanolone (5α-pregnan-3α-ol-20-one), 3,5-tetrahydroprogesterone, pregnanolone (5β-pregnan-3α-ol-20-one), isopregnanolone (5α-pregnan-3β-ol-20-one), epipregnanolone (5β-pregnan-3β-ol-20-one), 21-hydroallopregnanolone, or an analogue or prodrug thereof.

In some embodiments,

is not selected from alfadolone (3α,21-dihydroxy-5α-pregnane-11,20-dione), alfaxolone (3α-hydroxy-5α-pregnane-11,20-dione), ganaxolone (3α-hydroxy-3β-methyl-5α-pregnan-20-one), hydroxydione (21-hydroxy-5β-pregnane-3,20-dione), minaxolone (11α-(dimethylamino)-20-ethoxy-3α-hydroxy-5α-pregnan-20-one), Org 20599 (21-chloro-3α-hydroxy-20-morpholin-4-yl-5β-pregnan-20-one), Org 21465 (20-(2,2-dimethyl-4-morpholinyl)-3α-hydroxy-11,20-dioxo-5α-pregnan-2l-yl methanesulfonate), renanolone (3α-hydroxy-5β-pregnan-11,20-dione), or SAGE-217 (1-(2-((3R,5R,8R,9R,10S,13S,14S,17S)-3-hydroxy-3,13-dimethylhexadecahydro-1H-cyclopenta[a]phenanthren-17-yl)-2-oxoethyl)-1H-pyrazole-4-carbonitrile).

In some embodiments,

is not selected from pregnanolone, pregnenolone, 3β-dihydropregesterone, isopregnanolone, epipregnanolone, or 21-hydroxyallopregnanolone.

In some embodiments,

the neurosteroid is a naturally-occurring or non naturally-occurring (e.g., synthetic) inhibitory neurosteroid. In some embodiments, the neurosteroid is a naturally-occurring inhibitory neurosteroid selected from:
  3α-Dihydroprogesterone (3α-DHP): pregn-4-en-3α-ol-20-one,
  5α-Dihydroprogesterone (5α-DHP; allopregnanedione): 5α-pregnane-3,20-dione,
  5β-Dihydroprogesterone (5β-DHP; pregnanedione): 5β-pregnane-3,20-dione,
  Allopregnanediol: 5α-pregnane-3α,20α-diol,
  Allopregnanolone (brexanolone; SAGE-547): 5α-pregnan-3α-ol-20-one,
  Dihydrodeoxycorticosterone (DHDOC): 21-hydroxy-5α-pregnan-20-one,
  Pregnanediol: 5β-pregnan-3α,20α-diol,
  Pregnanolone (eltanolone): 5β-pregnan-3α-ol-20-one,
  Tetrahydrodeoxycorticosterone (THDOC): 3α,21-dihydroxy-5α-pregnan-20-one,
  Deoxycorticosterone (desoxycortone): 21-hydroxypregn-4-ene-3,20-dione,
  Pregnenolone (P5): (pregn-5-en-3β-ol-20-one), and
  Progesterone (P4) (pregn-4-ene-3,20-dione).

In some embodiments,

is a non naturally-occurring (e.g., synthetic) inhibitory neurosteroid selected from:
  Alfadolone: 3α,21-dihydroxy-5α-pregnane-11,20-dione,
  Alfadolone acetate: 3α,21-dihydroxy-5α-pregnane-11,20-dione 21-acetate,
  Alfaxalone: 3α-hydroxy-5α-pregnane-11,20-dione,
  EIDD-036 (P4-20-O): 20-(hydroxyimino)pregn-4-en-3-one,
  Ganaxolone: 3β-methyl-5α-pregnan-3α-ol-20-one,
  Hydroxydione: 21-hydroxy-5β-pregnane-3,20-dione,
  Minaxolone: 11α-(dimethylamino)-20-ethoxy-5α-pregnan-3α-ol-20-one,
  ORG-20599: 21-chloro-20-morpholin-4-yl-5β-pregnan-3α-ol-20-one,
  ORG-21465: 20-(2,2-dimethyl-4-morpholinyl)-3α-hydroxy-11,20-dioxo-5α-pregnan-2l-yl methanesulfonate,
  Renanolone: 5β-pregnan-3α-ol-11,20-dione,
  SGE-516,
  SGE-872,
  SAGE-217 (Zuranolone): 3α-hydroxy-3β-methyl-21-(4-cyano-1H-pyrazol-1'-yl)-19-nor-5β-pregnan-20-one, or
  a proneurosteroid, such as:
  EIDD-1723,
  P1-185, and
  Progesterone carboxymethyloxime (P4-3-CMO).

In some embodiments,

is a naturally-occurring or non naturally-occurring (e.g., synthetic) excitatory neurosteroid. In some embodiments,

is a naturally-occurring excitatory neurosteroid selected from:
  3β-Dihydroprogesterone (3β-DHP): pregn-4-en-3β-ol-20-one,
  Epipregnanolone: 5β-pregnan-3β-ol-20-one,
  Isopregnanolone (sepranolone): 5α-pregnan-3β-ol-20-one,
  Pregnenolone sulfate (PS): pregn-5-en-3β-ol-20-one 3β-sulfate, or
  Pregnenolone (P5): pregn-5-en-3β-ol-20-one.

In some embodiments,

is epipregnanolone sulfate (5β-pregnan-3β-ol-20-one 3β-sulfate).

In some embodiments,

is a naturally-occurring or non naturally-occurring (e.g., synthetic) neurotrophic neurosteroid. In some embodiments,

is:
BNN-27: 17α,20R-epoxypregn-5-ene-3β,21-diol.
In some embodiments,

is a naturally-occurring or non naturally-occurring (e.g., synthetic) antineurotrophic neurosteroid. In some embodiments,

is:
Dexamethasone: 9α-fluoro-11,17α,21-trihydroxy-16α-methylpregna-1,4-diene-3,20-dione or an analogue thereof.
In some embodiments,

is selected from naturally-occurring or non naturally-occurring (e.g., synthetic) pheromones and pherines. In some embodiments,

is selected from:
Pregnadienedione (PDD): pregna-4,20-dien-3,6-dione, PH10, PH15, PH30, PH56, PH78, PH84, and Salubrin (PH80).
In some embodiments,

is selected from:
Pregnenolone (P5): pregn-5-en-3β-ol-20-one,
Progesterone (P4): pregn-4-ene-3,20-dione,
3β-Methoxypregnenolone (MAP-4343): 3β-methoxypregn-5-en-20-one,
Cyclopregnol (neurosterone): 6β-hydroxy-3:5-cyclopregnan-20-one.

In some embodiments,

is a compound selected from those described in WO209094724, the content of each of which is incorporated by reference in its entirety. In some embodiments

is a compound of formulas IA, IB, II or III, as described in WO2019094724:

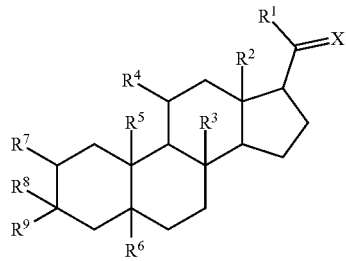

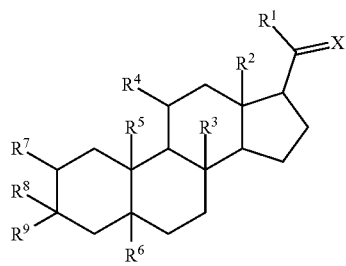

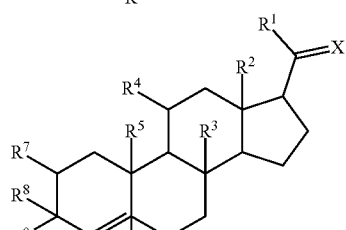

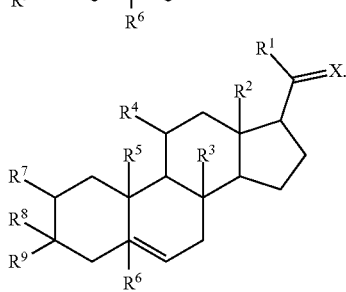

In some embodiments,

is selected from Co26749/WAY-141839, Co134444, and Co177843:

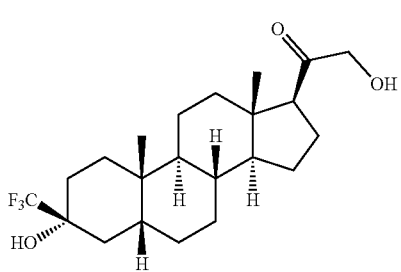

Co26749/WAY-141839

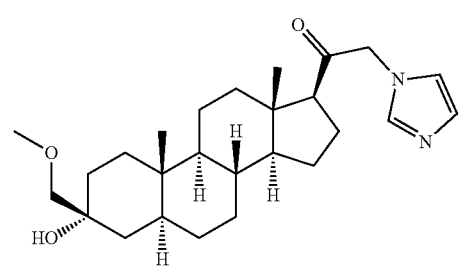

Co134444

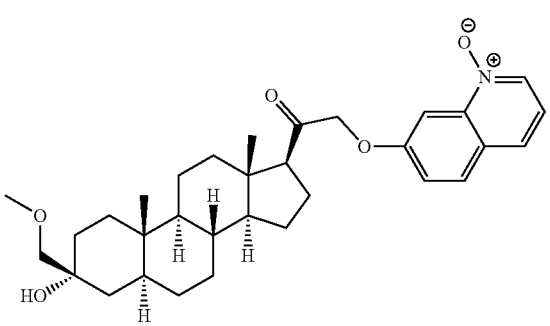

Co177843

In some embodiments,

is a compound selected from those described in US 2016/0229887, the content of which is incorporated by reference in its entirety.

In some embodiments,

is a compound selected from those described in Martinez Botella G. et al., *J. Med. Chem.* 2015, 58, 8, 3500-3511, the content of which is incorporated by reference in its entirety.

In some embodiments,

is a compound selected from those described in Paul S. M. et al., J Neurosci. 2013, 33(44):1'7290-300, the contents of which is incorporated by reference in its entirety.

In some embodiments,

is a compound selected from the following table:

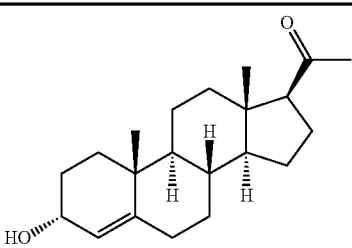

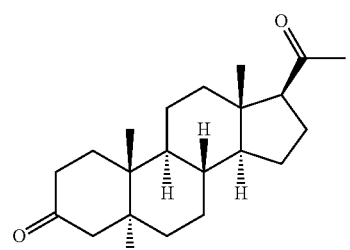

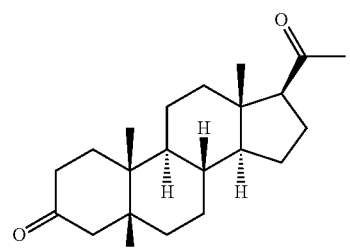

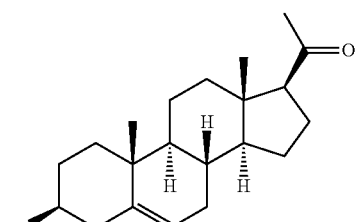

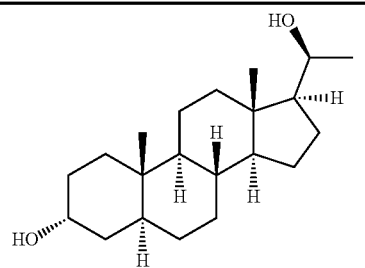
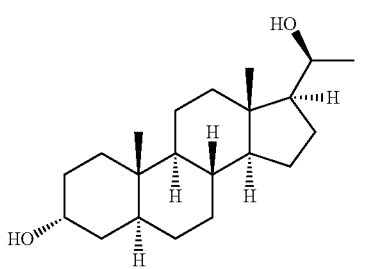
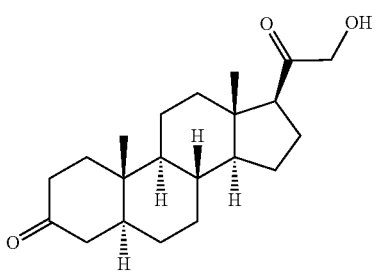
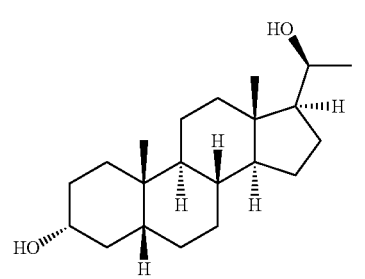
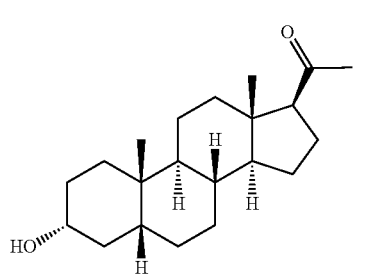
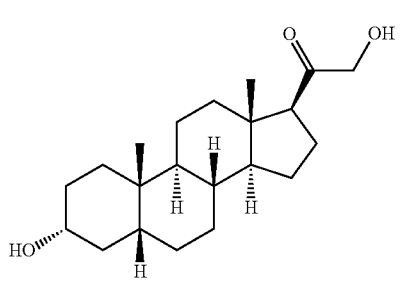
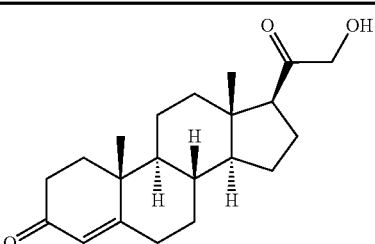
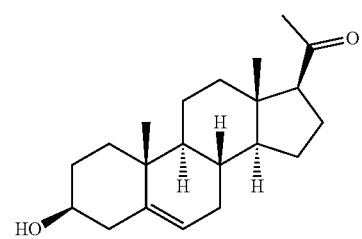
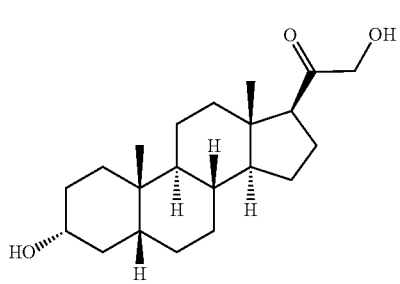
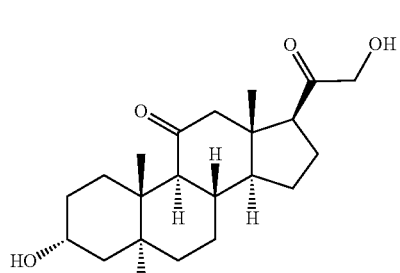
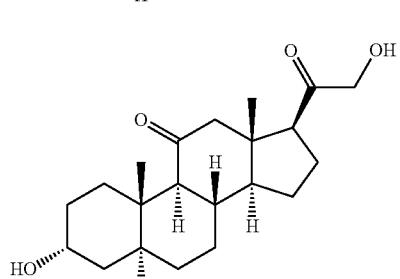
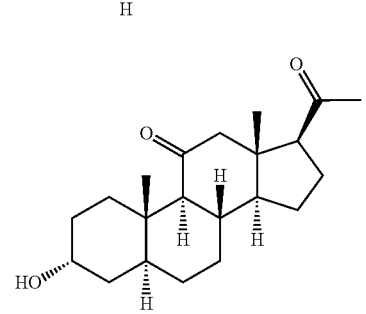

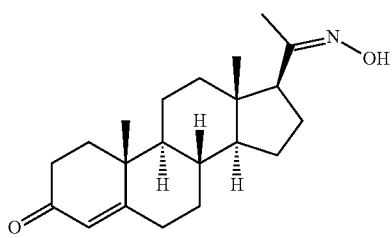
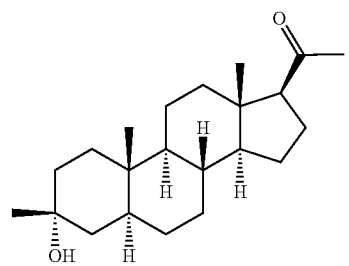
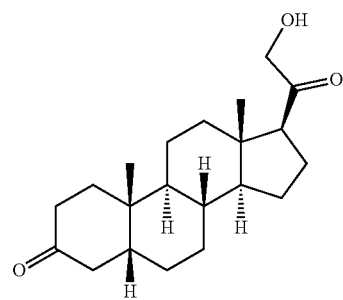
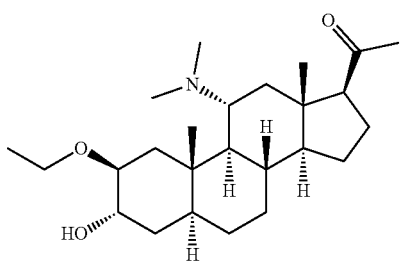
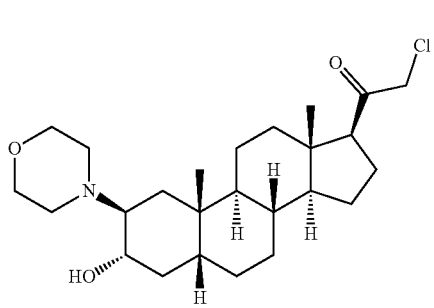
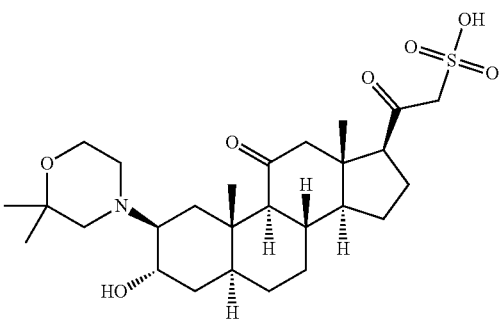
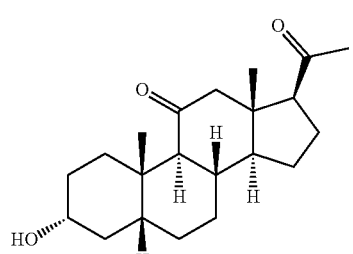
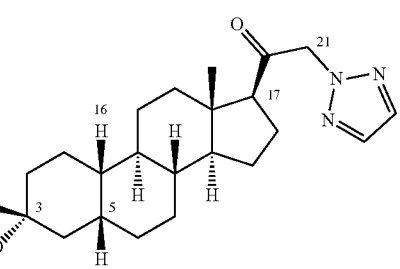
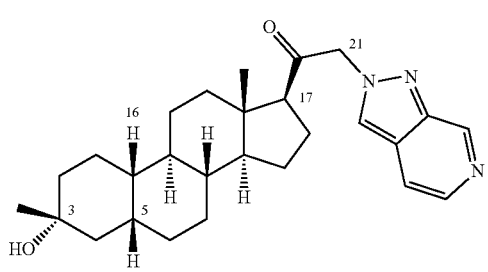

61
-continued
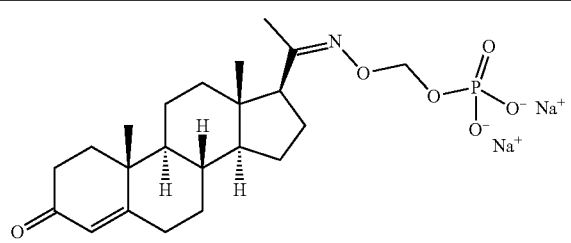
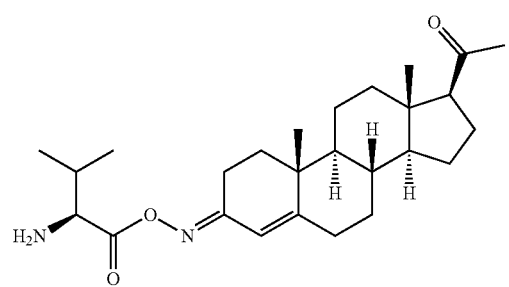
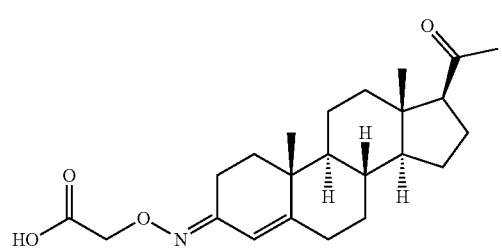
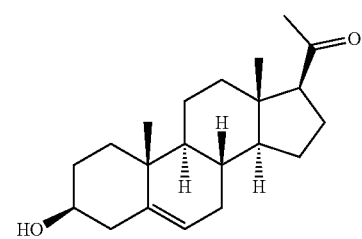
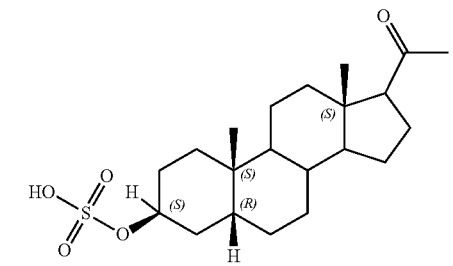
62
-continued
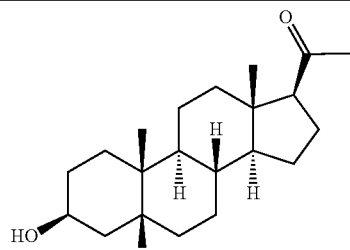
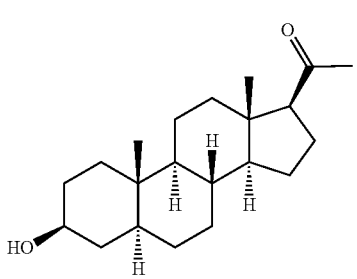
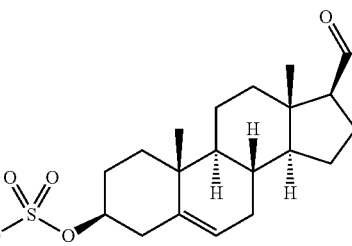
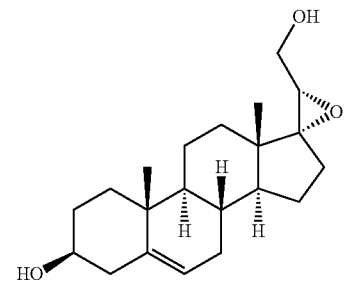
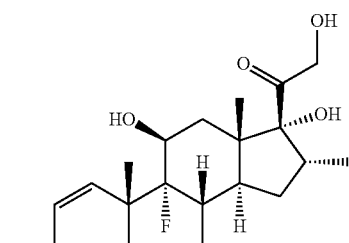
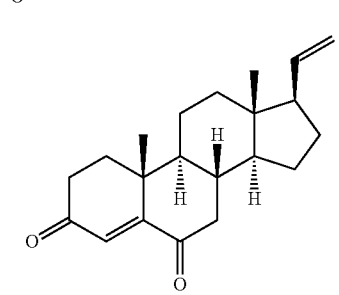

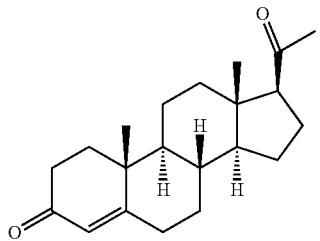

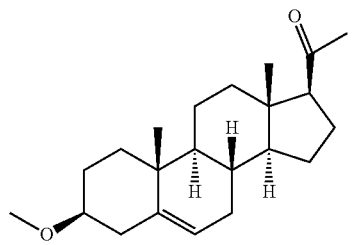

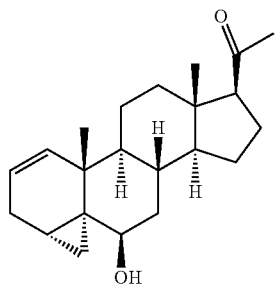

One of ordinary skill in the art will appreciate that certain lipid prodrugs shown in Table 1 are in the form of prodrugs. Thus, it will be appreciated that a lipid prodrug moiety of the present invention is attached to the therapeutic agent or the active form thereof. For the purpose of clarity, and by way of example, it will be understood that a provided lipid prodrug moiety is attached at any modifiable oxygen, sulfur, or nitrogen atom of a pregnane neurosteroid. For example, allopregnanolone has the following structure:

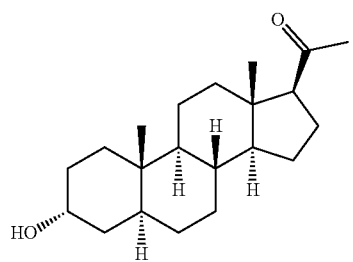

and may be attached to the lipid prodrug moiety e.g., via its hydroxyl (OH) group or at another chemically modifiable position such as the ketone.

As used herein, depiction of brackets around a therapeutic agent,

means that the

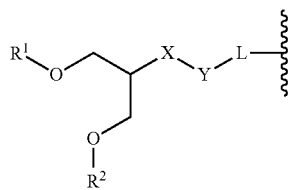

moiety is covalently attached to

at any available modifiable nitrogen, oxygen, or sulfur atom. For purposes of clarity and by way of non-limiting examples, available modifiable nitrogen, oxygen, or sulfur atoms in the following therapeutic agent compound structures are depicted below, wherein each wavy bond defines the point of attachment to formula I or another of the formulae depicted herein:

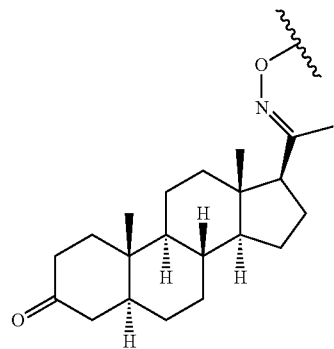

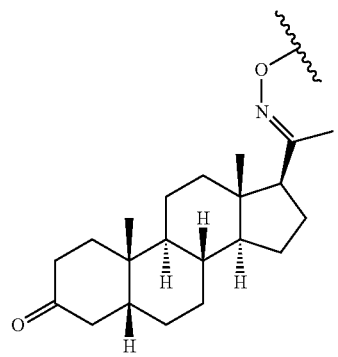

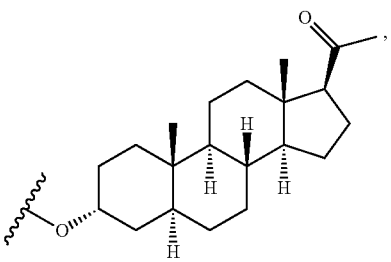

65
-continued
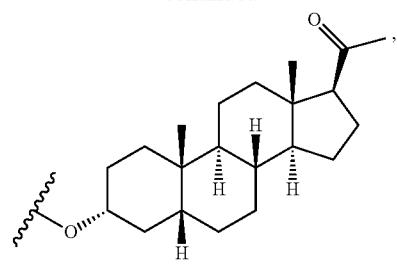
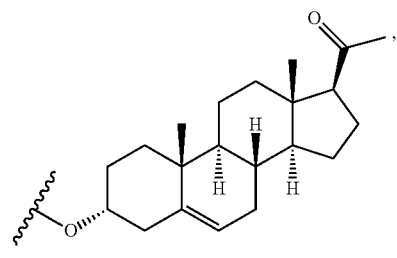
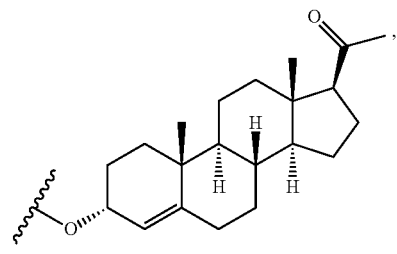
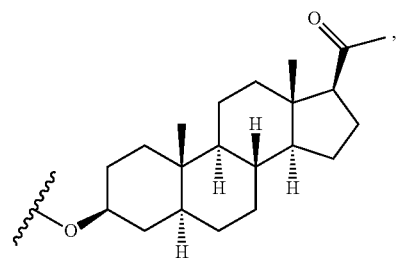
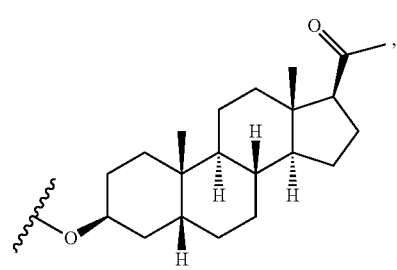
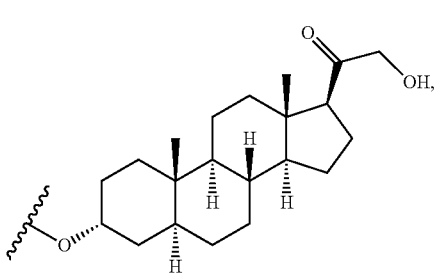
66
-continued
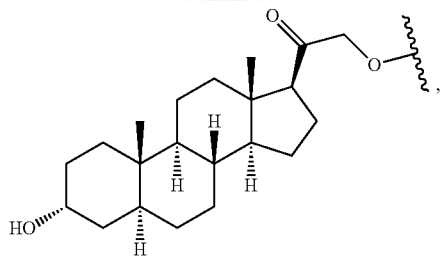
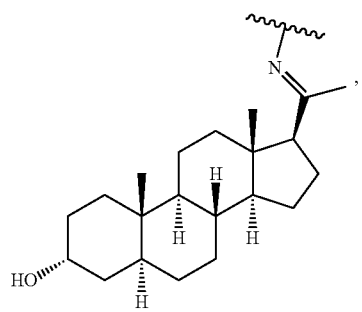
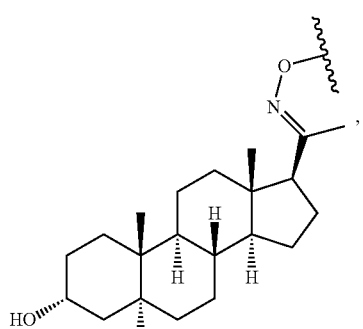
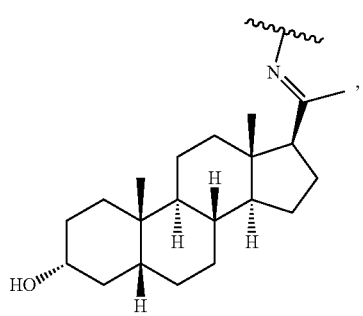
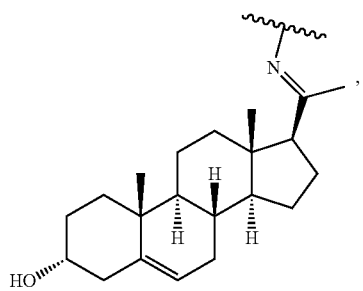

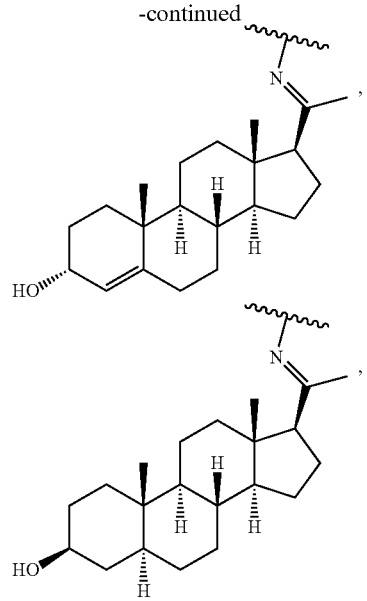,
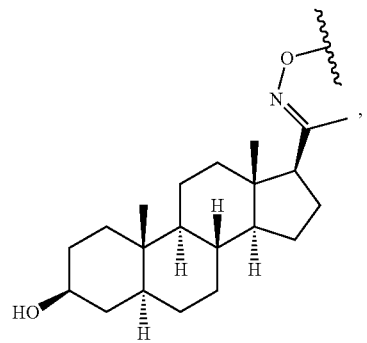,
, or
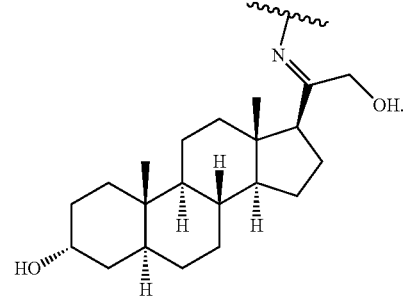
In some embodiments,
is
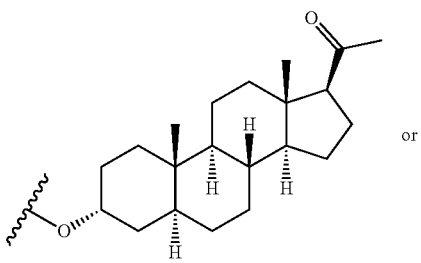
or
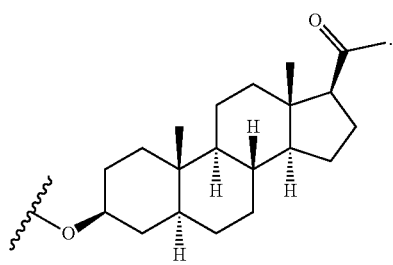
In some embodiments, is
is
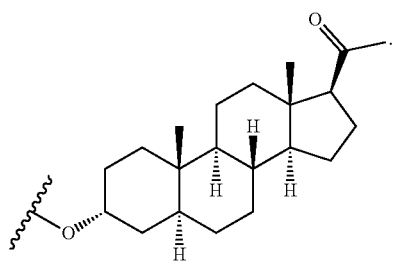
In some embodiments,
is
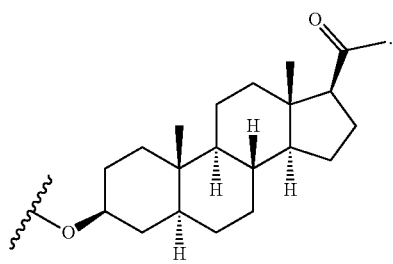

In some embodiments, the present invention provides a compound of Formula I-a:

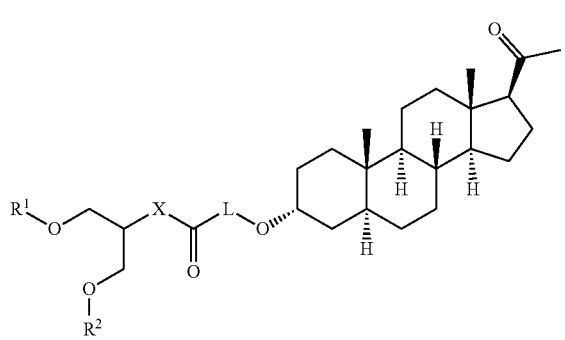

I-a or a pharmaceutically acceptable salt thereof, wherein each of L, $R^1$, $R^2$, and X is as defined above and described in embodiments herein, both singly and in combination.

In some embodiments, the present invention provides a compound of Formula I-b:

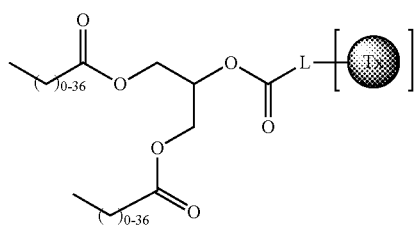

I-b or a pharmaceutically acceptable salt thereof, wherein each of L and

is as defined above and described in embodiments herein, both singly and in combination.

In some embodiments, the present invention provides a compound of Formula I-c:

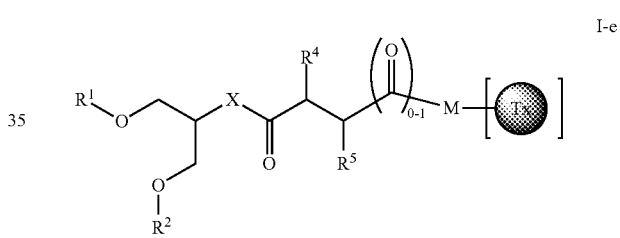

I-c or a pharmaceutically acceptable salt thereof, wherein each of L, $R^1$, $R^2$, and X is as defined above and described in embodiments herein, both singly and in combination.

In some embodiments, the present invention provides a compound of Formula I-d:

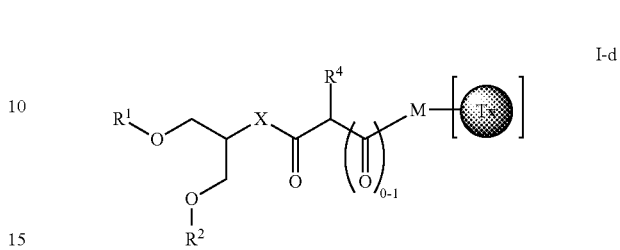

I-d or a pharmaceutically acceptable salt thereof, wherein each of $R^1$, $R^2$, $R^4$, $R^5$, X, M, and

is as defined above and described in embodiments herein, both singly and in combination.

In some embodiments, the present invention provides a compound of Formula I-e:

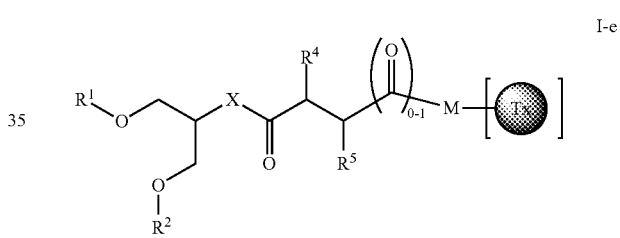

I-e or a pharmaceutically acceptable salt thereof, wherein each of $R^1$, $R^2$, $R^4$, $R^5$, X, M, and

is as defined above and described in embodiments herein, both singly and in combination.

In some embodiments, the present invention provides a compound of Formula I-f:

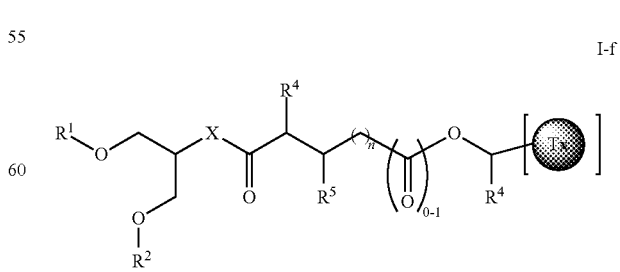

I-f or a pharmaceutically acceptable salt thereof, wherein each of $R^1$, $R^2$, $R^4$, $R^5$, X, n, and

is as defined above and described in embodiments herein, both singly and in combination.

In some embodiments, the present invention provides a compound of Formula I-g:

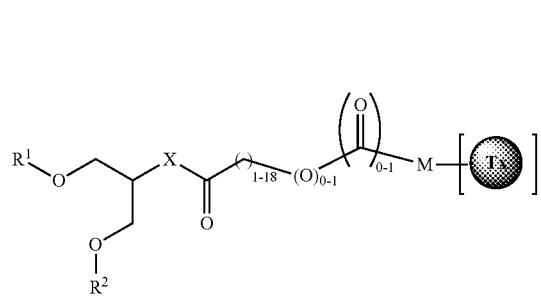

I-g or a pharmaceutically acceptable salt thereof, wherein each of $R^1$, $R^2$, X, M, and

is as defined above and described in embodiments herein, both singly and in combination.

In some embodiments, the present invention provides a compound of Formula I-h:

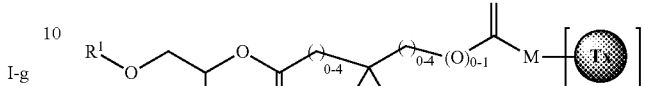

I-h or a pharmaceutically acceptable salt thereof, wherein each of $R^1$, $R^2$, $R^4$, $R^5$, M, and

is as defined above and described in embodiments herein, both singly and in combination.

In some embodiments, the present invention provides a compound of Formula VIII-a, VIII-b, VIII-c, VIII-d, VIII-e, VIII-f, or VIII-g:

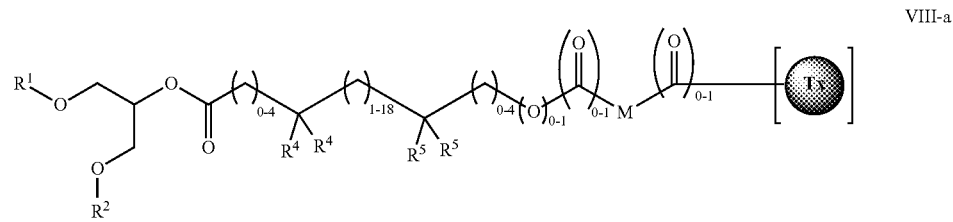

VIII-a

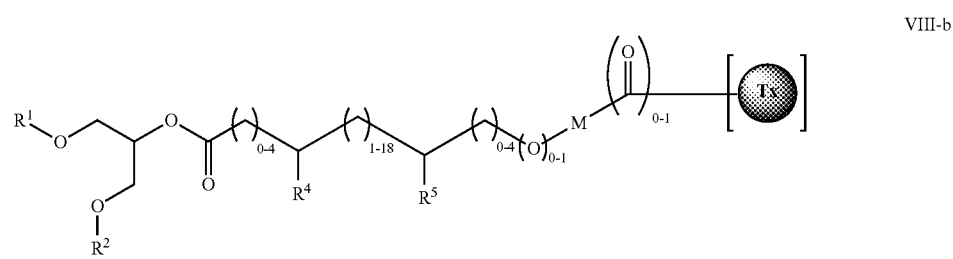

VIII-b

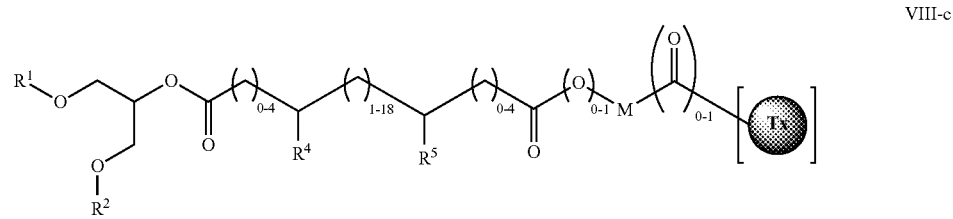

VIII-c

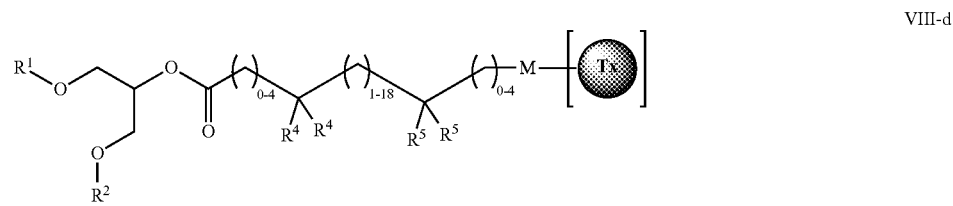

VIII-d

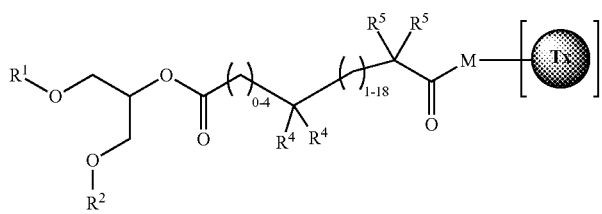
VIII-e
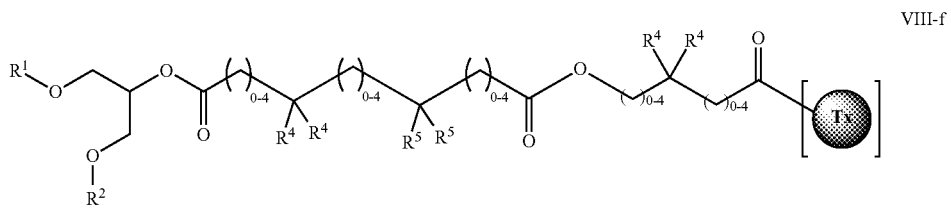
VIII-f
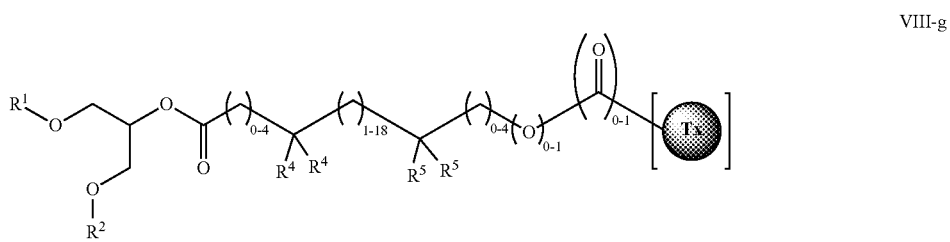
VIII-g
or a pharmaceutically acceptable salt thereof, wherein each of $R^1$, $R^2$, $R^4$, $R^5$, M, and
is as defined above and described in embodiments herein, both singly and in combination.
In some embodiments, the present invention provides a compound of Formula IX-a or IX-b:
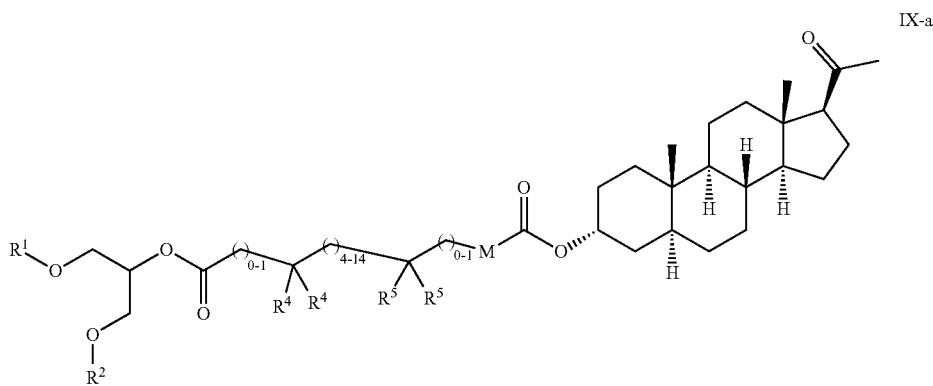
IX-a

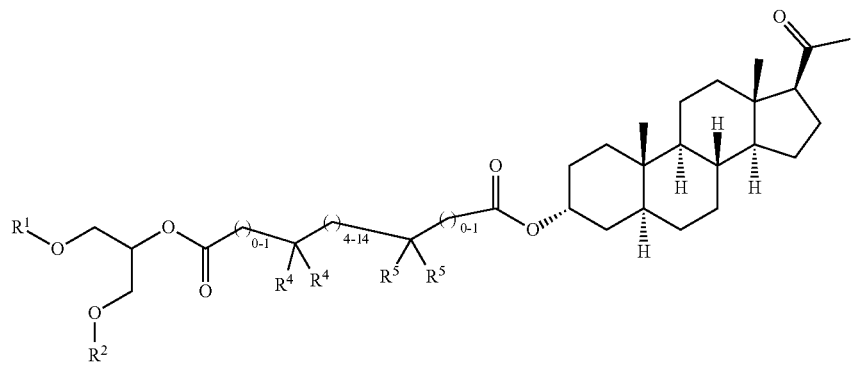

IX-b or a pharmaceutically acceptable salt thereof, wherein each of $R^1$, $R^2$, $R^4$, $R^5$, and M is as defined above and described in embodiments herein, both singly and in combination.

In some embodiments, the present invention provides a compound of Formula IX-c or IX-d:

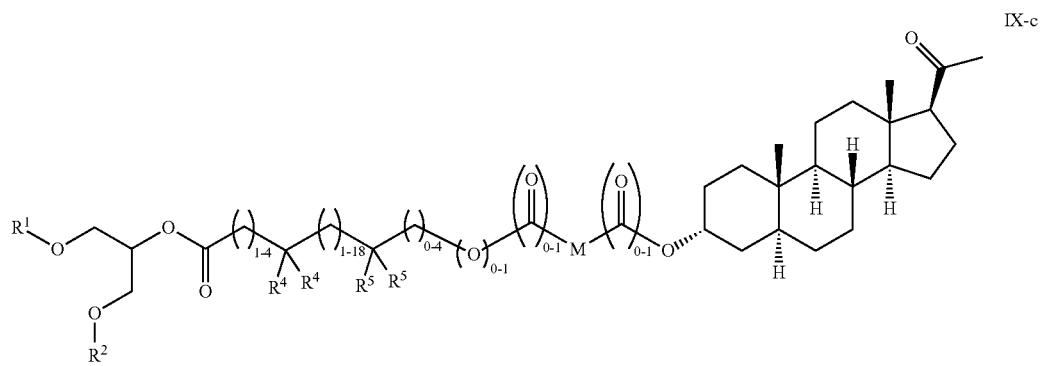

IX-c

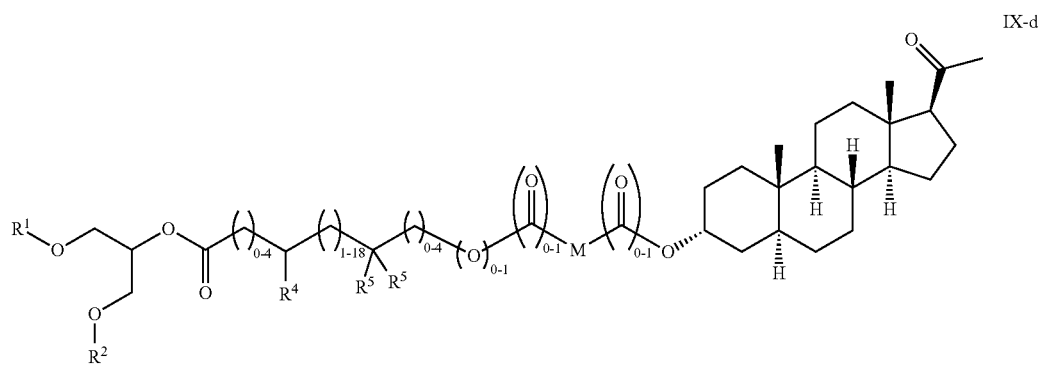

IX-d or a pharmaceutically acceptable salt thereof, wherein each of $R^1$, $R^2$, $R^4$, $R^5$, and M is as defined above and described in embodiments herein, both singly and in combination.

In some embodiments, the present invention provides a compound of Formula X:

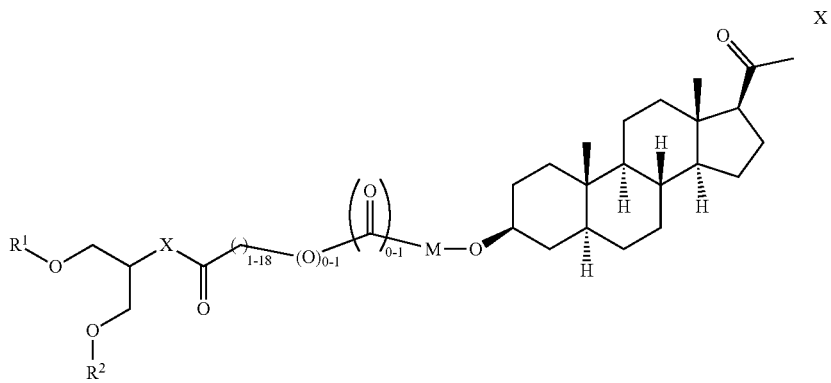

or a pharmaceutically acceptable salt thereof, wherein each of $R^1$, $R^2$, X, and M is as defined above and described in embodiments herein, both singly and in combination.

In some embodiments, the present invention provides a compound of Formula XI:

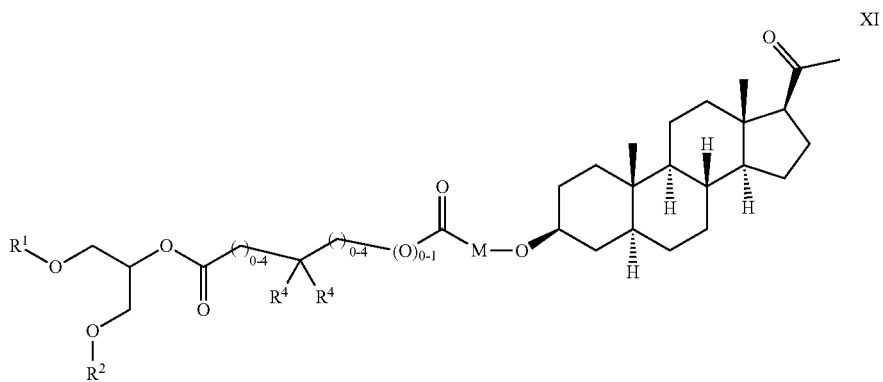

or a pharmaceutically acceptable salt thereof, wherein each of $R^1$, $R^2$, $R^4$, and M is as defined above and described in embodiments herein, both singly and in combination.

In some embodiments, the present invention provides a compound of Formula XII-a, XII-b, XII-c, XII-d, XII-e, XII-f, or XII-g:

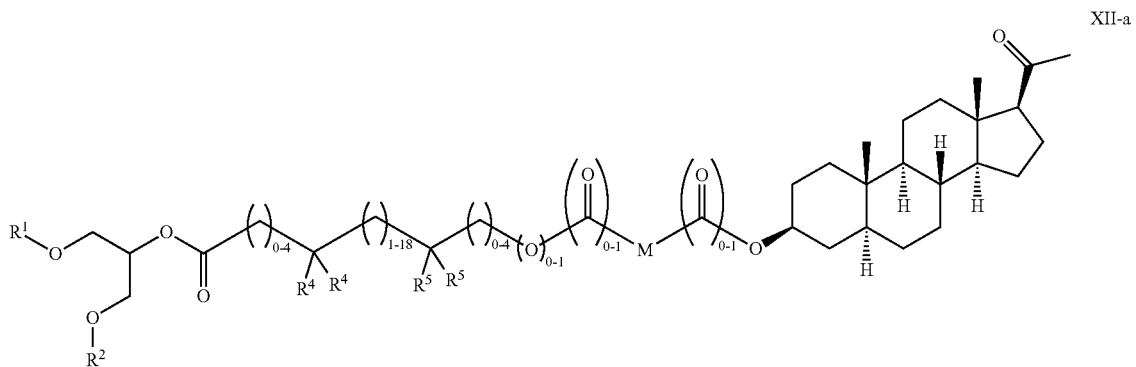

-continued
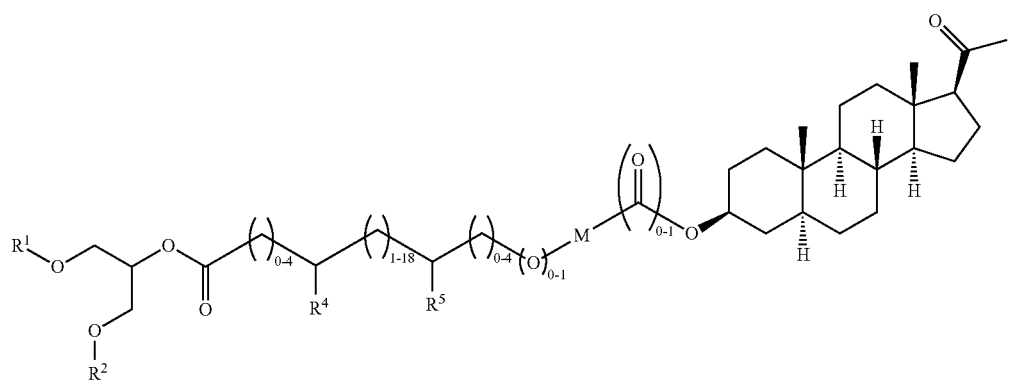
XII-b
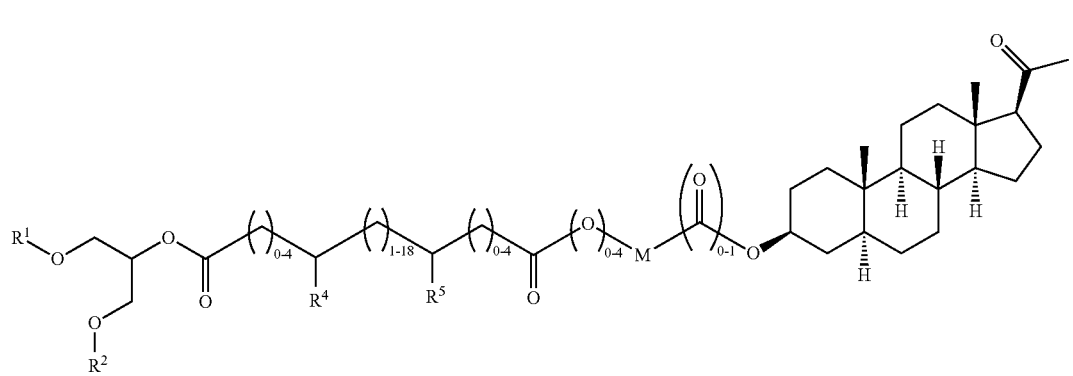
XII-c
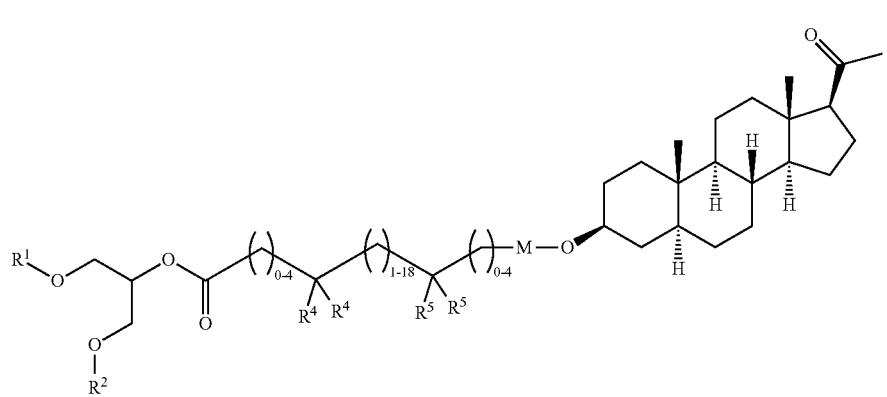
XII-d
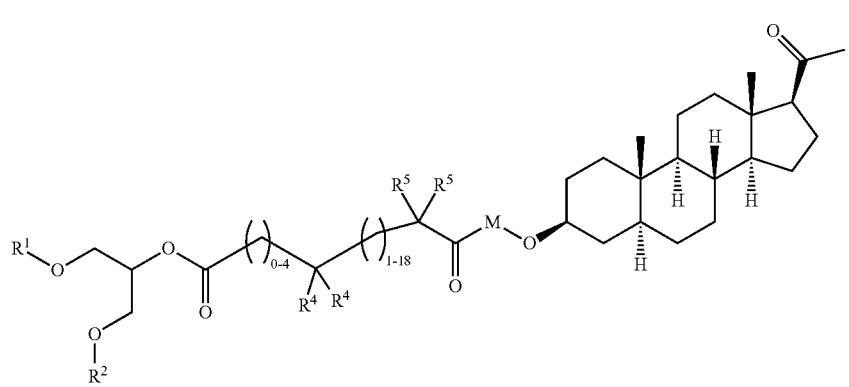
XII-e -continued
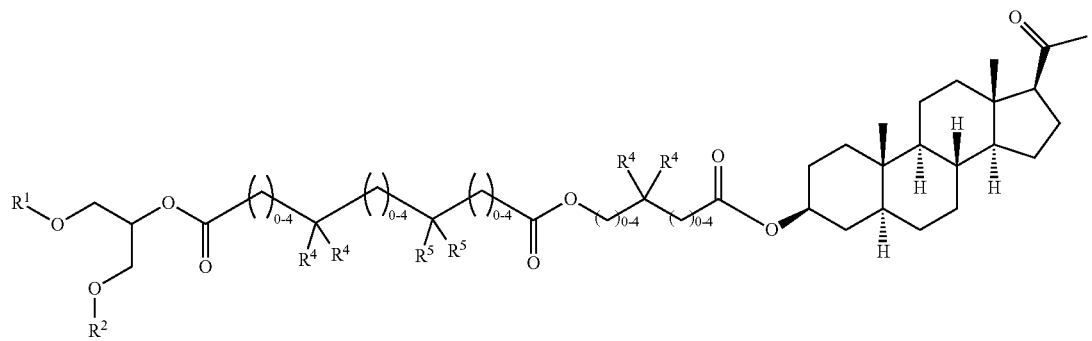
XII-f
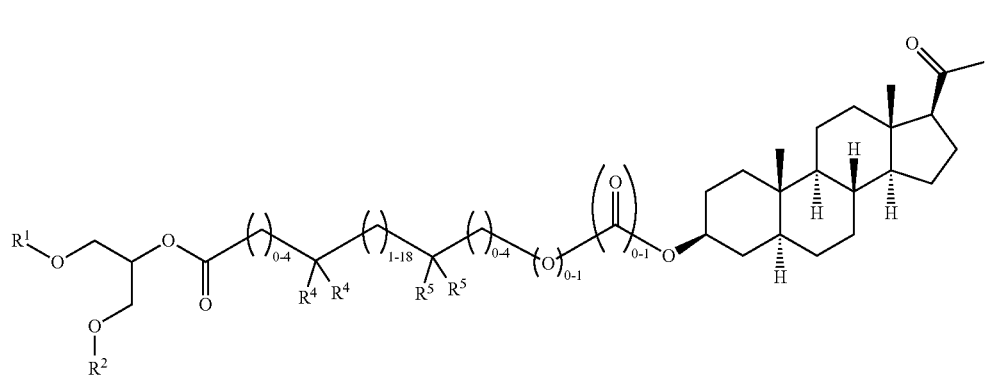
XII-g
or a pharmaceutically acceptable salt thereof, wherein each of $R^1$, $R^2$, $R^4$, $R^5$, and M is as defined above and described in embodiments herein, both singly and in combination.
In some embodiments, the present invention provides a compound of Formula XIII-a or XIII-b:
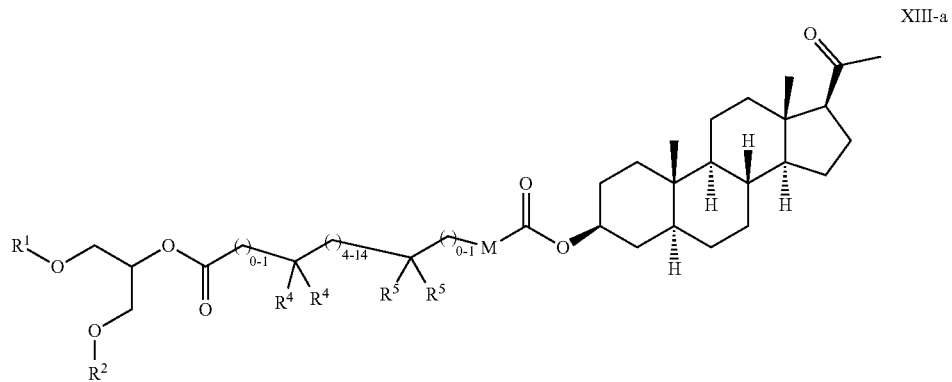
XIII-a

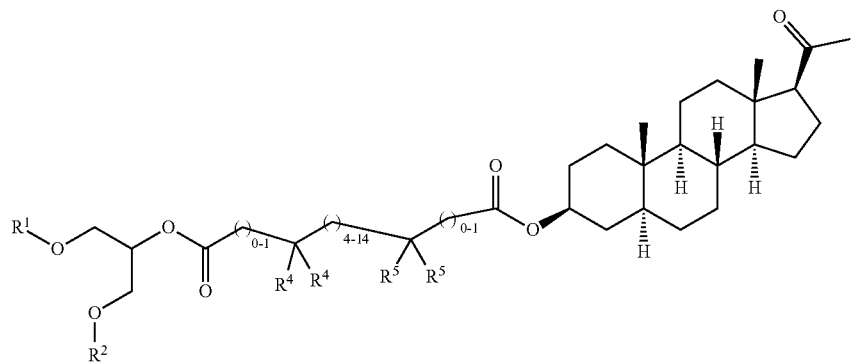

XIII-b or a pharmaceutically acceptable salt thereof, wherein each of $R^1$, $R^2$, $R^4$, $R^5$, and -M- is as defined above and described in embodiments herein, both singly and in combination.

In some embodiments, the present invention provides a compound of Formula XIII-c or XIII-d:

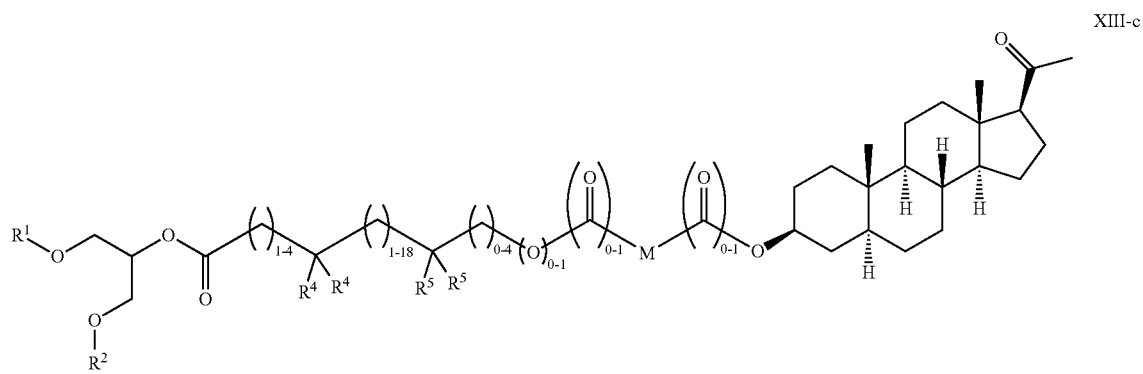

XIII-c

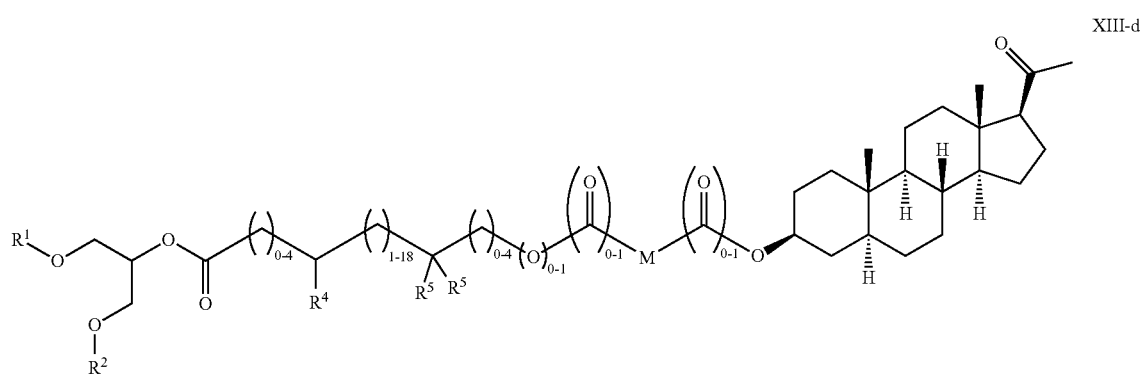

XIII-d or a pharmaceutically acceptable salt thereof, wherein each of $R^1$, $R^2$, $R^4$, $R^5$, and M is as defined above and described in embodiments herein, both singly and in combination.

In the above formulae, when a range of numbers, such as 0-4 or 1-18, is disclosed, individual integers within the range are also specifically disclosed. Thus, the above range of 0-4 includes 0, 1, 2, 3, and 4. The range 1-18 includes 1, 2, 3, 4, 5, 6, 7, 8, 9, 10, 11, 12, 13, 14, 15, 16, 17, and 18. The range 0-1 includes 0 and 1, i.e. the group is optionally present. Where more than one range is disclosed in a formula, each range is independently and optionally selected from the disclosed range. For example, in Formula VIII-c above, each 0-4 and 1-18 range is varied independently of the others.

In another aspect, the present invention provides a compound of Formula XIV:

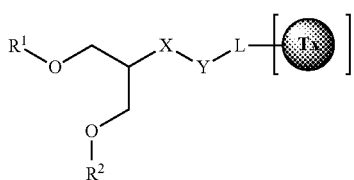

(XIV)

or a pharmaceutically acceptable salt thereof, wherein:
$R^1$ and $R^2$ are each independently hydrogen or —C(O)$R^3$;
each $R^3$ independently is a saturated or unsaturated, straight or branched, optionally substituted $C_{1-37}$ hydrocarbon chain;
X is —O—;
Y is —C(O)—;
L is a saturated or unsaturated, straight or branched, optionally substituted bivalent $C_{3-20}$ hydrocarbon chain, wherein 0-2 methylene units of L are independently replaced by -Cy-, —O—, —N(R)— —S—, —OC(O)—, —C(O)O—, or —C(O)—; and wherein 1 methylene unit of L is optionally replaced with -M-; or L is

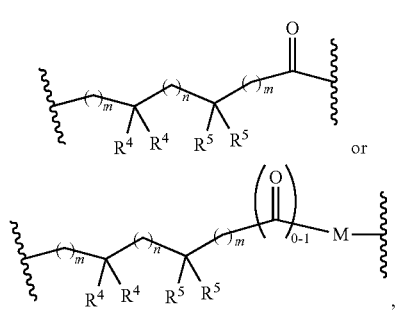

wherein the right-hand side of L is attached to

each -Cy- independently is an optionally substituted 3-6 membered bivalent saturated, partially unsaturated, or aromatic ring having 0-4 heteroatoms independently selected from nitrogen, oxygen, or sulfur;
each R independently is hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^4$ and $R^5$ independently is hydrogen, deuterium, halogen, —CN, —OR, —NR$_2$, —SR, a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or the $C_{1-6}$ aliphatic is optionally substituted with 1, 2, 3, 4, 5, or 6 deuterium or halogen atoms; or
two instances of $R^4$ or $R^5$ attached to the same carbon atom, taken together with the carbon atom to which they are attached, form a 3-6 membered spirocyclic saturated monocyclic carbocyclic ring or 3-6 membered spirocyclic saturated heterocyclic ring having 1-2 heteroatoms independently selected from nitrogen, oxygen, or sulfur;
-M- is a self-immolative group;
n is 0-18;
each m independently is 0-6; and

is a therapeutic agent selected from a naturally-occurring or non naturally occurring pregnane neurosteroid or an analogue or prodrug thereof.
In some embodiments, L is

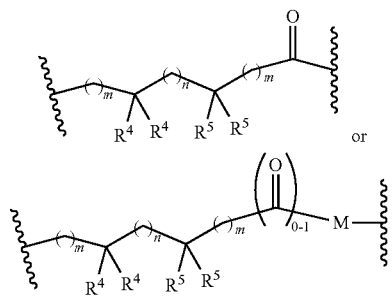

In some embodiments, L is

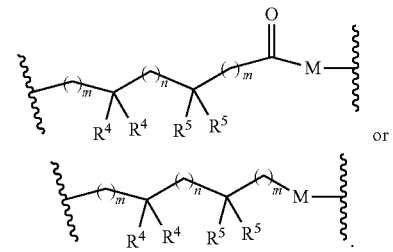

In some embodiments, L

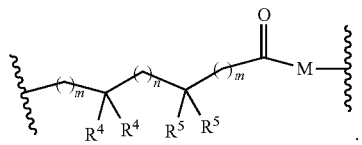

In some embodiments, L is

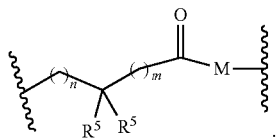

In some embodiments, L is

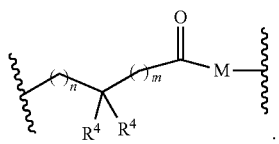

In some embodiments, L is

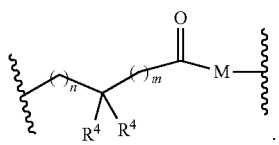

In some embodiments, n is 0, 1, 2, 3, 4, 5, 6, 7, 8, 9, 10, 11, or 12; or 0-12, 0-10, 0-8, or 0-6; or 1-12, 1-10, 1-8, or 1-6; or 2-12, 2-10, 2-8, or 2-6; or 0-4. In some embodiments, each m independently is 0, 1, 2, or 3; or each m independently is 0 or 1. In some embodiments, each m is 0. In some embodiments, each m is 1. In some embodiments, each m is 0 or 1 and n is 2-12.

In some embodiments, -M- is

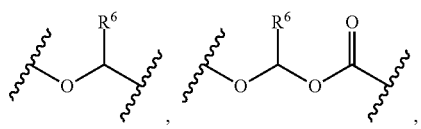

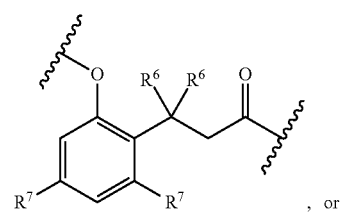

, or

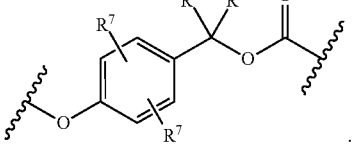

In some embodiments, -M- is

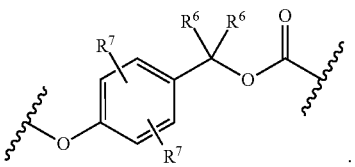

In some embodiments, -M- is

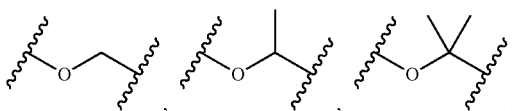

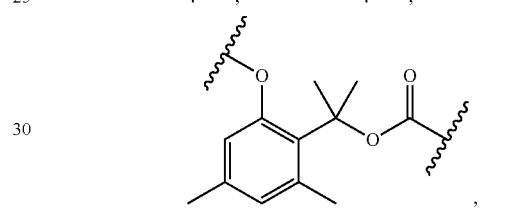

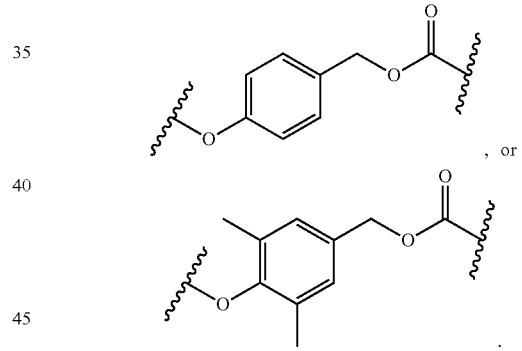

, or

In some embodiments, -M- is

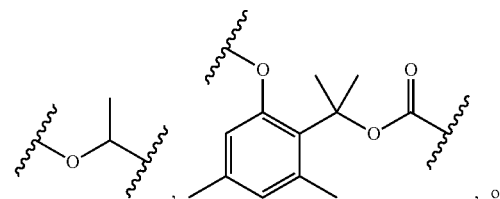

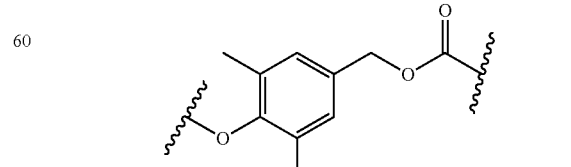

, or

In some embodiments, -M- is

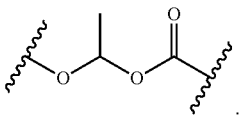 [SMILES: *OC(C)OC(*)=O]

In some embodiments, -M- is

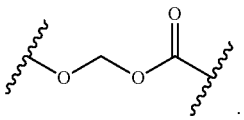 [SMILES: *OCOC(*)=O]

In some embodiments the right-hand side of the above embodiments of -M- is attached to

, such as at an available O atom of

.

In some embodiments, -M- is

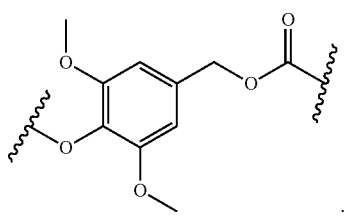 [SMILES: *Oc1c(OC)cc(COC(*)=O)cc1OC]

In some embodiments, -M- is

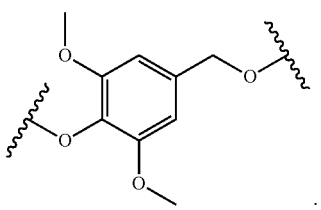 [SMILES: *OCc1cc(OC)c(O*)c(OC)c1]

In some embodiments, -M- is

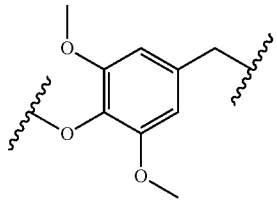

In some embodiments, the right-hand side of the above embodiments of -M- is attached to

, such as at an available O atom of

.

In some embodiments, one instance of $R^4$ is hydrogen and one instance of $R^5$ is hydrogen. In some embodiments, each $R^4$ and $R^5$ independently is hydrogen, deuterium, halogen, —CN, or $C_{1-6}$ aliphatic optionally substituted with —OR or 1, 2, 3, 4, 5, or 6 deuterium or halogen atoms.

In some embodiments, one instance of $R^4$ or $R^5$ is $C_{1-6}$ alkyl, such as $C_{1-3}$ alkyl, for example, methyl. In some embodiments, two instances of $R^4$ and $R^5$ are each independently $C_{1-6}$ alkyl, such as $C_{1-3}$ alkyl, for example, methyl.

In some embodiments, -M- is present. In some embodiments, -M- is present and at least one of $R^4$ or $R^5$ is not hydrogen. In some embodiments, -M- is present and at least one of $R^4$ or $R^5$ is $C_{1-6}$ alkyl, such as $C_{1-3}$ alkyl, for example, methyl. In some embodiments, -M- is present and at least two instances of $R^4$ and $R^5$ are independently $C_{1-6}$ alkyl, such as $C_{1-3}$ alkyl, for example, methyl.

In some embodiments, -M- is not present. In some embodiments, -M- is not present and at least one of $R^4$ or $R^5$ is not hydrogen. In some embodiments, -M- is not present and at least one of $R^4$ or $R^5$ is $C_{1-6}$ alkyl, such as $C_{1-3}$ alkyl, for example, methyl. In some embodiments, -M- is not present and at least two instances of $R^4$ and $R^5$ are independently $C_{1-6}$ alkyl, such as $C_{1-3}$ alkyl, for example, methyl. In some embodiments, two instances of $R^4$, two instances of $R^5$, or one instance of $R^4$ and one instance of $R^5$ are present; and each $R^4$ and $R^5$ independently is selected from $C_{1-6}$ alkyl, such as $C_{1-3}$ alkyl, for example, methyl, optionally substituted with 1, 2, 3, 4, 5, or 6 deuterium or halogen atoms.

In some embodiments,

is allopregnanolone. In some embodiments,

is isoallopregnanolone.

In some embodiments, L is

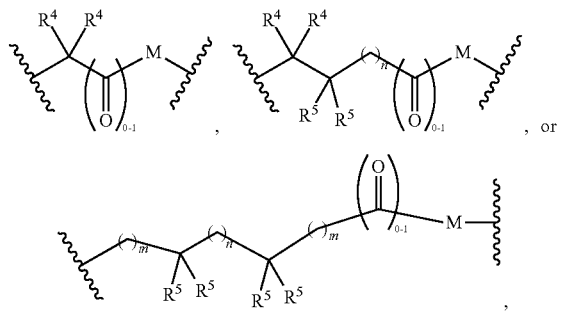

, or wherein either the right-hand side or left-hand side of L is attached to

;

and -M- is:

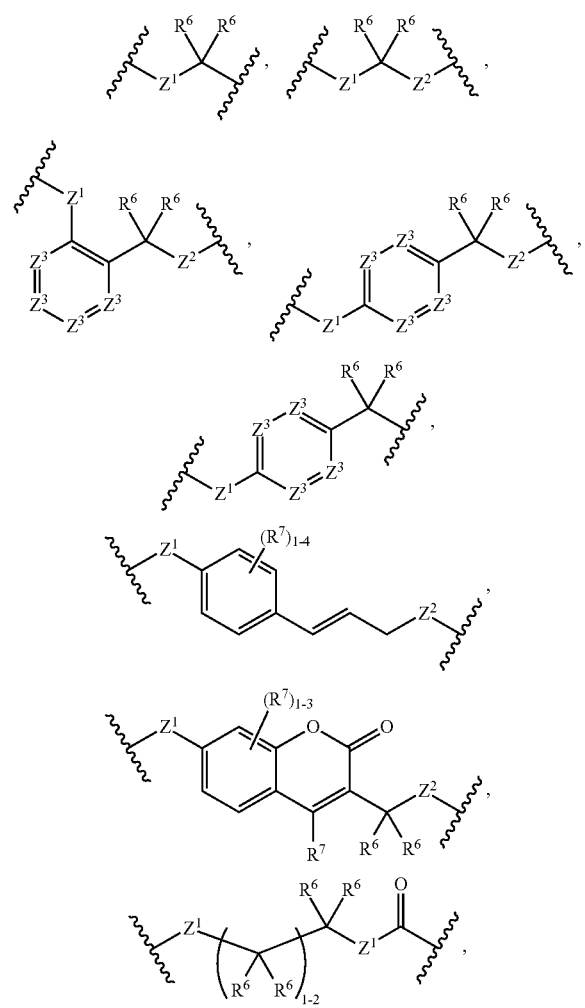

-continued

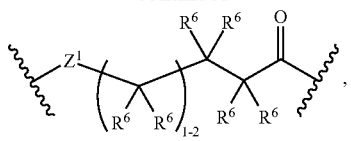

,

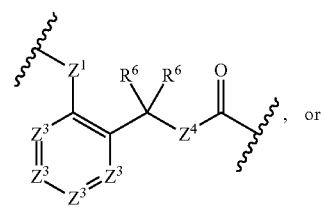

, or

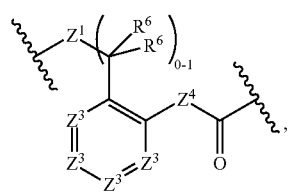

, wherein each $R^6$ independently is selected from hydrogen, deuterium, $C_{1-10}$ aliphatic, halogen, or —CN;

each $R^7$ independently is selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;

each $Z^1$ independently is selected from —O—, —NR—, or —S—;

each $Z^2$ independently is selected from —O—, —NR—, —S—, —OC(O)—, —NRC(O)O—, or —OC(O)NR—;

each $Z^3$ independently is selected from =N— or =C(R$^7$)—; and each $Z^4$ independently is selected from —O—, —NR— —S— —C(R$^6$ or a covalent bond.

In some embodiments, and -M- is
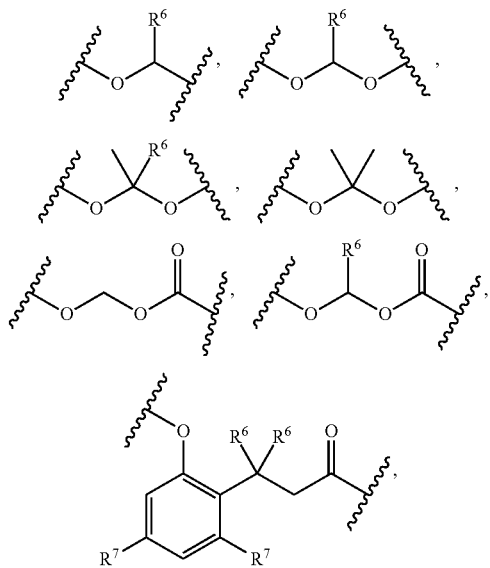
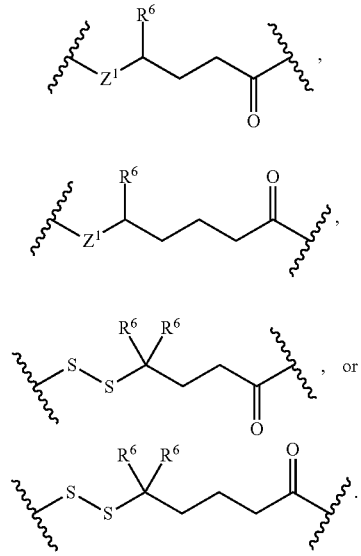
In another aspect, provided herein is a compound of Formula XV:
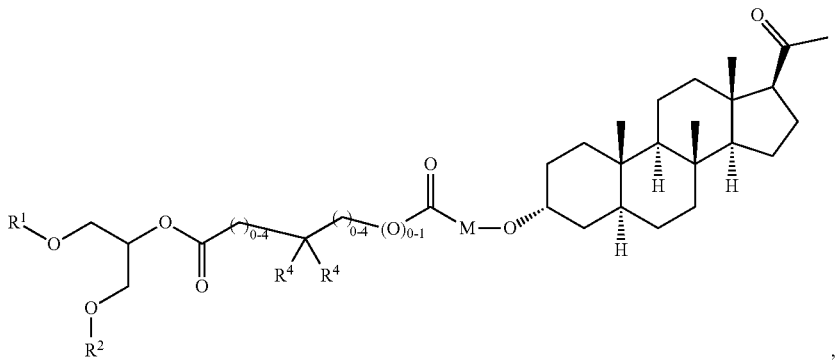
or a pharmaceutically acceptable salt thereof, wherein:
each of $R^1$ and $R^2$ independently is a fatty acid;
each $R^4$ independently is hydrogen, deuterium, halogen, —CN, or a $C_{1-6}$ aliphatic group
optionally substituted with halogen, —CN, —OR, —NR$_2$, or —SR; and
-M- is
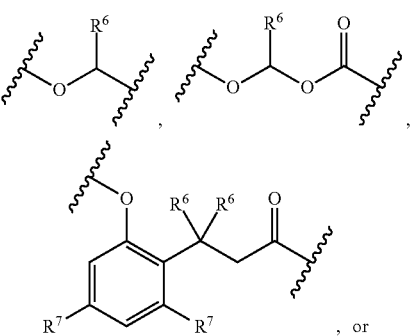
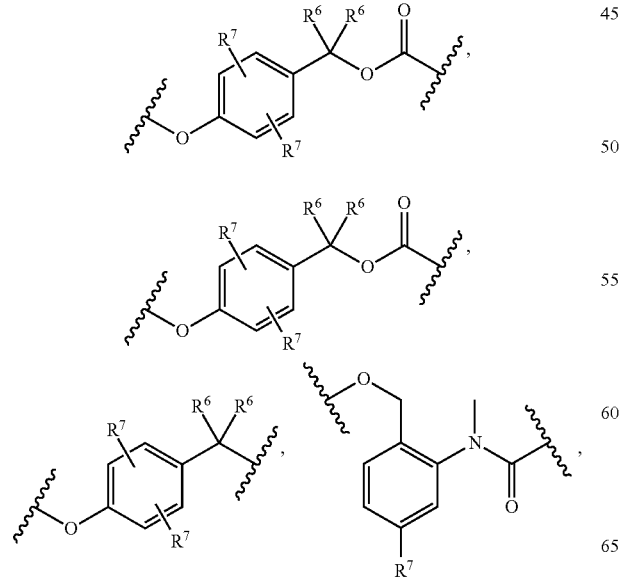

-continued

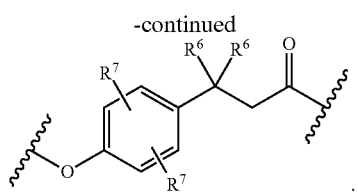

In some embodiments of Formula XV, each of $R^1$ and $R^2$ is heptanoic acid. In some embodiments of Formula XV, each of $R^1$ and $R^2$ is octanoic acid. In some embodiments of Formula XV, each of $R^1$ and $R^2$ is nonanoic acid.

In some embodiments of Formula XV, each $R^4$ is hydrogen. In some embodiments of Formula XV, each $R^4$ is methyl.

In some embodiments of Formula XV, -M- is

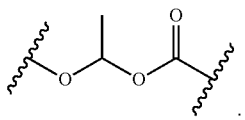 [SMILES: *OC(C)OC(*)=O]

In some embodiments of Formula XV, -M- is

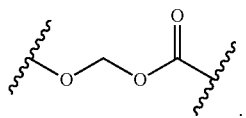 [SMILES: *OCOC(*)=O]

In some embodiments of Formula XV, -M- is

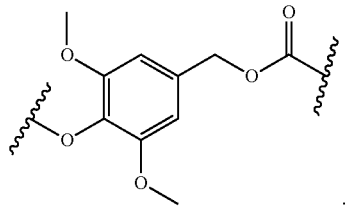 [SMILES: *Oc1c(OC)cc(COC(*)=O)cc1OC]

In one aspect, the present invention provides a lipid prodrug compound shown in Table 1:

TABLE 1

Exemplary Compounds

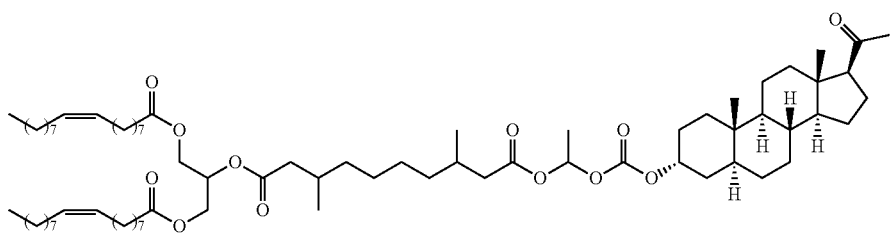

ALL-CMSI-C10b'bMe-2-TG-oleate

I-1

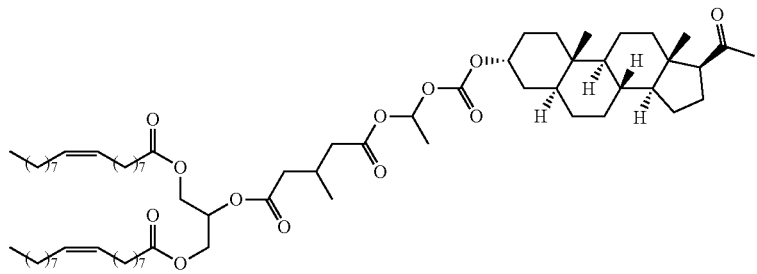

ALL-CMSI-C5bMe-2-TG-oleate

I-2

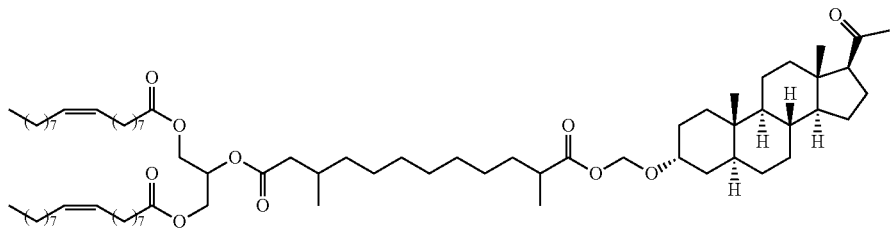

ALL-ASI-C12a'bMe-2-TG-oleate

I-3

TABLE 1-continued
Exemplary Compounds
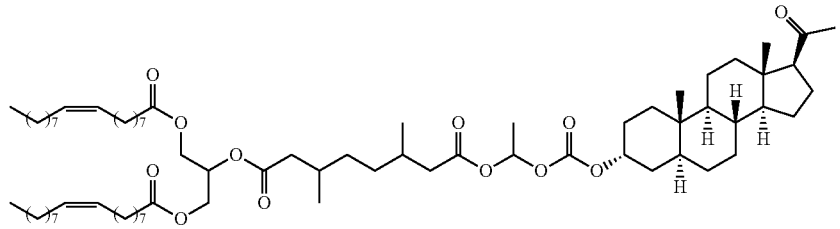
ALL-CMSI-C8b'bMe-2-TG-oleate
I-4
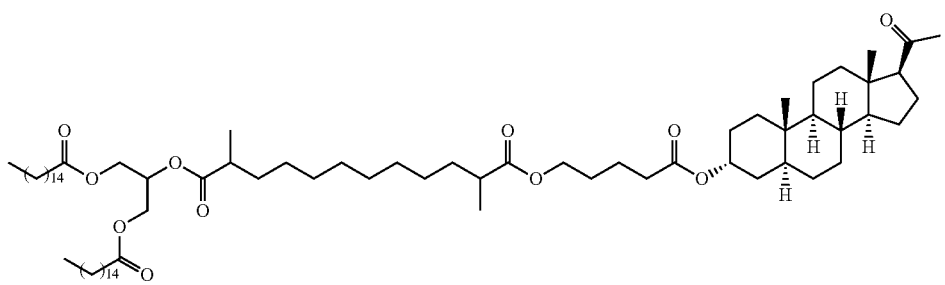
ALL-FSI5-C12a'aMe-2-TG
I-5
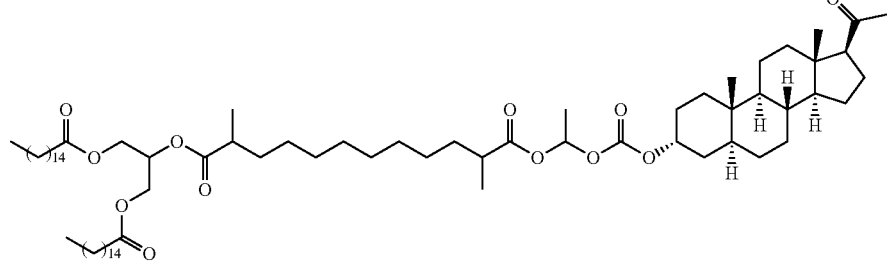
ALL-CMSI-C12a'aMe-2-TG
I-6
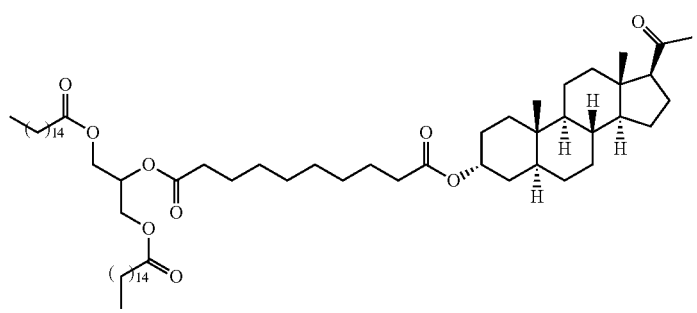
ALL-C10-2-TG
I-7
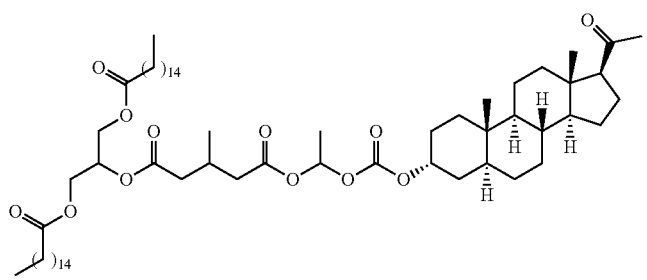
ALL-CMSI-C5bMe-2-TG
I-8

TABLE 1-continued
Exemplary Compounds
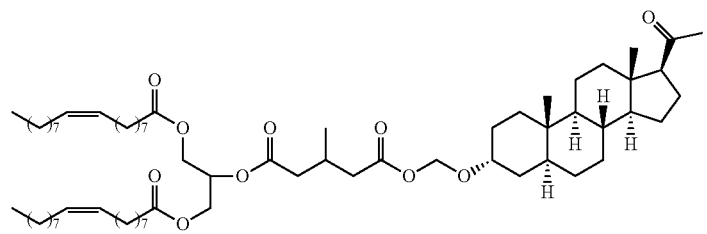
ALL-ASI-C5bMe-2-TG-oleate
I-9
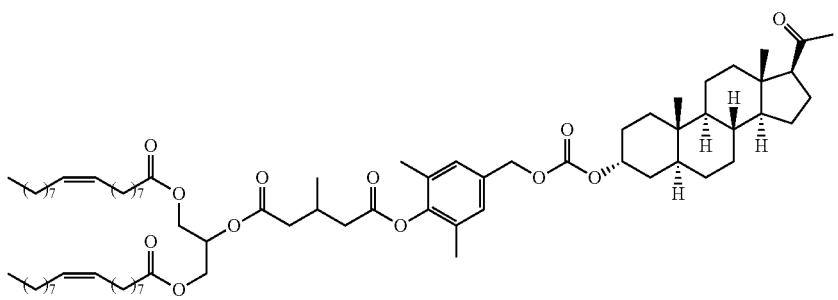
ALL-CDMPHB-C5bMe-2-TG-oleate
I-10
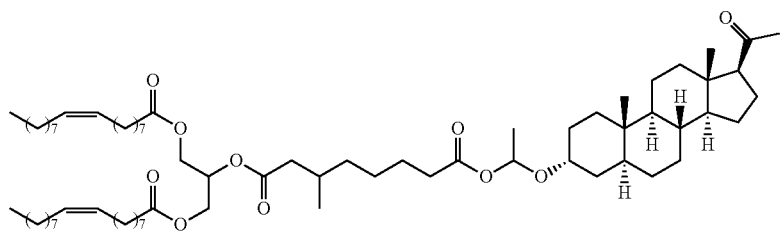
ALL-MASI-C8bMe-2-TG-oleate
I-11
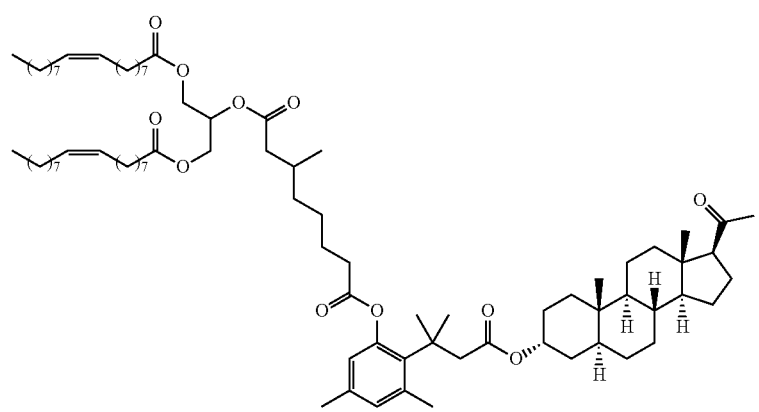
ALL-TML-C8bMe-2-TG oleate
I-12

TABLE 1-continued
Exemplary Compounds
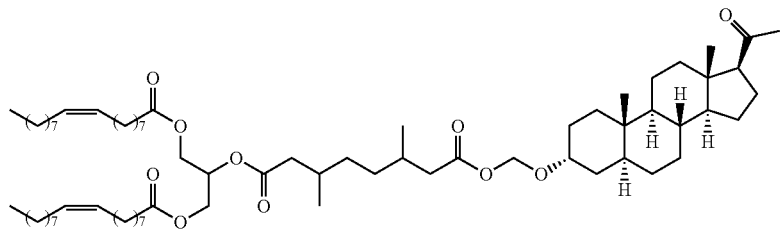
ALL-ASI-C8b'bMe-2-TG-oleate
I-13
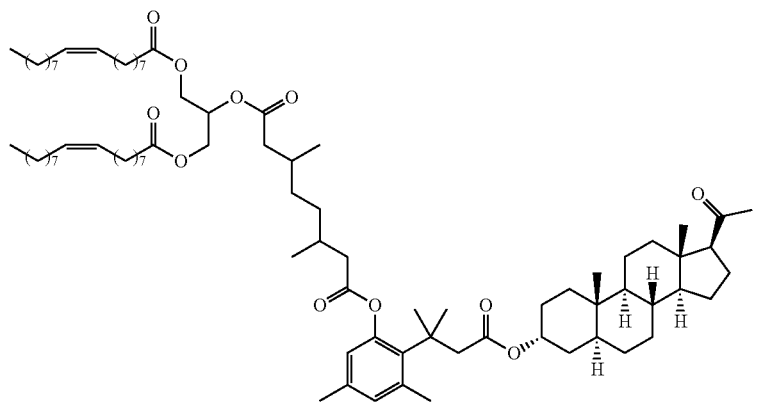
ALL-TML-C8b'bMe-2-TG oleate
I-14
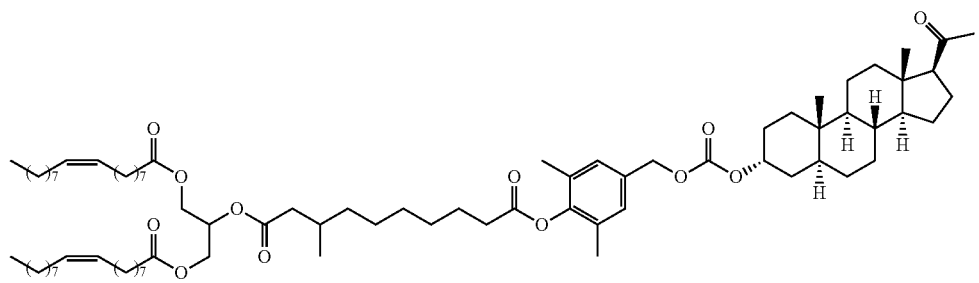
ALL-CDMPHB-C10bMe-2-TG-oleate
I-15
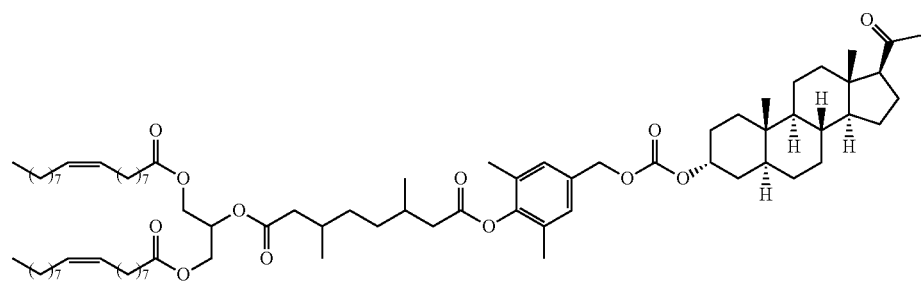
ALL-CDMPHB-C8b'bMe-2-TG-oleate
I-16

TABLE 1-continued
Exemplary Compounds
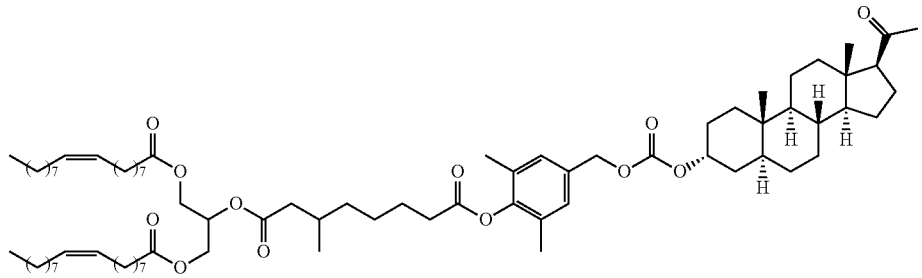
ALL-CDMPHB-C8bMe-2-TG-oleate
I-17
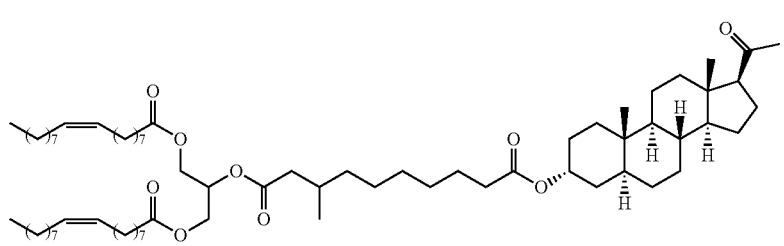
ALL-C10bMe-2-TG-oleate
I-18
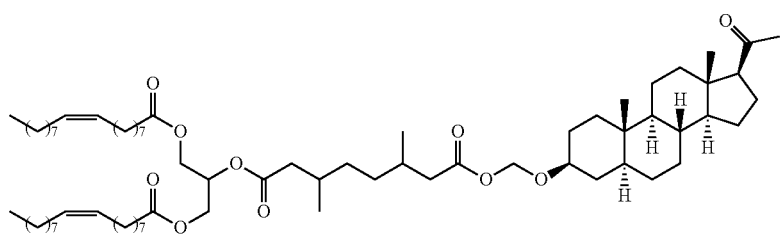
IAL-ASI-C8b'bMe-2-TG-oleate
I-19
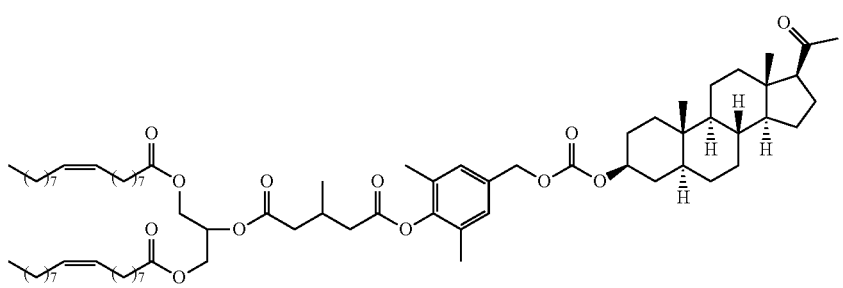
IAL-CDMPHB-C5bMe-2-TG-oleate
I-20
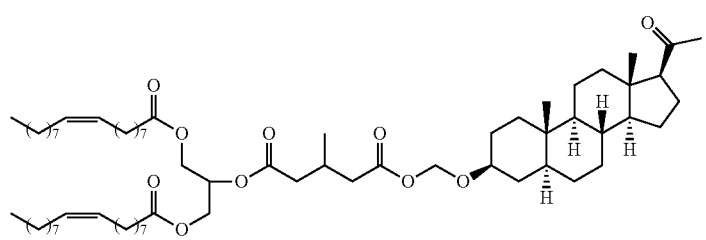
IAL-ASI-C5bMe-2-TG-oleate
I-21

TABLE 1-continued
Exemplary Compounds
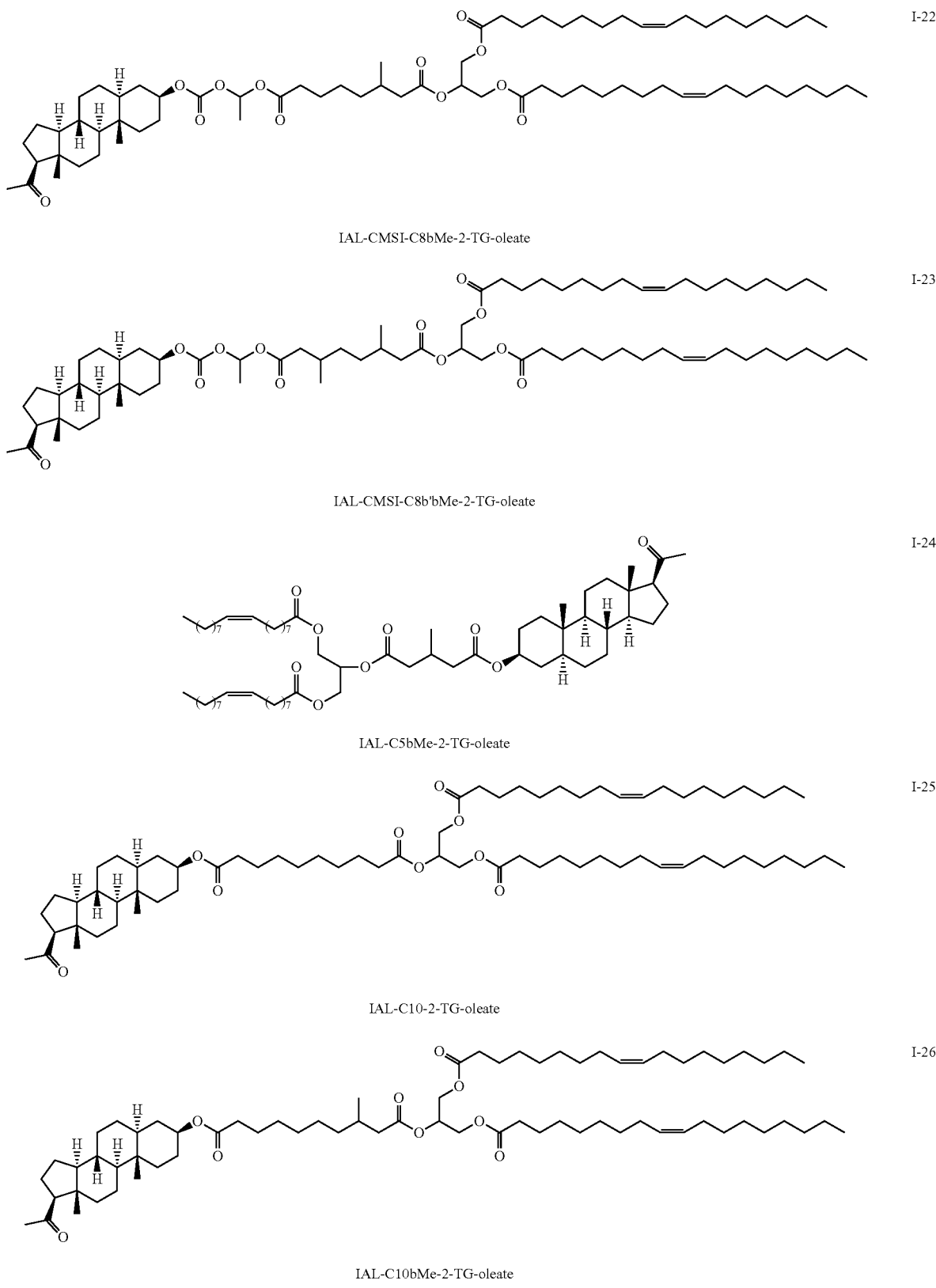
IAL-CMSI-C8bMe-2-TG-oleate  I-22
IAL-CMSI-C8b'bMe-2-TG-oleate  I-23
IAL-C5bMe-2-TG-oleate  I-24
IAL-C10-2-TG-oleate  I-25
IAL-C10bMe-2-TG-oleate  I-26

TABLE 1-continued
Exemplary Compounds
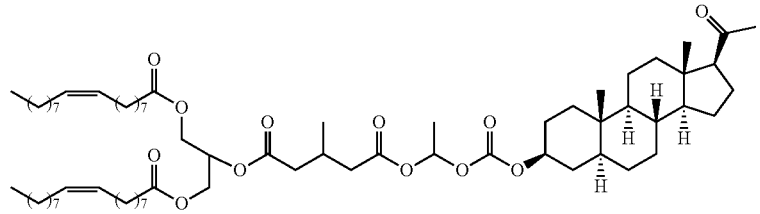
IAL-CMSI-C5bMe-2-TG-oleate
I-27
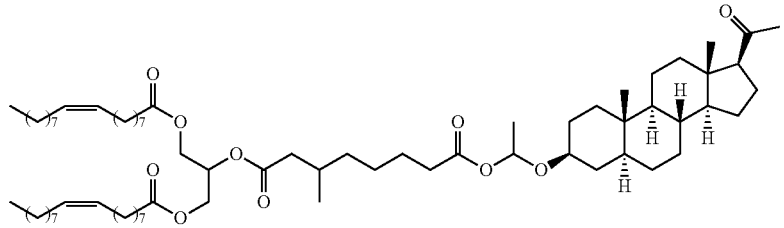
IAL-MASI-C8bMe-2-TG-oleate
I-28
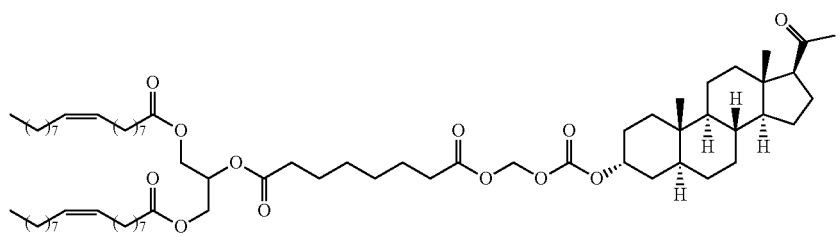
ALL-CASI-C8-2-TG-oleate
I-29
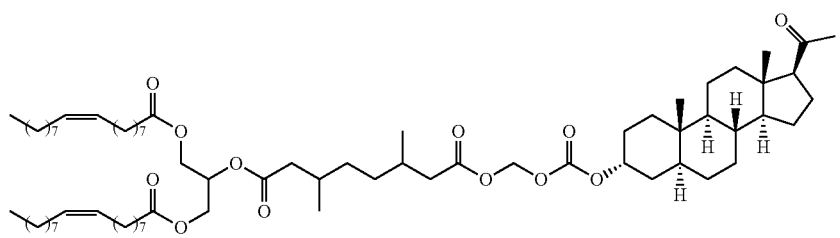
ALL-CASI-C8b'bMe-2-TG-oleate
I-30
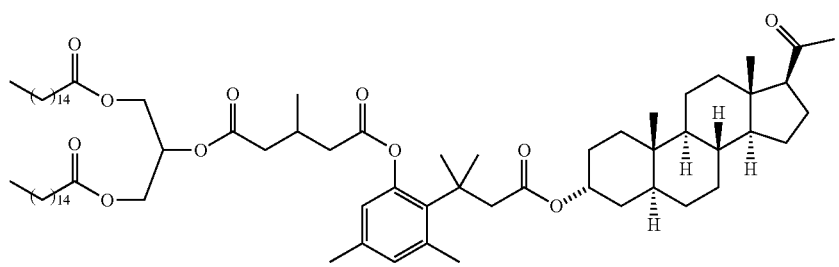
ALL-TML-C5bMe-2-TG
I-31

TABLE 1-continued
Exemplary Compounds
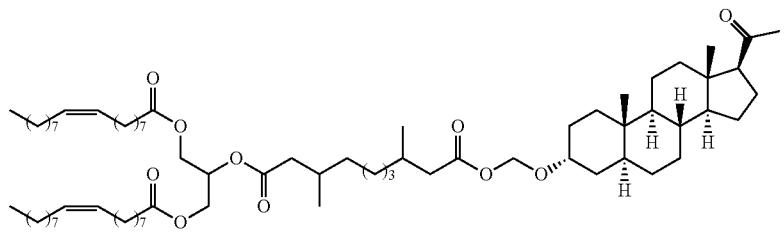
ALL-ASI-C10b'bMe-2-TG-oleate
I-32
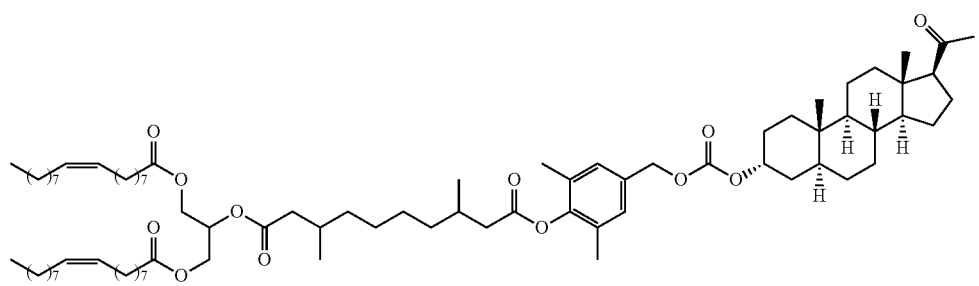
ALL-CDMPHB-C10b'bMe-2-TG-oleate
I-33
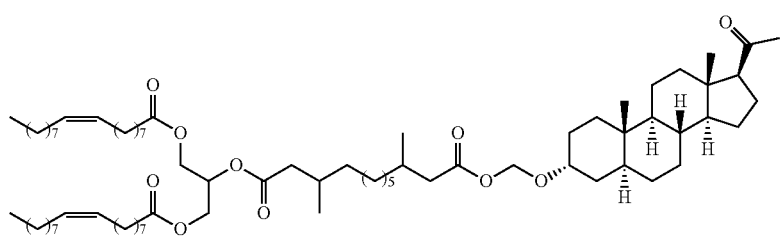
ALL-ASI-C12b'bMe-2-TG-oleate
I-34
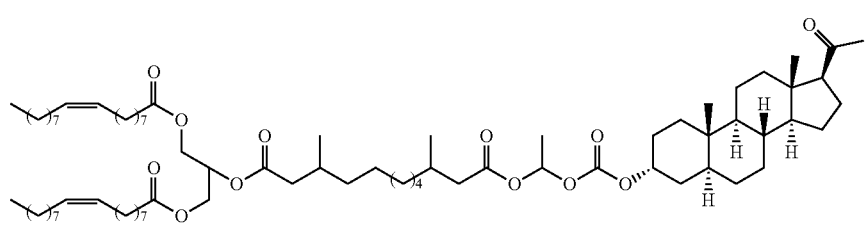
ALL-CMSI-C12b'bMe-2-TG-oleate
I-35
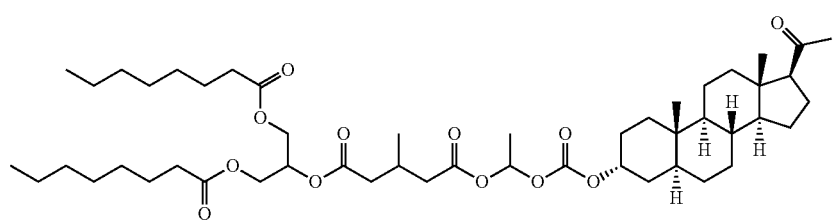
ALL-CMSI-C5bMe-2-TG-octanoate
I-36

TABLE 1-continued
Exemplary Compounds
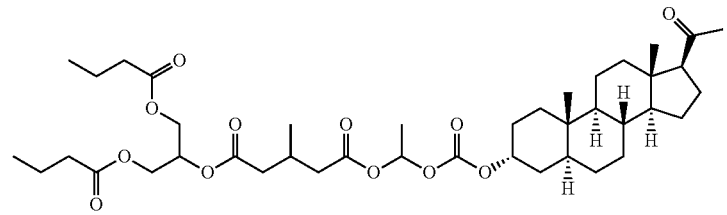
ALL-CMSI-C5bMe-2-TG-butyrate
I-37
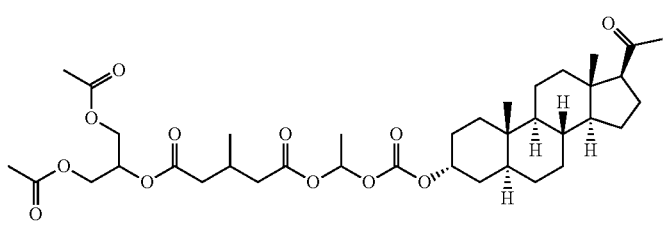
ALL-CMSI-C5bMe-2-TG-acetate
I-38
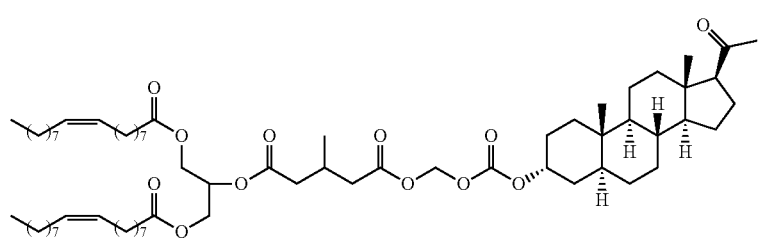
ALL-CASI-C5bMe-2-TG-oleate
I-39
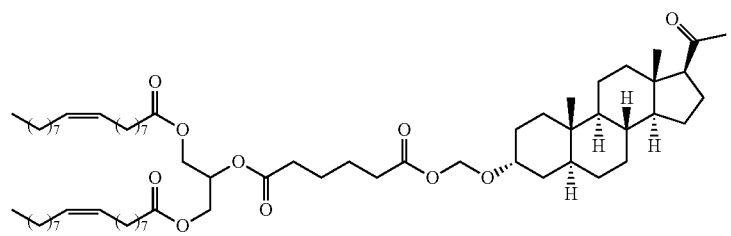
ALL-ASI-C6-2-TG-oleate
I-40
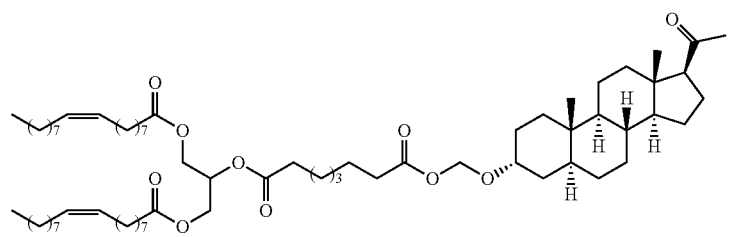
ALL-ASI-C8-2-TG-oleate
I-41

TABLE 1-continued
Exemplary Compounds
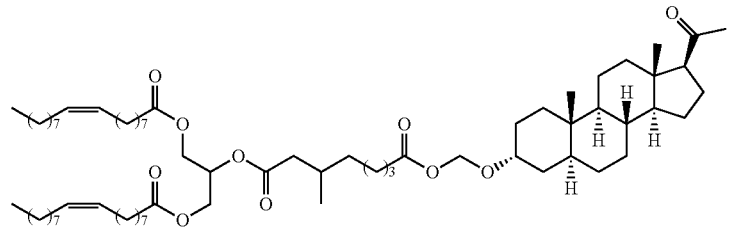
ALL-ASI-C8bMe-2-TG-oleate
I-42
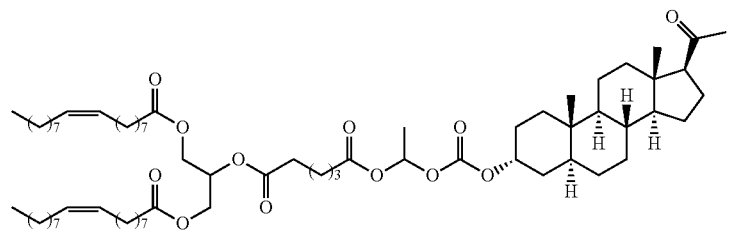
ALL-CMSI-C6-2-TG-oleate
I-43
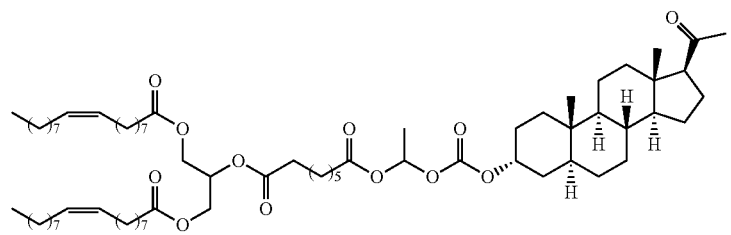
ALL-CMSI-C8-2-TG-oleate
I-44
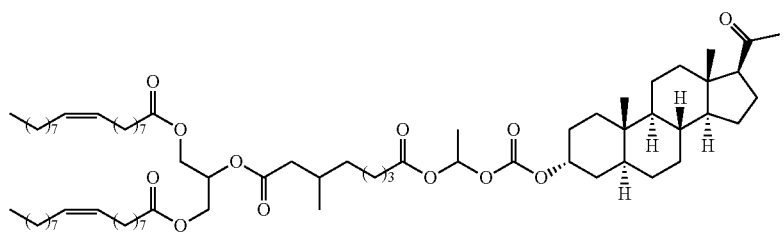
ALL-CMSI-C8bMe-2-TG-oleate
I-45
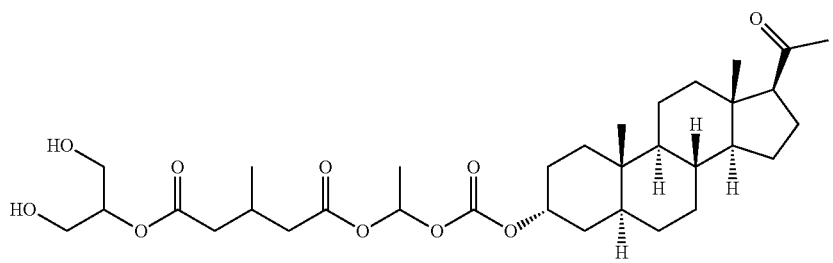
ALL-CMSI-C5bMe-2-MG
I-46

TABLE 1-continued
Exemplary Compounds
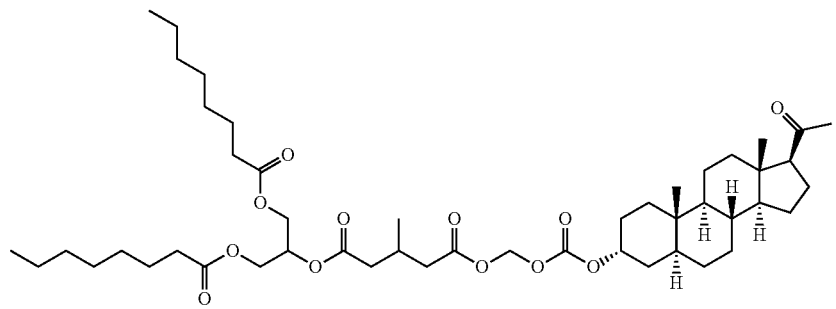
ALL-CASI-C5bMe-octanoate
I-47
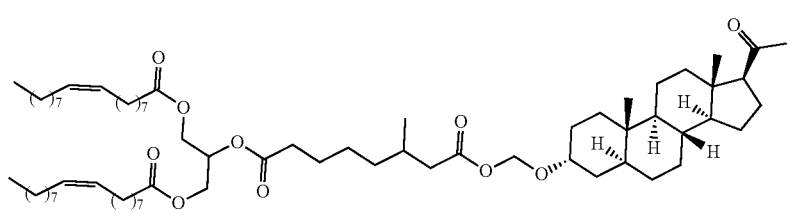
ALL-ASI-C8b'Me-2-TG-oleate
I-48
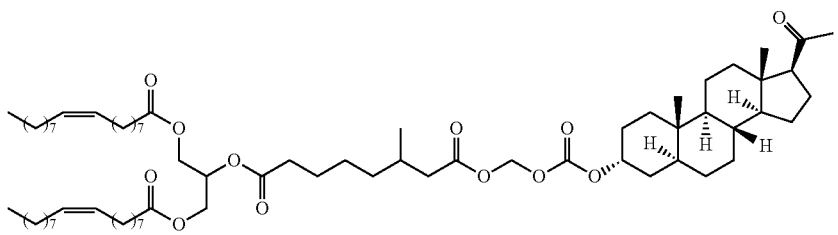
ALL-CASI-C8b'Me-2-TG-oleate
I-49
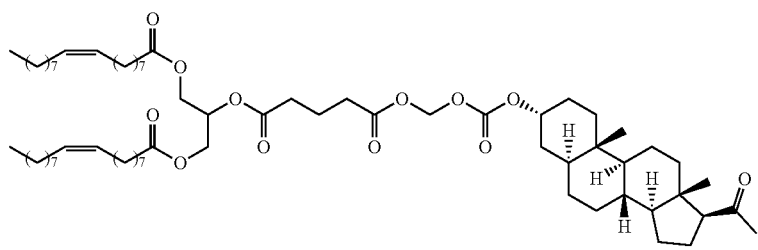
ALL-CASI-C5-2-TG-oleate
I-50
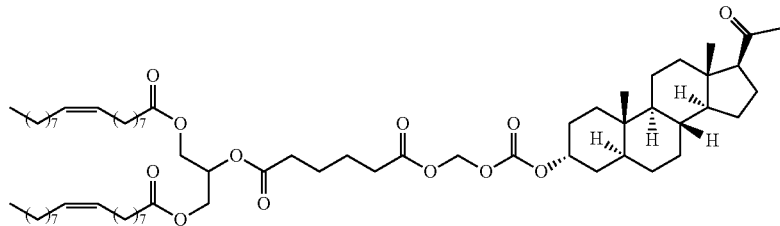
ALL-CASI-C6-2-TG-oleate
I-51

TABLE 1-continued
Exemplary Compounds
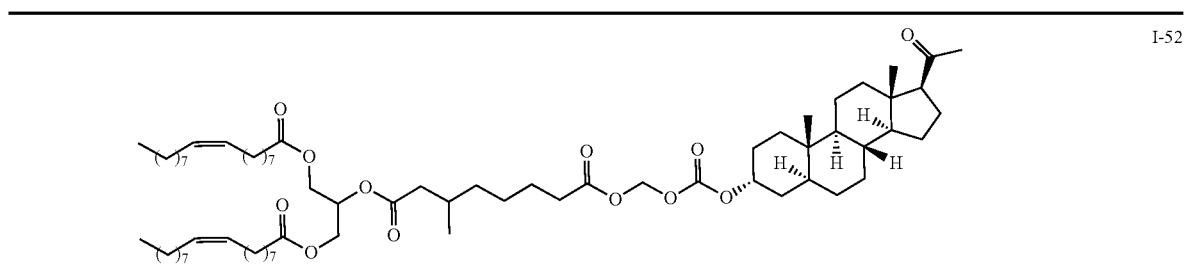
ALL-CASI-C8bMe-2-TG-oleate
I-52
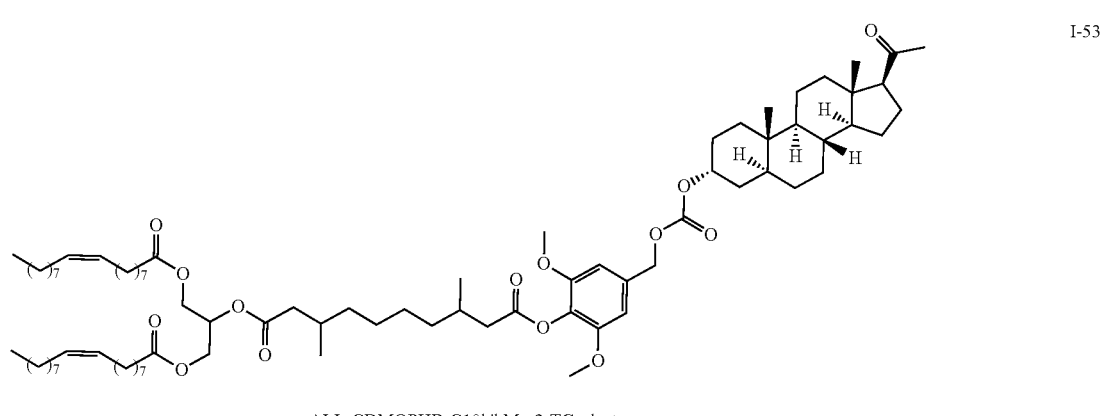
ALL-CDMOPHB-C10b'bMe-2-TG-oleate
I-53
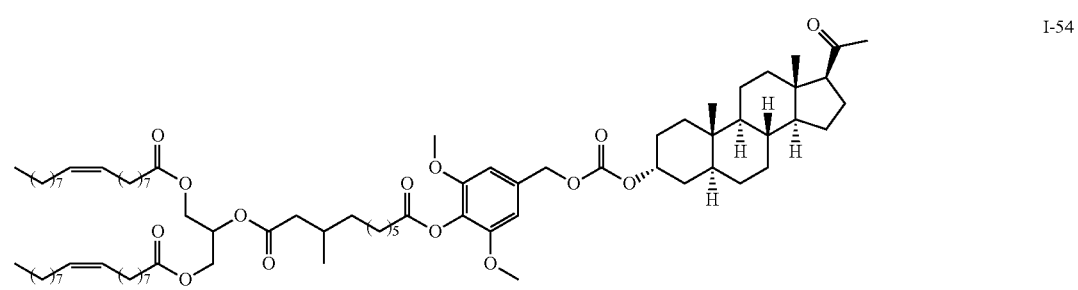
ALL-CDMOPHB-C10bMe-2-TG-oleate
I-54
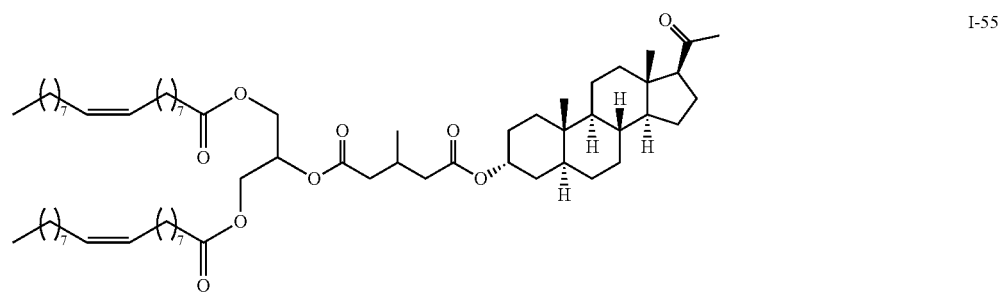
ALL-C5bMe-2-TG-oleate
I-55

TABLE 1-continued
Exemplary Compounds
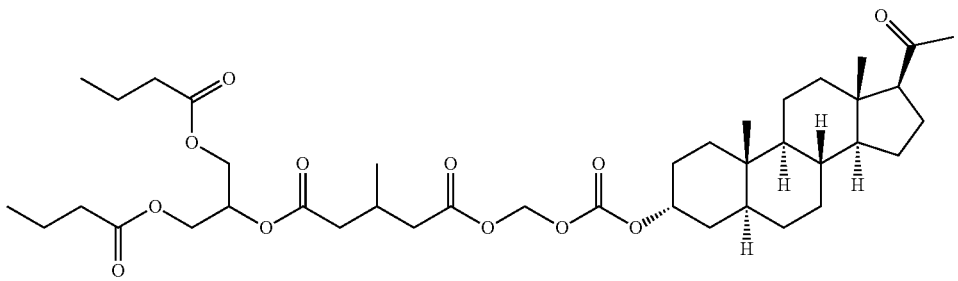
ALL-CASI-C5bMe-2-TG-butyrate
I-56
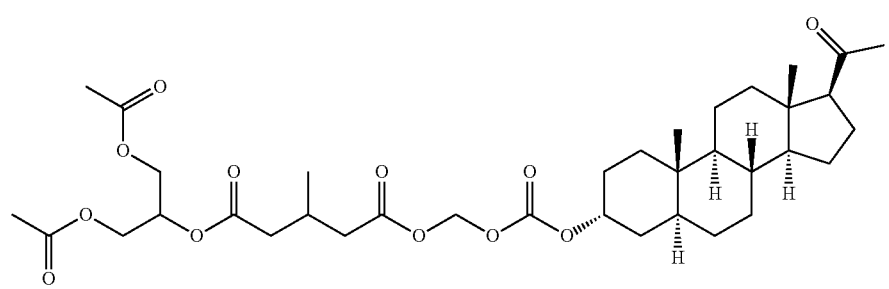
ALL-CASI-C5bMe-2-TG-acetate
I-57
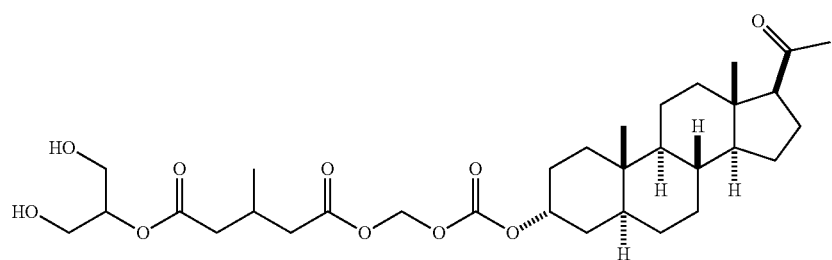
ALL-CASI-C5bMe-2-MG
I-58
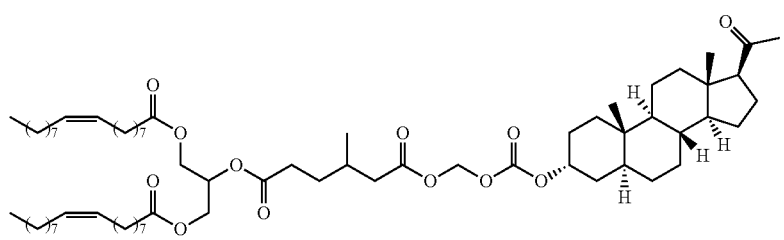
ALL-CASI-C6b'Me-2-TG-oleate
I-59
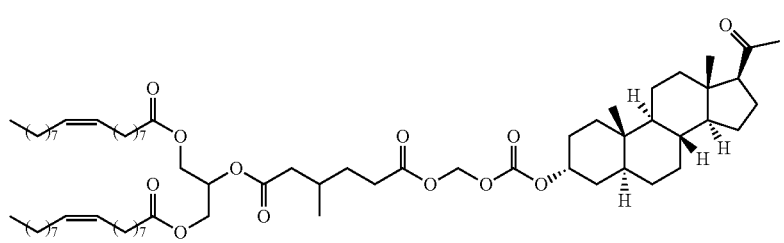
ALL-CASI-C6bMe-2-TG-oleate
I-60

In some embodiments, the present invention provides a compound as depicted in Table 1, above, wherein one or both of the fatty acids depicted above (at the $R^1$ and $R^2$ positions of the Formulae depicted herein) independently are replaced with another fatty acid.

Lipids, Including Fatty Acids, Phospholipids, Lipid-Processing Mimetics, and Mixtures Thereof for Use in Disclosed Lipid Prodrugs Lipid prodrugs according to the present disclosure mimic the lipid-processing that takes place in the human body.

A variety of lipids are suitable for use in lipid prodrugs of the present disclosure. In some embodiments, the lipid prodrug comprises a fatty acid, phosphatide, phospholipid, or analogue thereof (e.g., phosphatidylcholine, lecithin, phosphatidylethanolamine, cephalin, or phosphatidylserine or analogue or portion thereof, such as a partially hydrolyzed portion thereof), or other lipid-processing mimetic (e.g., a group cleaved by lipases, other digestive enzymes, or other mechanisms in the GI tract that enables the lipid prodrug to mimic dietary lipid processing). In some embodiments, the fatty acid is a short-chain, medium-chain, or long-chain fatty acid. In some embodiments, the fatty acid is a saturated fatty acid. In some embodiments, the fatty acid is an unsaturated fatty acid. In some embodiments, the fatty acid is a mono-unsaturated fatty acid. In some embodiments, the fatty acid is a polyunsaturated fatty acid, such as an ω-3 (omega-3) or CO-6 (omega-6) fatty acid. In some embodiments, the lipid, e.g., fatty acid, has a $C_2$-$C_{60}$ chain. In some embodiments, the lipid, e.g., fatty acid, has a $C_2$-$C_{28}$ chain. In some embodiments, the lipid, e.g., fatty acid, has a $C_2$-$C_{40}$ chain. In some embodiments, the lipid, e.g., fatty acid, has a $C_2$-$C_{12}$ or $C_4$-$C_{12}$ chain. In some embodiments, the lipid, e.g., fatty acid, has a $C_4$-$C_{40}$ chain. In some embodiments, the lipid, e.g., fatty acid, has a $C_4$-$C_{40}$, $C_2$-$C_{38}$, $C_2$-$C_{36}$, $C_2$-$C_{34}$, $C_2$-$C_{32}$, $C_2$-$C_{30}$, $C_4$-$C_{30}$, $C_2$-$C_{28}$, $C_4$-$C_{28}$, $C_2$-$C_{26}$, $C_4$-$C_{26}$, $C_2$-$C_{24}$, $C_4$-$C_{24}$, $C_6$-$C_{24}$, $C_5$-$C_{24}$, $C_{10}$-$C_{24}$, $C_2$-$C_{22}$, $C_4$-$C_{22}$, $C_6$-$C_{22}$, $C_5$-$C_{22}$, $C_{10}$-$C_{22}$, $C_2$-$C_{20}$, $C_4$-$C_{20}$, $C_6$-$C_{20}$, $C_5$-$C_{20}$, $C_{10}$-$C_{20}$, $C_2$-$C_{18}$, $C_4$-$C_{18}$, $C_6$-$C_{18}$, $C_8$-$C_{18}$, $C_{10}$-$C_{18}$, $C_{12}$-$C_{18}$, $C_{14}$-$C_{18}$, $C_{16}$-$C_{18}$, $C_2$-$C_{16}$, $C_4$-$C_{16}$, $C_6$-$C_{16}$, $C_8$-$C_{16}$, $C_{10}$-$C_{16}$, $C_{12}$-$C_{16}$, $C_{14}$-$C_{16}$, $C_2$-$C_{15}$, $C_4$-$C_{15}$, $C_6$-$C_{15}$, $C_5$-$C_{15}$, $C_9$-$C_{15}$, $C_{10}$-$C_{15}$, $C_{11}$-$C_{15}$, $C_{12}$-$C_{15}$, $C_{13}$-$C_{15}$, $C_2$-$C_{14}$, $C_4$-$C_{14}$, $C_6$-$C_{14}$, $C_5$-$C_{14}$, $C_9$-$C_{14}$, $C_{10}$-$C_{14}$, $C_{11}$-$C_{14}$, $C_{12}$-$C_{14}$, $C_2$-$C_{13}$, $C_4$-$C_{13}$, $C_6$-$C_{13}$, $C_7$-$C_{13}$, $C_8$-$C_{13}$, $C_9$-$C_{13}$, $C_{10}$-$C_{13}$, $C_{10}$-$C_{13}$, $C_{11}$-$C_{13}$, $C_2$-$C_{12}$, $C_4$-$C_{12}$, $C_6$-$C_{12}$, $C_7$-$C_{12}$, $C_5$-$C_{12}$, $C_9$-$C_{12}$, $C_{10}$-$C_{12}$, $C_2$-$C_{11}$, $C_4$-$C_{11}$, $C_6$-$C_{11}$, $C_7$-$C_{11}$, $C_5$-$C_{11}$, $C_9$-$C_{11}$, $C_2$-$C_{10}$, $C_4$-$C_{10}$, $C_2$-$C_9$, $C_4$-$C_9$, $C_2$-$C_8$, $C_4$-$C_8$, $C_2$-$C_7$, $C_4$-$C_7$, $C_2$-$C_6$, or $C_4$-$C_6$, chain. In some embodiments, the lipid, e.g., fatty acid, has a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, $C_{50}$, $C_{51}$, $C_{52}$, $C_{53}$, $C_{54}$, $C_{55}$, $C_{56}$, $C_{57}$, $C_{58}$, $C_{59}$, or $C_{60}$ chain. In some embodiments, the lipid prodrug comprises two fatty acids, each of which independently is selected from a fatty acid having a chain with any one of the foregoing ranges or numbers of carbon atoms. In some embodiments, one of the fatty acids independently is a fatty acid with a $C_6$-$C_{21}$ chain and one independently is a fatty acid with a $C_{12}$-$C_{36}$ chain. In some embodiments, each fatty acid independently has a chain of 11, 12, 13, 14, 15, 16, or 17 carbon atoms.

In some embodiments, the lipid prodrug comprises two lipids. In some embodiments, the two lipids, e.g., fatty acids, taken together have 6-80 carbon atoms (an equivalent carbon number (ECN) of 6-80). In some embodiments, the lipids, e.g., fatty acids, have an ECN of 6-80, 8-80, 10-80, 12-80, 14-80, 16-80, 18-80, 20-80, 22-80, 24-80, 26-80, 28-80, 30-80, 4-76, 6-76, 8-76, 10-76, 12-76, 14-76, 16-76, 18-76, 20-76, 22-76, 24-76, 26-76, 28-76, 30-76, 6-72, 8-72, 10-72, 12-72, 14-72, 16-72, 18-72, 20-72, 22-72, 24-72, 26-72, 28-72, 30-72, 6-68, 8-68, 10-68, 12-68, 14-68, 16-68, 18-68, 20-68, 22-68, 24-68, 26-68, 28-68, 30-68, 6-64, 8-64, 10-64, 12-64, 14-64, 16-64, 18-64, 20-64, 22-64, 24-64, 26-64, 28-64, 30-64, 6-60, 8-60, 10-60, 12-56, 14-56, 16-56, 18-56, 20-56, 22-56, 24-56, 26-56, 28-56, 30-56, 6-52, 8-52, 10-52, 12-52, 14-52, 16-52, 18-52, 20-52, 22-52, 24-52, 26-52, 28-52, 30-52, 6-48, 8-48, 10-48, 12-48, 14-48, 16-48, 18-48, 20-48, 22-48, 24-48, 26-48, 28-48, 30-48, 6-44, 8-44, 10-44, 12-44, 14-44, 16-44, 18-44, 20-44, 22-44, 24-44, 26-44, 28-44, 30-44, 6-40, 8-40, 10-40, 12-40, 14-40, 16-40, 18-40, 20-40, 22-40, 24-40, 26-40, 28-40, 30-40, 6-36, 8-36, 10-36, 12-36, 14-36, 16-36, 18-36, 20-36, 22-36, 24-36, 26-36, 28-36, 30-36, 6-32, 8-32, 10-32, 12-32, 14-32, 16-32, 18-32, 20-32, 22-32, 24-32, 26-32, 28-32, or 30-32.

Suitable fatty acids include saturated straight-chain fatty acids, saturated branched fatty acids, unsaturated fatty acids, hydroxy fatty acids, and polycarboxylic acids. In some embodiments, such fatty acids have up to 32 carbon atoms.

Examples of useful saturated straight-chain fatty acids include those having an even number of carbon atoms, such as butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, and heptacosanoic acid.

Examples of suitable saturated branched fatty acids include isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyldecanoic acid, α-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.). Suitable saturated odd-carbon branched fatty acids include anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid, and 26-methyloctacosanoic acid.

Examples of suitable unsaturated fatty acids include 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12,15-octadecatetraenoic acid, parinaric acid, 5,8,11,14-eicosatetraenoic acid, 5,8,11,14,17-eicosapentaenoic acid, 7,10,13,16,19-docosapentaenoic acid, 4,7,10,13,16,19-docosahexaenoic acid, and the like.

Examples of suitable hydroxy fatty acids include α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10, 12-octadecadienic acid, kamolenic acid, ipurolic acid, 9,10-dihydroxystearic acid, 12-hydroxystearic acid and the like.

Examples of suitable polycarboxylic acids include oxalic acid, malonic acid, succinic acid, glutaric acid, adipic acid, pimelic acid, suberic acid, azelaic acid, sebacic acid, D,L-malic acid, and the like.

In some embodiments, each fatty acid independently is selected from Propionic acid, Butyric acid, Valeric acid, Caproic acid, Enanthic acid, Caprylic acid, Pelargonic acid, Capric acid, Undecylic acid, Laurie acid, Tridecylic acid, Myristic acid, Pentadecylic acid, Palmitic acid, Margaric acid, Stearic acid, Nonadecylic acid, arachidic acid, Heneicosylic acid, Behenic acid, Tricosylic acid, Lignoceric acid, Pentacosylic acid, Cerotic acid, Heptacosylic acid, Montanic acid, Nonacosylic acid, Melissic acid, Henatriacontylic acid, Lacceroic acid, Psyllic acid, geddic acid, ceroplastic acid, hexatriacontylic acid, heptatriacontanoic acid, or octatriacontanoic acid.

In some embodiments, each fatty acid independently is selected from α-linolenic acid, stearidonic acid, eicosapentaenoic acid, docosahexaenoic acid, linoleic acid, gamma-linoleic acid, dihomo-gamma-linoleic acid, arachidonic acid, docosatetraenoic acid, palmitoleic acid, vaccenic acid, paullinic acid, oleic acid, elaidic acid, gondoic acid, erucic acid, nervonic acid, mead acid, adrenic acid, bosseopentaenoic acid, ozubondo acid, sardine acid, herring acid, docosahexaenoic acid, or tetracosanolpentaenoic acid, or another monounsaturated or polyunsaturated fatty acid.

In some embodiments, one or both of the fatty acids is an essential fatty acid. In view of the beneficial health effects of certain essential fatty acids, the therapeutic benefits of disclosed lipid prodrugs may be increased by including such fatty acids in the lipid prodrug. In some embodiments, the essential fatty acid is an n-6 or n-3 essential fatty acid selected from the group consisting of linolenic acid, gamma-linolenic acid, dihomo-gamma-linolenic acid, arachidonic acid, adrenic acid, docosapentaenoic n-6 acid, alpha-linolenic acid, stearidonic acid, the 20:4n-3 acid, eicosapentaenoic acid, docosapentaenoic n-3 acid, or docosahexaenoic acid.

In some embodiments, each fatty acid independently is selected from all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid, or lipoic acid. In other embodiments, the fatty acid is selected from eicosapentaenoic acid, docosahexaenoic acid, or lipoic acid. Other examples of fatty acids include all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15, 18,21-docosahexaenoic acid), or tetracosahexaenoic acid (nisinic acid or all-cis-6,9,12,15,18,21-tetracosenoic acid). In some embodiments, the fatty acid is a medium-chain fatty acid such as lipoic acid.

Fatty acid chains differ greatly in the length of their chains and may be categorized according to chain length, e.g., as short to very long.

Short-chain fatty acids (SCFA) are fatty acids having about five or less carbons (e.g., butyric acid). In some embodiments, each of the fatty acids independently is a SCFA. In some embodiments, one of the fatty acids independently is a SCFA.

Medium-chain fatty acids (MCFA) include fatty acids having about 6-12 carbons, which can form medium-chain triglycerides. In some embodiments, each of the fatty acids independently is a MCFA. In some embodiments, one of the fatty acids independently is a MCFA.

Long-chain fatty acids (LCFA) include fatty acids having about 13-21 carbons. In some embodiments, each of the fatty acids independently is a LCFA. In some embodiments, one of the fatty acids independently is a LCFA.

Very long chain fatty acids (VLCFA) include fatty acids having about 22 or more carbons, such as 22-60, 22-50, or 22-40 carbons. In some embodiments, each of the fatty acids independently is a VLCFA. In some embodiments, one of the fatty acids independently is a VLCFA.

In some embodiments, one of the fatty acids independently is a MCFA and one independently is a LCFA.

Therapeutic Agents and Exemplary Associated Diseases

In accordance with the present invention, a variety of therapeutic agents may be covalently conjugated to the lymphatic system-directing lipids, e.g., triglyceride scaffolds, described herein. In some embodiments, by conjugating a therapeutic agent to a lymphatic system-directing lipid, the present invention provides enhanced desirable properties of the therapeutic agent such as improving oral bioavailability, minimizing destruction of the agent in the gut, avoiding liver first-pass effect, improving therapeutic agent delivery to a target tissue, or increasing the solubility and stability of the therapeutic agents, including the solubility and stability of the agents in vivo.

As described herein, the present invention provides a compound of formula I, wherein the therapeutic agent is a pregnane neurosteroid or an analogue or prodrug thereof.

In general, neurotransmitters regulate the conductance of ions across neuronal membranes. Gamma aminobutyric acid (GABA) exerts a profound effect on overall neuron excitability by regulating the conductance of chloride ions via the GABA receptor-chloride ionophore complex (GR). As intracellular chloride levels increase, neurons become hyperpolarized and less susceptible to excitatory inputs. It is well-known that through this mechanism, GR complex mediates anxiety, seizure activity, and sedation.

Certain endogenous steroids, such as the A-ring reduced metabolites of progesterone, act as selective allosteric modulators of the GR complex without classical steroid hormone activity. In particular, pregnane neurosteroids, such as allopregnanolone (3α-hydroxy-5α-pregnane-20-one) and allotetrahydrodeoxycorticosterone (5α,3α-THDOC), act as potent positive allosteric modulators of GR and produce anxiolytic (Bitran, D. et al. J. Neuroendocrinol 7(3): 171-7 (1995)), anti-conflict (Perche, F. et al. Aggress Behav 27(2): 130-8 (2001)), antiseizure (Frye, C. A. Brain Res. 643 (1-2): 194-203 (1995)), and antinociceptive (Wiebe, J. P. & Kavaliers, M. Brain Res. 461(1): 150-7 (1988)) as well as neuroprotective effects. Further, the antidepressant effect of allopregnane is well-established in animal models (e.g., Frye, C. A. & Walf, A. A. Horm Behav 41(3): 306-15 (2002)) and low levels of allopregnanolone are associated with various depressive-mood disorders (e.g., Anréen, L. et al. Psychoneuroendocrinology 34(8): 1121-32 (2009)).

Additionally, pregnane neurosteroid treatment has been shown to have positive effects in various neurological conditions (e.g., Alzheimer's disease, Parkinson's disease, multiple sclerosis, Niemann-Pick Type C, fragile X-associate tremor/ataxia syndrome (FXTAS), diabetic neuropathy, status epilepticus (including benzodiazepine resistant), and traumatic brain injury (Irwin, R. W. et al. Front. Cell. Neurosci. 8:203. doi: 10.3389/fncel.2014.00203).

Still, neurosteroids are susceptible to metabolism and have poor bioavailability (Rupprecht, R. Psychoneuroendocrinology, 28(2): 139-68 (2003)). Consequently, there exists a need for neurosteroid (e.g., allopreganolone) prodrugs that have improved bioavailability and circumvent first pass metabolism by the liver.

In some embodiments, a disclosed lipid prodrug comprises a therapeutic agent selected from neuroactive steroids, such as allopregnanolone, pregnanolone, pregnenolone, 30-dihydroprogesterone, isopregnanolone, epipregnanolone, and 21-hydroxyallopregnanolone, or others disclosed herein. In some embodiments, the neuroactive steroid is selected from allopregnanolone or 21-hydroxyallopregnanolone.

The compounds disclosed herein can be used to treat a variety of diseases, or one or more symptom(s) thereof, including, for example, post-partum depression (Osborne, L. M. et al. Psychoneuroendocrinology 79: 116-21 (2017)), depression (Almeida, F. B. et al. *Neurobiology of Stress* 12 (2020) 100218; Melón, L. et al. *Front. Endocrinol.* 9:703. (2018); Almeida, F. B. et al. *Physiology & Behavior* 194 (2018) 246-251), anxiety (Schüle, C. et al. Prog. Neurobiol. 113: 79-87 (2014)), Niemann-Pick disease or associated neurological and physical symptoms (Griffin, L. D. et al. Nat. Med. 10(7): 704-11 (2004)), Status Epilecticus (Rogawski, M. A. et al. *Epilepsia* 54(s6): 93-8 (2013)); Alzheimer's disease, Parkinson's disease, multiple sclerosis, Niemann-Pick Type C, fragile X-associate tremor/ataxia syndrome, diabetic neuropathy, seizures (Kaminski, R. M. et al. *Epilepsia*, 45(7):864-867, (2004)), or traumatic brain injury (Irwin, R. W. et al. Front. Cell. Neurosci. 8:203. doi: 10.3389/fncel.2014.00203; Irwin, R. W. & Brinton, R. D. Prog. Neuobiol 113: 40-55 (2014)). In some embodiments, provided herein are methods for treating a neurological disease or condition, e.g., post-partum depression, depression, anxiety, Niemann-Pick disease, Status Epilecticus, Alzheimer's disease, Parkinson's disease, multiple sclerosis, Niemann-Pick Type C, fragile X-associate tremor/ataxia syndrome, diabetic neuropathy, seizures, or traumatic brain injury, comprising administering to a subject in need thereof a compound of the present invention.

In other embodiments, the present invention provides a method of treating or preventing a disease, disorder, or condition in which an increased level of a pregnane neurosteroid, such as allopregnanolone, is beneficial, or a disease, disorder, or condition caused by a deficiency in a pregnane neurosteroid, such as an allopregnanolone deficiency, comprising administering to a subject in need thereof an effective amount of a disclosed lipid prodrug.

In some embodiments, the present invention provides a method of treating a $GABA_A$-related disease, disorder, or condition, comprising administering to a subject in need thereof an effective amount of a disclosed lipid prodrug.

In some embodiments, the present invention provides a method of treating a disease, disorder, or condition caused by deficient activation of $GABA_A$, comprising administering to a subject in need thereof an effective amount of a disclosed lipid prodrug.

In some embodiments, the disease, disorder, or condition is selected from post-partum depression, depression, major depressive disorder, bipolar disorder, a mood disorder, anxiety, post-traumatic stress disorder (PTSD), premenstrual dysphoric disorder (PMDD), premenstrual syndrome, generalized anxiety disorder, seasonal affective disorder (SAD), social anxiety, memory loss, poor stress tolerance, Niemann-Pick disease type C or an associated neurological or physical symptom, epilepsy, essential tremor, epileptiform disorders, NMDA hypofunction, migraines, status epilepticus, a sleep disorder such as insomnia, Fragile X Syndrome, depression induced by another medication (such as finasteride or another 5 alpha reductase inhibitor), PCDH19 female pediatric epilepsy, sexual dysfunction, Parkinson's disease, or Alzheimer's disease. In some embodiments, the status epilepticus is super-refractory status epilepticus (SRSE), a severe form of uncontrolled seizures. In some embodiments, the disease, disorder, or condition is depression induced by another medication (such as finasteride or another 5 alpha reductase inhibitor). In some embodiments, the depression induced by another medication is postfinasteride syndrome.

In some embodiments, the disease, disorder, or condition is selected from post-partum depression, depression, major depressive disorder, bipolar disorder, Niemann-Pick disease type C, epilepsy, essential tremor, epileptiform disorders, NMDA hypofunction, status epilepticus, Parkinson's disease, or Alzheimer's disease. In some embodiments, the status epilepticus is super-refractory status epilepticus (SRSE), a severe form of uncontrolled seizures.

In some embodiments, the present invention provides a method of treating a depressive mood disorder (e.g., major depressive disorder, bipolar disorder, seasonal affective disorder (SAD), cyclothymic disorder, premenstrual dysphoric disorder, persistent depressive disorder, disruptive mood dysregulation disorder, depression related to medical illness, postpartum depression) and/or anxiety disorder (e.g., panic disorder and post-traumatic stress disorder) comprising administering to a subject in need thereof a disclosed lipid prodrug.

In some embodiments, the present invention provides a method of treating multiple sclerosis, traumatic brain injury, ischemia, stroke, peripheral neuropathy, neuropathic pain, spinal cord trauma, or a non-REM sleep disorder associated with Alzheimer's Disease (AD) or Parkinson's Disease (PD), comprising administering to a subject in need thereof a disclosed lipid prodrug. See, e.g., Biol Psychiatry. 2010 Nov. 15; 68(10): 956-963, which is hereby incorporated by reference in its entirety.

In some embodiments, the present invention provides a method of reducing neuroinflammation in a subject, comprising administering to a subject in need thereof a disclosed lipid prodrug. In some embodiments, the subject has AD or PD. See, e.g., Canelif Yilmaz, et al., Frontiers in Neuroendocrinology, https://doi.org/10.1016/j.yfrne.2019.100788, which is hereby incorporated by reference in its entirety.

Allopregnanolone (ALLO; Brexanolone; SAGE-547) is currently being investigated as treatment for postpartum depression (NCT2614547; Kanes, S. et al. Lancet 390 (10093): 480-9 (2017)).

In some embodiments, the present invention provides a method of treating Fragile X syndrome or Fragile X-associated syndrome in a subject, comprising administering to a subject in need thereof a disclosed lipid prodrug. In some embodiments, the present invention provides a method of treating Fragile X syndrome in a subject, comprising administering to a subject in need thereof a disclosed lipid prodrug. In some embodiments, the present invention provides a method of treating Fragile X-associated syndrome in a subject, comprising administering to a subject in need thereof a disclosed lipid prodrug. In some embodiments, the present invention provides a method of treating Fragile X-associated tremor/ataxia syndrome in a subject, comprising administering to a subject in need thereof a disclosed lipid prodrug.

In some embodiments, the present invention provides a method of treating epilepsy and related epileptic disorders in a subject, comprising administering to a subject in need thereof a disclosed lipid prodrug. In some embodiments, the epileptic disorder is acute repetitive seizures. In some embodiments, the epileptic disorder is treatment refeactive seizures. In some embodiments, the epileptic disorder is status epilepticus. In some embodiments, the epileptic disorder is a convulsive state including, but not limited to, status epilepticus, epileptic seizures or spasms. Specific types of epileptic seizures include, but are not limited to, tonic-clonic (Grand Mal) seizure, partial (Focal) seizure, catamenial seizure, acute repetitive seizure, psychomotor (complex partial) seizure, absence (Petit Mal) seizure, and myoclonic seizure.

In some embodiments, the present invention provides a method of treating a demyelinating disease in a subject, comprising administering to a subject in need thereof a disclosed lipid prodrug. In some embodiments, the demyelinating disease is selected from multiple sclerosis, neuromyelitis optica, optic neuritis, transverse myelitis, acute disseminated encephalomyelitis, adrenoleukodystrophy and adrenomyeloneuropathy, Guillain-Barre syndrome, anti-myelin associated glycoprotein peripheral neuropathy, Charcot-Marie-Tooth disease, progressive inflammatory neuropathy, chronic inflammatory demyelinating polyneuropathy, and amyotrophic lateral sclerosis (ALS). In some embodiments, the demyelinating disease is multiple sclerosis. In some embodiments, the multiple sclerosis is relapsing remitting multiple sclerosis (RRMS) or primary progressive multiple sclerosis.

In some embodiments, the present invention provides a method of treating a lysosomal storage disorder in a subject, comprising administering to a subject in need thereof a disclosed lipid prodrug. In some embodiments, the lysosomal storage disorder is selected from Farber disease, Krabbe disease, Fabry disease, Schindler disease, GM1 gangliosidosis, GM2 gangliosidosis, Tay-Sachs disease, Sandhoff disease, Gaucher disease, lysosomal acid lipase deficiency, Niemann-Pick disease, sulfatidosis, metachromatic leukodystrophy, Hurler syndrome, Scheie syndrome, Hurler-Scheie syndrome, Hunter syndrome, Sanfilippo syndrome, Morquio syndrome, Maroteaux-Lamy syndrome, Sly syndrome, hyaluronidase deficiency, sialidosis, I-cell disease, phosphotransferase deficiency, mucolipidin 1 deficiency, neuronal ceroid lipofuscinoses, Wolman disease, alpha-mannosidosis, beta-mannosidosis, aspartylglucosaminuria, fucosidosis, cystinosis, pycnodysostosis, Salla disease, infantile free sialic acid storage disease, Pompe disease, Danon disease, cholesteryl ester storage disease, and lysosomal disease.

In some embodiments, the present invention provides a method of treating a nervous system disorder in a subject, comprising administering to a subject in need thereof a disclosed lipid prodrug. In some embodiments, the nervous system disorder is Angelman syndrome, Rett syndrome, Dravet syndrome, Lennox-Gastaut syndrome, or catamenial epilepsy. In some embodiments, the nervous system disorder is Angelman syndrome, Rett syndrome, or Dravet syndrome.

In some embodiments, the nervous system disorder is Lennox-Gastaut syndrome or catamenial epilepsy.

In some embodiments, the present invention provides a method of treating a sleep disorder in a subject, comprising administering to a subject in need thereof a disclosed lipid prodrug. In some embodiments, the sleep disorder is secondary to rheumatoid arthritis. In some embodiments, the sleep disorder is obstructive sleep apnea, insomnia, or restless legs syndrome.

In some embodiments, the present invention provides a method of treating hepatic encephalopathy in a subject, comprising administering to a subject in need thereof a disclosed lipid prodrug.

In some embodiments, the present invention provides a method of treating chronic pain in a subject, comprising administering to a subject in need thereof a disclosed lipid prodrug.

In some embodiments, the therapeutic agent is ganaxolone or allopregnanolone.

2. Definitions

While the terms used herein are believed to be well understood by one of ordinary skill in the art, definitions are set forth herein to facilitate explanation of the presently-disclosed subject matter.

As used herein, the term "about," when referring to a numerical value or range of a parameter such as mass, weight, volume, time, concentration, biological activity, c Log P, or percentage, is meant to encompass variations of, e.g., ±20%, in some embodiments ±10%, in some embodiments ±5%, in some embodiments ±1%, in some embodiments ±0.5%, and in some embodiments ±0.1% from the specified value or range.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "lipid," as used herein, refers to natural and non-natural hydrophobic and/or lipophilic fats, oils, polymers, hydrocarbons, and other such materials. In some embodiments, suitable lipids, when incorporated into a lipid prodrug, are processed or metabolized similarly to triglycerides in the GI tract or mimic such processing or metabolism. The term "glyceride" refers to an ester of glycerol (1,2,3-propanetriol) with acyl radicals of fatty acids or other lipids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. The carbons of the glycerol backbone are designated sn-1, sn-2 and sn-3, with sn-2 being in the middle and sn-1 and sn-3 being the ends of the glycerol.

Naturally occurring oils and fats consist largely of triglycerides wherein the 3 fatty acyl residues may or may not be identical. The term "long chain triglycerides" (or "LCT") means both a simple and mixed triglyceride containing fatty acids with more than 12 carbon atoms (long chain fatty acids, "LCFA"), whereas the term "medium chain triglycerides" (or "MCT") means both a simple and mixed triglyceride containing fatty acids with 4 to 12 carbon atoms.

The term "ECN" or "equivalent carbon number" means the sum of the number of carbon atoms in the acyl chains of a glyceride molecule. For example, tripalmitin (tripalmitic glycerol), which is a simple triglyceride containing 3 acyl radicals of 16 carbon atoms, has an ECN of 3×16=48. Conversely, a triglyceride with an ECN=40 may have "mixed" acyl chain lengths of 8, 16 and 16; 10, 14 and 16; 8, 14 and 18, etc. Naturally occurring oils are frequently "mixed" with respect to specific fatty acids, but tend not to contain LCFAs and MCFAs on the same glycerol backbone. Thus, triacylglycerols with ECNs of 24-30 typically contain predominately medium chain fatty acids, while triacylglycerols with ECNs of greater than 43 typically contain predominantly long chain fatty acids. Triacylglycerols having an ECNs of 32-42 typically contain one or two MCFA in combination with one or two LCFAs to "fill" the triglyceride. Triacylglycerols with ECNs in the range of greater than 30 to less than 48 typically represent mixed triacylglycerol species that are absent from or are present in significantly lower concentrations in physical mixtures. The fatty acids that occur in foods usually contain an even number of carbon atoms in an unbranched chain, e.g., lauric or dodecanoic acid.

The term "self-immolative group," as used herein, refers to a bivalent chemical moiety that comprises a covalent, scissile bond as one of its bivalent bonds and a stable, covalent bond with a therapeutic agent as its other bivalent bond, wherein the bond with the therapeutic agent becomes labile upon cleavage of the scissile bond. Examples of self-immolative groups include, but are not limited to, disulfide groups, hydrazones, acetal self-immolative groups, carboxyacetal self-immolative groups, carboxy(methylacetal) self-immolative groups, para-hydroxybenzyl carbonyl self-immolative groups, flipped ester self-immolative groups, and trimethyl lock, or 2-hydroxyphenyl carbamate (2-HPC) self-immolative groups. A number of other suitable self-immolative groups are known in the art as described, for example, in C. A. Blencowe et al., Polym. Chem. 2011, 2, 773-790 and F. Kratz et al., ChemMedChem. 2008, 3(1), 20-53; Huvelle, S. et al., *Org. Biomol. Chem.* 2017, 15(16), 3435-3443; and Alouane, A. et al., *Angewandte Chemie International Edition* 2015, 54 (26), 7492-7509; and Levine, M. N. et al., *Chem. Sci. VL—IS*-3 (8), 2412-2420; each of which is hereby incorporated by reference in its entirety.

As used here in, the term "therapeutic agent," "active pharmaceutical agent," "active agent," or "pharmaceutical agent" includes any therapeutic agent or imaging (contrasting) agent which would benefit from transport via the intestinal lymphatic system, for example, to enable oral administration (e.g., of an intravenously administered therapeutic agent), to avoid first pass metabolism, avoid liver toxicity or other toxicity, or for targeted delivery within the lymphatic system.

Lipid prodrug compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, Handbook of Chemistry and Physics, 98$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphonates and phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

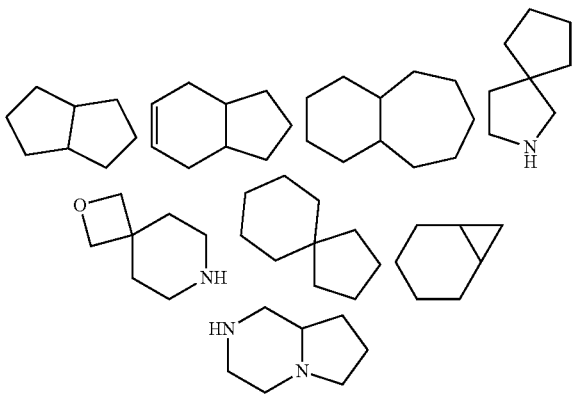

Exemplary bridged bicyclics include:

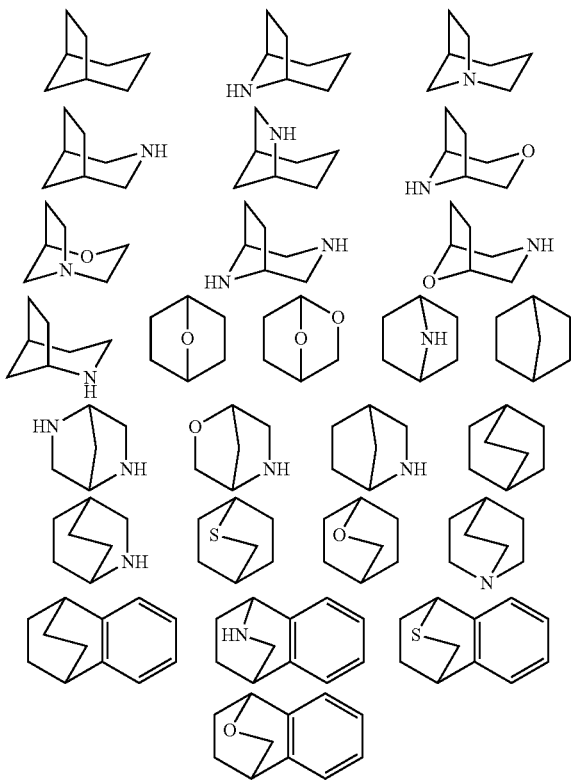

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of boron, oxygen, sulfur, nitrogen, phosphorus, or silicon (including any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain" refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —C(S)SR°; —SC(S)SR°, —$(CH_2)_{0-4}OC(O)NR°2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$S(O)(NR°)R°$; —$S(O)_2N=C(NR°_2)_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —($C_{1-4}$ straight or branched alkylene)O—$N(R°)_2$; or —($C_{1-4}$ straight or branched alkylene)C(O)O—$N(R°)_2$.

Each R° independently is hydrogen, $C_{1-6}$ aliphatic, —$CH_2Ph$, —$O(CH_2)_{0-1}Ph$, —$CH_2$—(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of R° selected from =O and =S; or each R° is optionally substituted with a monovalent substituent independently selected from halogen, —$(CH_2)_{0-2}R^•$, -(haloR$^•$), —$(CH_2)_{0-2}$OH, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —C(O)SR$^•$, —($C_{1-4}$ straight or branched alkylene)C(O)OR$^•$, or —SSR$^•$.

Each R$^•$ independently is selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each R$^•$ is unsubstituted or where preceded by halo is substituted only with one or more halogens; or wherein an optional substituent on a saturated carbon is a divalent substituent independently selected from =O, =S, =NNR*$_2$, =NNHC(O)R*, =NNHC(O)OR*, =NNHS(O)$_2$ R*, =NR*, =NOR*, —O(C(R*$_2$))$_{2-3}$O—, or —S(C(R*$_2$))$_{2-3}$S—, or a divalent substituent bound to vicinal substitutable carbons of an "optionally substituted" group is —O(CR*$_2$)$_{2-3}$O—, wherein each independent occurrence of R* is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ independently is selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each R$^•$ is unsubstituted or where preceded by halo is substituted only with one or more halogens.

An optional substituent on a substitutable nitrogen independently is —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† independently is hydrogen, C$_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R† is C$_{1-6}$ aliphatic, R† is optionally substituted with halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ independently is selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R˙ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts include salts of an amino group (or other basic group) formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^3$C- or $^{14}$C-enriched carbon are within the scope of this invention. Such compounds are useful, for example, as analytical tools, as probes in biological assays, or as therapeutic agents in accordance with the present invention.

3. Uses, Formulation and Administration

Uses of Lymphatic-Directing Lipid Prodrugs

Disclosed lymphatic-directing lipid prodrugs, as well as pharmaceutically acceptable compositions comprising a disclosed lipid prodrug, and a pharmaceutically acceptable excipient, diluent, or carrier, are useful for treating a variety of diseases, disorders or conditions. Such diseases, disorders, or conditions include those described herein.

One of ordinary skill in the art will recognize and appreciate that each of the therapeutic agents described herein are known to be associated with treatment of one or more diseases, disorders, or conditions. Accordingly, it will be appreciated that, in certain embodiments, the present invention provides a method of treating a disease, disorder, or condition in a patient in need thereof comprising administering to said patient a disclosed lipid prodrug.

The presently disclosed lipid prodrugs are useful for the stable transport of pharmaceutical agents to the intestinal lymph and release of the pharmaceutical agents in the lymph, lymphocytes, lymphoid tissues, tissues with high lipase activity such as adipose tissue, certain cancers, the liver, or in the systemic circulation. Disclosed lipid prodrugs are particularity useful for the transport and release of pharmaceutical agents that benefit from avoidance of first pass metabolism, for example, therapeutic agents that exhibit greater than about 50% first pass metabolism when administered orally. In some embodiments, the therapeutic agent exhibits greater than about 60% first pass metabolism when administered orally. In some embodiments, the therapeutic agent exhibits greater than about 70%, 80%, or 90% first pass metabolism when administered orally.

Therapeutic agents that may benefit from the stable transport to the intestinal lymph and release in the lymph, lymphocytes, lymphoid tissues, tissues with high lipase activity such as adipose tissue, certain cancers, the liver, or in the systemic circulation include, but are not limited to, therapeutic agents listed herein such as allopregnanolone, pregnanolone, pregnenolone, 30-dihydroprogesterone, isopregnanolone, epipregnanolone, ganaxolone, or 21-hydroxyallopregnanolone.

The presently disclosed lipid prodrugs are also useful for the targeted release of the therapeutic agent within the lymphatic system, for example, in the lymph, lymphocytes and lymphoid tissues, as well as in tissues with high lipase activity such as adipose tissue, certain cancers, or the liver. In some embodiments, the therapeutic agent exhibits poor lymphatic transport when administered orally. In some embodiments, the therapeutic exhibits less than 70%, 60%, 50%, 40%, 30%, 20%, 15%, 10%, 8%, 5%, 4%, 3%, 2%, 1%, 0.5%, 0.25%, 0.2%, 0.15%, or 0.1% when administered orally. In contrast, the present invention provides for improved lymphatic transport of such therapeutic agents. In some embodiments, a disclosed lipid prodrug exhibits at least 1%, 5%, 7.5%, 10%, 12.5%, 15%, 20%, 25%, 30%, 35%, 40%, or 50% lymphatic transport when administered orally. In some embodiments, a disclosed lipid prodrug exhibits about 1-50%, 5-40%, 10-30%, 15-25%, or about 50%, 40%, 30%, 25%, 20%, 15%, 12.5%, 10%, 7.5%, 5%, 2.5%, or 1% lymphatic transport when administered orally, as measured by either w/w % of the lipid prodrug administered or w/w % of the therapeutic agent in its lipid prodrug form vs. the unmodified therapeutic agent.

In some embodiments, a disclosed lipid prodrug is delivered to the central nervous system (CNS) or crosses the blood-brain barrier (BBB) via the lymphatic system.

In some embodiments, the present invention provides a method of treating or preventing a disease, disorder, or condition, comprising administering to a subject in need thereof an effective amount of a disclosed lipid prodrug that comprises a pregnane neurosteroid therapeutic.

In some embodiments, the present invention provides a pharmaceutical composition comprising a disclosed lipid prodrug formulated substantially as described in one of the Examples below or another exemplary formulation herein. In some embodiments, such a pharmaceutical composition provides a pharmacokinetic result upon administration to a subject as described in Tables B, C, D, or E below.

Pharmaceutically Acceptable Compositions

According to another embodiment, the present invention provides a composition comprising a lipid prodrug of the present disclosure and a pharmaceutically acceptable carrier, adjuvant, or vehicle. The amount of lipid prodrug in the composition is an amount effective to treat the relevant disease, disorder, or condition in a patient in need thereof (an "effective amount"). In some embodiments, a composition of the present disclosure is formulated for oral administration to a patient.

The term "pharmaceutically acceptable carrier, adjuvant, or vehicle" refers to a non-toxic carrier, adjuvant, or vehicle that does not destroy the pharmacological activity of the agent with which it is formulated. Pharmaceutically acceptable carriers, adjuvants or vehicles that may be used in the disclosed compositions include, but are not limited to, ion exchangers, alumina, stearates such as aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In some embodiments, the composition is formulated as a lipophilic mixture, such as a lipid-based composition.

Compositions of the present invention may be administered orally, parenterally, enterally, intracisternally, intraperitoneally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the composition is administered orally, intraperitoneally, or intravenously. In some embodiments, the composition is a transmucosal formulation. In some embodiments, the composition is injected directly into the lymphatic system. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

To aid in delivery of the composition, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, pharmaceutically acceptable compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

In some embodiments, the pharmaceutically acceptable composition is formulated for oral administration. Such formulations may be administered with or without food. In some embodiments, the pharmaceutically acceptable composition is administered without food. In other embodiments, the pharmaceutically acceptable composition is administered with food.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Therapeutic agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the lipid prodrug is formulated as an orally administerable, lipid-based formulation. Lipid-based formulations for oral delivery are known in the art and may include, for example, substantially non-aqueous vehicles which typically contain one or more lipid components. The lipid vehicles and resulting lipid formulations may be usefully classified as described below according to their shared common features according to the lipid formulation classification system (LFCS) (Pouton, C. W., Eur. J. Pharm. Sci. 11 (Supp 2), S93-S98, 2000; Pouton, C. W., Eur. J. Pharm. Sci. 29 278-287, 2006).

Lipid vehicles, and the resulting lipid formulations, may contain oil/lipids and/or surfactants, optionally with co-solvents. In the LFCS terminology, Type I formulations include oils or lipids which require digestion, such as mono, di and tri-glycerides and combinations thereof. Type II formulations are water-insoluble self emulsifying drug delivery systems (SEDDS) which contain lipids and oils used in Type I formulations, with additional water insoluble surfactants. Type III formulations are SEDDS or self-microemulsifying drug delivery systems (SMEDDS) which contain lipids and oils used in Type I formulations, with additional water-soluble surfactants and/or co-solvents (Type IIIa) or a greater proportion of water-soluble components (Type IIIb). Type IV formulations contain predominantly hydrophilic surfactants and co-solvents (e.g., PEG, propylene glycol and diethylene glycol monoethyl ether) and are useful for drugs which are poorly water soluble but not lipophilic. Any such lipid formulation (Type I-IV) is contemplated herein for use with a disclosed lipid prodrug or pharmaceutical composition thereof.

In some embodiments, the lipid vehicle contains one or more oils or lipids, without additional surfactants, co-surfactants or co-emulsifiers, or co-solvents, i.e. it consists essentially of one or more oils or lipids. In some further embodiments, the lipid vehicle contains one or more oils or lipids together with one or more water-insoluble surfactants, optionally together with one or more co-solvents. In some embodiments, the lipid vehicle contains one or more oils or lipids together with one or more water-soluble surfactants, optionally together with one or more co-solvents. In some embodiments, the lipid vehicle contains a mixture of oil/lipid, surfactant and co-solvent. In some embodiments, the lipid vehicle consists essentially of one or more surfactants/co-surfactants/co-emulsifiers, and/or solvents/co-solvents.

Examples of oils or lipids which may be used in the present invention include almond oil, babassu oil, blackcurrant seed oil, borage oil, canola oil, castor oil, coconut oil, cod liver oil, corn oil, cottonseed oil, evening primrose oil, fish oil, grape seed oil, mustard seed oil, olive oil, palm kernel oil, palm oil, peanut oil, rapeseed oil, safflower oil, sesame oil, shark liver oil, soybean oil, sunflower oil, walnut oil, wheat germ oil, avocado oil, bran oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl monolaurate, glyceryl behenate, glyceryl monolinoleate, glyceryl trilinolenate, glyceryl trioleate, glyceryl triundecanoate, glyceryl tristearate linoleic glycerides, saturated polyglycolized glycerides, synthetic medium chain triglycerides containing primarily $C_{8-12}$ fatty acid chains, medium chain triglycerides containing primarily $C_{8-12}$ fatty acid chains, long chain triglycerides containing primarily $>C_{12}$ fatty acid chains, modified triglycerides, fractionated triglycerides, and mixtures thereof.

Examples of mono and diglycerides which may be used in such formulations include glycerol mono- and diesters having fatty acid chains from 8 to 40 carbon atoms, including hydrolysed coconut oils (e.g., Capmul® MCM), hydrolysed corn oil (e.g., Maisine™35-1). In some embodiments, the monoglycerides and diglycerides are mono- or di-saturated fatty acid esters of glycerol having fatty acid chains of 8 to 18 carbon chain length (e.g., glyceryl monostearate, glyceryl distearate, glyceryl monocaprylate, glyceryl dicaprylate, glyceryl monocaprate and glyceryl dicaprate). Mixtures of fatty acids ("structured glycerides") adapted for enhancing the absorption and transport of lipid soluble compounds are disclosed in, e.g., U.S. Pat. No. 6,013,665, which is hereby incorporated by reference.

Suitable surfactants for use in the lipid formulations include propylene glycol mono- and di-esters of $C_{8-22}$ fatty acids, such as, but not limited to, propylene glycol monocaprylate, propylene glycol dicaprylate, propylene glycol monolaurate, sold under trade names such as Capryol® 90, Labrafac® PG, Lauroglycol® FCC, sugar fatty acid esters, such as, but not limited to, sucrose palmitate, sucrose laurate, and sucrose stearate; sorbitan fatty acid esters such as, but not limited to, sorbitan laurate, sorbitan palmitate, and sorbitan oleate; polyoxyethylene sorbitan fatty acid esters such as, but not limited to, polysorbate 20, polysorbate 40, polysorbate 60, polysorbate 80, and polysorbate 85; polyoxyethylene mono- and di-fatty acid esters including, but not limited to, polyoxyl 40 stearate and polyoxyl 40 oleate; a mixture of polyoxyethylene mono- and di-esters of $C_{8-22}$ fatty acids and glyceryl mono-, di-, and tri-esters of $C_{8-22}$ fatty acids as sold under tradenames such as Labrasol®, Gelucire® 44/14, Gelucire® 50/13, and Labrafil®; polyoxyethylene castor oils compound such as, but not limited to, polyoxyl 35 castor oil, polyoxyl 40 hydrogenated castor oil, and polyoxyl 60 hydrogenated castor oil, as are sold under tradenames such as Cremophor®/Kolliphor EL, Cremophor®/Kolliphor® RH40, and Cremophor®/Kolliphor® RH60; polyoxyethylene alkyl ethers including, but not limited to, polyoxyl 20 cetostearyl ether and polyoxyl 10 oleyl ether; DL-α-tocopheryl polyethylene glycol succinate; glyceryl mono-, di-, and tri-esters; glyceryl mono-, di-, and tri-esters of $C_{8-22}$ fatty acids; sucrose mono-, di-, and tri-esters; sodium dioctylsulfosuccinate; polyoxyethylene-polyoxypropylene copolymers such as, but not limited to poloxamer 124, poloxamer 188, and poloxamer 407; polyoxyethylene ethers of $C_{8-22}$ fatty alcohols including, but not limited to, polyoxyethylenelauryl alcohol, polyoxyethylenecetyl alcohol, polyoxyethylene stearyl alcohol, polyoxyethyleneoleyl alcohol, as sold under tradenames such as Brij® 35, Brij® 58, Brij® 78, Brij® 98, or a mixture of any two or more thereof.

A co-emulsifier, or co-surfactant, may be used in the formulation. A suitable co-emulsifier or co-surfactant may be a phosphoglyceride; a phospholipid, for example lecithin, or a free fatty acid that is liquid at room temperature, for example, iso-stearic acid, oleic acid, linoelic acid, linolenic acid, palmitic acid, stearic acid, lauric acid, capric acid, caprylic acid, and caproic acid.

Suitable solvents/co-solvents include ethanol, propylene glycol, polyethylene glycol, diethylene glycol monoethyl ether, and glycerol.

A polymer may also be used in the formulation to inhibit drug precipitation or to alter the rate of drug release. A range of polymers have been shown to impart these properties and are well known to those skilled in the art. Suitable polymers include hydroxypropylmethylcellulose, hydroxypropylmethylcellulose acetyl succinate, other cellulose-derived polymers such as methylcellulose; poly(meth)acrylates, such as the Eudragit series of polymers, including Eudragit E100, polyvinylpyrrolidone, or others as described in, e.g., Warren et al., Mol. Pharmaceutics 2013, 10, 2823-2848.

Formulations may be chosen specifically to provide for sustained release of the active in the gastrointestinal (GI) tract in order to control the rate of absorption. Many different approaches may be used to achieve these ends including the use of high melting point lipids that disperse/erode slowly in the GI tract, or polymers that form a matrix that slowly erodes. These formulations may take the form of large monolithic dose forms or may be present as micro or nano-particulate matrices as described in, for example, in Mishra, Handbook of Encapsulation and Controlled Release, CRC Press, Boca Raton, (2016) ISBN 978-1-4822-3234-9, Wilson and Crowley Controlled Release in Oral Drug Delivery, Springer, NY, ISBN 978-1-4614-1004-1 (2011) or Wise, Handbook of Pharmaceutical Controlled Release Technology, Marcel Dekker, NY, ISBN 0-82467-0369-3 (2000).

Formulations may also contain materials commonly known to those skilled in the art to be included in lipid-based formulations, including antioxidants, for example, butylated hydroxyanisole (BHA) or butylated hydroxytoluene (BHT) and solidifying agents such as microporous silica, for example magnesium alumino-metasilicate (Neusilin).

In some embodiments, the lipid prodrug may be co-administered orally with an enzyme inhibitor to increase stability of the prodrug in the gastrointestinal tract or enterocyte. In certain embodiments, the enzyme inhibitor inhibits pancreatic lipases, examples of which include, but are not limited to, Alli® (orlistat). In other embodiments it is envisaged that the enzyme inhibitor will inhibit cellular lipase enzymes such as monoacylglycerol lipase, an example of which includes, but is not limited to, JZL184 (4-nitrophenyl-4-[bis(1,3-benzodioxol-5-yl)(hydroxy) methyl]piperidine-1-carboxylate).

Combination Therapies

A provided lipid prodrug, or pharmaceutically acceptable composition thereof, may be administered to a patient in need thereof in combination with one or more additional therapeutic agents and/or therapeutic processes.

The lipid prodrug or pharmaceutically acceptable composition thereof can be administered alone or in combination with one or more other therapeutic compounds, possible combination therapy taking the form of fixed combinations or the administration of the lipid prodrug or composition and one or more other therapeutic compounds being staggered or given independently of one another, or the combined administration of fixed combinations and one or more other therapeutic compounds. A disclosed lipid prodrug or composition can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a provided lipid prodrug or composition, as part of a multiple dosage regimen. Alternatively, those agents may be part of a single dosage form, mixed together with a disclosed lipid prodrug in a single composition. If administered as part of a multiple dosage regime, the two active agents may be submitted simultaneously, sequentially or within a period of time from one another.

As used herein, the term "combination," "combined," and related terms refers to the simultaneous or sequential administration of therapeutic agents in accordance with the present disclosure. For example, a disclosed lipid prodrug may be administered with another therapeutic agent simultaneously or sequentially in separate unit dosage forms or together in a single unit dosage form. Accordingly, the present disclosure provides a single unit dosage form comprising a disclosed lipid prodrug, an additional therapeutic agent, and a pharmaceutically acceptable carrier, adjuvant, or vehicle. In some embodiments, the additional agent is formulated in a separate composition from the lipid prodrug.

The amount of both a disclosed lipid prodrug and additional therapeutic agent (in those compositions which comprise an additional therapeutic agent as described above) that may be combined with the carrier materials to produce a single dosage form will vary depending upon the patient treated and the particular mode of administration. In certain embodiments, compositions of this invention should be formulated so that a dosage of between about 0.01-500 mg/kg body weight/day of a disclosed lipid prodrug can be administered.

In those compositions which comprise an additional therapeutic agent, that additional therapeutic agent and the disclosed lipid prodrug may act synergistically. Therefore, the amount of additional therapeutic agent in such compositions will be less than that required in a monotherapy utilizing only that therapeutic agent. In such compositions, a dosage of between about 0.01 µg/kg to 100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Examples of agents with which the lipid prodrugs of this invention may be combined include, without limitation: treatments for Alzheimer's Disease such as Aricept® and Exelon®; treatments for HIV such as ritonavir; treatments for Parkinson's Disease such as L-DOPA/carbidopa, entacapone, ropinirole, pramipexole, bromocriptine, pergolide, trihexyphendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention include a monoclonal antibody or a siRNA therapeutic.

In another embodiment, the present invention provides a method of treating an inflammatory disease, disorder or condition such as a neuroinflammatory disease or Alzheimer's disease, by administering to a patient in need thereof a disclosed lipid prodrug and one or more additional therapeutic agents. Such additional therapeutic agents may be small molecules or a biologic and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiments, the present invention provides a method of treating a depressive mood disorder (e.g., major depressive disorder, bipolar disorder, seasonal affective disorder (SAD), cyclothymic disorder, premenstrual dysphoric disorder, persistent depressive disorder, disruptive mood dysregulation disorder, depression related to medical illness, postpartum depression) and/or anxiety disorder (e.g., panic disorder and post-traumatic stress disorder) comprising administering to a patient in need thereof a disclosed lipid prodrug and one or more additional therapeutic agents selected from citalopram (Celexa®), escitalopram (Lexapro®), fluoxetine (Prozac®), fluvoxamine (Luvox®/Luvox CR®), paroxetine (Paxil®/Paxil CR®), sertraline (Zoloft®), desvenlafaxine (Pristiq®), duloxetine (Cymbalta®), venlafaxine (Effexor®/Effexor XR®), milnacipran (Savella®), levomilnacipran (Fetzima®), amitriptyline (Elavil®), desipramine (Norpramin®), doxepine (Sinequan®), imipramine (Tofranil®), nortriptyline (Pamelor®), amoxapine, clomipramine (Anafranil®), maprotiline (Ludiomil®), trimipramine (Surmontil®), protriptyline (Vivactil®), phenelzine (Nardil®), selegiline (Emsam®), tranylcypromine (Parnate®), bupropion (Wellbutrin®), mirtazapine (Remeron®), nefazodone (Serzone®), trazodone (Desyrel®, Oleptro®), vilazodone (Viibryd®), and vortioxetine (Brintellix®).

In some embodiments, the present invention provides a method of treating Alzheimer's disease comprising administering to a patient in need thereof a disclosed lipid prodrug and one or more additional therapeutic agents selected from donepezil (Aricept®), rivastigmine (Exelon®), galantamine (Razadyne®), tacrine (Cognex®), and memantine (Namenda®).

The disclosed lipid prodrugs and compositions, and any co-administered additional therapeutic agents, according to the method of the present invention, may be administered using any amount and any route of administration effective for treating or lessening the severity of a disease, disorder, or condition such as an inflammatory disorder, a neurodegenerative or neurological disorder, or schizophrenia. The exact amount required will vary from subject to subject, depending on the species, age, and general condition of the subject, the severity of the infection, the particular agent, its mode of administration, and the like. Disclosed lipid prodrugs are preferably formulated in dosage unit form for ease of administration and uniformity of dosage. The expression "dosage unit form" as used herein refers to a physically discrete unit of agent appropriate for the patient to be treated. It will be understood, however, that the total daily usage of a disclosed lipid prodrug or composition thereof and any co-administered additional therapeutic agents will be decided by the attending physician within the scope of sound medical judgment. The specific effective dose level for any particular patient or organism will depend upon a variety of factors including the disorder being treated and the severity of the disorder; the activity of the specific lipid prodrug employed; the specific composition employed; the age, body weight, general health, sex and diet of the patient; the time of administration, route of administration, and rate of excretion of the specific lipid prodrug or composition; the duration of the treatment; drugs used in combination or coincidental with the specific lipid prodrug or composition employed, and like factors well known in the medical arts. The term "subject" or "patient," as used herein, means an animal, preferably a mammal, and most preferably a human.

In some embodiments, a dose is selected to account for lymphatic uptake, metabolism, and release of the parent drug allopregnanolone (allo). For example, if a given dose of lipid prodrug is absorbed more efficiently than an equivalent oral or intravenous dose of allopregnanolone, the dose of lipid prodrug is decreased by an appropriate amount to result in the desired plasma or lymphatic system concentration of allopregnanolone. In some embodiments, the dose is selected such that an orally-administered dose of lipid prodrug provides, upon lymphatic uptake in the patient, metabolism, and release of the parent drug allopregnanolone, a desired, effective concentration, e.g., a plasma or lymphatic system concentration, of allopregnanolone to treat a disease, disorder, or condition, such as those disclosed herein.

In some embodiments, the dose of lipid prodrug or a pharmaceutically acceptable salt thereof is about 0.01 mg/kg to about 100 mg/kg. In some embodiments, the dose of lipid prodrug or a pharmaceutically acceptable salt thereof is about 0.1 mg/kg to about 25 mg/kg. In some embodiments, the dose of lipid prodrug or a pharmaceutically acceptable salt thereof is about 0.5 mg/kg to about 15 mg/kg. In some embodiments, the dose of lipid prodrug or a pharmaceutically acceptable salt thereof is about 1 mg/kg to about 10 mg/kg. In some embodiments, the dose of lipid prodrug or a pharmaceutically acceptable salt thereof is about 2 mg/kg to about 7.5 mg/kg. In some embodiments, the dose of lipid prodrug or a pharmaceutically acceptable salt thereof is about 3.0 mg/kg to about 7.0 mg/kg. In some embodiments, the dose of lipid prodrug or a pharmaceutically acceptable salt thereof is about 0.1, 0.2, 0.3, 0.4, 0.5, 0.6, 0.7, 0.8, 0.9, 1.0, 1.3, 1.5, 1.7, 2.0, 2.5, 3.0, 3.5, 4.0, 5.0, 6.0, 7.0, 8.0, 9.0, or 10.0 mg/kg.

In some embodiments, the dose is about 1 mg to about 5 g of lipid prodrug or a pharmaceutically acceptable salt thereof. In some embodiments, the dose is about 10 mg to about 2.5 g of lipid prodrug or a pharmaceutically acceptable salt thereof. In some embodiments, the dose is about 100 mg to about 2.0 g of lipid prodrug or a pharmaceutically acceptable salt thereof. In some embodiments, the dose is about 250 mg to about 1.0 g of lipid prodrug or a pharmaceutically acceptable salt thereof. In some embodiments, the dose is about 500 mg to about 1.0 g of lipid prodrug or a pharmaceutically acceptable salt thereof.

In some embodiments, the dose of lipid prodrug or a pharmaceutically acceptable salt thereof is calculated to provide a particular dose of allopregnanolone when the prodrug is administered orally. In some embodiments, the dose of lipid prodrug or a pharmaceutically acceptable salt thereof is calculated to provide about 0.01 mg/kg to about 100 mg/kg of allopregnanolone, 0.1 mg/kg to about 25 mg/kg, about 0.5 mg/kg to about 15 mg/kg, about 1 mg/kg to about 10 mg/kg, about 2 mg/kg to about 7.5 mg/kg, about 3.0 mg/kg to about 7.0 mg/kg of allopregnanolone. In some embodiments, the dose of lipid prodrug or a pharmaceutically acceptable salt thereof is calculated to provide about 0.1, 0.2, 0.3, 0.4, 0.5, 0.6, 0.7, 0.8, 0.9, 1.0, 1.3, 1.5, 1.7, 2.0, 2.5, 3.0, 3.5, 4.0, 5.0, 6.0, 7.0, 8.0, 9.0, or 10.0 mg/kg of allopregnanolone when the prodrug is administered orally.

In some embodiments, the dose of lipid prodrug or a pharmaceutically acceptable salt thereof is calculated to provide about 5 mg to about 3 g of allopregnanolone when the prodrug is administered orally. In some embodiments, the dose is calculated to provide about 50 mg to about 2.5 g of allopregnanolone, or about 100 mg to about 1.5 g, or about 250 mg to about 1.0 g of allopregnanolone.

4. Methods of Making Lipid Prodrugs

General Methods for Making Lipid Prodrugs

The lipid prodrug compounds of this invention may be prepared or isolated in general by synthetic and/or semi-synthetic methods known to those skilled in the art for analogous compounds and by methods described in detail in the Examples, herein.

The therapeutic agents comprised in disclosed lipid prodrugs (e.g., conjugated to a glyceride-based prodrug) may be purchased commercially or prepared by organic synthesis, semi-synthesis, fermentation (e.g., with viral vectors), and like methods known in the art.

In some embodiments, protecting groups (as defined below) can be used to manipulate therapeutic agents in preparation for conjugation to the remainder of the lipid prodrug structure, for example, to prevent undesired side reactions from taking place.

In the synthesis methods described herein, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 7$^{th}$ Edition, John Wiley & Sons, 2013, *Comprehensive Organic Transformations*, R. C. Larock, 3$^{rd}$ Edition, John Wiley & Sons, 2018, and *Protective Groups in Organic Synthesis*, P. G. M. Wuts, 5$^{th}$ edition, John Wiley & Sons, 2014, the entirety of each of which is hereby incorporated herein by reference.

As used herein, the phrase "leaving group" (LG) includes, but is not limited to, halogens (e.g., fluoride, chloride, bromide, iodide), sulfonates (e.g., mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protective Groups in Organic Synthesis*, P. G. M. Wuts, 5$^{th}$ edition, John Wiley & Sons, 2014, and Philip Kocienski, in *Protecting Groups*, Georg Thieme Verlag Stuttgart, New York, 1994, the entireties of which are incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protective Groups in Organic Synthesis*, P. G. M. Wuts, 5$^{th}$ edition, John Wiley & Sons, 2014, and Philip Kocienski, in *Protecting Groups*, Georg Thieme Verlag Stuttgart, New York, 1994, the entireties of which are incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxycarbonyl, methyloxycarbonyl, trichloroethyloxycarbonyl, allyloxycarbonyl (Alloc), benzyloxocarbonyl (Cbz), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, March's Advanced Organic Chemistry: Reactions, Mechanisms, and Structure, M. B. Smith and J. March, 7$^{t}$ Edition, John Wiley & Sons, 2013, the entirety of which is incorporated herein by reference. Such interconversions may require one or more of the aforementioned techniques, and certain methods for synthesizing compounds of the invention are described below.

As a general strategy, compounds of the present invention may be synthesized via one of the following routes:

Scheme 1. Synthesis of compounds of formula iii-a.

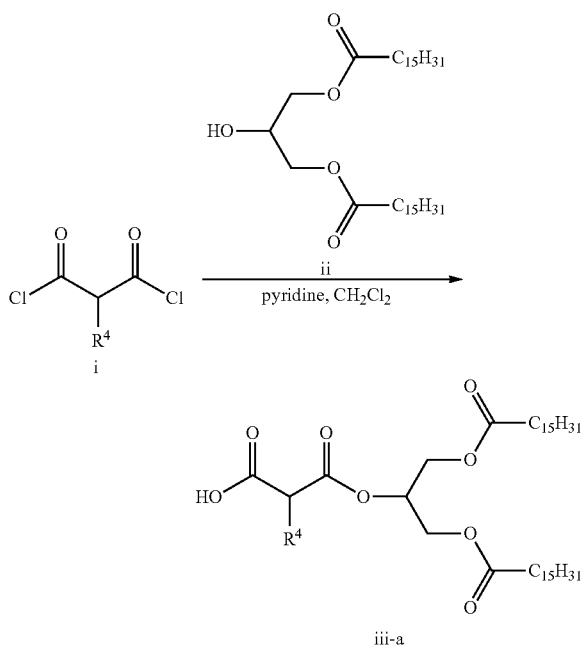

Diacid chlorides i, which are readily available from the corresponding malonic acids, can be reacted with a diglyceride such as ii in the presence of pyridine or another appropriate base to give acid-triglyceride (acid-TG) iii-a (see Scheme 1). Formula iii-a is shown with $C_{15}H_{31}$ fatty acid side chains, but other fatty acids (such as those described above) can be substituted in this and other Formulas described below.

Scheme 2. Synthesis of compounds of formula iii-b.

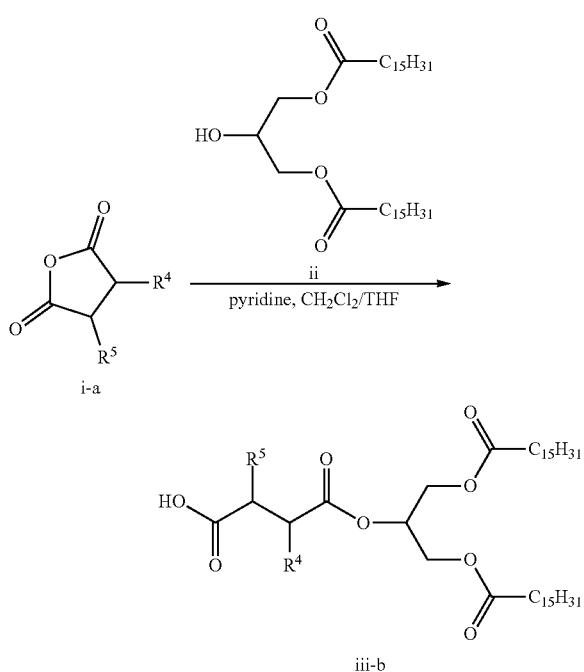

In cases where acid anhydride i-a is available, acid-TG iii-b can be generated by ring-opening with diglyceride ii in the presence of pyridine or another appropriate base (Scheme 2). This method works best when $R^4$ and $R^5$ of acid anhydride i-a are identical, e.g. both Me, but will result in a regioisomeric mixture of acid-TG products iv when $R^4$ and $R^5$ differ from each other. Consequently, other methods, such as that outlined in Scheme 3, can advantageously be employed in this circumstance.

Scheme 3. Synthesis of compounds of formula iv where $R^4$ = Me, Alkyl, etc. and $R^5$ = H.

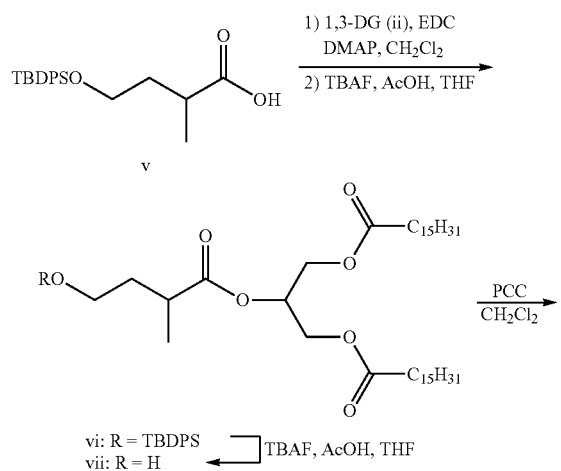

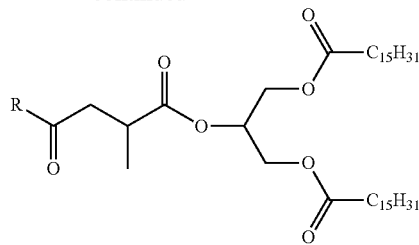

To obtain acid-TG iv-a as a single regioisomer in the specific example where $R^4$=Me or other alkyl or substitution and $R^5$=H, the known carboxylic acid v (Lienard, B. M. R. et al., *Org. Biomol. Chem.* 2008, 6, (13), 2282-2292) can be used as a starting point (see Scheme 3). Coupling of acid v with 1,3-DG ii under standard conditions produces TBDPS protected triglyceride vi, which can be treated with appropriate conditions such as TBAF and AcOH to afford alcohol vii. A two-step oxidation process (for example, PCC, then $KMnO_4$) can then be used to transform alcohol vii into the desired acid-TG iv via the intermediate aldehyde viii.

Scheme 4. Synthesis of compounds of formula x wherein -M- is an acetal self-immolative (ASI) group.

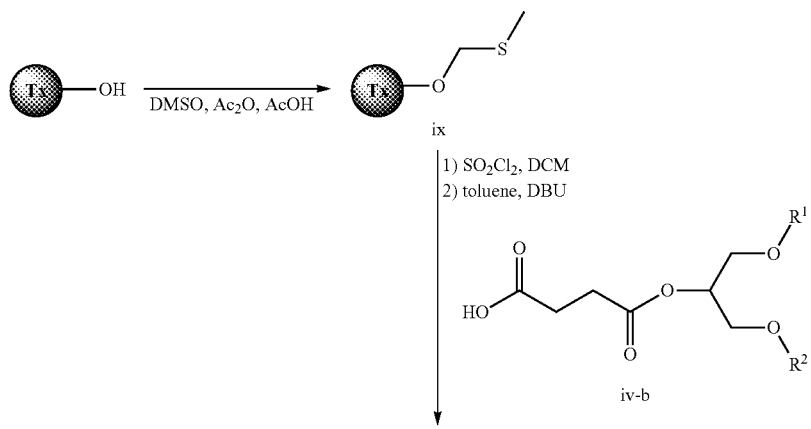

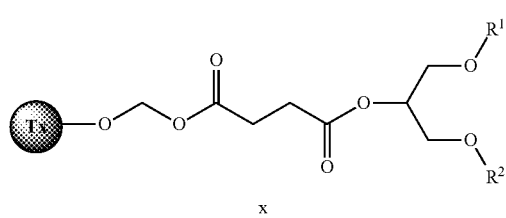

For the synthesis of compounds containing an acetal self-immolative (ASI) group between the pharmaceutical agent and the alkyl spacer, the alcohol-bearing parent molecule must be functionalized and activated prior to conjugation with acid-triglyceride iii as outlined above in Scheme 4. Treatment of an alcohol with DMSO in a mixture of acetic anhydride and acetic acid results in the formation of (methylthio)methyl (MTM) ether ix. Activation of MTM ether ix using sulfuryl chloride forms a presumed sulfoxide species that can react with the carboxylate of acid-triglyceride iv-b to give the target compound x.

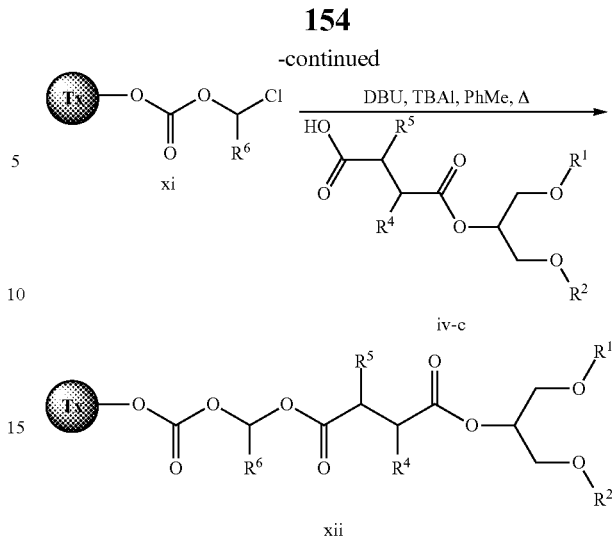

In cases where the pharmaceutical agent contains an alcohol, phenol or amine (primary or secondary) functional group, a modified version of the acetal self-immolative group can be used where an additional carboxy group is included. Reaction of the parent drug with a chloroalkyl chloroformate gives chloroalkyl carbonates (shown) or carbamates xi (see Scheme 5). Displacement of the halide leaving group is then accomplished by treatment with the carboxylate derived from acid-TG iv-c in an appropriate solvent such as refluxing toluene to afford the target compound xii.

Scheme 5. Synthesis of compounds of formula xii wherein -M- is a carboxyacetal (CASI) or carboxy(methylacetal) (CMSI) self-immolative group.

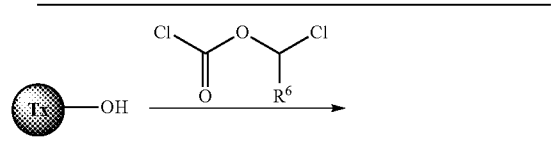

Scheme 6. Synthesis of compounds of formula xviii wherein -M- is a trimethyl-lock (TML) self-immolative group.

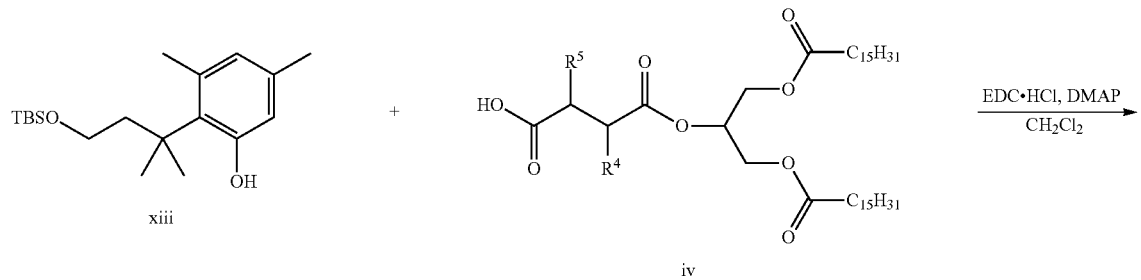

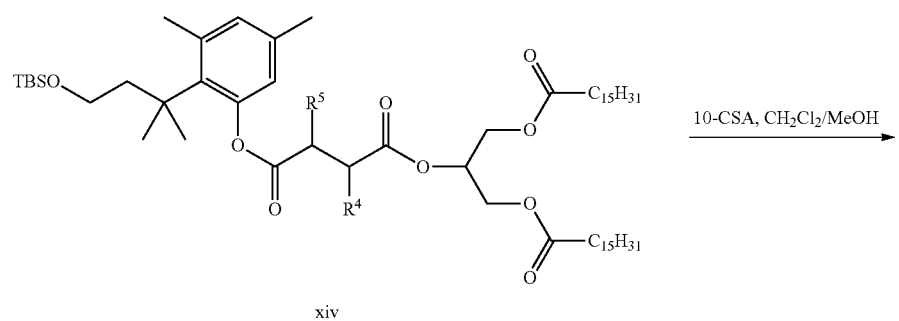

-continued

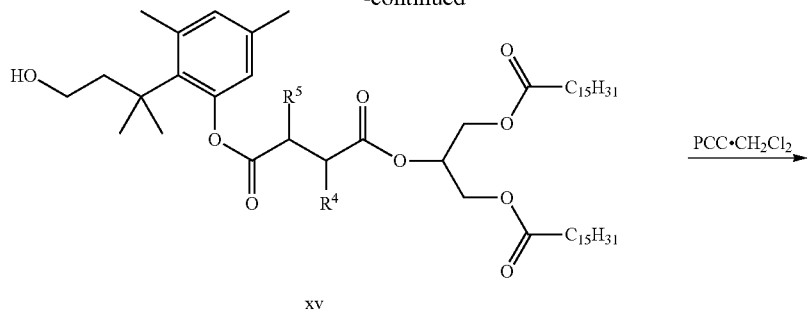

xv

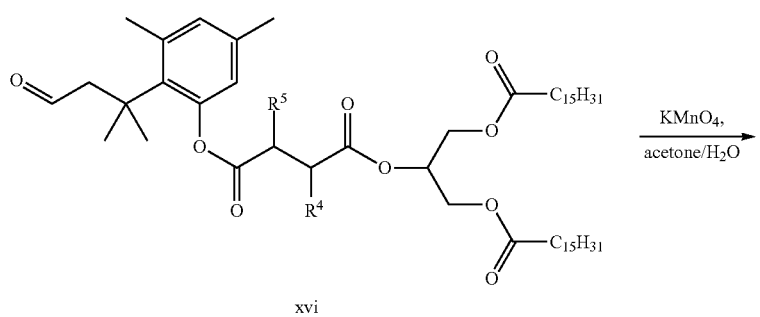

xvi

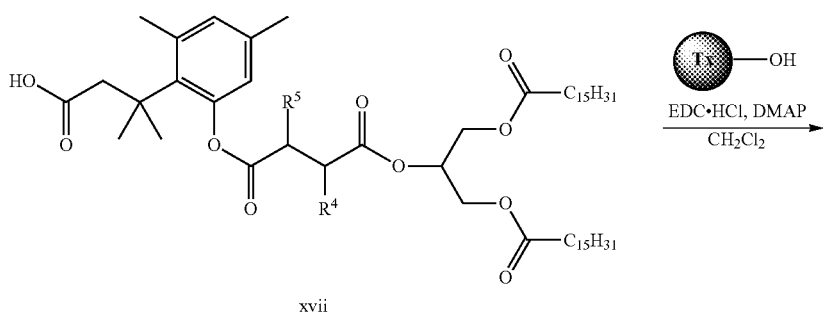

xvii

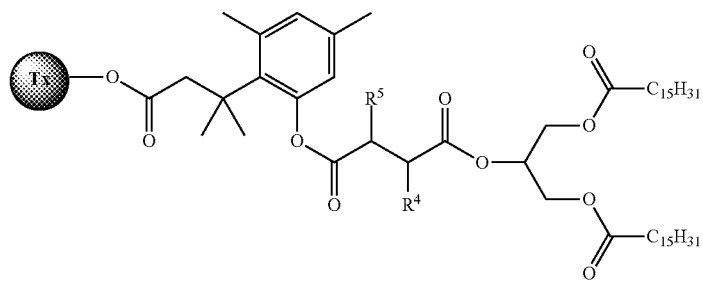

xviii

For the synthesis of prodrugs containing a trimethyl lock (TML) self-immolative group (Levine, M. N.; Raines, R. T. Chem. Sci. 2012, 3, 2412-2420, hereby incorporated by reference) between the pharmaceutical agent and the alkyl spacer to facilitate systemic release of the parent molecule, the acid-triglyceride iv is typically functionalized with the TML moiety prior to conjugation with a pharmaceutical agent as outlined in Scheme 6. Coupling of acid-TG iv with TML phenol xiii under standard conditions gives triglyceride xiv, which can be deprotected under acidic conditions (10-camphorsulfonic acid) to give alcohol xv. Sequential oxidation of alcohol xv firstly to aldehyde xvi and then acid xvii, followed by coupling to either an alcohol (shown), amine or sulfonamide-containing pharmaceutical agent under standard conditions can give the target compound xviii.

Scheme 7. Synthesis of compounds of formula xxiv wherein -M- is a p-hydroxybenzyl carbonyl (PHB) self-immolative group.
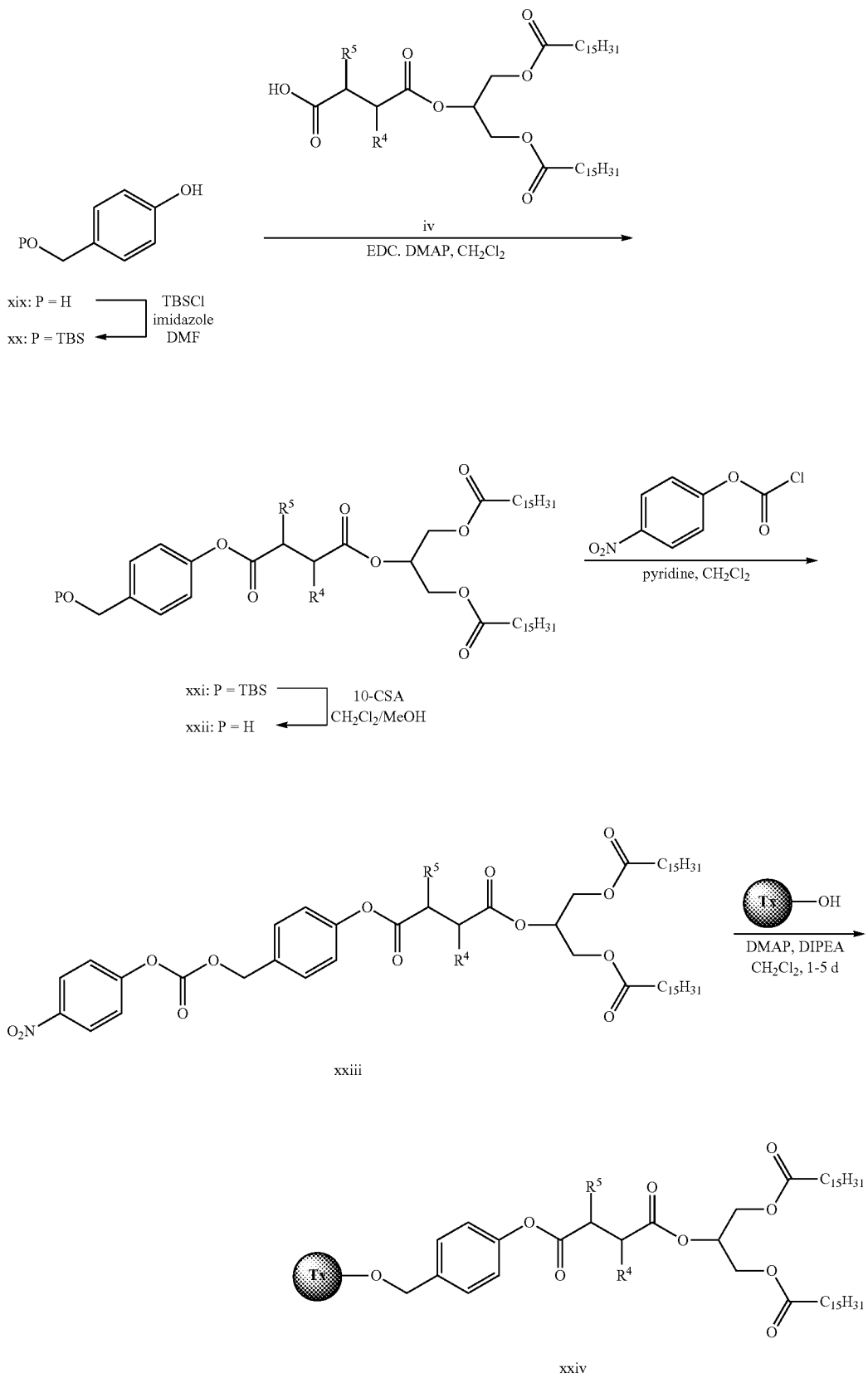

For the synthesis of compounds containing a p-hydroxybenzyl (PHB) carbonyl self-immolative group, the primary hydroxyl group of p-hydroxybenzyl alcohol (xix) is first protected as a silyl ether and the free phenolic hydroxyl group coupled with acid-TG iv to give PHB triglyceride xxi (see Scheme 7). After removal of the silicon protecting group, primary alcohol xxii can be activated by treatment with p-nitrophenyl (PNP) chloroformate to give PNP carbonate xxiii. Displacement of the PNP group is then achieved by reaction with a pharmaceutical agent (A-OH shown) under basic conditions to give the desired compound xxiv.

Scheme 8. Synthesis of compounds of formula III wherein -M- is a flipped-ester self-immolative (FSI) group.

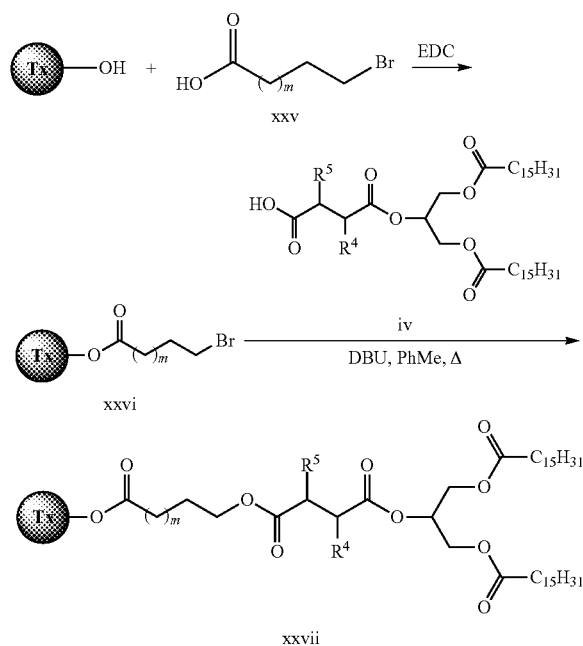

Without wishing to be bound by theory, it is believed that the flipped-ester self-immolative (FSI) group can liberate the free pharmaceutical agent by a cyclization mechanism, resulting in loss of either a four-carbon (FSI-4) or five-carbon (FSI-5) lactone. Alternatively, liberation of the agent may occur by a chemical or enzymatic mechanism in vivo. FSI prodrugs can be synthesized by coupling the pharmaceutical agent (A-OH shown) with either 4-bromobutyric acid (m=1) or 5-bromovaleric acid (m=2) (xxv) to give bromide xxvi (see Scheme 8). Displacement of bromide xxvi using the carboxylate derived from acid-TG iv generates the desired ester bond in target compound xxvii.

EXEMPLIFICATION

Example 1: Synthesis of Intermediates

List of Abbreviations
equiv or eq: molar equivalents
rt: room temperature
UV: ultra violet
HPLC: high pressure liquid chromatography
Rt: retention time
LCMS or LC-MS: liquid chromatography-mass spectrometry
NMR: nuclear magnetic resonance
TLC: thin layer chromatography
sat: saturated
aq: aqueous
Ac: acetyl
BINAP: (±)-2,2'-Bis(diphenylphosphino)-1,1'-binaphthalene
Bn: Benzyl
DBU: 1,8-Diazabicyclo[5.4.0]undec-7-ene
DCC: N,N'-Dicyclohexylcarbodiimide
DCM: Dichloromethane
DCE: Dichloroethane
DEA: Diethylamine
DIPA: Diisopropylamine
DM water: demineralized water
DMF: N,N-dimethylformamide
DMSO: dimethylsulfoxide
DMPU: N,N'-Dimethylpropyleneurea
ACN or MeCN: acetonitrile
DIPEA: diisopropylethylamine
EA or EtOAc: ethyl acetate
EDCI, EDC, or EDAC: 1-Ethyl-3-(3-dimethylaminopropyl)carbodiimide
TEA: triethylamine
THF: tetrahydrofuran
TBS: tert-butyldimethylsilyl
KHMDS: potassium hexamethyl disilylazide
Tf: trifluoromethanesulfonate
Ms: methanesulfonyl
NBS: N-bromosuccinimide
PCC: Pyridinium chlorochromate
PE: petroleum ether
TFA: trifluoroacetic acid
MMPP: magnesium monoperoxyphthalate
HATU: 1-[Bis(dimethylamino)methylene]-1H-1,2,3-triazolo[4,5-b]pyridinium 3-oxid Hexafluorophosphate
Cy: cyclohexyl
Tol: toluene
DMP: Dess-Martin periodinane
IBX: 2-iodoxybenzoic acid
PMB: p-methoxybenzyl
SEM: [2-(Trimethylsilyl)ethoxy]methyl
1,3-DG (Int-2):

Scheme 9. Synthesis of Int-2.

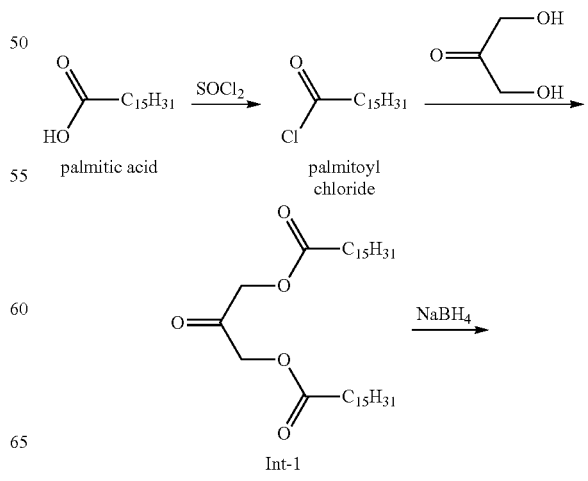

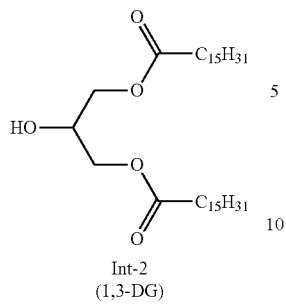

Int-2
(1,3-DG)

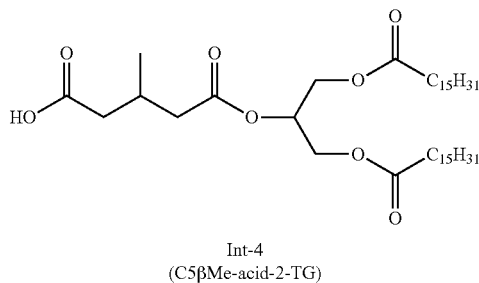

Int-4
(C5βMe-acid-2-TG)

DMF (1 mL, 13.7 mmol) was added into a mixture of palmitic acid (433 g, 1.69 mol) in thionyl chloride (500 mL, 6.3 mol) at room temperature. The resultant reaction mixture was heated under reflux for 3 h. It was concentrated to dryness to afford palmitoyl chloride (453 g, 1.64 mol, 97% yield) as a yellowish oil, which was used in the next step without further purification.

To a mixture of 1,3-dihydroxypropan-2-one (77 g, 0.855 mol) and anhydrous pyridine (140 g, 1.76 mol) in anhydrous dichloromethane (2500 mL) under nitrogen at room temperature, was added with palmitic chloride (453 g, 1.64 mol). The mixture was stirred at room temperature for 16 h. It was diluted with MeOH (1000 mL) and water (2000 mL) and stirred for 30 min. The precipitate was collected by filter and dried to afford Int-1 (462 g, 0.815 mmol, 95% yield) as a white solid.

Int-1 (220 g, 388 mmol) was dissolved in a solution of THF (3000 mL) and water (200 mL) at 0° C. Sodium borohydride (22 g, 579 mmol) was added portion wise. After addition, the mixture was filtered to afford a cake, which was dried to afford compound Int-2 (1,3-DG) (177 g, 311 mmol, 80% yield) as a white solid. LC-MS: MS m/z=591 (M+Na+), RT=4.39 min; $^1$H NMR (400 MHz, chloroform-d) δ 4.20-4.05 (m, 5H), 2.35 (t, J=7.6 Hz, 4H), 1.62 (t, J=7.6 Hz, 4H), 1.25 (s, 48H), 0.88 (t, J=6.6 Hz, 6H).

C5βMe-acid-2-TG (Int-4):

Scheme 10. Synthesis of Int-4.

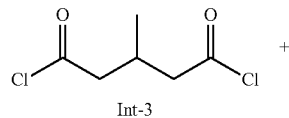

Int-3

A mixture of 3-methylglutaric acid (500 mg, 3.42 mmol) and DMF (two drops) in thionyl chloride (2.48 mL, 34.2 mmol) was heated at reflux for two hours. The reaction was cooled to room temperature, diluted with toluene (5 mL) and concentrated under reduced pressure to give diacid chloride Int-3 (584 mg, 83%) as a yellow oil that was used without purification. $^1$H NMR (400 MHz, CDCl$_3$) δ 3.02 (dd, J=17.3, 6.1 Hz, 2H), 2.89 (dd, J=17.3, 7.2 Hz, 2H), 2.61 (m, 1H), 1.13 (d, J=6.8 Hz, 2H).

A solution of Int-2 (1,3-DG) (50.0 mg, 0.0879 mmol) and pyridine (71.1 μL, 0.879 mmol) in dichloromethane (2 mL) was added to acid chloride Int-3 (80.4 mg, 0.439) in dichloromethane (1.5 mL) and the mixture heated at reflux for two hours. The reaction was cooled to room temperature, diluted with ethyl acetate (15 mL) and 1 M HCl (5 mL) and the organic phase separated. The aqueous layer was further extracted with ethyl acetate (2×20 mL) and the combined organic extracts washed with 1 M HCl (20 mL) and brine (2×30 mL), dried (MgSO$_4$) and concentrated under reduced pressure to give the crude product. Purification by silica gel chromatography (20% to 45% ethyl acetate/hexanes) gave Int-4 (54.0 mg, 88%) as a colorless solid. $^1$H NMR (400 MHz, CDCl$_3$) δ 5.27 (m, 1H), 4.311 (dd, J=11.9, 4.2 Hz, 1H), 4.305 (dd, J=11.9, 4.2 Hz, 1H), 4.14 (dd, J=11.9, 5.6 Hz, 2H), 2.52-2.39 (m, 3H), 2.36-2.24 (m, 6H), 1.66-1.55 (m, 4H), 1.37-1.17 (m, 48H), 1.06 (d, J=6.3 Hz, 3H), 0.88 (t, J=6.8 Hz, 6H); $^{13}$C NMR (101 MHz, CDCl$_3$) δ 178.1 (C), 173.5 (2C; C), 171.4 (C), 69.3 (CH), 62.2 (2C; CH$_2$), 40.7 (CH$_2$), 40.4 (CH$_2$), 34.1 (2C; CH$_2$), 32.1 (2C; CH$_2$), 29.82 (6C; CH$_2$), 29.78 (4C; CH$_2$), 29.74 (2C; CH$_2$), 29.6 (2C; CH$_2$), 29.5 (2C; CH$_2$), 29.4 (2C; CH$_2$), 29.2 (2C; CH$_2$), 27.3 (CH), 25.0 (2C; CH$_2$), 22.8 (2C; CH$_2$), 19.8 (CH$_3$), 14.2 (2C; CH$_3$); ESI-HRMS: calcd. for C$_{41}$H$_{76}$NaO$_8$ [M+Na$^+$] 719.5432; found 719.5451.

Alternate Procedure (Larger Scale):

Scheme 11. Alternate Synthesis of Int-4.

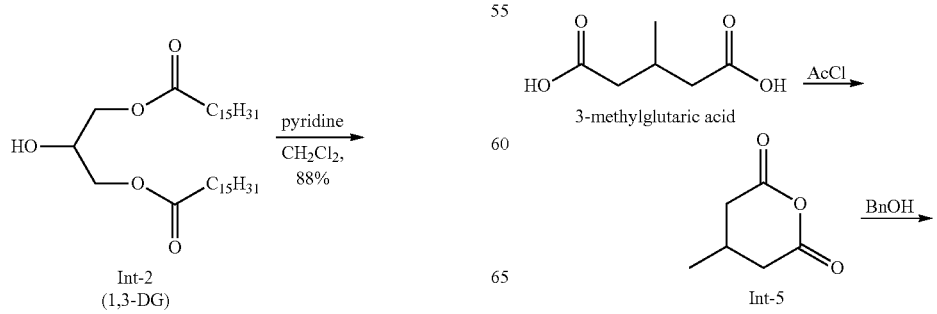

Int-2
(1,3-DG)

3-methylglutaric acid

Int-5

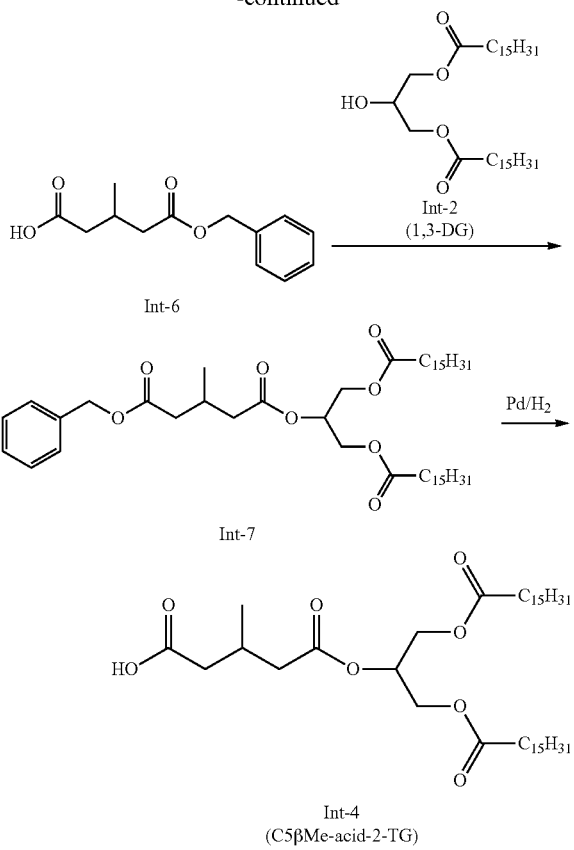

Int-6

(1,3-DG)

Int-7

Pd/H$_2$

Int-4
(C5βMe-acid-2-TG)

(68 g, 86.5 mmol, 29% yield) as a white solid. $^1$H NMR (400 MHz, chloroform-d) δ 7.40-7.32 (m, 5H), 5.30-5.24 (m, 1H), 5.12 (s, 2H), 4.31-4.27 (m, 2H), 4.17-4.10 (m, 2H), 2.50-2.38 (m, 3H), 2.34-2.28 (m, 6H), 1.61-1.55 (m, 4H), 1.35-1.20 (m, 48H), 1.02 (d, J=6.4 Hz, 3H), 0.88 (t, J=6.6 Hz, 6H).

Int-7 (68 g, 86.5 mmol) and palladium on carbon (3 g) were suspended in THF (400 mL). The mixture was hydrogenated under hydrogen atmosphere at 30° C. for 16 h, then filtered and concentrated to dryness. The residue was further purified by trituration with hexane to afford Int-4 (C5βMe-acid-2-TG) (51 g, 73.2 mmol, 84% yield) as a white solid. LC-MS: MS m/z=719 (M+Na+), RT=3.83 min. $^1$H NMR (400 MHz, chloroform-d) δ 5.31-5.25 (m, 1H), 4.34-4.29 (m, 2H), 4.16-4.12 (m, 2H), 2.49-2.40 (m, 3H), 2.33-2.28 (m, 6H), 1.62-1.57 (m, 4H), 1.35-1.20 (m, 48H), 1.06 (d, J=6.4 Hz, 3H), 0.88 (t, J=6.6 Hz, 6H).

C5βMe-acid-2-TG-oleate (Int-210):

Using the procedures depicted in Scheme 10 for the synthesis of Int-4, compound Int-210 was prepared from Int-112:

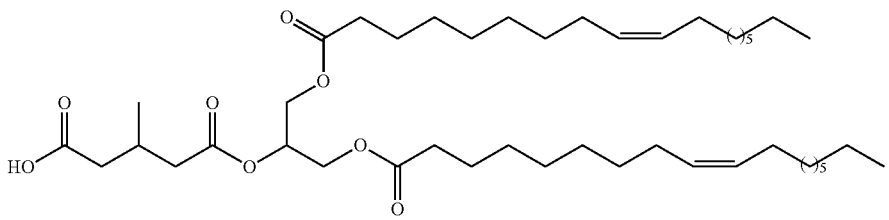 [SMILES: CCCC/C=C\CCCCCCCC(=O)OCC(COC(=O)CCCCCCC/C=C\CCCC)OC(=O)CC(C)CC(=O)O]

A mixture of 3-methylglutaric acid (100 g, 685 mmol) and acetyl chloride (250 mL, 3.53 mol) was heated under reflux for 16 h, then concentrated to dryness before adding into a solution of pyridine (270 g, 3.4 mol) and benzyl alcohol (100 g, 926 mmol) in dichloromethane (1500 mL) at room temperature. The mixture was stirred for 72 h. The reaction was concentrated and the residue was purified by silica column chromatography, eluting with from 0 to 50% ethyl acetate in petroleum ether to afford Int-6 (70 g, 297 mmol, 43% yield) as a yellowish oil. $^1$H NMR (400 MHz, chloroform-d) δ 7.39-7.30 (m, 5H), 5.12 (s, 2H), 2.52-2.25 (m, 5H), 1.04 (d, J=6.6 Hz, 3H).

To a mixture of Int-6 (70 g, 297 mmol) and Int-2 (1,3-DG) (80 g, 140 mmol) in dichloromethane (1500 mL) was added EDCI (115 g, 600 mmol) and DMAP (3.66 g, 30 mmol). Triethylamine (100 mL, 719 mmol) was added drop wise at 0° C. The mixture was stirred at room temperature for 72 h. The reaction was concentrated to dryness and the residue was purified by silica column chromatography, eluting with ethyl acetate in petroleum ether from 0 to 50% to afford Int-7

$^1$H NMR (400 MHz, CDCl$_3$) δ 5.41 (m, 4H), 5.30 (m, 1H), 4.35 (m, 2H), 4.20 (m, 2H), 2.54 (d, 2H), 2.39 (m, 4H), 2.36 (m, 2H), 2.05 (m, 8H), 1.74 (m, 1H), 1.73 (m, 4H), 1.1-1.3 (m, 40H), 1.05 (d, 3H), 0.9 (t, 6H); $^{13}$C NMR (101 MHz, CDCl$_3$) δ 176.7 (1C, C=O), 173.3 (2C, C=O), 171.8 (1C, C=O), 130.01 (2C), 129.74 (2C), 68.86 (C, CH), 62.13 (2C), 42.26 2C), 40.9 (2C), 37.09 (1C), 33.99 (2C), 31.91 (2C), 29.78-29.10 (14C), 27.7 (3C), 24.82 (2C), 22.71 (2C), 19.7 (1C), 16.32 (1C) 14.14 (2C); MS (ESI, –ve) m/z: 784.4 (M–1).

C10-acid-2-TG:

Scheme 12. Synthesis of Int-9.

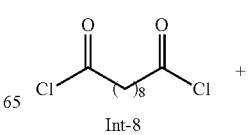

Int-8

-continued

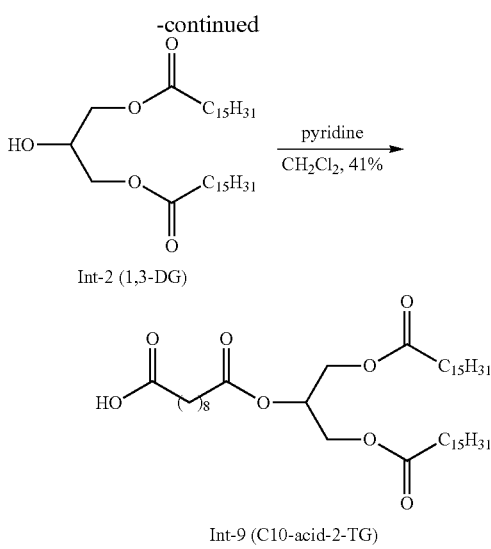

A mixture of sebacic acid (88.0 mg, 0.435 mmol) and DMF (one drop) in thionyl chloride (316 µL, 4.35 mmol) was heated at reflux for 1.5 hours. The reaction was cooled to RT, diluted with toluene (5 mL) and concentrated under reduced pressure to give diacid chloride Int-8 (104 mg, quant.) as a yellow oil that was used without purification. $^1$H NMR (400 MHz, chloroform-d) δ 2.88 (t, J=7.3 Hz, 4H), 1.76-1.66 (m, 4H), 1.42-1.26 (m, 8H).

A solution of Int-2 (1,3-DG) (45.0 mg, 0.0791 mmol) and pyridine (64.0 µL, 0.791 mmol) in dichloromethane (1.5 mL) was added to diacid chloride Int-8 (104 mg, 0.435 mmol) in dichloromethane (1.5 mL) and the mixture stirred at rt for 1.5 hours. The reaction was diluted with ethyl acetate (5 mL), water (10 mL) and 1 M HCl (3 mL) and the aqueous layer extracted with ethyl acetate (3×15 mL). The combined organic extracts were washed with 1 M HCl (30 mL) and brine (30 mL), dried (MgSO$_4$) and concentrated under reduced pressure to give the crude product. Purification by silica gel chromatography (20% to 50% ethyl acetate/hexanes) gave Int-9 (C10-acid-2-TG) (24.3 mg, 41%) as a pale yellow solid. $^1$H NMR (400 MHz, CDCl$_3$) δ 5.26 (m, 1H), 4.29 (dd, J=11.9, 4.4 Hz, 2H), 4.14 (dd, J=11.9, 5.9 Hz, 2H), 2.37-2.27 (m, 8H), 1.70-1.53 (m, 8H), 1.39-1.19 (m, 56H), 0.87 (t, J=6.9 Hz, 6H); $^{13}$C NMR (101 MHz, CDCl$_3$) δ 178.6 (C), 173.5 (2C; C), 173.0 (C), 69.0 (CH), 62.2 (CH$_2$), 34.3 (CH$_2$), 34.2 (2C; CH$_2$), 33.9 (CH$_2$), 32.01 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 29.2 (2C; CH$_2$), 29.11 (CH$_2$), 29.10 (CH$_2$), 25.00 (2C; CH$_2$), 24.95 (CH$_2$), 24.8 (CH$_2$), 22.8 (2C; CH$_2$), 14.3 (2C; CH$_3$).

Alternate Procedure (Larger Scale):

Scheme 13. Synthesis of Int-9.

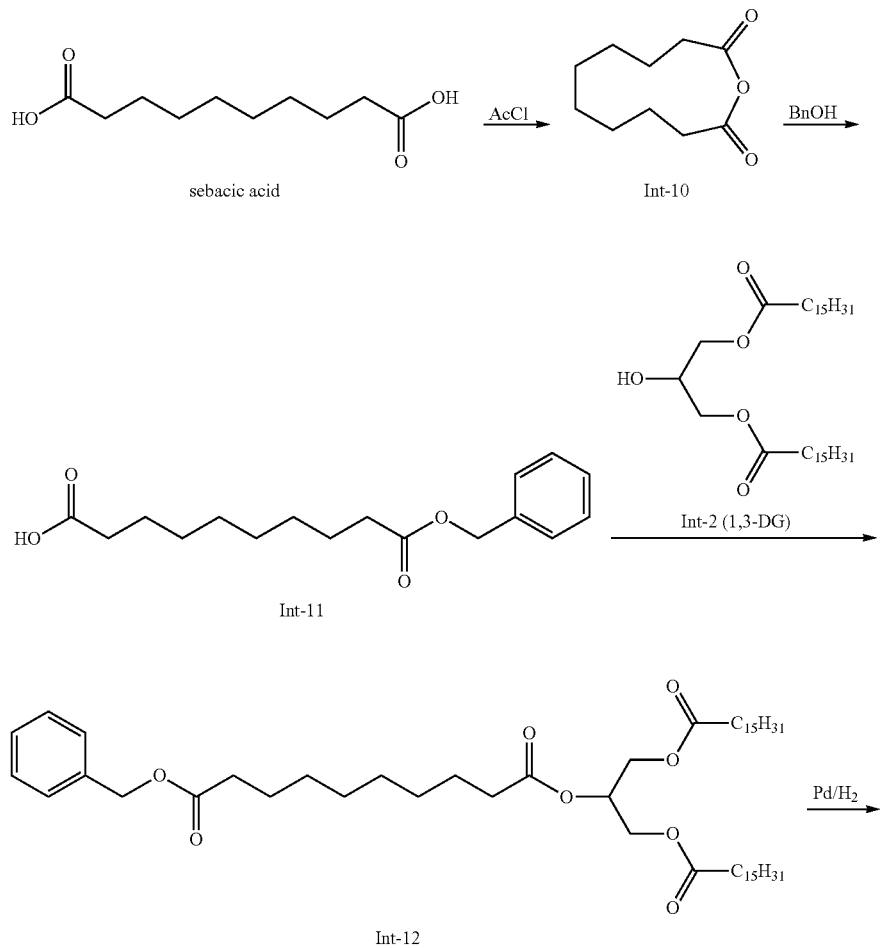

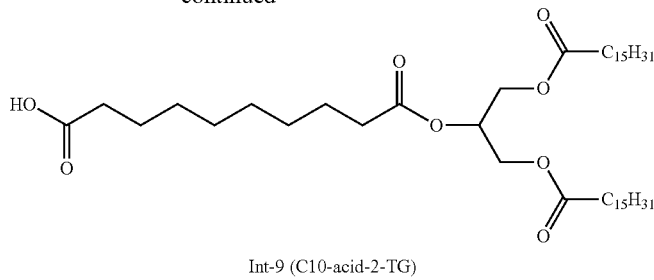

Int-9 (C10-acid-2-TG)

A mixture of sebacic acid (100 g, 495 mmol) and acetyl chloride (250 mL, 3.53 mol) was heated under reflux for 16 h, then cooled and concentrated to dryness. It was added into a solution of pyridine (270 g, 3.4 mol) and benzyl alcohol (100 g, 926 mmol) in dichloromethane (1500 mL) at room temperature and the mixture was stirred for 72 h. The reaction was concentrated and the residue was purified by column chromatography, eluting with from 0 to 50% ethyl acetate in petroleum ether to afford Int-11 (82 g, 281 mmol, 57% yield) as a yellowish oil. LC-MS: MS m/z=293 (M+H+), RT=1.45 min.

To a mixture of Int-11 (82 g, 281 mmol) and Int-2 (1,3-DG) (80 g, 140 mmol) in dichloromethane (1500 mL) was added EDCI (115 g, 600 mmol) and DMAP (3.66 g, 30 mmol). Then triethylamine (100 mL, 719 mmol) was added dropwise at 0° C. The mixture was stirred at room temperature for 72 h. The reaction was concentrated to dryness and the residue was purified by column chromatography, eluting with ethyl acetate in petroleum ether from 0 to 50% to afford Int-12 (65 g, 77 mmol, 27% yield) as a white solid. $^1$H NMR (400 MHz, chloroform-d) δ 7.38-7.29 (m, 5H), 5.27-5.25 (m, 1H), 5.11 (s, 2H), 4.31-4.27 (m, 2H), 4.17-4.12 (m, 2H), 2.37-2.29 (m, 8H), 1.65-1.57 (m, 8H), 1.35-1.20 (m, 56H), 0.88 (t, J=6.6 Hz, 6H).

Int-12 (65 g, 77 mmol) and palladium on carbon (3 g) were suspended in THF (400 mL). The mixture was hydrogenated under hydrogen atmosphere at 30° C. for 16 h, then it was filtered and the filtrate concentrated to dryness and then further purified by trituration with hexane to afford Int-9 (C10-acid-2-TG) (50 g, 66.4 mmol, 86% yield) as a white solid. LC-MS: MS m/z=775 (M+Na+), RT=5.95 min; $^1$H NMR (400 MHz, chloroform-d) δ 5.29-5.24 (m, 1H), 4.31-4.27 (m, 2H), 4.19-4.12 (m, 2H), 2.37-2.39 (m, 8H), 1.65-1.58 (m, 8H), 1.35-1.20 (m, 56H), 0.88 (t, J=6.6 Hz, 6H).

Int-120 was Prepared Using Similar Methods:

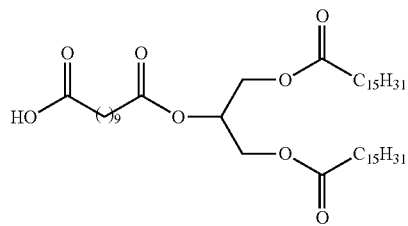

$^1$H NMR (401 MHz, CDCl$_3$) δ 5.25 (m, 1H), 4.28 (dd, J=11.9, 4.3 Hz, 2H), 4.13 (dd, J=11.9, 5.9 Hz, 2H), 2.35-2.26 (m, 8H), 1.65-1.54 (m, 8H), 1.35-1.18 (m, 58H), 0.86 (t, J=6.9 Hz, 6H); $^{13}$C NMR (101 MHz, CDCl$_3$) δ 179.9 (C), 173.4 (2C; C), 173.0 (C), 69.0 (CH), 62.2 (2C; CH$_2$), 34.3 (CH$_2$), 34.2 (2C; CH$_2$), 34.1 (CH$_2$), 32.0 (2C; CH$_2$), 29.81 (6C; CH$_2$), 29.77 (4C; CH$_2$), 29.74 (2C; CH$_2$), 29.59 (2C; CH$_2$), 29.48 (2C; CH$_2$), 29.38 (2C; CH$_2$), 29.36 (CH$_2$), 29.31 (2C; CH$_2$), 29.22 (2C; CH$_2$), 29.15 (CH$_2$), 29.13 (CH$_2$), 25.0 (3C; CH$_2$), 24.8 (CH$_2$), 22.8 (2C; CH$_2$), 14.2 (2C; CH$_3$). ESI-HRMS: calcd. for C$_{46}$H$_{86}$NaO$_8$ [M+Na$^+$] 789.6215; found 789.6218.

C12α'βMe-acid-2-TG (Int-23 and Int-27):

Scheme 14. Synthesis of Int-23 and Int-27.

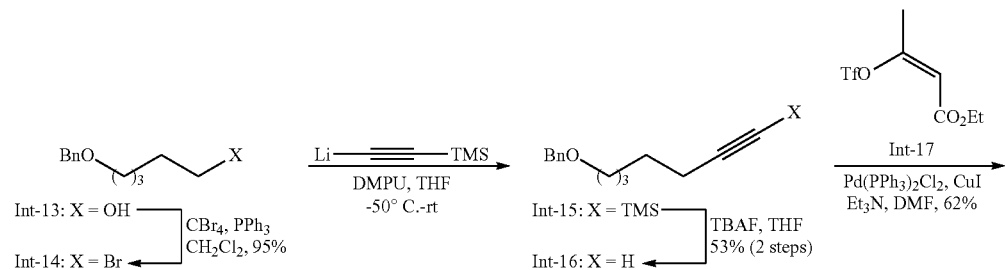

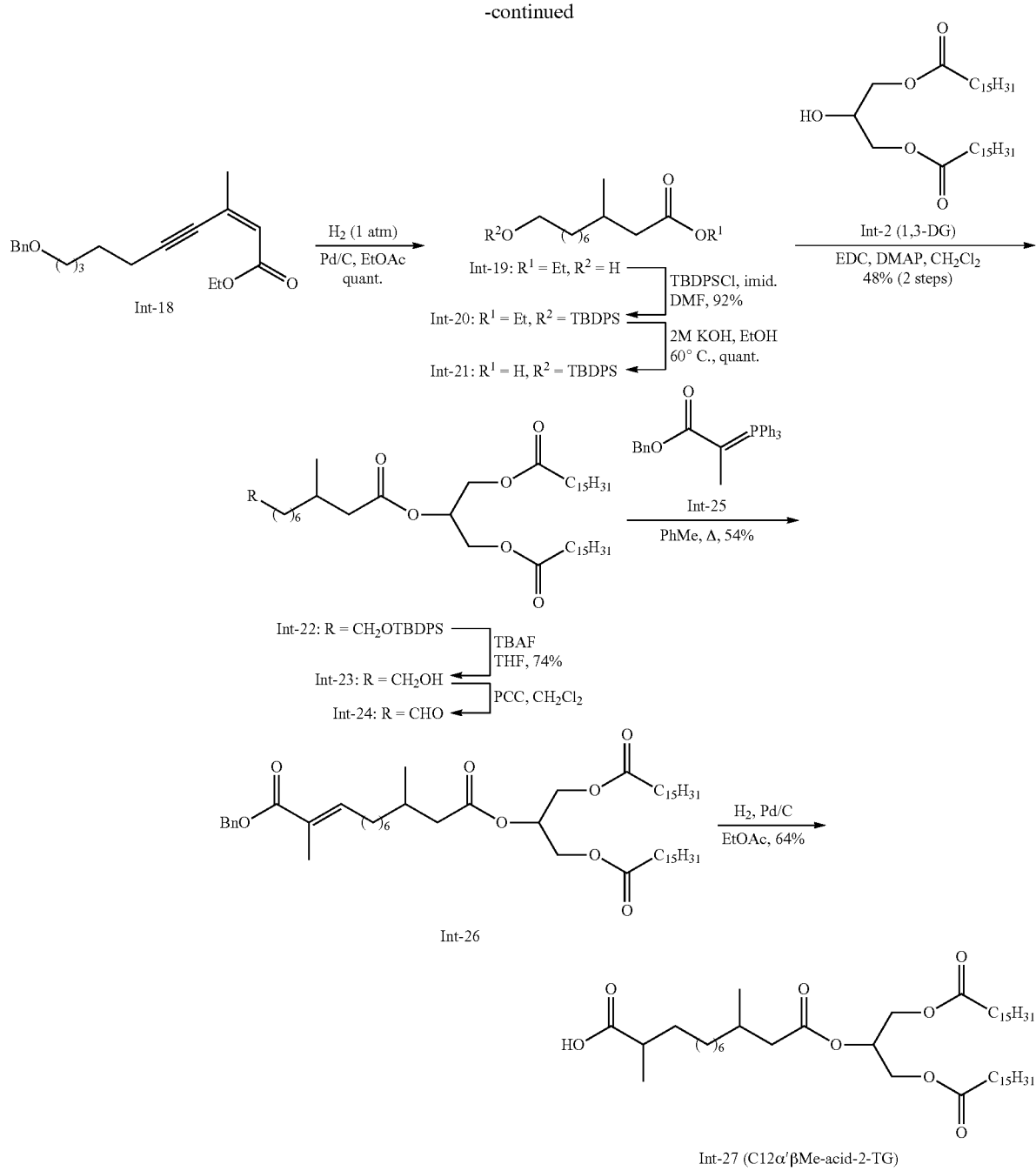

Int-27 (C12α'βMe-acid-2-TG)

Int-13: prepared according to: Young, I. S.; Kerr, M. A. *J. Am. Chem. Soc.* 2007, 129, 1465-1469.

Int-14: prepared according to: Chowdhury, R.; Ghosh, S. K. *Org. Lett.* 2009, 11, 3270-3273.

n-Butyllithium (n-BuLi, 1.6 M in hexanes, 765 μL, 1.23 mmol) was added slowly to a solution of TMS-acetylene (198 μL, 1.40 mmol) in THF (1.5 mL) at −78° C. and the mixture stirred at −78° C. for five minutes then warmed to rt and stirred for a further 15 minutes. The reaction was re-cooled to −50° C., a solution of bromide Int-14 (90.0 mg, 0.350 mmol) in THF (1 mL) was added dropwise and the mixture stirred at −50° C. for 15 minutes and then at room temperature for 17 hours. The reaction was diluted with brine (15 mL) and the aqueous phase extracted with ethyl acetate (3×15 mL). The combined organic extracts were washed with brine (30 mL), dried (MgSO$_4$) and concentrated under reduced pressure to give the crude product. Purification by silica gel chromatography (4% to 5% ethyl acetate/hexanes) gave TMS alkyne Int-15 (45.9 mg, 48%) as a colorless oil also containing desilylated alkyne Int-16 (9.7 mg, 14% by $^1$H NMR integration) and small amounts of PPh$_3$. $^1$H NMR (400 MHz, CDCl$_3$) δ 7.37-7.26 (m, 5H), 4.50 (s, 2H), 3.48 (t, J=6.5 Hz, 2H), 2.23 (t, J=7.0 Hz, 2H), 1.68-1.60 (m, 2H), 1.58-1.42 (m, 4H), 0.14 (s, J=3.4 Hz, 7H).

Tetrabutylammonium fluoride (TBAF, 1.0 M in THF, 201 μL, 0.201 mmol) was added dropwise to a 7:2 mixture of silylalkyne Int-15 and alkyne Int-16 (55.6 mg combined, 0.215 mmol) in THF (1 mL) at 0° C. and the mixture stirred at room temperature for one hour. The reaction was diluted with water (5 mL) and sat. aq. NH$_4$Cl (3 mL) and the aqueous phase extracted with ethyl acetate (3×10 mL). The combined organic extracts were washed with brine (20 mL), dried (MgSO$_4$) and concentrated under reduced pressure to give the crude product. Purification by silica gel chromatography (4% ethyl acetate/hexanes) gave alkyne Int-16 (37.5 mg, 53% over two steps) as a colorless oil. $^1$H NMR (400 MHz, CDCl$_3$) δ 7.39-7.27 (m, 5H), 4.51 (s, 2H), 3.49 (t, J=6.5 Hz, 2H), 2.21 (td, J=6.9, 2.6 Hz, 2H), 1.95 (t, J=2.7 Hz, 1H), 1.70-1.61 (m, 2H), 1.60-1.48 (m, 4H); $^{13}$C NMR (101 MHz, CDCl$_3$) δ 138.7 (C), 128.5 (2C; CH), 127.7 (2C; CH), 127.6 (CH), 84.6 (C), 73.0 (CH$_2$), 70.3 (CH$_2$), 68.4 (CH), 29.4 (CH$_2$), 28.4 (CH$_2$), 25.5 (CH$_2$), 18.5 (CH$_2$).

Int-17: prepared according to: Kim, H.-O. et al. *Synlett* 1998, 1059-1060.

A suspension of PdCl$_2$(PPh$_3$)$_2$ (16.8 mg, 0.0240 mmol) in DMF (1.5 mL) was degassed using N$_2$ gas for five minutes, and then CuI (9.1 mg, 0.0480 mmol), Et$_3$N (66.8 µL, 0.480 mmol) and a degassed solution of alkyne Int-16 (48.5 mg, 0.240 mmol) and enol triflate Int-17 (94.3 mg, 0.360 mmol) in DMF (2 mL) were added. The mixture was degassed using a stream of N$_2$ for a further five minutes and then heated at 50° C. for one hour. The reaction mixture was cooled to room temperature, diluted with ethyl acetate (30 mL), washed with 1 M HCl, sat. aq. NaHCO$_3$, water and brine (20 mL each), dried (MgSO$_4$) and concentrated under reduced pressure to give the crude product. Silica gel chromatography (4% to 5% ethyl acetate/hexanes) gave enyne Int-18 (46.6 mg, 62%) as a pale yellow oil. $^1$H NMR (400 MHz, CDCl$_3$) δ 7.37-7.24 (m, 5H), 5.92 (m, 1H), 4.50 (s, 2H), 4.17 (q, J=7.1 Hz, 2H), 3.48 (t, J=6.5 Hz, 2H), 2.45 (t, J=7.0 Hz, 2H), 2.01 (d, J=1.4 Hz, 3H), 1.69-1.59 (m, 4H), 1.56-1.49 (m, 2H), 1.27 (t, J=7.1 Hz, 3H); $^{13}$C NMR (101 MHz, CDCl$_3$) δ 165.4 (C), 138.8 (C), 135.9 (C), 128.5 (2C; CH), 127.7 (2C; CH), 127.6 (CH), 123.4 (CH), 102.9 (C), 80.0 (C), 73.0 (CH$_2$), 70.4 (CH$_2$), 60.0 (CH$_2$), 29.4 (CH$_2$), 28.4 (CH$_2$), 26.0 (CH$_3$), 25.7 (CH$_2$), 20.1 (CH$_2$), 14.4 (CH$_3$).

A solution of benzyl ether Int-18 (31.4 mg, 0.100 mmol) in ethyl acetate (8 mL) in a three-neck round-bottom flask was twice evacuated and flushed with N$_2$ gas, then palladium on carbon (10% w/w, 26.6 mg, 0.0250 mmol) was added and the resulting suspension re-evacuated and flushed with N$_2$ three times. The flask was fitted with a H$_2$ balloon, evacuated and flushed with H$_2$ three times and the reaction mixture stirred at RT under 1 atm of H$_2$ for one hour. The flask was then evacuated and flushed with N$_2$ and the reaction mixture filtered through a pad of Celite, washing with ethyl acetate (30 mL). The filtrate was concentrated under reduced pressure to give saturated alcohol Int-19 (23.0 mg, quant.) as a colorless oil that was used without purification. $^1$H NMR (400 MHz, CDCl$_3$) δ 4.12 (q, J=7.1 Hz, 2H), 3.63 (t, J=6.6 Hz, 2H), 2.28 (dd, J=14.6, 6.1 Hz, 1H), 2.09 (dd, J=14.6, 8.1 Hz, 1H), 1.94 (m, 1H), 1.60-1.50 (m, 2H), 1.25 (t, J=6.6 Hz, 3H), 1.40-1.13 (m, 10H), 0.92 (d, J=6.6 Hz, 3H); $^{13}$C NMR (101 MHz, CDCl$_3$) δ 173.6 (C), 63.2 (CH$_2$), 60.2 (CH$_2$), 42.1 (CH$_2$), 36.8 (CH$_2$), 32.9 (CH$_2$), 30.5 (CH), 29.8 (CH$_2$), 29.5 (CH$_2$), 26.9 (CH$_2$), 25.8 (CH$_2$), 19.9 (CH$_3$), 14.4 (CH$_3$).

Imidazole (9.6 mg, 0.141 mmol) and tert-butyl(chloro)diphenylsilane (TBDPSCl, 50.8 µL, 0.195 mmol) were added to a solution of alcohol Int-19 (18.0 mg, 0.0781 mmol) in DMF (3 mL) and the mixture stirred at RT for 16 hours. The reaction was diluted with ethyl acetate (20 mL), washed with brine (2×20 mL), dried (MgSO$_4$), and concentrated under reduced pressure to give the crude product. Purification by silica gel chromatography (4% ethyl acetate/hexanes with 0.5% Et$_3$N) gave TBDPS ether Int-20 (33.7 mg, 92%) as a colorless oil. $^1$H NMR (400 MHz, CDCl$_3$) δ 7.70-7.64 (m, 4H), 7.45-7.33 (m, 6H), 4.13 (q, J=7.1 Hz, 2H), 3.65 (t, J=6.5 Hz, 2H), 2.28 (dd, J=14.6, 6.0 Hz, 1H), 2.09 (dd, J=14.6, 8.2 Hz, 1H), 1.94 (m, 1H), 1.60-1.50 (m, 2H), 1.38-1.21 (m, 3H), 1.05 (s, J=2.9 Hz, 2H), 1.05 (s, 9H), 0.93 (d, J=6.6 Hz, 3H); $^{13}$C NMR (101 MHz, CDCl$_3$) δ 173.6 (C), 135.7 (4C; CH), 134.3 (2C; C), 129.6 (2C; CH), 127.7 (4C; CH), 64.1 (CH$_2$), 60.2 (CH$_2$), 42.1 (CH$_2$), 36.9 (CH$_2$), 32.7 (CH$_2$), 30.5 (CH), 29.9 (CH$_2$), 29.5 (CH$_2$), 27.01 (3C; CH$_3$), 26.99 (CH$_2$), 25.9 (CH$_2$), 19.9 (CH$_3$), 19.4 (C), 14.4 (CH$_3$).

A solution of potassium hydroxide (2.0 M, 427 µL, 0.853 mmol) was added to ester Int-20 (40.0 mg, 0.0853 mmol) in ethanol (2 mL) and the mixture heated at 80° C. for two hours. The reaction was cooled to RT, acidified to pH 1 by addition of 1 M HCl and the organic solvent removed under reduced pressure. The residue was diluted with water (5 mL) and the aqueous phase extracted with ethyl acetate (3×15 mL). The combined organic extracts were washed with brine (30 mL), dried (MgSO$_4$) and concentrated under reduced pressure to give crude acid Int-21 (37.6 mg, quant.) as a colorless oil that was used without purification. $^1$H NMR (400 MHz, CDCl$_3$) δ 7.74-7.63 (m, 4H), 7.45-7.34 (m, 6H), 3.65 (t, J=6.5 Hz, 2H), 2.35 (dd, J=15.0, 5.9 Hz, 1H), 2.14 (dd, J=15.0, 8.2 Hz, 1H), 1.95 (m, 1H), 1.61-1.50 (m, 2H), 1.38-1.18 (m, 10H), 1.04 (s, 9H), 0.96 (d, J=6.6 Hz, 3H); $^{13}$C NMR (101 MHz, CDCl$_3$) δ 179.5 (C), 135.7 (4C; CH), 134.3 (2C; C), 129.6 (2C; CH), 127.7 (4C; CH), 64.1 (CH$_2$), 41.7 (CH$_2$), 36.8 (CH$_2$), 32.7 (CH$_2$), 30.3 (CH), 29.8 (CH$_2$), 29.5 (CH$_2$), 27.01 (3C; CH$_3$), 26.97 (CH$_2$), 25.9 (CH$_2$), 19.8 (CH$_3$), 19.4 (C). Note: While two sets of signals were observed in both the $^1$H and $^{13}$C NMR spectra, only the major set of signals are reported above. It was unclear if the doubling was due to the presence of two closely-related compounds or the presence of both monomeric and dimeric species due to the high concentration of the NMR sample.

DMAP (10.1 mg, 0.0831 mmol), EDC·HCl (39.8 mg, 0.208 mmol) and Int-2 (1,3-DG) (70.9 mg, 0.125 mmol) were added to a solution of acid Int-21 (36.6 mg, 0.0831 mmol) in dichloromethane (2.5 mL) and the mixture stirred at room temperature for 21 hours. The reaction was diluted with dichloromethane (5 mL), silica gel was added and the mixture concentrated under reduced pressure. Purification by silica gel chromatography (4% to 5% ethyl acetate/hexanes) gave triglyceride Int-22 (39.9 mg, 48% over two steps) as a colorless solid. $^1$H NMR (400 MHz, CDCl$_3$) δ 7.69-7.64 (m, 4H), 7.44-7.34 (m, 6H), 5.28 (m, 1H), 4.289/4.287 (each dd, J=11.8, 4.2 Hz, 2H), 4.14 (dd, J=12.0, 5.9 Hz, 2H), 3.65 (t, J=6.5 Hz, 2H), 2.37-2.27 (m, 5H), 2.11 (dd, J=14.7, 8.4 Hz, 1H), 1.92 (m, 1H), 1.67-1.50 (m, 8H), 1.39-1.14 (m, 56H), 1.04 (s, 9H), 0.93 (d, J=6.6 Hz, 3H), 0.88 (t, J=6.9 Hz, 6H); $^{13}$C NMR (101 MHz, CDCl$_3$) δ 173.5 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 34.2 (2C; CH$_2$), 32.7 (CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.6 (2C; CH$_2$), 29.54 (CH$_2$), 29.51 (2C; CH$_2$), 29.4 (2C; CH$_2$), 29.3 (2C; CH$_2$), 27.02 (CH$_2$), 27.00 (3C; CH$_3$), 25.9 (CH$_2$), 25.0 (2C; CH$_2$), 22.8 (2C; CH$_2$), 19.7 (CH$_3$), 19.4 (C), 14.3 (2C; CH$_3$).

Tetrabutylammonium fluoride (TBAF, 1.0 M in THF, 98.3 µL, 98.3 µmol) was added to a solution of TBDPS ether Int-22 (39.0 mg, 39.3 µmol) in THF (2.5 mL) at 0° C. and the mixture stirred at room temperature for three hours. The reaction was diluted with water (10 mL), extracted with ethyl acetate (3×15 mL), and the organic extracts washed with brine (30 mL), dried (MgSO₄) and concentrated under reduced pressure to give the crude product. Purification by silica gel chromatography (10% to 20% ethyl acetate/hexanes) gave alcohol Int-23 (21.8 mg, 74%) as a colorless solid. $^1$H NMR (400 MHz, CDCl₃) δ 5.28 (m, 1H), 4.29 (dd, J=11.9, 4.3 Hz, 2H), 4.14 (dd, J=11.9, 5.9 Hz, 2H), 3.64 (t, J=6.6 Hz, 2H), 2.36-2.27 (m, 5H), 2.12 (dd, J=14.7, 8.2 Hz, 1H), 1.93 (m, 1H), 1.65-1.52 (m, 6H), 1.39-1.16 (m, 58H), 0.93 (d, J=6.6 Hz, 3H), 0.88 (t, J=6.9 Hz, 6H); $^{13}$C NMR (101 MHz, CDCl₃) δ 173.5 (2C; C), 172.5 (C), 68.9 (CH), 63.2 (CH₂), 62.3 (2C; CH₂), 41.8 (CH₂), 36.7 (CH₂), 34.2 (2C; CH₂), 32.9 (CH₂), 32.1 (2C; CH₂), 30.5 (CH), 29.84 (4C; CH₂), 29.83 (2C; CH₂), 29.80 (4C; CH₂), 29.77 (2C; CH₂), 29.6 (2C; CH₂), 29.5 (3C; CH₂), 29.4 (2C; CH₂), 29.3 (3C; CH₂), 26.9 (CH₂), 25.8 (CH₂), 25.0 (2C; CH₂), 22.8 (2C; CH₂), 19.7 (CH₃), 14.3 (2C; CH₃).

Pyridinium chlorochromate (PCC, 12.0 mg, 55.8 μmol) was added to a suspension of alcohol Int-23 (21.0 mg, 27.9 μmol) and celite (15 mg) in dichloromethane (1.5 mL) at 0° C. and the mixture stirred at room temperature for 1.75 hours. The reaction was filtered through a short pad of silica gel, eluting with ethyl acetate, and the filtrate concentrated under reduced pressure to give crude aldehyde Int-24 (20.9 mg, quant.) as a yellow oil that was used without purification.

$^1$H NMR (400 MHz, CDCl₃) δ 9.76 (s, 1H), 5.28 (m, 1H), 4.29 (dd, J=11.6, 3.5 Hz, 2H), 4.14 (dd, J=11.6, 5.7 Hz, 2H), 2.42 (t, J=7.1 Hz, 2H), 2.36-2.25 (m, 5H), 2.12 (dd, J=14.5, 8.3 Hz, 1H), 1.93 (m, 1H), 1.72-1.53 (m, 6H), 1.42-1.05 (m, 56H), 0.93 (d, J=6.5 Hz, 3H), 0.88 (t, J=6.6 Hz, 6H).

Int-25: prepared according to: Gossauer, A.; Kuhne, G. *Liebigs. Ann. Chem.* 1977, 664-686.

A solution of ylide Int-25 (8.1 mg, 19.0 μmol) in toluene (0.4 mL) was added to aldehyde Int-24 (11.0 mg, 14.6 μmol) in toluene (0.6 mL) and the mixture heated at reflux for four hours. The reaction was cooled to rt and concentrated under reduced pressure to give the crude product. Purification by silica gel chromatography (5% to 10% ethyl acetate/hexanes) gave α,β-unsaturated benzyl ester Int-26 (7.1 mg, 54%) as a yellow oil. $^1$H NMR (401 MHz, CDCl₃) δ 7.41-7.27 (m, 5H), 6.81 (td, J=7.5, 1.4 Hz, 1H), 5.27 (m, 1H), 5.18 (s, 2H), 4.29 (dd, J=11.9, 4.3 Hz, 2H), 4.14 (dd, J=11.9, 6.0 Hz, 2H), 2.36-2.27 (m, 5H), 2.20-2.08 (m, 3H), 1.93 (m, 1H), 1.85 (d, J=1.2 Hz, 3H), 1.67-1.54 (m, 6H), 1.47-1.38 (m, 2H), 1.37-1.19 (m, 54H), 0.93 (d, J=6.6 Hz, 3H), 0.88 (t, J=6.9 Hz, 6H); $^{13}$C NMR (101 MHz, CDCl₃) δ 173.4 (2C; C), 172.4 (C), 168.2 (C), 143.2 (CH), 136.6 (C), 128.7 (2C; CH), 128.2 (CH), 128.1 (2C; CH), 127.6 (C), 69.0 (CH), 66.3 (CH₂), 62.3 (2C; CH₂), 41.8 (CH₂), 36.8 (CH₂), 34.2 (2C; CH₂), 32.1 (2C; CH₂), 30.5 (CH), 29.85 (6C; CH₂), 29.81 (4C; CH₂), 29.77 (2C; CH₂), 29.74 (CH₂), 29.63 (2C; CH₂), 29.56 (CH₂), 29.51 (2C; CH₂), 29.4 (2C; CH₂), 29.3 (2C; CH₂), 28.9 (CH₂), 28.7 (CH₂), 27.0 (CH₂), 25.0 (2C; CH₂), 22.8 (2C; CH₂), 19.7 (CH₂), 14.3 (2C; CH₂), 12.6 (CH₂).

A solution of benzyl ether Int-26 (48.5 mg, 54.0 μmol) in ethyl acetate (2.5 mL) in a two-neck flask was evacuated and flushed with N₂ gas (three times each), then palladium on carbon (10% w/w, 11.5 mg, 10.8 μmol) was added and the resulting suspension re-evacuated and flushed with N₂ (three times each). The flask was fitted with a H₂ balloon, evacuated and flushed with H₂ (three times each) and the reaction mixture stirred at room temperature under 1 atm of H₂ for three hours. The reaction was filtered through a pad of celite, washing with ethyl acetate, and concentrated under reduced pressure to give the crude product. Purification by silica gel chromatography (10% to 20% ethyl acetate/hexanes) gave saturated acid Int-27 (C12α'βMe-acid-2-TG) (28.1 mg, 64%) as a colorless oil. $^1$H NMR (401 MHz, CDCl₃) δ 5.27 (m, 1H), 4.29 (dd, J=11.9, 4.3 Hz, 2H), 4.14 (dd, J=11.9, 6.1 Hz, 2H), 2.46 (m, 1H), 2.37-2.26 (m, 5H), 2.12 (dd, J=14.7, 8.2 Hz, 1H), 1.94 (m, 1H), 1.73-1.55 (m, 5H), 1.41 (m, 1H), 1.37-1.20 (m, 60H), 1.18 (d, J=7.0 Hz, 3H), 0.93 (d, J=6.6 Hz, 3H), 0.88 (t, J=6.9 Hz, 6H); $^{13}$C NMR (101 MHz, CDCl₃) δ 182.3 (C), 173.5 (2C; C), 172.5 (C), 69.0 (CH), 62.3 (2C; CH₂), 41.8 (CH₂), 39.4 (CH), 36.8 (CH₂), 34.2 (2C; CH₂), 33.7 (CH₂), 32.1 (2C; CH₂), 30.5 (CH), 29.84 (6C; CH₂), 29.80 (4C; CH₂), 29.77 (2C; CH₂), 29.62 (2C; CH₂), 29.60 (CH₂), 29.57 (CH₂), 29.5 (2C; CH₂), 29.4 (2C; CH₂), 29.3 (2C; CH₂), 27.3 (CH₂), 27.0 (CH₂), 25.0 (2C; CH₂), 22.8 (2C; CH₂), 19.7 (CH₃), 17.0 (CH₃), 14.3 (2C; CH₃).

C4-acid-2-TG (Int-28):

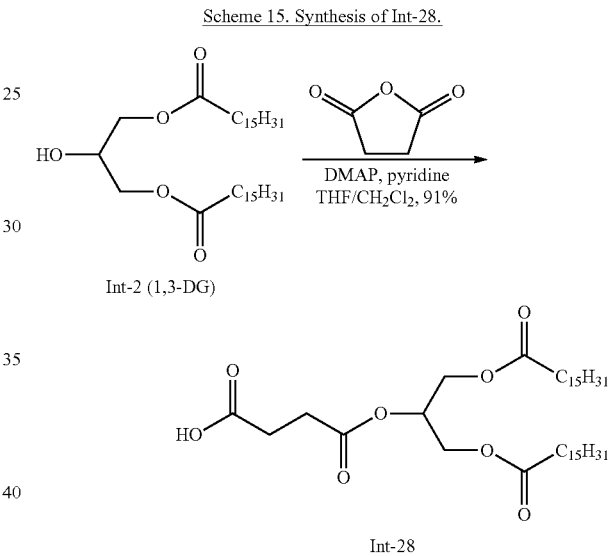

Scheme 15. Synthesis of Int-28.

4-(Dimethylamino)pyridine (DMAP, 15.5 mg, 0.127 mmol) was added to a solution of 1,3-diglyceride Int-2 (72.2 mg, 0.127 mmol) and succinic anhydride (25.4 mg, 0.254 mmol) in pyridine/THF/CH₂Cl₂ (0.5 mL each) and the mixture stirred at room temperature for 17 hours. An extra portion of succinic anhydride (25.4 mg, 0.254 mmol) and DMAP (15.5 mg, 0.127 mmol) was added and the solution heated at 40° C. for a further 22 hours. The reaction was diluted with ethyl acetate (25 mL), washed with 1 M HCl (20 mL) and brine (2×30 mL), dried (MgSO₄) and concentrated under reduced pressure to give the crude product. Silica gel chromatography (15% to 25% ethyl acetate/hexanes) gave acid-TG Int-28 (77.0 mg, 91%) as a colorless solid. $^1$H NMR (400 MHz, CDCl₃) δ 5.27 (m, 1H), 4.30 (dd, J=12.0, 4.3 Hz, 2H), 4.15 (dd, J=12.0, 5.8 Hz, 2H), 2.72-2.61 (m, 4H), 2.31 (t, J=7.6 Hz, 4H), 1.67-1.54 (m, 4H), 1.36-1.19 (m, 48H), 0.88 (t, J=6.9 Hz, 6H); $^{13}$C NMR (101 MHz, CDCl₃) δ 176.9 (C), 173.5 (2C; C), 171.4 (C), 69.8 (CH), 62.0 (2C; CH₂), 34.2 (2C; CH₂), 32.1 (2C; CH₂), 29.84 (6C; CH₂), 29.81 (4C; CH₂), 29.77 (2C; CH₂), 29.6 (2C; CH₂), 29.5 (2C; CH₂), 29.4 (2C; CH₂), 29.3 (2C; CH₂), 29.0 (CH₂), 28.8 (CH₂), 25.0 (2C; CH₂), 22.8 (2C; CH₂), 14.3 (2C; CH₃).

C6-acid-2-TG (Int-29):

Scheme 16. Synthesis of Int-29.

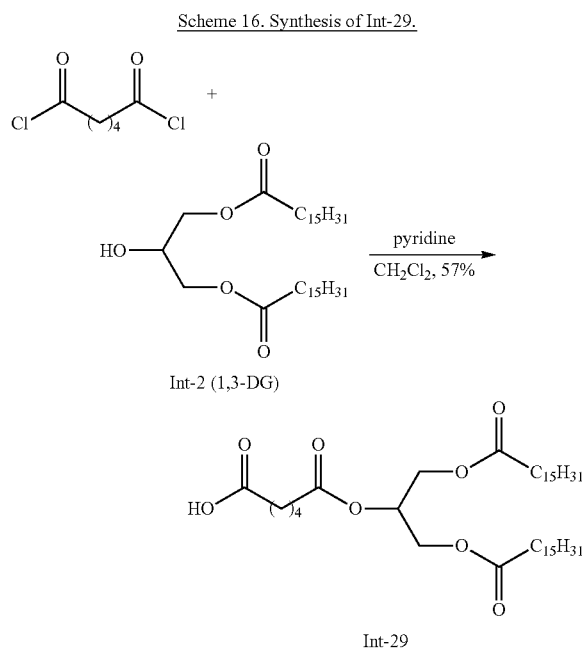

A solution of 1,3-diglyceride Int-2 (75.0 mg, 0.132 mmol) and pyridine (107 μL, 1.32 mmol) in CH$_2$Cl$_2$ (2.5 mL) was added to diacid chloride 1 (96.1 mL, 0.659 mmol) in CH$_2$Cl$_2$ (2.5 mL) and the mixture heated at reflux for 3.5 hours. The reaction was cooled to room temperature, diluted with ethyl acetate (30 mL) and the organic extract washed with 1 M HCl (20 mL) and brine (2×20 mL), dried (MgSO$_4$) and concentrated under reduced pressure to give the crude product. Purification by silica gel chromatography (15% to 25% ethyl acetate/hexanes) gave acid-TG Int-29 (52.7 mg, 57%) as a colorless solid. $^1$H NMR (400 MHz, CDCl$_3$) δ 5.26 (m, 1H), 4.30 (dd, J=11.9, 4.3 Hz, 2H), 4.14 (dd, J=11.9, 5.9 Hz, 2H), 2.41-2.34 (m, 4H), 2.31 (t, J=7.6 Hz, 4H), 1.72-1.65 (m, 4H), 1.65-1.56 (m, 4H), 1.35-1.20 (m, 48H), 0.88 (t, J=6.8 Hz, 6H); $^{13}$C NMR (101 MHz, CDCl$_3$) δ 178.3 (C), 173.5 (2C; C), 172.4 (C), 69.3 (CH), 62.2 (2C; CH$_2$), 34.2 (2C; CH$_2$), 33.8 (CH$_2$), 33.5 (CH$_2$), 32.1 (2C; CH$_2$), 29.84 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 24.3 (CH$_2$), 24.1 (CH$_2$), 22.8 (2C; CH$_2$), 14.3 (2C; CH$_2$).

C10βMe-acid-2-TG (Int-30):

Scheme 17. Synthesis of Int-30.

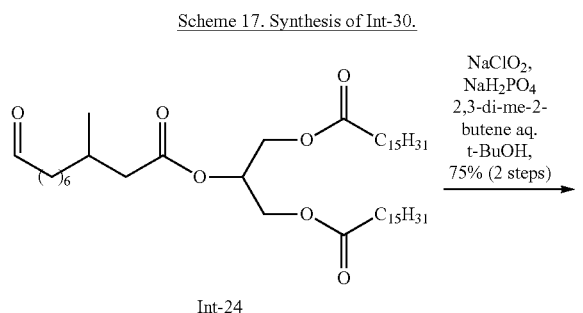

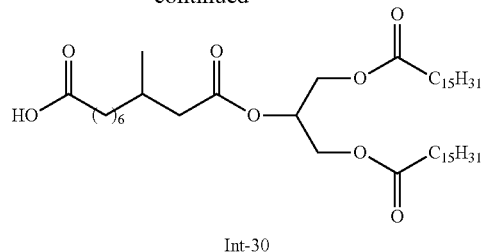

A solution of sodium chlorite (22.7 mg, 0.251 mmol) and sodium phosphate monobasic (NaH$_2$PO$_4$, 23.4 mg, 0.195 mmol) in water (1 mL) was added dropwise to aldehyde Int-24 (20.9 mg, 0.0279 mmol) in t-BuOH (1.5 mL) and 2,3-dimethyl-2-butene (0.3 mL) and the reaction stirred at room temperature for 2.25 hours. The reaction was diluted with water (10 mL) and the aqueous layer extracted with ethyl acetate (3×15 mL). The combined organic extracts were washed with brine (30 mL), dried (MgSO$_4$) and concentrated under reduced pressure to give the crude product. Purification by silica gel chromatography (10% to 20% ethyl acetate/hexanes with 0.5% acetic acid) gave acid Int-30 (16.1 mg, 75%) as a colorless solid. $^1$H NMR (400 MHz, CDCl$_3$) δ 5.27 (m, 1H), 4.29 (dd, J=11.9, 4.3 Hz, 2H), 4.14 (dd, J=12.0, 6.0 Hz, 2H), 2.37-2.27 (m, 7H), 2.12 (dd, J=14.7, 8.2 Hz, 1H), 1.93 (m, 1H), 1.67-1.55 (m, 6H), 1.40-1.14 (m, 56H), 0.93 (d, J=6.6 Hz, 3H), 0.88 (t, J=6.9 Hz, 6H); $^{13}$C NMR (101 MHz, CDCl$_3$) δ 179.7 (C), 173.5 (2C; C), 172.4 (C), 69.0 (CH), 62.3 (2C; CH$_2$), 41.8 (CH$_2$), 36.7 (CH$_2$), 34.2 (2C; CH$_2$), 34.1 (CH$_2$), 32.1 (2C; CH$_2$), 30.4 (CH), 29.82 (6C; CH$_2$), 29.79 (4C; CH$_2$), 29.75 (2C; CH$_2$), 29.6 (2C; CH$_2$), 29.5 (3C; CH$_2$), 29.4 (2C; CH$_2$), 29.24 (2C; CH$_2$), 29.16 (CH$_2$), 26.8 (CH$_2$), 25.0 (2C; CH$_2$), 24.8 (CH$_2$), 22.8 (2C; CH$_2$), 19.7 (CH$_3$), 14.2 (2C; CH$_3$).

C12βMe-OH-2-TG (Int-121):

Using similar methods to those described above for Int-23 synthesis, Int-121 was prepared:

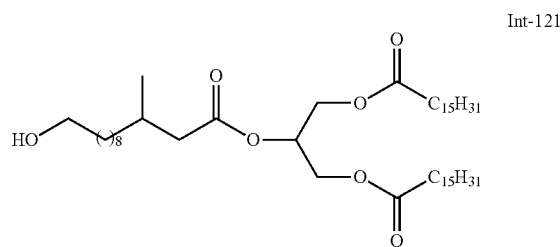

$^1$H NMR (401 MHz, CDCl$_3$) δ 5.28 (m, 1H), 4.29 (dd, J=11.9, 4.3 Hz, 2H), 4.14 (dd, J=11.8, 6.0 Hz, 2H), 3.64 (t, J=6.6 Hz, 2H), 2.32 (dd, J=14.6, 5.8 Hz, 1H), 2.30 (t, J=7.5 Hz, 4H), 2.12 (dd, J=14.6, 8.2 Hz, 1H), 1.94 (m, 1H), 1.64-1.49 (m, 6H), 1.40-1.13 (m, 62H), 0.93 (d, J=6.6 Hz, 3H), 0.88 (t, J=6.9 Hz, 6H); $^{13}$C NMR (101 MHz, CDCl$_3$) δ 173.3 (2C; C), 172.4 (C), 68.9 (CH), 62.9 (CH$_2$), 62.2 (2C; CH$_2$), 41.7 (CH$_2$), 36.7 (CH$_2$), 34.1 (2C; CH$_2$), 32.9 (CH$_2$), 32.0 (2C; CH$_2$), 30.4 (CH), 29.80 (CH$_2$), 29.76 (6C; CH$_2$), 29.72 (4C; CH$_2$), 29.68 (2C; CH$_2$), 29.65 (CH$_2$), 29.62 (CH$_2$), 29.53 (2C; CH$_2$), 29.50 (CH$_2$), 29.4 (2C; CH$_2$), 29.3 (2C; CH$_2$), 29.2 (2C; CH$_2$), 27.0 (CH$_2$), 25.8 (CH$_2$), 24.9 (2C; CH$_2$), 22.7 (2C; CH$_2$), 19.6 (CH$_3$), 14.2 (2C; CH$_3$).

C12α'βMe-OH-2-TG (Int-143):

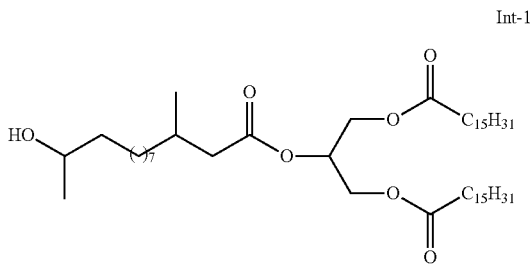

Pyridinium chlorochromate (16.5 mg, 0.0765 mmol) and Celite (16.5 mg) were added to a solution of alcohol Int-121 (40.0 mg, 0.0512 mmol) in $CH_2Cl_2$ (2.5 mL) at 0° C. and the resulting suspension stirred at 0° C. for 15 minutes and then at room temperature for three hours. The reaction mixture was filtered through a plug of silica gel, eluting with ethyl acetate (50 mL) and the filtrate concentrated under reduced pressure to give the corresponding aldehyde as a pale yellow oil that was used without purification.

The crude aldehyde was re-dissolved in diethyl ether (2.5 mL) and cooled to −10° C. (ice/brine bath). Methylmagnesium bromide (3.0 M in diethyl ether, 18.8 μL, 0.0563 mmol) was added and the reaction vessel transferred into the freezer (−20° C.) and allowed to stand for 19 hours. The mixture was warmed to −10° C., slowly quenched by the addition of sat. aq. $NH_4Cl$ solution (4 mL) and then warmed to room temperature. The aqueous layer was extracted with ethyl acetate (3×20 mL) and the combined organic extracts washed with water (25 mL) and brine (25 mL), dried ($MgSO_4$), and concentrated under reduced pressure to give the crude product. Silica gel chromatography (0% to 15% ethyl acetate/hexanes) gave alcohol Int-143 (21.6 mg, 53%) as a white solid. $^1H$ NMR (401 MHz, $CDCl_3$) δ 5.27 (m, 1H), 4.29 (dd, J=11.9, 3.8 Hz, 2H), 4.14 (dd, J=11.9, 6.0 Hz, 2H), 3.78 (m, 1H), 2.32 (dd, J=14.6, 5.8 Hz, 1H), 2.30 (t, J=7.5 Hz, 4H), 2.12 (dd, J=14.7, 8.2 Hz, 1H), 1.93 (m, 1H), 1.66-1.56 (m, 6H), 1.52-1.21 (m, 62H), 1.18 (d, J=6.2 Hz, 3H), 0.93 (d, J=6.6 Hz, 3H), 0.88 (t, J=6.9 Hz, 6H). $^{13}C$ NMR (101 MHz, $CDCl_3$) δ 173.5 (2C; C), 172.5 (C), 69.0 (CH), 68.3 (CH), 62.3 (2C; $CH_2$), 41.9 ($CH_2$), 39.5 ($CH_2$), 36.8 ($CH_2$), 34.2 (2C; $CH_2$), 32.1 (2C; $CH_2$), 30.5 (CH), 29.90 ($CH_2$), 29.85 (6C; $CH_2$), 29.81 (4C; $CH_2$), 29.78 (3C; $CH_2$), 29.75 ($CH_2$), 29.72 ($CH_2$), 29.6 (2C; $CH_2$), 29.5 (2C; $CH_2$), 29.4 (2C; $CH_2$), 29.3 (2C; $CH_2$), 27.1 ($CH_2$), 25.9 ($CH_2$), 25.0 (2C; $CH_2$), 23.7 ($CH_3$), 22.8 (2C; $CH_2$), 19.7 ($CH_3$), 14.3 (2C; $CH_3$).

C12α'βMe-OH-2-TG-oleate (Int-270):

Using similar methods to those described above for Int-143 synthesis, Int-269 and Int-270 were prepared from Int-235:

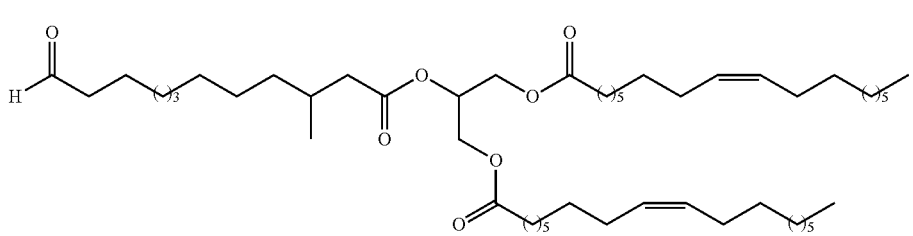

C12βMe-aldehyde-2-TG-oleate (Int-269) $^1H$ NMR (401 MHz, $CDCl_3$) δ 9.76 (t, J=1.8 Hz, 1H), 5.39-5.24 (m, 5H), 4.29 (dd, J=11.9, 4.2 Hz, 2H), 4.14 (dd, J=11.8, 6.1 Hz, 2H), 2.42 (td, J=7.3, 1.8 Hz, 2H), 2.32 (dd, J=14.7, 5.9 Hz, 1H), 2.30 (t, J=7.6 Hz, 4H), 2.12 (dd, J=14.7, 8.3 Hz, 1H), 2.05-1.87 (m, 9H), 1.69-1.50 (m, 6H), 1.38-1.14 (m, 52H), 0.93 (d, J=6.6 Hz, 3H), 0.88 (t, J=6.8 Hz, 6H).

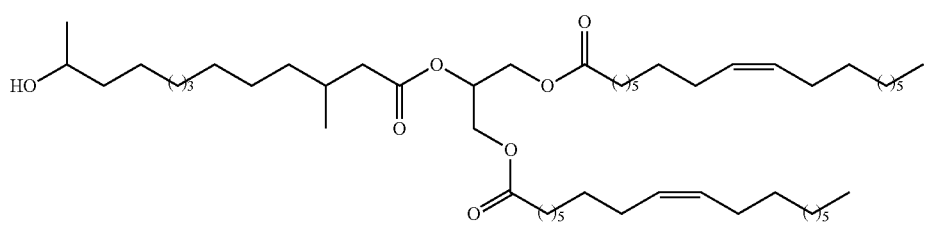

C12α'βMe-OH-2-TG-oleate (Int-270) $^1$H NMR (401 MHz, CDCl$_3$) δ 5.39-5.24 (m, 5H), 4.28 (dd, J=12.0, 4.0 Hz, 2H), 4.14 (dd, J=11.9, 6.1 Hz, 2H), 3.78 (m, 1H), 2.36-2.27 (m, 5H), 2.11 (dd, J=14.7, 8.2 Hz, 1H), 2.06-1.88 (m, 9H), 1.66-1.56 (m, 4H), 1.49-1.20 (m, 56H), 1.18 (d, J=6.2 Hz, 3H), 0.92 (d, J=6.6 Hz, 3H), 0.87 (t, J=6.9 Hz, 6H); $^{13}$C NMR (101 MHz, CDCl$_3$) δ 173.4 (2C; C), 172.5 (C), 130.1 (2C; CH), 129.8 (2C; CH), 68.9 (CH), 68.3 (CH), 62.3 (2C; CH$_2$), 41.8 (CH$_2$), 39.5 (CH$_2$), 36.8 (CH$_2$), 34.2 (2C; CH$_2$), 32.0 (2C; CH$_2$), 30.5 (CH), 29.89 (2C; CH$_2$), 29.88 (CH$_2$), 29.83 (2C; CH$_2$), 29.77 (CH$_2$), 29.72 (CH$_2$), 29.70 (CH$_2$), 29.65 (2C; CH$_2$), 29.45 (4C; CH$_2$), 29.30 (2C; CH$_2$), 29.24 (2C; CH$_2$), 29.22 (2C; CH$_2$), 27.4 (2C; CH$_2$), 27.3 (2C; CH$_2$), 27.0 (CH$_2$), 25.9 (CH$_2$), 25.0 (2C; CH$_2$), 23.6 (CH$_3$), 22.8 (2C; CH$_2$), 19.7 (CH$_3$), 14.2 (2C; CH$_3$); ESI-HRMS: calcd. for C$_{53}$H$_{98}$NaO$_7$ [M+Na$^+$] 869.7205; found 869.7206.

C12β'βMe-OH-2-TG (Int-148):

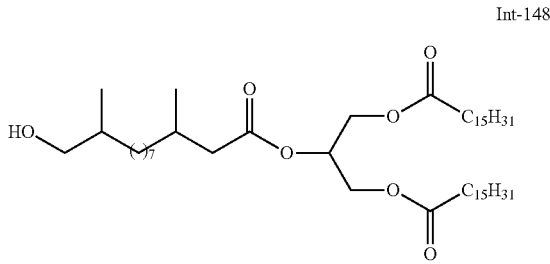

Int-148

Borane-dimethylsulfide complex (1.05 M in THF, 94.0 μL, 98.9 μmol) was added to a solution of carboxylic acid Int-27 (40.0 mg, 49.4 μmol) in THF (1.5 mL) at −5° C. and the mixture stirred at −5° C. for 40 minutes and then allowed to stand in refrigerator for 19 hours. The reaction was slowly diluted with cold water (20 mL) and the aqueous phase extracted with ethyl acetate (3×20 mL). The combined organic extracts were washed with brine (30 mL), dried (MgSO$_4$) and concentrated under reduced pressure to give the crude product. Purification by silica gel chromatography (5% to 15% ethyl acetate/hexanes) gave alcohol Int-148 (35.8 mg, 91%) as a colorless oil. $^1$H NMR (401 MHz, CDCl$_3$) δ 5.27 (m, 1H), 4.29 (dd, J=11.8, 4.2 Hz, 2H), 4.14 (dd, J=11.9, 5.9 Hz, 2H), 3.51 (dd, J=10.5, 5.8 Hz, 1H), 3.42 (dd, J=10.5, 6.5 Hz, 1H), 2.33 (dd, J=14.8, 6.0 Hz, 1H), 2.30 (t, J=7.6 Hz, 4H), 2.12 (dd, J=14.8, 8.2 Hz, 1H), 1.93 (m, 1H), 1.65-1.50 (m, 5H), 1.44-1.05 (m, 62H), 0.93 (d, J=6.7 Hz, 3H), 0.92 (d, J=6.7 Hz, 3H), 0.88 (t, J=6.9 Hz, 6H).

C12-acid-2-TG (Int-37):

Scheme 18. Synthesis of Int-37.

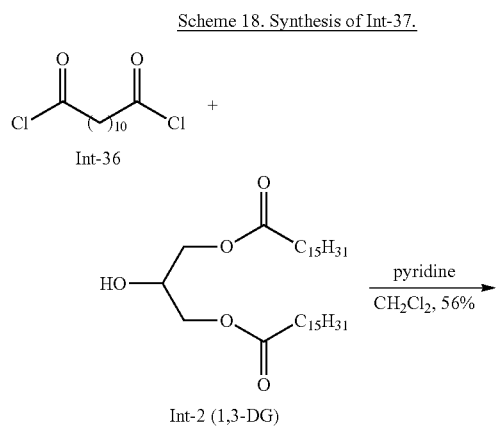

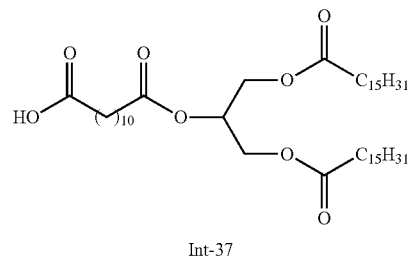

Int-37

A mixture of dodecanedioic acid (700 mg, 3.04 mmol) and DMF (two drops) in thionyl chloride (2.20 mL, 30.4 mmol) was heated at reflux for two hours. The reaction was cooled to room temperature, diluted with toluene (5 mL) and concentrated under reduced pressure to give diacid chloride Int-36 (812 mg, quant.) as a yellow oil that was used without purification. $^1$H NMR (400 MHz, CDCl$_3$): δ 2.88 (t, J=7.3 Hz, 4H), 1.76-1.65 (m, 4H), 1.42-1.23 (m, 12H).

A solution of 1,3-diglyceride Int-2 (40.0 mg, 0.0703 mmol) and pyridine (56.9 μL, 0.703 mmol) in CH$_2$Cl$_2$ (1.5 mL) was added to diacid chloride Int-36 (93.9 mg, 0.352 mmol) in CH$_2$Cl$_2$ (1.5 mL) and the mixture stirred at room temperature for 16 hours. The reaction was diluted with ethyl acetate (3 mL), water (10 mL) and 1 M HCl (2 mL) and the aqueous layer extracted with ethyl acetate (3×15 mL). The combined organic extracts were washed with 1 M HCl (30 mL) and brine (2×30 mL), dried (MgSO$_4$) and concentrated under reduced pressure to give the crude product. Purification by silica gel chromatography (20% to 45% ethyl acetate/hexanes) gave acid-TG Int-37 (30.7 mg, 56%) as a colorless solid. $^1$H NMR (400 MHz, CDCl$_3$): δ 5.26 (m, 1H), 4.29 (dd, J=11.9, 4.3 Hz, 2H), 4.14 (dd, J=11.9, 5.9 Hz, 2H), 2.38-2.26 (m, 8H), 1.69-1.54 (m, 8H), 1.38-1.19 (m, 60H), 0.87 (t, J=6.9 Hz, 6H).

C15βMe-acid-2-TG (Int-49):

Scheme 19. Synthesis of Int-49.

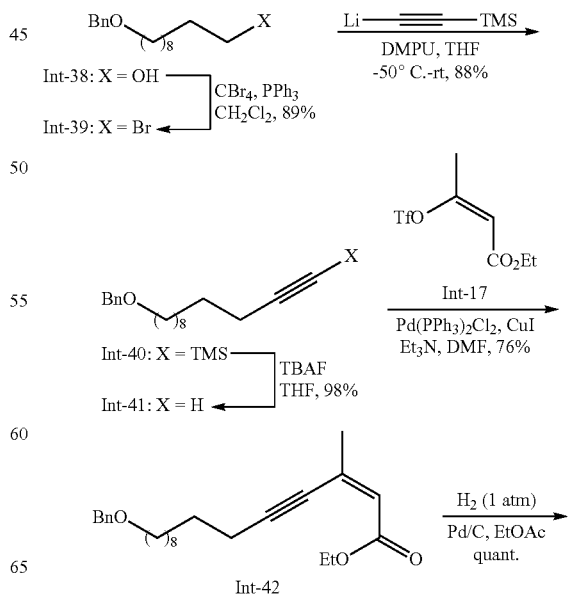

-continued

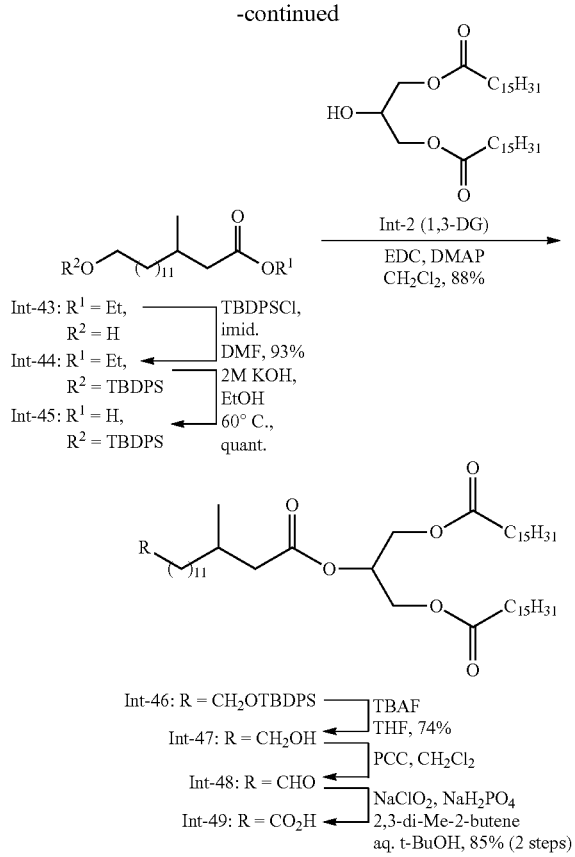

Int-43: R¹ = Et, R² = H
Int-44: R¹ = Et, R² = TBDPS
Int-45: R¹ = H, R² = TBDPS

TBDPSCl, imid. DMF, 93%
2M KOH, EtOH 60° C., quant.

Int-2 (1,3-DG)
EDC, DMAP
CH₂Cl₂, 88%

Int-46: R = CH₂OTBDPS
Int-47: R = CH₂OH
Int-48: R = CHO
Int-49: R = CO₂H

TBAF THF, 74%
PCC, CH₂Cl₂
NaClO₂, NaH₂PO₄ 2,3-di-Me-2-butene aq. t-BuOH, 85% (2 steps)

A solution of 1,10-decanediol (1.05 g, 6.00 mmol) in DMF (7 mL) was added dropwise to a suspension of sodium hydride (60% w/w in mineral oil, washed twice with dry petrol, 240 mg, 6.00 mmol) in DMF (8 mL) at 0° C. and the mixture stirred at room temperature for one hour. Benzyl bromide (784 µL, 3.50 mmol) was added dropwise and the mixture stirred at room temperature for 1.5 hours. The reaction was diluted with ethyl acetate (30 mL), quenched with water (20 mL) and the aqueous phase extracted with ethyl acetate (3×30 mL). The combined organic extracts washed with water and brine (60 mL each), dried (MgSO₄) and concentrated under reduced pressure to give the crude product. Purification by silica gel chromatography (20% to 30% ethyl acetate/hexanes) gave benzyl ether Int-38 (657 mg, 41%) as a colorless oil. ¹H NMR (400 MHz, CDCl₃) δ 7.39-7.24 (m, 5H), 4.50 (s, 2H), 3.64 (t, J=6.6 Hz, 2H), 3.46 (t, J=6.7 Hz, 2H), 1.65-1.52 (m, 4H), 1.40-1.25 (m, 12H).

Carbon tetrabromide (1.05 g, 3.17 mmol) and triphenylphosphine (1.07 g, 4.08 mmol) were added to a solution of alcohol Int-38 (600 mg, 1.11 mmol) in CH₂Cl₂ (20 mL) at 0° C. and the mixture stirred at room temperature for 2.5 hours. The reaction was diluted with CH₂Cl₂ (20 mL), silica gel was added and the solvent evaporated under reduced pressure. Purification by silica gel chromatography (3% to 4% ethyl acetate/hexanes) gave bromide Int-39 (658 mg, 89%) as a colorless oil. ¹H NMR (400 MHz, CDCl₃) δ 7.41-7.26 (m, 5H), 4.50 (s, 2H), 3.46 (t, J=6.6 Hz, 2H), 3.40 (t, J=6.9 Hz, 2H), 1.91-1.79 (m, 2H), 1.68-1.56 (m, 2H), 1.47-1.23 (m, 12H).

n-Butyllithium (n-BuLi, 1.6 M in hexanes, 4.01 mL, 6.42 mmol) was added slowly to a solution of TMS-acetylene (1.02 mL, 7.22 mmol) in THF (9 mL) at −78° C. and the mixture stirred at −78° C. for five minutes then warmed to room temperature and stirred for a further 15 minutes. The reaction was re-cooled to −50° C., a solution of bromide Int-39 (525 mg, 1.60 mmol) and DMPU (1.06 mL, 8.82 mmol) in THF (6 mL) was added dropwise and the mixture stirred at −50° C. for 30 minutes and then at room temperature for 22 hours. The reaction was diluted with brine (15 mL) and the organic solvent evaporated under reduced pressure. The aqueous residue was extracted with ethyl acetate (3×25 mL) and the combined organic extracts washed with brine (50 mL), dried (MgSO₄) and concentrated under reduced pressure to give the crude product. Purification by silica gel chromatography (3.5% to 4.5% ethyl acetate/hexanes) gave TMS alkyne Int-40 (489 mg, 88%) as a colorless oil containing small amounts of desilylated alkyne Int-41 (<10%). ¹H NMR (400 MHz, CDCl₃) δ 7.37-7.25 (m, 5H), 4.50 (s, 2H), 3.46 (t, J=6.7 Hz, 2H), 2.21 (t, J=7.2 Hz, 2H), 1.65-1.58 (m, 2H), 1.54-1.46 (m, 2H), 1.41-1.24 (m, 12H), 0.14 (s, 9H).

Tetrabutylammonium fluoride (TBAF, 1.0 M in THF, 1.61 mL, 1.61 mmol) was added dropwise to silylalkyne Int-40 (463 mg, 1.34 mmol) in THF (12 mL) at 0° C. and the mixture stirred at room temperature for 40 minutes. The reaction was diluted with water (10 mL) and the aqueous phase extracted with ethyl acetate (3×20 mL). The combined organic extracts were washed with brine (40 mL), dried (MgSO₄) and concentrated under reduced pressure to give the crude product. Purification by silica gel chromatography (4% to 5% ethyl acetate/hexanes) gave alkyne Int-41 (361 mg, 98%) as a colorless oil. ¹H NMR (400 MHz, CDCl₃) δ 7.38-7.25 (m, 5H), 4.50 (s, 2H), 3.46 (t, J=6.7 Hz, 2H), 2.18 (td, J=7.1, 2.6 Hz, 2H), 1.94 (t, J=2.7 Hz, 1H), 1.65-1.57 (m, 2H), 1.55-1.48 (m, 2H), 1.43-1.24 (m, 12H). ¹³C NMR (101 MHz, CDCl₃) δ 138.86 (C), 128.49 (2C; CH), 127.77 (2C; CH), 127.61 (CH), 84.97 (C), 73.00 (CH₂), 70.67 (CH₂), 68.18 (CH), 29.91 (CH₂), 29.67 (CH₂), 29.59 (CH₂), 29.57 (CH₂), 29.23 (CH₂), 28.89 (CH₂), 28.63 (CH₂), 26.33 (CH₂), 18.54 (CH₂).

A suspension of PdCl₂(PPh₃)₂ (32.2 mg, 0.0459 mmol) in DMF (4 mL) was degassed using a stream of N₂ gas for five minutes, and then CuI (35.0 mg, 0.184 mmol), Et₃N (256 µL, 1.84 mmol) and a degassed solution of alkyne Int-41 (250 mg, 0.918 mmol) and enol triflate Int-17 (313 mg, 1.19 mmol) in DMF (6 mL) were added. The mixture was degassed using a stream of N₂ for a further five minutes and then heated at 70° C. for one hour. The reaction was cooled to room temperature, diluted with ethyl acetate (40 mL), washed with 1 M HCl, sat. aq. NaHCO₃, water and brine (30 mL each), dried (MgSO₄) and concentrated under reduced pressure to give the crude product. Silica gel chromatography (4% to 5% ethyl acetate/hexanes) gave enyne Int-42 (269 mg, 76%) as a pale yellow oil. ¹H NMR (400 MHz, CDCl₃) δ 7.38-7.24 (m, 5H), 5.92 (m, 1H), 4.50 (s, 2H), 4.18 (t, J=7.1 Hz, 2H), 3.46 (t, J=6.7 Hz, 2H), 2.43 (t, J=7.2 Hz, 2H), 2.01 (d, J=1.4 Hz, 3H), 1.65-1.55 (m, 4H), 1.46-1.24 (m, 12H); ¹³C NMR (101 MHz, CDCl₃) δ 165.4 (C), 138.8 (C), 135.9 (C), 128.5 (2C; CH), 127.7 (2C; CH), 127.6 (CH), 123.3 (CH), 103.3 (C), 79.9 (C), 73.0 (CH₂), 70.6 (CH₂), 60.0 (CH₂), 29.9 (CH₂), 29.65 (CH₂), 29.59 (CH₂), 29.56 (CH₂), 29.2 (CH₂), 29.1 (CH₂), 28.6 (CH₂), 26.3 (CH₂), 26.0 (CH₃), 20.1 (CH₂), 14.4 (CH₃).

A solution of benzyl ether Int-42 (246 mg, 0.640 mmol) in ethyl acetate (25 mL) in a three-neck round-bottom flask was twice evacuated and flushed with N₂ gas, then palladium on carbon (10% w/w, 102 mg, 0.0960 mmol) was added and the resulting suspension re-evacuated and flushed with N₂ three times. The flask was fitted with a H₂ balloon, evacuated and flushed with H₂ three times and the reaction mixture stirred at room temperature under 1 atm of $H_2$ for one hour. The reaction mixture was then filtered through a pad of celite and the pad washed with ethyl acetate (40 mL). The filtrate was concentrated under reduced pressure to give saturated alcohol Int-43 (192 mg, quant.) as a colorless oil that was used without purification. $^1$H NMR (400 MHz, $CDCl_3$) δ 4.12 (q, J=7.1 Hz, 2H), 3.63 (t, J=6.6 Hz, 2H), 2.28 (dd, J=14.6, 6.0 Hz, 1H), 2.08 (dd, J=14.6, 8.1 Hz, 1H), 1.93 (m, 1H), 1.60-1.51 (m, 2H), 1.43-1.12 (m, 23H), 0.92 (d, J=6.6 Hz, 3H). $^{13}$C NMR (101 MHz, $CDCl_3$) δ 173.6 (C), 63.2 ($CH_2$), 60.2 ($CH_2$), 42.1 ($CH_2$), 36.9 ($CH_2$), 32.9 ($CH_2$), 30.5 (CH), 29.9 ($CH_2$), 29.74 (4C; $CH_2$), 29.70 ($CH_2$), 29.6 ($CH_2$), 27.0 ($CH_2$), 25.9 ($CH_2$), 19.9 ($CH_3$), 14.4 ($CH_3$).

Imidazole (32.0 mg, 0.0.469 mmol) and tert-butyl(chloro) diphenylsilane (TBDPSCl, 183 μL, 0.704 mmol) were added to a solution of alcohol Int-43 (70.5 mg, 0.235 mmol) in DMF (7 mL) and the mixture stirred at room temperature for 17 hours. The reaction was diluted with ethyl acetate (20 mL), washed with water (20 mL) and brine (2×20 mL), dried ($MgSO_4$) and concentrated under reduced pressure to give the crude product. Purification by silica gel chromatography (3% to 4% ethyl acetate/hexanes with 0.5% $Et_3N$) gave TBDPS ether Int-44 (117 mg, 93%) as a colorless oil. $^1$H NMR (400 MHz, $CDCl_3$) δ 7.70-7.63 (m, 4H), 7.44-7.34 (m, 6H), 4.12 (q, J=7.1 Hz, 2H), 3.65 (t, J=6.5 Hz, 2H), 2.29 (dd, J=14.6, 6.0 Hz, 1H), 2.09 (dd, J=14.6, 8.2 Hz, 1H), 1.95 (m, 1H), 1.60-1.50 (m, 2H), 1.38-1.14 (m, 23H), 1.04 (s, J=2.8 Hz, 9H), 0.92 (d, J=6.6 Hz, 3H); $^{13}$C NMR (101 MHz, $CDCl_3$) δ 173.5 (C), 135.7 (4C; CH), 134.3 (2C; C), 129.6 (2C; CH), 127.7 (4C; CH), 64.1 ($CH_2$), 60.2 ($CH_2$), 42.1 ($CH_2$), 36.9 ($CH_2$), 32.7 ($CH_2$), 30.5 (CH), 29.9 ($CH_2$), 29.79 (3C; $CH_2$), 29.77 (2C; $CH_2$), 29.5 ($CH_2$), 27.1 ($CH_2$), 27.0 (3C; $CH_3$), 25.9 ($CH_2$), 19.9 ($CH_3$), 19.4 (C), 14.4 ($CH_3$).

A solution of potassium hydroxide (2.0 M, 390 μL, 0.781 mmol) was added to ester Int-44 (42.1 mg. 0.0781 mmol) in ethanol (2 mL) and the mixture heated at 60° C. for 1.5 hours. The reaction was acidified to pH 1 by addition of 1 M HCl, diluted with water (10 mL) and the aqueous phase extracted with ethyl acetate (3×15 mL). The combined organic extracts were washed with brine (30 mL), dried ($MgSO_4$) and concentrated under reduced pressure to give crude acid Int-45 (39.9 mg, quant.) as a colorless oil that was used without purification. $^1$H NMR (400 MHz, $CDCl_3$) δ 7.75-7.66 (m, 4H), 7.46-7.35 (m, 6H), 3.67 (t, J=6.5 Hz, 2H), 2.36 (dd, J=15.0, 5.9 Hz, 1H), 2.15 (dd, J=14.9, 8.2 Hz, 1H), 1.97 (m, 1H), 1.61-1.52 (m, 2H), 1.41-1.17 (m, 20H), 1.06 (s, 9H), 0.98 (d, J=6.6 Hz, 3H); $^{13}$C NMR (101 MHz, $CDCl_3$) δ 179.7 (C), 135.7 (4C; CH), 134.3 (2C; C), 129.6 (2C; CH), 127.7 (4C; CH), 64.2 ($CH_2$), 41.7 ($CH_2$), 36.8 ($CH_2$), 32.7 ($CH_2$), 30.3 (CH), 29.9 ($CH_2$), 29.80 (2C; $CH_2$), 29.78 (2C; $CH_2$), 29.75 ($CH_2$), 29.5 ($CH_2$), 27.1 ($CH_2$), 27.0 (3C; $CH_3$), 25.9 ($CH_2$), 19.8 ($CH_3$), 19.4 (C).

4-(Dimethylamino)pyridine (DMAP, 9.5 mg, 0.0781 mmol), EDC·HCl (29.9 mg, 0.156 mmol) and 1,3-diglyceride Int-2 (53.3 mg, 0.0937 mmol) were added to a solution of acid Int-45 (39.9 mg, 0.0781 mmol) in $CH_2Cl_2$ (2.5 mL) and the mixture stirred at room temperature for 19 hours. The reaction was diluted with $CH_2Cl_2$ (5 mL), silica gel was added and the mixture concentrated under reduced pressure. Purification by silica gel chromatography (4% to 5% ethyl acetate/hexanes) gave triglyceride Int-46 (72.8 mg, 88% over two steps) as a colorless solid. $^1$H NMR (400 MHz, $CDCl_3$) δ 7.73-7.63 (m, 4H), 7.49-7.31 (m, 6H), 5.29 (m, 1H), 4.30 (dd, J=11.9, 4.2 Hz, 2H), 4.15 (dd, J=11.9, 6.1 Hz, 2H), 3.66 (t, J=6.5 Hz, 2H), 2.34 (dd, J=14.6, 6.0 Hz, 1H), 2.31 (t, J=7.5 Hz, 4H), 2.13 (dd, J=14.6, 8.3 Hz, 1H), 1.94 (m, 1H), 1.68-1.52 (m, 6H), 1.44-1.16 (m, 68H), 1.05 (s, 9H), 0.94 (d, J=6.6 Hz, 3H), 0.88 (t, J=6.8 Hz, 6H); $^{13}$C NMR (101 MHz, $CDCl_3$) δ 173.4 (2C; C), 172.5 (C), 135.7 (4C; CH), 134.3 (2C; C), 129.6 (2C; CH), 127.7 (4C; CH), 68.9 (CH), 64.1 ($CH_2$), 62.3 (2C; $CH_2$), 41.8 ($CH_2$), 36.8 ($CH_2$), 34.2 (2C; $CH_2$), 32.7 ($CH_2$), 32.1 (2C; $CH_2$), 30.5 (CH), 30.0 ($CH_2$), 29.84 (8C; $CH_2$), 29.80 (6C; $CH_2$), 29.76 (2C; $CH_2$), 29.61 (2C; $CH_2$), 29.54 ($CH_2$), 29.50 (3C; $CH_2$), 29.4 (2C; $CH_2$), 29.3 (2C; $CH_2$), 27.2 ($CH_2$), 27.0 (3C; $CH_3$), 25.9 ($CH_2$), 25.0 (2C; $CH_2$), 22.8 (2C; $CH_2$), 19.7 ($CH_3$), 19.3 (C), 14.3 (2C; $CH_3$).

Tetrabutylammonium fluoride (TBAF, 1.0 M in THF, 186 μL, 0.186 mmol) and acetic acid (10.6 μL, 0.186 mmol) were added dropwise to TBDPS ether Int-46 (65.7 mg, 0.0619 mmol) in THF (3 mL) at 0° C. and the mixture stirred at room temperature for 19 hours. The reaction was diluted with water (10 mL) and the aqueous phase extracted with ethyl acetate (3×15 mL). The combined organic extracts were washed with sat. aq. $NaHCO_3$ and brine (30 mL each), dried ($MgSO_4$) and concentrated under reduced pressure to give the crude product. Purification by silica gel chromatography (10% to 15% ethyl acetate/hexanes) gave alcohol Int-47 (34.2 mg, 67%) as a colorless oil. $^1$H NMR (400 MHz, $CDCl_3$) δ 5.27 (m, 1H), 4.28 (dd, J=11.9, 4.3 Hz, 2H), 4.14 (dd, J=11.8, 6.0 Hz, 2H), 3.63 (t, J=6.6 Hz, 2H), 2.32 (dd, J=14.6, 5.9 Hz, 1H), 2.30 (t, J=7.6 Hz, 4H), 2.11 (dd, J=14.6, 8.3 Hz, 1H), 1.92 (m, 1H), 1.66-1.52 (m, 6H), 1.40-1.13 (m, 68H), 0.92 (d, J=6.6 Hz, 3H), 0.87 (t, J=6.9 Hz, 6H); $^{13}$C NMR (101 MHz, $CDCl_3$) δ 173.5 (2C; C), 172.5 (C), 68.9 (CH), 63.2 ($CH_2$), 62.3 (2C; $CH_2$), 41.8 ($CH_2$), 36.8 ($CH_2$), 34.2 (2C; $CH_2$), 32.9 ($CH_2$), 32.1 (2C; $CH_2$), 30.5 (CH), 29.9 ($CH_2$), 29.84 (8C; $CH_2$), 29.80 (6C; $CH_2$), 29.76 (2C; $CH_2$), 29.73 ($CH_2$), 29.62 (2C; $CH_2$), 29.57 ($CH_2$), 29.5 (2C; $CH_2$), 29.4 (2C; $CH_2$), 29.3 (2C; $CH_2$), 27.1 ($CH_2$), 25.9 ($CH_2$), 25.0 (2C; $CH_2$), 22.8 (2C; $CH_2$), 19.7 ($CH_3$), 14.3 (2C; $CH_3$).

Pyridinium chlorochromate (PCC, 14.7 mg, 68.0 μmol) was added to a suspension of alcohol Int-47 (28.0 mg, 34.0 μmol) and celite (15 mg) in $CH_2Cl_2$ (1.5 mL) at 0° C. and the mixture stirred at room temperature for one hour. The reaction was filtered through a short pad of silica gel, eluting with ethyl acetate, and the filtrate concentrated under reduced pressure to give crude aldehyde Int-48 (27.9 mg, quant.) as a yellow oil that was used without purification. $^1$H NMR (400 MHz, $CDCl_3$) δ 9.76 (s, 1H), 5.28 (m, 1H), 4.29 (dd, J=11.6, 3.5 Hz, 2H), 4.14 (dd, J=11.9, 5.8 Hz, 2H), 2.42 (t, J=6.8 Hz, 2H), 2.36-2.25 (m, 5H), 2.12 (dd, J=14.4, 8.5 Hz, 1H), 1.94 (m, 1H), 1.69-1.51 (m, 6H), 1.42-1.09 (m, 66H), 0.93 (d, J=6.4 Hz, 3H), 0.88 (t, J=6.3 Hz, 6H).

A solution of sodium chlorite (27.6 mg, 0.306 mmol) and sodium phosphate monobasic ($NaH_2PO_4$, 28.8 mg, 0.238 mmol) in water (1.2 mL) was added dropwise to aldehyde Int-48 (27.9 mg, 0.0340 mmol) in t-BuOH (1.8 mL) and 2,3-dimethyl-2-butene (0.4 mL) and the reaction stirred at room temperature for 16 hours. The reaction was acidified to pH 2 using 1 M HCl, diluted with water (10 mL) and the aqueous layer extracted with ethyl acetate (3×15 mL). The combined organic extracts were washed with brine (30 mL), dried (($MgSO_4$)) and concentrated under reduced pressure to give the crude product. Purification by silica gel chromatography (10% to 15% ethyl acetate/hexanes with 0.5% acetic acid) gave acid Int-49 (24.3 mg, 85%) as a colorless solid. $^1$H NMR (400 MHz, $CDCl_3$) δ 5.29 (m, 1H), 4.29 (dd, J=11.9, 3.8 Hz, 2H), 4.14 (dd, J=11.9, 6.1 Hz, 2H), 2.37-2.27 (m, 7H), 2.11 (dd, J=14.7, 8.3 Hz, 1H), 1.92 (m, 1H), 1.68-1.54 (m, 6H), 1.40-1.13 (m, 66H), 0.93 (d, J=6.6 Hz, 3H), 0.87 (t, J=6.8 Hz, 6H); $^{13}$C NMR (101 MHz, $CDCl_3$)

δ 179.5 (C), 173.5 (2C; C), 172.5 (C), 68.9 (CH), 62.3 (2C; CH$_2$), 41.9 (CH$_2$), 36.8 (CH$_2$), 34.2 (2C; CH$_2$), 34.1 (CH$_2$), 32.1 (2C; CH$_2$), 30.5 (CH), 29.93 (CH$_2$), 29.85 (8C; CH$_2$), 29.81 (4C; CH$_2$), 29.77 (2C; CH$_2$), 29.73 (CH$_2$), 29.62 (2C; CH$_2$), 29.58 (CH$_2$), 29.51 (2C; CH$_2$), 29.42 (2C; CH$_2$), 29.39 (CH$_2$), 29.26 (2C; CH$_2$), 29.2 (CH$_2$), 27.1 (CH$_2$), 25.0 (2C; CH$_2$), 24.8 (CH$_2$), 22.8 (2C; CH$_2$), 19.7 (CH$_2$), 14.3 (2C; CH$_2$).

C8βMe-acid-2-TG-oleate (Int-178):

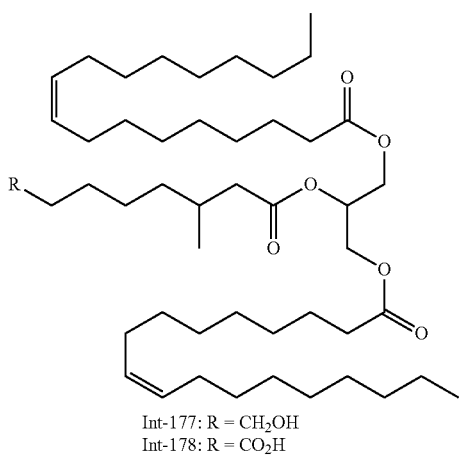

Int-177: R = CH$_2$OH
Int-178: R = CO$_2$H

Using the Pd-coupling, hydrogenation, EDC-coupling, and TBAF deprotection procedures described for the synthesis of Int-49, compound Int-177 (C8βMe-OH-2-TG-oleate) was prepared from 1-(tert-butyldiphenylsilyloxy)-pent-4-yne, benzyl (Z)-3-(((trifluoromethyl) sulfonyl)oxy) but-2-enoate (Int-198; prepared similarly to Int-17), and Int-112. $^1$H NMR (400 MHz, CDCl$_3$) δ 5.36 (m, 5H), 4.33 (dd, J=11.9, 4.2 Hz, 2H), 4.18 (dd, J=11.9, 6.1 Hz, 2H), 3.68 (t, J=6.6 Hz, 2H), 2.33 (dt, J=11.2, 5.6 Hz, 5H), 2.15 (m, 2H), 2.05 (q, J=6.3 Hz, 8H), 1.63 (dt, J=15.3, 7.5 Hz, 6H), 1.34 (p, J=6.9, 5.0 Hz, 46H), 0.95 (d, J=6.4 Hz, 3H), 0.90 (d, J=6.8 Hz, 6H); $^{13}$C NMR (101 MHz, CDCl$_3$) δ 173.30 (2C), 172.27 (1C), 130.04 (2C), 129.73 (2C), 68.87 (1C), 62.92 (1C), 62.16 (2C), 41.67 (1C), 36.56 (1C), 34.05 (2C), 32.72 (1C), 31.93 (2C), 30.27 (1C), 29.79-29.12 (16C), 27.24 (2C), 27.20 (2C), 26.67 (1C), 25.84 (1C), 24.86 (2C), 22.70 (2C), 19.60 (1C), 14.12 (2C); MS (ESI, +ve) m/z: 778.0 (M+1), 794.96 (M+18).

To a solution of Int-177 (4.0 g, 5.14 mmol) in acetone (40 mL) at 0° C. was added dropwise freshly prepared Jones' reagent (6.4 mL, 2.1 equiv.), and the resulting reaction mixture was stirred at 0° C. for 4 h. The reaction mixture was quenched with water (40 mL) and extracted with ethyl acetate (3×40 mL). The combined organic layer was dried over Na$_2$SO$_4$ and evaporated under reduced pressure. The residue was purified by column chromatography using silica gel (100-200 mesh), with product eluting at 8-10% ethyl acetate/hexane, to afford Int-178 (1.5 g, 37%) as a colorless oil. $^1$H NMR (400 MHz, CDCl$_3$) δ 5.35 (m, 5H), 4.32 (dd, J=11.9, 4.3 Hz, 2H), 4.31 (dd, J=12.4, 6.1 Hz, 2H), 2.38 (t, J=7.5 Hz, 5H), 2.20 (m, 2H), 2.02-2.01 (m, 8H), 1.63 (m, 6H), 1.24 (m, 46H), 0.95 (d, J=7.2 Hz, 3H), 0.89 (t, J=7.2 Hz, 6H); $^{13}$C NMR (101 MHz, CDCl$_3$) δ 178.66 (1C), 173.26 (2C), 172.13 (1C), 130.01 (2C), 129.71 (2C), 68.95 (1C), 65.32 (1C), 62.15 (2C), 36.21 (1C), 34.02 (2C), 33.89 (1C), 31.90 (2C), 30.15 (1C), 29.76-29.09 (14C), 27.22 (2C), 27.18 (2C), 26.36 (1C), 24.83 (2C), 23.39 (1C), 23.07 (2C), 22.67 (2C), 19.49 (1C), 14.07 (2C); MS (ESI, -ve) m/z: 790.15 (M-1).

C10βMe-acid-2-TG-oleate (Int-187):

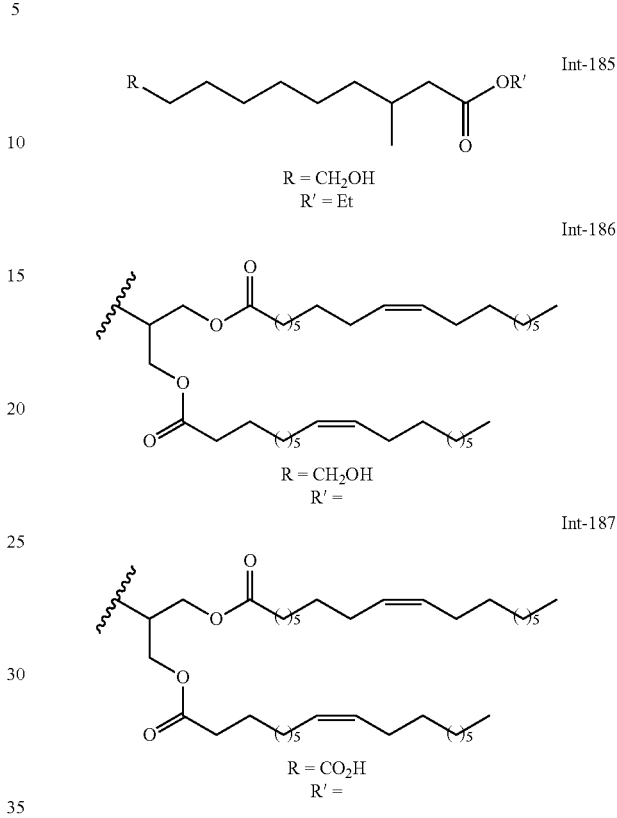

Compounds Int-185 and Int-186 were prepared from 1-benzyloxy-pentan-5-ol and Int-112 according to the procedures described for the synthesis of Int-43 and Int-47. Oxidation of Int-186 to Int-187 was conducted using the Jones' reagent according to the procedure described for preparation of Int-178.

Int-185 $^1$H NMR (400 MHz, CDCl$_3$) δ 4.12 (q, J=7.1 Hz, 2H), 3.63 (t, J=6.5 Hz, 2H), 2.27 (dd, J=14.6, 6.0 Hz, 1H), 2.08 (dd, J=14.6, 8.1 Hz, 1H), 1.93 (m, 1H), 1.60-1.51 (m, 2H), 1.43-1.12 (m, 15H), 0.92 (d, J=6.6 Hz, 3H).

C10βMe-OH-2-TG-oleate (Int-186) $^1$H NMR (400 MHz, CDCl$_3$) δ 5.495 (m, 4H), 5.376 (m, 1H), 4.367 (m, 2H), 4.176 (m, 2H), 3.657 (t, 2H), 2.345 (m, 6H), 2.178 (m, 2H), 2.108-1.980 (m, 8H), 1.335-1.303 (m, 56H), 0.975-0.898 (m, 9H); $^{13}$C NMR (101 MHz, CDCl$_3$) δ 173.31 (2C), 172.35 (1C), 130.02 (2C), 129.72 (2C), 68.79 (1C), 63.01 (1C), 62.16 (2C), 41.68 (2C), 36.61 (2C), 34.03 (2C), 32.77 (2C), 31.91 (2C), 30.33 (1C), 29.71 (4C), 29.53 (4C), 29.33 (4C), 29.12 (4C), 27.21 (2C), 26.81 (2C), 25.70 (2C), 24.84 (2C), 22.69 (2C), 19.58 (1C), 14.13 (1C); MS (ESI, +ve) m/z: 823.03 (M+18).

C10βMe-acid-2-TG-oleate (Int-187) $^1$H NMR (400 MHz, CDCl$_3$) δ 5.383 (m, 4H), 5.329 (m, 1H), 4.339 (m, 2H), 4.191 (m, 2H), 2.387 (m, 8H), 2.190-2.04 (m, 10H), 1.651 (m, 8H), 1.435-1.253 (m, 46H), 0.977-0.903 (m, 9H); $^{13}$C NMR (101 MHz, CDCl$_3$) δ 178.96 (1C), 173.29 (2C), 172.29 (1C), 130.01 (2C), 129.71 (2C), 68.82 (1C), 62.15 (1C), 41.66 (2C), 36.55 (1C), 34.03 (2C), 33.85 (2C), 31.90 (2C), 30.30 (1C), 29.77 (4C), 29.70 (4C), 29.52 (2C), 29.32 (2C), 29.17 (2C), 29.10 (2C), 29.02 (2C), 27.22 (1C), 27.17

(2C), 26.69 (2C), 24.83 (1C), 24.63 (2C), 22.68 (1C), 19.53 (1C), 14.11 (1C); MS (ESI, −ve) m/z: 818.01 (M−1).

C15βMe-acid-2-TG-oleate (Int-233):

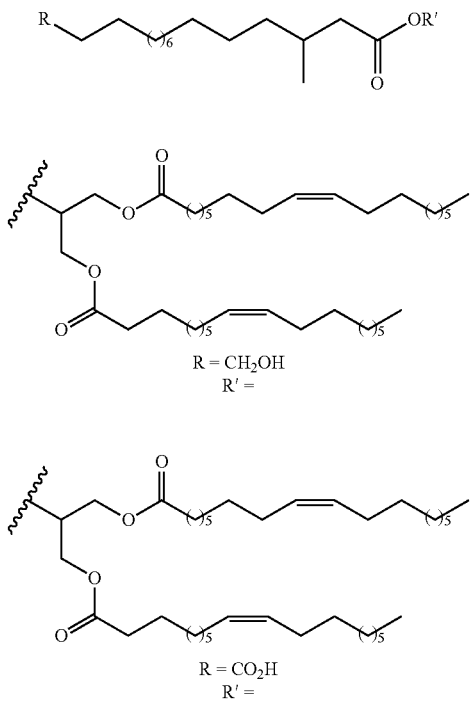

Compound Int-232 was prepared from Int-45 and Int-112 according to the procedures described for the conversion of Int-45 to Int-47. Oxidation of Int-232 to Int-233 was conducted using the Jones' reagent according to the procedure described for preparation of Int-178.

C15βMe-OH-2-TG-oleate (Int-232) MS (ESI, +ve) m/z: 893.17 (M+18).

C15βMe-acid-2-TG-oleate (Int-233) MS (ESI, −ve) m/z: 888.23 (M−1).

C12βMe-acid-2-TG-oleate (Int-236):

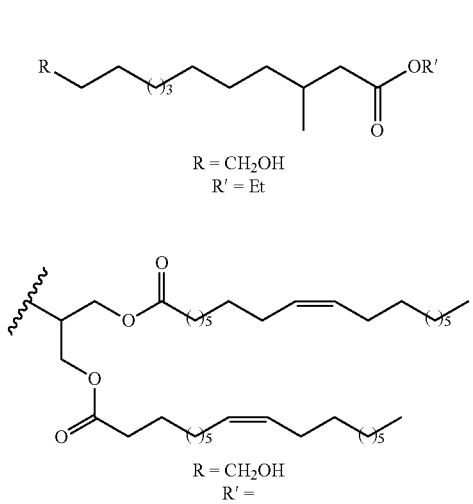

Compounds Int-234 and Int-235 were prepared from 1-benzyloxy-heptan-7-ol and Int-112 according to the procedures described for the synthesis of Int-43 and Int-47. Oxidation of Int-235 to Int-236 was conducted using the Jones' reagent according to the procedure described for preparation of Int-178.

Int-234 MS (ESI, +ve) m/z: 259.29 (M+1).

C12βMe-OH-2-TG-oleate (Int-235) $^1$H NMR (400 MHz, CDCl$_3$) 5.38-5.32 (m, 5H), 4.35 (dd, J=12.0, 4.0 Hz, 2H), 4.14 (dd, J=11.6, 5.3 Hz, 2H), 3.68 (t, J=6.4 Hz, 2H), 2.39-1.11 (m, 86H), 0.98 (d, J=6.6 Hz, 3H), 0.93 (t, J=6.4 Hz, 6H); $^{13}$C NMR (101 MHz, CDCl$_3$) 173.3, 172.4, 130.0, 129.75, 68.8, 63.1, 62.2, 41.7, 36.6, 34.0, 32.8, 31.9, 30.3, 29.7, 29.1, 27.2, 26.9, 25.7, 24.8, 22.7, 19.6, 14.1; MS (ESI, +ve) m/z: 851.13 (M+18).

C12βMe-acid-2-TG-oleate (Int-236) $^1$H NMR (400 MHz, CDCl$_3$) 5.38-5.32 (m, 5H), 4.35 (dd, J=16.0, 4.4 Hz, 2H), 4.17 (dd, J=12.0, 6.0 Hz, 2H), 2.39-1.11 (m, 88H), 0.98 (d, J=6.6 Hz, 3H), 0.93 (t, J=6.4 Hz, 6H); $^{13}$C NMR (101 MHz, CDCl$_3$) 179.4, 173.3, 172.4, 130.0, 129.74, 68.8, 62.2, 41.7, 36.6, 34.0, 33.9, 31.9, 30.3, 29.7, 29.5, 29.4, 29.3, 26.9, 24.8, 24.6, 22.7, 19.5, 14.1; MS (ESI, +ve) m/z: 845.93 (M+18).

C12βMe-acid-2-TG (Int-247):

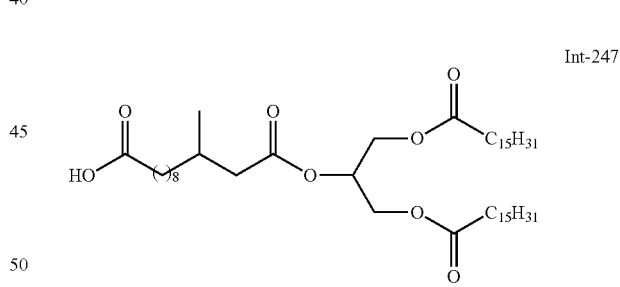

Compound Int-247 was prepared by oxidation of Int-121 using PCC and KMnO$_4$ according to the procedures described for preparation of Int-110 from Int-108.

C12βMe-acid-2-TG (Int-247) $^1$H NMR (400 MHz, CDCl$_3$) 5.32 (p, J=5.2 Hz, 1H), 4.33 (dd, J=11.9, 4.4 Hz, 2H), 4.18 (dd, J=11.9, 6.0 Hz, 2H), 2.36 (h, J=9.0, 8.1 Hz, 8H), 2.16 (dd, J=14.8, 8.1 Hz, 1H), 1.97 (s, 2H) 1.64 (s, 6H), 1.33 (s, 58H), 0.97 (d, J=6.4 Hz, 3H), 0.91 (t, J=6.0 Hz, 6H); $^{13}$C NMR (101 MHz, CDCl$_3$) 173.35 (2C), 172.37 (1C), 68.79 (1C), 63.033 (1C), 62.16 (1C), 41.70 (1C), 36.66 (1C), 34.05 (2C), 32.79 (1C), 31.94 (2C), 30.35 (1C), 29.71-29.06 (25C), 26.89 (1C), 25.73 (1C), 24.86 (2C), 22.71 (2C), 19.55 (1C), 14.15 (2C); MS (ESI, −ve) m/z: 793 (M−1); (ESI, +ve) m/z: 813 (M+18).

C15α'βMe-acid-2-TG (Int-62):
Scheme 20. Synthesis of Int-62.
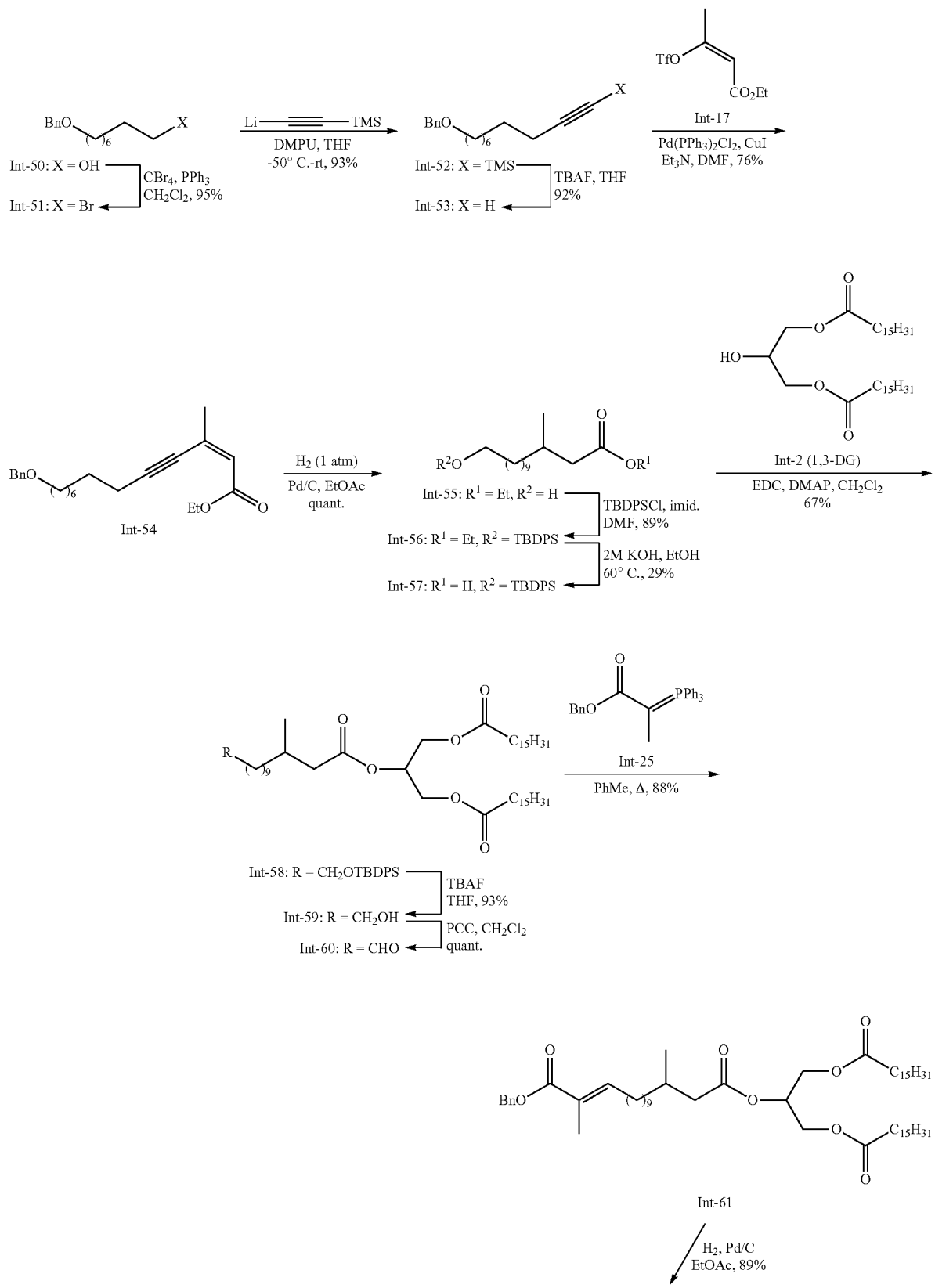

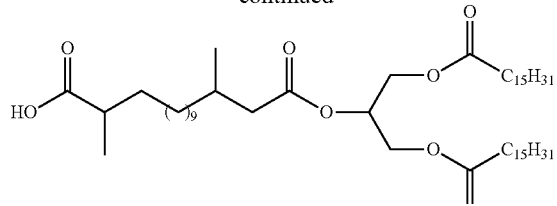

Int-62

Int-50: prepared according to: Subba Reddy, B. V. et al. Helv. Chim. Acta. 2013, 96, 1983-1990.

Int-51: known compound that may be prepared as disclosed in Takagi, Y. et A. Tetrahedron: Asymmr. 2004, 15, 2591-2594). $^1$H NMR (401 MHz, CDCl$_3$) δ 7.39-7.23 (m, 5H), 4.50 (s, 2H), 3.47 (t, J=6.6 Hz, 2H), 3.40 (t, J=6.9 Hz, 2H), 1.90-1.80 (m, 2H), 1.66-1.57 (m, 2H), 1.48-1.26 (m, 8H).

n-Butyllithium (n-BuLi, 2.0 M in cyclohexane, 18.1 mL, 36.3 mmol) was added slowly to a solution of TMS-acetylene (5.7 mL, 41.5 mmol) in THF (45 mL) at −78° C. and the mixture stirred at −78° C. for five minutes then warmed to room temperature and stirred for a further 15 minutes. The reaction was re-cooled to −78° C., a solution of bromide Int-51 (3.10 g, 10.4 mmol) and DMPU (6.3 mL, 51.8 mmol) in THF (30 mL) was added slowly and the mixture stirred at −78° C. for 30 minutes and then at room temperature for 18 hours. The reaction was diluted with water (60 mL) and the majority of the organic solvent removed under reduced pressure. The residue was diluted with brine (120 mL) and the aqueous phase extracted with ethyl acetate (3×100 mL). The combined organic extracts were washed with brine (3×100 mL), dried (MgSO$_4$) and concentrated under reduced pressure to give the crude product. Purification by silica gel chromatography (Reveleris 80 g column, 60 mL/min, 4% to 40% ethyl acetate/hexanes) gave TMS alkyne Int-52 (3.05 g, 93%) as a colorless oil. $^1$H NMR (401 MHz, CDCl$_3$) δ 7.36-7.25 (m, 5H), 4.50 (s, 2H), 3.46 (t, J=6.6 Hz, 2H), 2.21 (t, J=7.2 Hz, 2H), 1.65-1.57 (m, 2H), 1.55-1.46 (m, 2H), 1.41-1.27 (m, 8H), 0.15 (s, 9H).

Tetrabutylammonium fluoride (TBAF, 1.0 M in THF, 9.7 mL, 9.70 mmol) was added dropwise to silylalkyne Int-52 (3.05 g, 9.62 mmol) in THF (40 mL) at 0° C. and the mixture stirred at room temperature for one hour. The reaction was diluted with water (25 mL) and the organic solvent removed under reduced pressure. The resulting solution was diluted with brine (100 mL) and the aqueous phase extracted with ethyl acetate (3×50 mL). The combined organic extracts were washed with brine (3×50 mL), dried (MgSO$_4$) and concentrated under reduced pressure to give the crude product. Purification by silica gel chromatography (Reveleris 80 g column, 60 mL/min, 3% to 10% ethyl acetate/hexanes) gave alkyne Int-53 (2.17 g, 92%). $^1$H NMR (401 MHz, CDCl$_3$) δ 7.38-7.25 (m, 5H), 4.50 (s, 2H), 3.46 (t, J=6.6 Hz, 2H), 2.18 (td, J=7.1, 2.6 Hz, 2H), 1.94 (t, J=2.7 Hz, 1H), 1.66-1.56 (m, 2H), 1.57-1.48 (m, 2H), 1.43-1.27 (m, 8H); $^{13}$C NMR (101 MHz, CDCl$_3$) δ 138.8 (C), 128.4 (2C; CH), 127.7 (2C; CH), 127.6 (CH), 84.8 (C), 73.0 (CH), 70.6 (CH$_2$), 68.2 (CH), 29.8 (CH$_2$), 29.4 (CH$_2$), 29.1 (CH$_2$), 28.8 (CH$_2$), 28.6 (CH$_2$), 26.2 (CH$_2$), 18.5 (CH$_2$).

Int-17 was prepared as described above.

A suspension of PdCl$_2$(PPh$_3$)$_2$ (605 mg, 0.862 mmol) in DMF (40 mL) was degassed using N$_2$ gas for five minutes, and then CuI (335 mg, 1.76 mmol), Et$_3$N (2.40 mL, 17.2 mmol) and a degassed solution of alkyne Int-53 (2.11 g, 8.62 mmol) and enol triflate Int-17 (3.40 g, 13.00 mmol) in DMF (50 mL) were added. The mixture was degassed using a stream of N$_2$ for a further five minutes and then heated at 70° C. for one hour. The reaction was cooled to room temperature and concentrated under reduced pressure to about one-quarter of its original volume. The resulting solution was diluted with ethyl acetate (80 mL), washed with 1 M HCl, sat. aq. NaHCO$_3$, water and brine (30 mL each), dried (MgSO$_4$) and concentrated under reduced pressure to give the crude product. Silica gel chromatography (Reveleris 80 g column, 60 mL/min, 5% to 20% ethyl acetate/hexanes) gave enyne Int-54 (2.35 g, 76%) as a pale yellow oil. $^1$H NMR (401 MHz, CDCl$_3$) δ 7.37-7.24 (m, 5H), 5.92 (d, J=1.4 Hz, 1H), 4.50 (s, 2H), 4.18 (q, J=7.1 Hz, 2H), 3.46 (t, J=6.6 Hz, 2H), 2.43 (t, J=7.2 Hz, 2H), 2.01 (d, J=1.4 Hz, 3H), 1.65-1.55 (m, 4H), 1.46-1.30 (m, 8H), 1.28 (t, J=7.1 Hz, 3H); $^{13}$C NMR (101 MHz, CDCl$_3$) δ 165.4 (C), 138.8 (C), 135.9 (C), 128.5 (2C; CH), 127.7 (2C; CH), 127.6 (CH), 123.4 (CH), 103.2 (C), 79.9 (C), 73.0 (CH$_2$), 70.6 (CH$_2$), 60.0 (CH$_2$), 29.9 (CH$_2$), 29.4 (CH$_2$), 29.2 (CH$_2$), 29.0 (CH$_2$), 28.6 (CH$_2$), 26.3 (CH$_2$), 26.0 (CH$_3$), 20.1 (CH$_2$), 14.4 (CH$_3$).

A solution of benzyl ether Int-54 (707 mg, 1.98 mmol) in ethyl acetate (80 mL) in a three-neck round-bottom flask was twice evacuated and flushed with N$_2$ gas, then palladium on carbon (10% w/w, 525 mg, 0.494 mmol) was added and the resulting suspension re-evacuated and flushed with N$_2$ three times. The flask was fitted with a H$_2$ balloon, evacuated and flushed with H$_2$ three times and the reaction mixture stirred at room temperature under 1 atm of H$_2$ for two hours. The flask was then evacuated and flushed with N$_2$ and the reaction mixture filtered through a pad of celite, washing with ethyl acetate (80 mL). The filtrate was concentrated under reduced pressure to give saturated alcohol Int-55 (540 mg, quant.) as a colorless oil that was used without purification. $^1$H NMR (401 MHz, CDCl$_3$) δ 4.13 (q, J=7.1 Hz, 2H), 3.64 (t, J=6.6 Hz, 2H), 2.28 (dd, J=14.6, 6.0 Hz, 1H), 2.09 (dd, J=14.6, 8.1 Hz, 1H), 1.94 (m, 1H), 1.62-1.51 (m, 2H), 1.39-1.21 (m, 16H), 1.25 (t, J=7.1 Hz, 3H), 0.93 (d, J=6.6 Hz, 3H).

Imidazole (670 mg, 9.85 mmol) and tert-butyl(chloro)diphenylsilane (TBDPSCl, 3.5 mL, 13.6 mmol) were added to a solution of alcohol Int-55 (1.48 g, 5.42 mmol) in CH$_2$Cl$_2$ (80 mL) at 0° C. and the mixture stirred at room temperature for 2.5 hours. The reaction was concentrated to half its volume under reduced pressure, washed with water (2×20 mL) and brine (30 mL), dried (MgSO$_4$) and concentrated under reduced pressure to give the crude product. Purification by silica gel chromatography (Reveleris 80 g column, 60 mL/min, 1% to 16% ethyl acetate/hexanes) gave TBDPS ether Int-56 (2.46 g, 89%) as a colorless oil. $^1$H NMR (401 MHz, CDCl$_3$) δ 7.75-7.64 (m, 4H), 7.46-7.35 (m, 6H), 4.13

(q, J=7.1 Hz, 2H), 3.65 (t, J=6.5 Hz, 2H), 2.29 (dd, J=14.6, 6.0 Hz, 1H), 2.09 (dd, J=14.6, 8.2 Hz, 1H), 1.95 (m, 1H), 1.61-1.50 (m, 2H), 1.38-1.20 (m, 19H), 1.05 (s, 9H), 0.93 (d, J=6.6 Hz, 3H).

A solution of potassium hydroxide (2.0 M, 11.3 mL, 22.6 mmol) was added to ester Int-56 (1.15 g, 2.26 mmol) in ethanol (40 mL) and the mixture stirred at room temperature for 19 hours. The reaction was adjusted to pH 2 by addition of 1 M HCl and the organic solvent removed under reduced pressure. The residue was diluted with water (15 mL) and the aqueous phase extracted with ethyl acetate (3×20 mL). The combined organic extracts were washed with brine (30 mL), dried ($MgSO_4$) and concentrated under reduced pressure to give the crude product. Silica gel chromatography (5% to 25% ethyl acetate/hexanes) gave a pure sample of acid Int-57 (321 mg, 29%) as a pale yellow oil that was used for analytical purposes. An additional >750 mg of 9 was obtained containing slight contamination by an unknown TBDPS species—this material was carried forward and purified at a later stage in the reaction sequence. $^1$H NMR (401 MHz, $CDCl_3$) δ 7.70-7.64 (m, 4H), 7.44-7.34 (m, 6H), 3.65 (t, J=6.5 Hz, 2H), 2.35 (dd, J=15.0, 5.9 Hz, 1H), 2.14 (dd, J=15.0, 8.2 Hz, 1H), 1.95 (m, 1H), 1.60-1.51 (m, 2H), 1.39-1.16 (m, 16H), 1.04 (s, 9H), 0.96 (d, J=6.6 Hz, 3H); $^{13}$C NMR (101 MHz, $CDCl_3$) δ 179.3 (C), 135.7 (4C; CH), 134.4 (2C; C), 129.6 (2C; CH), 127.7 (4C; CH), 64.2 ($CH_2$), 41.7 ($CH_2$), 36.8 ($CH_2$), 32.7 ($CH_2$), 30.3 (CH), 29.9 ($CH_2$), 29.76 (2C; $CH_2$), 29.72 ($CH_2$), 29.5 ($CH_2$), 27.1 ($CH_2$), 27.0 (3C; $CH_3$), 25.9 ($CH_2$), 19.8 ($CH_3$), 19.4 (C).

DMAP (80.8 mg, 0.661 mmol), EDC·HCl (230 mg, 1.20 mmol) and 1,3-diglyceride Int-2 (374 mg, 0.658 mmol) were added to a solution of acid Int-57 (288 mg, 0.597 mmol) in $CH_2Cl_2$ (20 mL) and the mixture stirred at room temperature for 20 hours. The reaction was diluted with $CH_2Cl_2$ (20 mL), silica gel was added and the mixture concentrated under reduced pressure. Purification by silica gel chromatography (5% to 8% ethyl acetate/hexanes) gave triglyceride Int-58 (416 mg, 67%) as a colorless solid. $^1$H NMR (401 MHz, $CDCl_3$) δ 7.69-7.64 (m, 4H), 7.44-7.34 (m, 6H), 5.28 (m, 1H), 4.289/4.288 (each dd, J=11.9, 4.3 Hz, 2H), 4.14 (dd, J=12.0, 6.0 Hz, 2H), 3.65 (t, J=6.5 Hz, 2H), 2.34 (dd, J=15.0, 5.9 Hz, 1H), 2.30 (t, J=7.5 Hz, 4H), 2.12 (dd, J=14.6, 8.3 Hz, 1H), 1.93 (m, 1H), 1.66-1.50 (m, 6H), 1.45-1.14 (m, 64H), 1.04 (s, 9H), 0.93 (d, J=6.6 Hz, 3H), 0.88 (t, J=6.6 Hz, 6H).

Tetrabutylammonium fluoride (TBAF, 1.0 M in THF, 574 µL, 0.574 mmol) and acetic acid (32.8 µL, 0.574 mmol) were added to a solution of TBDPS ether Int-58 (395 mg, 0.383 mmol) in THF (15 mL) at 0° C. and the mixture stirred at room temperature for 17 hours. The reaction was concentrated under reduced pressure and the residue diluted with ethyl acetate (30 mL), washed with water (2×20 mL) and brine (30 mL), dried ($MgSO_4$) and concentrated under reduced pressure to give the crude product. Purification by silica gel chromatography (5% to 25% ethyl acetate/hexanes) gave alcohol Int-59 (282 mg, 93%) as a colorless solid. $^1$H NMR (401 MHz, $CDCl_3$) δ 5.28 (m, 1H), 4.286/4.285 (each dd, J=11.8, 4.2 Hz, 2H), 4.14 (dd, J=11.9, 5.7 Hz, 2H), 3.63 (t, J=6.6 Hz, 2H), 2.33 (dd, J=15.0, 5.9 Hz, 1H), 2.30 (t, J=7.5 Hz, 4H), 2.12 (dd, J=14.7, 8.3 Hz, 1H), 1.93 (m, 1H), 1.68-1.52 (m, 6H), 1.49-1.15 (m, 64H), 0.93 (d, J=6.6 Hz, 3H), 0.88 (t, J=6.6 Hz, 6H); $^{13}$C NMR (101 MHz, $CDCl_3$) δ 173.5 (2C; C), 172.5 (C), 69.0 (CH), 63.2 ($CH_2$), 62.3 (2C; $CH_2$), 41.9 ($CH_2$), 34.2 (2C; $CH_2$), 33.0 ($CH_2$), 32.1 (2C; $CH_2$), 30.5 (CH), 29.9 ($CH_2$), 29.84 (6C; $CH_2$), 29.81 (4C; $CH_2$), 29.77 (2C; $CH_2$), 29.74 ($CH_2$), 29.71 ($CH_2$), 29.62 (2C; $CH_2$), 29.57 ($CH_2$), 29.5 (2C; $CH_2$), 29.4 (2C; $CH_2$), 29.3 (3C; $CH_2$), 27.1 ($CH_2$), 25.9 ($CH_2$), 25.0 (2C; $CH_2$), 22.8 (2C; $CH_2$), 19.7 ($CH_3$), 14.3 (2C; $CH_3$).

Pyridinium chlorochromate (PCC, 143 mg, 0.664 mmol) was added to a suspension of alcohol Int-59 (263 mg, 0.331 mmol) and Celite (150 mg) in $CH_2Cl_2$ (18 mL) at 0° C. and the mixture stirred at room temperature for four hours. The reaction was filtered through a short pad of silica gel, eluting with ethyl acetate, and the filtrate concentrated under reduced pressure to give crude aldehyde Int-60 (262 mg, quant.) as a yellow oil that was used without purification. $^1$H NMR (401 MHz, $CDCl_3$) δ 9.76 (t, J=1.8 Hz, 1H), 5.27 (m, 1H), 4.29 (dd, J=11.8, 4.1 Hz, 2H), 4.14 (dd, J=11.8, 6.0 Hz, 2H), 2.42 (td, J=7.4, 1.8 Hz, 2H), 2.33 (dd, J=15.0, 5.9 Hz, 1H), 2.30 (t, J=7.5 Hz, 4H), 2.12 (dd, J=14.7, 8.3 Hz, 1H), 1.93 (m, 1H), 1.69-1.53 (m, 6H), 1.45-1.16 (m, 62H), 0.93 (d, J=6.6 Hz, 3H), 0.88 (t, J=6.8 Hz, 6H).

Int-25 was prepared as described above.

A solution of ylide Int-25 (270 mg, 0.637 mmol) in toluene (10 mL) was added to aldehyde Int-60 (262 mg, 0.331 mmol) in toluene (8 mL) and the mixture heated at reflux for 20 hours. The reaction was cooled to room temperature and concentrated under reduced pressure to give the crude product. Purification by silica gel chromatography (5% to 15% ethyl acetate/hexanes) gave α,β-unsaturated benzyl ester Int-61 (273 mg, 88%) as a yellow oil. $^1$H NMR (401 MHz, $CDCl_3$) δ 7.40-7.27 (m, 5H), 6.82 (td, J=7.5, 1.4 Hz, 1H), 5.28 (m, 1H), 5.18 (s, 2H), 4.29 (dd, J=11.9, 4.3 Hz, 2H), 4.14 (dd, J=11.9, 6.0 Hz, 2H), 2.33 (dd, J=15.0, 5.9 Hz, 1H), 2.30 (t, J=7.5 Hz, 4H), 2.20-2.07 (m, 3H), 1.92 (m, 1H), 1.85 (d, J=1.2 Hz, 3H), 1.65-1.53 (m, 4H), 1.47-1.37 (m, 2H), 1.36-1.14 (m, 62H), 0.93 (d, J=6.6 Hz, 3H), 0.88 (t, J=6.9 Hz, 6H); $^{13}$C NMR (101 MHz, $CDCl_3$) δ 173.4 (2C; C), 172.5 (C), 168.2 (C), 143.3 (CH), 136.6 (C), 128.6 (2C; CH), 128.13 (CH), 128.11 (2C; CH), 127.5 (C), 68.9 (CH), 66.3 ($CH_2$), 62.3 (2C; $CH_2$), 41.8 ($CH_2$), 36.8 ($CH_2$), 34.2 (2C; $CH_2$), 32.1 (2C; $CH_2$), 30.5 (CH), 29.9 ($CH_2$), 29.84 (6C; $CH_2$), 29.80 (4C; $CH_2$), 29.76 (2C; $CH_2$), 29.70 ($CH_2$), 29.61 (3C; $CH_2$), 29.57 ($CH_2$), 29.5 (2C; $CH_2$), 29.4 (2C; $CH_2$), 29.3 (3C; $CH_2$), 28.9 ($CH_2$), 28.7 ($CH_2$), 27.1 ($CH_2$), 25.0 (2C; $CH_2$), 22.8 (2C; $CH_2$), 19.7 ($CH_3$), 14.3 (2C; $CH_3$), 12.5 ($CH_3$).

A solution of benzyl ester Int-61 (246 mg, 0.262 mmol) in ethyl acetate (10 mL) in a two-neck flask was evacuated and flushed with $N_2$ gas (three times each), then palladium on carbon (10% w/w, 55.7 mg, 0.0524 mmol) was added and the resulting suspension re-evacuated and flushed with $N_2$ (three times each). The flask was fitted with a $H_2$ balloon, evacuated and flushed with $H_2$ (three times each) and the reaction mixture stirred at room temperature under 1 atm of $H_2$ for 1.5 hours. The reaction was filtered through a pad of celite, washing with ethyl acetate, and concentrated under reduced pressure to give the crude product. Purification by silica gel chromatography (5% to 20% ethyl acetate/hexanes) gave saturated acid Int-62 (193 mg, 87%) as a colorless solid. $^1$H NMR (401 MHz, $CDCl_3$) δ 5.28 (m, 1H), 4.291/4.289 (each dd, J=11.8, 4.2 Hz, 2H), 4.147/4.144 (each dd, J=11.9, 6.0 Hz, 2H), 2.46 (m, 1H), 2.33 (dd, J=15.0, 5.9 Hz, 1H), 2.31 (t, J=7.5 Hz, 4H), 2.12 (dd, J=14.7, 8.2 Hz, 1H), 1.94 (m, 1H), 1.73-1.55 (m, 5H), 1.50-1.21 (m, 67H), 1.18 (d, J=7.0 Hz, 3H), 0.93 (d, J=6.6 Hz, 3H), 0.88 (t, J=6.9 Hz, 6H).

C15α'βMe-acid-2-TG-butyrate (Int-219)

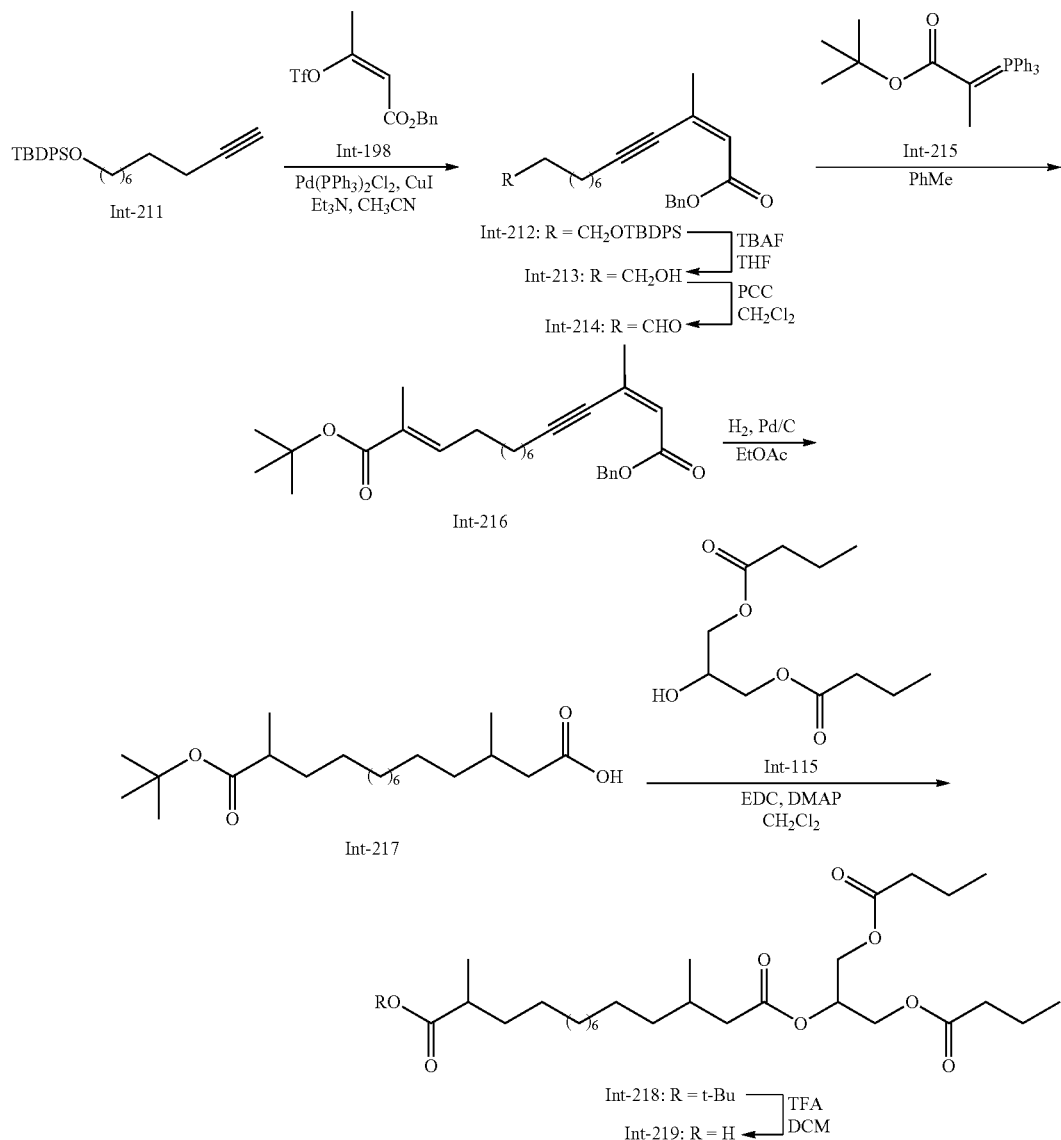

Int-211 was prepared from dec-9-yn-1-ol and TBDPSCl using the procedure for preparation of Int-56, above. $^1$H NMR (400 MHz, CDCl$_3$) δ 7.72 (dd, J=6.4, 1.8 Hz, 4H), 7.48-7.40 (m, 6H), 3.71 (t, J=6.4 Hz, 2H), 2.24 (td, J=6.8, 2.4 Hz, 2H), 1.98 (s, 1H), 1.63 (dq, J=6.4 Hz, 2H), 1.47 (m, 4H), 1.40 (m, 6H), 1.09 (s, 9H).

A suspension of PdCl$_2$(PPh$_3$)$_2$ (6.44 g, 9.18 mmol) in CH$_3$CN (180 mL) was degassed using N$_2$ gas for five minutes, and then CuI (1.74 g, 9.18 mmol), Et$_3$N (18.54 g, 183.7 mmol) and a degassed solution of alkyne Int-211 (36.0 g, 91.8 mmol) and Int-198 (29.75 g, 91.83 mmol) in CH$_3$CN (180 mL) were added. The mixture was degassed using a stream of N$_2$ for a further five minutes and then heated at 60° C. for two hours. The reaction was cooled to room temperature, diluted with water (360 mL), and extracted with EtOAc (3×360 mL). The combined organic layers were dried over sodium sulfate and concentrated under reduced pressure. The resulting oil was purified by column chromatography using silica gel (100-200 mesh), with product eluting at 4-7% EtOAc in hexane, to afford Int-212 (33.0 g, 63.5%). $^1$H NMR (400 MHz, CDCl$_3$) δ 7.71 (d, J=6.0 Hz, 4H), 7.43 (dd, J=18.4, 10.7, 8.0 Hz, 11H), 6.02 (s, 1H), 5.22 (s, 2H), 3.69 (t, 2H), 2.44 (t, 2H), 2.06 (s, 3H), 1.59 (dq, 2H), 1.38 (ddd, J=15.2, 10.9, 6.1 Hz, 4H), 1.31 (dd, J=7.3, 3.8 Hz, 6H), 1.08 (s, 9H).

Int-213 was prepared from Int-212 by analogy to the procedure for preparation of Int-59, above. $^1$H NMR (400 MHz, CDCl$_3$) δ 7.41 (dd, J=12.7, 4.8 Hz, 5H), 6.09 (s, 1H), 5.21 (d, J=11.2 Hz, 2H), 3.69 (t, J=6.4 Hz, 2H), 2.44 (t, J=7.2 Hz, 2H), 2.08 (s, 3H), 1.58 (p, J=7.1 Hz, 2H), 1.48-1.43 (m, 10H).

Int-214 was prepared from Int-213 by analogy to the procedure for preparation of Int-60, above.

To a solution of Int-214 (19 g, 58.2 mmol) in toluene (190 mL) at room temperature under nitrogen atmosphere was added Int-215 (68.19 g, 174.8 mmol; prepared from triphenyl phosphine and t-butyl 2-bromopropanoate). The resulting reaction mixture was heated at 90° C. for 2 hours. The reaction mixture was cooled to room temperature and concentrated under reduced pressure. The resulting oil was purified by column chromatography using silica gel (100-200 mesh), with product eluting at 2-4% EtOAc in hexane, to afford Int-216 (15.0 g, 58.9%). $^1$H NMR (400 MHz, CDCl$_3$) δ 7.43-7.35 (m, 5H), 6.69 (t, J=7.2 Hz, 1H), 6.09 (s, 1H), 5.19 (s, 2H), 2.39 (t, J=12.8 Hz, 2H), 2.18 (q, J=7.4 Hz, 2H), 2.03 (s, 3H), 1.82 (s, 3H), 1.61-1.55 (m, 12H), 1.45 (s, 9H).

Palladium on carbon (10% w/w, 19 g) was added to a solution of Int-216 (19 g, 43.37 mmol) in ethyl acetate (190 mL) in an autoclave, and the autoclave was evacuated and re-filled with N$_2$ three times. The autoclave was evacuated and pressurized with 10 kg/cm$^2$H$_2$ pressure, and the reaction mixture was stirred at room temperature for 72 h. The reaction mixture was filtered through a pad of Celite, which was washed with additional ethyl acetate (380 mL). The filtrate was concentrated under reduced pressure to afford Int-217 (13 g, 84.2%) as a colorless oil, which was used for the next step without further purification. $^1$H NMR (400 MHz, CDCl$_3$) δ 2.39-2.29 (m, 3H), 2.19-2.12 (m, 1H), 1.96 (s, 2H), 1.46 (s, 9H), 1.27 (s, 18H), 1.10 (d, J=6.8 Hz, 3H), 0.97 (d, J=6.6 Hz, 3H).

To a stirred solution of Int-217 (6.0 g, 16.4 mmol) and Int-115 (3.81 g, 16.4 mmol) in DCM (120.0 mL) at room temperature was added EDC·HCl (7.8 g, 41.1 mmol) and DMAP (2.0 g, 16.4 mmol). The reaction mixture was stirred at room temperature for 18 h. The reaction mixture was concentrated under vacuum. The resulting residue was purified by column chromatography using silica gel, eluting with 4-5% EtOAc in n-hexane, to afford Int-218 (6.0 g, 62.5%) as a brownish viscous liquid. $^1$H NMR (400 MHz, CDCl$_3$) δ 5.34-5.23 (m, 1H), 4.33 (dd, J=12.1, 4.2 Hz, 2H), 4.17 (dd, J=11.9, 6.0 Hz, 2H), 2.30 (dd, J=8.7, 6.2 Hz, 5H), 2.12 (dd, J=14.7, 8.3 Hz, 2H), 1.93 (s, 1H), 1.66 (p, J=7.4 Hz, 6H), 1.44 (s, 9H), 1.35-1.15 (m, 18H), 1.08 (d, J=7.0 Hz, 3H), 0.99-0.88 (m, 9H).

To a stirred solution of Int-218 (6.0 g, 10.5 mmol) in DCM (120 mL) at room temperature was added TFA (12.0 mL, 2.0 vol.), and the solution was stirred at room temperature for 3.0 hours. The reaction mixture was concentrated under vacuum. The residue was diluted with water (500 mL) and extracted with ethyl acetate (2×500 mL). The combined organic layers were washed with sodium bicarbonate solution and brine, then dried over sodium sulfate, filtered and concentrated under vacuum to afford Int-219 (5.1 g, 94%) as a yellowish viscous liquid. $^1$H NMR (400 MHz, CDCl$_3$) δ 5.33 (ddd, J=10.3, 6.0, 4.2 Hz, 1H), 4.30 (dd, J=11.9, 4.3 Hz, 2H), 4.16 (dd, J=11.9, 6.0 Hz, 2H), 2.47 (h, J=6.9 Hz, 2H), 2.31 (q, J=8.2, 7.6 Hz, 6H), 2.12 (dd, J=14.6, 8.3 Hz, 1H), 1.64 (dt, J=14.8, 7.4 Hz, 6H), 1.27 (m, 15H), 1.18 (d, J=6.9 Hz, 6H), 1.01-0.84 (m, 9H); $^{13}$C NMR (101 MHz, CDCl$_3$) δ 183.51 (1C), 173.61 (2C), 172.85 (1C), 68.92 (1C), 62.26 (2C), 41.72 (1C), 39.38 (1C), 36.66 (1C), 35.93 (2C), 33.52 (1C), 30.39 (1C), 29.76-29.45 (6C), 27.12 (1C), 26.91 (1C), 19.53 (1C), 18.33 (2C), 16.80 (1C), 13.60 (2C); MS (ESI, +ve) m/z: 532.70 (M+18).

C15α'βMe-acid-2-TG-octanoate (Int-220):

Using the procedures described for the synthesis of Int-219, compound Int-220 was prepared from Int-217 and Int-192:

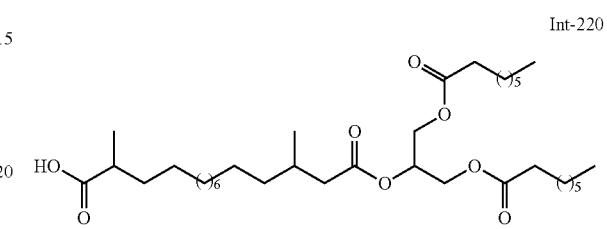

$^1$H NMR (400 MHz, CDCl$_3$) δ 5.32 (t, J=12.4 Hz, 2H), 4.33 (dd, J=11.6, 4.0 Hz, 2H), 4.19 (dd, J=12.0, 6.0 Hz, 2H), 2.51 (m, 1H), 2.37 (m, 6H), 2.17 (m, 1H), 1.71 (m, 6H), 1.30 (d, J 10.4 Hz, 34H), 1.21 (d, J=6.8 Hz, 3H), 0.96-0.88 (m, 9H); $^{13}$C NMR (101 MHz, CDCl$_3$) δ 182.71 (1C), 173.44 (2C), 172.49 (1C), 69.84 (1C), 62.21 (2C), 41.74 (1C), 39.30 (1C), 36.70 (1C), 34.07 (2C), 33.55 (2C), 31.69 (1C), 30.39 (1C), 29.80-28.93 (14C), 27.16 (1C), 26.95 (1C), 19.58 (1C), 16.85 (1C), 14.09 (2C); MS (ESI, +ve) m/z: 644.89 (M+18).

C15α'βMe-acid-2-TG-oleate (Int-221):

Using the procedures described for the synthesis of Int-219, compound Int-221 was prepared from Int-217 and Int-112:

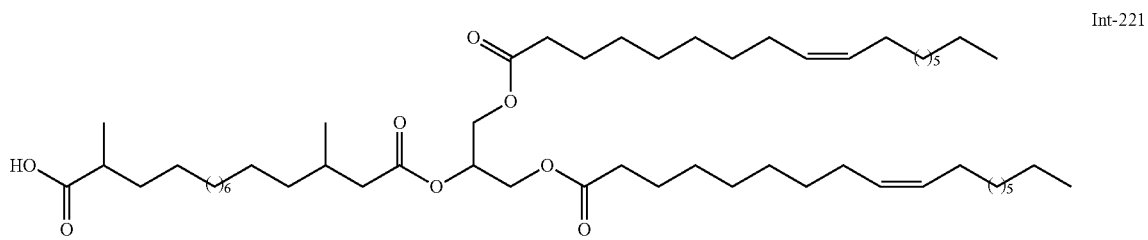 [SMILES: CCCC/C=C\CCCCCCCC(=O)OCC(COC(=O)CCCCCCC/C=C\CCCC)OC(=O)CC(C)CCCCCC(C)C(=O)O]

$^1$H NMR (400 MHz, CDCl$_3$) δ 5.38-5.32 (m, 5H), 4.35-4.32 (dd, J=4.4 Hz, 12.0 Hz, 2H), 4.20-4.15 (dd, J=6.0 Hz, 11.6 Hz, 2H), 2.49 (m, 1H), 2.34 (t, J=7.2 Hz, 2H), 2.09-2.04 (m, 5H), 1.71-1.64 (m, 6H), 1.34-1.30 (m, 66H), 1.13 (d, J=6.9 Hz, 3H), 0.96 (d, J=6.9 Hz, 3H), 0.91 (t, J=6.0 Hz, 6H); $^{13}$C NMR (101 MHz, CDCl$_3$) δ 182.72 (1C), 173.33 (2C), 172.42 (1C), 130.03 (2C), 129.73 (2C), 68.83 (1C), 62.19 (2C), 41.71 (1C), 39.31 (1C), 36.69 (1C), 34.05 (2C), 33.53 (1C), 31.94 (2C), 30.36 (1C), 29.79-29.12 (23C), 27.21 (4C), 26.97 (1C), 24.85 (2C), 22.71 (2C), 19.57 (1C), 16.85 (1C), 14.14 (2C); MS (ESI, −ve) m/z: 902 (M−1). (ESI, +ve) m/z: 921 (M+18).

C18α'βMe-acid-2-TG-oleate (Int-224):

Using the procedures described for the synthesis of Int-219, compounds Int-222, Int-223, and Int-224 were prepared from Int-112 and tert-butyldimethyl(tridec-12-yn-1-yloxy)silane, which was prepared from dodecan-1,12-diol by mono-TBS protection (with TBSCl, imidazole, and DMAP in a mixture of DCM and DMF) followed by PCC oxidation and Ohira reagent homologation (by analogy to the procedures for synthesizing Int-197 from Int-195).

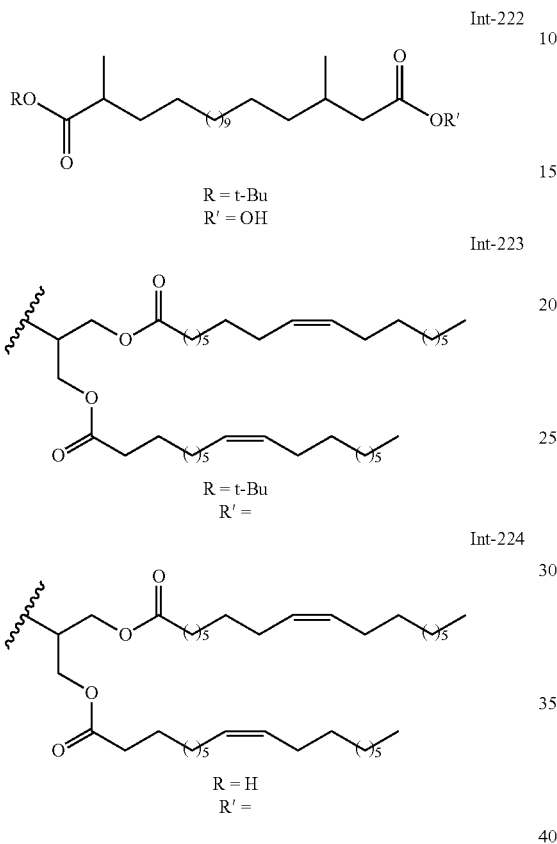

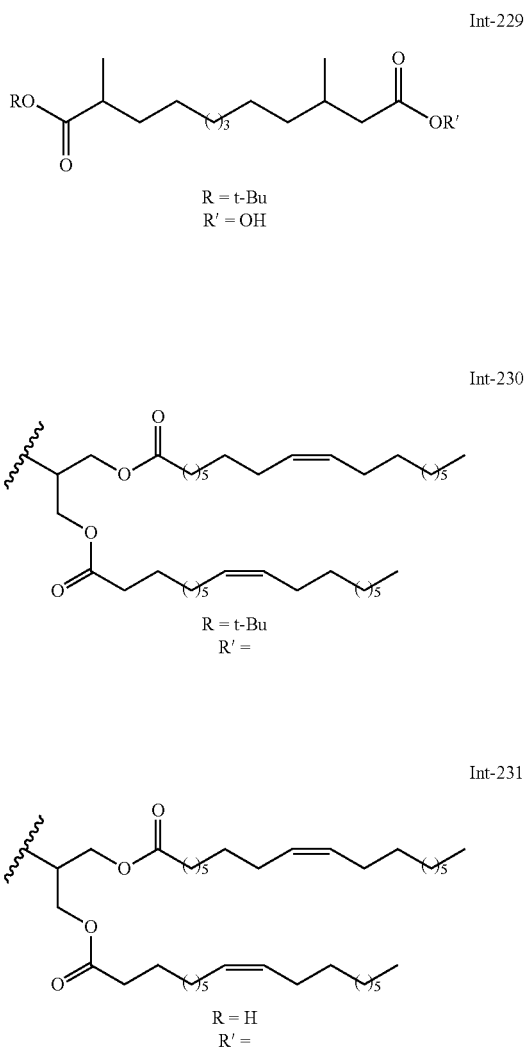

Int-222 ¹H NMR (400 MHz, CDCl₃) 2.42-2.31 (m, 2H), 2.21-2.14 (m, 1H), 2.00 (m, 1H), 1.49 (s, 9H), 1.29 (m, 26H), 1.13 (d, J=7.2 Hz, 3H), 0.99 (d, J=6.4 Hz, 3H).

C18α'βMe-CO₂tBu-2-TG-oleate (Int-223) ¹H NMR (400 MHz, CDCl₃) δ 5.40-5.32 (m, 5H), 4.35-4.31 (dd, J=4.4 Hz, 12.0 Hz, 2H), 4.20-4.16 (dd, J=6.0 Hz, 11.6 Hz, 2H), 2.39-2.31 (m, 6H), 2.16 (m, 1H), 2.05 (m, 9H), 1.64 (m, 6H), 1.49 (s, 9H), 1.41-1.27 (m, 64H), 1.13 (d, J=6.9 Hz, 3H), 0.96 (d, J=6.9 Hz, 3H), 0.90 (m, 6H).

C18α'βMe-acid-2-TG-oleate (Int-224) ¹H NMR (400 MHz, CDCl₃) δ 5.41-5.31 (m, 5H), 4.35-4.31 (dd, J=4.4 Hz, 12.0 Hz, 2H), 4.20-4.15 (dd, J=6.0 Hz, 11.6 Hz, 2H), 2.54 (m, 1H), 2.39-2.33 (m, 4H), 2.19-2.13 (m, 1H), 2.09-2.02 (m, 6H), 1.75-1.63 (m, 6H), 1.34-1.30 (m, 68H), 1.23-1.21 (d, J=6.8 Hz, 3H), 0.98-0.87 (m, 9H); ¹³C NMR (101 MHz, CDCl₃) δ 182.21 (1C), 173.32 (2C), 172.40 (1C), 130.03 (2C), 129.74 (2C), 68.83 (1C), 62.21 (2C), 41.73 (1C), 39.24 (1C), 36.73 (1C), 34.06 (2C), 33.57 (1C), 31.93 (2C), 30.40 (1C), 29.79-29.12 (26C), 27.25 (2C), 27.20 (2C), 26.97 (1C), 24.86 (2C), 22.71 (2C), 19.59 (1C), 16.85 (1C), 14.14 (2C); MS (ESI, +ve) m/z: 963.09 (M+18).

C12α'βMe-acid-2-TG-oleate (Int-231):

Using the procedures described for the synthesis of Int-219, compounds Int-229, Int-230, and Int-231 were prepared from Int-112 and hept-6-yn-1-ol.

Int-229 ¹H NMR (400 MHz, CDCl₃) 2.38-2.28 (m, 3H), 2.18-2.12 (m, 2H), 1.96 (s, 2H), 1.45 (s, 9H), 1.28 (s, 12H), 1.10 (d, J=6.9 Hz, 3H), 0.97 (d, J=6.6 Hz, 3H).

C12α'βMe-CO₂tBu-2-TG-oleate (Int-230) ¹H NMR (400 MHz, CDCl₃) δ 5.38-5.32 (m, 5H), 4.33 (dd, J=11.6 Hz, 4.0 Hz, 2H), 4.18 (dd, J=11.6 Hz, 6.0 Hz, 2H), 2.39-2.33 (m, 6H), 2.18-1.97 (m, 10H), 1.64-1.61 (m, 6H), 1.48 (s, 9H), 1.33-1.30 (m, 52H), 1.13 (d, J=13.0 Hz, 3H), 0.97 (d, J=7.2 Hz, 3H), 0.92 (t, J=6.0 Hz, 6H).

C₁₂α'βMe-acid-2-TG-oleate (Int-231) ¹H NMR (400 MHz, CDCl₃) δ 5.42-5.29 (m, 5H), 4.33 (dd, J=4.4 Hz, 12.0 Hz, 2H), 4.18 (dd, J=6.0 Hz, 11.6 Hz, 2H), 2.55-2.46 (m, 1H), 2.39-2.33 (t, J=7.2 Hz, 5H), 2.16 (q, J=6.4 Hz, 1H), 2.05-1.97 (m, 8H), 1.74-1.63 (m, 5H), 1.49-1.44 (m, 2H), 1.34-1.30 (m, 52H), 1.13 (d, J=13.0 Hz, 3H), 0.97 (d, J=7.2 Hz, 3H), 0.92 (t, J=6.0 Hz, 6H); ¹³C NMR (101 MHz, CDCl₃) δ 182.75 (1C), 173.32 (2C), 172.38 (1C), 130.03 (2C), 129.73 (2C), 68.83 (1C), 62.19 (2C), 41.71 (1C), 39.31 (1C), 36.69 (1C), 34.05 (2C), 33.53 (1C), 31.94 (2C), 30.36 (1C), 29.79-29.12 (19C), 27.25 (2C), 27.20 (2C), 27.15 (2C), 24.85 (2C), 22.71 (2C), 19.57 (1C), 16.85 (1C), 14.14 (2C); MS (ESI, -ve) m/z: 859.93 (M-1); (ESI, +ve) m/z: 878.94 (M+18).

Ph-C3-phenol-2-TG (Int-67):

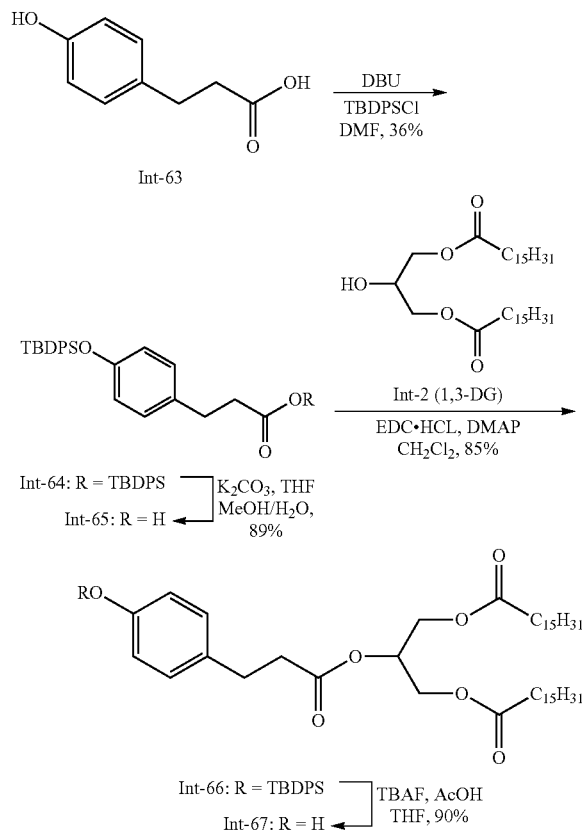

DBU (108 μL, 1.08 mmol) and t-butyldiphenylsilyl chloride (TBDPSCl, 338 PL, 1.30 mmol) were added to a solution of (4-hydroxyphenyl)propionic acid (Int-63; commercially available) (120 mg, 0.722 mmol) in DMF (4 mL) and the mixture stirred at room temperature for one hour. The reaction was diluted with ethyl acetate (15 mL) and organic phase washed with water and brine (15 mL each), dried (MgSO$_4$) and concentrated under reduced pressure to give the crude product. Silica gel chromatography (4.5% ethyl acetate/hexanes) gave silyl ester Int-64 (165 mg, 36%) as a colorless oil. $^1$H NMR (400 MHz, CDCl$_3$): δ 7.75-7.70 (m, 4H), 7.63-7.58 (m, 4H), 7.46-7.31 (m, 12H), 6.97-6.91 (m, 2H), 6.71-6.67 (m, 2H), 2.87 (t, J=7.6 Hz, 2H), 2.72 (t, J=7.6 Hz, 2H), 1.11 (s, 9H), 1.07 (s, 9H); $^{13}$C NMR (101 MHz, CDCl$_3$): δ 172.3 (C), 154.1 (C), 135.7 (4C; CH), 135.4 (4C; CH), 133.2 (2C; C), 133.0 (C), 132.0 (2C; C), 130.1 (2C; CH), 130.0 (2C; CH), 129.2 (2C; CH), 127.9 (4C; CH), 127.8 (4C; CH), 119.7 (2C; CH), 37.9 (CH$_2$), 30.4 (CH$_2$), 27.0 (3C; CH$_3$), 26.7 (3C; CH$_3$), 19.6 (C), 19.2 (C).

Potassium carbonate (157 mg, 1.14 mmol) was added to a solution of TBDPS ester Int-64 (147 mg, 0.228 mmol) in THF (3 mL), methanol (1.5 mL) and water (1.5 mmol) and the mixture stirred at room temperature for 2.5 hours. The reaction was acidified to pH 2 by the addition of 1 M HCl and the aqueous layer extracted with ethyl acetate (3×15 mL). The combined organic extracts were washed with water (30 mL), sat. aq. NaHCO$_3$ (30 mL) and brine (30 mL), dried (MgSO$_4$) and concentrated under reduced pressure to give the crude product. Purification by silica gel chromatography (20% to 35% to 50% ethyl acetate/hexanes) gave acid Int-65 (82.4 mg, 89%) as a colorless solid. $^1$H NMR (400 MHz, CDCl$_3$) δ 7.74-7.67 (m, 4H), 7.45-7.32 (m, 6H), 6.95-6.88 (m, 2H), 6.71-6.65 (m, 2H), 2.82 (t, J=7.8 Hz, 2H), 2.58 (t, J=7.8 Hz, 2H), 1.09 (s, 9H); $^{13}$C NMR (101 MHz, CDCl$_3$): δ 179.2 (C), 154.3 (C), 135.7 (4C; CH), 133.1 (2C; C), 132.7 (C), 130.0 (2C; CH), 129.1 (2C; CH), 127.9 (4C; CH), 119.8 (2C; CH), 35.9 (CH$_2$), 29.9 (CH$_2$), 26.7 (3C; CH$_3$), 19.6 (C).

DMAP (8.2 mg, 0.0667 mmol), EDC·HCl (25.6 mg, 0.133 mmol) and 1,3-diglyceride Int-2 (41.7 mg, 0.0734 mmol) were added to a solution of acid Int-65 (27.0 mg, 0.0666 mmol) in CH$_2$Cl$_2$ (2 mL) and the mixture stirred at room temperature for 19 hours. The reaction was diluted with CH$_2$Cl$_2$ (3 mL), silica gel was added and the mixture concentrated under reduced pressure. Purification by silica gel chromatography (5% to 7.5% ethyl acetate/hexanes) gave triglyceride Int-66 (54.4 mg, 85%) as a colorless solid. $^1$H NMR (400 MHz, CDCl$_3$) δ 7.74-7.66 (m, 4H), 7.45-7.33 (m, 6H), 6.94-6.87 (m, 2H), 6.71-6.64 (m, 2H), 5.24 (m, 1H), 4.25 (dd, J=11.9, 4.3 Hz, 2H), 4.11 (dd, J=11.9, 5.9 Hz, 2H), 2.81 (t, J=7.8 Hz, 2H), 2.60-2.51 (m, 2H), 2.28 (t, J=7.5 Hz, 4H), 1.64-1.56 (m, 4H), 1.35-1.20 (m, 48H), 1.09 (s, 9H), 0.88 (t, J=6.8 Hz, 6H); $^{13}$C NMR (101 MHz, CDCl$_3$) δ 173.4 (2C; C), 172.2 (C), 154.2 (C), 135.7 (4C; CH), 133.1 (2C; C), 132.7 (C), 130.0 (2C; CH), 129.1 (2C; CH), 127.9 (4C; CH), 119.8 (2C; CH), 69.2 (CH), 62.1 (2C; CH$_2$), 36.0 (CH$_2$), 34.2 (2C; CH$_2$), 32.1 (2C; CH$_2$), 30.1 (CH$_2$), 29.85 (2C; CH$_2$), 29.81 (2C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.7 (3C; CH$_3$), 25.0 (2C; CH$_2$), 22.8 (2C; CH$_2$), 19.6 (C), 14.3 (2C; CH$_3$).

Acetic acid (6.5 μL, 0.114 mmol) and tetrabutylammonium fluoride (TBAF, 1.0 M in THF, 114 μL, 0.114 mmol) were added to a solution of TBDPS ether Int-66 (54.5 mg, 0.0570 mmol) in THF (1.2 mL) at 0° C. and the mixture stirred at room temperature for 30 minutes. The reaction was diluted with water (10 mL) and the aqueous layer extracted with ethyl acetate (3×10 mL). The combined organic extracts were washed with sat. aq. NaHCO$_3$ (20 mL) and brine (20 mL), dried (MgSO$_4$) and concentrated under reduced pressure to give the crude product. Purification by silica gel chromatography (10% to 15% ethyl acetate/hexanes) gave phenol Int-67 (37.0 mg, 90%) as a colorless solid. $^1$H NMR (400 MHz, CDCl$_3$) δ 7.09-7.03 (m, 2H), 6.78-6.72 (m, 2H), 5.25 (m, 1H), 4.62 (s, 1H), 4.25 (dd, J=11.9, 4.4 Hz, 2H), 4.11 (dd, J=11.9, 5.8 Hz, 2H), 2.88 (t, J=7.7 Hz, 2H), 2.61 (t, J=7.7 Hz, 2H), 2.29 (t, J=7.6 Hz, 4H), 1.64-1.56 (m, 4H), 1.34-1.18 (m, 48H), 0.88 (t, J=6.9 Hz, 6H); $^{13}$C NMR (101 MHz, CDCl$_3$) δ 173.6 (2C; C), 172.3 (C), 154.4 (C), 132.3 (C), 129.5 (2C; CH), 115.5 (2C; CH), 69.2 (CH), 62.2 (2C; CH$_2$), 36.2 (CH$_2$), 34.2 (2C; CH$_2$), 32.1 (2C; CH$_2$), 30.2 (CH$_2$), 29.83 (6C; CH$_2$), 29.79 (4C; CH$_2$), 29.76 (2C; CH$_2$), 29.6 (2C; CH$_2$), 29.5 (2C; CH$_2$), 29.4 (2C; CH$_2$), 29.2 (2C; CH$_2$), 25.0 (2C; CH$_2$), 22.8 (2C; CH$_2$), 14.3 (2C; CH$_3$).

DMPh-C10βMe-phenol-2-TG-oleate (Int-202):

Scheme 21-A. Synthesis of Int-202.

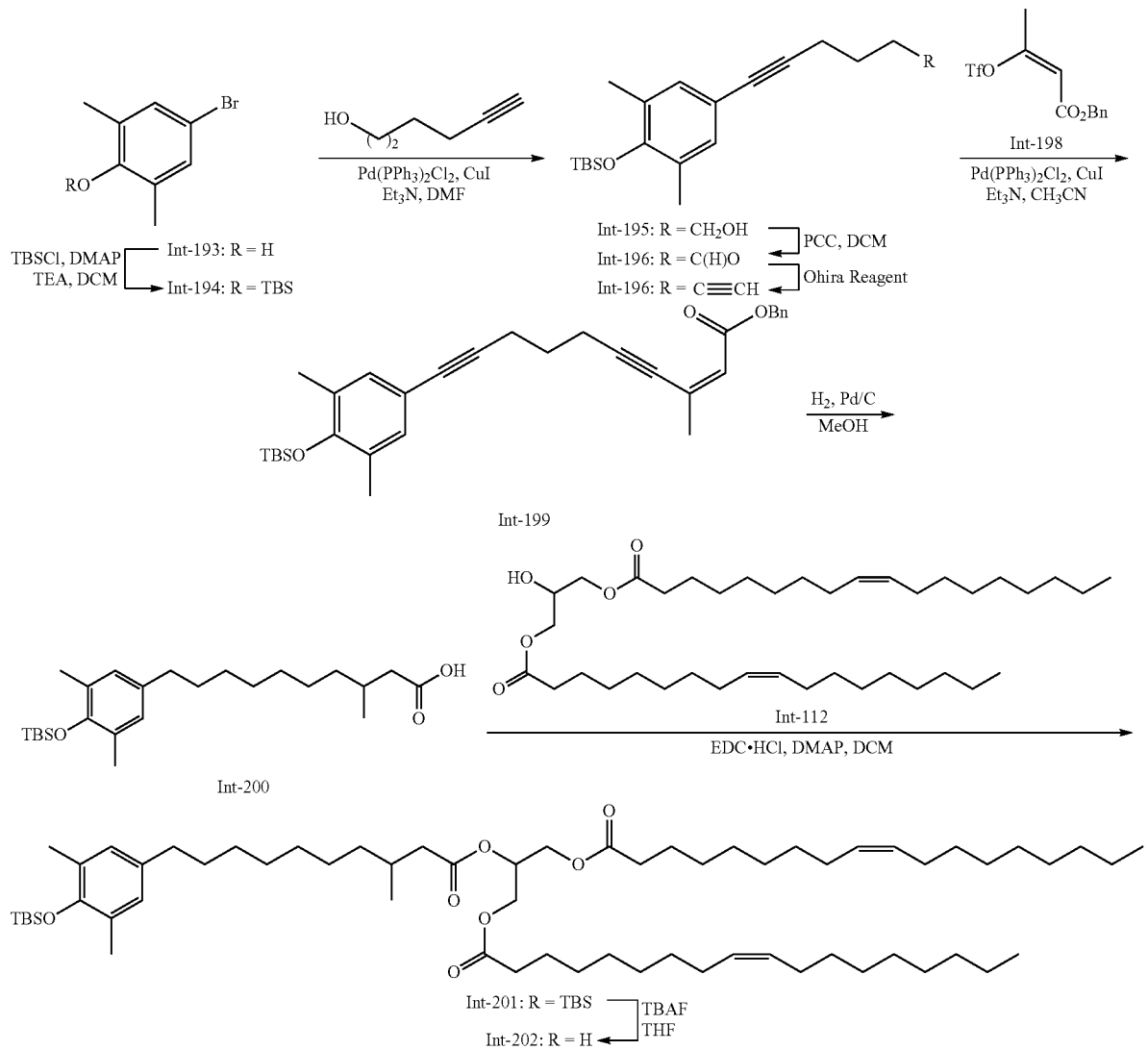

To a stirred solution of Int-193 (40.0 g, 199 mmol) at RT in DCM (400 mL) was added DMAP (24.27 g, 199.0 mmol) and TEA (40.19 g, 398.0 mmol). To the reaction mixture was added TBDMSCl (44.9 g, 298.4 mmol) in portions, and the resulting reaction mixture was stirred at RT for 2 hours. The reaction mixture was diluted with water (400 mL) and extracted with DCM (3×400 mL). The combined organic layers were dried over sodium sulfate and evaporated under vacuum. The resulting materials was purified by column chromatography using silica gel (100-200 mesh). Desired product was eluted at 100% hexane as a mobile phase. Pure fractions were concentrated under vacuum to afford Int-194 (60.0 g, 95.7%). $^1$H NMR (400 MHz, CDCl$_3$): δ 7.11 (s, 2H), 2.19 (s, 6H), 1.04 (s, 9H), 0.66 (s, 6H).

A suspension of PdCl$_2$(PPh$_3$)$_2$ (5.11 g, 7.29 mmol) in DMF (230 mL) was degassed using N$_2$ gas for five minutes, and then CuI (1.38 g, 7.29 mmol), Et$_3$N (29.46 g, 291 mmol) and a degassed solution of Int-194 (23 g, 87.5 mmol) and hex-5-yn-1-ol (8.59 g, 87.5 mmol) was added. The mixture was degassed using a stream of N$_2$ for a further five minutes and then heated at 60° C. for 2 h. The reaction mixture was cooled to room temperature, diluted with cold water (300 mL), and extracted with ethyl acetate (3×250 mL). The combined organic layers were dried over sodium sulfate and evaporated under reduced pressure. The resulting material was purified by column chromatography using silica gel (100-200 mesh). Desired product eluted at 10% ethyl acetate/hexane as a mobile phase. Pure fractions were concentrated under vacuum to afford Int-195 (21.0 g, 43.3%). $^1$H NMR (400 MHz, CDCl$_3$) δ 7.03 (s, 2H), 2.57 (s, 6H), 2.48 (t, 2H), 2.47 (t, 2H), 1.80 (m, 4H), 1.32 (s, 9H), 0.95 (s, 6H).

To a stirred solution of Int-195 (5.0 g, 15.0 mmol) in DCM (50 mL) at 0° C. was slowly added PCC (6.49 g, 30.1 mmol). The reaction mixture was brought to RT and stirred for 2 h. The reaction mixture was filtered through a bed of Celite. The filtrate was evaporated under vacuum to afford Int-196 (4.16 g, 83.3%), which was used directly in the next step without further purification. $^1$H NMR (400 MHz, CDCl$_3$): δ 9.88 (s, 1H), 7.07 (s, 2H), 2.71 (t, J=14.4 Hz, 2H), 2.53 (t, J=13.6 Hz, 2H), 2.09 (s, 6H), 1.23 (m, 2H), 0.98 (s, 9H), 0.20 (s, 6H).

To a stirred solution of Int-196 (6.0 g, 18 mmol) in MeOH (60 mL) at 0° C. was added K$_2$CO$_3$ (10.3 g, 72.7 mmol) and then Ohira reagent (6.98 g, 36.4 mmol) was added dropwise. The reaction mixture was slowly allowed to warm to RT then stirred at RT for 3.5 h. The reaction mixture was evaporated under vacuum. The residue was diluted with water (60 mL) and extracted with ethyl acetate (5×60 mL). The combined organic layer was dried over sodium sulfate and evaporated under reduced pressure. The resulting material was purified by column chromatography using silica gel (100-200 mesh). Desired product was eluted at 2% ethyl acetate/hexane as a mobile phase. Pure fractions were concentrated under vacuum to afford Int-197 (21.0 g, 64.8%). $^1$H NMR (400 MHz, CDCl$_3$): δ 7.41 (s, 2H), 2.59-2.51 (m, 6H), 2.24 (s, 6H), 1.88-1.80 (m, 2H), 1.30 (s, 1H), 1.09 (s, 9H), 0.20 (s, 6H).

A suspension of PdCl$_2$(PPh$_3$)$_2$ (1.20 g, 1.71 mmol) in MeCN (56 mL) was degassed using N$_2$ gas for five minutes, and then CuI (0.326 g, 1.71 mmol), Et$_3$N (6.93 g, 68.7 mmol) and a degassed solution of Int-197 (5.6 g, 17.2 mmol) and Int-198 (13.91 g, 42.90 mmol; prepared similarly to Int-17) was added. The mixture was degassed using a stream of N$_2$ for a further five minutes and then stirred at RT for 3.5 h. The reaction mixture was diluted with water (60 mL), and extracted with ethyl acetate (3×60 mL). The combined organic layers were dried over sodium sulfate and evaporated under reduced pressure. The resulting oil was purified by column chromatography using silica gel (100-200 mesh). Desired product eluted at 2% ethyl acetate/hexane as a mobile phase. Pure fractions were concentrated under vacuum to afford Int-199 (3.0 g, 35%). $^1$H NMR (400 MHz, CDCl$_3$) δ 7.42-7.06 (m, 7H), 6.02 (s, 1H), 5.21 (s, 2H), 2.64-2.52 (m, 4H), 2.12 (s, 9H), 1.90-1.84 (m, 2H), 1.04 (s, 9H), 0.22 (s, 6H).

To a solution of Int-199 (6.0 g, 12.0 mmol) in ethyl acetate (60 mL) was added palladium on carbon (10% w/w, 5.3 g), and the resulting suspension was evacuated and filled with H$_2$ three times. The reaction mixture was stirred at RT for 48 h under H$_2$ pressure in an autoclave. The reaction mixture was filtered through a pad of Celite, which was washed with ethyl acetate (120 mL). The filtrate was evaporated under vacuum to afford Int-200 (4.5 g, 89%), which was used directly in the next step without further purification. $^1$H NMR (400 MHz, CDCl$_3$): δ 6.81 (s, 2H), 2.66 (t, J=15.6 Hz, 2H), 2.40 (dd, J=5.6, 14.8 Hz, 2H), 2.20 (s, 6H), 2.07 (m, 1H), 1.46 (m, 2H), 1.13-1.27 (m, 14H), 1.05 (s, 9H), 0.20 (s, 6H).

To a solution of Int-200 (4.5 g, 10.7 mmol) in DCM (45 mL) at RT were added 4-(dimethylamino)pyridine (1.30 g, 10.7 mmol), EDC·HCl (4.10 g, 21.4 mmol), and Int-112 (5.307 g, 8.56 mmol), and the reaction mixture was stirred at RT for 3 h. The reaction mixture was concentrated, then diluted with water (40 mL) and extracted with DCM (3×40 mL). The combined organic layer was dried over sodium sulfate and evaporated under reduced pressure. The resulting material was purified by column chromatography using silica gel (100-200 mesh). Desired product eluted at 2% ethyl acetate/hexane as a mobile phase. Pure fractions were concentrated under vacuum to afford Int-201 (3.7 g, 34%). $^1$H NMR (400 MHz, CDCl$_3$): δ 6.80 (s, 2H), 5.41 (m, 5H), 4.35 (dd, J=4.0, 4.4 Hz, 2H), 4.20 (dd, J=6.0, 6.1 Hz, 2H), 2.52 (t, J=15.6 Hz, 2H), 2.39-2.34 (m, 8H), 2.26 (m, 6H), 2.15 (d, J=8.4 Hz, 2H), 2.05 (dd, J=12.0 Hz, 12H), 1.66-1.43 (m, 6H), 1.34-1.30 (m, 51H), 0.978 (s, 9H), 0.92 (s, 6H).

A solution of Int-201 (2.5 g, 2.44 mmol) in THF (30 mL) was cooled at 0° C., and then TBAF (2M in THF, 6.10 mL, 6.1 mmol) was added dropwise over 10 min. The reaction mixture was stirred at RT for 3 h. The reaction mixture was diluted with water (30 mL) and extracted with ethyl acetate (3×30 mL). The combined organic layer was dried over sodium sulfate and then evaporated under reduced pressure. The resulting material was purified by column chromatography using silica gel (100-200 mesh). Desired product eluted at 6% ethyl acetate/hexane as a mobile phase. Pure fractions were concentrated under vacuum to afford Int-202 (0.920 g, 41.4%). $^1$H NMR (400 MHz, CDCl$_3$): δ 6.82 (s, 2H), 5.42 (m, 5H), 4.35 (dd, J=4.0, 4.4 Hz, 2H), 4.20 (dd, J=6.0, 6.1 Hz, 2H), 2.52 (t, J=15.6 Hz, 2H), 2.39-2.34 (m, 8H), 2.26 (m, 6H), 2.15 (d, J=8.4 Hz, 2H), 2.05 (dd, J=12.0 Hz, 9H), 1.66-1.43 (m, 6H), 1.34-1.30 (m, 42H), 1.04-0.96 (m, 14H); $^{13}$C NMR (101 MHz, CDCl$_3$): δ 173.34 (3C), 172.40 (2C), 150.10 (1C), 134.52 (1C), 130.05 (3C), 129.75 (2C), 128.46 (3C), 122.75 (1C), 68.83 (2C), 62.21 (3C), 60.45 (1C), 41.73 (2C), 36.72 (2C), 35.13 (2C), 34.06 (2C), 31.95 (3C), 30.40 (4C), 29.37 (8C), 29.26 (2C), 27.26 (3C), 22.73 (2C), 19.59 (2C), 15.98 (2C), 14.18 (2C). HPLC (UV, 285 nm): 15.99 min, 97.43% purity; HPLC(ELSD): 16.00 min, 100% purity; MS (ESI, +ve) m/z: 927.17 (M+18).

C6-ET-alcohol-2-TG (Int-73):

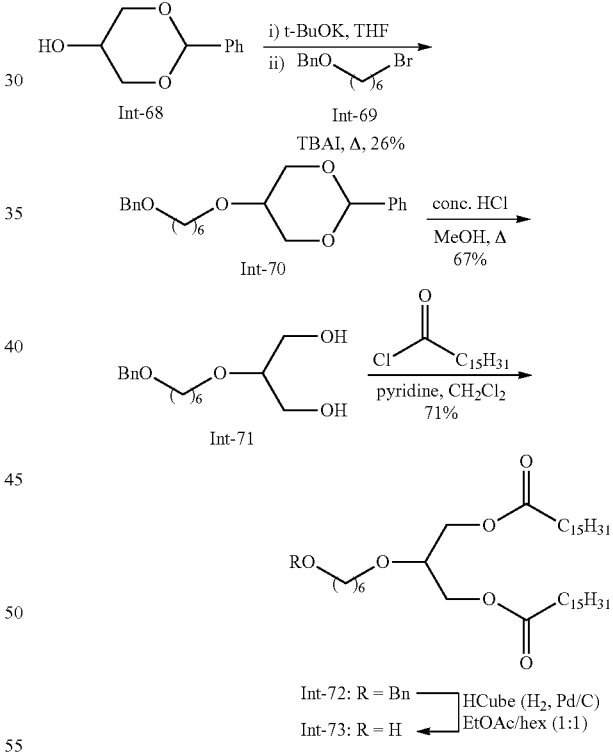

Int-69 is a known compound that may be prepared as described in, e.g., Sang-sup, J. et al. *Tetrahedron: Asymmetry* 1997, 8, 1187-1192).

Alcohol Int-68 (commercially available; 90.0 mg, 0.499 mmol) was added in a single portion to a suspension of t-BuOK (84.1 mg, 0.749 mmol) in THF (2 mL) and the mixture stirred at room temperature for one hour. A solution of bromide Int-69 (190 mg, 0.699 mmol) in THF (1 mL) and TBAI (36.9 mg, 0.100 mmol) were then added and the resulting mixture heated at reflux for 20 hours. The reaction was cooled to room temperature and diluted with ethyl acetate (10 mL), quenched with water (15 mL) and the aqueous phase extracted with ethyl acetate (3×20 mL). The combined organic extracts were washed with water and brine (50 mL each), dried (MgSO$_4$) and concentrated under reduced pressure to give the crude product. Silica gel chromatography (5 to 15% to 25% ethyl acetate/hexanes) gave a sample of semi-pure product, which was re-subjected to column chromatography (5% to 12.5% ethyl acetate/toluene) to give ether-linked glycerol Int-70 (48.0 mg, 26%) as a colorless oil. $^1$H NMR (400 MHz, CDCl$_3$): δ 7.54-7.49 (m, 2H), 7.39-7.26 (m, 8H), 5.55 (s, 1H), 4.50 (s, 2H), 4.33 (dd, J=12.5, 1.4 Hz, 2H), 4.07-4.01 (m, 2H), 3.55 (t, J=6.7 Hz, 2H), 3.47 (t, J=6.6 Hz, 2H), 3.25 (m, 1H), 1.71-1.59 (m, 4H), 1.45-1.39 (m, 4H).

A mixture of benzylidene acetal Int-70 (46.0 mg, 0.124 mmol), conc. HCl (2 drops) and MeOH (1.5 mL) was heated at reflux for two hours and then cooled to room temperature. The reaction was diluted with ethyl acetate (30 mL) and water (10 mL), and the organic phase washed sat. aq. NaHCO$_3$, water and brine (30 mL each), dried (MgSO$_4$) and concentrated under reduced pressure to give the crude product. Silica gel chromatography (40% to 80% ethyl acetate/hexanes) gave diol Int-71 (23.5 mg, 67%) as a colorless oil. $^1$H NMR (400 MHz, CDCl$_3$): δ 7.36-7.27 (m, 5H), 4.50 (s, 2H), 3.76 (dd, J=11.6, 4.4 Hz, 2H), 3.67 (dd, J=11.6, 5.1 Hz, 2H), 3.57 (t, J=6.6 Hz, 2H), 3.50-3.42 (m, 3H), 1.67-1.56 (m, 4H), 1.43-1.36 (m, 4H).

A solution of freshly-prepared palmitoyl chloride (91.6 mg, 0.333 mmol) in CH$_2$Cl$_2$ (1.5 mL) and pyridine (30.3 µL, 0.375 mmol) were added to the diol Int-71 (23.5 mg, 0.0833 mmol) and the reaction stirred at room temperature for 16 hours. The reaction mixture was diluted with CH$_2$Cl$_2$ (30 mL) and quenched with water (10 mL). The organic phase was washed with water, sat. aq. NaHCO$_3$ and brine (30 mL each), dried (MgSO$_4$) and concentrated under reduced pressure to give the crude product. Silica gel chromatography (5% to 10% ethyl acetate/hexanes) gave glyceride Int-72 (44.8 mg, 71%) as a colorless solid. $^1$H NMR (400 MHz, CDCl$_3$): δ 7.36-7.26 (m, 5H), 4.50 (s, 2H), 4.18 (dd, J=11.6, 4.9 Hz, 2H), 4.11 (dd, J=11.6, 5.5 Hz, 2H), 3.68 (dd, J=10.4, 5.3 Hz, 1H), 3.55 (t, J=6.6 Hz, 2H), 3.46 (t, J=6.6 Hz, 2H), 2.32 (t, J=7.6 Hz, 4H), 1.67-1.54 (m, 8H), 1.34-1.21 (m, 52H), 0.88 (t, J=6.9 Hz, 6H); $^{13}$C NMR (100 MHz, CDCl$_3$): δ 173.7 (2C; C), 138.8 (C), 128.5 (2C; CH), 127.7 (2C; CH), 127.6 (CH), 75.3 (CH), 73.0 (CH$_2$), 70.7 (CH$_2$), 70.5 (CH$_2$), 63.2 (2C; CH$_2$), 34.3 (2C; CH$_2$), 32.1 (2C; CH$_2$), 30.0 (CH$_2$), 29.87 (CH$_2$), 29.84 (2C; CH$_2$), 29.80 (2C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.2 (CH$_2$), 26.0 (CH$_2$), 25.1 (2C; CH$_2$), 22.8 (2C; CH$_2$), 14.3 (2C; CH$_3$).

A solution of benzyl ether Int-72 (43.5 mg, 57.3 µmol) in ethyl acetate/hexanes (10 mL each) was subjected to hydrogenolysis using an HCube hydrogenation apparatus under recycling conditions (10% Pd/C cartridge, full H$_2$ mode at 6 bar, flow rate=1 mL/min), with the column temperature set at 25° C. for 1.5 hours then at 35° C. for a further hour. Concentration of the reaction mixture under reduced pressure gave alcohol Int-73 (38.2 mg, quant.) as a colorless solid that was used without purification. $^1$H NMR (400 MHz, CDCl$_3$): δ 4.19 (dd, J=11.6, 4.9 Hz, 2H), 4.11 (dd, J=11.6, 5.5 Hz, 2H), 3.67 (m, 1H), 3.64 (t, J=6.5 Hz, 2H), 3.55 (t, J=6.5 Hz, 2H), 2.32 (t, J=7.6 Hz, 4H), 1.66-1.56 (m, 8H), 1.41-1.34 (m, 4H), 1.33-1.18 (m, 48H), 0.88 (t, J=6.8 Hz, 6H).

C4-ET-alcohol-2-TG (Int-78):

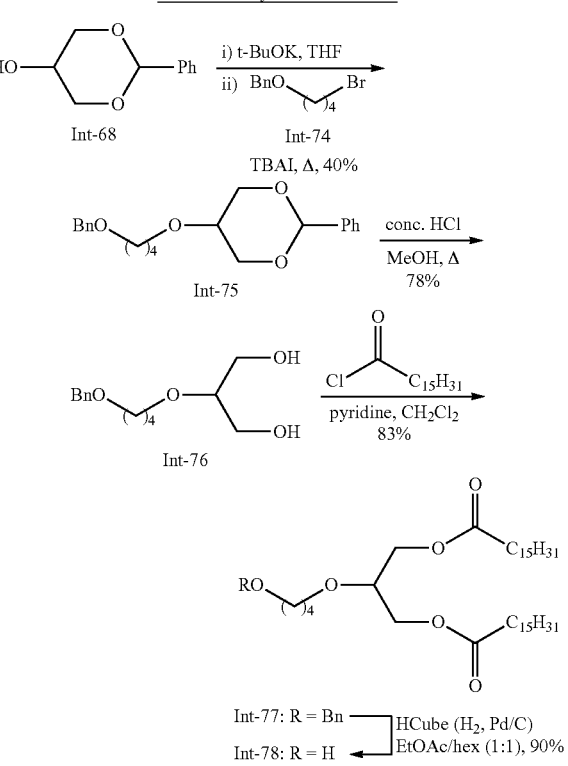

Int-74 is a known compound that may be prepared as described in Charette, A. B. et al. *J. Am. Chem. Soc.* 2001, 123, 11829-11830.

Alcohol Int-68 (commercially available; 135 mg, 0.749 mmol) was added in a single portion to a suspension of t-BuOK (118 mg, 1.05 mmol) in THF (2.5 mL) and the mixture stirred at RT for one hour. A solution of bromide Int-74 (273 mg, 1.12 mmol) in THF (2 mL) was then added and the resulting mixture heated at reflux for 26 hours. The reaction was cooled to room temperature and diluted with ethyl acetate (10 mL), quenched with water (20 mL) and the aqueous phase extracted with ethyl acetate (3×25 mL). The combined organic extracts were washed with water and brine (60 mL each), dried (MgSO$_4$) and concentrated under reduced pressure to give the crude product. Silica gel chromatography (10% to 20% ethyl acetate/hexanes) gave ether-linked glycerol Int-75 (103 mg, 40%) as a colorless oil. $^1$H NMR (400 MHz, CDCl$_3$): δ 7.53-7.48 (m, 2H), 7.38-7.27 (m, 8H), 5.55 (s, 1H), 4.50 (s, 2H), 4.37-4.27 (m, 2H), 4.08-3.98 (m, 2H), 3.61-3.55 (m, 2H), 3.54-3.50 (m, 2H), 3.25 (m, 1H), 1.82-1.65 (m, 4H); $^{13}$C NMR (100 MHz, CDCl$_3$): δ 138.8 (C), 138.3 (C), 128.9 (CH), 128.4 (2C; CH), 128.3 (2C; CH), 127.7 (2C; CH), 127.6 (CH), 126.3 (2C; CH), 101.4 (C), 73.0 (CH$_2$), 70.7 (CH), 70.3 (CH$_2$), 69.1 (2C; CH$_2$), 68.7 (CH$_2$), 26.7 (CH$_2$), 26.6 (CH$_2$).

A mixture of benzylidene acetal Int-75 (102 mg, 0.298 mmol), conc. HCl (2 drops) and MeOH (4 mL) was heated at reflux for two hours and then cooled to RT. The reaction was diluted with ethyl acetate (40 mL) and water (15 mL), and the organic phase washed sat. aq. NaHCO$_3$, water and brine (40 mL each), dried (MgSO$_4$) and concentrated under reduced pressure to give the crude product. Silica gel chromatography (25% to 65% to 90% ethyl acetate/hexanes) gave diol Int-76 (58.8 mg, 78%) as a colorless oil. $^1$H NMR (400 MHz, CDCl$_3$): δ 7.38-7.24 (m, 5H), 4.50 (s, 2H), 3.71 (dd, J=11.6, 4.6 Hz, 2H), 3.64 (dd, J=11.6, 4.9 Hz, 2H), 3.60-3.55 (m, 2H), 3.52-3.46 (m, 2H), 3.41 (m, 1H), 2.59 (br s, 2H), 1.75-1.61 (m, 4H); $^{13}$C NMR (100 MHz, CDCl$_3$): δ 138.5 (C), 128.5 (2C; CH), 127.8 (2C; CH), 127.7 (CH), 78.8 (CH), 73.0 (CH$_2$), 70.2 (CH$_2$), 69.8 (CH$_2$), 62.2 (2C; CH$_2$), 27.1 (CH$_2$), 26.4 (CH$_2$).

A solution of palmitoyl chloride (131 mg, 0.475 mmol) in CH$_2$Cl$_2$ (2 mL) and pyridine (48.0 µL, 0.594 mmol) were added to the diol Int-76 (30.2 mg, 0.119 mmol) and the reaction stirred at room temperature for 19 hours. The reaction mixture was diluted with CH$_2$Cl$_2$ (40 mL) and quenched with water (20 mL). The organic phase was washed with water, sat. aq. NaHCO$_3$ and brine (40 mL each), dried (MgSO$_4$) and concentrated under reduced pressure to give the crude product. Silica gel chromatography (6% ethyl acetate/hexanes) gave triglyceride Int-77 (72.4 mg, 83%) as a colorless solid. $^1$H NMR (400 MHz, CDCl$_3$): δ 7.38-7.26 (m, 5H), 4.50 (s, 2H), 4.18 (dd, J=11.6, 4.9 Hz, 2H), 4.11 (dd, J=11.6, 5.5 Hz, 2H), 3.67 (m, 1H), 3.58 (t, J=6.1 Hz, 2H), 3.48 (t, J=6.1 Hz, 2H), 2.31 (t, J=7.6 Hz, 4H), 1.73-1.55 (m, 8H), 1.37-1.19 (m, 48H), 0.88 (t, J=6.9 Hz, 6H); $^{13}$C NMR (100 MHz, CDCl$_3$): δ 173.7 (2C; C), 138.7 (C), 128.5 (2C; CH), 127.7 (2C; CH), 127.6 (CH), 75.4 (CH), 73.0 (CH$_2$), 70.4 (CH$_2$), 70.2 (CH$_2$), 63.1 (2C; CH$_2$), 34.3 (2C; CH$_2$), 32.1 (2C; CH$_2$), 29.82 (6C; CH$_2$), 29.79 (4C; CH$_2$), 29.74 (2C; CH$_2$), 29.6 (2C; CH$_2$), 29.5 (2C; CH$_2$), 29.4 (2C; H2), 29.3 (2C; CH$_2$), 26.8 (CH$_2$), 26.5 (CH$_2$), 25.0 (2C; CH$_2$), 22.8 (2C; CH$_2$), 14.2 (2C; CH$_3$).

A solution of benzyl ether Int-77 (70.0 mg, 95.8 µmol) in ethyl acetate/hexanes (25 mL each) was subjected to hydrogenolysis using an HCube hydrogenation apparatus under recycling conditions (10% Pd/C cartridge, full H$_2$ mode at 6 bar, flow rate=1 mL/min), with the column temperature set at 50° C. for 2.5 hours. Concentration of the reaction mixture under reduced pressure gave the crude product, which was purified by silica gel chromatography (10% to 30% ethyl acetate/hexanes) to give alcohol Int-78 (55.0 mg, 90%) as a colorless solid. $^1$H NMR (400 MHz, CDCl$_3$): δ 4.20 (dd, J=11.7, 4.8 Hz, 2H), 4.11 (dd, J=11.7, 5.5 Hz, 2H), 3.69 (m, 1H), 3.64 (t, J=5.9 Hz, 2H), 3.60 (t, J=5.8 Hz, 2H), 2.32 (t, J=7.5 Hz, 4H), 1.70-1.55 (m, 8H), 1.33-1.19 (m, 48H), 0.87 (t, J=6.8 Hz, 6H); $^{13}$C NMR (100 MHz, CDCl$_3$): δ 173.7 (2C; C), 75.5 (CH), 70.5 (CH$_2$), 63.0 (2C; CH$_2$), 62.6 (CH$_2$), 34.3 (2C; CH$_2$), 32.0 (2C; CH$_2$), 29.9 (CH$_2$), 29.82 (2C; CH$_2$), 29.78 (2C; CH$_2$), 29.7 (2C; CH$_2$), 29.6 (2C; CH$_2$), 29.5 (2C; CH$_2$), 29.4 (2C; CH$_2$), 29.3 (2C; CH$_2$), 26.7 (CH$_2$), 25.0 (2C; CH$_2$), 22.8 (2C; CH$_2$), 14.2 (2C; CH$_3$).

C5βpDiMe-acid-2-TG (Int-79):

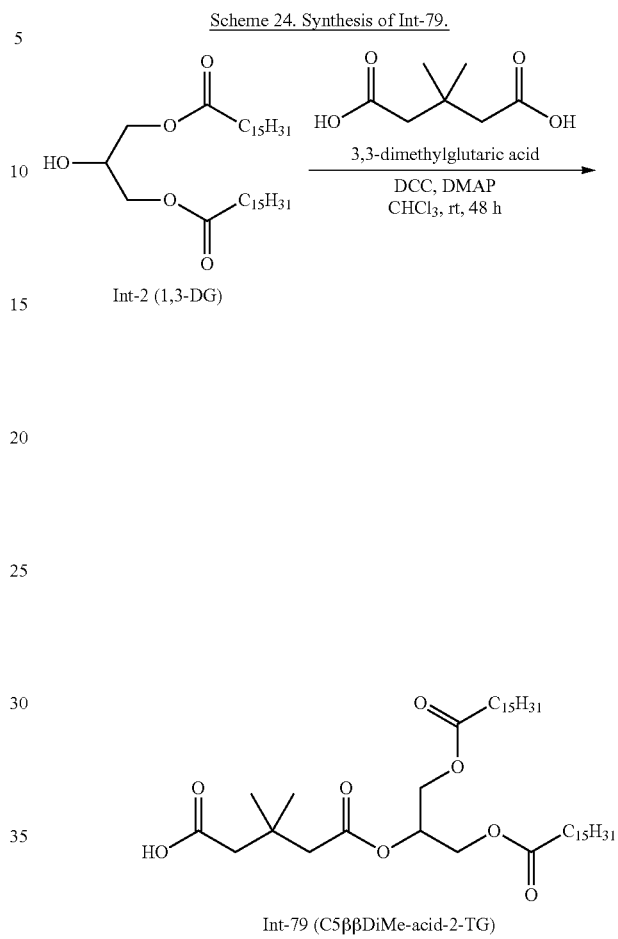

To a solution of compound Int-2 (5.0 g, 8.78 mmol) in chloroform (150 ml) was added DCC (3.62 g, 17.57 mmol) and DMAP (0.53 g, 4.39 mmol), followed by addition of 3,3-dimethylglutaric acid (2.81 g, 17.57 mmol) at room temperature and then stirring for 48 h. The reaction was monitored by TLC. After completion of the reaction, the reaction mixture was filtered through a celite bed and washed with dichloromethane (100 ml) and the filtrate was evaporated to give the crude desired compound, which was purified by combi-flash purification. The compound was eluted using 6% ethyl acetate in hexane and concentrated to give Int-79 (C5ββDiMe-acid-2-TG) (2.0 g, 32%) as off-white solid. $^1$H NMR (400 MHz, CDCl$_3$) δ 5.33 (m, 1H), 4.33 (m, 2H), 4.18 (m, 2H), 2.51 (s, 4H), 2.35 (t, 4H), 1.64 (t, 4H), 1.29 (m, 49H), 1.19 (s, 6H), 0.92 (t, 6H); $^{13}$C NMR (101 MHz, CDCl$_3$) δ 176.4 (1C), 173.3 (2C), 171.0 (1C), 69.1 (1C), 62.1 (2C), 45.0 (1C) 44.7 (1C), 34.0 (3C), 32.6 (1C), 31.9 (3H), 29.7-29.1 (14C), 27.7 (3C), 24.8 (3C), 22.7 (3C), 14.1 (3C); HPLC (ELSD): 10.07 min, 97.74% purity; MASS (ESI, −ve) m/z: 710 (M−1).

C12a'aMe-acid-2-TG (Int-81):

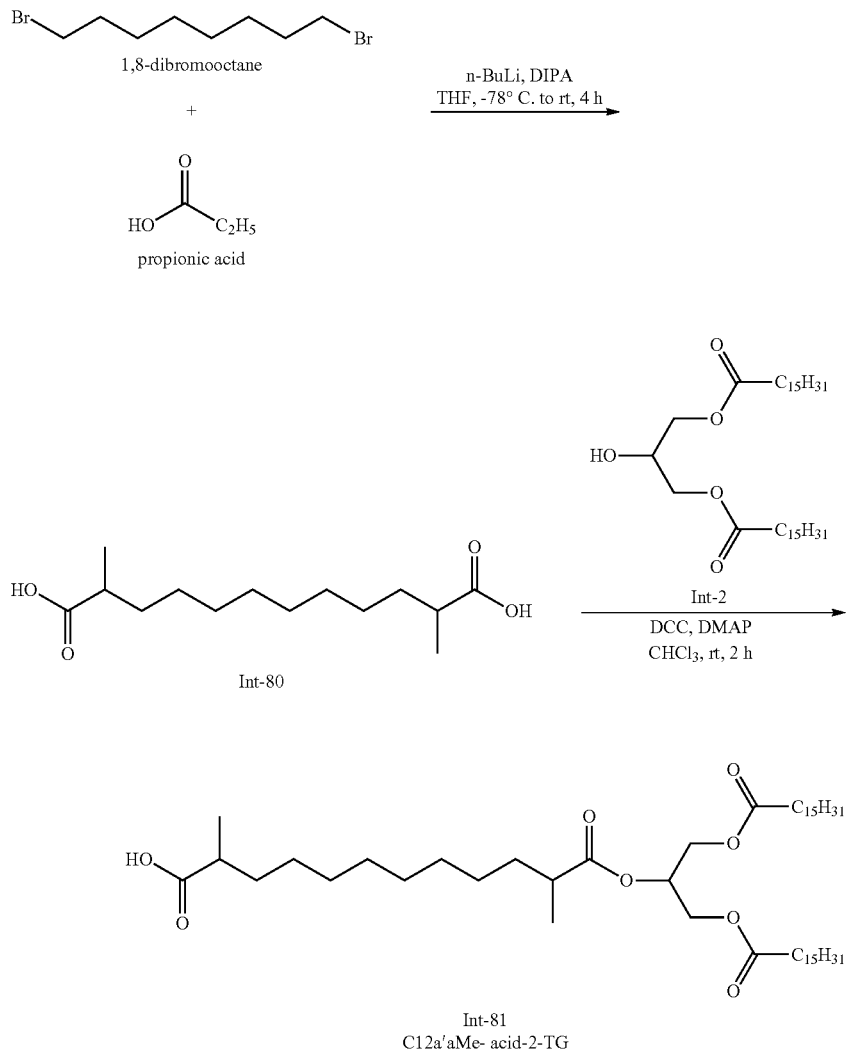

To a solution of diisopropylamine (DIPA) (3.18 g, 81.08 mmol) in dry THF (45 mL) was added n-BuLi (2.5 M in hexane) (32 mL, 81.08 mmol) at −78° C. The reaction mixture was stirred at −78° C. for 30 min, then then propionic acid (1.5 g, 20.27 mmol) was added and the reaction mixture was stirred at −78° C. for further 30 min. 1,8-dibromooctane (2.75 g, 10.13 mmol) was added and the reaction mixture was stirred and allowed to warm from −78° C. to room temperature over 3 h. The reaction was monitored by TLC for completeness. An additional identical batch starting with 1.5 g propionic acid was prepared and the two batches combined before workup. The combined reaction mixture was diluted with water (100 mL) and acidified with 1N HCl (25 ml) and extracted with ethyl acetate (3×100 ml), and the combined organic layer was dried over $Na_2SO_4$ and evaporated to give crude compound. The title compound was purified by combi flash purification, eluting with 10% ethyl acetate/hexane as the mobile phase. After evaporation, Int-80 (0.99 g, 9.5%) was obtained as an off-white solid. $^1$H NMR (400 MHz, $CDCl_3$) δ 2.57-2.39 (m, 2H), 1.71 (m, 2H), 1.50-1.43 (m, 2H), 1.40-1.25 (m, 14H), 1.22 (d, J=7.2 Hz 6H).

To a solution of compound Int-2 (2.7 g, 4.74 mmol) in chloroform (50 ml) was added DCC (1.95 g, 9.49 mmol) and DMAP (0.28 g, 2.30 mmol), then the reaction was stirred at room temperature for 30 min. Int-80 (2.44 g, 9.49 mmol) was added at room temperature and stirred for 2 h. The reaction was monitored by TLC until completion, after which the reaction mixture was filtered through celite and washed with DCM (45 ml), then evaporated to give the crude product, which was purified by combi flash purification, eluting with 7% ethyl acetate/hexane. After evaporation, Int-81 (C12a'aMe-acid-2-TG) (1.7 g, 44.3%) was obtained as an off-white solid. $^1$H NMR (400 MHz, $CDCl_3$) δ 5.32 (m, 1H), 4.33 (m, 2H), 4.19 (m, 2H), 2.49 (m, 2H), 2.34 (m, 4H), 1.72-1.62 (m, 4H), 1.49-1.40 (m, 4H). 1.38-1.29 (m, 59H), 1.24-1.17 (m, 8H), 0.92 (m, 6H); $^{13}$C NMR (101 MHz, $CDCl_3$) δ 181.7 (1C), 176.0 (1C), 173.4 (2C), 68.7 (2C), 62.2 (3C), 39.6 (2C), 39.2 (1C), 34.1 (3C), 33.7 (1C), 32.0 (3C), 29.7-29.2 (17C), 27.2 (1C), 24.9 (3C), 22.7 (3C), 17.1 (2C), 16.9 (1C), 14.2 (3C).

C12a'aMe-acid-2-TG-oleate (Int-260):
Using the procedure described for the synthesis of Int-81, compound Int-260 was prepared from Int-80 and Int-112:

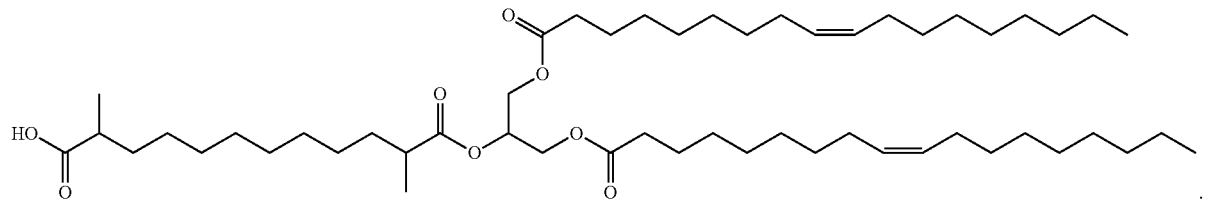
Int-260

Bromotriglyceride Int-91:

Iodotriglyceride Int-95:

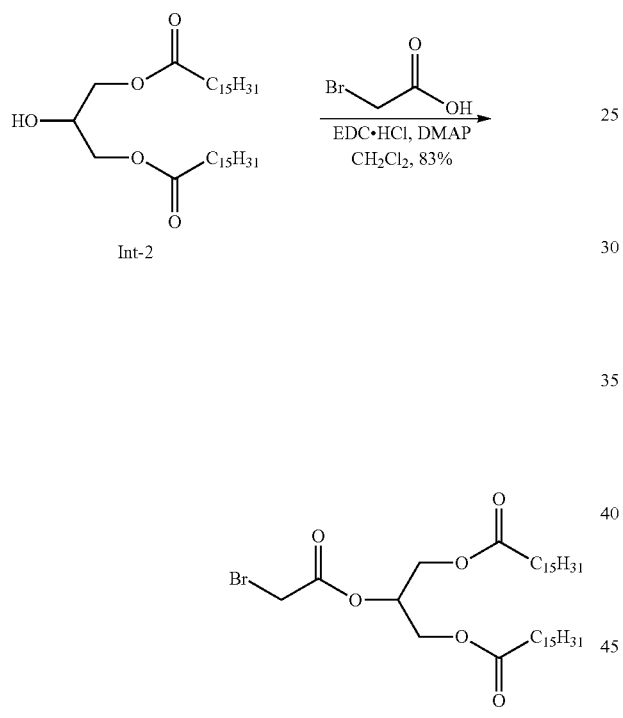

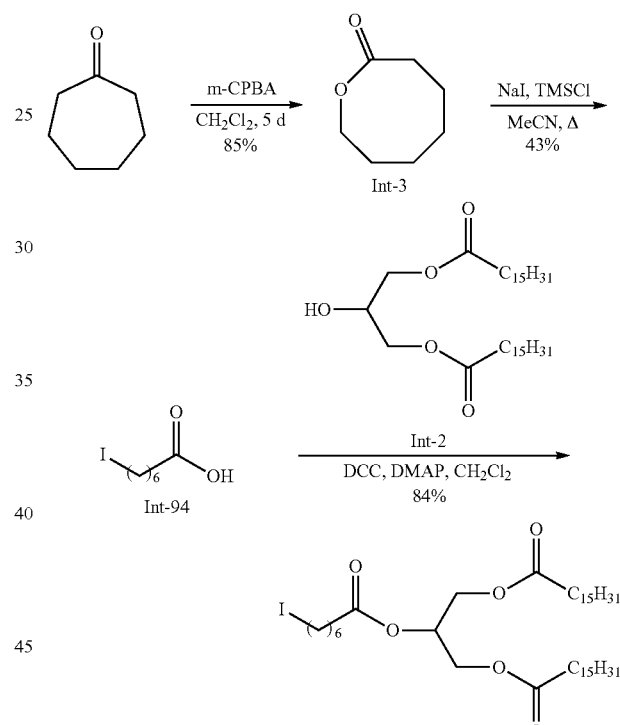

DMAP (10.7 mg, 0.0979 mmol) and EDC·HCl (41.8 mg, 0.220 mmol) were added to a solution of bromoacetic acid (24.4 mg, 0.176 mmol) and Int-2 (50.0 mg, 0.0879 mmol) in $CH_2Cl_2$ (2 mL) and the mixture stirred at RT for 22 hours. The reaction was diluted with $CH_2Cl_2$ (5 mL), silica gel was added, and the solvent removed under reduced pressure. Silica gel chromatography (4% ethyl acetate/hexanes) gave bromotriglyceride Int-91 (50.3 mg, 83%) as a colorless solid. $^1$H NMR (400 MHz, $CDCl_3$) δ 5.31 (m, 1H), 4.34 (dd, J=12.1, 4.0 Hz, 2H), 4.17 (dd, J=12.1, 6.1 Hz, 2H), 3.84 (s, 2H), 2.32 (t, J=7.6 Hz, 4H), 1.66-1.56 (m, 4H), 1.35-1.20 (m, 48H), 0.88 (t, J=6.9 Hz, 6H); $^{13}$C NMR (101 MHz, $CDCl_3$) δ 173.4 (2C; C), 166.7 (C), 71.3 (CH), 61.9 (2C; $CH_2$), 34.1 (2C; $CH_2$), 32.1 (2C; $CH_2$), 29.84 (2C; $CH_2$), 29.80 (2C; $CH_2$), 29.75 (2C; $CH_2$), 29.6 (2C; $CH_2$), 29.5 (2C; $CH_2$), 29.4 (2C; $CH_2$), 29.3 (2C; $CH_2$), 25.5 ($CH_2$), 25.0 (2C; $CH_2$), 22.8 (2C; $CH_2$), 14.3 (2C; $CH_2$).

Int-93 is a known compound prepared from cycloheptanone as shown above (see Kai, K. et al. *Tetrahedron* 2008, 64, 6760-6769). To prepare Int-94, chlorotrimethylsilane (TMSCl, 208 µL, 1.64 mmol) was added to a suspension of lactone Int-93 (70.0 mg, 0.546 mmol) and sodium iodide (246 mg, 1.64 mmol) in acetonitrile (1.5 mL) and the mixture heated at reflux for 16 hours. The reaction was cooled to RT, diluted with ethyl acetate and water (10 mL each), and extracted with ethyl acetate (3×15 ml). The combined organic extracts were washed with 1 M $Na_2S2O3$ and brine (40 mL each), dried ($MgSO_4$) and concentrated under reduced pressure to give the crude product. Silica gel chromatography (100% $CH_2Cl_2$ to 50% ethyl acetate/hexanes) gave semi-pure acid Int-94 (59.8 mg, 43%) as a yellow oil. However, an accurate yield and clean NMR spectra could not be obtained due to the presence of the m-CPBA impurities, which were carried forward to the next step. ¹H NMR (400 MHz, CDCl₃) δ 3.19 (t, J=7.0 Hz, 2H), 2.37 (t, J=7.4 Hz, 2H), 1.88-1.80 (m, 2H), 1.71-1.61 (m, 2H), 1.46-1.33 (m, 4H).

DMAP (15.2 mg, 0.124 mmol) and DCC (51.3 mg, 0.248 mmol) were added sequentially to a solution of acid Int-94 (35.0 mg, 0.137 mmol) and 1,3-diglyceride Int-2 (70.7 mg, 0.124 mmol) in CH₂Cl₂ (4 mL) and the mixture stirred at RT for 17 hours. The resulting suspension was diluted with CH₂Cl₂, cooled to 0° C. and filtered through Celite, washing with further CH₂Cl₂. The organic phase was washed with 1 M HCl, sat. aq. NaHCO₃ and brine, dried (MgSO₄) and concentrated under reduced pressure to give the crude product. Silica gel chromatography (3.5% to 4.5% ethyl acetate/hexanes) gave semi-pure iodotriglyceride Int-95 (83.6 mg, 84%) as a colorless solid. However, an accurate yield and clean NMR spectra could not be obtained due to the presence of the m-CPBA impurities, which were carried forward to the next step. ¹H NMR (400 MHz, CDCl₃) δ 5.26 (m, 1H), 4.30 (dd, J=11.9, 4.4 Hz, 2H), 4.14 (dd, J=11.9, 5.9 Hz, 2H), 3.18 (t, J=7.0 Hz, 2H), 2.36-2.27 (m, 6H), 1.86-1.77 (m, 2H), 1.68-1.52 (m, 6H), 1.45-1.18 (m, 52H), 0.88 (t, J=6.9 Hz, 6H).

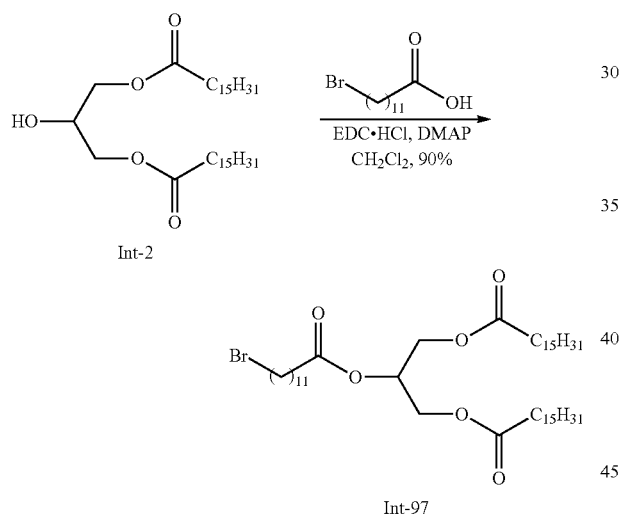

Scheme 28. Synthesis of Int-97.

Int-2 Int-97

DMAP (17.2 mg, 0.141 mmol) and EDC·HCl (67.4 mg, 0.352 mmol) were added to a solution of 1,3-diglyceride Int-2 (80.0 mg, 0.141 mmol) and 12-bromododecanoic acid (51.0 mg, 0.183 mmol) in CH₂Cl₂ (2.5 mL) and the mixture stirred at RT for 18 hours. The reaction was diluted with CH₂Cl₂ (10 mL), silica gel was added, and the mixture concentrated under reduced pressure. Purification by silica gel chromatography (5% to 10% ethyl acetate/hexanes) gave bromotriglyceride Int-97 (105 mg, 90%) as a colorless solid. ¹H NMR (401 MHz, CDCl₃) δ 5.25 (m, 1H), 4.28 (dd, J=11.9, 4.3 Hz, 2H), 4.13 (dd, J=11.9, 5.9 Hz, 2H), 3.38 (t, J=6.9 Hz, 2H), 2.30 (t, J=7.5 Hz, 2H), 2.29 (t, J=7.5 Hz, 4H), 1.88-1.79 (m, 2H), 1.65-1.55 (m, 6H), 1.45-1.36 (m, 2H), 1.34-1.18 (m, 60H), 0.86 (t, J=6.8 Hz, 6H); ¹³C NMR (101 MHz, CDCl₃) δ 173.4 (2C; C), 172.9 (C), 69.0 (CH), 62.2 (2C; CH₂), 34.3 (CH₂), 34.2 (2C; CH₂), 34.0 (CH₂), 33.0 (CH₂), 32.1 (2C; CH₂), 29.82 (6C; CH₂), 29.78 (4C; CH₂), 29.74 (2C; CH₂), 29.60 (3C; CH₂), 29.54 (2C; CH₂), 29.48 (2C; CH₂), 29.39 (2C; CH₂), 29.38 (CH₂), 29.23 (2C; CH₂), 29.17 (CH₂), 28.9 (CH₂), 28.3 (CH₂), 25.0 (2C; CH₂), 22.8 (2C; CH₂), 14.2 (2C; CH₃).

Int-105:

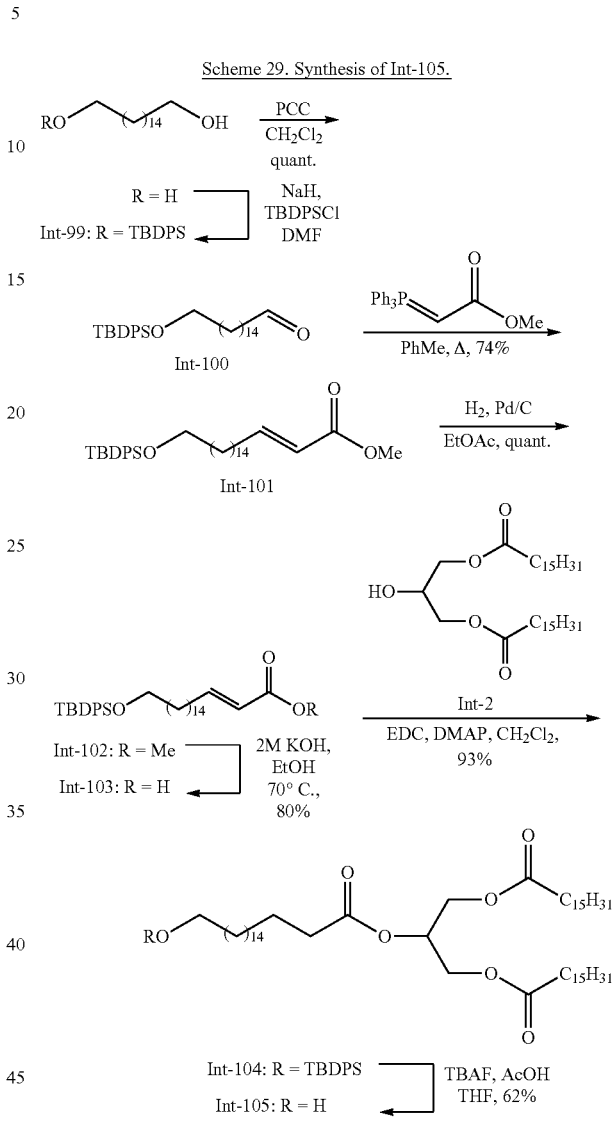

Scheme 29. Synthesis of Int-105.

Int-99:

A suspension of 1,16-hexanediol (200 mg, 0.774 mmol) in DMF (2 mL) was added a suspension of NaH (34.1 mg, 60% w/w dispersion in mineral oil, washed twice with dry petrol, 8.51 mmol) in DMF (1 mL) at 0° C. and the mixture stirred at 0° C. for 10 minutes and then at rt for 30 minutes. TBDPSCl (221 μL, 0.851 mmol) was added and the mixture stirred at rt for 17 hours. The reaction was diluted with ethyl acetate (50 mL), washed with water and brine (2×40 mL each), dried (MgSO₄) and concentrated under reduced pressure to give the crude product. Silica gel chromatography (15% ethyl acetate/hexanes) gave TBDPS ether Int-99 (124 mg, 32%) as a colorless solid. ¹H NMR (401 MHz, CDCl₃) δ 7.70-7.63 (m, 4H), 7.45-7.34 (m, 6H), 3.64 (td, J=6.5, 3.6 Hz, 4H), 1.61-1.46 (m, 4H), 1.39-1.19 (m, 24H), 1.04 (s, 9H).

Int-100:

Pyridinium chlorochromate (PCC, 106 mg, 0.491 mmol) and Celite (100 mg) were added to alcohol Int-99 (122 mg, 0.246 mmol) in CH$_2$Cl$_2$ (6 mL) at 0° C. and the mixture stirred at 0° C. for 10 minutes and then at rt for 1.5 hours. The reaction was filtered through a short pad of silica gel, eluting with 50% ethyl acetate/hexanes (80 mL), and the filtrate concentrated under reduced pressure to give crude aldehyde Int-100 (121 mg, quant.) as a yellow oil that was immediately used without purification.

Int-101:

Ylide methyl 2-(triphenyl-$\lambda^5$-phosphaneylidene)acetate (205 mg, 0.614 mmol) was added to crude aldehyde Int-100 (121 mg, 0.246 mmol) in toluene (6 mL) and the mixture heated at reflux for one hour. The reaction was cooled to rt and concentrated under reduced pressure to give the crude product. Purification by silica gel chromatography (4% ethyl acetate/hexanes) gave alpha,beta-unsaturated methyl ester Int-101 (100 mg, 74%, 6:1 mixture of E/Z isomers) as a yellow oil. NMR data is provided for the major isomer. $^1$H NMR (401 MHz, CDCl$_3$) δ 7.74-7.66 (m, 4H), 7.48-7.36 (m, 6H), 7.01 (dt, J=15.6, 7.0 Hz, 1H), 5.85 (dt, J=15.6, 1.5 Hz, 1H), 3.74 (s, 3H), 3.69 (t, J=6.5 Hz, 2H), 2.22 (qd, J=7.3, 1.5 Hz, 2H), 1.64-1.55 (m, 2H), 1.47 (dd, J=13.9, 6.9 Hz, 2H), 1.42-1.25 (m, 22H), 1.09 (s, 9H); $^{13}$C NMR (101 MHz, CDCl$_3$) δ 167.3 (C), 149.9 (CH), 135.7 (4C; CH), 134.3 (2C; C), 129.6 (2C; CH), 127.7 (4C; CH), 120.9 (CH), 64.1 (CH$_2$), 51.4 (CH$_3$), 32.7 (CH$_2$), 32.3 (CH$_2$), 29.79 (2C; CH$_2$), 29.75 (2C; CH$_2$), 29.74 (CH$_2$), 29.66 (CH$_2$), 29.52 (CH$_2$), 29.50 (CH$_2$), 29.3 (CH$_2$), 28.1 (CH$_2$), 27.0 (3C; CH$_2$), 25.9 (CH$_2$), 19.3 (C).

Int-102:

A solution of alkene Int-101 (99.0 mg, 0.180 mmol) in ethyl acetate (5 mL) in a two-neck flask was evacuated and flushed with N$_2$ gas three times each, then palladium on carbon (10% w/w, 28.7 mg, 0.0270 mmol) was added and the resulting suspension re-evacuated and flushed with N$_2$ three times. The flask was fitted with a H$_2$ balloon, evacuated and flushed with H$_2$ three times and the reaction mixture stirred at rt under 1 atm of H$_2$ for one hour. The reaction was filtered through a pad of Celite, washing with ethyl acetate (80 mL), and concentrated under reduced pressure to give saturated methyl ester Int-102 (99.4 mg, quant.) as a colorless oil that was used without purification. $^1$H NMR (401 MHz, CDCl$_3$) δ 7.75-7.67 (m, 4H), 7.47-7.36 (m, 6H), 3.69 (t, J=6.5 Hz, 2H), 3.68 (s, 3H), 2.33 (t, J=7.5 Hz, 2H), 1.70-1.54 (m, 4H), 1.43-1.23 (m, 26H), 1.09 (s, 9H); $^{13}$C NMR (101 MHz, CDCl$_3$) δ 174.4 (C), 135.7 (4C; CH), 134.3 (2C; C), 129.6 (2C; CH), 127.7 (4C; CH), 64.1 (CH$_2$), 51.5 (CH$_3$), 34.2 (CH$_2$), 32.7 (CH$_2$), 29.82 (2C; CH$_2$), 29.81 (2C; CH$_2$), 29.78 (CH$_2$), 29.76 (CH$_2$), 29.75 (CH$_2$), 29.73 (CH$_2$), 29.6 (CH$_2$), 29.5 (CH$_2$), 29.4 (CH$_2$), 29.3 (CH$_2$), 27.0 (3C; CH$_3$), 25.9 (CH$_2$), 25.1 (CH$_2$), 19.3 (C).

Int-103:

A solution of potassium hydroxide (2.0 M, 530 μL, 1.06 mmol) was added to ester Int-102 (26.0 mg. 0.0854 mmol) in ethanol (3 mL) and the mixture heated at 70° C. for 50 minutes. The reaction was acidified to pH 3 by addition of 1 M HCl and diluted with ethyl acetate (40 mL). The organic phase was washed with water (2×30 mL) and brine (30 mL), dried (MgSO$_4$) and concentrated under reduced pressure to give the crude product. Purification by silica gel chromatography (15% ethyl acetate/hexanes) gave acid Int-103 (76.8 mg, 80%) as a colorless oil. $^1$H NMR (401 MHz, CDCl$_3$) δ 7.73-7.67 (m, 4H), 7.44-7.37 (m, 6H), 3.68 (t, J=6.5 Hz, 2H), 2.37 (t, J=7.5 Hz, 2H), 1.70-1.53 (m, 4H), 1.41-1.23 (m, 26H), 1.07 (s, 9H); $^{13}$C NMR (101 MHz, CDCl$_3$) δ 180.4 (C), 135.7 (4C; CH), 134.3 (2C; C), 129.6 (2C; CH), 127.7 (4C; CH), 64.2 (CH$_2$), 34.2 (CH$_2$), 32.7 (CH$_2$), 29.83 (4C; CH$_2$), 29.81 (CH$_2$), 29.78 (2C; CH$_2$), 29.76 (CH$_2$), 29.6 (CH$_2$), 29.5 (CH$_2$), 29.4 (CH$_2$), 29.2 (CH$_2$), 27.0 (3C; CH$_3$), 25.9 (CH$_2$), 24.8 (CH$_2$), 19.4 (C).

Int-104:

DMAP (10.2 mg, 0.0839 mmol), EDC·HCl (40.2 mg, 0.210 mmol) and 1,3-diglyceride Int-2 (52.5 mg, 0.0923 mmol) were added to a solution of acid Int-103 (45.2 mg, 0.0839 mmol) in CH$_2$Cl$_2$ (4 mL) and the mixture stirred at RT for 22 hours. The reaction was diluted with CH$_2$Cl$_2$ (10 mL), silica gel was added and the mixture concentrated under reduced pressure. Purification by silica gel chromatography (4% to 6% ethyl acetate/hexanes) gave triglyceride Int-104 (84.9 mg, 93%) as a colorless solid. $^1$H NMR (401 MHz, CDCl$_3$) δ 7.71-7.65 (m, 4H), 7.45-7.34 (m, 6H), 5.28 (m, 1H), 4.31 (dd, J=11.9, 4.3 Hz, 2H), 4.16 (dd, J=11.9, 6.0 Hz, 2H), 3.66 (t, J=6.5 Hz, 2H), 2.325 (t, J=7.5 Hz, 2H), 2.319 (t, J=7.5 Hz, 4H), 1.69-1.52 (m, 8H), 1.42-1.20 (m, 74H), 1.06 (s, 9H), 0.89 (t, J=6.8 Hz, 6H); $^{13}$C NMR (101 MHz, CDCl$_3$) δ 173.4 (2C; C), 173.0 (C), 135.7 (4C; CH), 134.3 (2C; C), 129.6 (2C; CH), 127.7 (4C; CH), 69.0 (CH), 64.1 (CH$_2$), 62.2 (2C; CH$_2$), 34.3 (CH$_2$), 34.2 (2C; CH$_2$), 32.7 (CH$_2$), 32.1 (2C; CH$_2$), 29.86 (2C; CH$_2$), 29.84 (9C; CH$_2$), 29.80 (5C; CH$_2$), 29.77 (2C; CH$_2$), 29.76 (2C; CH$_2$), 29.65 (CH$_2$), 29.61 (2C; CH$_2$), 29.53 (CH$_2$), 29.50 (2C; CH$_2$), 29.44 (CH$_2$), 29.41 (2C; CH$_2$), 29.25 (2C; CH$_2$), 29.22 (CH$_2$), 27.0 (3C; CH$_3$), 25.9 (CH$_2$), 25.04 (CH$_2$), 24.99 (2C; CH$_2$), 22.8 (2C; CH$_2$), 19.3 (C), 14.2 (2C; CH$_3$).

Int-105:

Tetrabutylammonium fluoride (TBAF, 1.0 M in THF, 154 μL, 0.154 mmol) and acetic acid (8.8 μL, 0.154 mmol) were added to a solution of TBDPS ether Int-104 (84.0 mg, 0.0771 mmol) in THF (3 mL) at 0° C. and the mixture stirred at 0° C. for 15 minutes and then at rt for seven hours. The reaction was diluted with ethyl acetate (40 mL), washed with water (30 mL) and brine (2×30 mL), dried (MgSO$_4$) and concentrated under reduced pressure to give the crude product. Purification by silica gel chromatography (7.5% to 20% ethyl acetate/hexanes) gave alcohol Int-105 (40.5 mg, 62%) as a colorless solid. $^1$H NMR (401 MHz, CDCl$_3$) δ 5.26 (m, 1H), 4.29 (dd, J=11.9, 4.3 Hz, 2H), 4.14 (dd, J=11.9, 6.0 Hz, 2H), 3.64 (t, J=6.6 Hz, 2H), 2.31 (t, J=7.5 Hz, 2H), 2.30 (t, J=7.5 Hz, 4H), 1.67-1.51 (m, 8H), 1.44-1.17 (m, 74H), 0.88 (t, J=6.8 Hz, 6H); $^{13}$C NMR (101 MHz, CDCl$_3$) δ 173.5 (2C; C), 173.1 (C), 69.0 (CH), 63.3 (CH$_2$), 62.3 (2C; CH$_2$), 34.4 (CH$_2$), 34.2 (2C; CH$_2$), 33.0 (CH$_2$), 32.1 (2C; CH$_2$), 29.82 (10C; CH$_2$), 29.80 (6C; CH$_2$), 29.76 (3C; CH$_2$), 29.75 (CH$_2$), 29.65 (CH$_2$), 29.63 (2C; CH$_2$), 29.59 (CH$_2$), 29.51 (2C; CH$_2$), 29.45 (CH$_2$), 29.42 (2C; CH$_2$), 29.27 (2C; CH$_2$), 29.23 (2C; CH$_2$), 25.9 (CH$_2$), 25.1 (CH$_2$), 25.0 (2C; CH$_2$), 22.8 (2C; CH$_2$), 14.3 (2C; CH$_3$).

Int-110 (TML(CO₂H)—C₄₋₂-TG):

Scheme 30. Synthesis of Int-110.

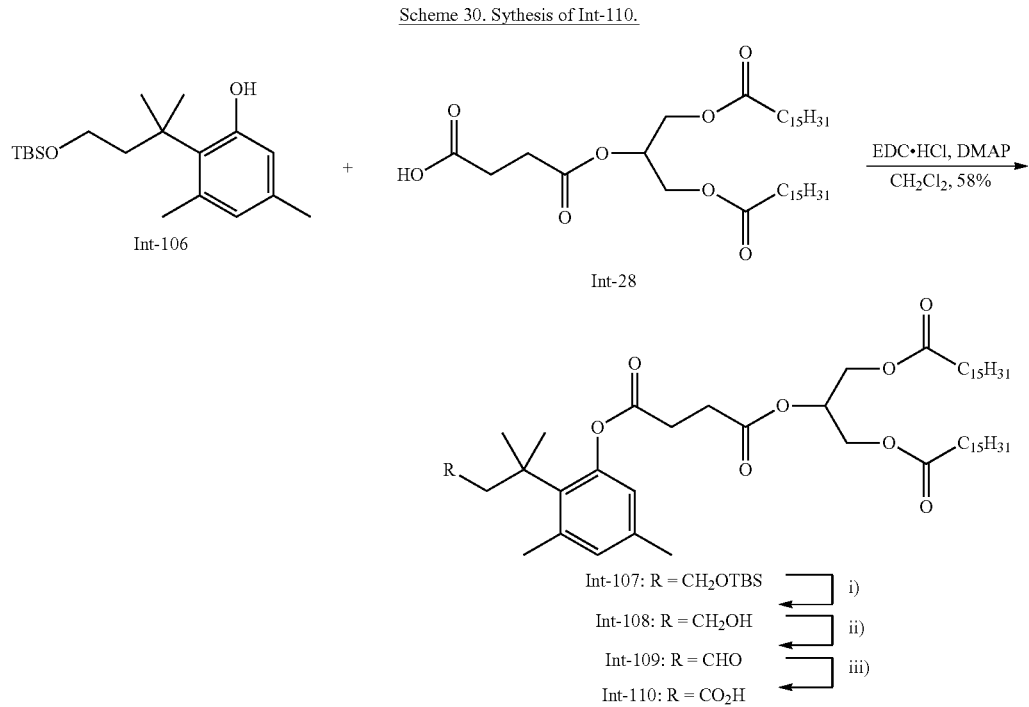

i) 10-CSA, CH₂Cl₂/MeOH, 81%;
ii) PCC, CH₂Cl₂;
iii) KMnO₄, acetone/H₂O, 50% (2 steps)

Int-106: prepared according to: Amsberry, K. L. et al. Pharm Res. 1991, 8, 455-461.

DMAP (18.3 mg, 0.149 mmol) and EDC·HCl (71.6 mg, 0.374 mmol) were added to a solution of Int-28 (100 mg, 0.149 mmol) and phenol Int-106 (53.0 mg, 0.164 mmol) in CH₂Cl₂ (4 mL) and the mixture stirred at room temperature for 19 hours. The reaction was diluted with CH₂Cl₂ (5 mL), silica gel was added, and the mixture concentrated under reduced pressure. Purification by silica gel chromatography (3% to 7.5% ethyl acetate/hexanes) gave TML-TG Int-107 (84.6 mg, 58%) as a colourless oil. ¹H NMR (400 MHz, CDCl₃) δ 6.80 (d, J=2.0 Hz, 1H), 6.55 (d, J=1.9 Hz, 1H), 5.29 (m, 1H), 4.31 (dd, J=11.9, 4.4 Hz, 2H), 4.16 (dd, J=12.0, 5.8 Hz, 2H), 3.51-3.44 (m, 2H), 2.85 (t, J=6.9 Hz, 2H), 2.75 (t, J=6.9 Hz, 2H), 2.51 (s, 3H), 2.30 (t, J=7.6 Hz, 4H), 2.22 (s, 3H), 2.06-1.99 (m, 2H), 1.65-1.56 (m, 4H), 1.46 (s, 6H), 1.37-1.20 (m, 48H), 0.88 (t, J=6.9 Hz, 6H), 0.84 (s, 9H), −0.03 (s, 6H); ¹³C NMR (101 MHz, CDCl₃) δ 173.4 (2C; C), 171.5 (C), 171.3 (C), 149.7 (C), 138.5 (C), 136.1 (C), 134.1 (C), 132.5 (CH), 123.1 (CH), 69.8 (CH), 62.0 (2C; CH₂), 60.9 (CH₂), 46.1 (CH₂), 39.2 (C), 34.1 (2C; CH₂), 32.1 (2C; CH₂), 31.9 (2C; CH₃), 29.9 (CH₂), 29.83 (6C; CH₂), 29.79 (4C; CH₂), 29.75 (2C; CH₂), 29.6 (2C; CH₂), 29.5 (2C; CH₂), 29.4 (2C; CH₂), 29.2 (2C; CH₂), 29.0 (CH₂), 26.1 (3C; CH₃), 25.4 (CH₃), 25.0 (2C; CH₂), 22.8 (2C; CH₂), 20.3 (CH₃), 18.3 (C), 14.3 (2C; CH₃), −5.21 (2C; CH₃). ESI-HRMS: calcd. for C₅₈H₁₀₅O₉Si [M+H⁺] 973.7522; found 973.7515.

10-Camphorsulfonic acid (3.0 mg, 12.9 μmol) was added to TBS ether Int-107 (83.7 mg, 86.0 μmol) in CH₂Cl₂ (1 mL) and MeOH (1 mL) and the mixture stirred at room temperature for one hour. The reaction was diluted with CH₂Cl₂ (20 mL) and the organic phase washed with sat. aq. NaHCO₃ and brine (20 mL each), dried (MgSO₄) and concentrated under reduced pressure to give the crude product. Purification by silica gel chromatography (15% to 25% ethyl acetate/hexanes) gave alcohol Int-108 (59.9 mg, 81%) as a colourless oil. ¹H NMR (400 MHz, CDCl₃) δ 6.81 (d, J=2.0 Hz, 1H), 6.56 (d, J=1.4 Hz, 1H), 5.28 (m, 1H), 4.30 (dd, J=12.0, 4.4 Hz, 2H), 4.17 (dd, J=12.0, 5.8 Hz, 2H), 3.51 (t, J=6.8 Hz, 2H), 2.88 (t, J=6.6 Hz, 2H), 2.75 (t, J=6.6 Hz, 2H), 2.52 (s, 3H), 2.29 (t, J=7.6 Hz, 4H), 2.22 (s, 3H), 2.05 (t, J=7.4 Hz, 2H), 1.65-1.57 (m, 4H), 1.50 (s, 6H), 1.37-1.20 (m, 48H), 0.88 (t, J=6.9 Hz, 6H); ¹³C NMR (101 MHz, CDCl₃) δ 173.5 (2C; C), 171.71 (C), 171.70 (C), 149.8 (C), 138.5 (C), 136.3 (C), 133.9 (C), 132.6 (CH), 123.2 (CH), 69.8 (CH), 62.0 (2C; CH₂), 60.5 (CH₂), 45.9 (CH₂), 39.2 (C), 34.1 (2C; CH₂), 32.1 (2C; CH₃), 32.0 (2C; CH₂), 29.84 (CH₂), 29.80 (6C; CH₂), 29.77 (4C; CH₂), 29.72 (2C; CH₂), 29.6 (2C; CH₂), 29.5 (2C; CH₂), 29.4 (2C; CH₂), 29.2 (2C; CH₂), 28.9 (CH₂), 25.5 (CH₃), 24.9 (2C; CH₂), 22.8 (2C; CH₂), 20.3 (CH₃), 14.2 (2C; CH₃). ESI-HRMS: calcd. for C₅₂H₉₀NaO₉ [M+Na⁺] 881.6477; found 881.6489.

Pyridinium chlorochromate (PCC, 30.1 mg, 0.139 mmol) was added to a suspension of alcohol Int-108 (59.9 mg, 0.0697 mmol) and Celite (30 mg) in CH₂Cl₂ (3 mL) at 0° C. and the mixture stirred at room temperature for two hours. The reaction was filtered through a short pad of silica gel, eluting with 50% ethyl acetate/hexanes (50 mL), and the filtrate concentrated under reduced pressure to give crude aldehyde Int-109 (59.8 mg, quant.) as a yellow oil that was used without purification. ¹H NMR (400 MHz, CDCl₃) δ 9.54 (t, J=2.6 Hz, 1H), 6.84 (d, J=2.0 Hz, 1H), 6.60 (d, J=1.4 Hz, 1H), 5.28 (m, 1H), 4.30 (dd, J=12.0, 4.3 Hz, 2H), 4.16

(dd, J=12.0, 5.8 Hz, 2H), 2.86 (t, J=6.7 Hz, 2H), 2.83 (d, J=2.6 Hz, 2H), 2.75 (t, J=6.3 Hz, 2H), 2.53 (s, 3H), 2.30 (t, J=7.6 Hz, 4H), 2.23 (s, 3H), 1.64-1.58 (m, 4H), 1.56 (s, 3H), 1.55 (s, 3H), 1.32-1.22 (m, 48H), 0.88 (t, J=6.9 Hz, 6H).

Potassium permanganate (12.2 mg, 76.7 μmol) in 1:1 acetone/water (1.6 mL total) was added to aldehyde Int-109 (59.8 mg, 69.7 μmol) in acetone (1.6 mL) and the mixture stirred at room temperature for 17 hours. The reaction was diluted with water (10 mL), acidified to pH 2 using 1 M HCl, and the aqueous layer extracted with $CH_2Cl_2$ (3×15 mL). The combined organic extracts were washed with brine (40 mL), dried ($MgSO_4$) and concentrated under reduced pressure to give the crude product. Purification by silica gel chromatography (10% to 25% ethyl acetate/hexanes) gave acid Int-110 (30.4 mg, 50%) as a colorless solid. $^1$H NMR (400 MHz, $CDCl_3$) δ 6.81 (d, J=1.6 Hz, 1H), 6.58 (d, J=1.4 Hz, 1H), 5.28 (m, 1H), 4.30 (dd, J=11.9, 4.4 Hz, 2H), 4.16 (dd, J=12.0, 5.8 Hz, 2H), 2.88 (t, J=6.6 Hz, 2H), 2.84 (s, 2H), 2.75 (t, J=6.6 Hz, 2H), 2.53 (s, 3H), 2.29 (t, J=7.6 Hz, 4H), 2.22 (s, 3H), 1.64-1.58 (m, J=9.3 Hz, 4H), 1.57 (s, 6H), 1.34-1.20 (m, 48H), 0.88 (t, J=6.8 Hz, 6H); $^{13}$C NMR (101 MHz, $CDCl_3$) δ 176.1 (C), 173.6 (2C; C), 171.6 (C), 171.4 (C), 149.5 (C), 138.2 (C), 136.5 (C), 133.4 (C), 132.7 (CH), 123.0 (CH), 69.8 (CH), 62.0 (2C; $CH_2$), 47.6 ($CH_2$), 38.8 (C), 34.1 (2C; $CH_2$), 32.1 (2C; $CH_2$), 31.5 (2C; $CH_3$), 29.9 ($CH_2$), 29.84 (6C; $CH_2$), 29.80 (4C; $CH_2$), 29.76 (2C; $CH_2$), 29.6 (2C; $CH_2$), 29.5 (2C; $CH_2$), 29.4 (2C; $CH_2$), 29.2 (2C; $CH_2$), 29.0 ($CH_2$), 25.4 ($CH_3$), 25.0 (2C; $CH_2$), 22.8 (2C; $CH_2$), 20.4 ($CH_3$), 14.3 (2C; $CH_3$). ESI-HRMS: calcd. for $C_{52}H_{88}NaO_{10}$ [M+Na$^+$] 895.6270; found 895.6266.

Using similar methods, Int-119 was prepared by EDC coupling with Int-37 in 84% yield:

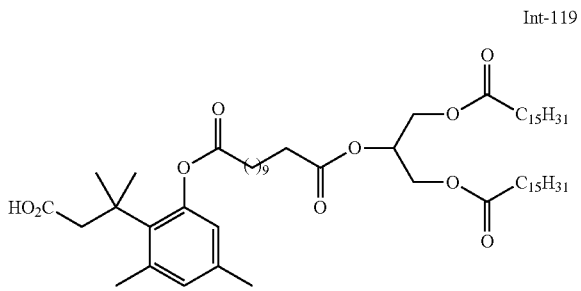

Int-119

$^1$H NMR (401 MHz, $CDCl_3$) δ 6.80 (d, J=1.9 Hz, 1H), 6.55 (d, J=1.7 Hz, 1H), 5.26 (m, 1H), 4.29 (dd, J=11.9, 4.4 Hz, 2H), 4.14 (dd, J=11.9, 5.9 Hz, 2H), 2.83 (s, 2H), 2.55 (t, J=7.5 Hz, 2H), 2.53 (s, 3H), 2.32 (t, J=7.5 Hz, 2H), 2.31 (t, J=7.5 Hz, 4H), 2.22 (s, 3H), 1.78-1.69 (m, 2H), 1.67-1.54 (m, 6H), 1.57 (s, 6H), 1.45-1.20 (m, 60H), 0.88 (t, J=6.8 Hz, 6H); $^{13}$C NMR (101 MHz, $CDCl_3$) δ 176.3 (C), 173.5 (2C; C), 173.1 (C), 173.0 (C), 149.7 (C), 138.2 (C), 136.4 (C), 133.5 (C), 132.5 (CH), 123.2 (CH), 69.0 (CH), 62.2 (2C; $CH_2$), 47.4 ($CH_2$), 38.9 (C), 35.2 ($CH_2$), 34.3 ($CH_2$), 34.2 (2C; $CH_2$), 32.1 (2C; $CH_2$), 31.4 (2C; $CH_3$), 29.84 (6C; $CH_2$), 29.80 (4C; $CH_2$), 29.76 (2C; $CH_2$), 29.62 (2C; $CH_2$), 29.53 (2C; $CH_2$), 29.50 (2C; $CH_2$), 29.41 (2C; $CH_2$), 29.38 (2C; $CH_2$), 29.30 ($CH_2$), 29.26 (2C; $CH_2$), 29.19 ($CH_2$), 25.4 ($CH_3$), 25.0 (3C; $CH_2$), 24.8 ($CH_2$), 22.8 (2C; $CH_2$), 20.4 ($CH_3$), 14.3 (2C; $CH_3$).

Int-122 was also prepared using similar methods:

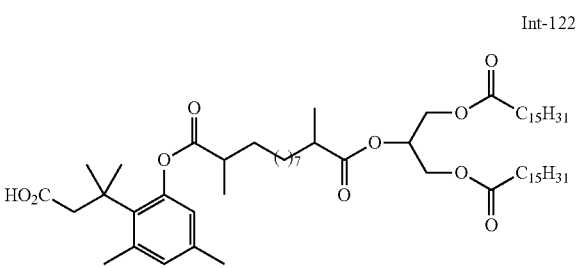

Int-122

$^1$H NMR (401 MHz, $CDCl_3$) δ 6.79 (d, J=1.9 Hz, 1H), 6.51 (d, J=1.8 Hz, 1H), 5.26 (m, 1H), 4.292/4.284 (each dd, J=11.8, 4.2 Hz, 2H), 4.14 (dd, J=11.9, 6.1 Hz, 2H), 2.84 (s, 2H), 2.67 (m, 1H), 2.53 (s, 3H), 2.44 (m, 1H), 2.30 (t, J=7.6 Hz, 4H), 2.22 (s, 3H), 1.84 (m, 1H), 1.69-1.45 (m, 7H), 1.573 (s, 3H), 1.567 (s, 3H), 1.45-1.19 (m, 63H), 1.14 (d, J=7.0 Hz, 3H), 0.88 (t, J=6.9 Hz, 6H); $^{13}$C NMR (101 MHz, $CDCl_3$) δ 176.1 (2C; C), 175.9 (C), 173.5 (2C; C), 150.1 (C), 138.2 (C), 136.4 (C), 133.6 (C), 132.5 (CH), 123.0 (CH), 68.9 (CH), 62.30/62.27 (2C; $CH_2$), 47.3 ($CH_2$), 40.2 (CH), 39.7 (CH), 39.0 (C), 34.2 (2C; $CH_2$), 33.8 ($CH_2$), 33.6 ($CH_2$), 32.1 (2C; $CH_2$), 31.5 ($CH_3$), 29.84 (2C; $CH_2$), 29.80 (2C; $CH_2$), 29.76 (2C; $CH_2$), 29.65 (2C; $CH_2$), 29.61 (2C; $CH_2$), 29.59 (2C; $CH_2$), 29.5 (2C; $CH_2$), 29.4 (2C; $CH_2$), 29.28/29.27 (2C; $CH_2$), 27.34 ($CH_2$), 27.28 ($CH_2$), 25.5 ($CH_3$), 25.0 (2C; $CH_2$), 22.8 (2C; $CH_2$), 20.4 ($CH_3$), 17.2 ($CH_3$), 16.9 ($CH_3$), 14.3 (2C; $CH_3$).

TML-C8βMe-acid-2-TG-oleate (Int-267):

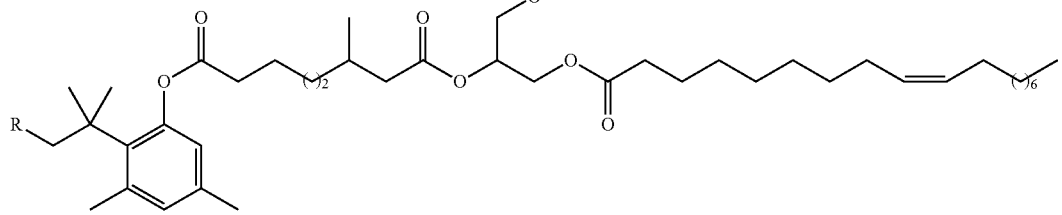

Int-266: R = CH$_2$OH
Int-267: R = CO$_2$H

Using similar methods as described for the synthesis of alcohol Int-108, compound Int-266 was prepared from Int-106 and Int-178. $^1$H NMR (400 MHz, CDCl$_3$) δ 6.81 (s, 1H), 6.53 (s, 1H), 5.31 (m, 4H), 5.20 (s, 1H), 4.29 (d, J=14.0 Hz, 2H), 4.14 (dd, J=11.6, 6.4 Hz, 2H), 3.18 (s, 2H), 2.47 (s, 4H), 2.33 (m, 5H), 2.16 (m, 2H), 1.98 (d, J=5.2 Hz, 4H), 1.91 (t, J=15.6 Hz 2H), 1.59-1.38 (m, 12H), 1.23 (s, 54H), 0.89 (m, 8H).

Oxidation of Int-266 to Int-267 was conducted using the Jones' reagent according to the procedure described for preparation of Int-178. $^1$H NMR (400 MHz, CDCl$_3$) δ 6.85 (s, 1H), 6.59 (s, 1H), 5.38 (m, 5H), 4.35 (d, J=11.6 Hz, 3H) 4.20 (dd, J=11.6 Hz, J=5.9 Hz, 2H), 2.86 (s, 1H), 2.63 (t, J=19.3 Hz, 5H), 2.41 (m, 5H), 2.26 (s, 3H), 2.21 (m, 2H), 2.05 (d, J=5.2 Hz, 8H), 1.80 (t, J=14.4 Hz, 2H), 1.62 (s, 5H), 1.45 (s, 4H), 1.33 (m, 46H), 0.99 (d, J=6.4 Hz, 3H), 0.91 (t, J=12.8 Hz, 6H); $^{13}$C NMR (101 MHz, CDCl$_3$) δ 176.33 (1C), 173.38 (2C), 172.64 (1C), 172.30 (1C), 149.45 (1C), 138.05 (1C), 136.29 (1C), 133.36 (1C), 132.45 (1C), 130.03 (2C), 129.73 (2C), 123.02 (1C), 69.00 (1C), 62.15 (2C), 47.36 (1C), 41.57 (1C), 38.68 (1C), 36.24 (1C), 34.91 (1C), 34.03 (2C), 31.93 (2C), 31.28 (2C), 30.13 (1C), 29.78-29.13 (18C), 27.23 (2C), 26.45 (1C), 25.34 (1C), 24.84 (2C), 24.71 (1C), 22.71 (2C), 20.28 (1C), 19.48 (1C), 14.16 (2C); MS (ESI, +ve) m/z: 1013.15 (M+18).

TML-C8β'βMe-acid-2-TG-oleate (Int-268):

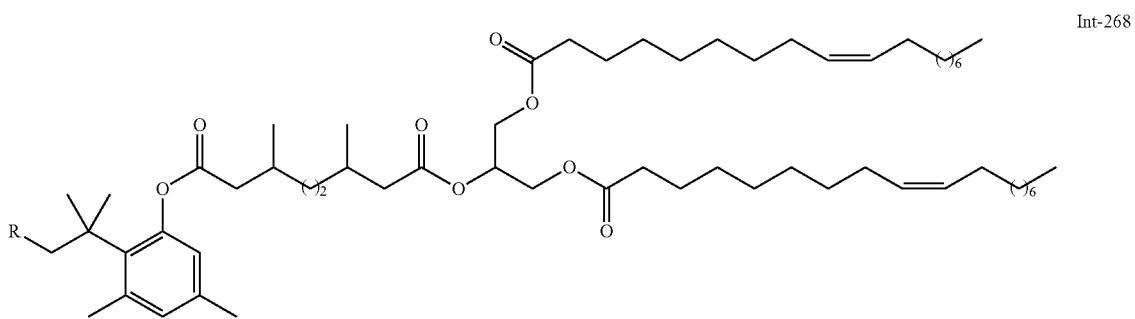

Using similar methods as described for the synthesis of Int-267, compound Int-268 was prepared from Int-106 and Int-176. $^1$H NMR (400 MHz, CDCl$_3$) δ 6.85 (s, 1H), 6.59 (s, 1H), 5.33 (m, 5H), 4.34 (d, J=11.6 Hz, 2H) 4.20 (dd, J=11.6 Hz, J=6.0 Hz, 2H), 2.90 (s, 2H), 2.64 (t, J=19.3 Hz, 4H), 2.49-2.32 (m, 8H), 2.26 (s, 3H), 2.22 (m, 2H), 2.16-2.05 (m, 10H), 1.76 (t, J=14.4 Hz, 2H), 1.64-1.55 (m, 3H), 1.51-1.30 (m, 47H), 1.17 (d, J=6.0 Hz, 3H), 1.077 (d, J=6.4 Hz, 3H), 0.917 (d, J=6.4 Hz, 6H); $^{13}$C NMR (101 MHz, CDCl$_3$) δ 175.65 (1C), 173.41 (2C), 172.41 (1C), 172.30 (1C), 149.45 (1C), 138.10 (1C), 136.28 (1C), 133.40 (1C), 133.36 (1C), 132.45 (1C), 130.26 (2C), 129.74 (2C), 122.99 (1C), 68.96 (1C), 62.15 (2C), 47.36 (1C), 41.57 (1C), 38.68 (1C), 36.24 (1C), 34.91 (1C), 34.03 (2C), 31.93 (2C), 31.28 (2C), 30.19 (1C), 29.80-29.12 (17C), 27.23 (2C), 26.45 (1C), 25.34 (1C), 24.84 (2C), 22.72 (1C), 20.30 (2C), 19.97 (1C), 19.48 (2C), 14.16 (2C); MS (ESI, +ve) m/z: 1027.18 (M+18).

Int-112 1,3-di-oleoyl glycerol (1,3-DG-oleate):

Scheme 31. Synthesis of Int-112.

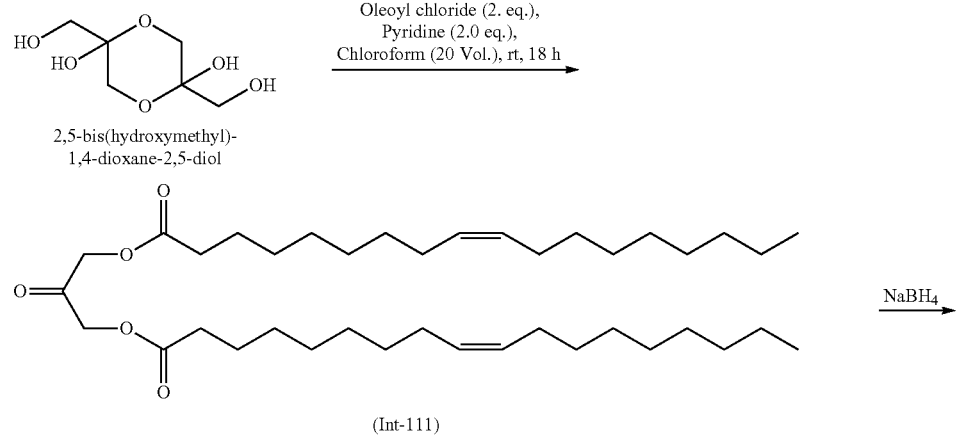

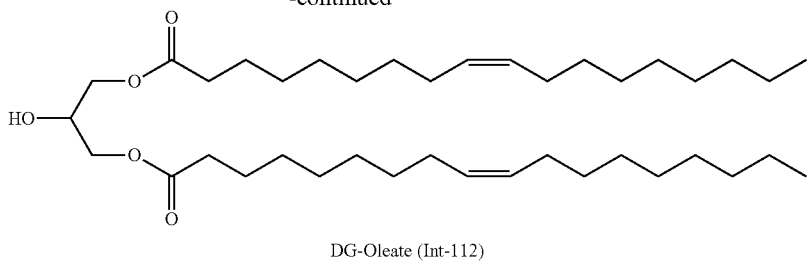

DG-Oleate (Int-112)

To a solution of 2,5-bis(hydroxymethyl)-1,4-dioxane-2,5-diol (5 g, 27.7 mol) in chloroform (20 vol) was added pyridine (5.5 mL, 69.4 mol) followed by oleoyl chloride (11 mL, 54.9 mol) and the mixture was stirred at room temperature for 1 h. The solvent was evaporated and the reaction mixture dissolved in ethyl acetate (30 vol) and washed with 1N HCl (10 vol). The organic layer was dried and solvent evaporated under vacuum. The crude material was recrystallized with cold methanol (20 vol). The solid obtained was further washed with cold methanol, and dried to give ketone Int-111 (11 g, 62%) as a white solid. $^1$H NMR (400 MHz, CDCl$_3$) δ 5.36 (t, J=11.6 Hz, 4H), 4.78 (s, 4H), 2.47 (m, 4H), 2.38 (m, 8H), 1.71 (m, 2H), 1.34-1.30 (m, 42H), 0.93 (m, 6H).

Sodium borohydride (NaBH$_4$, 307 mg, 8.09 mmol), was added to a solution of Int-111 (5 g, 8.09 mmol) in THF (20 vol) at 0° C. and then the reaction mixture was stirred at room temperature for 15 mins. The reaction was monitored by TLC and after completion, the reaction mixture was filtered through a celite bed to remove excess of sodium borohydride and the celite bed was washed with ethyl acetate (30 vol), the organic layer was washed with 1N solution of acetic acid (10 vol). The solvent was dried over Na$_2$SO$_4$ and solvent removed under vacuum. The crude material was column purified. The product was eluted at 5%-10% ethyl acetate/hexane to afford 1,3-DG-oleate (Int-112) (2 g, 39%) as viscous liquid. $^1$H NMR (400 MHz, CDCl$_3$) δ 5.39 (m, 4H), 4.20 (m, 5H), 2.44 (d, 1H), 2.36 (m, 4H), 2.01 (m, 8H), 2.47-2.25 (m, 12H), 2.17 (m, 1H), 2.02 (ddd, J=13.4, 4.9, 3.3 Hz, 1H), 1.85 (m, 1H), 1.77 (m, 1H), 1.64 (m, 2H), 1.57-1.26 (m, 42H), 0.9 (t, 6H); $^{13}$C NMR (101 MHz, CDCl$_3$) δ 173.9 (2C, C=O), 130.1 (2C), 129.7 (2C), 68.4 (C, CH), 65.1 (2C), 34.1 (2C), 31.9 (2C), 29.8-29.1 (18C), 27.3 (2C), 24.9 (2C), 22.7 (2C), 14.1 (2C). HPLC (ELSD): 9.62 min, 99.27% purity. MS (ESI, +ve) m/z: 639.2 (MH$^+$+H$_2$O).

Int-113 (C10-acid-TG-oleate):

Scheme 32. Synthesis of Int-113.

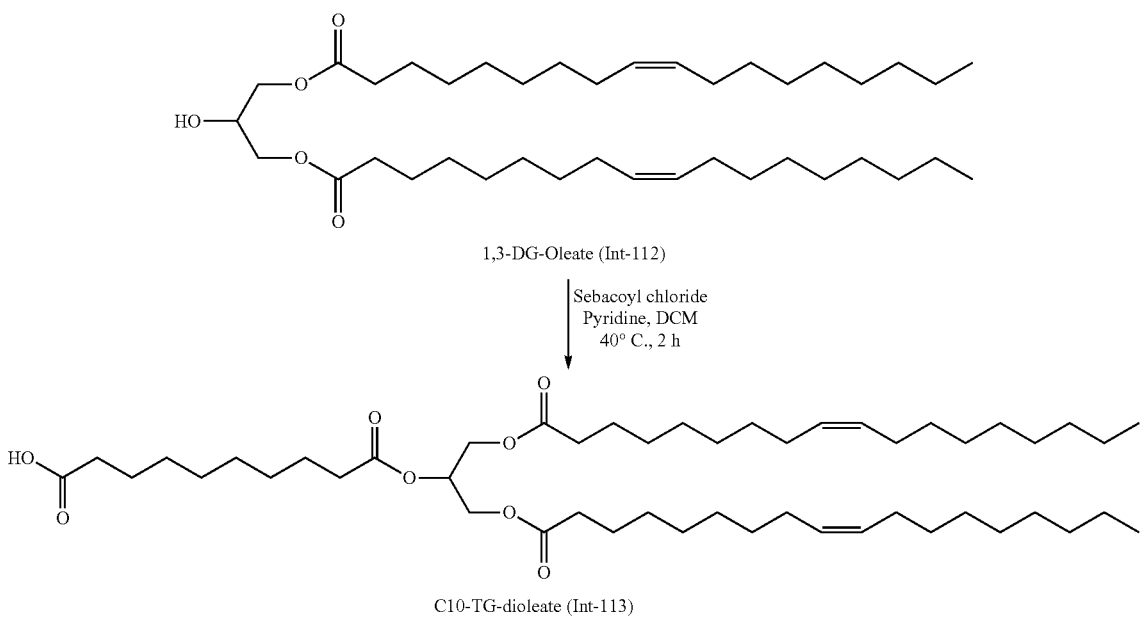

Pyridine (0.19 mL, 2.41 mmol) was added to a suspension of DG-oleate Int-112 (150 mg, 0.241 mmol) in DCM (20 Vol). After 5 min, sebacoyl chloride (289 mg, 1.2 mmol) was added dropwise with stirring at room temperature. Reaction mixture allowed to stir at 40° C. for 2 h. The reaction was monitored by TLC and after completion, diluted with DCM (20 vol), washed with water (20 vol), aqueous sodium bicarbonate (10 vol) and brine (10 vol). The obtained organic layer was dried over Na$_2$SO$_4$, filtered and solvent was removed under reduced pressure. The crude material was column purified. The product was eluted at 5-10% ethyl acetate/hexane to afford $C_{10}$-acid-TG-oleate Int-113 (60 mg, 30%) as viscous liquid. $^1$H NMR (400 MHz, CDCl$_3$) δ 5.43 (m, 4H), 5.29 (m, 1H), 4.35 (d, 2H), 4.20 (m, 2H), 2.40 (m, 8H), 2.05 (m, 8H), 1.65 (m, 10H), 1.33-1.18 (m 46H), 0.93 (t, 6H); $^{13}$C NMR (101 MHz, CDCl$_3$) δ 1.78 (1C, C=O, 173.3 (2C, C=O), 172.8 (1C, C=O), 130.1 (2C), 129.8 (2C), 68.9 (C, CH), 62.1 (2C), 60.5 (2C), 34.2 (4C), 31.9 (2C), 29.8-29.0 (18C), 27.3 (4C), 24.9 (4C), 22.7 (2C), 14.2 (2C). HPLC (ELSD): 10.90 min, 99% purity. MS (ESI, +ve) m/z: 823.8 (MH$^+$+H$_2$O).

Alternate Procedure (Larger Scale):

To a stirred solution of Int-112 (3.00 g, 4.80 mmol) and sebacic acid (1.94 g, 9.60 mmol) in DCM (45 ml) was added 4-(dimethylamino)pyridine (DMAP, 0.58 g, 4.80 mmol) followed by EDC·HCl (1.82 g, 9.60 mmol). The resulting reaction mixture was stirred at room temperature for 6 h. Progress of the reaction was monitored by TLC. After completion of reaction, the reaction mixture was concentrated under reduced pressure yielding a crude sticky material, which was purified by column chromatography using silica gel (100-200 mesh). Pure compound was eluted at 15% ethyl acetate and hexane as the mobile phase. Pure fractions were concentrated under reduced pressure to afford pure Int-113 (2.95 g, 75.8%) as a viscous liquid.

Int-115 (1,3-DG-butyrate):

evaporated under vacuum. The crude material was purified by column. The product was eluted at 5-10% ethyl acetate/hexane to afford Int-114 (1.4 g, 54%) as viscous liquid. $^1$H NMR (400 MHz, CDCl$_3$) δ 4.8 (s, 4H), 2.45 (t, 4H), 1.79-1.69 (m, 4H), 1.04-0.98 (t, 6H); $^{13}$C NMR (101 MHz, CDCl$_3$) δ 198.2 (1C=O), 172.2 (2C=O), 66.1 (2C), 35.9 (2C), 18.3 (2C), 14.1 (2C). HPLC (ELSD): 1.73 min, 99.8% purity.

Sodium borohydride (NaBH$_4$, 230 mg, 6.10 mmol), was added to a solution of Int-114 (1.3 g, 6.1 mmol) in THF (26 ml) at 0° C. and then the reaction mixture was stirred at room temperature for 15 mins. The reaction was monitored by TLC and after completion, the reaction mixture was filtered through a celite bed to remove excess sodium borohydride, the celite bed was washed with ethyl acetate (40 ml), and the combined organic layer was washed with a 1N solution of acetic acid (13 ml). The organic layer was dried over Na$_2$SO$_4$ and solvent removed under vacuum. The crude material was purified by column. The product was eluted at 5-10% ethyl acetate/hexane to afford Int-115 (1.0 g, 70.6%) as a viscous liquid. $^1$H NMR (400 MHz, CDCl$_3$) δ 4.25-4.13 (m, 5H), 2.4 (s, 1H), 2.38 (t, 4H), 1.75-1.66 (m, 4H), 1.01-0.98 (t, 6H); $^{13}$C NMR (101 MHz, CDCl$_3$) δ 173.8 (2C=O), 68.3 (1C), 65.0 (2C), 35.9 (2C), 18.4 (2C), 13.6 (2C). HPLC (ELSD): 1.8 min, 100% purity. MS (ESI, +ve) m/z: 255.37 (M$^+$+23).

Int-125:

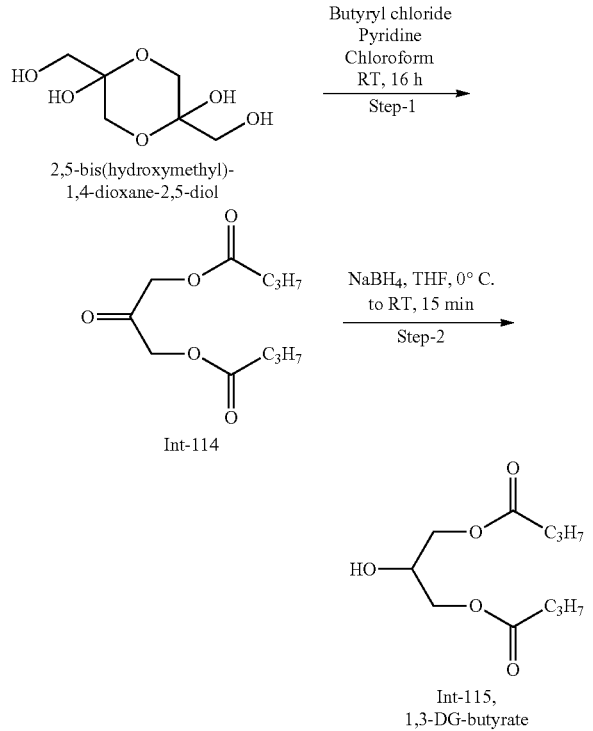

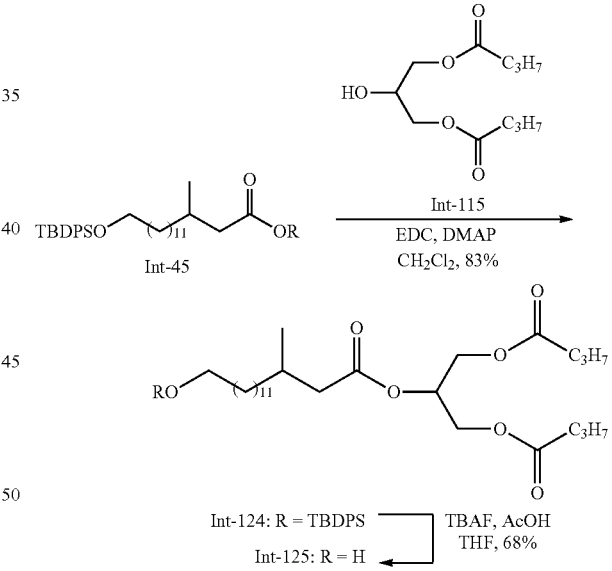

To a solution of 2,5-bis-(hydroxymethyl)-1,4-dioxane-2,5-diol (2.0 g, 1.11 mmol) in chloroform (40 ml) was added pyridine (2.2 mL, 2.77 mmol) followed by butyryl chloride (2.3 mL, 2.22 mol) before stirring at room temperature for 16 h. After completion, the solvent was evaporated and re-dissolved in ethyl acetate (60 ml) and washed with 1N HCl (20 ml). The combined organic layer was dried and Int-45 was prepared as described above and coupled with Int-115 using EDC and DMAP similarly to methods described above to provide Int-124. Int-124: $^1$H NMR (401 MHz, CDCl$_3$) δ 7.70-7.64 (m, 4H), 7.42-7.35 (m, 6H), 5.29 (m, 1H), 4.307/4.305 (each dd, J=11.9, 4.2 Hz, 2H), 4.159/4.157 (each dd, J=11.9, 6.0 Hz, 2H), 3.66 (t, J=6.5 Hz, 2H), 2.34 (dd, J=14.7, 5.9 Hz, 1H), 2.30 (t, J=7.4 Hz, 4H), 2.13 (dd, J=14.7, 8.3 Hz, 1H), 1.95 (m, 1H), 1.70-1.50 (m, 6H), 1.37-1.17 (m, 20H), 1.05 (s, 9H), 0.95 (t, J=7.5 Hz, 6H). 0.94 (d, J=6.4 Hz, 3H); $^{13}$C NMR (101 MHz, CDCl$_3$) δ 173.2 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 36.0 (2C; CH$_2$), 32.7 (CH$_2$), 30.5 (CH), 29.9 (CH$_2$), 29.80 (3C; CH$_2$), 29.76 (CH$_2$), 29.75 (CH$_2$), 29.5 (CH$_2$), 27.1 (CH$_2$), 27.0 (3C; CH$_3$), 25.9 (CH$_2$), 19.7 (CH$_3$), 19.3 (C) 18.5 (2C; CH$_2$), 13.7 (2C; CH$_3$).

Int-125:

Tetrabutylammonium fluoride (TBAF, 1.0 M in THF, 243 µL, 0.243 mmol) and AcOH (13.9 L, 0.243 mmol) were added dropwise to TBDPS ether Int-124 (58.7 mg, 0.0809 mmol) in THF (4 mL) at 0° C. and the mixture stirred at rt for 19 hours. The reaction was diluted with water (10 mL) and the aqueous phase extracted with ethyl acetate (3×15 mL). The combined organic extracts were washed with sat. aq. NaHCO$_3$ and brine (30 mL each), dried (MgSO$_4$) and concentrated under reduced pressure to give the crude product. Purification by silica gel chromatography (6% to 20% ethyl acetate/hexanes) gave alcohol Int-125 (26.7 mg, 68%) as a colorless oil. $^1$H NMR (401 MHz, CDCl$_3$) δ 5.28 (m, 1H), 4.298/4.295 (each dd, J=11.9, 4.3 Hz, 2H), 4.153/4.151 (each dd, J=11.9, 6.0 Hz, 2H), 3.64 (t, J=6.6 Hz, 2H), 2.33 (dd, J=14.7, 5.9 Hz, 1H), 2.30 (t, J=8.4, 6.5 Hz, 4H), 2.12 (dd, J=14.7, 8.3 Hz, 1H), 1.93 (m, 1H), 1.70-1.46 (m, 8H), 1.38-1.16 (m, 18H), 0.95 (t, J=7.4 Hz, 6H), 0.93 (d, J=6.7 Hz, 3H); $^{13}$C NMR (101 MHz, CDCl$_3$) δ 173.3 (2C; C), 172.5 (C), 69.0 (CH), 63.2 (CH$_2$), 62.3 (2C; CH$_2$), 41.9 (CH$_2$), 36.8 (CH$_2$), 36.1 (2C; CH$_2$), 33.0 (CH$_2$), 30.5 (CH), 29.9 (CH$_2$), 29.78 (CH$_2$), 29.76 (2C; CH$_2$), 29.74 (CH$_2$), 29.71 (CH$_2$), 29.6 (CH$_2$), 27.1 (CH$_2$), 25.9 (CH$_2$), 19.7 (CH$_3$), 18.5 (2C; CH$_2$), 13.8 (2C; CH$_3$).

Int-126:

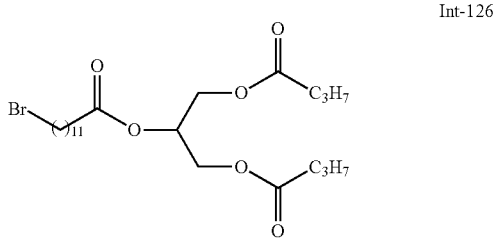

Int-126

Prepared using similar methods as those shown above. $^1$H NMR (401 MHz, CDCl$_3$) δ 5.23 (m, 1H), 4.26 (dd, J=11.9, 4.3 Hz, 2H), 4.11 (dd, J=11.9, 6.0 Hz, 2H), 3.36 (t, J=6.9 Hz, 2H), 2.28 (t, J=7.4 Hz, 2H), 2.26 (t, J=7.4 Hz, 4H), 1.84-1.75 (m, 2H), 1.66-1.52 (m, 6H), 1.42-1.33 (m, 2H), 1.31-1.19 (m, 12H), 0.90 (t, J=7.4 Hz, 6H); $^{13}$C NMR (101 MHz, CDCl$_3$) δ 173.1 (2C; C), 172.9 (C), 68.9 (CH), 62.1 (2C; CH$_2$), 35.9 (2C; CH$_2$), 34.2 (CH$_2$), 34.0 (CH$_2$), 32.9 (CH$_2$), 29.5 (CH$_2$), 29.43 (CH$_2$), 29.42 (CH$_2$), 29.3 (CH$_2$), 29.1 (CH$_2$), 28.8 (CH$_2$), 28.2 (CH$_2$), 24.9 (CH$_2$), 18.4 (2C; CH$_2$), 13.7 (2C; CH$_3$); ESI-HRMS: calcd. for C$_{23}$H$_{41}$$^{79}$BrNaO$_6$ [M+Na$^+$]515.1979; found 515.1995.

Int-117 1,3-bis-decanoyl glycerol (1,3-DG-decanoate):

Scheme 35. Synthesis of Int-117.

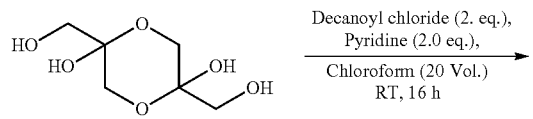

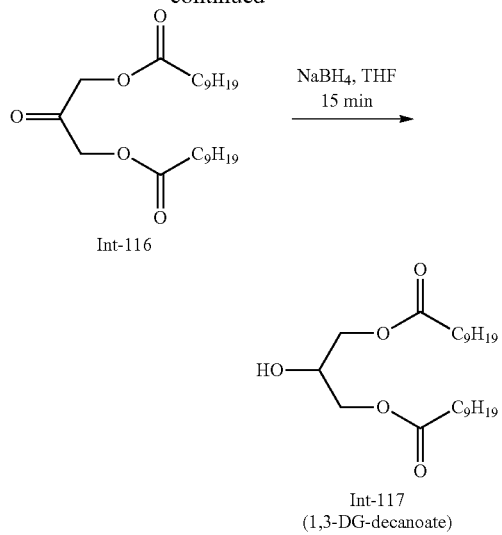

To a solution of 2, 5-bis-(hydroxymethyl)-1,4-dioxane-2,5-diol (0.2 g, 1.11 mmol) in chloroform (4.0 ml) was added pyridine (0.22 mL, 2.77 mmol) followed by decanoyl chloride (0.45 mL, 2.22 mmol) and stirred at room temperature for 16 h. The solvent was evaporated and re-dissolved in ethyl acetate (6 ml) and washed with 1N HCl (2 ml). The organic layer was dried and solvent evaporated under vacuum. The crude material was purified by column. The product was eluted at 5-10% ethyl acetate/hexane to afford Int-116 (0.09 g, 20.36%) as viscous liquid. $^1$H NMR (400 MHz, CDCl$_3$) δ 4.8 (m, 4H), 2.46 (m, 4H), 1.73-1.66 (m, 4H), 1.30 (m, 24H), 0.91 (t, 6H); $^{13}$C NMR (101 MHz, CDCl$_3$) δ 198.2 (1C=O), 172.0 (2C=O), 66.1 (2C), 33.7 (2C), 31.8 (2C), 29.3 (2C), 29.2 (2C), 29.0 (2C), 24.8 (2C), 22.6 (2C), 14.12 (2C). HPLC (ELSD): 2.88 min, 100% purity.

Sodium borohydride (NaBH$_4$) (7 mg, 0.2 mmol), was added to a solution of Int-116 (80 mg, 0.2 mmol) in THF (2 ml) at 0° C. and then the reaction mixture was stirred at room temperature for 15 mins. The reaction was monitored by TLC and after completion, the reaction mixture was filtered through a celite bed to remove excess sodium borohydride and the celite bed was washed with ethyl acetate (3 ml). The organic layer was washed with 1 M acetic acid (1 ml). The solvent was dried over Na$_2$SO$_4$ and solvent removed under vacuum. The crude material was purified by column. The product was eluted at 5-10% ethyl acetate/hexane to afford Int-117 (70 mg, 100%) as viscous liquid. $^1$H NMR (400 MHz, CDCl$_3$) δ 4.2-4.1 (m, 5H), 2.51 (s, 1H), 2.38 (t, 4H), 1.68-1.64 (m, 4H), 1.32-1.29 (m, 22H), 0.91 (t, 6H); $^{13}$C NMR (101 MHz, CDCl$_3$) δ 173.0 (2C=O), 68.3 (1C), 65.0 (2C), 34.1 (2C), 31.8 (2C), 29.7 (2C), 29.4 (2C), 29.3 (2C), 29.1 (2C), 24.9 (2C), 22.7 (2C), 14.1 (2C). HPLC (ELSD): 10.70 min, 97.6% purity.

Int-192 1,3-bis-octanoyl glycerol (1,3-DG-octanoate):

Scheme 35-A. Synthesis of Int-192.

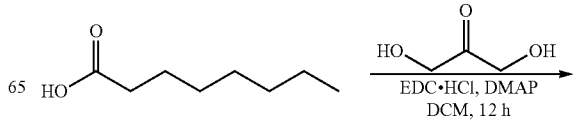

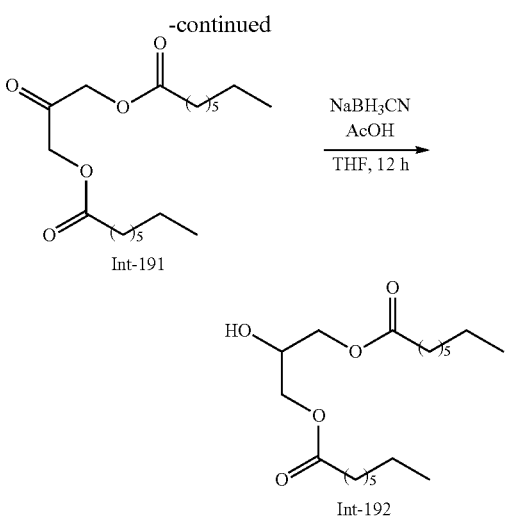

To a solution of octanoic acid (60 g, 416 mmol) and 1,3-dihydroxypropan-2-one (37.5 g, 416 mmol) in DCM (500 mL) at room temperature, was added EDC·HCl (199.68 g, 1.04 mol) followed by DMAP (50.90 g, 0.416 mmol). The reaction mixture was allowed to stir at room temperature for 12 hours. The reaction mixture was diluted with DCM (200 mL), and washed with water (200 mL). The organic layer was dried over Na$_2$SO$_4$, and solvent was removed under vacuum. The resulting material was purified by column chromatography using 100-200 mesh silica gel. The desired compound was eluted at 10% ethyl acetate/hexane to afford Int-191 (44 g, 31%) as a white solid. $^1$H NMR (400 MHz, CDCl$_3$) δ 4.77 (m, 4H), 2.44 (t, 4H), 1.70-1.58 (m, 4H), 1.32-1.30 (m, 16H), 0.89 (t, 6H).

To a solution of Int-191 (44 g, 128 mmol) in THF (500 mL) was added acetic acid (9.2 mL) dropwise at 0° C., and then sodium cyanoborohydride (9.7 g, 154 mmol) was added in portions. The reaction mixture was allowed to warm to RT and stirred for 12 h. The reaction mixture was diluted with ethyl acetate (500 mL) and washed with water (300 mL). The organic layer was dried over Na$_2$SO$_4$, and solvent was removed under vacuum. The resulting material was purified by column chromatography using 100-200 mesh silica gel. The desired compound was eluted at 9% ethyl acetate/hexane to afford Int-192 (25 g, 56%) as a viscous liquid. $^1$H NMR (400 MHz, CDCl$_3$) δ 4.25-4.12 (m, 5H), 2.47 (d, 1H), 2.41-2.37 (t, 4H), 1.69-1.604 (m, 4H), 1.49-1.32 (m, 16H), 1.00-0.90 (t, 6H); $^{13}$C NMR (101 MHz, CDCl$_3$) δ 173.97 (2C), 68.38 (1C), 65.05 (2C), 34.12 (2C), 31.66 (2C), 29.09 (2C), 28.92 (2C), 24.90 (2C), 22.61 (2C), 14.08 (2C). HPLC (ELSD): 12.48 min, 100% purity; MS (ESI, +ve) m/z: 362 (MH$^+$+18).

Int-123:

Scheme 36. Synthesis of Int-123.

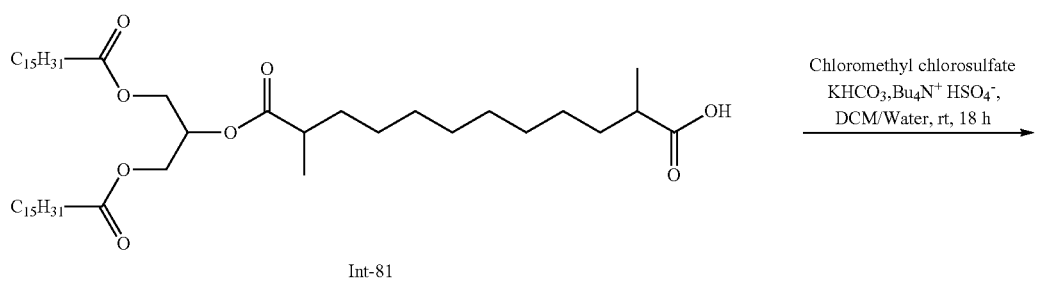

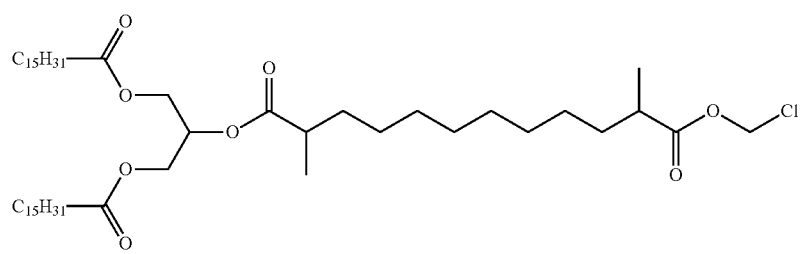

Tetra-n-butyl ammonium hydrogen sulfate (0.034 g, 0.098 mmol) and potassium bicarbonate (0.198 g, 1.977 mmol) in distilled water (10 ml) was added to a stirred solution of Int-81 (0.4 g, 0.494 mmol) and tetra-n-butyl ammonium hydrogen sulfate (0.034 g, 0.098 mmol) in dichloromethane (10 ml) at rt and stirred for 0.5 h. Then chloromethyl chlorosulfate (0.062 ml, 0.618 mmol) was added dropwise at rt and stirred vigorously at rt for 18 h. The reaction was monitored by TLC, and after completion of reaction, the reaction mixture was diluted with DCM (25 ml). The organic phase was separated and the aqueous phase extracted with DCM (2×50 ml). Combined organic layers were washed with water (50 ml), brine (50 mL), dried over sodium sulphate, filtered and concentrated at reduced pressure to get crude material. Crude material was purified by column chromatography over silica 100-200 mesh; compound eluted at 20% ethyl acetate/hexane as a mobile phase; visualization was with KMnO$_4$ solution. Int-123 (0.250 g, 59%) was obtained as a viscous liquid. $^1$H NMR (400 MHz, CDCl$_3$) δ 5.75 (m, 2H), 5.32-5.30 (m, 1H), 4.33 (dd, J=11.9, 4.3 Hz, 2H), 4.18 (dd, J=11.9, 6.0 Hz, 2H), 2.56-2.45 (m, 2H), 2.36-2.32 (t, J=7.2 Hz, 4H), 1.66-1.62 (m, 4H), 1.48-1.40 (m, 8H), 1.29 (m, 56H), 1.19 (dd, J=11.2, 7.0 Hz, 6H), 0.92 (t, J=6.7 Hz, 6H).

Using Similar Methods, Int-155 was Prepared:

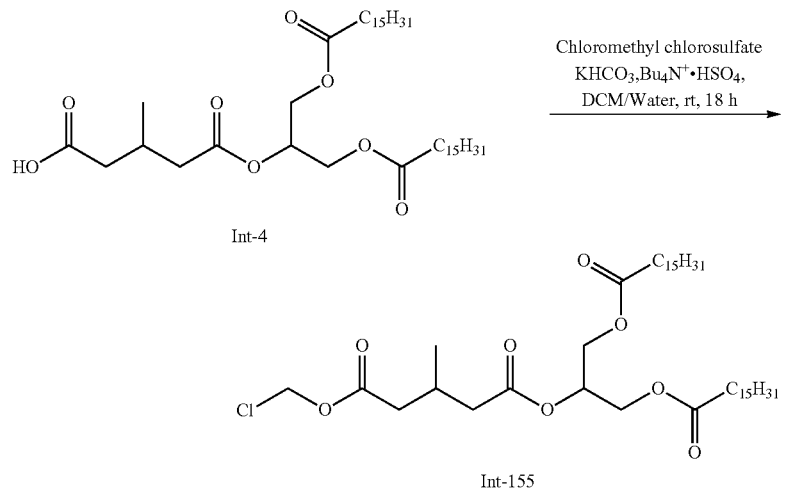

Tetra-n-butyl ammonium hydrogen sulfate (24 mg, 0.072 mmol) and potassium bicarbonate (286 mg, 2.86 mmol) in distilled water (10 ml) was added to a stirred solution of acid linker Int-4 (0.5 g, 0.72 mmol) and tetra-n-butyl ammonium hydrogen sulfate (24 mg, 0.072 mmol) in dichloromethane (10 ml) at rt and stir for 0.5 h. Then chloromethyl chlorosulfate (0.092 ml, 0.89 mmol) was dropwise added at room temperature and stirred vigorously at rt for 18 h. The reaction was monitored by TLC, after completion of reaction; reaction mixture was diluted with DCM (5 ml). The organic phase was separated and the aqueous phase was extracted with DCM (2×5 ml). The combined organic layers were washed with water (10 ml), brine (10 mL), dried over sodium sulfate, filtered and concentrated at reduced pressure to get crude material. Crude material was purified by column chromatography over silica, compound eluted at 15% ethyl acetate/hexane as a mobile phase. Pure fractions were concentrated in the rotavap to give Int-155 C5bMe-chloromethyl ester: (0.250 g, 47%) as white solid. $^1$H NMR (400 MHz, CDCl$_3$) δ 5.76 (s, 2H), 5.33 (m, 1H), 4.34 (dd, 2H), 4.18 (dd, 2H), 2.5-2.3 (m, 8H), 1.66-1.64 (m, 2H), 1.60 (s, 3H), 1.29 (m, 48H), 1.09 (d, 3H), 0.91 (t, 6H). MS (ESI, +ve) m/z: 763 (MH$^+$+18).

C15-acid-2-TG (Int-129):

Scheme 37. Synthesis of Int-129.

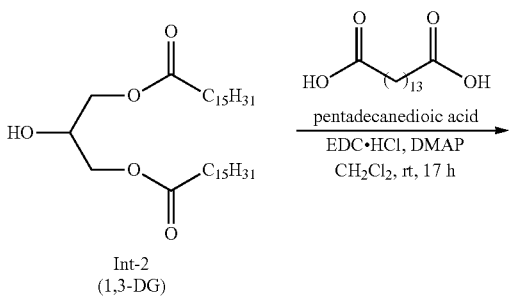

Int-2
(1,3-DG)

-continued

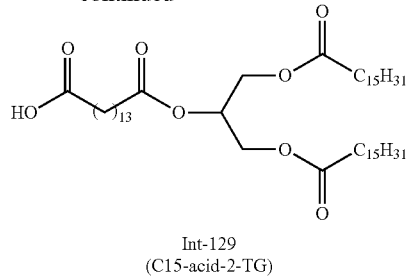

Int-129
(C15-acid-2-TG)

4-(Dimethylamino)pyridine (22.5 mg, 0.184 mmol) and N—(3-dimethylaminopropyl)-N'-ethyl-carbodiimide (EDC·HCl, 88.3 mg, 0.461 mmol) were added to a solution of pentadecanedioic acid (100 mg, 0.369 mmol) and compound Int-2 (105 mg, 0.184 mmol) in CH$_2$Cl$_2$ (5 mL) and the mixture stirred at room temperature for 17 hours. The reaction was diluted with CH$_2$Cl$_2$ (10 mL), silica gel was added and the mixture concentrated under reduced pressure. Purification by silica gel chromatography (15% to 25% ethyl acetate/hexanes) gave Int-129 (C15-acid-2-TG) (113 mg, 75%) as a colourless solid. $^1$H NMR (401 MHz, CDCl$_3$) δ 5.26 (m, 1H), 4.29 (dd, J=11.9, 4.3 Hz, 2H), 4.14 (dd, J=11.9, 6.0 Hz, 2H), 2.34 (t, J=7.5 Hz, 2H), 2.31 (t, J=7.5 Hz, 2H), 2.30 (t, J=7.5 Hz, 4H), 1.67-1.56 (m, 8H), 1.38-1.17 (m, 66H), 0.87 (t, J=6.8 Hz, 6H); $^{13}$C NMR (101 MHz, CDCl$_3$) δ 179.6 (C), 173.5 (2C; C), 173.0 (C), 69.0 (CH), 62.2 (2C; CH$_2$), 34.4 (CH$_2$), 34.2 (2C; CH$_2$), 34.1 (CH$_2$), 32.1 (2C; CH$_2$), 29.84 (6C; CH$_2$), 29.80 (4C; CH$_2$), 29.76 (2C; CH$_2$), 29.75 (2C; CH$_2$), 29.72 (CH$_2$), 29.62 (2C; CH$_2$), 29.58 (CH$_2$), 29.50 (2C; CH$_2$), 29.43 (CH$_2$), 29.41 (2C; CH$_2$), 29.38 (CH$_2$), 29.25 (2C; CH$_2$), 29.21 (2C; CH$_2$), 25.03 (CH$_2$), 25.00 (2C; CH$_2$), 24.8 (CH$_2$), 22.8 (2C; CH$_2$), 14.3 (2C; CH$_3$).

MASI-C12α'αMe-chloride-2-TG (Int-136):

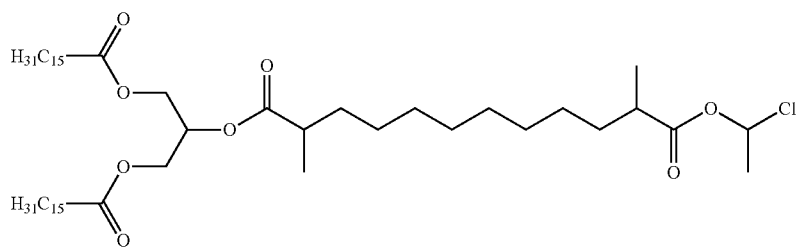

Int-136

A solution of Int-81 (0.5 g, 0.618 mmol) in DCM (5 ml), DMF (two drops) and oxalyl chloride (1.1 ml, 12.36 mmol) was added at 0° C. then reaction mixture was stirred at RT for 2 h. The reaction mixture was concentrated under reduced pressure, and then co-evaporated three times with DCM (5 mL each) and dried under reduced pressure. The resulting acid chloride was dissolved in DCM (20 ml), then ZrCl$_4$ (0.33 g, 1.45 mmol) in DCM (10 mL) was added dropwise to the reaction mixture at 0° C. and stirred at 0° C. for 10 minutes. Then paraldehyde (0.383 g, 2.90 mmol) was added and the reaction mixture was stirred at 0° C. for 0.5 h and RT for 1 h. The reaction mixture was diluted with DCM (50 mL) and water (50 mL). The organic layer was washed with water (25 mL) and brine (25 mL), dried over Na$_2$SO$_4$, and concentrated under reduced pressure to give the crude product. Purification by column chromatography over silica gel eluting with 5% to 15% ethyl acetate/hexanes gave Int-136 (0.135 g, 21%) as a viscous oil. $^1$H NMR (400 MHz, CDCl3) δ 6.61-6.57 (q, 1H), 5.32 (m, 1H), 4.33 (dd, J=11.6, 3.7 Hz, 2H), 4.19 (dd, J=11.9, 6.1 Hz, 2H), 2.49 (m, 2H), 2.34 (t, J=7.6 Hz, 4H), 1.83 (d, J=5.6 Hz, 2H), 1.72-1.62 (m, 4H), 1.49-1.40 (m, 5H). 1.38-1.29 (m, 60H), 1.24-1.17 (m, 6H), 0.92 (t, 6H).

MASI-C12α'βMe-chloride-2-TG (Int-142):

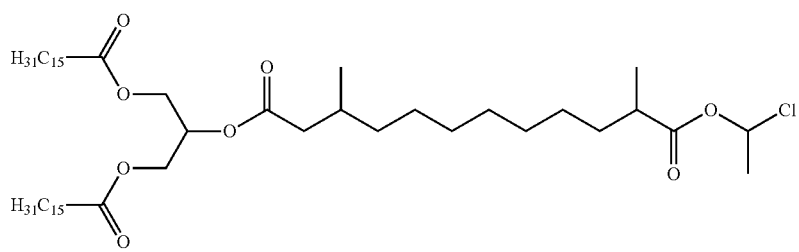

Int-142

A solution of Int-27 (0.5 g, 0.618 mmol) in DCM (5 ml), DMF (two drops) and oxalyl chloride (1.1 ml, 12.36 mmol) was added at 0° C., then the reaction mixture was stirred at RT for 2 h. The reaction mixture was concentrated under reduced pressure, and then co-evaporated three times with DCM (5 mL each) and dried under reduced pressure. The resulting acid chloride was dissolved in DCM (20 ml), then $ZrCl_4$ (0.33 g, 1.45 mmol) in DCM (10 mL) was added dropwise to the reaction mixture at 0° C. and stirred at 0° C. for 10 minutes. Then paraldehyde (0.383 g, 2.90 mmol) was added and the reaction mixture was stirred at 0° C. for 0.5 h and RT for 1 h. The reaction mixture was diluted with DCM (50 mL) and water (50 mL). The organic layer was washed with water (25 mL) and brine (25 mL), dried over $Na_2SO_4$, and concentrated under reduced pressure to give the crude product. Purification by column chromatography over silica gel eluting with 5% to 15% ethyl acetate/hexanes gave Int-142 (0.170 g, 32%) as a viscous oil. $^1$H NMR (400 MHz, $CDCl_3$) δ 6.61-6.57 (q, J=5.6 Hz, 1H), 5.32 (m, 1H), 4.33 (dd, J=11.6, 3.7 Hz, 2H), 4.19 (dd, J=11.9, 6.1 Hz, 2H), 2.49 (m, 2H), 2.39-2.32 (t, J=7.6 Hz, 6H), 2.18-2.12 (m, 2H), 2.08-1.97 (m, 2H), 1.83 (d, J=5.6 Hz, 3H), 1.64-1.56 (m, 8H), 1.38-1.29 (m, 54H), 1.21-1.19 (m, 6H), 0.92 (t, J=6.0 Hz, 6H).

MASI-C10-chloride-2-TG (Int-165):

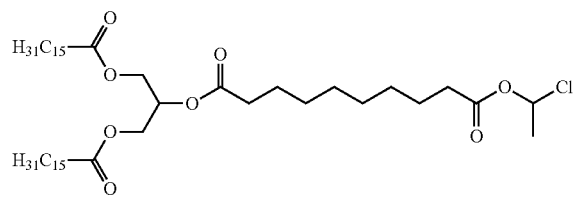

Int-165

A solution of Int-9 (1.0 g, 1.32 mmol) in DMF (two drops) and $SOCl_2$ (0.98 mL, 13.29 mmol) was heated at reflux for 1.25 h. The reaction mixture was cooled to RT, concentrated under reduced pressure, co-evaporated three times with toluene (5 mL each), and dried under reduced pressure. The resulting acid chloride was dissolved in DCM (20 mL) and cooled to 0° C. A solution of $ZrCl_4$ (309 mg, 1.32 mmol) in DCM (10 mL) was added dropwise, and the mixture was stirred at 0° C. for 10 minutes. Paraldehyde (351 mg, 2.65 mmol) was added and the reaction mixture was stirred at 0° C. for 0.5 hour and RT for 1 h. The reaction mixture was diluted with DCM (10 mL) and water (10 mL). The organic phase was washed with water and brine (10 mL each), dried over $Na_2SO_4$, and concentrated under reduced pressure. The resulting material was purified by silica gel column chromatography, with the compound eluting at 5% to 15% ethyl acetate/hexane, and concentrated under reduced pressure to afford Int-165 (300 mg, 30%) as a brown oil. $^1$H NMR (400 MHz, $CDCl_3$) δ 6.59 (d, J=5.8 Hz, 1H), 5.30 (t, J=5.5 Hz, 1H), 4.26 (dd, J=11.9, 5.1 Hz, 2H), 4.18 (dd, J=11.6, 5.9 Hz, 2H), 2.40-2.33 (m, 8H), 1.83 (d, J=5.9 Hz, 3H), 1.67 (m, 12H), 1.32 (s, 52H), 0.92 (t, J=6.6 Hz, 6H).

MASI-C5βMe-chloride-2-TG (Int-166):

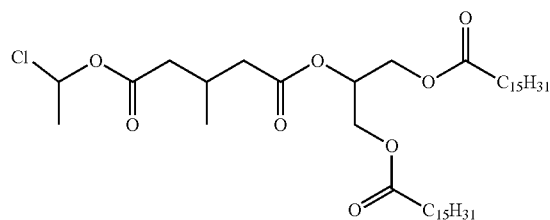

Using the method described for the synthesis of Int-165, compound Int-166 was prepared from Int-4. $^1$H NMR (400 MHz, $CDCl_3$) δ 6.59 (d, J=5.8 Hz, 1H), 5.46-5.22 (m, 1H), 4.35 (dd, J=12.0, 4.2 Hz, 2H), 4.18 (dd, J=11.9, 6.0 Hz, 2H), 2.56-2.41 (m, 3H), 2.40-2.27 (m, 6H), 1.83 (d, J=5.8 Hz, 3H), 1.64 (m, 4H), 1.31 (d, J=9.6 Hz, 48H), 1.09 (dd, J=6.6, 2.6 Hz, 3H), 0.92 (t, J=6.7 Hz, 6H).

CMSI-C5βMe-2-TG (Int-228):

Scheme 38. Synthesis of Int-228.

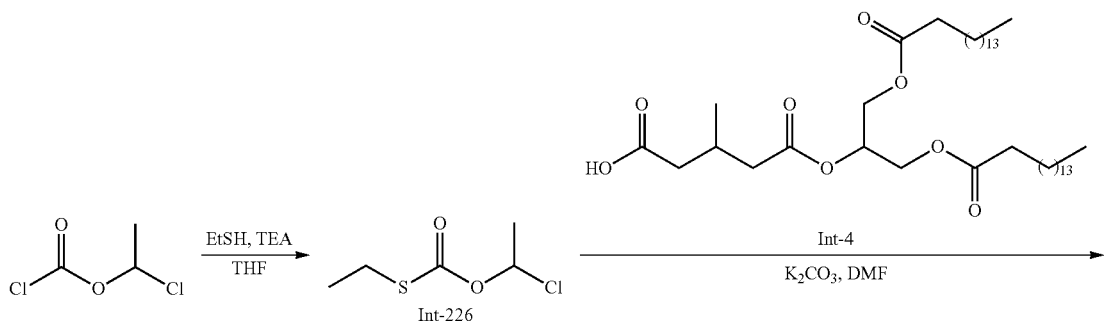

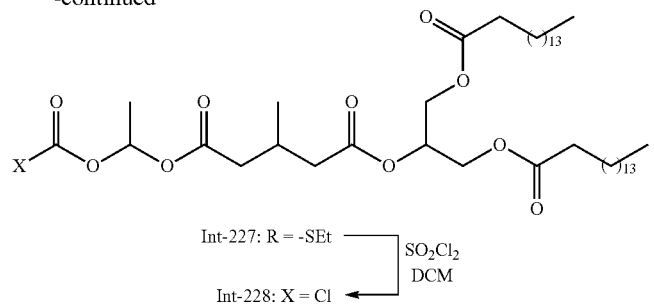

Int-227: R = -SEt
Int-228: X = Cl
SO₂Cl₂
DCM

To a solution of ethanethiol (1.0 g, 16 mmol) in THF (10 mL) was added TEA (3.25 g, 32.3 mmol), and the reaction mixture was stirred at room temperature for 30 min. Then (1-chloroeth-1-yl)chloroformate (1.74 mL, 16.1 mmol) was added, and the resulting reaction mixture was stirred at room temperature for 24 h. The reaction mixture was concentrated. The residue was purified by Combiflash, with product eluting at 5% ethyl acetate/hexane, to afford Int-226 (2.4 g, 88%) as a viscous oil. ¹H NMR (400 MHz, CDCl₃) δ 6.64 (tt, J=8.6, 4.3 Hz, 1H), 2.96 (q, J=4.3, 3.7 Hz, 2H), 1.62 (d, J=3.2 Hz, 3H), 1.38 (t, J=7.4 Hz, 3H).

To a solution of Int-226 (1.0 g, 5.95 mmol) in DMF (10 mL), K₂CO₃ (4.1 g, 29.8 mmol) was added, and the reaction mixture was stirred at room temperature for 30 min. Then Int-4 (2.4 g, 3.6 mmol) was added, and the resulting reaction mixture was stirred at 100° C. for 2 h. The reaction mixture was diluted with water (50 mL), and extracted with ethyl acetate (3×50 mL). The combined organic layers were dried over sodium sulfate then evaporated under reduced pressure. The residue was purified by Combiflash purification, with compound eluting at 5% ethyl acetate/hexane, to afford Int-227 (0.8 g, 73%) as a viscous oil. ¹H NMR (400 MHz, CDCl₃) δ δ 7.01 (q, J=10.8, 5.6 Hz, 1H), 5.31 (m, 1H), 4.36 (dd, J=11.9, 4.3 Hz, 2H), 4.17 (dd, J=11.9, 6.0 Hz, 2H), 2.95-2.87 (m, 2H), 2.56-2.41 (m, 4H), 2.34 (q, J=11.1, 9.4 Hz, 6H), 1.69-1.60 (m, 4H), 1.55 (d, J=5.4 Hz, 3H), 1.33 (m, 50H), 1.07 (d, J=6.0 Hz, 3H), 0.92 (t, J=6.6 Hz, 6H).

To a solution of Int-227 (0.500 g, 0.603 mmol) in DCM (10 mL) under N₂ atmosphere at 0° C. was added SO₂C₂ (0.203 g, 1.507 mmol), and the reaction mixture was stirred at rt for 3 h. The reaction mixture was evaporated under reduced pressure to afford Int-228, which was used directly in the next step without further purification.

C10α'αMe-acid-2-TG (Int-150):

Scheme 39. Synthesis of Int-150.

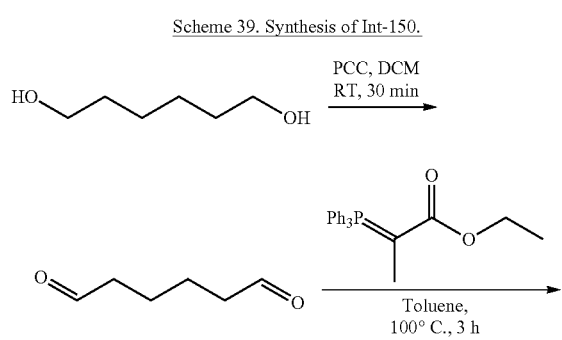

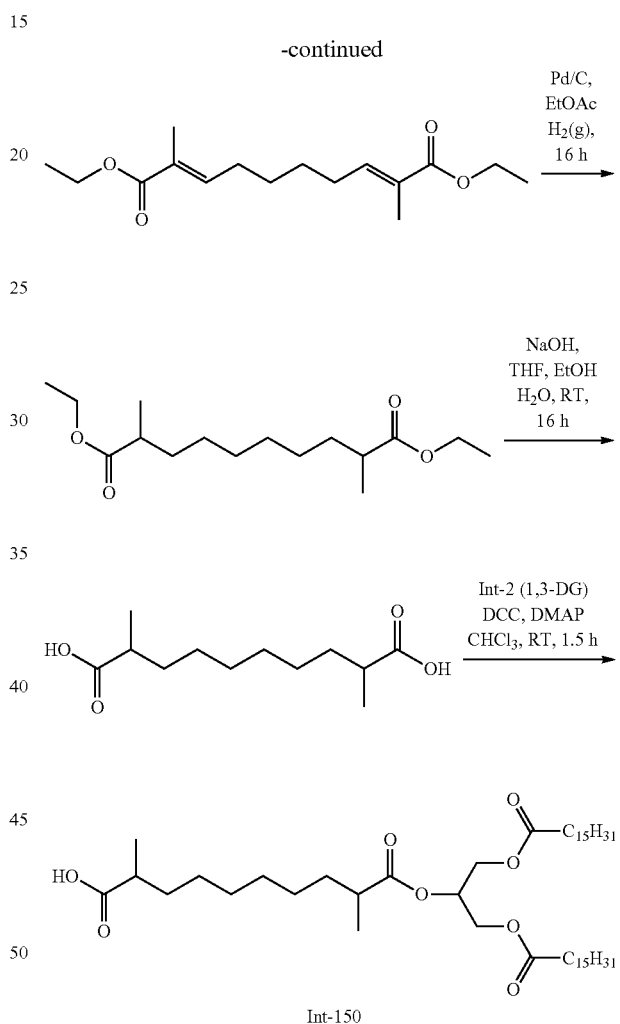

Int-150

Intermediate C10α'αMe-acid-2-TG (Int-150) was prepared from hexane-1,6-diol as shown in Scheme 39, using methods described above. ¹H NMR (400 MHz, CDCl₃) δ 5.35-5.24 (m, 1H), 4.31 (dd, J=11.8, 4.0 Hz, 2H), 4.17 (dd, J=11.9, 6.0 Hz, 2H), 2.47 (p, J=7.2 Hz, 2H), 2.33 (t, J=7.7 Hz, 6H), 1.69-1.60 (m, 6H), 1.44-1.39 (m, 4H), 1.27 (s, 52H), 1.18 (dd, J=14.8, 7.0 Hz, 6H), 0.89 (t, J=6.4 Hz, 6H); ¹³C NMR (101 MHz, CDCl₃) δ 182.44 (1C), 175.90 (1C), 173.36 (2C), 68.72 (1C), 62.16 (2C), 39.54 (1C), 39.27 (1C), 34.08 (2C), 33.61 (1C), 33.51 (1C), 31.97 (3C), 29.74-28.98 (22C), 27.12 (1C), 24.89 (2C), 22.73 (2C), 17.07 (1C), 16.89 (1C), 14.17 (2C); MS (ESI, +ve) m/z: 798.6 (M+18).

C10ααMe-acid-2-TG (Int-151):

Scheme 40. Synthesis of Int-151.

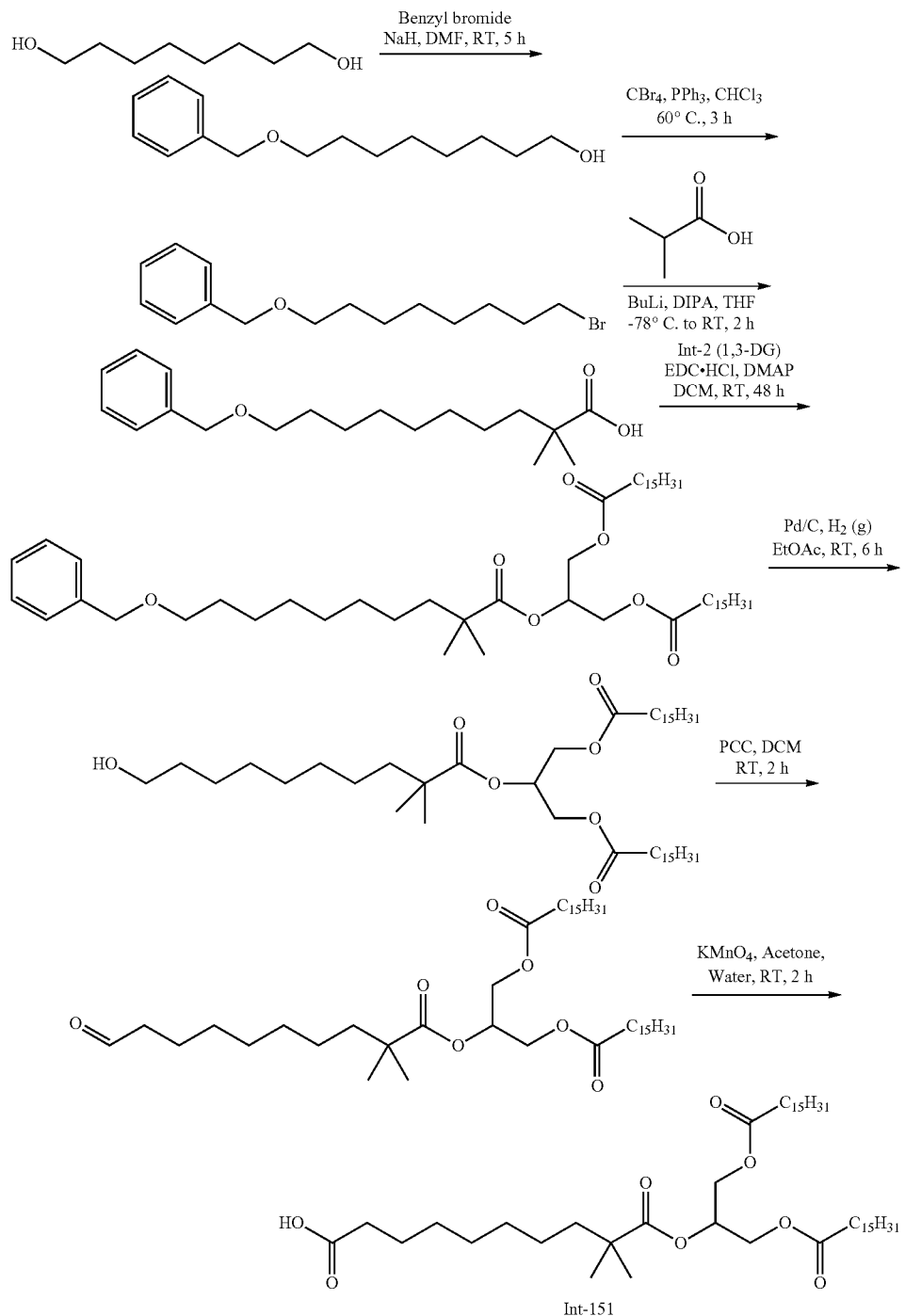

Intermediate C10ααMe-acid-2-TG (Int-151) was prepared from octane-1,8-diol as shown in Scheme 40, using methods described above. $^1$H NMR (400 MHz, CDCl$_3$) δ 5.28 (m, 1H), 4.34 (dd, J=11.8, 4.2 Hz, 2H), 4.18 (dd, J=11.8, 6.1 Hz, 2H), 2.36 (dt, J=17.1, 7.5 Hz, 4H), 1.65-1.51 (m, 8H), 1.29 (s, 58H), 1.19 (s, 6H), 0.91 (t, J=6.5 Hz, 6H); $^{13}$C NMR (101 MHz, CDCl$_3$) δ 179.57 (1C), 177.49 (1C), 173.33 (2C), 68.94 (1C), 62.16 (1C), 42.40 (1C), 40.63 (1C), 34.24 (2C), 31.96 (2C), 30.06-29.15 (26C), 25.07 (1C), 24.89 (2C), 24.81 (1C), 24.65 (1C), 22.73 (2C), 14.16 (2C); MS (ESI, −ve) m/z: 780.08 (M−1); MS (ESI, +ve) m/z: 799.16 (M+18).

C12ααMe-acid-2-TG (Int-167):

Intermediate C12ααMe-acid-2-TG (Int-167) was prepared using the procedures shown in Scheme 40, using decane-1,10-diol in place of octane-1,8-diol.

Int-167
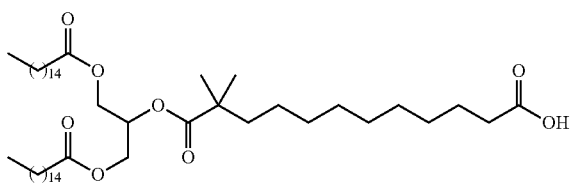
$^1$H NMR (400 MHz, CDCl$_3$) δ 5.30 (m, 1H), 4.33 (dd, J=11.8, 4.3 Hz, 2H), 4.18 (dd, J=11.9, 6.1 Hz, 2H), 2.36 (dt, J=18.5, 7.5 Hz, 6H), 1.73-1.58 (m, 8H), 1.53 (dd, J=9.8, 5.6 Hz, 2H), 1.29 (s, 58H), 1.19 (s, 6H), 0.92 (t, J=6.6 Hz, 6H); $^{13}$C NMR (101 MHz, CDCl$_3$) δ 179.79 (1C), 177.07 (1C), 173.31 (2C), 68.76 (1C), 62.15 (2C), 42.39 (1C), 40.54 (1C), 34.06 (2C), 34.02 (1C), 31.94 (3C), 30.17 (1C), 29.72-29.06 (24C), 25.05 (2C), 24.86 (2C), 24.67 (1C), 22.71 (2C), 14.15 (2C). HPLC (ELSD): 15.32 min, 100% purity. MS (ESI, −ve) m/z: 807.04 (M−1). MS (ESI, +ve) m/z: 826.6 (M+18).
C11αMe-acid-2-TG (Int-152):
Scheme 41. Synthesis of Int-152.
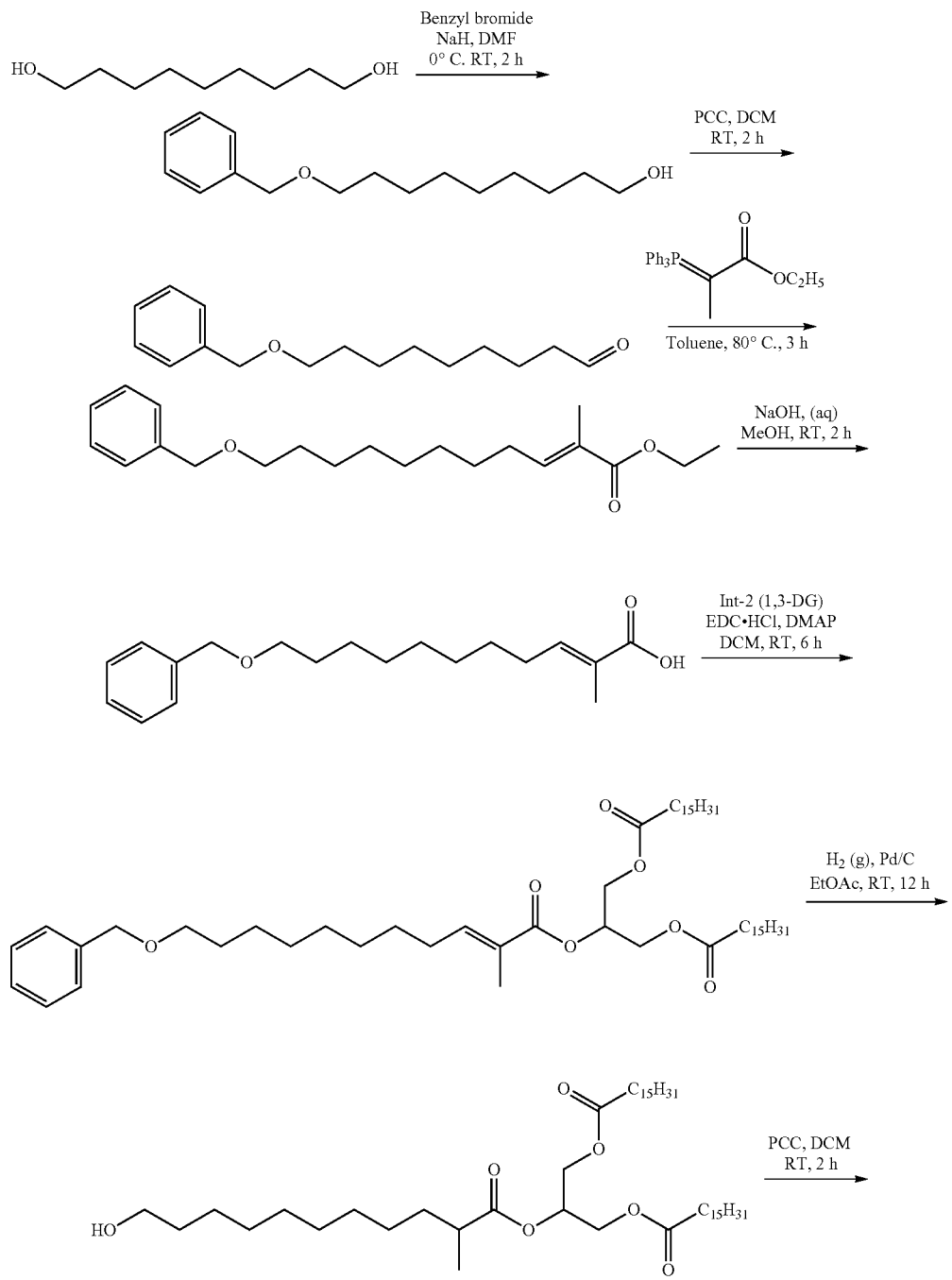

-continued

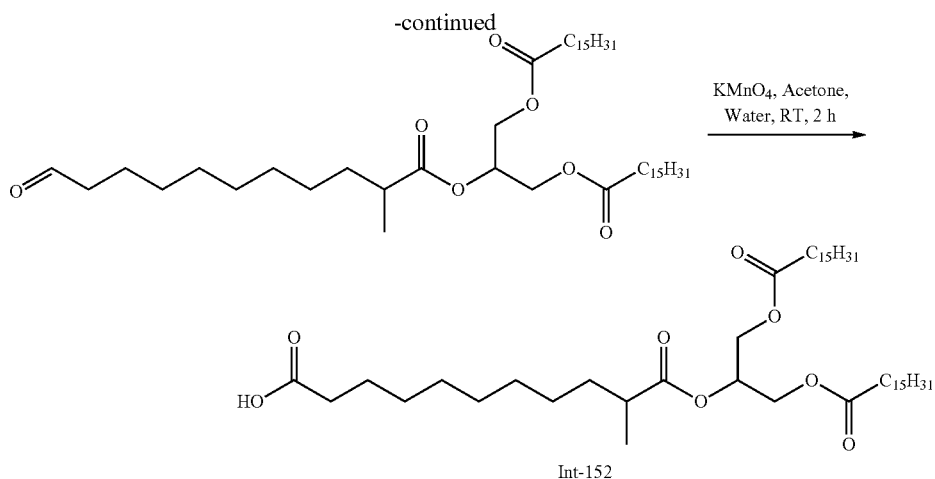

Int-152

Intermediate C11αMe-acid-2-TG (Int-152) was prepared from nonane-1,9-diol as shown in Scheme 41, using methods described above. $^1$H NMR (400 MHz, CDCl$_3$) δ 5.32 (m, 1H), 4.33 (dd, J=11.8, 3.7 Hz, 2H), 4.19 (dd, J=11.9, 6.0 Hz, 2H), 2.48 (h, J=6.9 Hz, 1H), 2.37 (dt, J=15.5, 7.5 Hz, 6H), 1.71-1.58 (m, 8H), 1.29 (m, 58H), 1.18 (d, J=6.9 Hz, 3H), 0.91 (t, J=6.5 Hz, 6H); $^{13}$C NMR (101 MHz, CDCl$_3$) δ 179.64 (1C), 175.92 (1C), 173.34 (2C), 68.73 (1C), 62.18 (2C), 39.54 (1C), 34.08 (2C), 34.01 (1C), 33.63 (1C), 31.96 (2C), 29.73-29.07 (23C), 27.14 (1C), 24.88 (2C), 24.68 (1C), 22.73 (3C), 17.05 (1C), 14.16 (2C); MS (ESI, −ve) m/z: 779.0 (M−1); MS (ESI, +ve) m/z: 798.0 (M+18).

C12αMe-acid-TG (Int-156):

Using similar methods to those used for Int-152, Int-156 was prepared.

INT-156

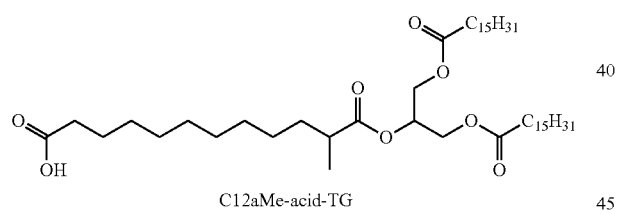

C12aMe-acid-TG $^1$H NMR (400 MHz, CDCl$_3$) δ 5.34-5.29 (m, 1H), 4.34 (dd, J=11.8, 3.8 Hz, 2H), 4.19 (dd, J=11.8, 6.0 Hz, 2H), 2.50-2.45 (m, 1H), 2.40-2.32 (m, 6H), 1.69-1.64 (m, 8H), 1.29 (s, 60H), 1.18 (d, J=6.9 Hz, 3H), 0.92 (t, J=6.7 Hz, 6H); $^{13}$C NMR (101 MHz, CDCl$_3$) δ 179.38 (1C), 175.93 (1C), 173.33 (2C), 68.69 (1C), 62.17 (2C), 39.53 (1C), 34.06 (2C), 33.94 (1C), 33.63 (1C), 31.94 (2C), 29.71-29.05 (23C), 27.15 (1C), 24.86 (2C), 24.67 (1C), 22.71 (3C), 17.03 (1C), 14.14 (3C). HPLC (ELSD): 10.78 min, 100% purity. MASS (ESI, −ve) m/z: 794.0 (M−1).

C10αMe-alcohol-2-TG (Int-157) and C10αMe-acid-2-TG (Int-118):

Scheme 42. Synthesis of Int-157 and Int-188.

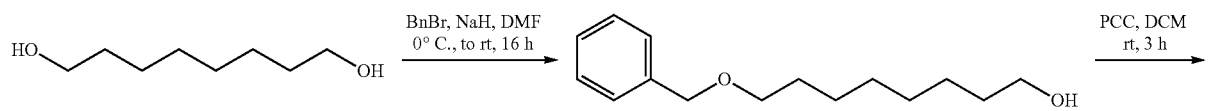

-continued
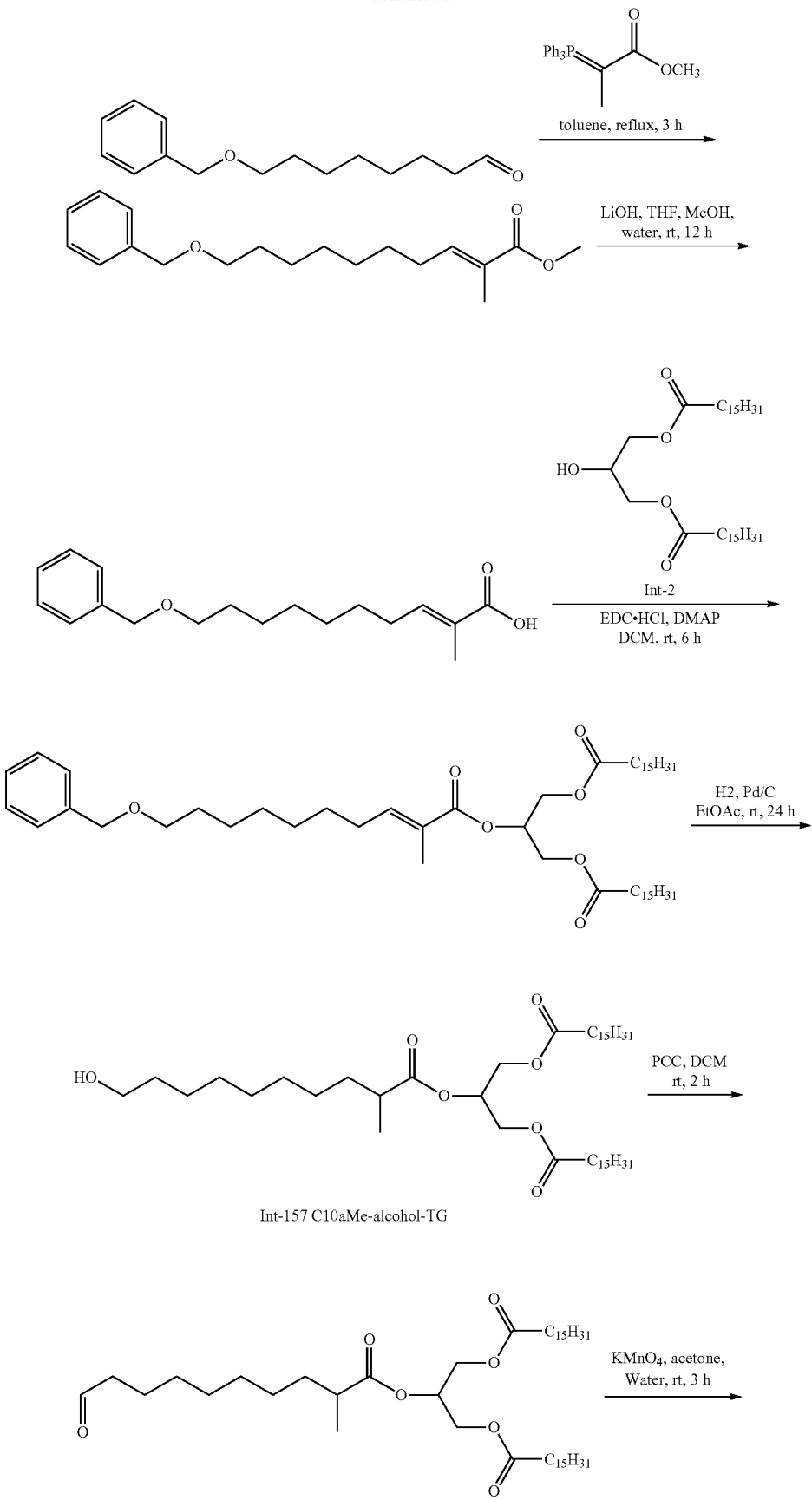

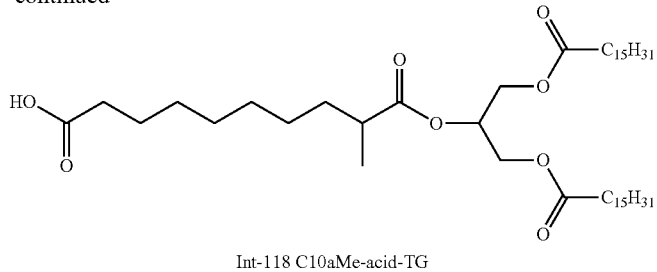

Int-118 C10αMe-acid-TG

Intermediates C10αMe-alcohol-2-TG (Int-157) and C10αMe-acid-2-TG (Int-118) were prepared from octane-1,8-diol as shown in Scheme 42, using methods described above.

C10αMe-alcohol-2-TG (Int-157) $^1$H NMR (400 MHz, CDCl3) δ 5.30 (t, J=4.4 Hz, 1H), 4.31 (dt, J=11.9, 4.0 Hz, 2H), 4.17 (dd, J=11.9, 6.1 Hz, 2H), 3.66 (q, J=6.2 Hz, 2H), 2.47 (p, J=6.9 Hz, 1H), 2.33 (t, J=7.6 Hz, 4H), 1.61 (d, J=14.4 Hz, 8H), 1.30 (s, 59H), 1.16 (d, J=7.0 Hz, 3H), 0.90 (t, J=6.7 Hz, 6H); $^{13}$C NMR (101 MHz, CDCl3) δ 175.9 (1C), 173.3 (2C), 68.7 (1C), 62.0 (1C), 62.1 (2C), 39.5 (1C), 34.1 (2C), 33.6 (1C), 32.8 (1C), 31.9 (3C), 29.7-29.1 (20), 27.1 (1C), 25.7 (1C), 24.9 (2C), 22.7 (3C), 17.0 (1C), 14.1 (3C); MS (ESI, +ve) m/z: 753.9 (M+1), 771.0 (M+18).

C10αMe-acid-2-TG (Int-118) $^1$H NMR (400 MHz, CDCl$_3$) δ 5.31 (s, 1H), 4.33 (dd, J=8.4, 4.4 Hz, 2H), 4.19 (dd, J=11.8, 5.9 Hz, 2H), 2.47 (m, 1H), 2.37 (dt, J=15.6, 7.4 Hz, 6H), 1.65 (s, 7H), 1.31 (d, J=13.3 Hz, 58H), 1.18 (d, J=6.9 Hz, 3H), 0.92 (t, J=6.6 Hz, 6H); $^{13}$C NMR (101 MHz, CDCl$_3$) δ 179.73 (1C), 175.87 (1C), 173.31 (2C), 68.70 (1C), 62.13 (1C), 39.50 (1C), 34.04 (3C), 33.57 (1C), 31.93 (4C), 29.71-29.01 (18C), 27.07 (1C), 24.85 (3C), 24.62 (1C), 22.70 (4C), 17.03 (1C), 14.14 (3C). MASS (ESI, −ve) m/z: 766.0 (M−1). (ESI, +ve) m/z: 785.0 (M+18).

C5(carbonate)-chloride-2-TG (Int-85):

Scheme 43. Synthesis of Int-85.

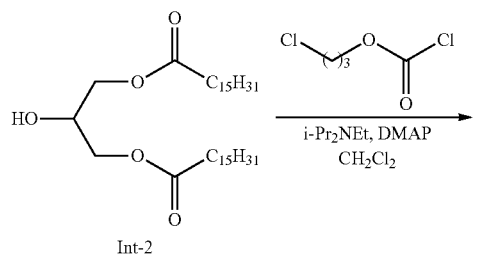

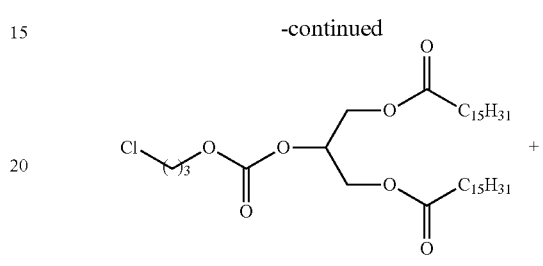

Int-85

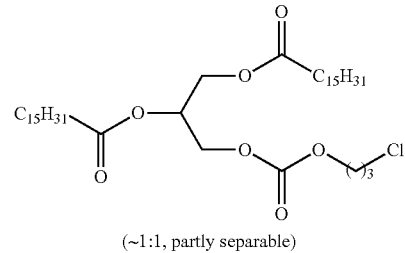

(~1:1, partly separable)

3-Chloropropyl chloroformate (20.3 μL, 0.169 mmol) and N,N-diethylisopropylamine (DIPEA, 54.2 μL, 0.316 mmol) were added to 1,3-diglyceride Int-2 (60.0 mg, 0.105 mmol) and DMAP (2.6 mg, 0.0211 mmol) in CH$_2$Cl$_2$ (3 mL) at 0° C. and the mixture stirred at RT for 18 hours. The reaction was diluted with CH$_2$Cl$_2$ (30 mL) and the organic phase washed with water, sat. aq. NaHCO$_3$ and brine (25 mL each), dried (MgSO$_4$) and concentrated under reduced pressure to give the crude product. Silica gel chromatography (4% to 5.5% ethyl acetate/hexanes) gave a mixture of chloropropyl carbonates Int-85 and a regioisomer (ca. 1:1 ratio, 49.8 mg, 69%) as a colorless solid. $^1$H NMR (400 MHz, CDCl$_3$) δ 5.28 (m, 1H), 4.38-4.13 (m, 6H), 3.63 (t, J=6.3 Hz, 2H), 2.35-2.29 (m, 4H), 2.18-2.10 (m, 2H), 1.66-1.56 (m, 4H), 1.36-1.19 (m, 48H), 0.88 (t, J=6.9 Hz, 6H). Note: The $^1$H NMR spectrum was acquired using a sample enriched in target carbonate Int-85.

DMPHB-C12α'βMe-bromide-2-TG (Int-135):

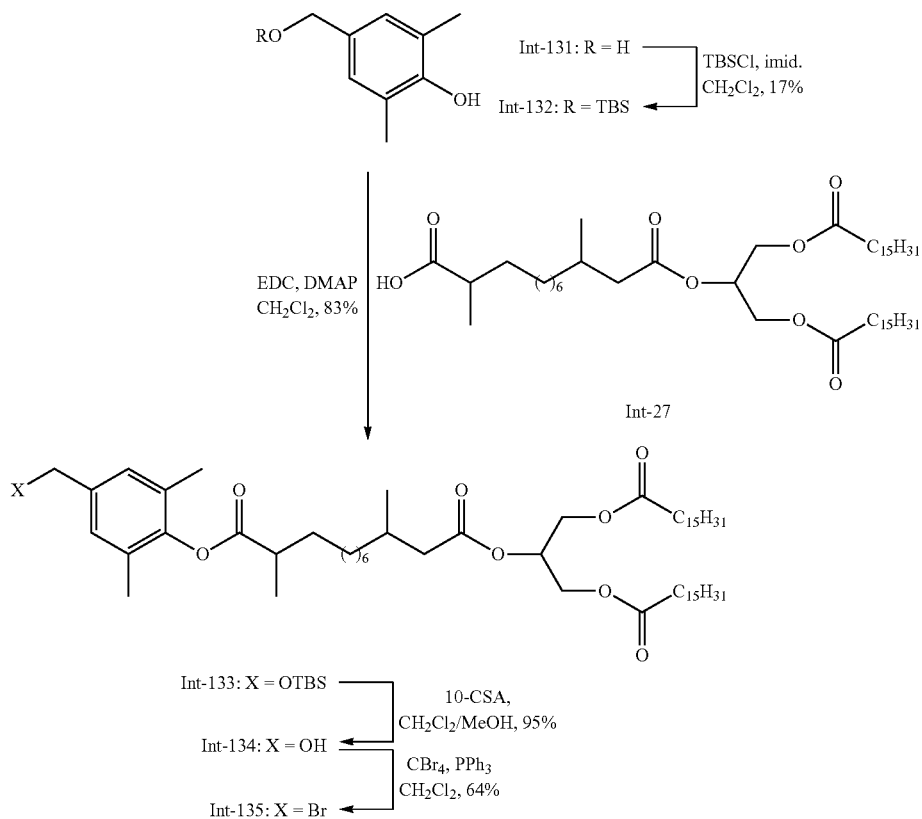

Scheme 44. Synthesis of Int-135.

Sodium borohydride (378 mg, 9.99 mmol) was added in 4-5 portions to a solution of 4-hydroxy-3,5-dimethylbenzaldehyde (500 mg, 3.33 mmol) in methanol (8 mL) at 0° C. and the resulting mixture stirred at 0° C. for 45 minutes. The reaction mixture was acidified to pH 2 by the addition of 1 M HCl (10-15 mL) and the organic solvent removed under reduced pressure. The aqueous residue was extracted with $CH_2Cl_2$ (2×20 mL) and the combined organic extracts dried ($MgSO_4$) and concentrated under reduced pressure to give crude diol Int-131 (600 mg), which was used in the next step without further purification.

Imidazole (161 mg, 2.37 mmol) and tert-butyl(chloro)dimethylsilane (TBSCl, 297 mg, 1.97 mmol) were added to a solution of Int-131 (300 mg of crude material described above) in $CH_2Cl_2$ (8 mL) at 0° C. and the mixture stirred at RT for 45 minutes. The reaction was diluted with $CH_2Cl_2$ (40 mL), washed with water and brine (40 mL each), dried ($MgSO_4$) and concentrated under reduced pressure to give the crude product. Purification by silica gel chromatography (12.5% to 17.5% ethyl acetate/hexanes) gave TBS ether Int-132 (90.5 mg, 17%) as a colorless oil. $^1H$ NMR (401 MHz, $CDCl_3$) δ 6.93 (s, 2H), 4.60 (s, 2H), 2.24 (s, 6H), 0.93 (s, 9H), 0.09 (s, 6H).

4-(Dimethylamino)pyridine (DMAP, 11.5 mg, 0.0938 mmol) and EDC·HCl (36.0 mg, 0.188 mmol) were added to a solution of Int-27 (79.7 mg, 0.0985 mmol) and phenol Int-132 (25.0 mg, 0.0938 mmol) in $CH_2Cl_2$ (4 mL) and the mixture stirred at RT for about three days. The reaction was diluted with $CH_2Cl_2$ (10 mL), silica gel was added and the mixture concentrated under reduced pressure. Purification by silica gel chromatography (8% to 10% ethyl acetate/hexanes) gave Int-133 (82.8 mg, 83%) as a colorless oil. $^1H$ NMR (401 MHz, $CDCl_3$) δ 7.00 (s, 2H), 5.28 (m, 1H), 4.65 (s, 2H), 4.29 (dd, J=11.9, 3.9 Hz, 2H), 4.14 (dd, J=11.8, 5.9 Hz, 2H), 2.72 (m, 1H), 2.33 (dd, J=14.6, 6.0 Hz, 1H), 2.30 (t, J=7.5 Hz, 4H), 2.13 (s, 6H), 2.12 (dd, J=14.6, 8.4 Hz, 1H), 1.97-1.81 (m, 2H), 1.66-1.48 (m, 5H), 1.34 (d, J=7.0 Hz, 3H), 1.46-1.13 (m, 60H), 0.94 (s, 9H), 0.93 (d, J=6.9 Hz, 3H), 0.88 (t, J=6.9 Hz, 6H), 0.09 (s, 6H); $^{13}C$ NMR (101 MHz, $CDCl_3$) δ 174.6 (C), 173.4 (2C; C), 172.4 (C), 147.1 (C), 138.7 (C), 129.9 (2C; C), 126.4 (2C; CH), 68.9 (CH), 64.7 ($CH_2$), 62.3 (2C; $CH_2$), 41.8 ($CH_2$), 39.9 (CH), 36.8 ($CH_2$), 34.2 (2C; $CH_2$), 33.8 ($CH_2$), 32.1 (2C; $CH_2$), 30.5 (CH), 29.87 ($CH_2$), 29.82 (6C; $CH_2$), 29.79 (4C; $CH_2$), 29.75 (2C; $CH_2$), 29.67 ($CH_2$), 29.65 ($CH_2$), 29.60 (2C; $CH_2$), 29.5 (2C; $CH_2$), 29.4 (2C; $CH_2$), 29.2 (2C; $CH_2$), 27.5 ($CH_2$), 27.0 ($CH_2$), 26.1 (3C; $CH_3$), 25.0 (2C; $CH_2$), 22.8 (2C; $CH_2$), 19.7 ($CH_3$), 17.6 ($CH_3$), 16.6 (2C; $CH_3$), 14.2 (2C; $CH_3$), −5.1 (2C; $CH_3$).

10-Camphorsulfonic acid (3.6 mg, 15.1 μmol) was added to Int-133 (80.0 mg, 75.6 μmol) in $CH_2Cl_2$ (1 mL) and MeOH (1 mL) and the mixture stirred at RT for one hour. The reaction was diluted with $CH_2Cl_2$ (30 mL), washed with sat. aq. $NaHCO_3$ and brine (25 mL each), dried ($MgSO_4$) and concentrated under reduced pressure to give the crude product. Purification by silica gel chromatography (20% ethyl acetate/hexanes) gave alcohol Int-134 (67.7 mg, 95%) as a colorless oil. $^1H$ NMR (401 MHz, $CDCl_3$) δ 7.05 (s, 2H), 5.27 (m, 1H), 4.58 (s, 2H), 4.28 (dd, J=11.9, 4.3 Hz, 2H), 4.13 (dd, J=11.9, 6.0 Hz, 2H), 2.73 (m, 1H), 2.32 (dd, J=14.6, 6.0 Hz, 1H), 2.30 (t, J=7.5 Hz, 4H), 2.13 (s, 6H), 2.11 (dd, J=14.7, 8.2 Hz, 1H), 1.98-1.80 (m, 2H), 1.64-1.49 (m, 5H), 1.34 (d, J=7.0 Hz, 3H), 1.46-1.17 (m, 60H), 0.93 (d, J=6.6 Hz, 3H), 0.87 (t, J=6.8 Hz, 6H); $^{13}$C NMR (101 MHz, CDCl$_3$) δ 174.6 (C), 173.4 (2C; C), 172.4 (C), 147.7 (C), 138.4 (C), 130.4 (2C; C), 127.4 (2C; CH), 68.9 (CH), 65.0 (CH$_2$), 62.3 (2C; CH$_2$), 41.8 (CH$_2$), 39.9 (CH), 36.8 (CH$_2$), 34.2 (2C; CH$_2$), 33.8 (CH$_2$), 32.0 (2C; CH$_2$), 30.5 (CH), 29.83 (CH$_2$), 29.81 (6C; CH$_2$), 29.77 (4C; CH$_2$), 29.74 (2C; CH$_2$), 29.63 (CH$_2$), 29.62 (CH$_2$), 29.59 (2C; CH$_2$), 29.5 (2C; CH$_2$), 29.4 (2C; CH$_2$), 29.2 (2C; CH$_2$), 27.5 (CH$_2$), 27.0 (CH$_2$), 25.0 (2C; CH$_2$), 22.8 (2C; CH$_2$), 19.7 (CH$_3$), 17.5 (CH$_3$), 16.6 (2C; CH$_3$), 14.2 (2C; CH$_3$).

Carbon tetrabromide (CBr$_4$, 28.6 mg, 86.4 μmol) and triphenylphosphine (PPh$_3$, 27.2 mg, 104 μmol) were added to alcohol Int-134 (32.6 mg, 34.6 μmol) in CH$_2$Cl$_2$ (2 mL) at 0° C. and the reaction stirred at RT for 1.5 hours. The reaction was diluted with CH$_2$Cl$_2$ (5 mL), silica gel was added, and the solvent removed under reduced pressure. Purification by silica gel chromatography (5% to 6% ethyl acetate/hexanes) gave bromide Int-135 (22.2 mg, 64%) as a colorless oil. $^1$H NMR (401 MHz, CDCl$_3$) δ 7.09 (s, 2H), 5.27 (m, 1H), 4.42 (s, 2H), 4.29 (dd, J=11.9, 3.8 Hz, 2H), 4.14 (dd, J=11.9, 6.0 Hz, 2H), 2.73 (m, 1H), 2.33 (dd, J=14.8, 5.8 Hz, 1H), 2.30 (t, J=7.5 Hz, 4H), 2.123 (s, 6H), 2.118 (dd, J=14.6, 8.4 Hz, 1H), 1.97-1.80 (m, 2H), 1.65-1.48 (m, 5H), 1.34 (d, J=7.0 Hz, 3H), 1.46-1.14 (m, 60H), 0.93 (d, J=6.6 Hz, 3H), 0.88 (t, J=6.9 Hz, 6H); $^{13}$C NMR (101 MHz, CDCl$_3$) δ 174.4 (C), 173.4 (2C; C), 172.5 (C), 148.4 (C), 135.1 (C), 130.9 (2C; C), 129.5 (2C; CH), 69.0 (CH), 62.3 (2C; CH$_2$), 41.8 (CH$_2$), 39.9 (CH), 36.8 (CH$_2$), 34.2 (2C; CH$_2$), 33.8 (CH$_2$), 33.3 (CH$_2$), 32.1 (2C; CH$_2$), 30.5 (CH), 29.88 (CH$_2$), 29.84 (6C; CH$_2$), 29.80 (4C; CH$_2$), 29.77 (2C; CH$_2$), 29.67 (CH$_2$), 29.66 (CH$_2$), 29.62 (2C; CH$_2$), 29.5 (2C; CH$_2$), 29.4 (2C; CH$_2$), 29.3 (2C; CH$_2$), 27.5 (CH$_2$), 27.1 (CH$_2$), 25.0 (2C; CH$_2$), 22.8 (2C; CH$_2$), 19.7 (CH$_3$), 17.6 (CH$_3$), 16.6 (2C; CH$_3$), 14.3 (2C; CH$_3$).

PHB-C12'βMe-bromide-2-TG (Int-140):

Using similar methods, Int-140 was prepared from 4-(((tert-butyldimethylsilyl)oxy)methyl)phenol (a known compound that may be prepared as described in, e.g., Smith, J. H. et al. *Angew. Chem. Int. Ed.* 2011, 50, 5075-5080):

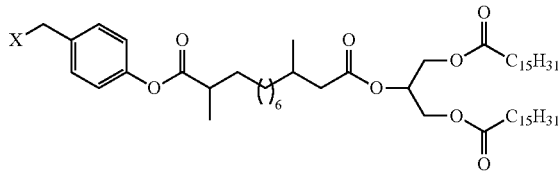

Int-138: X = OTBS
Int-139: X = OH
Int-140: X = Br 4-(Dimethylamino)pyridine (DMAP, 7.7 mg, 0.0629 mmol) and EDC·HCl (24.1 mg, 0.126 mmol) were added to a solution of Int-27 (56.0 mg, 0.0692 mmol) and 4-(((tert-butyldimethylsilyl)oxy)methyl)phenol (15.0 mg, 0.0629 mmol) in CH$_2$Cl$_2$ (1.5 mL) and the mixture stirred at RT for 19 hours. The reaction was diluted with CH$_2$Cl$_2$ (5 mL), silica gel was added, and the mixture was concentrated under reduced pressure. Purification by silica gel chromatography (7.5% to 10% ethyl acetate/hexanes) gave Int-138 (31.0 mg, 48%) as a colorless oil. $^1$H NMR (401 MHz, CDCl$_3$) δ 7.34-7.29 (m, 2H), 7.04-6.99 (m, 2H), 5.28 (m, 1H), 4.72 (s, 2H), 4.29 (dd, J=11.9, 3.9 Hz, 2H), 4.14 (dd, J=11.9, 5.8 Hz, 2H), 2.66 (m, 1H), 2.33 (dd, J=14.7, 8.3 Hz, 1H), 2.30 (t, J=7.5 Hz, 4H), 2.12 (dd, J=14.7, 8.3 Hz, 1H), 1.94 (m, 1H), 1.80 (m, 1H), 1.66-1.48 (m, 6H), 1.45-1.15 (m, 59H), 1.28 (d, J=6.9 Hz, 3H), 0.94 (s, 9H), 0.88 (d, J=6.6 Hz, 3H), 0.88 (t, J=6.8 Hz, 6H), 0.09 (s, 6H); $^{13}$C NMR (101 MHz, CDCl$_3$) δ 175.5 (C), 173.4 (2C; C), 172.5 (C), 149.8 (C), 139.0 (C), 127.1 (2C; CH), 121.4 (2C; CH), 69.0 (CH), 64.6 (CH$_2$), 62.3 (2C; CH$_2$), 41.8 (CH$_2$), 39.8 (CH), 36.8 (CH$_2$), 34.2 (2C; CH$_2$), 33.9 (CH$_2$), 32.1 (2C; CH$_2$), 30.5 (CH), 29.89 (CH$_2$), 29.84 (6C; CH$_2$), 29.80 (4C; CH$_2$), 29.77 (2C; CH$_2$), 29.69 (CH$_2$), 29.67 (CH$_2$), 29.62 (2C; CH$_2$), 29.5 (2C; CH$_2$), 29.4 (2C; CH$_2$), 29.3 (2C; CH$_2$), 27.4 (CH$_2$), 27.1 (CH$_2$), 26.1 (3C; CH$_3$), 25.0 (2C; CH$_2$), 22.8 (2C; CH$_2$), 19.7 (CH$_3$), 17.2 (CH$_3$), 14.3 (2C; CH$_3$), -5.1 (2C; CH$_3$); ESI-HRMS: Calcd. for C$_{62}$H$_{112}$NaO$_9$Si [M+Na+] 1051.7968; Found 1051.7962.

10-Camphorsulfonic acid (1.4 mg, 6.0 ∝mol) was added to TBS ether Int-138 (31.0 mg, 30.1 ∝mol) in CH$_2$Cl$_2$ (0.6 mL) and MeOH (0.6 mL) and the mixture stirred at RT for one hour. The reaction was diluted with CH$_2$Cl$_2$ (20 mL), washed with sat. aq. NaHCO$_3$ and brine (20 mL each), dried (MgSO$_4$), and concentrated under reduced pressure to give the crude product. Purification by silica gel chromatography (15% to 25% ethyl acetate/hexanes) gave alcohol Int-139 (22.0 mg, 80%) as a colorless oil. $^1$H NMR (401 MHz, CDCl$_3$) δ 7.41-7.34 (m, 2H), 7.08-7.03 (m, 2H), 5.27 (m, 1H), 4.68 (s, 2H), 4.283/4.281 (each dd, J=11.8, 4.3 Hz, 2H), 4.14 (dd, J=11.8, 6.0 Hz, 2H), 2.67 (m, 1H), 2.32 (dd, J=14.7, 5.8 Hz, 1H), 2.30 (t, J=7.6 Hz, 1H), 2.11 (dd, J=14.7, 8.3 Hz, 1H), 1.93 (m, 1H), 1.80 (m, 1H), 1.70 (br s, 1H), 1.65-1.49 (m, 5H), 1.45-1.16 (m, 63H), 0.93 (d, J=6.6 Hz, 3H), 0.88 (t, J=6.9 Hz, 6H); $^{13}$C NMR (101 MHz, CDCl$_3$) δ 175.5 (C), 173.5 (2C; C), 172.5 (C), 150.4 (C), 138.5 (C), 128.2 (2C; CH), 121.8 (2C; CH), 69.0 (CH), 64.9 (CH$_2$), 62.3 (2C; CH$_2$), 41.8 (CH$_2$), 39.8 (CH), 36.8 (CH$_2$), 34.2 (2C; CH$_2$), 33.9 (CH$_2$), 32.1 (2C; CH$_2$), 30.5 (CH), 29.84 (7C; CH$_2$), 29.80 (4C; CH$_2$), 29.77 (2C; CH$_2$), 29.6 (4C; CH$_2$), 29.5 (2C; CH$_2$), 29.4 (2C; CH$_2$), 29.3 (2C; CH$_2$), 27.4 (CH$_2$), 27.0 (CH$_2$), 25.0 (2C; CH$_2$), 22.8 (2C; CH$_2$), 19.7 (CH$_3$), 17.2 (CH$_3$), 14.3 (2C; CH$_3$); ESI-HRMS: Calcd. for C$_{56}$H$_{98}$NaO$_9$ [M+Na$^+$] 937.7103; Found 937.7136.

Carbon tetrabromide (CBr$_4$, 15.0 mg, 58.7 μmol) and triphenylphosphine (PPh$_3$, 18.5 mg, 70.5 μmol) were added to alcohol Int-139 (21.5 mg, 23.5 μmol) in CH$_2$Cl$_2$ (1.5 mL) at 0° C. and the reaction stirred at rt for one hour. The reaction was diluted with CH$_2$Cl$_2$ (5 mL), silica gel was added, and the solvent removed under reduced pressure. Purification by silica gel chromatography (2% to 6% ethyl acetate/hexanes) gave bromide Int-140 (20.1 mg, 87%) as a colorless oil. $^1$H NMR (401 MHz, CDCl$_3$) δ 7.42-7.37 (m, 2H), 7.06-7.02 (m, 2H), 5.27 (m, 1H), 4.49 (s, 2H), 4.288/4.287 (each dd, J=11.8, 4.2 Hz, 2H), 4.14 (dd, J=11.9, 6.0 Hz, 2H), 2.67 (m, 1H), 2.33 (dd, J=14.7, 5.8 Hz, 1H), 2.30 (t, J=7.5 Hz, 4H), 2.12 (dd, J=14.7, 8.3 Hz, 1H), 1.93 (m, 1H), 1.79 (m, 1H), 1.66-1.50 (m, 5H), 1.45-1.14 (m, 63H), 0.93 (d, J=6.6 Hz, 3H), 0.88 (t, J=6.9 Hz, 6H); $^{13}$C NMR (101 MHz, CDCl$_3$) δ 175.3 (C), 173.4 (2C; C), 172.5 (C), 150.9 (C), 135.3 (C), 130.3 (2C; CH), 122.1 (2C; CH), 69.0 (CH), 62.3 (2C; CH$_2$), 41.8 (CH$_2$), 39.8 (CH), 36.8 (CH$_2$), 34.2 (2C; CH$_2$), 33.9 (CH$_2$), 32.9 (CH$_2$), 32.1 (2C; CH$_2$), 30.5 (CH), 29.87 (CH$_2$), 29.84 (6C; CH$_2$), 29.81 (4C; CH$_2$), 29.77 (2C; CH$_2$), 29.66 (CH$_2$), 29.65 (CH$_2$), 29.62 (2C; CH$_2$), 29.5 (2C; CH$_2$), 29.4 (2C; CH$_2$), 29.3 (2C; CH$_2$), 27.4 (CH$_2$), 27.1 (CH$_2$), 25.0 (2C; CH$_2$), 22.8 (2C; CH$_2$), 19.7 (CH$_3$), 17.1 (CH$_3$), 14.3 (2C; CH$_3$).

PHB-OH-C10-2-TG (Int-272):

Using similar methods as described for the synthesis of Int-139, compound Int-272 was prepared from 4-(((tert-butyldimethylsilyl)oxy)methyl)phenol and Int-9:

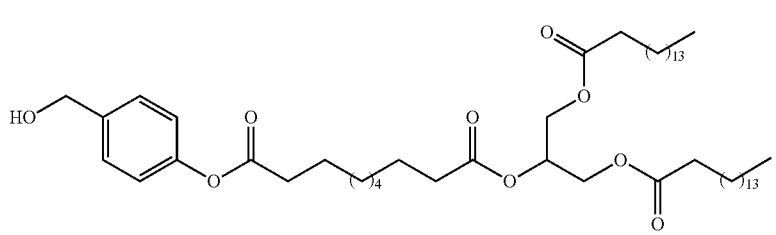

Int-272

¹H NMR (400 MHz, CDCl₃) δ 7.41-7.32 (m, 2H), 7.10-7.01 (m, 2H), 5.25 (m, 1H), 4.67 (s, 2H), 4.28 (dd, J=11.9, 4.3 Hz, 2H), 4.14 (dd, J=11.9, 5.9 Hz, 2H), 2.54 (t, J=7.5 Hz, 2H), 2.31 (t, J=7.5 Hz, 2H), 2.30 (t, J=7.5 Hz, 4H), 1.89 (br s, 1H), 1.78-1.70 (m, 2H), 1.65-1.55 (m, 6H), 1.46-1.20 (m, 56H), 0.87 (t, J=6.9 Hz, 6H); ¹³C NMR (101 MHz, CDCl₃) δ 173.5 (2C; C), 173.0 (C), 172.4 (C), 150.2 (C), 138.6 (C), 128.2 (2C; CH), 121.8 (2C; CH), 69.0 (CH), 64.8 (CH₂), 62.2 (2C; CH₂), 34.5 (CH₂), 34.3 (CH₂), 34.2 (2C; CH₂), 32.1 (2C; CH₂), 29.82 (6C; CH₂), 29.78 (4C; CH₂), 29.75 (2C; CH₂), 29.6 (2C; CH₂), 29.5 (2C; CH₂), 29.4 (2C; CH₂), 29.23 (2C; CH₂), 29.19 (2C; CH₂), 29.15 (CH₂), 29.10 (CH₂), 25.0 (3C; CH₂), 24.9 (CH₂), 22.8 (2C; CH₂), 14.3 (2C; CH₂).

DMPHB-C10βMe-bromide-2-TG (Int-147):

Using similar methods as described for the synthesis of Int-135, compound Int-147 was prepared from Int-132 and Int-30:

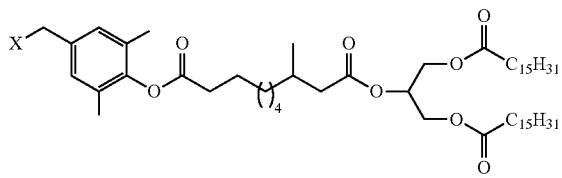

Int-145: X = OTBS
Int-146: X = OH
Int-147: X = Br 4-(Dimethylamino)pyridine (DMAP, 6.9 mg, 0.0563 mmol) and EDC·HCl (21.6 mg, 0.113 mmol) were added to a solution of acid-TG Int-30 (45.3 mg, 0.0591 mmol) and phenol Int-132 (15.0 mg, 0.0563 mmol) in CH₂Cl₂ (3 mL) and the mixture stirred at room temperature for three days. The reaction was diluted with CH₂Cl₂ (10 mL), silica gel was added, and the mixture concentrated under reduced pressure. Purification by silica gel chromatography (8% to 10% ethyl acetate/hexanes) gave ester Int-145 (46.6 mg, 81%) as a colorless oil. ¹H NMR (401 MHz, CDCl₃) δ 7.00 (s, 2H), 5.28 (m, 1H), 4.65 (s, 2H), 4.29 (dd, J=11.8, 4.1 Hz, 2H), 4.14 (dd, J=11.9, 6.0 Hz, 2H), 2.58 (t, J=7.6 Hz, 2H), 2.33 (dd, J=14.6, 6.0 Hz, 1H), 2.31 (t, J=7.5 Hz, 4H), 2.13 (s, 6H), 2.12 (dd, J=14.7, 8.2 Hz, 1H), 1.96 (m, 1H), 1.83-1.74 (m, 2H), 1.69-1.54 (m, 4H), 1.47-1.19 (m, 56H), 0.94 (s, 9H), 0.88 (d, J=6.2 Hz, 3H), 0.88 (t, J=6.8 Hz, 6H), 0.09 (s, 6H); ¹³C NMR (101 MHz, CDCl₃) δ 173.4 (2C; C), 172.4 (C), 171.7 (C), 147.1 (C), 138.8 (C), 129.9 (2C; C), 126.4 (2C; CH), 69.0 (CH), 64.7 (CH₂), 62.3 (2C; CH₂), 41.8 (CH₂), 36.8 (CH₂), 34.2 (3C; CH₂), 32.1 (2C; CH₂), 30.5 (CH), 29.84 (6C; CH₂), 29.80 (4C; CH₂), 29.76 (2C; CH₂), 29.61 (2C; CH₂), 29.55 (CH₂), 29.50 (2C; CH₂), 29.41 (2C; CH₂), 29.26 (2C; CH₂), 26.9 (CH₂), 26.1 (3C; CH₃), 25.3 (CH₂), 25.0 (2C; CH₂), 22.8 (2C; CH₂), 19.7 (CH₃), 16.6 (2C; CH₃), 14.3 (2C; CH₃), −5.1 (2C; CH₃); ESI-HRMS: calcd. for C₆₁H₁₁₀NaO₉Si [M+Na⁺] 1037.7811; found 1037.7815.

10-Camphorsulfonic acid (2.1 mg, 8.9 ∝mol) was added to TBS ether Int-145 (45.0 mg, 44.3 ∝mol) in CH₂Cl₂ (1 mL) and MeOH (1 mL) and the mixture stirred at room temperature for one hour. The reaction was diluted with CH₂Cl₂ (30 mL), washed with sat. aq. NaHCO₃ and brine (25 mL each), dried (MgSO₄) and concentrated under reduced pressure to give the crude product. Purification by silica gel chromatography (20% ethyl acetate/hexanes) gave alcohol Int-146 (30.4 mg, 76%) as a colorless oil. ¹H NMR (401 MHz, CDCl₃) δ 7.06 (s, 2H), 5.27 (m, 1H), 4.60 (s, 2H), 4.287/4.285 (each dd, J=11.8, 4.2 Hz, 2H), 4.14 (dd, J=11.9, 6.0 Hz, 2H), 2.59 (t, J=7.6 Hz, 2H), 2.33 (dd, J=14.6, 6.0 Hz, 1H), 2.30 (t, J=7.5 Hz, 4H), 2.14 (s, 6H), 2.12 (dd, J=14.7, 8.3 Hz, 1H), 1.95 (m, 1H), 1.84-1.73 (m, 2H), 1.69 (br s, 1H), 1.65-1.54 (m, 4H), 1.46-1.18 (m, 56H), 0.94 (d, J=6.6 Hz, 3H), 0.87 (t, J=6.8 Hz, 6H); ¹³C NMR (101 MHz, CDCl₃) δ 173.4 (2C; C), 172.4 (C), 171.6 (C), 147.7 (C), 138.4 (C), 130.4 (2C; C), 127.4 (2C; CH), 69.0 (CH), 65.1 (CH₂), 62.3 (2C; CH₂), 41.8 (CH₂), 36.7 (CH₂), 34.2 (2C; CH₂), 34.1 (CH₂), 32.1 (2C; CH₂), 30.4 (CH), 29.83 (6C; CH₂), 29.79 (4C; CH₂), 29.76 (2C; CH₂), 29.61 (2C; CH₂), 29.53 (CH₂), 29.50 (2C; CH₂), 29.40 (2C; CH₂), 29.39 (CH₂), 29.25 (2C; CH₂), 26.9 (CH₂), 25.2 (CH₂), 25.0 (2C; CH₂), 22.8 (2C; CH₂), 19.7 (CH₃), 16.5 (2C; CH₃), 14.3 (2C; CH₃); ESI-HRMS: calcd. for C₅₅H₉₆NaO₉ [M+Na⁺] 923.6947; found 923.6973.

Carbon tetrabromide (CBr₄, 26.7 mg, 80.4 ∝mol) and triphenylphosphine (PPh₃, 25.3 mg, 96.5 ∝mol) were added to alcohol Int-146 (29.0 mg, 32.2 ∝mol) in CH₂Cl₂ (1.5 mL) at 0° C. and the reaction stirred at room temperature for 50 minutes. The reaction was diluted with CH₂Cl₂ (5 mL), silica gel was added and the solvent was removed under reduced pressure. Purification by silica gel chromatography (6% to 10% ethyl acetate/hexanes) gave bromide Int-147 (23.6 mg, 76%) as a colorless oil; ¹H NMR (401 MHz, CDCl₃) δ 7.09 (s, 2H), 5.28 (m, 1H), 4.42 (s, 2H), 4.29 (dd, J=11.9, 4.3 Hz, 2H), 4.14 (dd, J=11.9, 6.0 Hz, 2H), 2.59 (t, J=7.6 Hz, 2H), 2.33 (dd, J=14.6, 6.0 Hz, 1H), 2.30 (t, J=7.5 Hz, 4H), 2.13 (dd, J=14.7, 8.3 Hz, 1H), 2.12 (s, 6H), 1.94 (m, 1H), 1.83-1.72 (m, 2H), 1.66-1.55 (m, 4H), 1.47-1.17 (m, 56H), 0.94 (d, J=6.6 Hz, 3H), 0.88 (t, J=6.9 Hz, 6H); ¹³C NMR (101 MHz, CDCl₃) δ 173.4 (2C; C), 172.4 (C), 171.4 (C), 148.4 (C), 135.2 (C), 130.8 (2C; C), 129.5 (2C; CH), 69.0 (CH), 62.3 (2C; CH₂), 41.8 (CH₂), 36.7 (CH₂), 34.2 (2C; CH₂), 34.1 (CH₂), 33.3 (CH₂), 32.1 (2C; CH₂), 30.4 (CH), 29.84 (6C; CH₂), 29.80 (4C; CH₂), 29.77 (2C; CH₂), 29.62 (2C; CH₂), 29.54 (CH₂), 29.51 (2C; CH₂), 29.41 (2C; CH₂), 29.39 (CH₂), 29.27 (2C; CH₂), 26.9 (CH₂), 25.2 (CH₂), 25.0 (2C; CH₂), 22.8 (2C; CH₂), 19.7 (CH₃), 16.5 (2C; CH₃), 14.3 (2C; CH₃).

DMPHB-OH-C15βMe-2-TG-oleate (Int-273):

Using similar methods as described for the synthesis of Int-146, but replacing CSA with TsOH in the deprotection step, compound Int-273 was prepared from Int-132 and Int-233:

Int-273

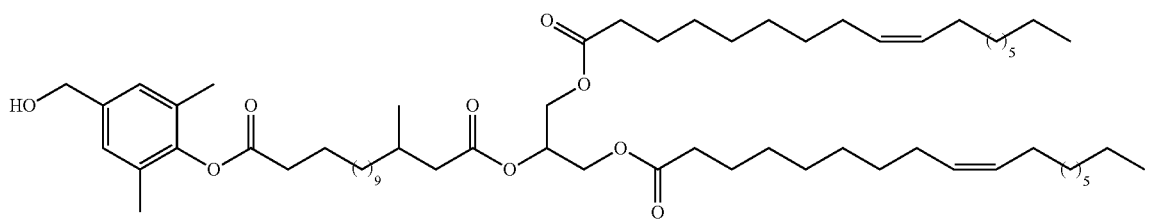

$^1$H NMR (401 MHz, CDCl$_3$) δ 7.04 (s, 2H), 5.39-5.23 (m, 5H), 4.57 (s, 2H), 4.28 (dd, J=11.9, 3.8 Hz, 2H), 4.13 (dd, J=11.8, 6.0 Hz, 2H), 2.58 (t, J=7.6 Hz, 2H), 2.32 (dd, J=14.7, 5.9 Hz, 1H), 2.29 (t, J=7.5 Hz, 4H), 2.12 (s, 6H), 2.11 (dd, J=14.7, 8.3 Hz, 1H), 2.05-1.88 (m, 9H), 1.82-1.73 (m, 2H), 1.66-1.54 (m, 4H), 1.48-1.12 (m, 58H), 0.92 (d, J=6.6 Hz, 3H), 0.87 (t, J=6.9 Hz, 6H); $^{13}$C NMR (101 MHz, CDCl$_3$) δ 173.3 (2C; C), 172.4 (C), 171.7 (C), 147.6 (C), 138.4 (C), 130.3 (2C; C), 130.1 (2C; CH), 129.8 (2C; CH), 127.3 (CH), 68.9 (CH), 64.9 (CH$_2$), 62.2 (2C; CH$_2$), 41.8 (CH$_2$), 36.8 (CH$_2$), 34.12 (CH$_2$), 34.09 (2C; CH$_2$), 32.0 (2C; CH$_2$), 30.4 (CH), 29.89 (CH$_2$), 29.84 (2C; CH$_2$), 29.78 (2C; CH$_2$), 29.75 (CH$_2$), 29.71 (CH$_2$), 29.68 (CH$_2$), 29.61 (2C; CH$_2$), 29.56 (CH$_2$), 29.40 (4C; CH$_2$), 29.35 (2C; CH$_2$), 29.25 (2C; CH$_2$), 29.19 (2C; CH$_2$), 29.16 (2C; CH$_2$), 27.30 (2C; CH$_2$), 27.25 (2C; CH$_2$), 27.0 (CH$_2$), 25.2 (CH$_2$), 24.9 (2C; CH$_2$), 22.8 (2C; CH$_2$), 19.6 (CH$_3$), 16.5 (2C; CH$_3$), 14.2 (2C; CH$_3$); ESI-HRMS: calcd. for C$_{64}$H$_{110}$O$_9$ [M+H$^+$] 1045.8042; found 1045.8027.

FSI5-C12α'αMe-acid-2-TG (Int-160):

then the reaction mixture was stirred at room temperature for 1 h. The reaction mixture was filtered through a celite bed, and washed with DCM (200 mL). The filtrate was concentrated under reduced pressure. The resulting crude material was purified by silica gel column chromatography, with the compound eluting at 10% ethyl acetate/hexane, to afford Int-158 (3.3 g, 50.6%) as a viscous oil. $^1$H NMR (400 MHz, CDCl$_3$) δ 7.38-7.30 (m, 2H), 6.98-6.89 (m, 2H), 5.10 (s, 2H), 3.86 (s, 3H), 3.44 (t, J=6.5 Hz, 2H), 2.41 (t, J=7.2 Hz, 2H), 1.99-1.87 (m, 2H), 1.83 (dddd, J=12.5, 9.5, 6.1, 3.4 Hz, 2H).

To a solution of Int-81 (0.50 g, 0.61 mmol) and Int-158 (0.27 g, 0.92 mmol) in DMF (5 mL) was added K$_2$CO$_3$ (3.1 mmol) followed by TBAI (0.228 g, 0.61 mmol) at room temperature, and then the reaction mixture was stirred at 100° C. for 18 h. The reaction mixture was poured into water (20 mL) and extracted with ethyl acetate (3×50 mL). The combined organic layers were dried over Na$_2$SO$_4$, filtered, and concentrated under reduced pressure. The resulting crude material was purified by silica gel column chroma- Scheme 45. Synthesis of Int-160.

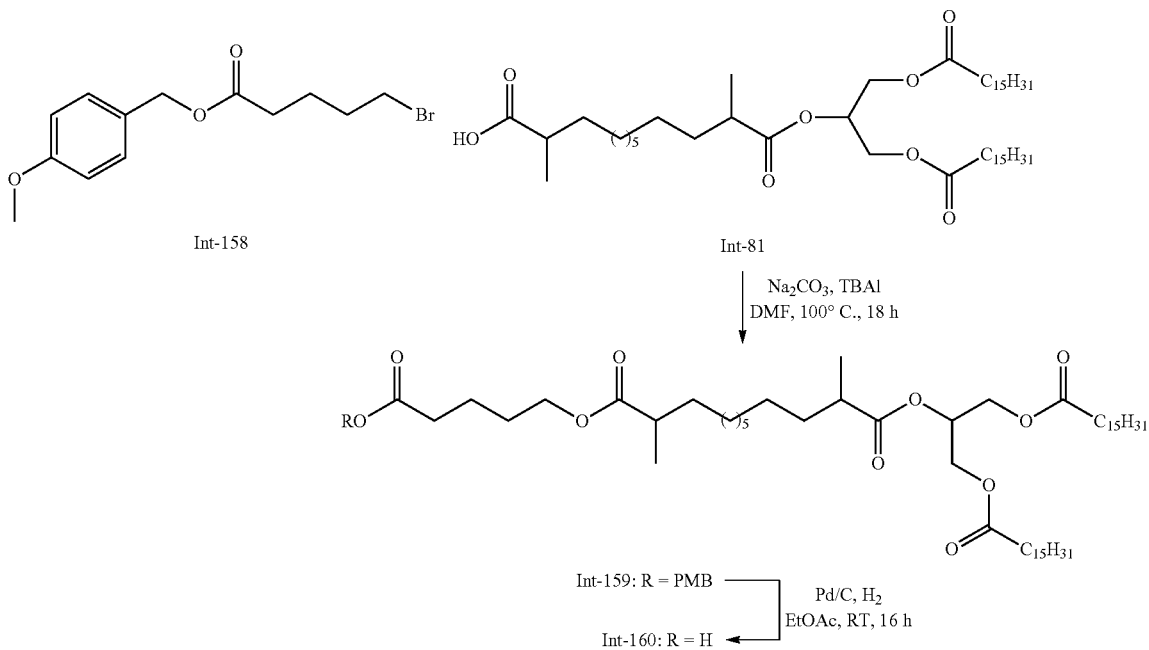

tography, with the compound eluting at 20% ethyl acetate/hexane, to afford Int-159 (400 mg, 63%) as a viscous oil. $^1$H NMR (400 MHz, CDCl$_3$) δ 7.39-7.30 (m, 2H), 6.98-6.89 (m, 2H), 5.31 (m, 1H), 5.09 (s, 2H), 4.33 (dd, J=11.9, 4.3 Hz, To a solution of 4-methoxybenzyl alcohol (3.0 g, 21.73 mmol) and 5-bromopentanoic acid (7.8 g, 43.47 mmol) in DCM (30 mL) at room temperature was added DMAP (5.3 g, 43.47 mmol) followed by DCC (8.0 g, 43.47 mmol), and 2H), 4.19 (dd, J=11.9, 5.9 Hz, 2H), 4.09 (t, J=6.0 Hz, 2H), 3.85 (s, 3H), 2.53-2.26 (m, 8H), 1.74-1.59 (m, 8H), 1.43-1.39 (m, 4H), 1.26 (m, 60H), 1.17 (dd, J=7.0, 4.8 Hz, 6H), 0.92 (t, J=6.7 Hz, 6H).

In an autoclave, to a solution of Int-159 (0.4 g, 0.38 mmol) in ethyl acetate (50 mL) was added 10% Pd/C (300 mg) under nitrogen atmosphere. The reaction mixture was stirred at room temperature for 16 h under 100 psi hydrogen pressure. The reaction mixture was filtered on a celite bed and washed with ethyl acetate (50 mL). The filtrate was concentrated under reduced pressure. The resulting crude material was purified by flash column chromatography using silica gel, eluting with 30% to 50% ethyl acetate/hexane, to afford Int-160 (300 mg, 85%) as a white solid. $^1$H NMR (400 MHz, CDCl$_3$) δ 5.31 (m, 1H), 4.33 (dd, J=11.9, 4.3 Hz, 2H), 4.19 (dd, J=11.9, 5.9 Hz, 2H), 4.14 (t, J=6.0 Hz, 2H), 2.53-2.26 (m, 8H), 1.74-1.59 (m, 8H), 1.43-1.39 (m, 4H), 1.26 (m, 60H), 1.17 (dd, J=7.0, 4.8 Hz, 6H), 0.92 (t, J=6.7 Hz, 6H).

FSI5-C5βMe-acid-2-TG (Int-162):

Using similar methods as described for the synthesis of Int-160, compound Int-162 was prepared from Int-158 and Int-4:

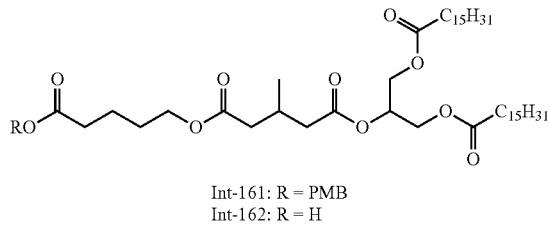

Int-161: R = PMB
Int-162: R = H

To a solution of Int-4 (0.50 g, 0.71 mmol) in DMF (5 mL) was added Na$_2$CO$_3$ (0.45 g, 4.31 mmol) followed by TBAI (0.130 g, 0.35 mmol) and Int-158 (0.21 g, 0.71 mmol) at room temperature, and then the reaction mixture was stirred at 100° C. for 18 h. The reaction mixture was poured into water (20 mL) and extracted with ethyl acetate (3×50 mL). The combined organic layers were dried over Na$_2$SO$_4$, filtered, and concentrated under reduced pressure. The resulting crude material was purified by silica gel column chromatography, with the compound eluting at 20% ethyl acetate/hexane, to afford Int-161 (500 mg, 76%) as a viscous oil. $^1$H NMR (400 MHz, CDCl$_3$) δ 7.37-7.30 (m, 2H), 6.96-6.89 (m, 2H), 5.31 (m, 1H), 5.09 (s, 2H), 4.34 (ddd, J=12.0, 4.4, 2.0 Hz, 2H), 4.25-4.07 (m, 4H), 3.85 (s, 3H), 2.56-2.21 (m, 8H), 1.81-1.58 (m, 8H), 1.29 (m, 51H), 1.05 (d, J=6.3 Hz, 3H), 0.92 (t, J=6.7 Hz, 6H).

In an autoclave, to a solution of Int-161 (0.5 g, 0.54 mmol) in ethyl acetate (10 mL) was added 10% Pd/C (150 mg) under nitrogen atmosphere. The reaction mixture was stirred at room temperature for 16 h under 100 psi hydrogen pressure. The reaction mixture was filtered on a celite bed and washed with ethyl acetate (50 mL). The filtrate was concentrated under reduced pressure. The resulting crude material was purified by flash column chromatography using silica gel, eluting with 30% to 50% ethyl acetate/hexane, to afford Int-162 (300 mg, 69%) as a white solid. $^1$H NMR (400 MHz, CDCl$_3$) δ 5.31 (p, J=5.0 Hz, 1H), 4.34 (dd, J=12.2, 4.3 Hz, 2H), 4.23-4.11 (m, 4H), 2.56-2.23 (m, 8H), 1.75 (h, J=3.1 Hz, 2H), 1.69-1.60 (m, 6H), 1.29 (m, 52H), 1.06 (d, J=6.3 Hz, 3H), 0.92 (t, J=6.7 Hz, 6H); MS (ESI, −ve) m/z: 796.52 (MH-1).

FSI5-C10-acid-2-TG (Int-164):

Using similar methods as described for the synthesis of Int-160 and Int-162, compound Int-164 was prepared from Int-158 and Int-9:

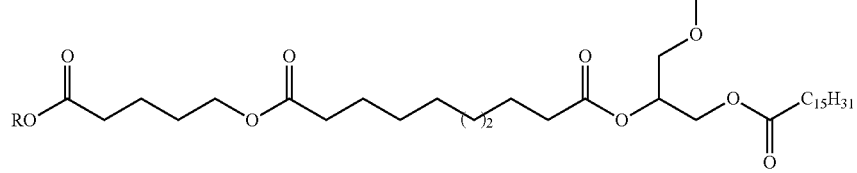

Int-163: R = PMB
Int-164: R = H

To a solution of Int-158 (0.520 g, 1.72 mmol) and Int-9 (1.0 g, 1.3 mmol) in DMF (5 mL) was added K$_2$CO$_3$ (0.91 g, 6.64 mmol) followed by TBAI (0.491 g, 1.32 mmol) at room temperature, and then the reaction mixture was stirred at 100° C. for 18 h. The reaction mixture was poured into water (20 mL) and extracted with ethyl acetate (3×50 mL). The combined organic layers were dried over Na$_2$SO$_4$, filtered, and concentrated under reduced pressure. The resulting crude material was purified by silica gel column chromatography, with the compound eluting at 20% ethyl acetate/hexane, to afford Int-163 (900 mg, 70%) as a viscous oil. $^1$H NMR (400 MHz, CDCl$_3$) δ 7.33 (d, J=8.3 Hz, 2H), 6.97-6.89 (m, 2H), 5.30 (t, J=4.4 Hz, 1H), 5.09 (s, 2H), 4.33 (dd, J=11.9, 4.3 Hz, 2H), 4.23-4.06 (m, 4H), 3.85 (s, 3H), 2.45-2.27 (m, 10H), 1.74-1.64 (m, 14H), 1.29 (m, 54H), 0.92 (t, J=6.7 Hz, 6H).

In an autoclave, to a solution of Int-163 (0.9 g, 0.92 mmol) in ethyl acetate (30 mL) was added 10% Pd/C (250 mg) under nitrogen atmosphere. The reaction mixture was stirred at room temperature for 16 h under 100 psi hydrogen pressure. The reaction mixture was filtered on a celite bed and washed with ethyl acetate (50 mL). The filtrate was concentrated under reduced pressure. The resulting crude material was purified by flash column chromatography using silica gel, eluting with 30% to 50% ethyl acetate/hexane, to afford Int-164 (400 mg, 51%) as a white solid. $^1$H NMR (400 MHz, CDCl$_3$) δ 5.28 (t, J=4.4 Hz, 1H), 4.32 (dd, J=11.9, 4.3 Hz, 2H), 4.22-4.07 (m, 4H), 2.46-2.36 (m, 2H), 2.32 (q, J=7.5 Hz, 8H), 1.73 (dt, J=6.7, 3.4 Hz, 4H), 1.62 (p, J=7.4, 6.0 Hz, 8H), 1.36-1.27 (m, 57H), 0.90 (t, J=6.7 Hz, 6H); MS (ESI, +ve) m/z: 852.6 (MH+1).

FSI5-C12β'βMe-acid-2-TG-oleate (Int-262):

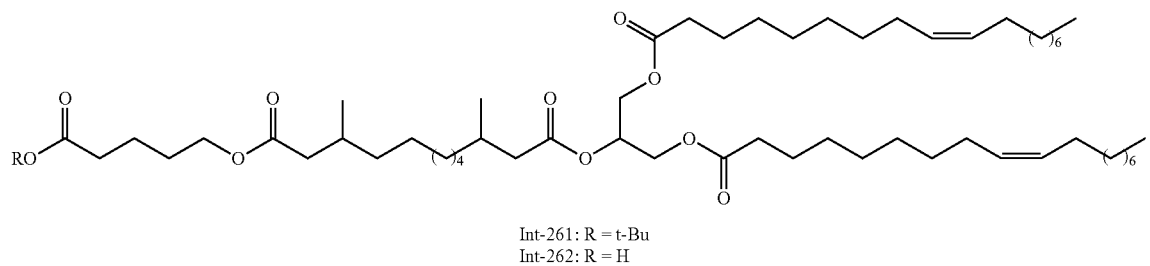

Int-261: R = t-Bu
Int-262: R = H

Using similar methods as described for the synthesis of Int-163, compound Int-261 was prepared from Int-174 and t-butyl 5-bromopentanoate. $^1$H NMR (400 MHz, CDCl$_3$) δ 5.31 (m, 5H), 4.29 (dd, J=12.0, 4.3 Hz, 2H), 4.17 (dd, J=11.9, 6.0 Hz, 2H), 4.09 (t, J=6.5 Hz, 2H), 2.35 (t, J=6.8 Hz, 6H), 2.12 (m, 2H), 2.00 (d, J=5.8 Hz, 6H), 1.93 (m, 2H), 1.58 (m, 8H), 1.44 (s, 9H), 1.28 (m, 56H), 0.94 (d, J=6.4 Hz, 6H), 0.94 (t, J=7.2 Hz, 6H).

Trifluoroacetic acid (3.6 mL) was added dropwise over 10 minutes to a solution of Int-261 (1.2 g, 1.10 mmol) in DCM (12 mL) at 0° C., and the reaction mixture was stirred at RT for 3 hours. The reaction mixture was concentrated under reduced pressure, and the residue was purified by column chromatography using silica gel (100-200 mesh), with product eluting at 12% ethyl acetate/hexane. Pure fractions were concentrated under reduced pressure to afford Int-262 (0.580 g, 51.1%) as a colourless oil. $^1$H NMR (400 MHz, CDCl$_3$) δ 5.31 (m, 5H), 4.30 (dd, J=12.0, 4.3 Hz, 2H), 4.17 (dd, J=11.9, 6.0 Hz, 2H), 4.11 (t, J=6.5 Hz, 2H), 2.42 (t, J=6.8 Hz, 6H), 2.12 (m, 2H), 2.00 (d, J=5.8 Hz, 8H), 1.73 (m, 4H), 1.62 (m, 4H), 1.28 (m, 56H), 0.94 (d, J=6.4 Hz, 6H), 0.94 (t, J=7.2 Hz, 6H).

FSI5-C12βMe-acid-2-TG-oleate (Int-263):

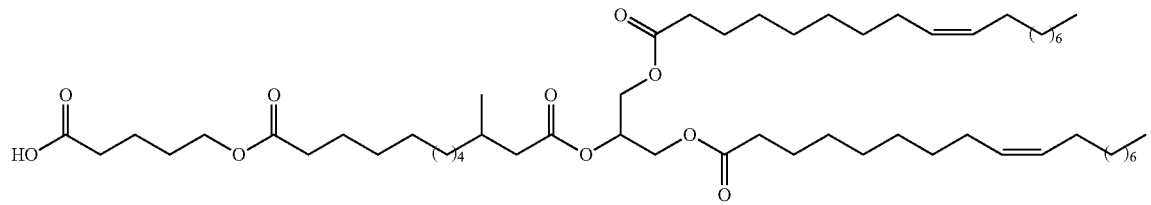

Int-263

Using similar methods as described for the synthesis of Int-262, compound Int-263 was prepared from Int-236 and t-butyl 5-bromopentanoate. $^1$H NMR (400 MHz, CDCl$_3$) δ 5.31 (m, 5H), 4.30 (dd, J=12.0, 4.3 Hz, 2H), 4.17 (dd, J=11.9, 6.0 Hz, 2H), 4.11 (t, J=6.5 Hz, 2H), 2.42 (t, J=6.8 Hz, 6H), 2.12 (m, 1H), 2.00 (d, J=5.8 Hz, 8H), 1.73 (m, 4H), 1.62 (m, 6H), 1.28 (m, 57H), 0.94 (d, J=6.4 Hz, 3H), 0.88 (t, J=7.2 Hz, 6H).

FSI4-C12β'βMe-acid-2-TG-oleate (Int-264):

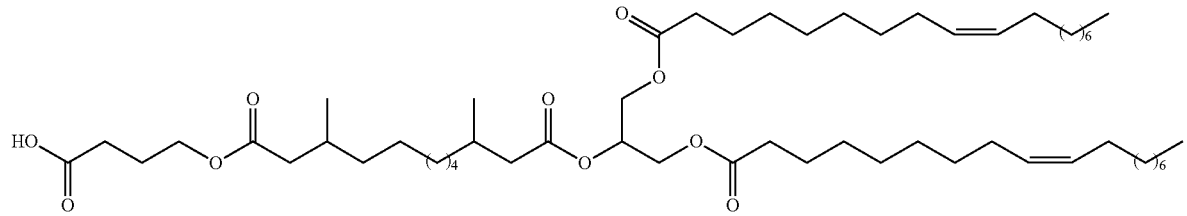

Int-264

Using similar methods as described for the synthesis of Int-262, compound Int-264 was prepared from Int-174 and t-butyl 4-bromobutanoate. $^1$H NMR (400 MHz, CDCl$_3$) δ 5.37 (m, 5H), 4.31 (m, 2H), 4.30 (m, 2H), 2.47 (m, 2H), 2.33 (q, J=7.7 Hz, 6H), 2.15 (m, 4H), 1.68-1.59 (m, 6H), 1.30 (d, J=13.9 Hz, 11H), 1.20 (m, 62H), 0.95 (d, J=6.4 Hz, 6H), 0.89 (dd, J=16.6, 9.5 Hz, 6H).

FSI4-C12βMe-acid-2-TG-oleate (Int-265):

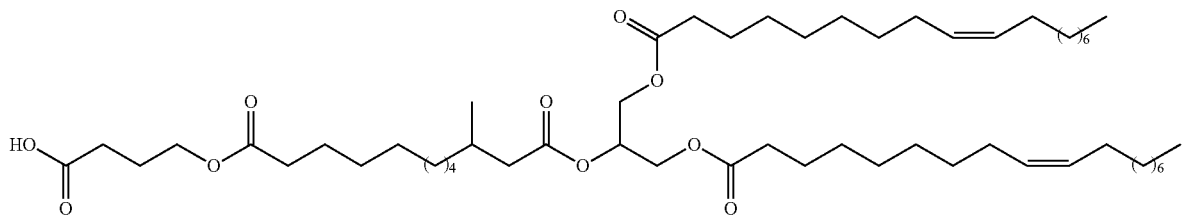

Using similar methods as described for the synthesis of Int-262, compound Int-265 was prepared from Int-236 and t-butyl 4-bromobutanoate. $^1$H NMR (400 MHz, CDCl$_3$) δ 5.40 (m, 5H), 4.33 (dd, J=11.6, 4.4 Hz, 2H), 4.14 (dd, J=25.7, 6.2 Hz, 4H), 2.40 (t, J=6.4 Hz, 2H), 2.33 (td, J=7.7, 4.3 Hz, 6H), 2.14 (m, 2H), 2.03-1.94 (m, 11H), 1.63 (dd, J=13.7, 5.8 Hz, 4H), 1.32 (d, J=11.2 Hz, 54H), 0.95 (td, J=18.9, 17.4, 9.1 Hz, 9H).

C10β'βMe-acid-2-TG-oleate (Int-172):

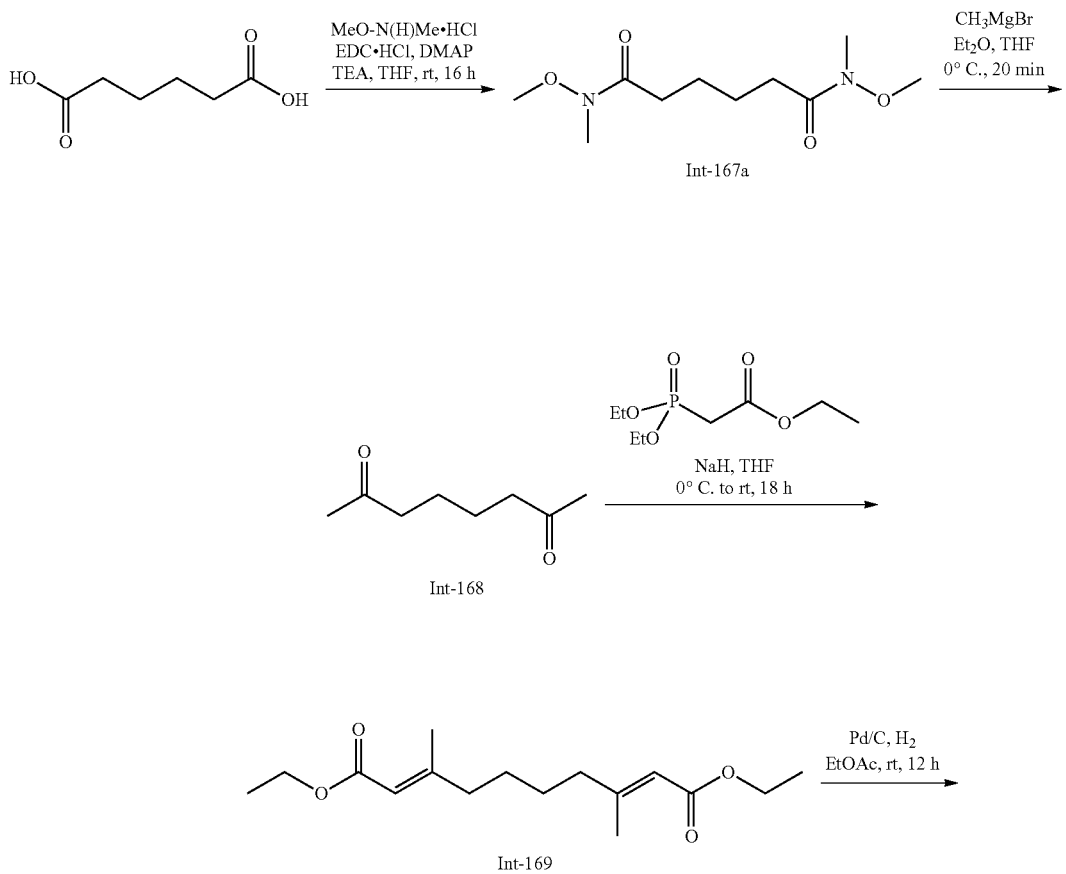

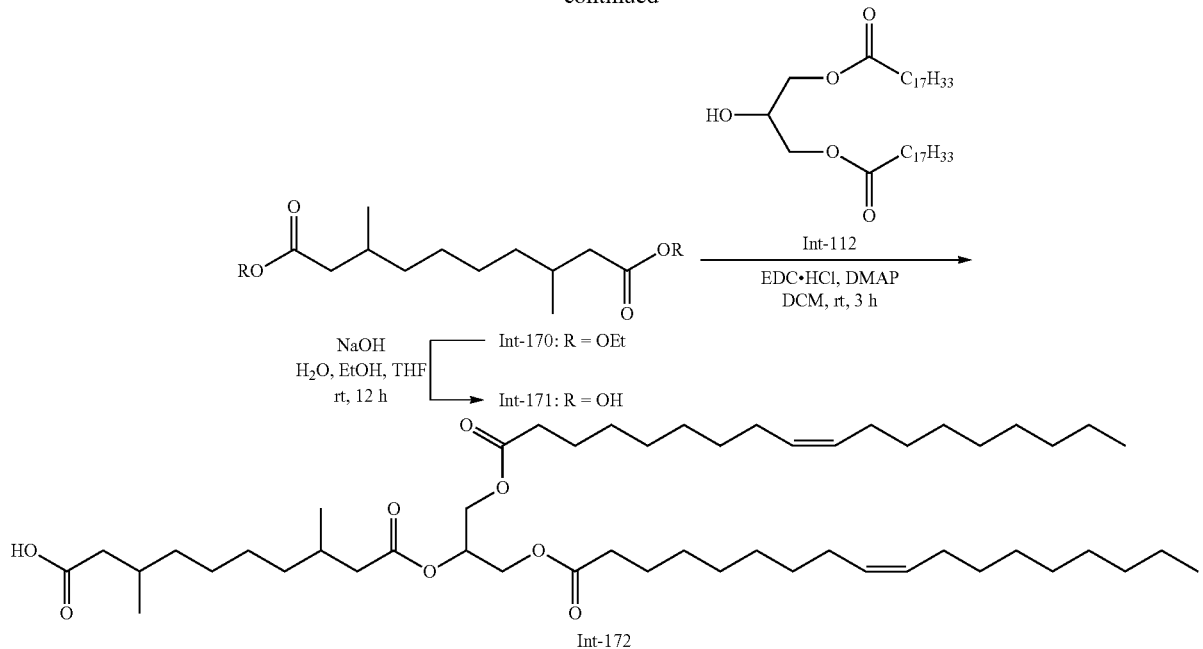

To a stirred solution of hexan-1,6-dioic acid (20.0 g, 136.85 mmol) in THF (500 mL) at room temperature were added N,O-dimethylhydroxylamine-HCl (40.04 g, 410.56 mmol), EDC·HCl (78.8 g, 410.56 mmol), DMAP (16.6 g, 136.85 mmol), and TEA (90 mL, 684.27 mmol). The resulting reaction mixture was stirred at rt for 16 h, then poured into 1N HCl solution (sufficient to achieve pH<7) and extracted with ethyl acetate (3×200 mL). The combined organic layer was dried over sodium sulphate and evaporated under vacuum. The residue was purified by column chromatography using silica gel (100-200 mesh), with product eluting at 50% ethyl acetate/hexane, to afford Int-167a (21.0 g, 66.1%) as a colorless oil. $^1$H NMR (400 MHz, CDCl$_3$) δ 3.65 (s, 6H), 3.15 (s, 6H), 2.43 (s, 4H), 1.66 (s, 4H).

To a stirred solution of Int-167a (5.0 g, 21.55 mmol) in dry THF (200 mL) at 0° C. was added dropwise methyl magnesium bromide solution (21.5 mL, 3.0 M in Et$_2$O, 64.65 mmol), then the resulting reaction mixture was stirred at 0° C. for 20 min. The reaction mixture was poured into 1N HCl Solution (sufficient to achieve pH<7) and extracted with ethyl acetate (3×100 mL). The combined organic layer was dried over sodium sulphate and evaporated under vacuum. The residue was purified by column chromatography using silica gel (100-200 mesh), with product eluting at 25% ethyl acetate/hexane, to afford Int-168 (2.0 g, 33%). $^1$H NMR (400 MHz, CDCl$_3$) δ 2.45 (s, 4H), 2.14 (s, 6H), 1.57 (s, 4H).

To a stirred mixture of 60% NaH (5.0 g, 126.6 mmol) in dry THF (100 mL) at 0° C. under nitrogen atmosphere was dropwise added ethyl 2-(diethoxyphosphoryl)acetate (28.4 g, 126.8 mmol) in THF (50 mL). The resulting reaction mixture was stirred at 0° C. for 30 min, then Int-168 (6.0 g, 42.25 mmol) in dry THF (50 mL) was added dropwise at 0° C. The reaction mixture was allowed to stir at room temperature for 18 h, then quenched with ice water (100 mL) and extracted with ethyl acetate (3×60 mL). The combined organic layer was dried over sodium sulphate and evaporated under vacuum. The residue was purified by column chromatography using silica gel (100-200 mesh), with product eluting at 15% ethyl acetate/hexane, to afford Int-169 (10.0 g, 84.0%). $^1$H NMR (400 MHz, CDCl$_3$) δ 5.65 (s, 2H), 4.14 (q, J=6.0 Hz, 4H), 2.63 (t, J=7.6 Hz, 4H), 2.14 (s, 6H), 1.28 (m, 10H).

To a solution of Int-169 (10.0 g, 35.5 mmol) in ethyl acetate (100 mL) was added palladium on carbon (10% w/w, 2.5 g), and the resulting suspension evacuated and re-filled with H$_2$ three times. The reaction mixture was stirred at room temperature for 12 h under hydrogen balloon pressure. The reaction mixture was filtered through a pad of Celite, washing with ethyl acetate (200 mL). The filtrate was concentrated under reduced pressure to give Int-170 (9.2 g, 91%) as a colorless oil that was used in the next step without further purification. $^1$H NMR (400 MHz, CDCl$_3$) δ 4.14 (q, J=6.0 Hz, 4H), 2.30 (dd, J=14.6, 6.0 Hz, 2H), 2.10 (dd, J=14.9, 7.4 Hz, 2H), 1.96 (bs, 2H), 1.27 (m, 8H), 1.2 (t, 6H), 0.94 (d, J=6.6 Hz, 6H).

To a solution of Int-170 (9.3 g, 32.5 mmol) in THF (75 mL), EtOH (75 mL), and water (75 ml) at room temperature was added NaOH (5.5 g, 137.5 mmol), then the reaction mixture was stirred at rt for 12 h. The reaction mixture was evaporated to remove organic solvent, then acidified by addition of 1 N HCl solution (until acidic pH), and extracted with ethyl acetate (3×75 mL). The combined organic layers were dried over sodium sulphate and evaporated under reduced pressure to afford Int-171 (7.8 g, quantitative) as an off-white solid, which was used in the next step without further purification. $^1$H NMR (400 MHz, CDCl$_3$) δ 2.35-2.30 (m, 2H), 2.22-2.2.12 (m, 2H), 1.97 (bs, 2H), 1.34-1.25 (m, 8H), 0.99-0.97 (d, J=6.4 Hz, 6H).

To a stirred solution of Int-171 (7.8 g, 33.91 mmol) and Int-112 (12.61 g, 20.33 mmol) in DCM (80 mL) was added 4-(dimethylamino)pyridine (DMAP, 4.13 g, 33.91 mmol) followed by EDC·HCl (12.88 g, 67.8 mmol), and the reaction mixture was stirred at room temperature for 3 h. The reaction mixture was evaporated under vacuum. The residue was purified by column chromatography using silica gel (100-200 mesh), with product eluting at 10-12% ethyl acetate/hexane, to afford Int-172 (8.5 g, 15%). $^1$H NMR (400 MHz, CDCl$_3$) δ 5.36-5.29 (m, 5H), 4.31 (dd, J=12.0, 4.4 Hz, 2H), 4.17 (dd, J=12.0, 4.4 Hz, 2H), 2.33 (t, J=12.0, 7.6 Hz, 6H), 2.21-2.12 (m, 2H), 2.02-1.98 (m, 10H), 1.63-1.61 (m, 4H), 1.44-1.29 (m, 48H), 0.97 (dd, J=14.0 Hz, 6.4 Hz, 6H), 0.88 (t, J=6.4 Hz, 6H); $^{13}$C NMR (101 MHz, CDCl$_3$) δ 177.95 (1C), 173.27 (2C), 172.25 (1C), 130.03 (2C), 129.72 (2C), 68.89 (1C), 62.17 (2C), 41.67 (1C), 41.33 (1C), 36.61

(2C), 34.05 (2C), 31.91 (2C), 30.33-29.11 (21C), 27.24 (2C), 27.15 (1C), 24.85 (2C), 22.68 (2C), 19.69 (1C), 19.55 (1C), 14.09 (2C); MS (ESI, −ve) m/z: 831.95 (MH−1).

C12β'βMe-acid-2-TG-oleate (Int-174):

Using the procedures described for the synthesis of Int-172, compounds Int-173 and Int-174 were prepared from octan-1,8-dioic acid and Int-112:

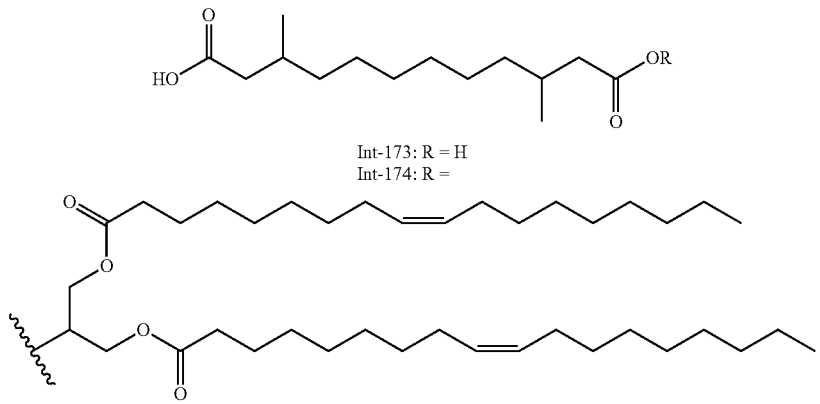

Int-173: R = H
Int-174: R =

C12β'βMe-acid (Int-173) $^1$H NMR (400 MHz, CDCl$_3$) δ 10.83 (bs, 1H), 2.36 (ddd, J=15.5, 9.6, 6.3 Hz, 2H), 2.18-1.81 (m, 4H), 1.33-1.14 (m, 12H), 0.98 (d, J=6.4 Hz, 6H); MS (ESI, −ve) m/z: 257.29 (M−1).

C12β'βMe-acid-2-TG-oleate (Int-174) $^1$H NMR (400 MHz, CDCl$_3$) δ 5.35-5.29 (m, 5H), 4.32 (dd, J=11.6 Hz, 4.0 Hz, 2H), 4.18 (dd, J=11.6, 6.0 Hz, 2H), 2.38-2.30 (m, 6H), 2.18-1.96 (m, 11H), 1.30-1.27 (m, 56H), 0.98-0.96 (m, 13H); $^{13}$C NMR (101 MHz, CDCl$_3$) δ 178.84 (1C), 173.31 (2C), 172.37 (1C), 130.03 (2C), 129.73 (2C), 68.85 (1C), 62.19 (2C), 41.71 (1C), 41.48-19.57 (39C), 14.13 (2C); MS (ESI, +ve) m/z: 878.82 (M+18), 861.15 (M+1).

C8β'βMe-acid-2-TG-oleate (Int-176):

Using the last four procedures described for the synthesis of Int-172, compounds Int-173 and Int-174 were prepared from hexan-2,5-dione and Int-112:

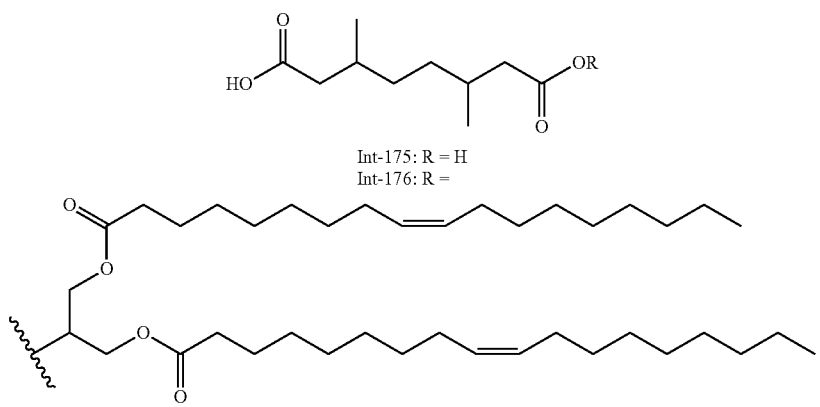

Int-175: R = H
Int-176: R =

C8β'βMe-acid (Int-175) $^1$H NMR (400 MHz, CDCl$_3$) δ 2.36 (ddd, J=15.5, 9.6, 6.3 Hz, 2H), 2.23 (m, 2H), 1.97 (m, 2H), 1.27 (t, J=7.1 Hz, 4H), 0.98 (d, J=6.4 Hz, 6H).

C8β'βMe-acid-2-TG-oleate (Int-176) $^1$H NMR (400 MHz, CDCl$_3$) δ 5.37 (m, 5H), 4.32 (dd, J=12.1 Hz, 4.4 Hz, 2H), 4.17 (dd, J=12.6, 6.0 Hz, 2H), 2.33 (t, J=7.6 Hz, 6H), 2.18 (m, 2H) 2.06-1.94 (m, 8H), 1.60 (m, 4H), 1.30 (m, 46H), 0.98 (d, J=6.4 Hz, 6H), 0.90 (t, J=6.8 Hz, 6H); $^{13}$C NMR (101 MHz, CDCl$_3$) δ 177.85 (1C), 173.27 (2C), 172.08 (1C), 130.02 (2C), 129.71 (2C), 68.96 (1C), 62.15 (2C), 41.65 (1C), 41.44-41.36 (4C), 34.04 (2C), 33.83 (1C), 31.91 (2C), 30.46-30.31 (2C), 29.78-29.11 (14C), 27.23 (2C), 27.18 (2C), 24.85 (2C), 22.67 (2C), 19.78-19.47 (2C), 14.08 (2C); MS (ESI, −ve) m/z: 803.98 (M−1).

C15β'βMe-acid-2-TG-oleate (Int-238):

Using the procedures described for the synthesis of Int-172, compounds Int-237 and Int-238 were prepared from undecan-1,11-dioic acid and Int-112:

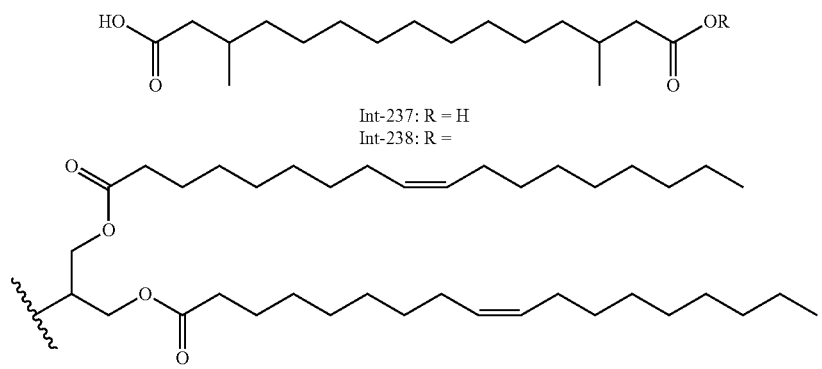

Int-237: R = H
Int-238: R =

C15β'βMe-acid (Int-237) $^1$H NMR (400 MHz, CDCl$_3$) δ 2.30-2.20 (m, 2H), 2.13 (s, 2H), 2.0 (bs, 2H), 1.40-1.30 (m, 18H), 1.00 (d, J=6.6 Hz, 6H); MS (ESI, −ve) m/z: 299.35 (M−1). (ESI, +ve) m/z: 301.37 (M+1).

C15β'βMe-acid-2-TG-oleate (Int-238) $^1$H NMR (400 MHz, CDCl$_3$) δ 5.36-5.29 (m, 5H), 4.31 (dd, J=12.0, 4.0 Hz, 2H), 4.17 (dd, J=12.0, 4.0 Hz, 2H), 2.44-2.31 (m, 6H), 2.19-2.11 (m, 2H), 2.04-1.98 (m, 10H), 1.63-1.61 (m, 10H), 1.32-1.28 (m, 52H), 0.97 (dd, J=14.0 Hz, 6.4 Hz, 6H), 0.90 (t, J=6.4 Hz, 6H); $^{13}$C NMR (101 MHz, CDCl$_3$) δ 173.24 (3C), 172.33 (1C), 130.01 (2C), 129.71 (2C), 68.87 (1C), 62.19 (2C), 41.71 (1C), 41.41 (1C), 36.70 (1C), 34.05 (2C), 31.91 (2C), 30.37 (1C), 30.17 (1C), 29.78-29.11 (23C), 27.23 (2C), 27.19 (2C), 26.93 (1C), 24.85 (2C), 22.68 (2C), 19.68 (2C), 14.08 (2C); MS (ESI, −ve) m/z: 902.04 (M−1). (ESI, +ve) m/z: 921.07 (M+18).

C12β'βMe-acid-2-TG (Int-252):

Using the procedures described for the synthesis of Int-172, compounds Int-252 was prepared from Int-173 and Int-2:

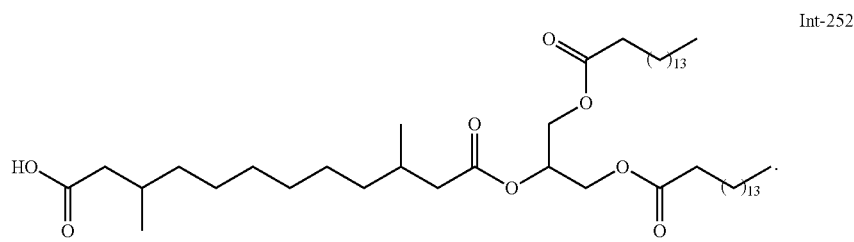

Int-252

C12β'βMe-acid-2-TG (Int-252) $^1$H NMR (400 MHz, CDCl$_3$) δ 5.32 (p, J=4.7 Hz, 1H), 4.33 (dd, J=11.9, 4.3 Hz, 2H), 4.19 (dd, J=12.0, 6.0 Hz, 2H), 2.44-2.28 (m, 6H), 2.26-2.10 (m, 2H), 2.02-1.95 (m, 2H), 1.65 (p, J=7.1 Hz, 6H), 1.32 (s, 58H), 1.05 (dd, J=10.8 Hz, 6.8 Hz, 6H), 0.94 (t, J=6.4 Hz, 6H); $^{13}$C NMR (101 MHz, CDCl$_3$) δ 178.90 (1C), 173.35 (2C), 172.38 (1C), 68.80 (2C), 62.15 (2C), 41.69 (1C), 41.48 (1C), 36.66 (1C), 36.63 (1C), 34.05 (2C), 31.94 (2C), 30.34 (1C), 30.13 (1C), 29.71-29.13 (21C), 26.87 (2C), 24.86 (2C), 22.71 (2C), 19.68 (1C), 19.56 (1C), 14.14 (2C); MS (ESI, −ve) m/z: 808.14 (M−1). (ESI, +ve) m/z: 827.10 (M+18).

DMPHB-C8β'βMe-bromide-2-TG-oleate (Int-181):

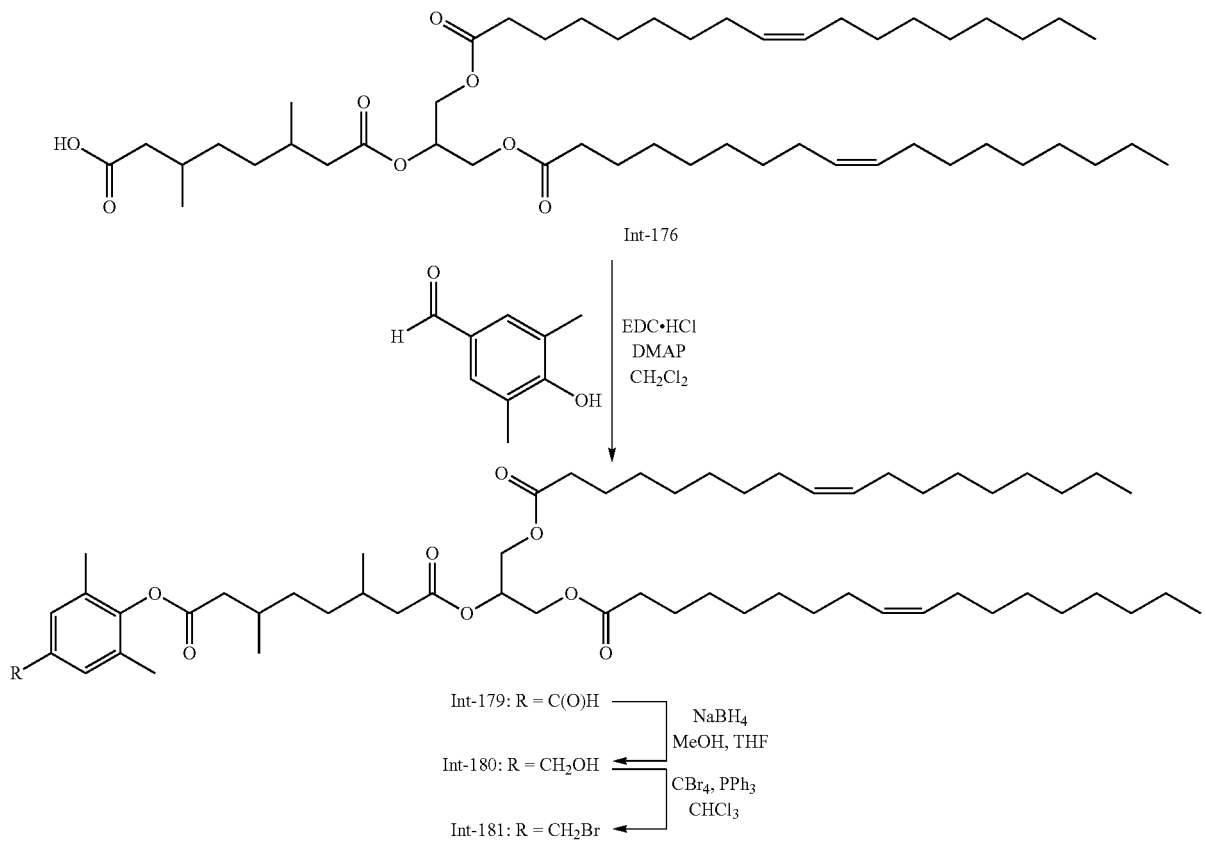

Scheme 47. Synthesis of Int-181.

4-(Dimethyl amino)pyridine (DMAP, 0.431 g, 2.33 mmol) and EDC·HCl (1.35 g, 4.66 mmol) were added to a solution of Int-176 (3.0 g, 2.44 mmol) and 4-hydroxy-3,5-dimethyl benzaldehyde (0.533 g, 2.33 mmol) in $CH_2Cl_2$ (30 mL), and the reaction mixture was stirred at rt for 2 h. The reaction mixture was concentrated under reduced pressure to afford Int-179 (3.5 g, quantitative), which was used in the next step without further purification. $^1$H NMR (400 MHz, CDCl3) δ 9.94 (s, 1H), 7.62 (s, 2H), 5.36 (d, J=16.8 Hz, 5H), 4.33 (dd, J=7.6, 6.0 Hz, 2H), 4.19 (dd, J=7.8, 5.5 Hz, 2H), 2.66 (m, 1H), 2.47 (m, 2H), 2.37 (t, J=7.2 Hz, 5H), 2.18 (s, 6H) 2.02 (m, 8H) 1.63 (m, 4H), 1.31 (m, 46H), 1.10 (d, J=6.9 Hz, 3H), 0.98 (d, J=6.8 Hz, 3H), 0.92 (t, J=6.8 Hz, 6H).

Sodium borohydride (0.139 g, 2.04 mmol) was added portionwise to a solution of Int-179 (3.5 g, 2.04 mmol) in methanol (10 mL) and THF (20 mL) at 0° C., and the resulting mixture was stirred at 0° C. for 10 min. The reaction mixture was acidified to pH 4 by addition of 1 N HCl (10 mL) and extracted with ethyl acetate (3×75 mL). The combined organic layer was dried over sodium sulphate and concentrated under reduced pressure. The residue was purified by column chromatography, eluting with 7-10% ethyl acetate/hexanes, to afford Int-180 (2.6 g, 75%). $^1$H NMR (400 MHz, $CDCl_3$) δ 7.09 (s, 2H), 5.36 (d, J=17.3 Hz, 5H), 4.63 (s, 2H), 4.33 (dd, J=7.6, 6.0 Hz, 2H), 4.19 (dd, J=7.8, 5.5 Hz, 2H), 2.66 (m, 1H), 2.47 (m, 2H), 2.37 (t, J=7.2 Hz, 5H), 2.18 (s, 6H) 2.02 (m, 8H) 1.59 (m, 4H), 1.31 (m, 46H), 1.10 (d, J=6.9 Hz, 3H), 0.98 (d, J=6.8 Hz, 3H), 0.90 (t, J=6.8 Hz, 6H).

Carbon tetrabromide (1.32 g, 2.15 mmol) and triphenylphosphine (1.25 g, 2.58 mmol) were added to Int-180 (1.5 g, 0.860 mmol) in $CHCl_3$ (15 mL) at room temperature. The reaction was stirred at 70° C. for 2 h. The reaction mixture was evaporated. The residue was purified by column chromatography using silica gel (100-200 mesh), with product eluting at 7-7.5% ethyl acetate/hexane, to afford Int-181 (500 mg, 31%) as a colorless liquid. $^1$H NMR (400 MHz, $CDCl_3$) δ 7.12 (s, 2H), 5.42-5.27 (m, 5H), 4.44 (s, 2H) 4.34 (dd, J=12.6 Hz, J=4.4 Hz, 2H), 4.19 (dd, J=12.6 Hz, J=4.4 Hz, 2H), 2.66 (m, 1H), 2.47 (m, 2H), 2.33 (t, J=7.2 Hz, 5H), 2.18 (s, 6H) 2.02 (m, 8H) 1.59 (m, 4H), 1.31 (m, 46H), 1.10 (d, J=6.9 Hz, 3H), 0.98 (d, J=6.8 Hz, 3H), 0.90 (t, J=6.8 Hz, 6H); $^{13}$C NMR (101 MHz, $CDCl_3$) δ 173.21 (2C), 172.07 (1C), 170.60 (1C), 148.31 (1C), 135.12 (1C), 130.70 (1C), 130.04 (2C), 129.72 (2C), 129.33 (1C), 69.00 (1C), 62.15 (2C), 41.65 (1C), 34.00 (2C), 33.97 (1C), 33.87 (1C), 33.81 (1C), 33.06 (1C), 31.91 (2C), 30.56 (1C), 30.50 (1C), 30.39 (1C), 30.33 (1C), 29.78-29.12 (18C), 27.24 (2C), 24.85 (2C), 22.68 (2C), 19.90 (1C), 19.71 (1C), 16.48 (2C), 14.10 (2C); MS (ESI, +ve) m/z: 1019.04 (M+18).

DMPHB-C10β'βMe-bromide-2-TG-oleate (Int-184):

Using the procedures described for the synthesis of Int-181, compounds Int-182, Int-183, and Int-184 were prepared from Int-172:

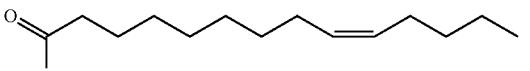
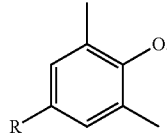

Int-182: R = C(O)H
Int-183: R = CH₂OH
Int-184: R = CH₂Br

DMPHB-C10β'βMe-aldehyde-2-TG-oleate (Int-182) ¹H NMR (400 MHz, CDCl₃) δ 9.94 (s, 1H), 7.63 (s, 2H), 5.36 (m, 5H), 4.33 (dd, J=7.6, 6.0 Hz, 2H), 4.19 (dd, J=7.8, 5.5 Hz, 2H), 2.68 (m, 1H), 2.48 (m, 2H), 2.37 (t, J=7.2 Hz, 5H), 2.18 (s, 6H) 2.02 (m, 8H) 1.64 (m, 4H), 1.32 (m, 50H), 1.09 (d, J=6.9 Hz, 3H), 0.99 (d, J=6.8 Hz, 3H), 0.92 (t, J=6.8 Hz, 6H).

DMPHB-C10β'βMe-OH-2-TG-oleate (Int-183) ¹H NMR (400 MHz, CDCl₃) δ 7.09 (s, 2H), 5.36 (m, 5H), 4.63 (s, 2H), 4.33 (dd, J=7.6, 6.0 Hz, 2H), 4.19 (dd, J=7.8, 5.5 Hz, 2H), 2.66 (m, 1H), 2.47 (m, 2H), 2.37 (t, J=7.2 Hz, 5H), 2.17 (s, 6H), 2.02 (m, 8H), 1.58 (m, 4H), 1.29 (m, 50H), 1.08 (d, J=6.9 Hz, 3H), 0.96 (d, J=6.8 Hz, 3H), 0.91 (t, J=6.8 Hz, 6H).

DMPHB-C10β'βMe-bromide-2-TG-oleate (Int-184) ¹H NMR (400 MHz, CDCl₃) δ 7.13 (s, 2H), 5.38 (m, 5H) 4.46 (s, 2H), 4.32 (dd, J=12.0, 4.2 Hz, 2H), 4.19 (dd, J=11.8, 6.0 Hz, 2H), 2.66 (m, 1H), 2.47 (m, 2H), 2.33 (t, J=7.2 Hz, 5H), 2.18 (s, 6H), 2.02 (m, 8H), 1.65 (m, 4H), 1.26 (m, 50H), 1.10 (d, J=6.4 Hz, 3H), 0.98 (d, J=20 Hz, 3H), 0.90 (t, J=6.8 Hz, 6H); ¹³C NMR (101 MHz, CDCl₃) δ 173.21 (2C), 172.07 (1C), 170.60 (1C), 148.31 (1C), 135.12 (1C), 130.70 (1C), 130.04 (2C), 129.72 (2C), 129.33 (1C), 69.00 (1C), 62.15 (2C), 41.65 (1C), 34.00 (2C), 33.97 (1C), 33.87 (1C), 33.81 (1C), 33.06 (1C), 31.91 (2C), 30.56 (1C), 30.50 (1C), 30.39 (1C), 30.33 (1C), 29.78-29.12 (20C), 27.24 (2C), 24.85 (2C), 22.68 (2C), 19.82 (1C), 19.53 (1C), 16.46 (2C), 14.08 (2C); MS (ESI, +ve) m/z: 1049.04 (M+18).

DMPHB-C10βMe-bromide-2-TG-oleate (Int-189):

Using the procedures described for the synthesis of Int-181, compounds Int-188, Int-189, and Int-190 were prepared from Int-187:

DMPHB-C10βMe-aldehyde-2-TG-oleate (Int-188) ¹H NMR (400 MHz, CDCl₃) δ 9.96 (s, 1H), 7.64 (s, 2H), 5.38-5.32 (m, 5H), 4.33 (dd, J=11.9, 4.3 Hz, 2H), 4.19 (dd, J=11.9, 6.0 Hz, 2H), 2.67 (t, J=7.0 Hz, 2H), 2.37 (dt, J=14.9, 6.8 Hz, 5H), 2.20 (s, 6H), 2.18 (m, 2H), 2.05-2.02 (m, 8H), 1.83 (t, J=7.5 Hz, 2H), 1.65-1.59 (m, 4H), 1.47-130 (m, 48H), 0.98 (d, J=6.8 Hz, 3H), 0.92 (t, J=6.8 Hz, 6H).

DMPHB-C10βMe-OH-2-TG-oleate (Int-189) ¹H NMR (400 MHz, CDCl₃) δ 7.11 (s, 2H), 5.42-5.31 (m, 5H), 4.65 (s, 2H), 4.33 (dd, J=11.9, 4.7 Hz, 2H), 4.19 (dd, J=12.2, 6.1 Hz, 2H), 2.63 (t, J=7.4 Hz, 2H), 2.37 (dt, J=14.9, 6.8 Hz, 5H), 2.18 (s, 6H), 2.16 (m, 2H), 2.05-2.02 (m, 8H), 1.83 (t, J=7.5 Hz, 2H), 1.65-1.59 (m, 4H), 1.47-130 (m, 48H), 0.98 (d, J=6.8 Hz, 3H), 0.92 (t, J=6.8 Hz, 6H).

DMPHB-C10βMe-bromide-2-TG-oleate (Int-190) ¹H NMR (400 MHz, CDCl₃) δ 7.13 (s, 2H), 5.38-5.32 (m, 5H), 4.46 (s, 2H), 4.33 (dd, J=12.6 Hz, J=4.4 Hz, 2H), 4.19 (dd, J=12.6 Hz, J=4.4 Hz, 2H), 2.63 (t, J=7.4 Hz, 2H), 2.37 (dt, J=14.9, 6.8 Hz, 5H), 2.18 (s, 6H), 2.16 (m, 2H), 2.05-2.02 (m, 8H), 1.83 (t, J=7.5 Hz, 2H), 1.65-1.59 (m, 4H), 1.47-1.30 (m, 48H), 0.98 (d, J=6.8 Hz, 3H), 0.92 (t, J=6.8 Hz, 6H); ¹³C NMR (101 MHz, CDCl₃) δ 173.26 (2C), 172.27 (1C), 171.31 (1C), 148.23 (1C), 135.08 (1C), 130.70 (2C), 130.02 (2C), 129.71 (2C), 129.31 (2C), 68.83 (1C), 62.14 (2C), 41.65 (1C), 36.60 (1C), 34.02 (2C), 33.16 (1C), 31.91 (2C), 30.30-29.11 (21C), 27.22 (2C), 26.76 (1C), 25.63 (1C), 25.06 (1C), 24.83 (2C), 22.69 (2C), 19.52 (1C), 16.38 (2C), 14.13 (2C); MS (ESI, +ve) m/z: 1033.16 (M+18).

DMPHB-C8βMe-bromide-2-TG-oleate (Int-205):

Using the procedures described for the synthesis of Int-181, compounds Int-203, Int-204, and Int-205 were prepared from Int-178:

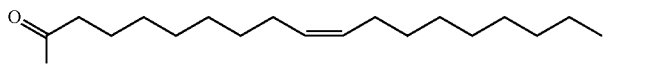
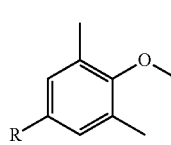

Int-188: R = C(O)H
Int-189: R = CH₂OH
Int-190: R = CH₂Br

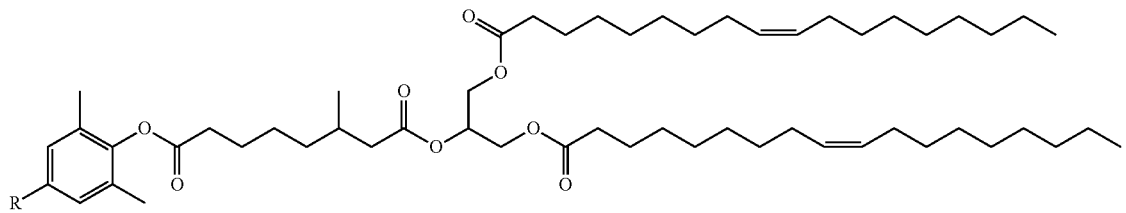

Int-203: R = C(O)H
Int-204: R = CH₂OH
Int-205: R = CH₂Br

DMPHB-C8βMe-aldehyde-2-TG-oleate (Int-203) ¹H NMR (400 MHz, CDCl₃) δ 9.96 (s, 1H), 7.64 (s, 2H), 5.36 (m, 5H), 4.36 (dd, J=7.6, 6.0 Hz, 2H), 4.20 (dd, J=7.8, 5.5 Hz, 2H), 2.71 (dt, J=21.3, 8.1 Hz, 1H), 2.48 (m, 2H), 2.35 (t, J=7.6 Hz, 5H), 2.25 (s, 6H), 2.03 (m, 8H), 1.64 (t, J=7.3 Hz, 4H), 1.49-1.26 (m, 46H), 1.18 (t, J=7.2 Hz, 2H), 0.99 (d, J=6.6 Hz, 3H), 0.91 (t, J=6.6 Hz, 6H).

DMPHB-C8βMe-OH-2-TG-oleate (Int-204) ¹H NMR (400 MHz, CDCl₃) δ 7.09 (s, 2H), 5.36 (m, 5H), 4.64 (d, J=5.6 Hz, 2H), 4.33 (dd, J=7.6, 6.0 Hz, 2H), 4.18 (dd, J=7.8, 5.5 Hz, 2H), 2.64 (t, J=12 Hz, 1H), 2.47 (m, 2H), 2.39 (m, 5H), 2.16 (s, 6H), 2.03 (q, J=6.5 Hz, 8H), 1.62 (d, J=17.5 Hz, 4H), 1.31-1.28 (m, 46H), 1.08 (d, J=6.9 Hz, 2H), 0.98 (d, J=6.7 Hz, 3H), 0.90 (t, J=6.7 Hz, 6H).

DMPHB-C8βMe-bromide-2-TG-oleate (Int-205) ¹H NMR (400 MHz, CDCl₃) δ 7.02 (s, 2H), 5.36 (d, J=16.0 Hz, 4H), 5.30 (s, 1H), 4.44 (s, 2H), 4.34 (dd, J=12.0, 4.0 Hz, 2H), 4.19 (dd, J=12.0, 6.0 Hz, 2H), 2.64 (t, J=14.8 Hz, 2H), 2.39 (m, 4H), 2.14 (s, 6H), 2.03 (d, J=5.6 Hz, 7H), 1.80 (s, 2H), 1.62 (t, J=20.4 Hz, 15H), 1.48-1.28 (m, 38H), 0.98 (d, J=6.4 Hz, 2H), 0.90 (m, 6H); ¹³C NMR (101 MHz, CDCl₃) δ 173.26 (2C), 172.13 (1C), 171.17 (1C), 148.24 (1C), 135.13 (1C), 130.70 (2C), 130.05 (2C), 129.73 (2C), 129.34 (2C), 68.96 (1C), 62.15 (2C), 41.60 (1C), 36.26 (1C), 34.05 (2C), 33.92 (1C), 33.13 (1C), 31.93 (2C), 30.18 (1C), 29.79-29.13 (16C), 27.25 (2C), 27.20 (1C), 26.57 (1C), 25.18 (1C), 24.86 (2C), 22.71 (2C), 19.49 (1C), 19.25 (1C), 16.39 (2C), 14.14 (2C); MS (ESI, +ve) m/z: 1004.94 (M+18).

DMPHB-C12α'βMe-bromide-2-TG-oleate (Int-241):
Using the procedures described for the synthesis of Int-181, compounds Int-239, Int-240, and Int-241 were prepared from Int-231:

DMPHB-C12α'βMe-aldehyde-2-TG-oleate (Int-239) ¹H NMR (400 MHz, CDCl₃) δ 9.96 (s, 1H), 7.64 (s, 2H), 5.42-5.30 (m, 5H), 4.33 (dd, J=11.9, 4.3 Hz, 2H), 4.1 (dd, J=11.9, 6.0 Hz, 2H), 2.80 (t, J=7.6 Hz, 1H), 2.32 (t, J=7.2 Hz, 5H), 2.26 (s, 6H), 2.13 (m, 2H), 2.05 (m, 8H), 1.91 (m, 2H), 1.64 (m, 7H), 1.48 (m, 2H), 1.34 (m, 50H), 0.98 (d, J=6.8 Hz, 3H), 0.92 (t, J=6.8 Hz, 6H).

DMPHB-C12α'βMe-OH-2-TG-oleate (Int-240) ¹H NMR (400 MHz, CDCl₃) δ 7.12 (s, 2H), 5.42-5.30 (m, 5H), 4.64 (s, 2H), 4.33 (dd, J=11.9, 4.7 Hz, 2H), 4.20-4.19 (dd, J=12.2, 6.1 Hz, 2H), 2.80 (t, J=7.6 Hz, 1H), 2.32 (t, J=7.2 Hz, 5H), 2.26 (s, 6H), 2.13 (m, 2H), 2.05 (m, 8H), 1.91 (m, 2H), 1.64 (m, 7H), 1.48 (m, 2H), 1.34 (m, 50H), 0.98 (d, J=6.8 Hz, 3H), 0.92 (t, J=6.8 Hz, 6H).

DMPHB-C12α'βMe-bromide-2-TG-oleate (Int-241) ¹H NMR (400 MHz, CDCl₃) δ 7.13 (s, 2H), 5.42-5.30 (m, 5H), 4.46 (s, 2H), 4.33 (dd, J=11.9, 4.7 Hz, 2H), 4.20-4.19 (dd, J=12.2, 6.1 Hz, 2H), 2.80 (t, J=7.6 Hz, 1H), 2.32 (t, J=7.2 Hz, 5H), 2.26 (s, 6H), 2.13 (m, 2H), 2.05 (m, 8H), 1.91 (m, 2H), 1.64 (m, 7H), 1.48 (m, 2H), 1.34 (m, 50H), 0.98 (d, J=6.8 Hz, 3H), 0.92 (t, J=6.8 Hz, 6H); ¹³C NMR (101 MHz, CDCl₃) δ 174.33 (1C), 173.31 (2C), 172.37 (1C), 148.23 (1C), 135.02 (1C), 130.74 (1C), 130.04 (2C), 129.74 (2C), 129.39 (3C), 68.82 (1C), 62.19 (2C), 41.72 (1C), 39.79 (1C), 36.72 (1C), 34.06 (2C), 33.67 (1C), 33.25 (1C), 31.95 (2C), 30.40 (1C), 29.81-29.13 (21C), 27.44 (1C), 27.21 (2C), 26.95 (1C), 24.87 (2C), 22.74 (2C), 19.59 (1C), 17.47 (1C), 16.49 (2C), 14.18 (2C); MS (ESI, +ve) m/z: 1077.01 (M+18).

DMPHB-C12βMe-bromide-2-TG-oleate (Int-245):
Using the procedures described for the synthesis of Int-181, compounds Int-243, Int-244, and Int-245 were prepared from Int-236:

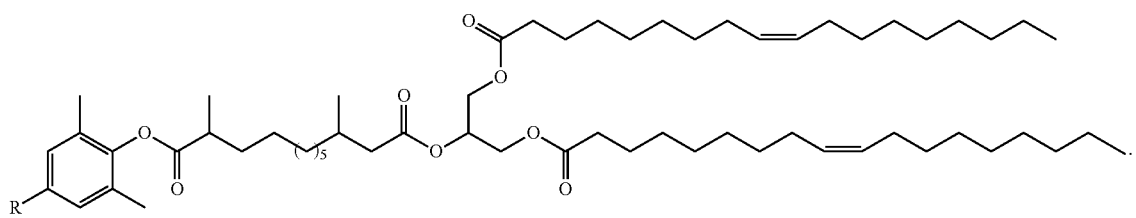

Int-239: R = C(O)H
Int-240: R = CH₂OH
Int-241: R = CH₂Br

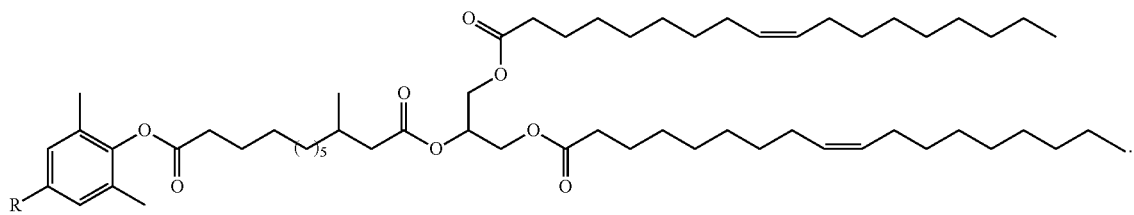

Int-243: R = C(O)H
Int-244: R = CH₂OH
Int-245: R = CH₂Br

DMPHB-C12βMe-aldehyde-2-TG-oleate (Int-243) ¹H NMR (400 MHz, CDCl₃) δ 9.96 (s, 1H), 7.64 (s, 2H), 5.45-5.28 (m, 5H), 4.33 (dd, J=11.9, 4.3 Hz, 2H), 4.19 (dd, J=11.9, 6.0 Hz, 2H), 2.67 (t, J=7.0 Hz, 2H), 2.37 (dt, J=14.9, 6.8 Hz, 5H), 2.26 (s, 6H), 2.13 (m, 2H), 2.05 (m, 8H), 1.83 (q, J=7.5 Hz, 2H), 1.63 (t, J=7.0 Hz, 4H), 1.48 (m, 2H), 1.34 (m, 50H), 0.97 (d, J=6.4 Hz, 3H), 0.92 (t, J=6.4 Hz, 6H).

DMPHB-C12βMe-OH-2-TG-oleate (Int-244) ¹H NMR (400 MHz, CDCl₃) δ 7.11 (s, 2H), 5.45-5.27 (m, 5H), 4.66 (d, J=2.5 Hz, 2H), 4.33 (dd, J=11.9, 4.3 Hz, 2H), 4.17 (dd, J=11.9, 6.0 Hz, 2H), 2.67 (t, J=7.0 Hz, 2H), 2.37 (dt, J=14.9, 6.8 Hz, 5H), 2.19 (s, 6H), 2.20-2.00 (m, 10H), 1.83 (q, J=7.5 Hz, 2H), 1.63 (t, J=7.0 Hz, 4H), 1.48 (m, 2H), 1.34 (m, 50H), 0.97 (d, J=6.4 Hz, 3H), 0.92 (t, J=6.4 Hz, 6H).

DMPHB-C12βMe-bromide-2-TG-oleate (Int-245) ¹H NMR (400 MHz, CDCl₃) δ 7.13 (s, 2H), 5.42-5.31 (m, 5H), 4.46 (s, 2H), ), 4.33 (dd, J=11.9, 4.3 Hz, 2H), 4.19 (dd, J=11.9, 6.0 Hz, 2H), 2.63 (t, J=7.0 Hz, 2H), 2.37 (dt, J=14.9, 6.8 Hz, 5H), 2.17 (s, 6H), 2.05 (m, 10H), 1.90 (dq, J=15.0, 7.5 Hz, 2H), 1.63 (tt, J=15.7, 7.0 Hz, 4H), 1.47 (m, 2H), 1.30 (m, 50H), 0.97 (d, J=6.4 Hz, 3H), 0.92 (t, J=6.4 Hz, 6H); ¹³C NMR (101 MHz, CDCl₃) δ 173.31 (2C), 172.37 (1C), 171.42 (1C), 148.27 (1C), 135.08 (1C), 130.74 (2C), 130.05 (2C), 129.74 (2C), 129.35 (2C), 68.82 (1C), 62.19 (1C), 41.72 (1C), 36.71 (1C), 34.06 (2C), 33.23 (1C), 31.95 (2C), 30.39 (1C), 29.81-29.13 (24C), 27.26 (2C), 27.21 (1C), 25.15 (1C), 24.87 (2C), 22.74 (2C), 19.59 (1C), 16.42 (2C), 14.18 (2C); MS (ESI, +ve) m/z: 1062.98 (M+18).

DMPHB-C12βMe-bromide-2-TG (Int-250):

Using the procedures described for the synthesis of Int-181, compounds Int-248, Int-249, and Int-250 were prepared from Int-247:

DMPHB-C12βMe-aldehyde-2-TG (Int-248) ¹H NMR (400 MHz, CDCl₃) δ 9.96 (s, 1H), 7.65 (s, 1H), 7.30 (s, 1H), 5.37-5.27 (m, 1H), 4.33 (dd, J=11.9, 4.3 Hz, 2H), 4.19 (dd, J=11.9, 6.0 Hz, 2H), 2.67 (t, J=7.6 Hz, 2H), 2.36 (t, J=7.2 Hz, 2H), 2.27 (s, 6H), 1.98 (s, 1H), 1.84 (p, J=7.5 Hz, 2H), 1.71-1.59 (m, 4H), 1.48 (dd, J=10.3, 5.3 Hz, 2H), 1.36-1.30 (m, 62H), 0.98 (d, J=6.8 Hz, 3H), 0.92 (t, J=6.8 Hz, 6H).

DMPHB-C12βMe-OH-2-TG (Int-249) ¹H NMR (400 MHz, CDCl₃) δ 7.12 (d, J=6.4 Hz, 2H), 5.37-5.27 (m, 1H), 4.66 (s, 2H), 4.33 (dd, J=11.9, 4.7 Hz, 2H), 4.19 (dd, J=12.2, 6.1 Hz, 2H), 2.64 (t, J=7.4 Hz, 2H), 2.35 (t, J=7.3 Hz, 2H), 2.19 (s, 6H), 1.98 (s, 1H), 1.83 (p, J=7.5 Hz, 2H), 1.69-1.59 (m, 4H), 1.48 (dd, J=10.3, 5.3 Hz, 2H), 1.29 (m, 62H), 0.98 (d, J=6.8 Hz, 3H), 0.92 (t, J=6.8 Hz, 6H).

DCPHB-C12βMe-OH-2-TG-oleate (Int-255):

Using the procedures described for the synthesis of Int-181, using 4-hydroxy-3,5-dichloro benzaldehyde instead of 4-hydroxy-3,5-dimethyl benzaldehyde, compounds Int-254 and Int-255 were prepared from Int-236:

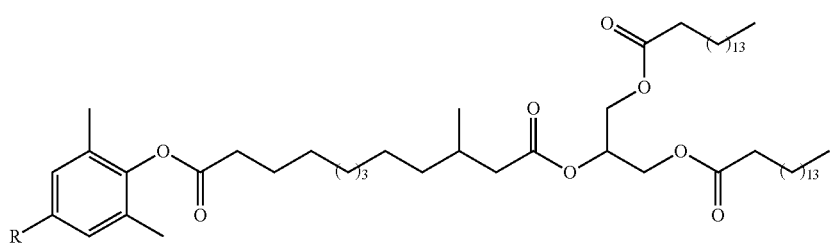

Int-248: R = C(O)H
Int-249: R = CH₂OH
Int-250: R = CH₂Br

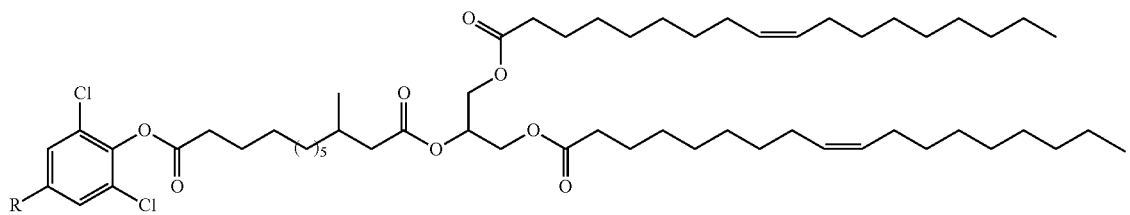

Int-254: R = C(O)H
Int-255: R = CH₂OH

DCPHB-C12βMe-aldehyde-2-TG-oleate (Int-254) $^1$H NMR (400 MHz, CDCl$_3$) δ 9.93 (s, 1H), 7.90 (s, 2H), 5.36-5.30 (m, 5H), 4.32-4.29 (dd, J=11.9, 6.0 Hz, 2H), 4.18-4.14 (dd, J=11.9, 6.0 Hz, 2H), 2.73 (m, 2H), 2.34-2.31 (m, 4H), 2.03 (m, 9H), 1.63 (m, 6H), 1.31 (m, 54H), 0.96 (m, 9H).

DCPHB-C12βMe-OH-2-TG-oleate (Int-255) $^1$H NMR (400 MHz, CDCl$_3$) δ 7.41 (s, 2H), 5.39-5.31 (m, 5H), 4.71 (s, 2H), 4.34 (dd, J=11.9, 6.0 Hz, 2H), 4.18 (dd, J=11.9, 6.0 Hz, 2H), 2.36 (m, 4H), 2.06 (m, 9H) 1.64 (m, 4H), 1.31 (m, 58H), 0.93 (m, 9H).

DCPHB-C12β'βMe-OH-2-TG-oleate (Int-258):
Using the procedures described for the synthesis of Int-181, using 4-hydroxy-3,5-dichloro benzaldehyde instead of 4-hydroxy-3,5-dimethyl benzaldehyde, compounds Int-257 and Int-258 were prepared from Int-174:

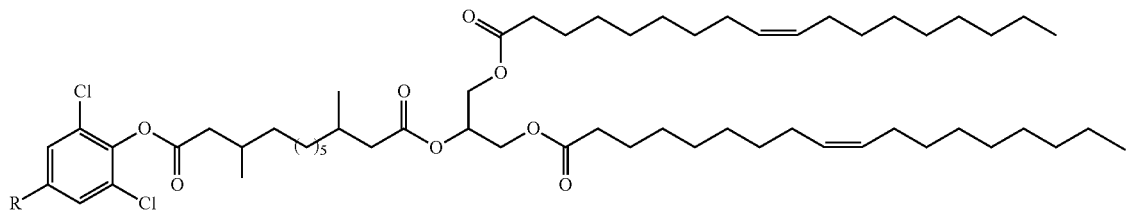

Int-257: R = C(O)H
Int-258: R = CH₂OH

DCPHB-C12β'βMe-aldehyde-2-TG-oleate (Int-257) $^1$H NMR (400 MHz, CDCl$_3$) δ 9.95 (s, 1H), 7.92 (s, 2H), 5.40-5.32 (m, 5H), 4.35-4.31 (dd, J=11.9, 6.0 Hz, 2H), 4.21-4.16 (dd, J=11.9, 6.0 Hz, 2H), 2.72 (m, 1H), 2.55 (m, 1H), 2.36 (m, 4H), 2.16 (m, 2H), 2.08 (m, 4H), 1.63 (m, 4H), 1.31 (m, 58H), 1.12 (m, J=6.8 Hz, 3H), 0.98 (m, J=6.8 Hz, 3H), 0.92 (m, 6H).

DCPHB-C12β'βMe-OH-2-TG-oleate (Int-258) $^1$H NMR (400 MHz, CDCl$_3$) δ 7.41 (s, 2H), 5.38-5.32 (m, 5H), 4.71 (s, 2H), 4.34 (dd, J=11.9, 6.0 Hz, 2H), 4.18 (dd, J=11.9, 6.0 Hz, 2H), 2.35 (m, 4H), 2.06 (m, 8H) 1.64 (m, 4H), 1.31 (m, 59H), 1.12 (d, J=6.4 Hz, 3H), 0.98 (d, J=6.4 Hz, 3H), 0.90 (m, 6H).

CDMPHB-(OPNP)-C10βMe-2-TG-oleate (Int-206):

Scheme 48. Synthesis of Int-206.

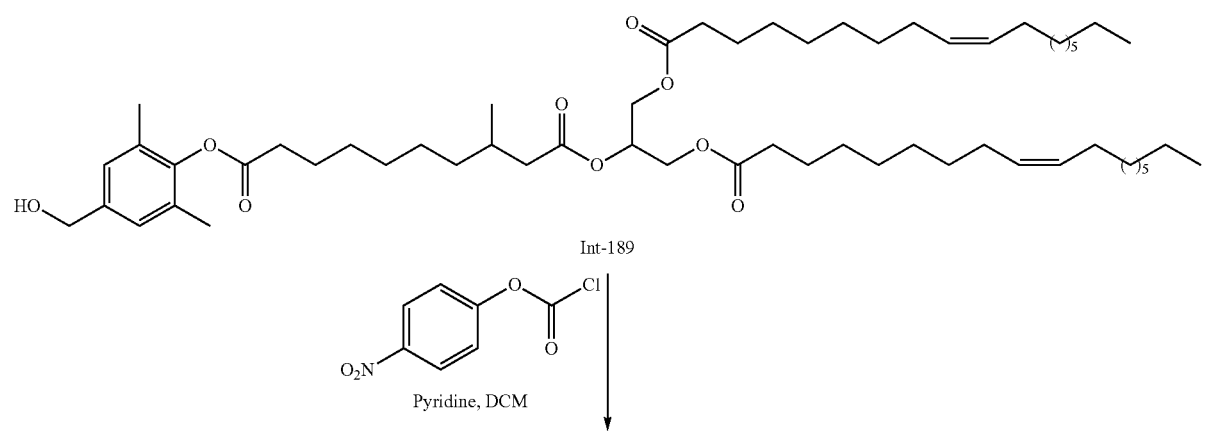

Int-189

Pyridine, DCM

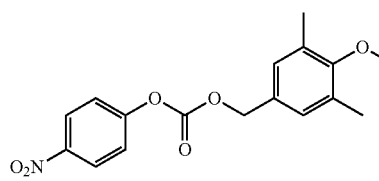 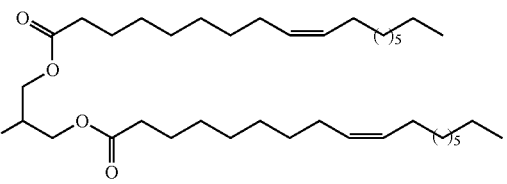

Int-206

Pyridine (0.52 mg, 6.63 mmol) was added dropwise to a stirred solution of Int-189 (2.4 g, 2.21 mmol) and 4-nitrophenylchloroformate (1.33 g, 6.63 mmol) in DCM (20 mL) at 0° C. The resulting reaction mixture was stirred at room temperature for 3 hours. The reaction mixture was concentrated then diluted with water (50 mL). The mixture was extracted with ethyl acetate (3×50 mL), and the combined organic layer was dried over sodium sulfate and concentrated under reduced pressure. The resulting oil was purified silica gel chromatography (9% ethyl acetate/hexanes) to afford Int-206 (1.5 g, 53%) as a yellowish oil. $^1$H NMR (400 MHz, CDCl$_3$) δ 8.33 (d, J=9.2 Hz, 2H), 7.44 (d, J=9.2 Hz, 2H), 7.19 (s, 2H) 5.38-5.32 (m, 5H), 5.25 (s, 2H), 4.35 (dd, J=12.0, 4.4 Hz, 2H), 4.21 (dd, J=12.0, 6.0 Hz, 2H), 2.66-2.63 (t, J=7.6 Hz, 2H), 2.40 (m, 4H), 2.20 (s, 6H), 2.05 (d, J=5.2 Hz, 8H), 1.84 (m, 2H), 1.61 (s, 4H), 1.46 (m, 2H), 1.33 (m, 46H), 0.98 (d, J=6.4 Hz, 3H), 0.93 (t, J=13.2 Hz, 9H).

CDMPHB-(OPNP)-C8βMe-2-TG-oleate (Int-207):

Using the procedures described for the synthesis of Int-206, compound Int-207 was prepared from Int-204:

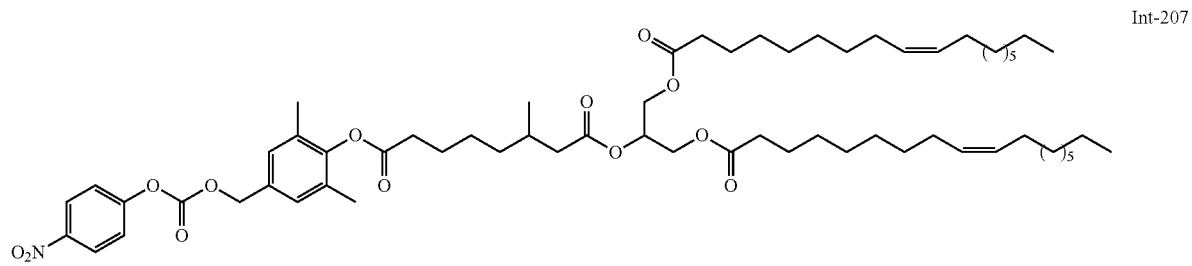

Int-207

$^1$H NMR (400 MHz, CDCl$_3$) δ 8.31 (d, J=8.8 Hz, 2H), 7.42 (d, J=8.8 Hz, 2H), 7.17 (s, 2H) 5.40-5.29 (m, 5H), 5.23 (s, 2H), 4.34 (dd, J=11.9, 4.3 Hz, 2H), 4.19 (dd, J=11.9, 5.9 Hz, 2H), 2.66-2.63 (m, 2H), 2.39 (m, 4H), 2.20 (s, 9H), 2.03 (m, 8H), 1.81 (s, 2H), 1.61 (m, 6H), 1.57 (m, 2H), 1.33 (m, 40H), 0.97 (d, J=6.4 Hz, 3H), 0.90 (t, J=6.8 Hz, 6H); $^{13}$C NMR (101 MHz, CDCl$_3$) δ 173.18 (2C), 172.19 (1C), 170.72 (1C), 155.58 (1C), 152.44 (1C), 148.87 (1C), 145.47 (1C), 131.57 (1C), 130.83 (2C), 130.03 (2C), 129.71 (2C), 129.11 (2C), 125.26 (2C), 121.77 (2C), 70.55 (1C), 68.93 (1C), 62.15 (2C), 41.66 (1C), 34.04 (2C), 33.98 (1C), 31.90 (2C), 30.55 (1C), 30.30 (1C), 29.77-29.11 (18C), 27.23 (2C), 27.18 (1C), 24.85 (2C), 22.66 (2C), 19.82 (1C), 19.54 (1C), 16.49 (2C), 14.19 (2C); MS (ESI, +ve) m/z: 1108.13 (M+18).

CDMPHB-(OPNP)-C10β'βMe-2-TG-oleate (Int-208):

Using the procedures described for the synthesis of Int-206, compound Int-208 was prepared from Int-183:

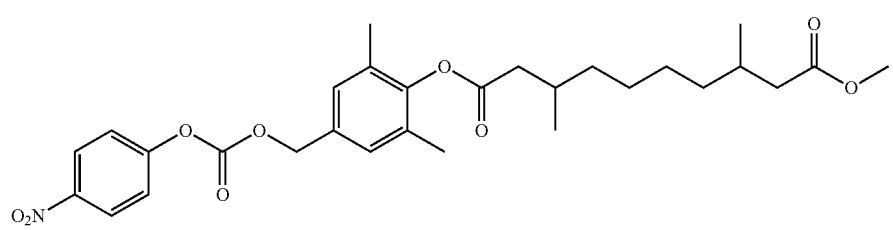

Int-208

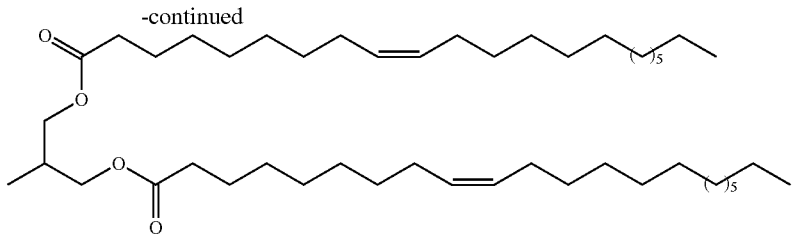

$^1$H NMR (400 MHz, CDCl$_3$) δ 8.31 (d, J=8.8 Hz, 2H), 7.42 (d, J=8.8 Hz, 2H), 7.19 (s, 2H) 5.38-5.32 (m, 5H), 5.25 (s, 2H), 4.34 (dd, J=11.9, 4.3 Hz, 2H), 4.19 (dd, J=11.9, 5.9 Hz, 2H), 2.64-2.63 (m, 1H), 2.48-2.46 (m, 2H), 2.36 (t, J=6.0 Hz, 5H), 2.21 (s, 6H), 2.14 (m, 2H), 2.04 (m, 6H), 1.65 (m, 4H), 1.33 (m, 50H), 1.09 (d, J=6.4 Hz, 3H), 0.97 (d, J=6.4 Hz, 3H), 0.90 (t, J=6.8 Hz, 6H); $^{13}$C NMR (101 MHz, CDCl$_3$) δ 173.18 (2C), 172.19 (1C), 170.72 (1C), 155.58 (1C), 152.44 (1C), 148.87 (1C), 145.47 (1C), 131.57 (1C), 130.83 (2C), 130.03 (2C), 129.71 (2C), 129.11 (2C), 125.26 (2C), 121.77 (2C), 70.55 (1C), 68.93 (1C), 62.15 (2C), 41.66 (1C), 34.04 (2C), 33.98 (1C), 31.90 (2C), 30.55 (1C), 30.30 (1C), 29.77-29.11 (20C), 27.23 (2C), 27.18 (2C), 24.85 (2C), 22.66 (2C), 19.82 (1C), 19.54 (1C), 16.49 (2C), 14.19 (2C); MS (ESI, +ve) m/z: 1150.15 (M+18).

CDMPHB-(OPNP)-C8β'βMe-2-TG-oleate (Int-209):
Using the procedures described for the synthesis of Int-206, compound Int-209 was prepared from Int-180:

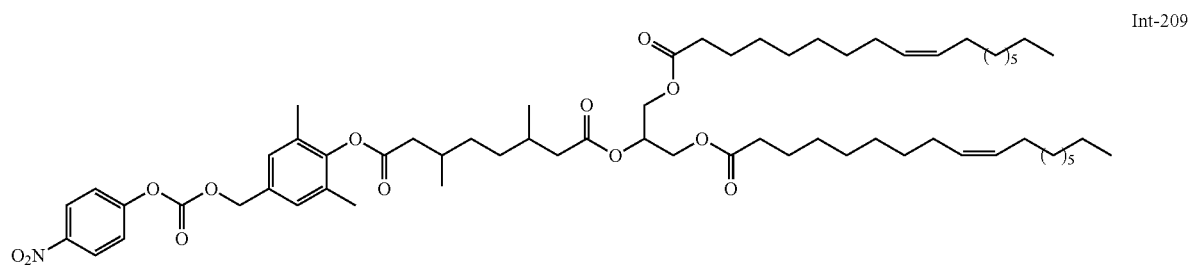

$^1$H NMR (400 MHz, CDCl$_3$) δ 8.31 (d, J=9.2 Hz, 2H), 7.41 (d, J=9.2 Hz, 2H), 7.17 (s, 2H), 5.41-5.30 (m, 5H), 5.23 (s, 2H), 4.34 (dd, J=11.9, 4.3 Hz, 2H), 4.19 (dd, J=11.9, 5.9 Hz, 2H), 2.66-2.61 (m, 1H), 2.48-2.45 (m, 1H), 2.36 (t, J=6.0 Hz, 4H), 2.15 (s, 6H), 2.03 (m, 6H), 1.58 (m, 4H), 1.24 (m, 50H), 1.08 (d, J=5.2 Hz, 3H), 0.98 (d, J=5.2 Hz, 3H), 0.90 (t, J=6.8 Hz, 6H); $^{13}$C NMR (101 MHz, CDCl$_3$) δ 173.20 (2C), 172.05 (1C), 170.61 (1C), 155.58 (1C), 152.44 (1C), 148.84 (1C), 145.47 (1C), 131.60 (1C), 130.81 (2C), 130.04 (2C), 129.71 (2C), 129.13 (2C), 125.28 (2C), 121.78 (2C), 70.55 (1C), 69.01 (1C), 62.13 (2C), 41.65 (1C), 34.04 (2C), 33.98 (1C), 31.90 (2C), 30.55 (1C), 30.51 (1C), 29.77-29.11 (19C), 27.24 (2C), 27.19 (1C), 24.85 (2C), 22.67 (2C), 19.90 (1C), 19.71 (1C), 16.51 (2C), 14.20 (2C); MS (ESI, +ve) m/z: 1122.06 (M+18).

CDMPHB-(OPNP)-C12α'βMe-2-TG (Int-225):
Using the procedures described for the synthesis of Int-206, compound Int-225 was prepared from Int-134:

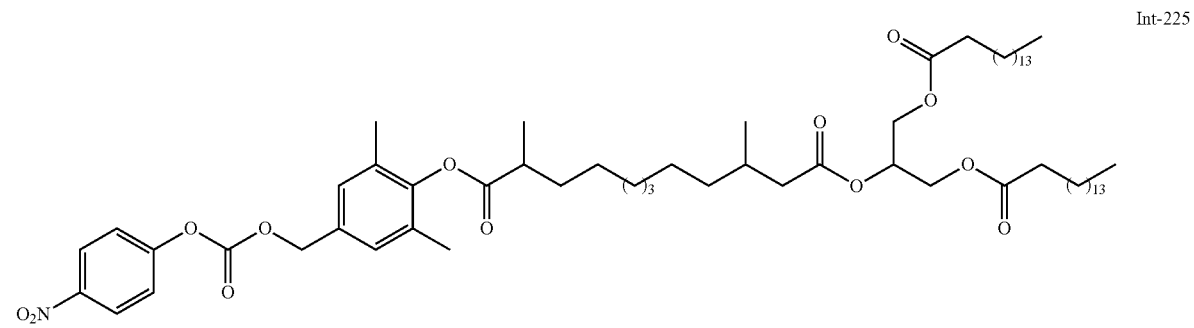

$^1$H NMR (401 MHz, CDCl$_3$) δ 8.29-8.24 (m, 2H), 7.41-7.35 (m, 2H), 7.14 (s, 2H), 5.27 (m, 1H), 5.21 (s, 2H), 4.29 (dd, J=11.9, 3.9 Hz, 2H), 4.14 (dd, J=11.9, 6.0 Hz, 2H), 2.74 (m, 1H), 2.33 (dd, J=14.8, 5.8 Hz, 1H), 2.30 (t, J=7.5 Hz, 4H), 2.16 (s, 6H), 2.12 (dd, J=14.8, 8.3 Hz, 1H), 1.99-1.81 (m, 2H), 1.66-1.50 (m, 5H), 1.47-1.17 (m, 60H), 1.35 (d, J=7.0 Hz, 3H), 0.93 (d, J=6.6 Hz, 3H), 0.87 (t, J=6.9 Hz, 6H); $^{13}$C NMR (101 MHz, CDCl$_3$) δ 174.4 (C), 173.4 (2C; C), 172.4 (C), 155.7 (C), 152.6 (C), 148.9 (C), 131.6 (C), 130.9 (2C; C), 129.3 (2C; CH), 125.4 (2C; CH), 121.9 (2C; CH), 70.7 (CH$_2$), 69.0 (CH), 62.3 (2C; CH$_2$), 41.8 (CH$_2$), 39.9 (CH), 36.8 (CH$_2$), 34.2 (2C; CH$_2$), 33.8 (CH$_2$), 32.1 (2C; CH$_2$), 30.5 (CH), 29.87 (CH$_2$), 29.83 (6C; CH$_2$), 29.79 (4C; CH$_2$), 29.75 (2C; CH$_2$), 29.66 (2C; CH$_2$), 29.60 (2C; CH$_2$), 29.5 (2C; CH$_2$), 29.4 (2C; CH$_2$), 29.3 (2C; CH$_2$), 27.5 (CH$_2$), 27.0 (CH$_2$), 25.0 (2C; CH$_2$), 22.8 (2C; CH$_2$), 19.7 (CH$_3$), 17.5 (CH$_3$), 16.6 (2C; CH$_3$), 14.2 (2C; CH$_3$).

CDMPHB-(OPNP)-C12α'βMe-2-TG-oleate (Int-242):

Using the procedures described for the synthesis of Int-206, compound Int-242 was prepared from Int-240:

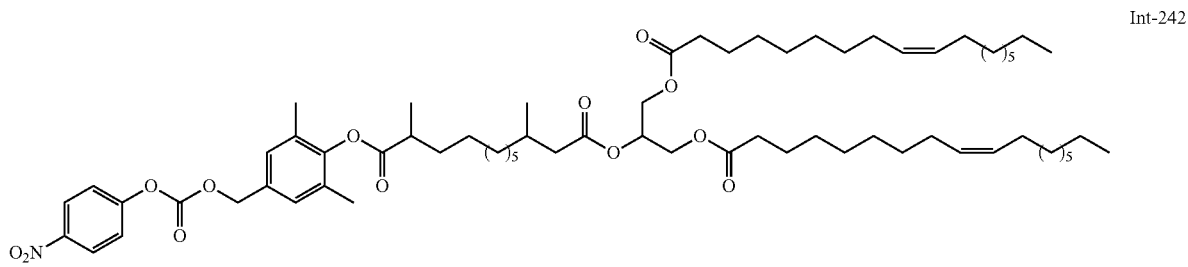

Int-242

$^1$H NMR (400 MHz, CDCl$_3$) δ 8.29 (d, J=9.2 Hz, 2H), 7.40 (d, J=9.2 Hz, 2H), 7.27 (s, 2H), 5.35-5.26 (m, 5H), 5.23 (s, 2H), 4.32-4.28 (dd, J=11.9, 4.3 Hz, 2H), 4.18-4.13 (dd, J=11.9, 6.0 Hz, 2H), 2.75 (m, 1H), 2.34 (t, J=7.4 Hz, 5H), 2.17 (s, 6H), 2.03 (p, J=7.2, 6.6 Hz, 8H), 1.86 (m, 2H), 1.63 (q, J=7.3 Hz, 4H), 1.49-1.09 (m, 57H), 0.95 (d, J=6.8 Hz, 3H), 0.89 (t, J=6.8 Hz, 6H); $^{13}$C NMR (101 MHz, CDCl$_3$) δ 173.35 (2C), 172.38 (1C), 171.46 (1C), 155.55 (1C), 152.46 (1C), 148.80 (1C), 145.42 (1C), 131.52 (1C), 130.84 (1C), 129.19 (2C), 125.27 (2C), 121.78 (2C), 70.60 (1C), 68.83 (1C), 62.17 (2C), 41.73 (1C), 36.71 (1C), 34.08 (2C), 31.97 (2C), 30.39 (1C), 29.74-29.16 (27C), 27.24 (2C), 27.19 (2C), 26.76 (1C), 25.07 (1C), 24.89 (2C), 22.74 (2C), 19.59 (1C), 16.45 (2C), 14.17 (2C); MS (ESI, +ve) m/z: 1178.26 (M+18).

CDMPHB-(OPNP)-C12βMe-2-TG-oleate (Int-246):

Using the procedures described for the synthesis of Int-206, compound Int-246 was prepared from Int-244:

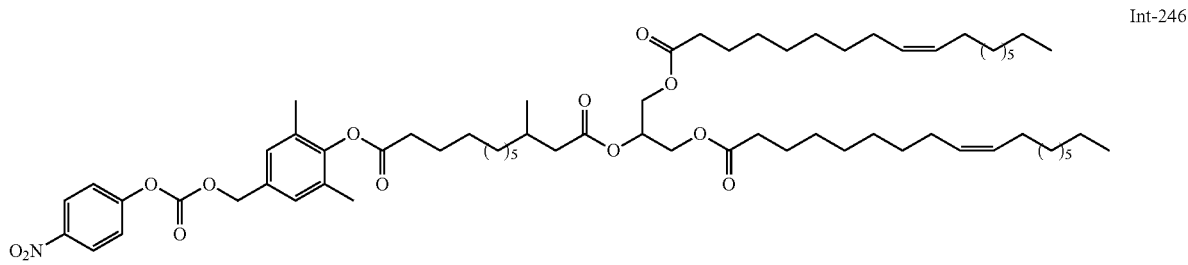

Int-246

$^1$H NMR (400 MHz, CDCl$_3$) δ 8.32 (d, J=8.7 Hz, 2H), 7.42 (d, J=8.9 Hz, 2H), 7.19 (s, 2H), 5.38-5.32 (m, 5H), 5.25 (s, 2H), 4.33 (dd, J=12.0, 4.4 Hz, 2H), 4.18 (dd, J=12.0, 6.0 Hz, 2H), 2.65 (t, J=7.6 Hz, 2H), 2.35 (t, J=7.4 Hz, 5H), 2.20 (s, 6H), 2.04 (q, J=6.6 Hz, 8H), 1.83 (p, J=7.5 Hz, 2H), 1.71-1.52 (m, 4H), 1.52-1.02 (m, 54H), 0.95 (d, J=6.4 Hz, 3H), 0.89 (t, J=6.8 Hz, 6H); $^{13}$C NMR (101 MHz, CDCl$_3$) δ 174.25 (1C), 173.20 (2C), 172.26 (1C), 155.56 (1C), 152.44 (1C), 148.82 (1C), 145.45 (1C), 131.55 (1C), 130.83 (1C), 130.02 (2C), 129.71 (2C), 129.11 (2C), 125.27 (2C), 121.78 (2C), 70.57 (1C), 68.88 (1C), 62.17 (2C), 41.70 (1C), 39.77 (1C), 36.70 (1C), 34.04 (2C), 33.65 (1C), 31.91 (2C), 30.36 (1C), 29.78-29.11 (19C), 27.41 (1C), 27.23 (2C), 27.19 (2C), 26.91 (1C), 24.86 (2C), 22.68 (2C), 19.57 (1C), 17.37 (1C), 16.39 (2C), 14.09 (2C); MS (ESI, +ve) m/z: 1164.16 (M+18).

CDMPHB-(OPNP)-C12βMe-2-TG (Int-251):
Using the procedures described for the synthesis of Int-206, compound Int-251 was prepared from Int-249:

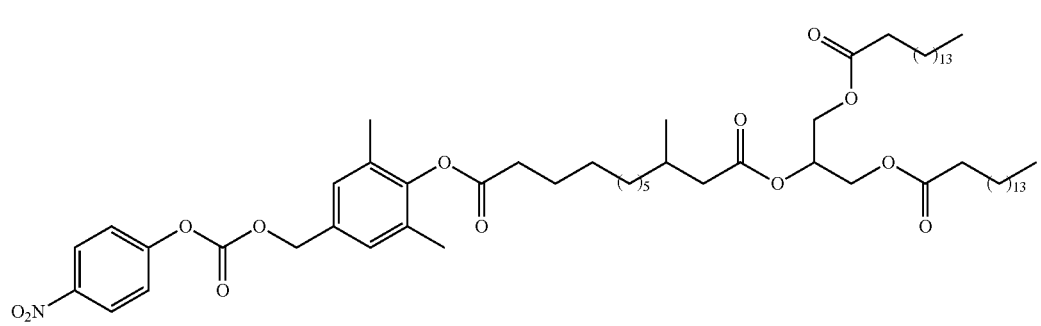
Int-251

¹H NMR (400 MHz, CDCl₃) δ 8.32 (d, J=8.7 Hz, 2H), 7.43 (d, J=8.9 Hz, 2H), 7.20 (s, 2H), 5.32 (s, 2H), 5.26 (m, 1H), 4.33 (dd, J=11.9, 4.3 Hz, 2H), 4.19 (dd, J=11.9, 6.0 Hz, 2H), 2.67 (t, J=7.4 Hz, 2H), 2.36 (t, J=7.3 Hz, 2H), 2.22 (s, 6H), 1.98 (m, 2H), 1.84 (m, 2H), 1.60 (m, 5H), 1.29 (m, 62H), 0.98 (d, J=6.8 Hz, 3H), 0.92 (t, J=6.8 Hz, 6H); ¹³C NMR (101 MHz, CDCl₃) δ 173.35 (2C), 172.38 (1C), 171.46 (1C), 155.55 (1C), 152.46 (1C), 148.80 (1C), 145.42 (1C), 131.52 (1C), 130.84 (1C), 129.19 (2C), 125.33 (2C), 121.84 (2C), 70.60 (1C), 68.83 (1C), 62.17 (1C), 41.73 (1C), 36.71 (1C), 34.08 (2C), 31.97 (2C), 30.39 (1C), 29.74-29.16 (27C), 26.95 (1C), 25.15 (1C), 24.89 (2C), 22.74 (2C), 19.59 (1C), 16.45 (2C), 14.17 (2C); MS (ESI, +ve) m/z: 1112.05 (M+18).

CDMPHB-(OPNP)-C10βMe-2-TG (Int-253):
Using the procedures described for the synthesis of Int-206, compound Int-253 was prepared from Int-146:

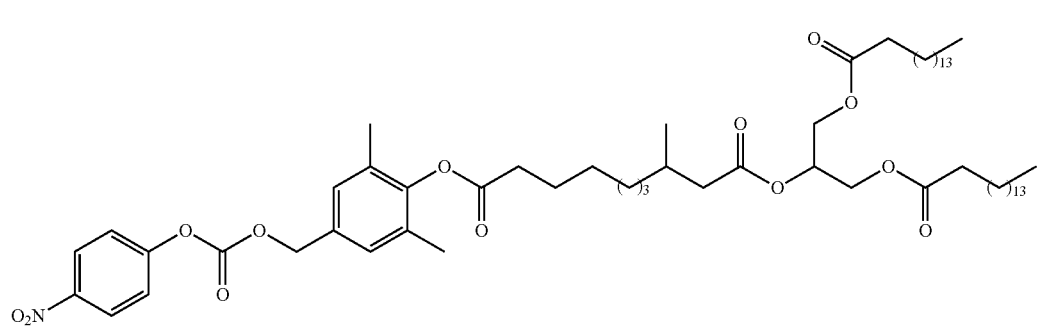
Int-253

¹H NMR (401 MHz, CDCl₃) δ 8.30-8.24 (m, 2H), 7.41-7.35 (m, 2H), 7.15 (s, 2H), 5.27 (m, 1H), 5.21 (s, 2H), 4.29 (dd, J=12.0, 4.1 Hz, 2H), 4.15 (dd, J=11.9, 6.0 Hz, 2H), 2.61 (t, J=7.6 Hz, 2H), 2.33 (dd, J=14.7, 5.8 Hz, 1H), 2.31 (t, J=7.4 Hz, 4H), 2.16 (s, 6H), 2.13 (dd, J=14.7, 8.3 Hz, 1H), 1.95 (m, 1H), 1.84-1.74 (m, 2H), 1.65-1.55 (m, 4H), 1.49-1.16 (m, 56H), 0.94 (d, J=6.6 Hz, 3H), 0.88 (t, J=6.9 Hz, 6H).

CDCPHB-(OPNP)-C12βMe-2-TG-oleate (Int-256):

Using the procedures described for the synthesis of Int-206, compound Int-256 was prepared from Int-255:

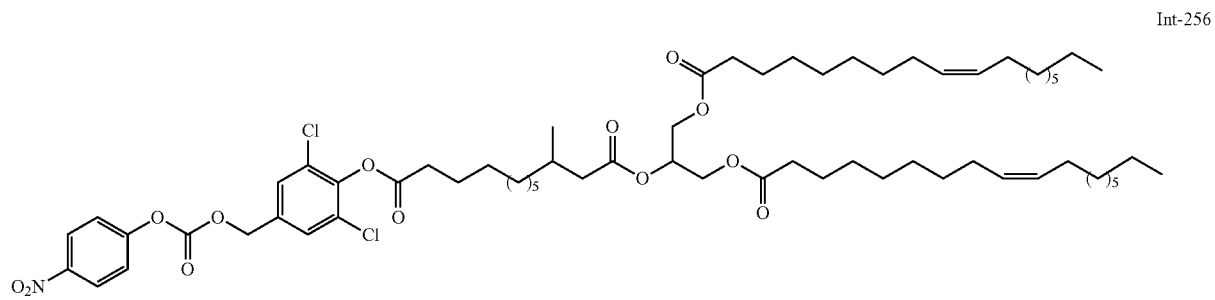
Int-256

¹H NMR (400 MHz, CDCl₃) δ 8.35-8.32 (d, J=8.8 Hz, 2H), 7.49 (m, 4H), 5.34 (m, 5H), 5.26 (s, 2H), 4.35-4.31 (dd, J=11.9, 4.3 Hz, 2H), 4.20-4.16 (dd, J=11.9, 5.9 Hz, 2H), 2.73 (t, J=7.6 Hz, 2H), 2.38 (m, 6H), 2.05 (m, 9H), 1.30 (m, 58H), 0.93 (m, 9H).

CDCPHB-(OPNP)-C12β'βMe-2-TG-oleate (Int-259):

Using the procedures described for the synthesis of Int-206, compound Int-259 was prepared from Int-258:

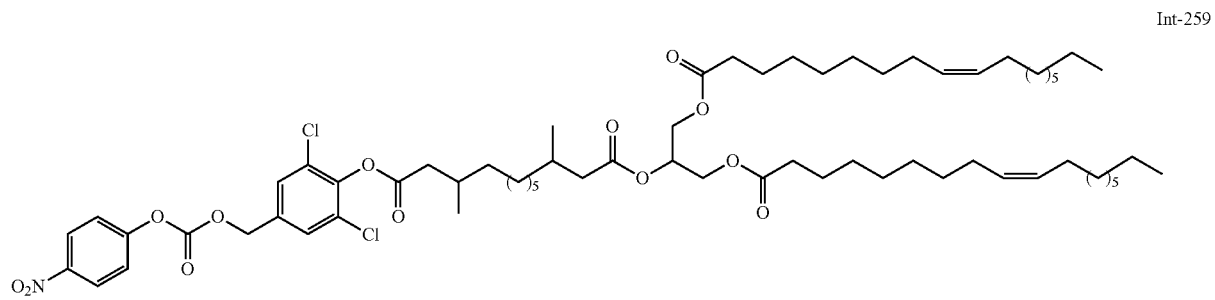
Int-259

¹H NMR (400 MHz, CDCl₃) δ 8.33-8.30 (d, J=9.2 Hz, 2H), 7.51 (m, 4H), 5.31 (m, 5H), 5.24 (s, 2H), 4.33-4.29 (dd, J=11.9, 4.3 Hz, 2H), 4.18-4.11 (dd, J=11.9, 5.9 Hz, 2H), 2.71 (m, 1H), 2.50 (m, 1H), 2.38 (m, 6H), 2.15 (m, 2H), 2.06 (m, 8H), 1.30 (m, 56H), 1.11 (d, J=6.4 Hz, 3H), 0.96 (d, J=6.8 Hz, 3H), 0.88 (m, 6H).

CPHB-(OPNP)-C10-2-TG (Int-274):

Using the procedures described for the synthesis of Int-206, compound Int-274 was prepared from Int-272:

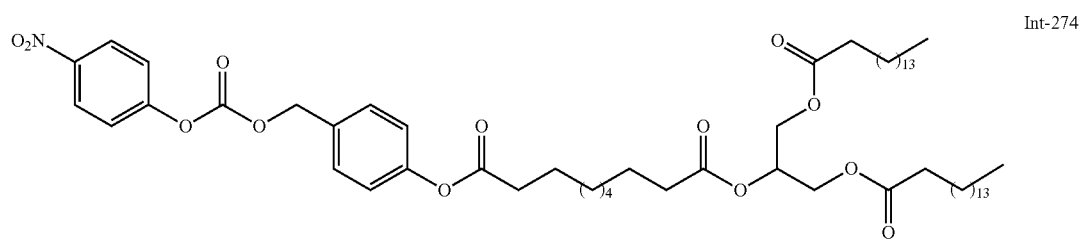
Int-274

$^1$H NMR (400 MHz, CDCl$_3$) δ 8.30-8.23 (m, 2H), 7.49-7.43 (m, 2H), 7.41-7.35 (m, 2H), 7.15-7.09 (m, 2H), 5.28 (s, 2H), 5.26 (m, 1H), 4.30 (dd, J=11.9, 4.3 Hz, 2H), 4.15 (dd, J=11.9, 5.9 Hz, 2H), 2.56 (t, J=7.5 Hz, 2H), 2.32 (t, J=7.5 Hz, 2H), 2.31 (t, J=7.5 Hz, 4H), 1.79-1.71 (m, 2H), 1.66-1.55 (m, 6H), 1.45-1.20 (m, 56H), 0.87 (t, J=6.9 Hz, 6H); $^{13}$C NMR (101 MHz, CDCl$_3$) δ 173.5 (2C; C), 173.0 (C), 172.3 (C), 155.6 (C), 152.6 (C), 151.4 (C), 145.5 (C), 131.8 (C), 130.2 (2C; CH), 125.4 (2C; CH), 122.2 (2C; CH), 121.9 (2C; CH), 70.4 (CH$_2$), 69.0 (CH), 62.2 (2C; CH$_2$), 34.5 (CH$_2$), 34.3 (CH$_2$), 34.2 (2C; CH$_2$), 32.1 (2C; CH$_2$), 29.82 (6C; CH$_2$), 29.78 (4C; CH$_2$), 29.75 (2C; CH$_2$), 29.6 (2C; CH$_2$), 29.5 (2C; CH$_2$), 29.4 (2C; CH$_2$), 29.24 (2C; CH$_2$), 29.21 (2C; CH$_2$), 29.17 (CH$_2$), 29.11 (CH$_2$), 24.98 (2C; CH$_2$), 24.96 (CH$_2$), 24.94 (CH$_2$), 22.8 (2C; CH$_2$), 14.3 (2C; CH$_3$).

C10-acid-2-TG-oleate (Int-275):

Scheme 48-A. Synthesis of Int-275.

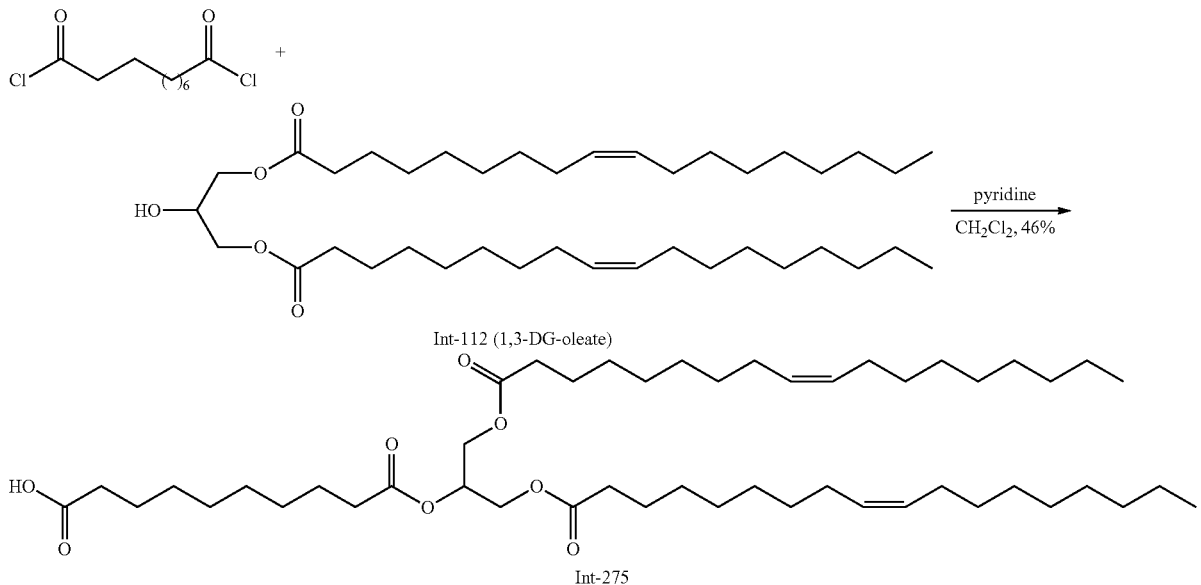

Sebacoyl chloride (0.86 mL, 4.03 mmol) was added to a mixture of Int-112 (500 mg, 0.81 mmol) and pyridine (0.65 mL, 8.05 mmol) in CH$_2$Cl$_2$ (5.0 mL). The resulting mixture was stirred at room temperature for 2 hours before being acidified using aqueous 2N HCl. The volatiles were removed in vacuo and the mixture was extracted with ethyl acetate. The combined organic layers were dried over sodium sulfate, filtered and concentrated in vacuo. The residue was purified by normal phase flash column chromatography on silica gel (Biotage Isolera, 40 g, Siliasep cartridge) using n-heptane and EtOAc (gradient: 1:0 to 2:3) to give Int-275 (298 mg, 46%) as a colourless oil. UPLC4_AP-MS: (BEHβ Long Acidic 70 to 95): R$_t$=3.53 min., 96% (ELS). MS (ESIpos) m/z=822.8 (M+H$_2$O+H)$^+$. $^1$H NMR (400 MHz, CDCl$_3$): δ(ppm)=5.40-5.22 (m, 5H), 4.29 (dd, J=4.4, 11.9 Hz, 2H), 4.14 (dd, J=5.9, 11.9 Hz, 2H), 2.46-2.26 (m, 9H), 2.06-1.96 (m, 7H), 1.68-1.53 (m, 9H), 1.40-1.18 (m, 51H), 0.87 (t, J=6.8 Hz, 6H). $^{13}$C NMR (100 MHz, CDCl$_3$): δ(ppm)=179.3, 173.42, 173.40, 173.0, 172.9, 169.6, 130.1, 129.8, 69.0, 62.2, 35.4, 34.3, 34.2, 34.0, 32.0, 29.9, 29.83, 29.79, 29.75, 29.7, 29.5, 29.3, 29.24, 29.21, 29.17, 29.11, 29.10, 29.0, 27.4, 27.3, 25.0, 24.8, 24.3, 22.8, 14.2.

C6-acid-2-TG-oleate (Int-276):

Scheme 49. Synthesis of Int-276.

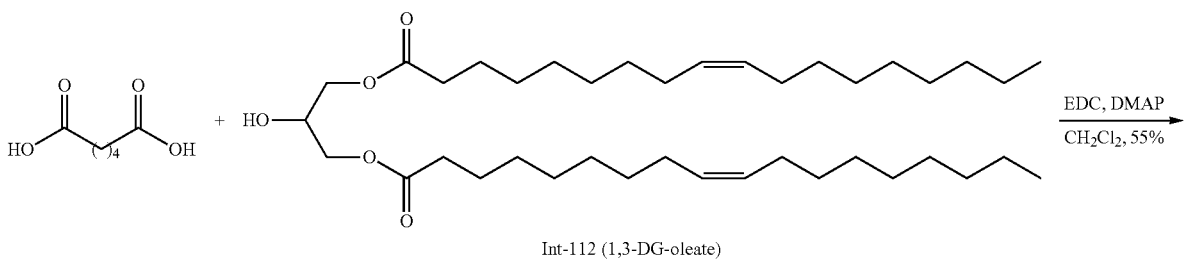

-continued

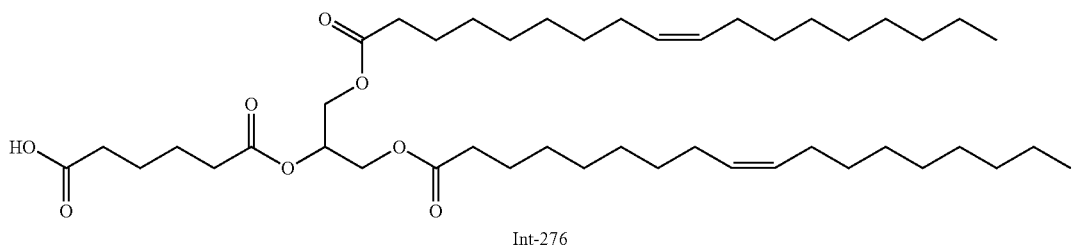

Int-276

4-(Dimethylamino)pyridine (59.0 mg, 0.483 mmol) and N—(3-dimethylamino-propyl)-N'-ethyl-carbodiimide (EDC·HCl, 232 mg, 1.21 mmol) were added to a solution of adipic acid (141 mg, 0.966 mmol) and Int-112 (300 mg, 0.483 mmol) in $CH_2Cl_2$ (15 mL) and the mixture stirred at rt for 40 minutes. The reaction was diluted with $CH_2Cl_2$ (15 mL), silica gel was added and the mixture concentrated under reduced pressure. Purification by silica gel chromatography (10% to 20% ethyl acetate/hexanes) gave Int-276 (199 mg, 55%) as a colourless oil; $^1$H NMR (401 MHz, $CDCl_3$) δ 5.40-5.22 (m, 5H), 4.30 (dd, J=11.9, 4.3 Hz, 2H), 4.14 (dd, J=12.1, 5.7 Hz, 2H), 2.41-2.33 (m, 4H), 2.31 (t, J=7.6 Hz, 4H), 2.05-1.97 (m, 8H), 1.71-1.55 (m, 8H), 1.41-1.17 (m, 40H), 0.88 (t, J=6.9 Hz, 6H); $^{13}$C NMR (101 MHz, $CDCl_3$) δ 173.5 (2C; C), 172.4 (C), 130.2 (2C; CH), 129.9 (2C; CH), 69.3 (CH), 62.2 (2C; $CH_2$), 34.1 (3C; $CH_2$), 33.8 ($CH_2$), 32.0 (2C; $CH_2$), 29.9 (2C; $CH_2$), 29.8 (2C; $CH_2$), 29.7 (2C; $CH_2$), 29.5 (4C; $CH_2$), 29.31 (2C; $CH_2$), 29.25 (2C; $CH_2$), 29.2 (2C; $CH_2$), 27.4 (2C; $CH_2$), 27.3 (2C; $CH_2$), 25.0 (2C; $CH_2$), 24.3 ($CH_2$), 24.1 ($CH_2$), 22.8 (2C; $CH_2$), 14.3 (2C; $CH_3$); Note: The signal for the carboxylic acid carbonyl group was not observed in the $^{13}$C NMR spectrum.

C8-acid-2-TG-oleate (Int-277):

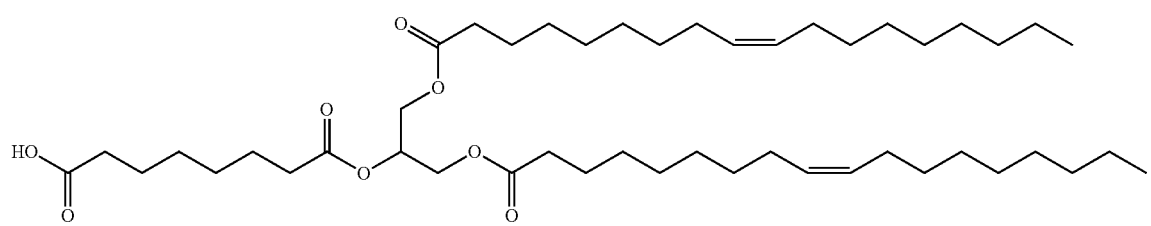

Int-277

Using similar methods as described for the synthesis of Int-276, Int-277 was prepared from suberic acid and Int-112. Purification by silica gel chromatography (10% to 20% ethyl acetate/hexanes) gave Int-277 (166 mg, 66%) as a colourless oil; $^1$H NMR (401 MHz, $CDCl_3$) δ 5.40-5.20 (m, 5H), 4.29 (dd, J=11.9, 4.4 Hz, 2H), 4.14 (dd, J=11.9, 5.9 Hz, 2H), 2.37-2.27 (m, 8H), 2.08-1.94 (m, 8H), 1.69-1.54 (m, 8H), 1.43-1.19 (m, 44H), 0.88 (t, J=6.9 Hz, 6H); $^{13}$C NMR (101 MHz, $CDCl_3$) δ 179.7 (C), 173.4 (2C; C), 172.8 (C), 130.1 (2C; CH), 129.8 (2C; CH), 69.0 (CH), 62.1 (2C; $CH_2$), 34.10 ($CH_2$), 34.08 (2C; $CH_2$), 34.0 ($CH_2$), 32.0 (2C; $CH_2$), 29.84 (2C; $CH_2$), 29.77 (2C; $CH_2$), 29.6 (2C; $CH_2$), 29.4 (4C; $CH_2$), 29.24 (2C; $CH_2$), 29.18 (2C; $CH_2$), 29.15 (2C; $CH_2$), 28.74 ($CH_2$), 28.72 ($CH_2$), 27.3 (2C; $CH_2$), 27.2 (2C; $CH_2$), 24.9 (2C; $CH_2$), 24.7 ($CH_2$), 24.5 ($CH_2$), 22.8 (2C; $CH_2$), 14.2 (2C; $CH_3$).

DMPHB(OH)-C5bMe-2-TG-oleate (Int-279):

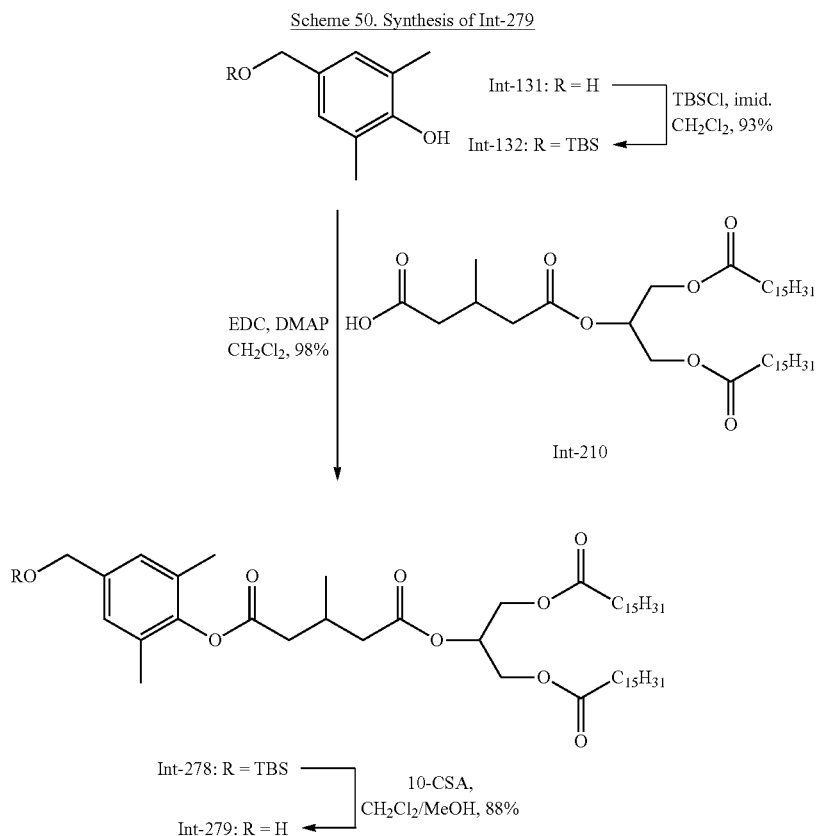

4-(Dimethylamino)pyridine (DMAP, 34.4 mg, 0.282 mmol) and EDC·HCl (108 mg, 0.563 mmol) were added to a solution of Int-210 (211 mg, 0.282 mmol) and Int-132 (75.0 mg, 0.282 mmol) in $CH_2Cl_2$ (15 mL) and the mixture stirred at rt for 17 hours. The reaction was diluted with $CH_2Cl_2$ (10 mL), silica gel was added and the mixture concentrated under reduced pressure. Purification by silica gel chromatography (6% to 10% ethyl acetate/hexanes) gave Int-278 (276 mg, 98%) as a colourless oil; $^1$H NMR (401 MHz, $CDCl_3$) δ 7.00 (s, 2H), 5.40-5.26 (m, 5H), 4.65 (s, 2H), 4.32 (dd, J=11.8, 4.0 Hz, 2H), 4.15 (dd, J=11.9, 6.0 Hz, 2H), 2.71 (dd, J=14.9, 5.4 Hz, 1H), 2.66-2.49 (m, 3H), 2.37 (dd, J=15.1, 7.4 Hz, 1H), 2.30 (t, J=7.5 Hz, 4H), 2.13 (s, 6H), 2.08-1.93 (m, 8H), 1.67-1.53 (m, 4H), 1.40-1.18 (m, 40H), 1.15 (d, J=6.4 Hz, 3H), 0.94 (s, 9H), 0.88 (t, J=6.9 Hz, 6H), 0.10 (s, 6H); $^{13}$C NMR (101 MHz, $CDCl_3$) δ 173.4 (2C; C), 171.4 (C), 170.2 (C), 147.0 (C), 139.0 (C), 130.1 (2C; CH), 129.9 (2C; CH), 129.8 (2C; C), 126.4 (2C; CH), 69.4 (CH), 64.6 ($CH_2$), 62.2 (2C; $CH_2$), 40.7 ($CH_2$), 40.3 ($CH_2$), 34.1 (2C; $CH_2$), 32.0 (2C; $CH_2$), 29.9 (2C; $CH_2$), 29.8 (2C; $CH_2$), 29.7 (2C; $CH_2$), 29.5 (4C; $CH_2$), 29.30 (2C; $CH_2$), 29.25 (2C; $CH_2$), 29.22 (2C; $CH_2$), 27.5 (CH), 27.4 (2C; $CH_2$), 27.3 (2C; $CH_2$), 26.1 (3C; $CH_3$), 25.0 (2C; $CH_2$), 22.8 (2C; $CH_2$), 19.9 ($CH_3$), 16.7 (2C; $CH_3$), 14.3 (2C; $CH_3$), −5.1 (2C; $CH_3$).

10-Camphorsulfonic acid (13.0 mg, 0.0547 mmol) was added to Int-278 (273 mg, 0.274 mmol) in $CH_2Cl_2$ (3 mL) and MeOH (3 mL) and the mixture was stirred at rt for one hour. The reaction was diluted with $CH_2Cl_2$ (40 mL), washed with sat. aq. $NaHCO_3$ and brine (40 mL each), dried ($MgSO_4$) and concentrated under reduced pressure to give the crude product. Purification by silica gel chromatography (20% ethyl acetate/hexanes) gave Int-279 (213 mg, 88%) as a colourless oil; $^1$H NMR (401 MHz, $CDCl_3$) δ 7.05 (s, 2H), 5.39-5.25 (m, 5H), 4.58 (s, 2H), 4.312/4.310 (each dd, J=11.9, 4.2 Hz, 2H), 4.138/4.134 (each dd, J=11.9, 6.0 Hz, 2H), 2.72 (dd, J=14.9, 5.2 Hz, 1H), 2.65-2.48 (m, 3H), 2.36 (dd, J=15.2, 7.2 Hz, 1H), 2.30 (t, J=7.6 Hz, 4H), 2.13 (s, 6H), 2.06-1.93 (m, 8H), 1.65-1.54 (m, 4H), 1.39-1.18 (m, 40H), 1.14 (d, J=6.4 Hz, 3H), 0.87 (t, J=6.9 Hz, 6H); $^{13}$C NMR (101 MHz, $CDCl_3$) δ 173.3 (2C; C), 171.4 (C), 170.1 (C), 147.6 (CH), 138.6 (CH), 130.2 (2C; CH), 130.1 (2C; CH), 129.8 (2C; CH), 127.3 (2C; CH), 69.3 (CH), 64.9 ($CH_2$), 62.2 (2C; $CH_2$), 40.7 ($CH_2$), 40.2 ($CH_2$), 34.1 (2C; $CH_2$), 32.0 (2C; $CH_2$), 29.9 (2C; $CH_2$), 29.8 (2C; $CH_2$), 29.6 (2C; $CH_2$), 29.4 (4C; $CH_2$), 29.3 (2C; $CH_2$), 29.20 (2C; $CH_2$), 29.17 (2C; $CH_2$), 27.5 (CH), 27.31 (2C; $CH_2$), 27.26 (2C; $CH_2$), 24.9 (2C; $CH_2$), 22.8 (2C; $CH_2$), 19.8 ($CH_3$), 16.6 (2C; $CH_3$), 14.2 (2C; $CH_3$).

TML-C5bMe-acid-2-TG (Int-154):

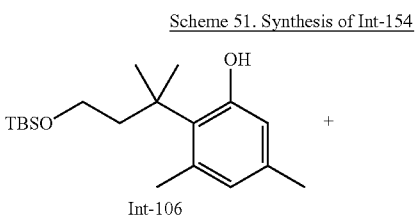

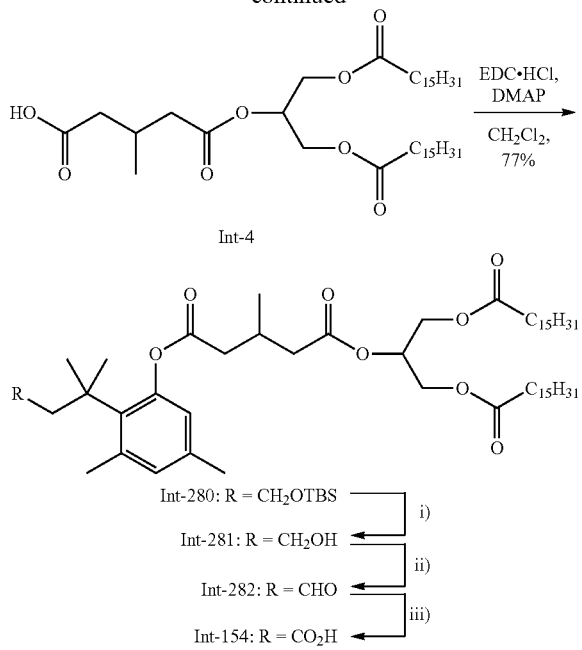

i) 10-CSA, CH$_2$Cl$_2$/MeOH, 89%
ii) PCC, CH$_2$Cl$_2$;
iii) KMnO$_4$, acetone/H$_2$O, 80% (2 steps)

4-(Dimethylamino)pyridine (DMAP, 3.4 mg, 27.8 µmol) and EDC·HCl (13.2 mg, 69.6 µmol) were added to a solution of Int-4 (19.4 mg, 27.8 µmol) and Int-106 (10.8 mg, 33.4 µmol) in CH$_2$Cl$_2$ (1 mL) and the mixture stirred at rt for three days. The reaction was diluted with CH$_2$Cl$_2$ (5 mL), silica gel was added and the mixture concentrated under reduced pressure. Purification by silica gel chromatography (5% to 7.5% ethyl acetate/hexanes) gave Int-280 (21.4 mg, 77%) as a colourless oil; $^1$H NMR (400 MHz, CDCl$_3$) δ 6.80 (d, J=1.8 Hz, 1H), 6.52 (d, J=1.7 Hz, 1H), 5.30 (m, 1H), 4.316 (dd, J=11.9, 4.2 Hz, 1H), 4.310 (dd, J=11.9, 4.2 Hz, 1H), 4.14 (dd, J=11.9, 6.0 Hz, 2H), 3.49 (t, J=7.3 Hz, 2H), 2.67-2.43 (m, 4H), 2.51 (s, 3H), 2.34 (dd, J=14.9, 7.2 Hz, 1H), 2.31 (t, J=7.3 Hz, 4H), 2.22 (s, 3H), 2.02 (t, J=7.8 Hz, 2H), 1.66-1.54 (m, 4H), 1.45 (s, 6H), 1.35-1.18 (m, 48H), 1.13 (d, J=6.4 Hz, 3H), 0.88 (t, J=6.8 Hz, 6H), 0.84 (s, 9H), −0.03 (s, 6H); $^{13}$C NMR (101 MHz, CDCl$_3$) δ 173.4 (2C; C), 171.5 (C), 171.4 (C), 149.7 (C), 138.5 (C), 136.1 (C), 134.2 (C), 132.5 (CH), 123.1 (CH), 69.3 (CH), 62.2 (2C; CH$_2$), 60.9 (CH$_2$), 46.1 (CH$_2$), 41.3 (CH$_2$), 40.7 (CH$_2$), 39.1 (C), 34.2 (2C; CH$_2$), 32.1 (2C; CH$_2$), 32.0 (2C; CH$_3$), 29.84 (6C; CH$_2$), 29.81 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 27.3 (CH), 26.1 (3C; CH$_3$), 25.4 (CH$_3$), 25.0 (2C; CH$_2$), 22.8 (2C; CH$_2$), 20.3 (CH$_3$), 19.9 (CH$_3$), 18.4 (C), 14.3 (2C; CH$_3$), −5.2 (2C; CH$_3$); ESI-HRMS: calcd. for C$_{60}$H$_{108}$NaO$_9$Si [M+Na$^+$] 1023.7655; found 1023.7643.

10-Camphorsulfonic acid (1.5 mg, 6.29 µmol) was added to Int-280 (21.0 mg, 21.0 µmol) in CH$_2$Cl$_2$ (0.5 mL) and MeOH (0.5 mL) and the mixture stirred at rt for one hour. The reaction was diluted with water (5 mL) and the aqueous layer extracted with ethyl acetate (3×15 mL). The combined organic extracts were washed with sat. aq. NaHCO$_3$ and brine (30 mL each), dried (MgSO$_4$) and concentrated under reduced pressure to give the crude product. Purification by silica gel chromatography (10% to 20% ethyl acetate/hexanes) gave Int-281 (16.5 mg, 89%) as a colourless oil; $^1$H NMR (400 MHz, CDCl$_3$) δ 6.82 (dd, J=1.4, 0.5 Hz, 1H), 6.53 (d, J=1.4 Hz, 1H), 5.29 (m, 1H), 4.317 (dd, J=11.9, 4.3 Hz, 1H), 4.314 (dd, J=11.9, 4.3 Hz, 1H), 4.15 (dd, J=11.9, 6.0 Hz, 1H), 3.53 (t, J=7.3 Hz, 2H), 2.72-2.45 (m, 4H), 2.52 (s, 3H), 2.37 (dd, J=15.2, 7.0 Hz, 1H), 2.33-2.27 (m, 4H), 2.23 (s, 3H), 2.05 (td, J=7.1, 2.5 Hz, 2H), 1.66-1.55 (m, 4H), 1.48 (s, 3H), 1.47 (s, 3H), 1.36-1.19 (m, 48H), 1.13 (d, J=6.5 Hz, 3H), 0.88 (t, J=6.9 Hz, 6H); $^{13}$C NMR (101 MHz, CDCl$_3$) δ 173.5 (2C; C), 171.8 (C), 171.5 (C), 149.7 (C), 138.6 (C), 136.3 (C), 133.9 (C), 132.6 (CH), 123.3 (CH), 69.4 (CH), 62.2 (2C; CH$_2$), 60.6 (CH$_2$), 45.9 (CH$_2$), 41.3 (CH$_2$), 40.7 (CH$_2$), 39.2 (C), 34.2 (2C; CH$_2$), 32.14 (CH$_3$), 32.11 (CH$_3$), 32.07 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 27.3 (CH), 25.5 (CH$_3$), 25.0 (2C; CH$_2$), 22.8 (2C; CH$_2$), 20.3 (CH$_3$), 20.0 (CH$_3$), 14.3 (2C; CH$_3$); ESI-HRMS: calcd. for C$_{54}$H$_{94}$NaO$_9$ [M+Na$^+$] 909.6790; found 909.6822.

Pyridinium chlorochromate (PCC, 7.8 mg, 36.1 µmol) was added to a suspension of Int-281 (16.0 mg, 18.0 µmol) and Celite (10 mg) in CH$_2$Cl$_2$ (1 mL) at 0° C. and the mixture stirred at rt for 2.5 hours. The reaction was filtered through a short pad of silica gel, eluting with 50% ethyl acetate/hexanes (50 mL), and the filtrate concentrated under reduced pressure to give crude Int-282 (16.0 mg, quant.) as a yellow oil that was used without purification; $^1$H NMR (400 MHz, CDCl$_3$) δ 9.53 (t, J=2.6 Hz, 1H), 6.85 (d, J=1.3 Hz, 1H), 6.58 (d, J=1.4 Hz, 1H), 5.29 (m, 1H), 4.320 (dd, J=11.9, 4.2 Hz, 1H), 4.317 (dd, J=11.9, 4.2 Hz, 1H), 4.15 (dd, J=11.9, 6.0 Hz, 2H), 2.86-2.75 (m, 2H), 2.67 (dd, J=15.5, 5.6 Hz, 1H), 2.53 (s, 3H), 2.63-2.44 (m, 3H), 2.36 (dd, J=15.3, 7.2 Hz, 1H), 2.30 (t, J=7.5 Hz, 4H), 2.24 (s, 3H), 1.64-1.57 (m, 4H), 1.56 (s, 3H), 1.55 (s, 3H), 1.36-1.19 (m, 48H), 1.13 (d, J=6.4 Hz, 3H), 0.88 (t, J=6.8 Hz, 6H).

Potassium permanganate (4.3 mg, 27.0 µmol) in 1:1 acetone/water (1 mL total) was added to Int-282 (16.0 mg, 18.0 µmol) in acetone (0.5 mL) and the mixture was stirred at rt for 16 hours. The reaction was diluted with water (5 mL), acidified to pH 2 using 1 M HCl, and the aqueous layer was extracted with ethyl acetate (3×15 mL). The combined organic extracts were washed with brine (30 mL), dried (MgSO$_4$) and concentrated under reduced pressure to give the crude product. Purification by silica gel chromatography (15% to 30% ethyl acetate/hexanes) gave Int-154 (13.0 mg, 80%) as a colourless solid; $^1$H NMR (400 MHz, CDCl$_3$) δ 6.81 (d, J=1.9 Hz, 1H), 6.56 (d, J=1.8 Hz, 1H), 5.28 (m, 1H), 4.31 (dd, J=11.9, 4.3 Hz, 2H), 4.15 (dd, J=11.9, 6.0 Hz, 2H), 2.88-2.76 (m, 2H), 2.67 (dd, J=15.2, 5.6 Hz, 1H), 2.64-2.46 (m, 3H), 2.54 (s, 3H), 2.36 (dd, J=15.2, 7.0 Hz, 1H), 2.33-2.28 (m, 4H), 2.23 (s, 3H), 1.64-1.53 (m, 4H), 1.57 (s, 3H), 1.56 (s, 3H), 1.34-1.19 (m, 48H), 1.13 (d, J=6.4 Hz, 3H), 0.88 (t, J=6.8 Hz, 6H); $^{13}$C NMR (101 MHz, CDCl$_3$) δ 175.17 (C), 173.60 (C), 173.58 (C), 171.5 (C), 171.4 (C), 149.4 (C), 138.3 (C), 136.4 (C), 133.4 (C), 132.7 (CH), 123.1 (CH), 69.4 (CH), 62.2 (2C; CH$_2$), 47.4 (CH$_2$), 41.2 (CH$_2$), 40.7 (CH$_2$), 38.8 (C), 34.2 (2C; CH$_2$), 32.1 (2C; CH$_2$), 31.51 (CH$_3$), 31.47 (CH$_3$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.3 (CH), 25.4 (CH$_3$), 25.0 (2C; CH$_2$), 22.8 (2C; CH$_2$), 20.4 (CH$_3$), 20.0 (CH$_3$), 14.3 (2C; CH$_3$); ESI-HRMS: calcd. for C$_{54}$H$_{92}$NaO$_{10}$ [M+Na$^+$] 923.6583; found 923.6620.

1,3-DG-acetate (Int-284):

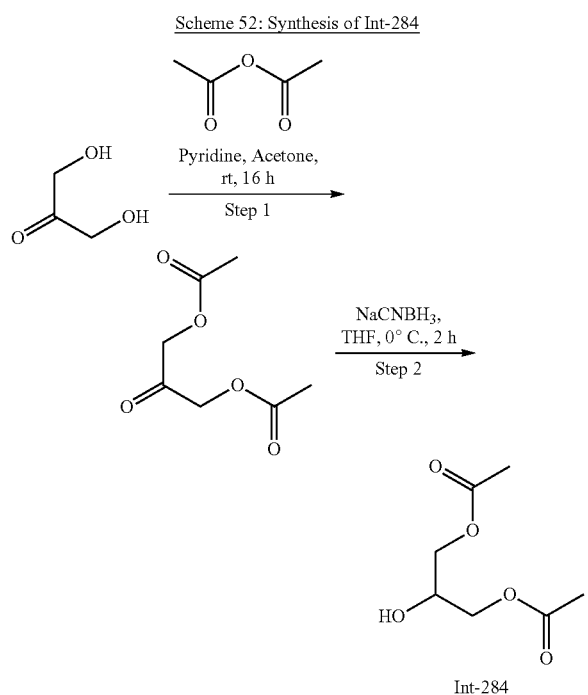

To a solution of 1,3-dihydroxypropan-2-one (5.0 g, 55.5 mmol) and acetic anhydride (11.33 g, 111.07 mmol) in acetone (50 ml) was added pyridine (9.66 g, 122.18 mmol) and the reaction mixture was stirred at room temperature for 16 hours. After completion of the reaction, the solution evaporated under vacuum, redissolved in DCM (50 ml) and washed with 1N HCl (50 ml), water (50 ml). The combined organic layer was dried over sodium sulphate and evaporated under vacuum to get crude. The crude material was purified by column chromatography using 100-200 mesh silica gel, and the desired product was eluted at 25% ethyl acetate/hexane to afford 2-oxopropane-1,3-diyl diacetate (8.0 g, 82.7%). $^1$H NMR (400 MHz, CDCl$_3$) δ 4.79 (s, 4H), 2.21 (s, 6H).

To a solution of 2-oxopropane-1,3-diyl diacetate (0.5 g, 2.87 mmol) in THF (5.0 ml) was added sodium cyanoborohydride (NaBH$_3$CN) (0.18 g, 2.87 mmol) at 0° C. and then the reaction mixture was stirred at 0° C. for 2 hours. After completion of the reaction, as determined by TLC, the reaction mixture was diluted with 1N HCl solution (20 ml), and the product was extracted with ethyl acetate (20 ml×3). The organic layer was dried over Na$_2$SO$_4$ and the solvent was removed under vacuum to get crude product. The crude material was purified by column chromatography using 100-200 mesh silica gel and the desired compound was eluted at 30% ethyl acetate/hexane to afford Int-284 (0.3 g, 59.3%) as viscous liquid. $^1$H NMR (400 MHz, CDCl$_3$) δ 4.14-4.36 (m, 5H), 2.15 (s, 6H). GC: RT 8.97 min, 97.14% purity. MASS (ESI, +ve) m/z: 193.9 (MH+18).

C8β'Me-acid-2-TG-oleate (Int-293):

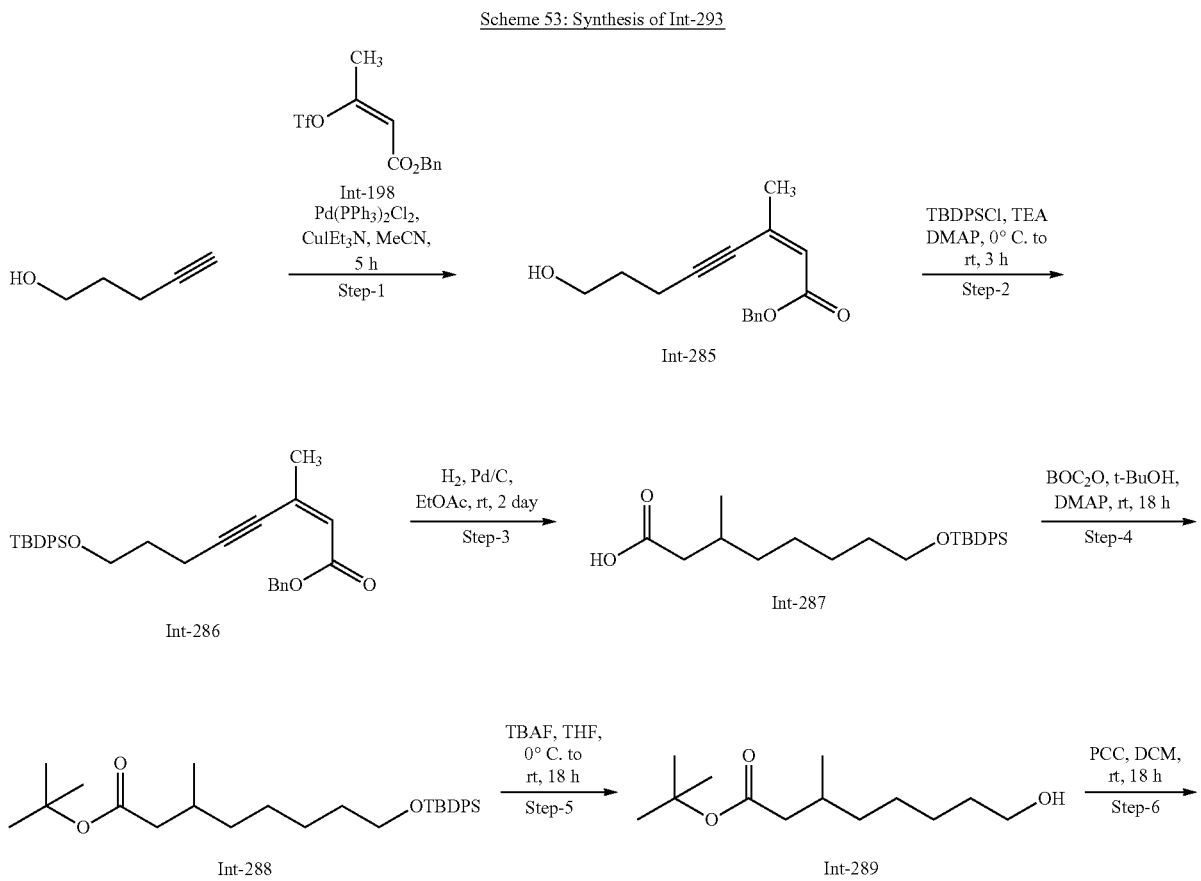

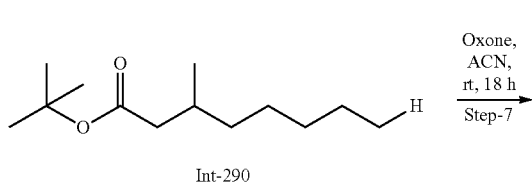

Int-290

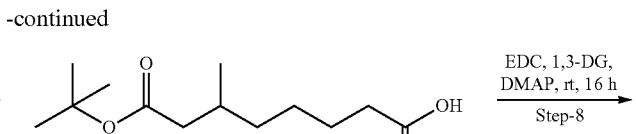

Int-291

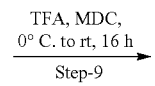

Int-292

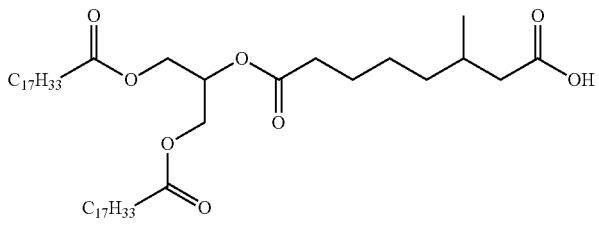

Int-293

A suspension of $PdCl_2(PPh_3)_2$ (0.83 g, 1.18 mmol) in ACN (30 ml) was degassed using $N_2$ gas for five minutes, and then CuI (0.45 g, 2.37 mmol), $Et_3N$ (6.7 mL, 47.5 mmol) and a degassed solution of Int-198 in ACN (15.40 g, 4.76 mmol) and pent-4-yn-1-ol (2.0 g, 2.38 mmol) were added. The mixture was degassed using a $N_2$ for a further five minutes and then heated at 50° C. for 5 h. Reaction was monitored by TLC, after completion of reactions, reaction mixture was cooled to RT, diluted with DM water (100 ml) and extracted with ethyl acetate (3×100 ml), and combined organic layer was dried over sodium sulphate and evaporated under reduced pressure to afford crude oil. Purification was done by column chromatography using silica gel (100-200 mesh). Pure product was eluted at 15% ethyl acetate/hexane as a mobile phase. Pure fractions were concentrated in the rota vapour to get pure Int-285 (5.1 g, 83.60%): $^1$H NMR (400 MHz, $CDCl_3$) δ 7.36 (m, 5H), 6.03 (s, 1H), 5.19 (s, 2H), 3.84 (t, J=5.6 Hz, 2H), 2.59 (t, J=6.4 Hz, 2H), 2.04 (s, 3H), 1.85 (dt, J=12.6, 5.6 Hz, 2H).

To a solution of Int-285 (5.0 g, 19.13 mmol) in DCM (50 ml) was added DMAP (0.47 g, 3.87 mmol) followed by TEA (3.5 ml, 25.10 mmol) under nitrogen atmosphere at 0° C. Stirred for 10 minutes, after that tert-butyl diphenyl silyl chloride (6.9 g, 25.1 mmol) was added drop wise at 0° C., and the resulting reaction mixture was stirred at RT for 3 h. Progress of reaction was monitored by TLC; after completion of reaction, the reaction mixture was quenched with water (200 ml) and extracted with DCM (3×150 ml). Combined organic layer was dried over $Na_2SO_4$, evaporated under reduced pressure to get crude material. Purification was done by column chromatography using silica gel (100-200 mesh). Pure compound was eluted at 5% ethyl acetate in hexane to get pure Int-286 (6.0 g, 62.5%) as colourless oil.

To a solution of Int-286 (5.0 g) in ethyl acetate (100 ml) palladium on carbon (10% w/w, 5 g) was added and the resulting suspension re-evacuated and flushed with $N_2$ three times. Then reaction mixture was stirred at RT for 2 days under 20 kg/$Cm^2$ (285 psi) $H_2$ pressure (in an autoclave), after completion of reaction, the reaction mixture was filtered through a pad of celite, and washed with ethyl acetate (240 ml). The filtrate was concentrated under reduced pressure to afford crude. Purification was done by column chromatography using silica gel (100-200 mesh). Pure compound was eluted at 15% ethyl acetate in hexane to get pure Int-287 (4.0 g, 96.38%) as colourless oil. $^1$H NMR (400 MHz, $CDCl_3$) δ 7.69 (d, J=7.0 Hz, 4H), 7.46-7.38 (dd, J=11.1, 7.0 Hz, 6H), 3.66 (t, J=6.4 Hz, 2H), 2.38 (m, 1H), 2.16 (m, 1H), 1.96 (m, 1H), 1.59-1.54 (p, J=6.8 Hz, 2H), 1.34 (m, 6H), 1.06 (s, 9H), 0.98 (d, J=7.0 Hz, 3H).

To a solution of Int-287 (2.0 g, 4.85 mmol) in Tert-BuOH (30 ml) was added DMAP (0.17 g, 1.45 mmol) followed by $BOC_2O$ (2.1 g, 9.7 mmol) at RT. The resulting reaction mixture was stirred at RT for 18 h. Progress of reaction was monitored by TLC; after completion of reaction, the reaction mixture was quenched with water (60 ml) and extracted with DCM (3×50 ml). Combined organic layer was dried over $Na_2SO_4$, evaporated under reduced pressure to get crude material. Purification was done by column chromatography using silica gel (100-200 mesh). Pure compound was eluted at 4% ethyl acetate in hexane to get pure Int-288 (1.5 g, 66.07%) as colourless oil. $^1$H NMR (400 MHz, $CDCl_3$) δ 7.72 (d, J=7.0 Hz, 4H), 7.44-7.38 (dd, J=11.1, 7.0 Hz, 6H), 3.66 (t, J=6.4 Hz, 2H), 2.37 (m, 1H), 2.16 (m, 1H), 1.95 (m, 1H), 1.58 (s, 9H), 1.59-1.56 (p, J=6.8 Hz, 2H), 1.34 (m, 6H), 1.06 (s, 9H), 0.98 (d, J=7.0 Hz, 3H).

To a solution of Int-288 (1.5 g, 3.21 mmol) in THF (20 ml) was added TBAF (1.6 g, 6.45 mmol) solution slowly dropwise at 0° C. The resulting reaction mixture was stirred at RT for 18 h. Progress of reaction was monitored by TLC; after completion of reaction, the reaction mixture was quenched with water (50 ml) and extracted with Ethyl acetate (3×50 ml). Combined organic layer was dried over $Na_2SO_4$, evaporated under reduced pressure to get crude material. Purification was done by column chromatography using silica gel (100-200 mesh). Pure compound was eluted at 10% ethyl acetate in hexane to get pure Int-289 (0.6 g, 82.19%) as colourless oil.

To a solution of Int-289 (0.6 g, 2.608 mmol) in DCM (20 ml) was added PCC (1.1 g, 5.217 mmol) at RT. The resulting reaction mixture was stirred at RT for 18 h. Progress of reaction was monitored by TLC; after completion of reaction, the reaction mixture was diluted with water (50 ml) and extracted with Ethyl acetate (3×50 ml). Combined organic layer was dried over $Na_2SO_4$, evaporated under reduced pressure to get crude Int-8 (0.7 g) as brown oil. Int-290 was used for next step without purification.

To a solution of Int-290 (0.7 g, 3.056 mmol) in ACN (20 ml) was added Oxone (2.2 g, 3.668 mmol) followed by $H_2O$ (0.5 ml) at RT. The resulting reaction mixture was stirred at RT for 18 h. Progress of reaction was monitored by TLC; after completion of reaction, the reaction mixture was diluted with water (50 ml) and extracted with Ethyl acetate (3×50 ml). Combined organic layer was dried over $Na_2SO_4$, evaporated under reduced pressure to get crude. Purification was done by column chromatography using silica gel (100-200 mesh). Pure compound was eluted at 10% ethyl acetate in hexane to get pure Int-291 (0.35 g) as colourless oil.

tography using silica gel (100-200 mesh). Pure product was eluted at 2-3% ethyl acetate/hexane as a mobile phase. Pure fractions were concentrated in the rota vapour to get pure Int-292 (0.40 g, 33.3%) as a colourless oil.

A solution of Int-292 (0.40 g) in DCM (10 ml) was added TFA (0.8 ml, 2V) 0° C. and reaction mixture was stirred at RT for 16 h. Reaction was monitored by TLC. After completion of reaction, reaction mixture was distilled out, diluted with water (50 ml) and extracted with Ethyl acetate (3×50 ml). Combined organic layer was dried over $Na_2SO_4$, evaporated under reduced pressure to get crude; Purification was done by column chromatography using silica gel (100-200 mesh). Pure product was eluted at 6-7% ethyl acetate: hexane as a mobile phase. Pure fractions were concentrated in the rota vapour to get pure Int-293 (0.200 g, 54.0 5%) as a colourless oil. $^1$H NMR (400 MHz, $CDCl_3$) δ 5.38-5.20 (m, 5H), 4.32 (dt, J=11.9, 3.6 Hz, 2H), 4.17 (dd, J=12.4, 5.9 Hz, 2H), 2.35 (t, J=7.5 Hz, 5H), 2.20 (m, 2H), 2.03 (m, 8H), 1.63 (m, 6H), 1.31 (m, 46H), 0.98 (d, J=7.2 Hz, 3H), 0.90 (t, J=7.2 Hz, 6H).

DMOPHB-alcohol-C10b'bMe-2-TG-oleate (Int-295):

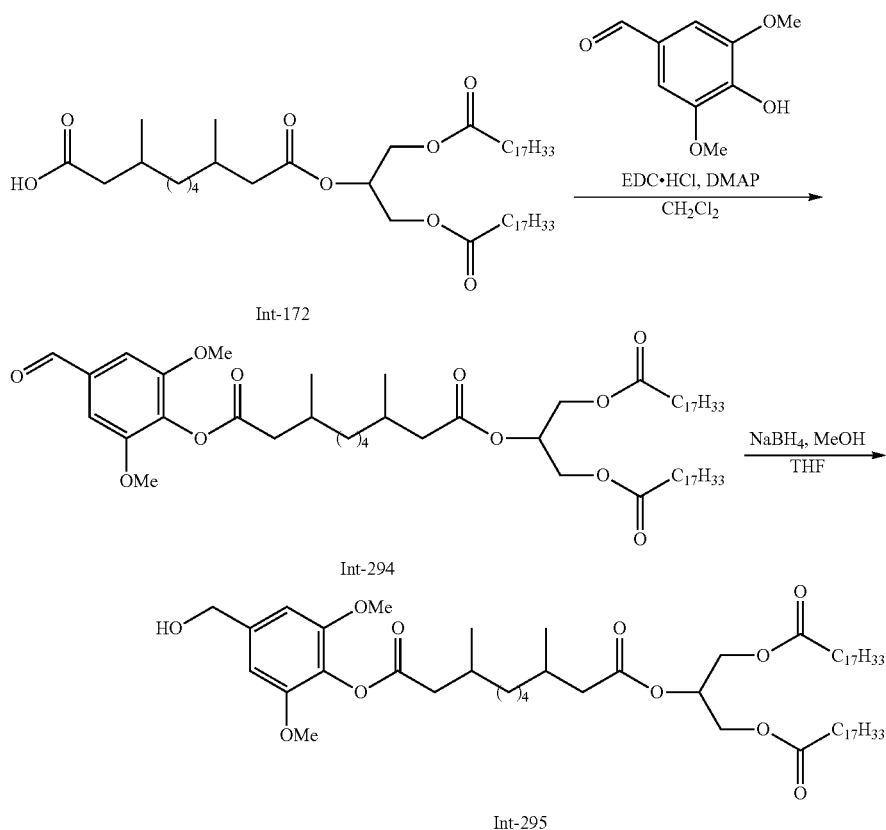

Scheme 54: Synthesis of Int-295

A solution of Int-291 (0.35 g, 1.435 mmol) in DCM (10 ml) was added DMAP (0.174 g, 1.435 mmol), EDC·HCl (0.550 g, 2.868 mmol) and 1,3-DG Oleate (0.445 g, 0.71 mmol) were added and the reaction mixture was stirred at RT for 16 h. Reaction was monitored by TLC. After completion of reaction, reaction mixture was distilled out to get crude material; Purification was done by column chroma- 4-(Dimethylamino)pyridine (DMAP, 440 mg, 3.60 mmol) and N—(3-dimethylaminopropyl)-N'-ethyl-carbodiimide (EDC·HCl, 920 mg, 4.80 mmol) were added to a solution of acid Int-172 (2.00 g, 2.40 mmol) and 4-hydroxy-3,5-dimethoxybenzaldehyde (437 mg, 2.40 mmol) in $CH_2Cl_2$ (30 mL) and the mixture stirred at room temperature overnight. The reaction was concentrated to near dryness and purified by normal phase flash column chromatography (Biotage Isolera, 80 g, Silicycle siliasep cartridge) using n-heptane and EtOAc (gradient: 1:0 to 7:3) to give the desired compound (1.89 g, 79%) as a colourless oil. UPLC4_AP-MS: (BEH C8 Long Acidic 70 to 95): $R_t$=4.37 min., 100% (ELS). MS (ESIpos) m/z=1014.9, 1015.9 (M+H$_2$O+H)$^+$. 1H NMR (400 MHz, CDCl$_3$): δ(ppm)=9.90 (s, 1H), 7.14 (s, 2H), 5.39-5.23 (m, 5H), 4.29 (dd, J=3.8, 11.9 Hz, 2H), 4.14 (dd, J=6.0, 11.9 Hz, 2H), 3.89 (s, 6H), 2.62 (dd, J=5.9, 14.7 Hz, 1H), 2.41 (dd, J=8.2, 14.7 Hz, 1H), 2.37-2.28 (m, 5H), 2.12 (dd, J=8.2, 14.7 Hz, 2H), 2.06-1.89 (m, 9H), 1.67-1.54 (m, 5H), 1.51-1.19 (m, 51H), 1.06 (d, J=6.6 Hz, 3H), 0.93 (d, J=6.6 Hz, 3H), 0.87 (t, J=6.8 Hz, 6H). $^{13}$C NMR (100 MHz, CDCl$_3$): δ(ppm)=191.2, 173.4, 172.4, 170.4, 153.1, 134.4, 134.1, 130.2, 129.8, 106.2, 69.0, 62.3, 56.4, 41.80, 41.78, 41.47, 41.45, 36.83, 36.77, 34.2, 32.0, 30.7, 30.5, 29.9, 29.84, 29.79, 29.75, 29.7, 29.5, 29.3, 29.24, 29.22, 27.4, 27.30, 27.26, 25.0, 22.8, 19.7, 19.64, 19.62, 19.60, 14.3.

Sodium borohydride (NaBH$_4$, 71 mg, 1.88 mmol) was added to a solution of 1-(1,3-bis(oleoyloxy)propan-2-yl) 10-(4-formyl-2,6-dimethoxyphenyl) 3,8-dimethyldecanedioate (1.88 g, 1.88 mmol) in MeOH (15 mL) and THF (30 mL). The mixture was stirred at room temperature for 1 hour before being quenched with water. The mixture was concentrated in vacuo and directly purified by normal phase flash column chromatography (Biotage Isolera, 80 g, Silicycle siliasep cartridge) using n-heptane and EtOAc (gradient: 1:0 to 1:1) to give the desired compound Int-295 (820 mg, 44%) as a colourless oil. UPLC4_AP-MS: (BEH C$_8$ Long Acidic 70 to 95): $R_t$=3.93 min., 99% (ELS). MS (ESIpos) m/z=1016.9, 1017.9 (M+H$_2$O+H)+. 1H NMR (400 MHz, CDCl$_3$): δ (ppm)=6.62 (s, 2H), 5.39-5.23 (m, 5H), 4.65 (s, 2H), 4.28 (ddd, J=1.1, 4.3, 11.9 Hz, 2H), 4.14 (dd, J=5.9, 12.1 Hz, 2H), 3.81 (s, 6H), 2.59 (dd, J=6.0, 14.6 Hz, 1H), 2.42-2.28 (m, 6H), 2.11 (dd, J=8.4, 14.6 Hz, 2H), 2.05-1.89 (m, 9H), 1.79 (s, 1H), 1.66-1.54 (m, 4H), 1.51-1.41 (m, 1H), 1.42-1.18 (m, 50H), 1.05 (d, J=6.6 Hz, 3H), 0.93 (d, J=6.6 Hz, 3H), 0.88 (t, J=6.8 Hz, 6H). $^{13}$C NMR (100 MHz, CDCl$_3$): δ(ppm)=173.4, 172.4, 171.1, 152.4, 139.5, 130.2, 129.9, 128.0, 103.4, 69.0, 65.6, 62.3, 60.5, 56.2, 41.81, 41.79, 41.6, 41.5, 36.9, 36.8, 36.8, 34.2, 32.0, 30.8, 30.50, 30.48, 29.9, 29.84, 29.76, 29.7, 29.5, 29.31, 29.25, 29.2, 27.4, 27.31, 27.28, 27.25, 27.2, 25.0, 22.8, 21.2, 19.7, 19.64, 19.62, 14.33, 14.25.

DMOPHB-alcohol-C10bMe-2-TG-oleate (Int-297):

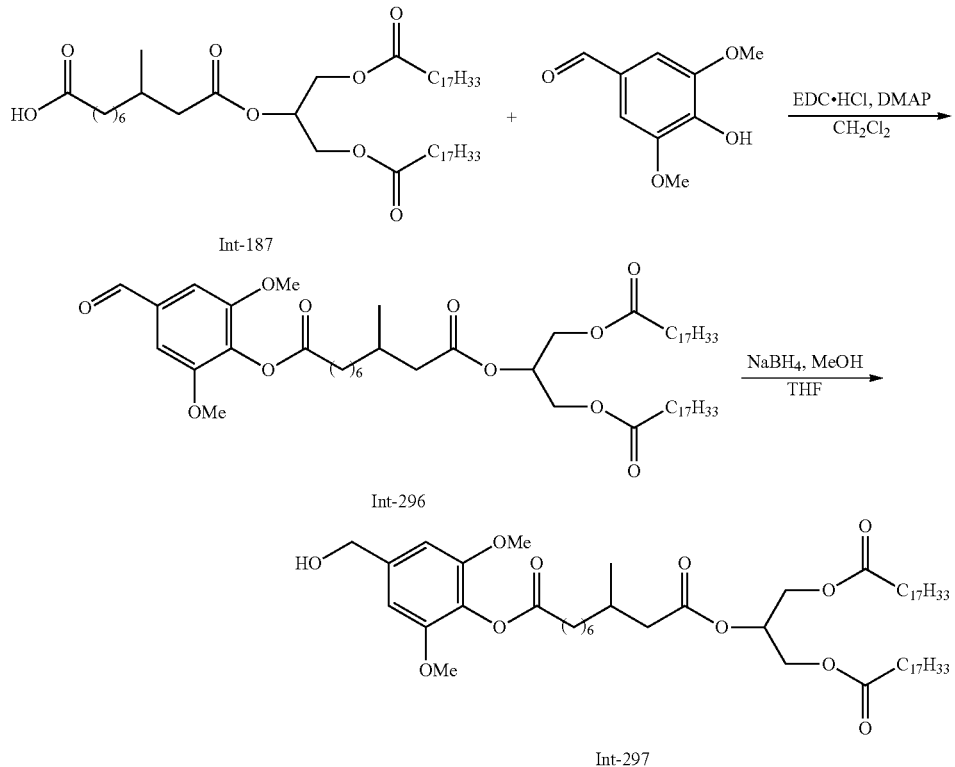

Scheme 55: Synthesis of Int-297

4-(Dimethylamino)pyridine (DMAP, 447 mg, 3.66 mmol) and N—(3-dimethylaminopropyl)-N'-ethyl-carbodiimide (EDC·HCl, 935 mg, 4.88 mmol) were added to a solution of acid Int-187 (2.00 g, 2.44 mmol) and 4-hydroxy-3,5-dimethoxybenzaldehyde (445 mg, 2.44 mmol) in CH$_2$Cl$_2$ (30 mL) and the mixture stirred at room temperature overnight. The reaction was concentrated to near dryness and purified by normal phase flash column chromatography (Biotage Isolera, 80 g, Silicycle siliasep cartridge) using n-heptane and EtOAc (gradient: 1:0 to 7:3) to give the desired compound Int-296 (1.30 g, 54%) as a colourless oil. UPLC4_AP-MS: (BEH C8 Long Acidic 70 to 95): $R_t$=4.12 min., 100% (ELS). MS (ESIpos) m/z=1000.9, 1001.9 (M+H$_2$O+H)+. $^1$H NMR (400 MHz, CDCl$_3$): δ(ppm)=9.90 (s, 1H), 7.14 (s, 2H), 5.39-5.22 (m, 5H), 4.29 (dd, J=4.1, 11.9 Hz, 2H), 4.14 (dd, J=6.0, 11.9 Hz, 2H), 3.89 (s, 6H), 2.62 (t, J=7.4 Hz, 2H), 2.37-2.27 (m, 5H), 2.12 (dd, J=8.4, 14.7 Hz, 1H), 2.06-1.88 (m, 8H), 1.82-1.72 (m, 2H), 1.67-1.53 (m, 4H), 1.50-1.18 (m, 51H), 0.93 (d, J=6.6 Hz, 3H), 0.87 (t, J=6.8 Hz, 6H). ¹³C NMR (100 MHz, CDCl₃): δ(ppm) =191.1, 173.4, 172.4, 171.0, 153.1, 134.4, 134.1, 130.1, 129.8, 106.2, 69.0, 62.3, 56.5, 41.8, 36.8, 34.1, 33.9, 32.0, 30.5, 29.9, 29.83, 29.79, 29.75, 29.7, 29.60, 29.55, 29.5, 29.44, 29.40, 29.3, 29.24, 29.22, 29.1, 27.34, 27.29, 26.9, 25.1, 25.0, 22.8, 19.7, 14.2.

Sodium borohydride (NaBH₄, 50 mg, 1.32 mmol) was added to a solution of 1-(1,3-bis(oleoyloxy)propan-2-yl) 10-(4-formyl-2,6-dimethoxyphenyl) 3-methyldecanedioate (1.30 g, 1.32 mmol) in MeOH (10 mL) and THF (20 mL). The mixture was stirred at room temperature for 1 hour before being quenched with water. The volatiles were removed in vacuo. The mixture was directly purified by normal phase flash column chromatography (Biotage Isolera, 80 g, Silicycle siliasep cartridge) using n-heptane and EtOAc (gradient: 1:0 to 1:1) to give the desired compound Int-297 (669 mg, 51%) as a colourless oil. UPLC4_AP-MS: (BEH C8 Long Acidic 70 to 95): R$_f$=3.81 min., 100% (ELS). MS (ESIpos) m/z=1002.9, 1003.9 (M+H₂O+H)⁺. 1H NMR (400 MHz, CDCl₃): δ(ppm)=6.62 (s, 2H), 5.39-5.23 (m, 5H), 4.65 (s, 2H), 4.28 (ddd, J=0.8, 4.2, 11.9 Hz, 2H), 4.14 (dd, J=6.0, 11.9 Hz, 2H), 3.81 (s, 6H), 2.60 (t, J=7.4 Hz, 2H), 2.37-2.28 (m, 5H), 2.11 (dd, J=8.4, 14.7 Hz, 1H), 2.05-1.88 (m, 8H), 1.82-1.70 (m, 3H), 1.67-1.53 (m, 4H), 1.49-1.38 (m, 2H), 1.39-1.18 (m, 48H), 0.93 (d, J=6.6 Hz, 3H), 0.88 (t, J=6.8 Hz, 6H). ¹³C NMR (100 MHz, CDCl₃): δ(ppm) =173.4, 172.4, 171.7, 152.4, 139.4, 130.2, 129.9, 128.0, 103.4, 69.0, 65.6, 62.3, 56.3, 41.8, 36.8, 34.2, 34.0, 32.0, 30.5, 29.9, 29.84, 29.79, 29.76, 29.7, 29.61, 29.56, 29.5, 29.31, 29.25, 29.2, 29.1, 27.4, 27.3, 26.9, 25.2, 25.0, 22.8, 19.7, 14.3.

ALL-CASI-C5bMe-acid (Int-298):

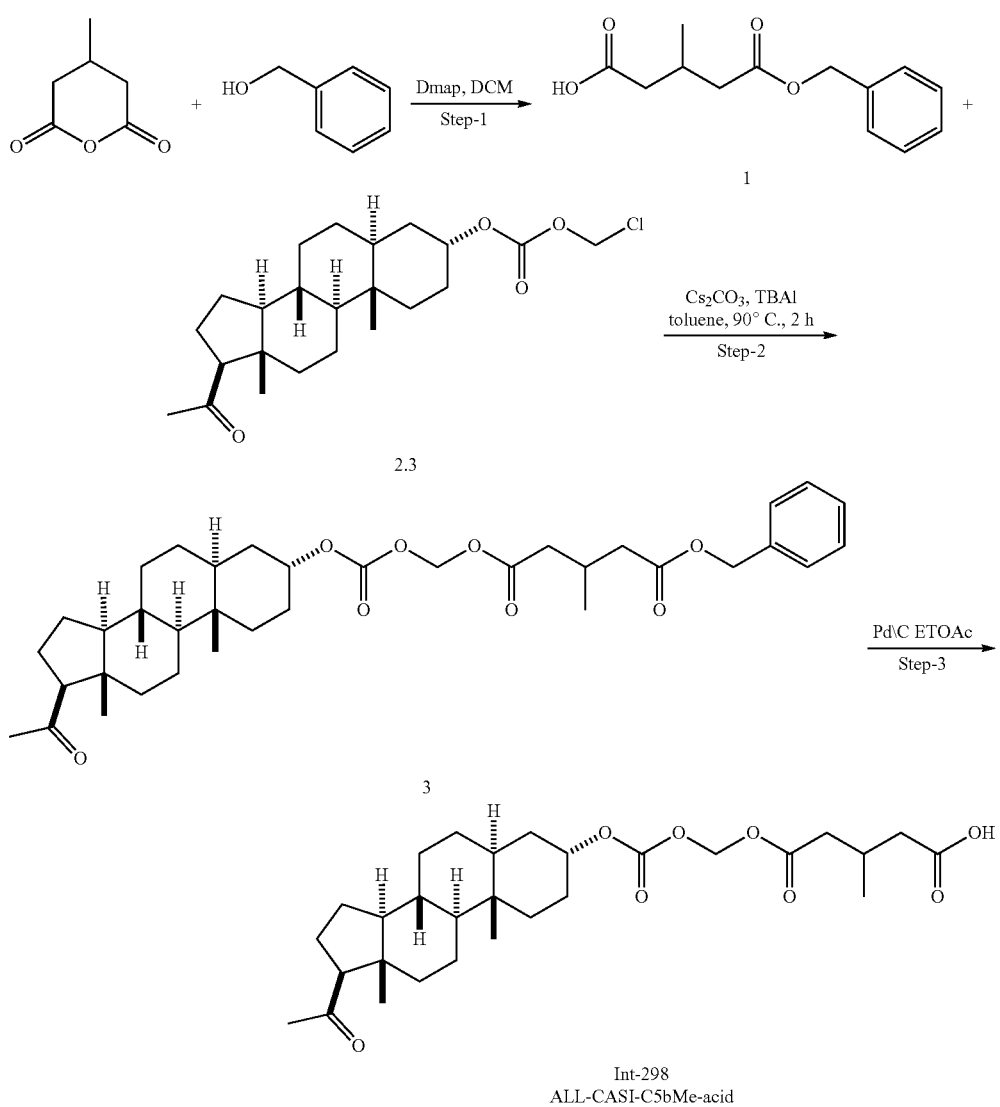

Int-298
ALL-CASI-C5bMe-acid

To a solution of 3-methylglutaric anhydride (5.0 g, 39.06 mmol) in DCM (60 ml) was added DMAP (2.38 g, 19.51 mmol). Reaction mixture was stirred at room temperature for 10 min, then benzyl alcohol (2.10 g, 19.51 mmol) was added. Stirred reaction mixture at room temperature for 16 hr. Reaction was monitored by TLC, after completion of reaction mixture was diluted with water (50 ml) and extracted with DCM (3×50 ml), combined organic layer dried over Na₂SO₄ and Distilled out under vacuum to get crude compound, which was purified by column chromatography using silica gel (100-200 mesh). Pure compound was eluted at 12% ethyl acetate and hexane as a mobile phase then pure fraction was conc. in the rota vapour to get Compound 1 (2.5 g, 30.17%): 1H NMR (400 MHz, CDCl3) δ 7.41-7.37 (m, 5H), 5.14 (s, 2H), 2.56-2.47 (m, 4H), 2.39-2.27 (m, 3H), 1.07 (d, J=6.4 Hz 3H).

To a solution of compound 2.3 (1.5 g, 3.65 mmol) in toluene (15 ml) was added $Cs_2CO_3$ (2.38 g, 7.31 mmol) and stirred at room temperature for 15 min, then 1 (0.86 g, 3.65 mmol) (pre dissolved in 8 ml Toluene) and TBAI (0.67 g, 1.82 mmol) was added at room temperature. Reaction mixture was stirred at 90° C. for 2 h. The reaction was monitored by TLC. After completion of the reaction, the reaction mixture was diluted with water (20 ml) and extracted with ethyl acetate (3×25 ml). The combined organic layer was dried over $Na_2SO_4$, and distilled under vacuum to get crude compound, which was purified by column chromatography using silica gel (100-200 mesh). Pure compound was eluted at 12% ethyl acetate and hexane as a mobile phase, then pure fraction was conc. in the rota vapour to get pure compound 3 (1.3 g, 59.09%): MASS (ESI, +ve) m/z: 610.7 (MH+18).

To a solution of 3 (1.3 g, 2.12 mmol) in ethyl acetate (30 ml), 20% Palladium on carbon (1.0 g, (20% moisture) was added and the resulting suspension was flushed with $N_2$ three times. The reaction mixture was then stirred at rt for 16 h under 120 psi $H_2$ pressure (in autoclave). After completion of the reaction, the reaction mixture was filtered through a pad of celite and washed with ethyl acetate (100 ml). The filtrate was concentrated under reduced pressure to afford crude material that was purified by column chromatography using silica gel (100-200 mesh). Pure compound was eluted at 15% ethyl acetate and hexane as a mobile phase and pure fractions were concentrated in the rota vapour to produce ALL-CASI-$C_5$bMe-acid (0.600 g, 54.54%): $^1$H NMR (400 MHz, Chloroform-d) δ 5.79 (s, 2H), 4.97 (m, 1H), 4.13 (m, 2H), 2.57-2.50 (m, 5H), 2.36 (t, J=7.6 Hz, 1H), 2.13 (s, 3H), 2.03 (t, J=14.4 Hz, 2H), 1.89 (m, 2H), 1.55 (d, J=5.2 Hz, 6H), 1.40-1.26 (m, 9H), 1.19 (d, J=16.0 Hz, 3H) 1.10-1.01 (m, 2H), 0.84 (d, J=14.4 Hz, 3H), 0.61 (s, 3H); ELSD: 5.35 min, 100% purity; MASS (ESI, +ve) m/z: 520.30 (MH+18).

C5bMe-acid-2-TG-octanoate (Int-299):

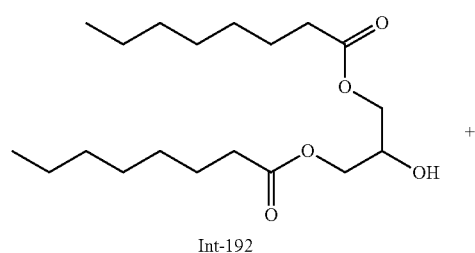

Int-192

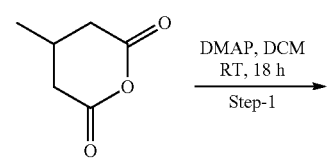

Step-1

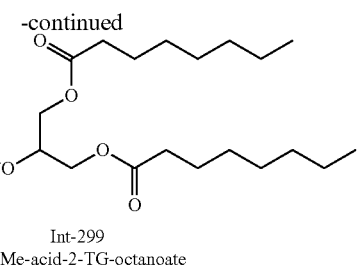

Int-299
C5bMe-acid-2-TG-octanoate

A solution of Int-192 (90.0 g, 261.0 mmol) and 3-methylglutaric anhydride (70.35 g, 549.1 mmol) in DCM (900 ml) was added DMAP (63.89 g, 522.9 mmol) at RT. The reaction was then stirred at RT for 18 h. The reaction was monitored by TLC. After completion of the reaction, the reaction mixture was diluted with water (1.0 lit), extracted with DCM (2×700 ml), dried over sodium sulphate, and concentrated under vacuum to obtain a crude residue. Purification was done by column chromatography using 5-6% Ethyl acetate in hexane as eluent to get pure Int-299 $C_5$bMe-acid-2-TG-octanoate (58 g, 46.97%) as viscus liquid: $^1$H NMR (400 MHz, Chloroform-d) 65.30 (m, 1H), 4.34 (ddd, J=12.0, 4.3, 2.7 Hz, 2H), 4.16 (dd, J=12.0, 6.0 Hz, 2H), 2.47 (ddt, J=15.7, 9.9, 4.9 Hz, 3H), 2.50-2.42 (m, 4H), 2.35-2.20 (m, 6H), 1.63 (p, J=7.6 Hz, 4H), 1.39-1.19 (m, 13H), 1.08 (d, J=6.1 Hz, 3H), 0.90 (t, J=6.6 Hz, 6H); $^{13}$C NMR (101 MHz, Chloroform-d) δ 178.03 (1C), 173.35 (2C), 171.32 (1C), 69.21 (2C), 62.09 (2C), 40.58 (1C), 40.34 (1C), 34.00 (2C), 31.63 (2C), 29.03 (2C), 28.88 (2C), 27.13 (1C), 24.82 (2C), 22.58 (2C), 19.61 (1C), 14.04 (1C); ELSD: 5.47 min, 100% purity.

C5-acid-2-TG-oleate (Int-300):

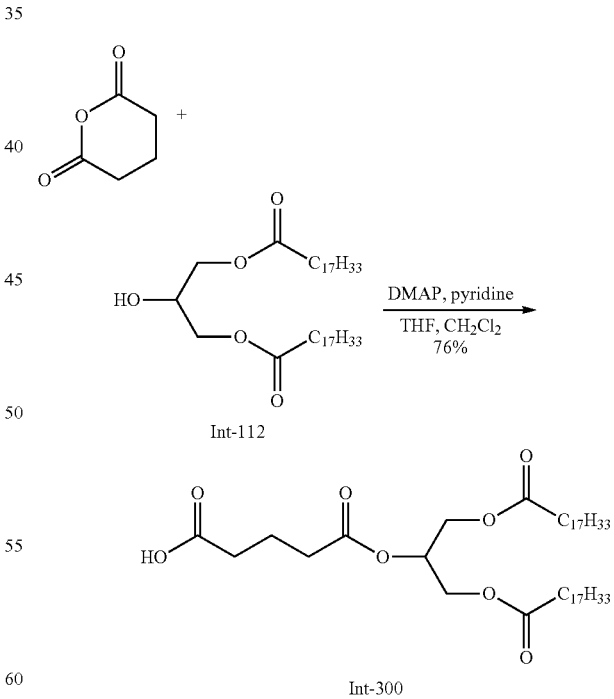

4-(Dimethylamino)pyridine (44.3 mg, 0.362 mmol) was added to a solution of Int-112 (225 mg, 0.362 mmol) and glutaric anhydride (82.7 mg, 0.725 mmol) in pyridine/THF/ $CH_2Cl_2$ (1.5 mL each) and the mixture stirred at rt for two days and 20 hours. The reaction was diluted with $CH_2Cl_2$ (40 mL), washed with water and brine (40 mL each), dried (MgSO$_4$) and concentrated under reduced pressure to give the crude product. Silica gel chromatography (10% to 25% ethyl acetate/hexanes) gave Int-300 (202 mg, 76%) as a colourless oil; $^1$H NMR (401 MHz, CDCl$_3$) δ 5.40-5.22 (m, 5H), 4.31 (dd, J=11.9, 4.3 Hz, 2H), 4.14 (dd, J=11.9, 5.9 Hz, 2H), 2.48-2.39 (m, 4H), 2.31 (t, J=7.6 Hz, 4H), 2.06-1.90 (m, 10H), 1.66-1.55 (m, 4H), 1.41-1.18 (m, 40H), 0.88 (t, J=6.9 Hz, 6H); $^{13}$C NMR (101 MHz, CDCl$_3$) δ 178.7 (C), 173.4 (2C; C), 172.0 (C), 130.1 (2C; CH), 129.8 (2C; CH), 69.4 (CH), 62.1 (2C; CH$_2$), 34.1 (2C; CH$_2$), 33.1 (CH$_2$), 32.9 (CH$_2$), 32.0 (2C; CH$_2$), 29.9 (2C; CH$_2$), 29.8 (2C; CH$_2$), 29.6 (2C; CH$_2$), 29.4 (4C; CH$_2$), 29.24 (2C; CH$_2$), 29.19 (2C; CH$_2$), 29.15 (2C; CH$_2$), 27.3 (2C; CH$_2$), 27.2 (2C; CH$_2$), 24.9 (2C; CH$_2$), 22.8 (2C; CH$_2$), 19.8 (CH$_2$), 14.2 (2C; CH$_3$).

C6bMe-acid-TG-oleate (Int-301):

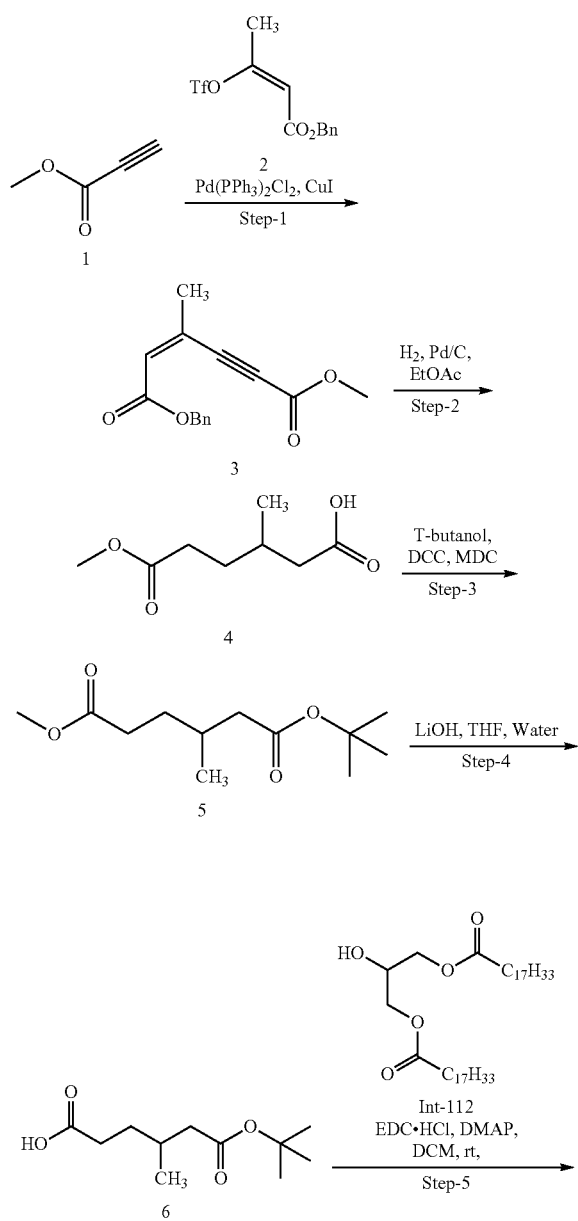

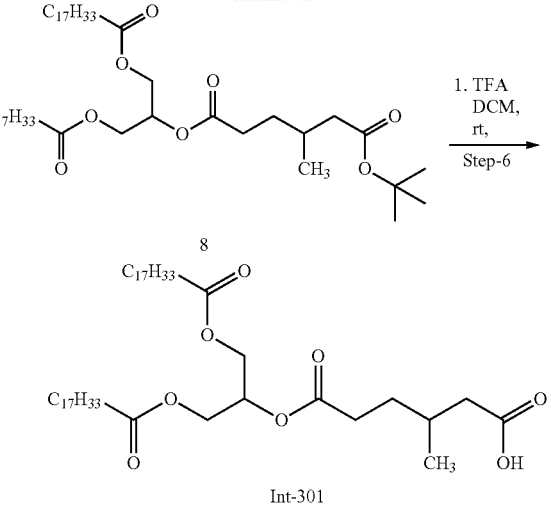

To a stirred solution of methyl propiolate (Compound 1, 5.0 g, 59.52 mmol) and benzyl (Z)-3-(((trifluoromethyl)sulfonyl)oxy)but-2-enoate (Compound 2, 15.4 g, 47.61 mmol) in tetrahydrofuran THF (50 mL) was added potassium carbonate (16.4 g, 118.9 mmol) and the reaction mixture was purged with nitrogen gas for 10 min. Copper iodide (0.226 g, 1.189 mmol) and bis (triphenylphosphine) palladium chloride (0.417 g, 0.594 mmol) were added and the reaction mixture was stirred at RT for 18 hr. The reaction was diluted with water (80 mL) and extracted with ethyl acetate (2*50 mL), and the organic layer was washed with water and brine solution, dried over Na$_2$SO$_4$, filtered and concentrated to give crude 1-benzyl 6-methyl (Z)-3-methylhex-2-en-4-ynedioate (Compound 3). Compound 3 was purified by column chromatography using 100-200 mesh silica gel (3% to 6.0% ethyl acetate/hexanes) to give pure Compound 3 (0.800 g) as a yellow oil. A second 5.0 gm batch yielded 0.60 g. Both batches were mixed and used in the next step: MASS (ESI, +ve) m/z: 275.93 (MH+18); $^1$H NMR (400 MHz, CDCl$_3$) δ 7.41-7.33 (m, 5H), 6.24 (d, J=1.2 Hz, 1H), 5.22 (s, 2H), 3.82 (s, 3H), 2.12 (5, 3H).

To a stirred solution of Compound 3 (1.3 g, 5.03 mmol) in ethyl acetate (50 mL) was added 20% palladium on carbon (1.0 g) and the reaction mixture was stirred under hydrogen gas (20 psi, RT) for 2 days. The reaction mixture was filtered through a celite bed and the filtrate was concentrated to give crude 6-methoxy-3-methyl-6-oxohexanoic acid (Compound 4) which was used in the next step (0.900 g, 95%) as a brown oil: MASS (ESI, +ve) m/z: 196.99 (MH+23); $^1$H NMR (400 MHz, CDCl$_3$) δ 3.71 (s, 3H), 2.49-2.35 (m, 3H), 2.26 (d, J=8.0 Hz, 1H), 2.08-1.99 (m, 1H), 1.89-1.80 (m, 1H), 1.17 (d, J=55 Hz, 3H), 0.99-0.89 (m, 1H).

To a stirred solution of Compound 4 (1.2 g, 6.88 mmol) in tert-butanol (12.0 mL) was added Di-tert-butyl dicarbonate (3.1 mL, 13.77 mmol) and DMAP (0.252 g, 2.06 mmol) and the reaction mixture was stirred at RT for 18 hr. The reaction was diluted with water and extracted with ethyl acetate. The organic layer was washed with water and brine solution, dried over Na$_2$SO$_4$, filtered and concentrated to give crude 1-(tert-butyl) 6-methyl 3-methylhexanedioate (Compound 5), which was purified by column chromatography using 100-200 mesh silica gel (8% to 12.0% ethyl acetate/hexanes) to yield Compound 5 (1.2 g) as a colourless oil: MASS (ESI, +ve) m/z: 230.92 (MH+1).

To a stirred solution of Compound 5 (1.2 g, 9.23 mmol) in tetrahydrofuran and water (1:1) (12.0 mL) was added lithium hydroxide (0.328, 13.84 mmol) at 0° C. and the reaction mixture was stirred at RT for 18 hours. The reaction was cooled and diluted with water, acidified with 2N HCl and extracted with ethyl acetate. The organic layer was washed with water and brine solution, dried over $Na_2SO_4$, filtered and concentrated to give crude 6-(tert-butoxy)-4-methyl-6-oxohexanoic acid (Compound 6). This crude material was purified by column chromatography using 100-200 mesh silica gel (5% to 15% ethyl acetate/hexanes) to give Compound 6 (0.900 g, 81.8%) as a yellow oil: MASS (ESI, −ve) m/z: 214.88 (MH-1); $^1$H NMR (400 MHz, $CDCl_3$) δ 2.45-2.41 (m, 1H), 2.40-2.25 (m, 1H), 2.23-2.10 (m, 1H), 2.04-1.98 (m, 1H), 1.78-1.72 (m, 1H), 1.62-1.58 (m, 1H), 1.51 (s, 9H), 1.01 (d, J=6.4 Hz, 3H).

4-(Dimethyl amino) pyridine (DMAP, 0.058 g, 0.483 mmol), N—(3-dimethylaminopropyl)-N'-ethylcarbodiimide hydrochloride (EDC·HCl, 0.184 g, 0.96 mmol), and Int-6 (0.313 g, 1.44 mmol) were added to a solution of Int-112 (0.300 g, 0.483 mmol) in DCM (5.0 mL) and the mixture was stirred at RT for 16 hours. The reaction was diluted with DCM (10 mL), silica gel was added and the mixture was concentrated under reduced pressure. Purification by Flash column chromatography (2% to 5% ethyl acetate/hexanes) gave Compound 8 (0.300 g) as a colorless oil: MASS (ESI, +ve) m/z: 836.40 (MH+18).

(TFA) Trifluoroacetic acid (1.0 mL), was added dropwise to a solution of Compound 8 (0.300 g, 0.366 mmol) in DCM (5.0 mL) at 0° C. and the reaction was then stirred at RT for 18 h, during which the reaction was monitored by TLC. After completion of the reaction, the reaction mixture was diluted with DCM and concentrated under vacuum to yield crude Int-301. Int-301 was purified by column chromatography using 12-15% Ethyl acetate and hexane as eluent to get pure Int-301 (279 mg yield 96%) as a colourless liquid: MASS (ESI, +ve) m/z: 780.37 (MH+18).

Example 2: Synthesis of Exemplary Compounds

Synthesis of IAL-CDMPHB-C$_5$bMe-2-TG-oleate:
1-(4-((((((3S,5S,8R,9S,10S,13S,14S,17S)-17-acetyl-10,13-dimethylhexadecahydro-1H-cyclopenta[a]phenanthren-3-yl)oxy)carbonyl)oxy)methyl)-2,6-dimethylphenyl) 5-(1,3-bis(oleoyloxy)propan-2-yl) 3-methylpentanedioate I-20

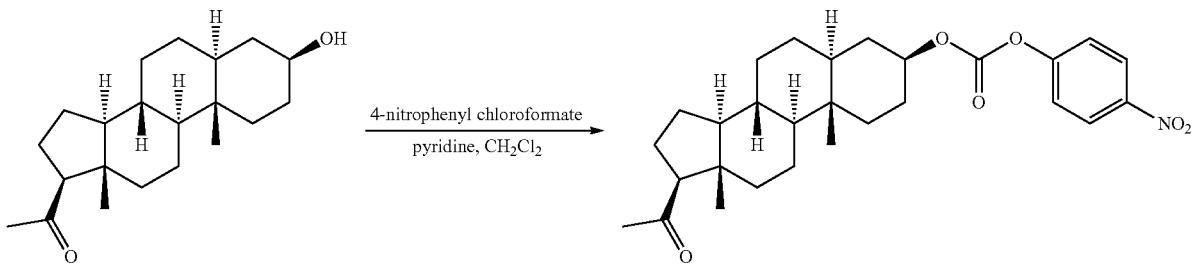

2.2

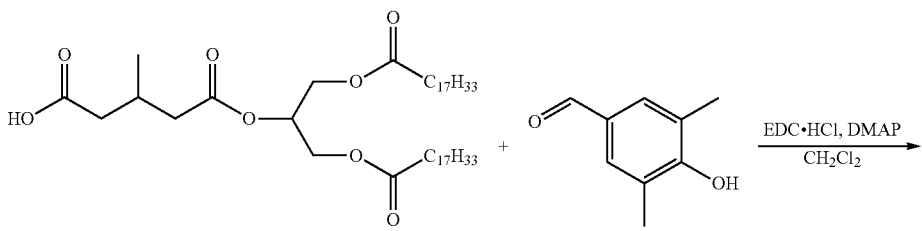

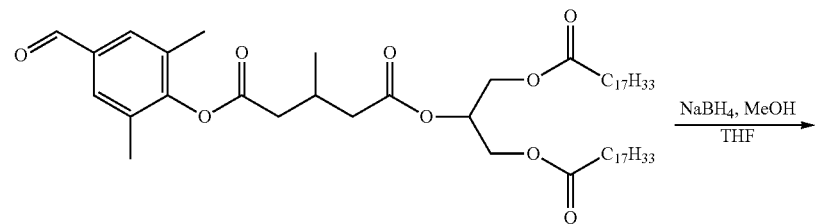

315

316

-continued

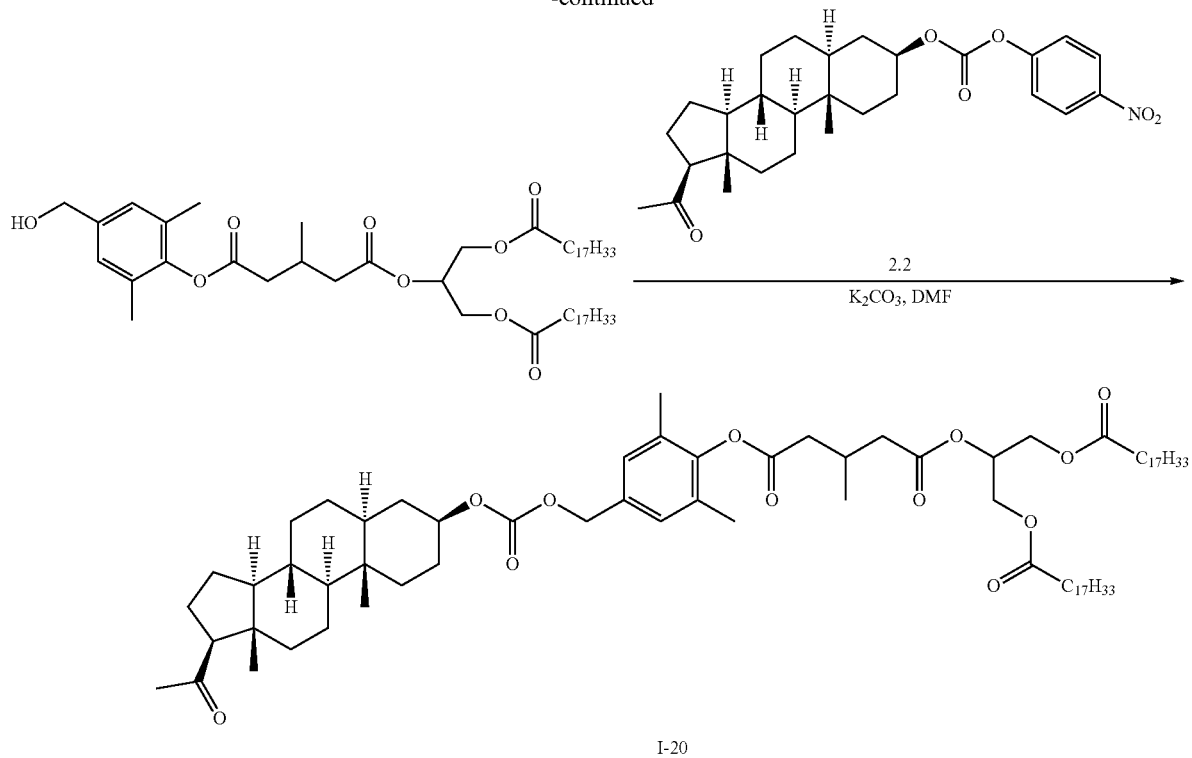

I-20

Step 1: (3S,5S,8R,9S,10S,13S,14S,17S)-17-acetyl-10,13-dimethylhexadecahydro-1H-cyclopenta[a]phenanthren-3-yl (4-nitrophenyl) carbonate 2.2

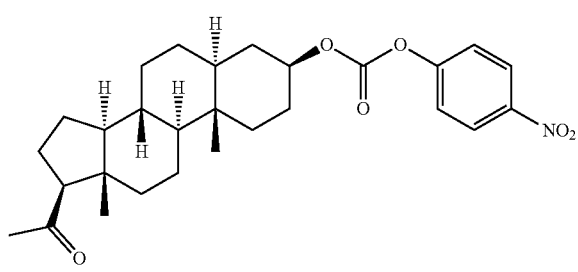

4-Nitrophenyl chloroformate (151 mg, 0.75 mmol) was added to a mixture of pyridine (95 µL, 1.18 mmol) and iso-allopregnanolone (150 mg, 0.47 mmol) in CH$_2$Cl$_2$ (5.0 mL). The resulting mixture was stirred at room temperature for 90 minutes before being concentrated in vacuo. The residue was purified by normal phase flash column chroma-tography (Biotage Isolera, 25 g, Silicycle siliasep cartridge) using n-heptane and EtOAc (gradient: 9:1 to 7:3). Fractions containing the desired compound were combined and concentrated in vacuo. The product was re-purified by normal phase flash column chromatography (Biotage Isolera, 25 g, Silicycle siliasep cartridge) using n-heptane and EtOAc (gradient: 1:0 to 4:1) to give the desired compound 2.2 (188 mg, 83%) as a white solid. $^1$H NMR (400 MHz, CDCl$_3$): δ(ppm)=8.30-8.25 (m, 2H), 7.40-7.35 (m, 2H), 4.74-4.65 (m, 1H), 2.52 (t, J=9.0 Hz, 1H), 2.21-2.11 (m, 4H), 2.05-1.95 (m, 2H), 1.85-1.75 (m, 2H), 1.73-1.57 (m, 5H), 1.55-1.48 (m, 3H), 1.46-1.14 (m, 8H), 1.08 (dt, J=3.6, 13.5 Hz, 1H), 0.99-0.85 (m, 4H), 0.72 (dt, J=3.7, 11.3 Hz, 1H), 0.61 (s, 3H).

Step 2: 1-(1,3-bis(oleoyloxy)propan-2-yl) 5-(4-formyl-2,6-dimethylphenyl) 3-methylpentanedioate

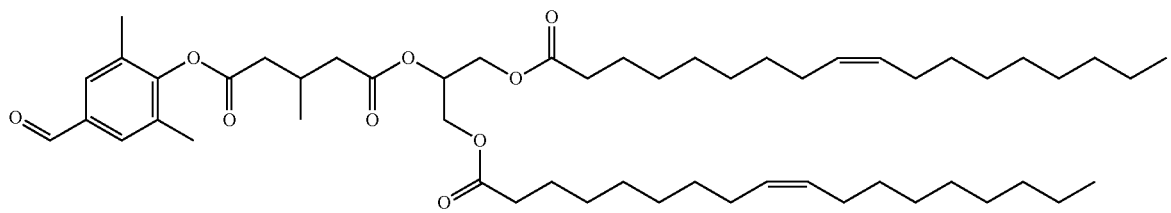 [SMILES: CCCCCCCC/C=C\CCCCCCCC(=O)OCC(COC(=O)CCCCCCC/C=C\CCCCCCCC)OC(=O)CC(C)CC(=O)Oc1c(C)cc(C=O)cc1C]

4-(Dimethylamino)pyridine (DMAP, 147 mg, 1.20 mmol) and N—(3-dimethylaminopropyl)-N'-ethyl-carbodiimide (EDC·HCl, 307 mg, 1.60 mmol) were added to a solution of the Int-210 (600 mg, 0.80 mmol) and 4-hydroxy-3,5-dimethylbenzaldehyde (120 mg, 0.80 mmol) in CH$_2$Cl$_2$ (40 mL) and the mixture stirred at room temperature overnight. The reaction was concentrated to near dryness and purified by normal phase flash column chromatography (Biotage Isolera, 40 g, Silicycle siliasep cartridge) using n-heptane and EtOAc (gradient: 1:0 to 7:3) to give the desired compound (555 mg, 79%) as a colourless oil. $^1$H NMR (400 MHz, CDCl$_3$): δ (ppm)=9.92 (s, 1H), 7.60 (s, 2H), 5.39-5.26 (m, 5H), 4.33 (dd, J=4.2, 11.9 Hz, 2H), 4.15 (ddd, J=0.8, 6.0, 12.0 Hz, 2H), 2.81-2.73 (m, 1H), 2.66-2.48 (m, 3H), 2.38 (dd, J=7.1, 15.3 Hz, 1H), 2.30 (t, J=7.6 Hz, 4H), 2.22 (s, 6H), 2.05-1.96 (m, 8H), 1.66-1.54 (m, 5H), 1.38-1.19 (m, 43H), 1.16 (d, J=6.4 Hz, 3H), 0.87 (t, J=6.9 Hz, 6H). $^{13}$C NMR (100 MHz, CDCl$_3$): δ(ppm)=191.5, 173.4, 171.3, 169.5, 153.2, 134.2, 131.6, 130.3, 130.2, 129.8, 69.5, 62.2, 40.6, 40.1, 34.1, 32.0, 29.9, 29.82, 29.79, 29.7, 29.5, 29.3, 29.24, 29.21, 27.39, 27.35, 27.3, 25.0, 22.8, 19.9, 16.7, 14.2.

Step 3: 1-(1,3-bis(oleoyloxy)propan-2-yl) 5-(4-(hydroxymethyl)-2,6-dimethylphenyl) 3-methylpentanedioate

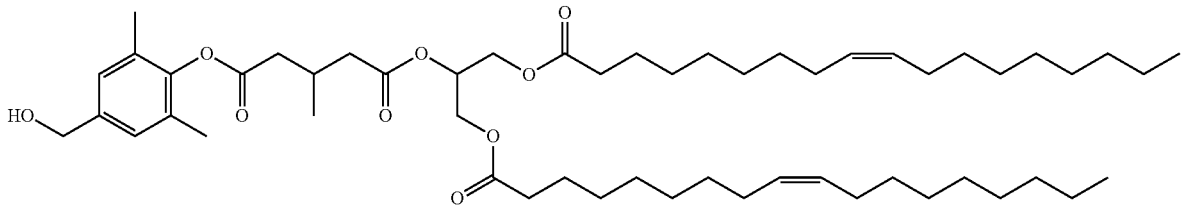 [SMILES: CCCCCCCC/C=C\CCCCCCCC(=O)OCC(COC(=O)CCCCCCC/C=C\CCCCCCCC)OC(=O)CC(C)CC(=O)Oc1c(C)cc(CO)cc1C]

Sodium borohydride (NaBH$_4$, 24 mg, 0.62 mmol) was added to a solution of 1-(1,3-bis(oleoyloxy)propan-2-yl) 5-(4-formyl-2,6-dimethylphenyl) 3-methylpentanedioate (550 mg, 0.62 mmol) in MeOH (5 mL) and THF (10 mL). The mixture was stirred at room temperature for 2 hours before being quenched by the addition of water. The volatiles were removed in vacuo and the mixture was acidified to pH=2 using an aqueous solution of 2N HCl. The mixture was extracted with ethyl acetate. The combined organic layers were dried over Na$_2$SO$_4$, filtered and concentrated in vacuo. The residue was purified by normal phase flash column chromatography (Biotage Isolera, 40 g, Silicycle siliasep cartridge) using n-heptane and EtOAc (gradient: 1:0 to 1:1) to give the desired compound (262 mg, 48%) as a colourless oil. $^1$H NMR (400 MHz, CDCl$_3$): δ(ppm)=7.07 (s, 2H), 5.39-5.26 (m, 5H), 4.61 (s, 2H), 4.32 (ddd, J=1.1, 4.2, 11.9 Hz, 2H), 4.14 (ddd, J=1.4, 6.0, 11.9 Hz, 2H), 2.73 (dd, J=5.2, 14.8 Hz, 1H), 2.67-2.49 (m, 3H), 2.37 (dd, J=7.2, 15.2 Hz, 1H), 2.30 (t, J=7.5 Hz, 4H), 2.14 (s, 6H), 2.05-1.94 (m, 8H), 1.67-1.54 (m, 6H), 1.39-1.19 (m, 42H), 1.15 (d, J=6.4 Hz, 3H), 0.88 (t, J=6.8 Hz, 6H). $^{13}$C NMR (100 MHz, CDCl$_3$): δ(ppm)=173.4, 171.4, 170.1, 147.7, 138.5, 130.4, 130.2, 129.9, 127.4, 69.4, 65.1, 62.2, 40.7, 40.3, 34.1, 32.1, 29.9, 29.8, 29.7, 29.5, 29.31, 29.26, 29.2, 27.5, 27.4, 27.3, 25.0, 22.8, 19.9, 16.6, 14.3.

Step 4: 1-(4-((((((3S,5S,8R,9S,10S,13S,14S,17S)-17-acetyl-10,13-dimethylhexadecahydro-1H-cyclopenta[a]phenanthren-3-yl)oxy)carbonyl)oxy)methyl)-2,6-dimethylphenyl) 5-(1,3-bis(oleoyloxy)propan-2-yl) 3-methylpentanedioate I-20

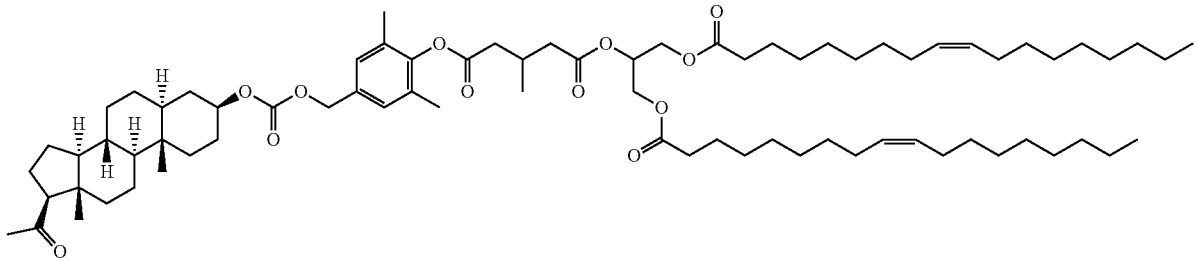

Potassium carbonate (K$_2$CO$_3$, 122 mg, 0.88 mmol) was added to a mixture of 1-(1,3-bis(oleoyloxy)propan-2-yl) 5-(4-(hydroxymethyl)-2,6-dimethylphenyl) 3-methylpentanedioate (130 mg, 0.15 mmol) in N,N-dimethylformamide (3.0 mL) at 0° C. The mixture was stirred at 0° C. for 30 min. Compound 2.2 (71 mg, 0.15 mmol) was added and the mixture was warmed to room temperature and left to stir at room temperature for 24 h and then at 70° C. for 24 h. The reaction mixture was cooled to room temperature. Water, brine and ethyl acetate were added. The layers were separated. The aqueous layer was extracted with ethyl acetate. The combined organic layers were dried over sodium sulfate, filtered and concentrated in vacuo. The residue was purified by normal phase flash column chromatography on silica gel (Biotage Isolera, 25 g, Siliasep cartridge) using n-heptane and EtOAc (gradient: 1:0 to 1:1). Fractions containing the pure product were combined. The residue was re-purified by normal phase flash column chromatography on silica gel (Biotage Isolera, 12 g, Siliasep cartridge) using n-heptane and EtOAc (gradient: 1:0 to 7:3) to give the desired compound (80 mg, 43%) as a colourless oil. UPLC3-MS: (XB BEH C4 Long Acidic 20 to 95): R$_t$=7.72 min., 100% (ELS). MS (ESIpos) m/z=1244.8, 1245.8 (M+NH$_4$+H)$^+$. $^1$H NMR (400 MHz, CDCl$_3$): δ(ppm)=7.07 (s, 2H), 5.38-5.24 (m, 5H), 5.04 (s, 2H), 4.61-4.50 (m, 1H), 4.31 (dd, J=4.2, 12.0 Hz, 2H), 4.14 (dd, J=6.0, 11.9 Hz, 2H), 2.72 (dd, J=5.1, 14.8 Hz, 1H), 2.65-2.48 (m, 4H), 2.36 (dd, J=7.2, 15.2 Hz, 1H), 2.30 (t, J=7.5 Hz, 4H), 2.19-2.09 (m, 10H), 2.06-1.85 (m, 10H), 1.79-1.49 (m, 12H), 1.48-1.08 (m, 55H), 1.02 (dt, J=3.8, 13.7 Hz, 1H), 0.97-0.84 (m, 8H), 0.80 (s, 3H), 0.69 (dt, J=3.7, 11.2 Hz, 1H), 0.59 (s, 3H). $^{13}$C NMR (100 MHz, CDCl$_3$): δ(ppm)=209.7, 173.3, 171.3, 170.0, 154.7, 148.3, 133.0, 130.4, 130.1, 129.8, 128.8, 77.9, 69.4, 68.9, 63.9, 62.2, 56.7, 54.2, 44.7, 44.3, 40.7, 40.2, 39.1, 36.8, 35.6, 35.5, 34.1, 33.9, 32.0, 31.6, 29.9, 29.8, 29.6, 29.4, 29.3, 29.21, 29.18, 28.5, 27.5, 27.4, 27.32, 27.27, 24.9, 24.5, 22.9, 22.8, 21.3, 19.8, 16.6, 14.2, 13.6, 12.3.

Synthesis of IAL-CMSI-C$_8$bMe-2-TG-oleate: 8-(1-(((((3S,5S,8R,9S,10S,13S,14S,17S)-17-acetyl-10,13-dimethylhexadecahydro-1H-cyclopenta[a]phenanthren-3-yl)oxy)carbonyl)oxy)ethyl) 1-(1,3-bis(oleoyloxy)propan-2-yl) 3-methyloctanedioate I-22

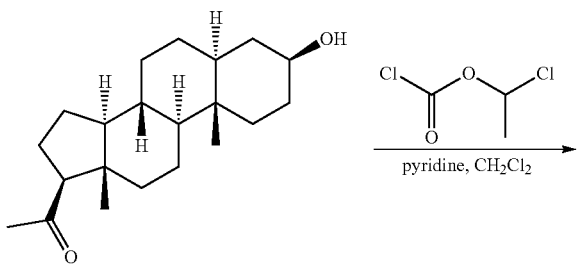 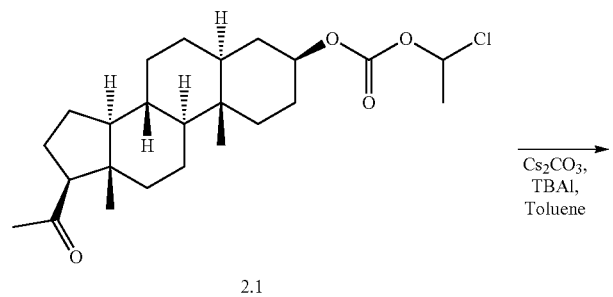

2.1

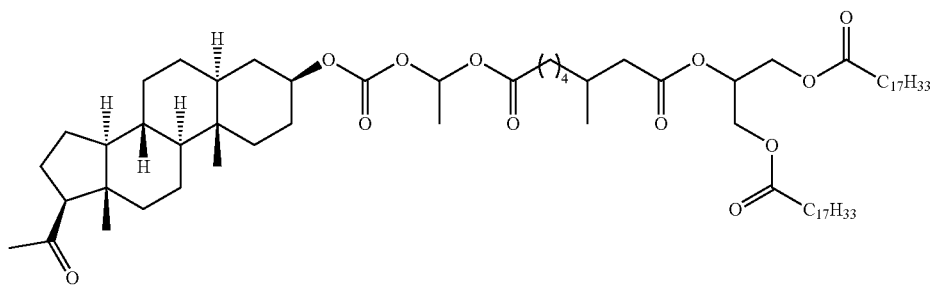

I-22

Pyridine (53 μL, 0.66 mmol) and 1-chloroethyl chloroformate (53 μL, 0.50 mmol) were added to a solution of iso-allopregnanolone (105 mg, 0.33 mmol) in CH$_2$Cl$_2$ (5.0 mL) at 0° C. The resulting mixture was stirred at 0° C. for 10 min and then warmed to room temperature and left to stir for 2 h. Water and CH$_2$Cl$_2$ were added. The layers were separated. The organic layer was washed with brine, dried over magnesium sulfate, filtered and concentrated in vacuo to give the desired compound 2.1 (157 mg, >100%) as a colourless oil which was used in the next step without further purification. $^1$H NMR (400 MHz, CDCl3): δ (ppm)= 6.40 (q, J=5.8 Hz, 1H), 4.67-4.57 (m, 1H), 2.49 (t, J=9.1 Hz, 1H), 2.20-2.05 (m, 4H), 2.03-1.85 (m, 2H), 1.84-1.08 (m, 21H), 1.03 (dt, J=4.6, 13.7 Hz, 1H), 0.95-0.84 (m, 1H), 0.79 (s, 3H), 0.68 (dt, J=3.8, 11.3 Hz, 1H), 0.58 (s, 3H). Pyridine remaining (8% w/w).

Caesium carbonate (277 mg, 0.85 mmol) was added to a mixture of Int-178 (335 mg, 0.42 mmol) in toluene (5.0 mL) and the mixture stirred at room temperature for 15 min. (3S,5S,8R,9S,10S,13S,14S,17S)-17-acetyl-10,13-dimethylhexadecahydro-1H-cyclopenta[a]phenanthren-3-yl (1-chloroethyl) carbonate 2.1 (157 mg, 0.37 mmol) and tetrabutylammonium iodide (TBAI, 68 mg, 0.19 mmol) were added and the mixture was stirred 80° C. for 2 h. The reaction mixture was cooled to room temperature. Water and ethyl acetate were added. The layers were separated. The aqueous layer was extracted with ethyl acetate. The combined organic layers were washed with brine, dried over magnesium sulfate, filtered and concentrated in vacuo. The residue was purified twice by normal phase flash column chromatography on silica gel (Biotage Isolera, 25 g, Siliasep cartridge) using n-heptane and EtOAc (gradient: 1:0 to 1:1). Fractions containing the pure product were combined and solvents removed by rotary evaporation to give the desired compound (327 mg, 75%) as a colourless oil. UPLC3-MS: (XB BEH C4 Long Acidic 20 to 95): $R_f$=7.68 min., 100% (ELS). MS (ESIpos) m/z=1196.9, 1197.8 $(M+NH_4+H)^+$. $^1$H NMR (400 MHz, CDCl$_3$): δ(ppm)=6.73 (q, J=5.4 Hz, 1H), 5.37-5.20 (m, 6H), 4.60-4.50 (m, 1H), 4.27 (dd, J=4.3, 11.9 Hz, 2H), 4.12 (dd, J=6.0, 11.9 Hz, 2H), 2.49 (t, J=9.1 Hz, 1H), 2.36-2.23 (m, 7H), 2.19-2.06 (m, 5H), 2.05-1.84 (m, 11H), 1.79-1.51 (m, 13H), 1.48 (d, J=5.4 Hz, 3H), 1.45-1.07 (m, 56H), 1.00 (dt, J=3.8, 13.6 Hz, 1H), 0.93-0.83 (m, 11H), 0.79 (s, 3H), 0.68 (dt, J=3.7, 11.2 Hz, 1H), 0.58 (s, 3H). $^{13}$C NMR (100 MHz, CDCl$_3$): δ (ppm)=209.6, 173.3, 172.2, 171.6, 152.6, 130.1, 129.8, 91.1, 78.3, 69.0, 63.9, 62.2, 56.7, 54.1, 53.5, 44.7, 44.6, 44.3, 41.6, 39.1, 36.7, 36.3, 35.53, 35.51, 34.1, 34.0, 33.8, 31.99, 31.97, 31.6, 30.2, 29.9, 29.79, 29.75, 29.7, 29.61, 29.56, 29.4, 29.3, 29.20, 29.17, 28.5, 27.31, 27.26, 26.4, 24.9, 24.7, 24.5, 22.9, 22.8, 21.3, 19.7, 19.5, 14.2, 13.5, 12.2.

Synthesis of IAL-CMSI-C8b'bMe-2-TG-oleate: 1-(1-(((((3S,5S,8R,9S,10S,13S,14S,17S)-17-acetyl-10,13-dimethylhexadecahydro-1H-cyclopenta[a]phenanthren-3-yl)oxy)carbonyl)oxy)ethyl) 8-(1,3-bis(oleoyloxy)propan-2-yl) 3,6-dimethyloctanedioate I-23

Cesium carbonate (274 mg, 0.84 mmol) was added to a mixture of Int-176 (338 mg, 0.42 mmol) in toluene (5.0 mL) and the mixture stirred at room temperature for 15 min. Compound 2.1, described above in the synthesis of I-22, (155 mg, 0.37 mmol) and tetrabutylammonium iodide (TBAI, 68 mg, 0.18 mmol) were added and the mixture was stirred 80° C. for 2 h. The reaction mixture was cooled to room temperature. Water and ethyl acetate were added. The layers were separated. The aqueous layer was extracted with ethyl acetate. The combined organic layers were washed with brine, dried over magnesium sulfate, filtered and concentrated in vacuo. The residue was purified twice by normal phase flash column chromatography on silica gel (Biotage Isolera, 25 g, Siliasep cartridge) using n-heptane and EtOAc (gradient: 1:0 to 1:1). Fractions containing the pure product were combined and solvents evaporated to give the desired compound (295 mg, 67%) as a colourless oil. UPLC3-MS: (XB BEH C4 Long Acidic 20 to 95): $R_f$=7.72 min., 100% (ELS). MS (ESIpos) m/z=1210.9, 1211.8 $(M+NH_4+H)^+$. $^1$H NMR (400 MHz, CDCl$_3$): δ (ppm)=6.75 (q, J=5.4 Hz, 1H), 5.39-5.23 (m, 6H), 4.61-4.51 (m, 1H), 4.28 (dd, J=4.3, 11.9 Hz, 2H), 4.13 (dd, J=6.0, 11.9 Hz, 2H), 2.51 (t, J=8.9 Hz, 1H), 2.37-2.27 (m, 6H), 2.18-2.07 (m, 6H), 2.04-1.84 (m, 12H), 1.80-1.52 (m, 12H), 1.49 (d, J=5.4 Hz, 3H), 1.45-1.08 (m, 58H), 1.02 (dt, J=3.8, 13.6 Hz, 1H), 0.93 (dd, J=1.7, 6.6 Hz, 7H), 0.87 (t, J=6.8 Hz, 7H), 0.80 (s, 3H), 0.69 (dt, J=3.6, 11.3 Hz, 1H), 0.59 (s, 3H). $^{13}$C NMR (100 MHz, CDCl$_3$): δ (ppm)=209.7, 173.4, 172.2, 171.1, 152.7, 130.1, 129.8, 91.1, 78.3, 69.0, 63.9, 62.3, 56.7, 54.2, 53.6, 44.7, 44.3, 41.8, 41.7, 41.6, 41.5, 39.1, 36.8, 35.57, 35.55, 34.14, 34.08, 34.03, 33.96, 33.9, 33.8, 32.03, 32.00, 31.6, 30.6, 30.5, 30.4, 30.3, 29.9, 29.83, 29.79, 29.75, 29.7, 29.5, 29.3, 29.24, 29.22,

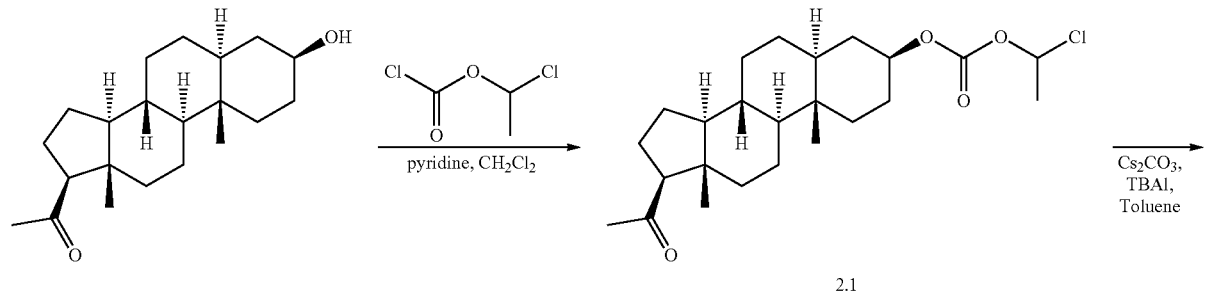

2.1

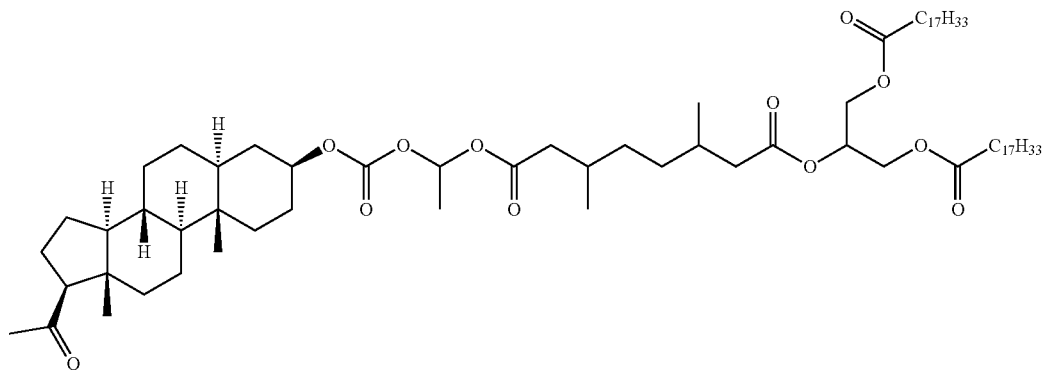

I-23

28.5, 27.4, 27.3, 25.0, 24.5, 22.9, 22.8, 21.3, 19.78, 19.75, 19.7, 19.59, 19.57, 19.5, 14.3, 13.6, 12.3.

Synthesis of IAL-C₅bMe-2-TG-oleate: 1-((3S,5S, 8R,9S,10S,13S,14S,17S)-17-acetyl-10,13-dimethyl-hexadecahydro-1H-cyclopenta[a]phenanthren-3-yl) 5-(1,3-bis(oleoyloxy)propan-2-yl) 3-methylpentanedioate I-24

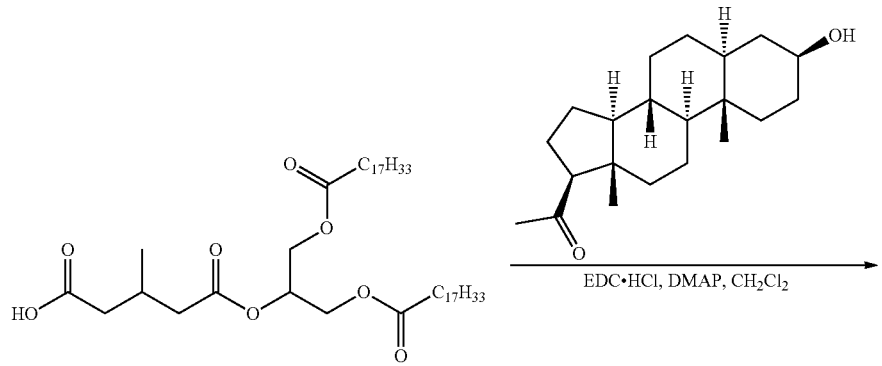

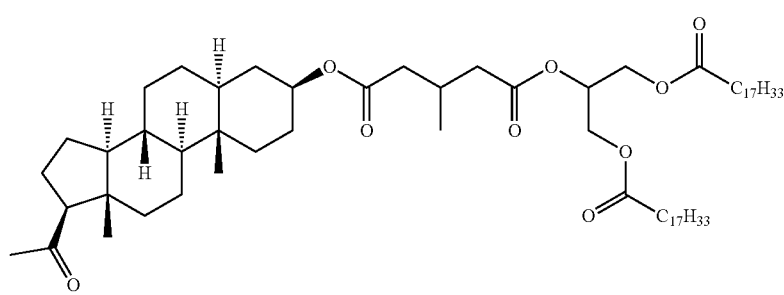

I-24

4-(Dimethylamino)pyridine (DMAP, 46 mg, 0.38 mmol) and N—(3-dimethylaminopropyl)-N'-ethyl-carbodiimide (EDC·HCl, 96 mg, 0.50 mmol) were added to a solution of iso-allopregnanolone (80 mg, 0.25 mmol) and Int-210 (187 mg, 0.25 mmol) in CH$_2$Cl$_2$ (3.0 mL) and the mixture stirred at room temperature for 18 hours before being concentrated in vacuo. The residue was purified by normal phase flash column chromatography on silica gel (Biotage Isolera, 25 g, Siliasep cartridge) using n-heptane and EtOAc (gradient: 1:0 to 7:3) to give the desired compound (200 mg, 76%) as a colourless oil. UPLC3-MS: (XB BEH C4 Long Acidic 20 to 95): R$_t$=7.64 min., 100% (ELS). MS (ESIpos) m/z=1066.78, 1067.71 (M+NH$_4$++H)$^+$. $^1$H NMR (400 MHz, CDCl$_3$): δ(ppm)=5.35-5.20 (m, 5H), 4.71-4.62 (m, 1H), 4.27 (ddd, J=1.4, 4.1, 12.0 Hz, 2H), 4.10 (dd, J=6.0, 12.0 Hz, 2H), 2.49 (t, J=8.9 Hz, 1H), 2.45-2.05 (m, 14H), 2.03-1.91 (m, 9H), 1.81-0.75 (m, 79H), 0.66 (dt, J=3.0, 11.6 Hz, 1H), 0.56 (s, 3H). $^{13}$C NMR (100 MHz, CDCl$_3$): δ (ppm)=209.5, 173.2, 171.7, 171.4, 130.0, 129.7, 73.6, 69.1, 63.8, 62.1, 56.7, 54.1, 44.7, 44.2, 41.1, 40.8, 39.1, 36.8, 35.6, 35.5, 34.0, 32.0, 31.5, 29.81, 29.75, 29.6, 29.4, 29.22, 29.16, 29.1, 28.5, 27.6, 27.5, 27.3, 27.2, 24.9, 24.4, 22.8, 22.7, 21.3, 19.6, 14.2, 13.5, 12.3.

Synthesis of IAL-C10-2-TG-oleate: 1-((3S,5S,8R, 9S,10S,13S,14S,17S)-17-acetyl-10,13-dimethyl-hexadecahydro-1H-cyclopenta[a]phenanthren-3-yl) 10-(1,3-bis(oleoyloxy)propan-2-yl) decanedioate I-25

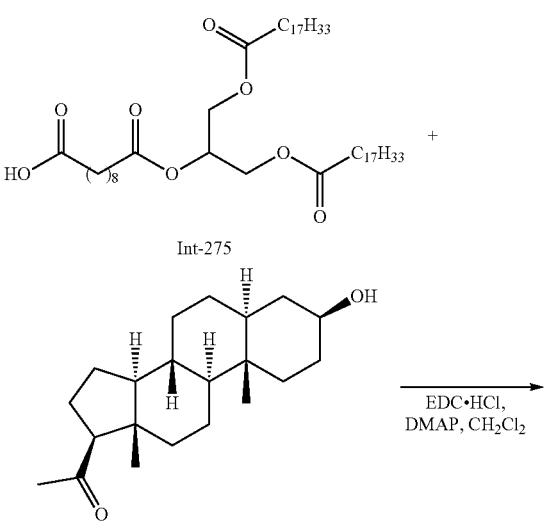

325

-continued

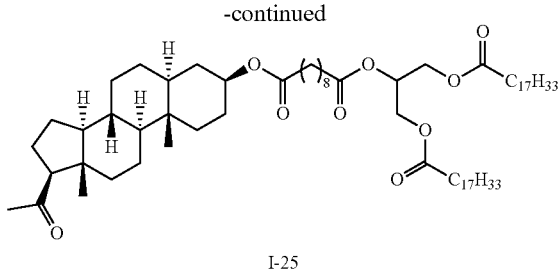

I-25

DMAP (66 mg, 0.54 mmol) and EDC·HCl (38 mg, 0.72 mmol) were added to a solution of iso-allopregnanolone (115 mg, 0.36 mmol) and Int-275 (290 mg, 0.36 mmol) in CH$_2$Cl$_2$ (7.0 mL) and the mixture was stirred at room temperature for 1 day before being concentrated in vacuo. The residue was purified by normal phase flash column chromatography on silica gel (Biotage Isolera, 25 g, Siliasep cartridge) using n-heptane and EtOAc (gradient: 1:0 to 1:1) to give the desired compound (231 mg, 58%) as a colourless gum. UPLC3-MS: (XB BEH C4 Long Acidic 20 to 95):

326

R$_t$=7.87 min., 100% (ELS). MS (ESIpos) m/z=1122.91, 1123.77 (M+NH$_4$++H)$^+$. $^1$H NMR (400 MHz, CDCl3): δ (ppm)=5.38-5.21 (m, 5H), 4.73-4.63 (m, 1H), 4.28 (dd, J=4.3, 11.9 Hz, 2H), 4.13 (dd, J=5.9, 11.9 Hz, 2H), 2.51 (t, J=8.9 Hz, 1H), 2.30 (t, J=7.5 Hz, 6H), 2.23 (t, J=7.5 Hz, 2H), 2.19-2.07 (m, 4H), 2.06-1.91 (m, 9H), 1.84-1.51 (m, 16H), 1.51-1.07 (m, 60H), 1.02 (dt, J=3.7, 13.5 Hz, 1H), 0.96-0.84 (m, 7H), 0.81 (s, 3H), 0.69 (dt, J=3.6, 11.3 Hz, 1H), 0.59 (s, 3H). $^{13}$C NMR (100 MHz, CDCl3): δ(ppm)=209.4, 173.3, 173.2, 172.7, 130.0, 129.7, 73.3, 68.9, 63.8, 62.1, 56.6, 54.1, 44.7, 44.2, 39.0, 36.8, 35.52, 35.48, 34.7, 34.2, 34.0, 31.9, 31.5, 29.8, 29.7, 29.64, 29.55, 29.5, 29.4, 29.34, 29.29, 29.2, 29.11, 29.09, 29.0, 28.5, 27.5, 27.23, 27.18, 25.0, 24.9, 24.4, 22.8, 22.7, 21.2, 14.1, 13.5, 12.2.

Synthesis of IAL-C10bMe-2-TG-oleate: 10-((3S,5S, 8R,9S,10S,13S,14S,17S)-17-acetyl-10,13-dimethyl-hexadecahydro-1H-cyclopenta[a]phenanthren-3-yl) 1-(1,3-bis(oleoyloxy)propan-2-yl) 3-methyldecane-dioate I-26

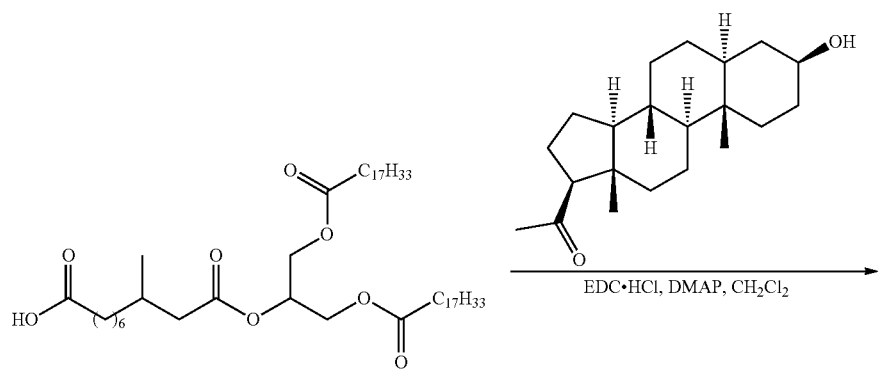

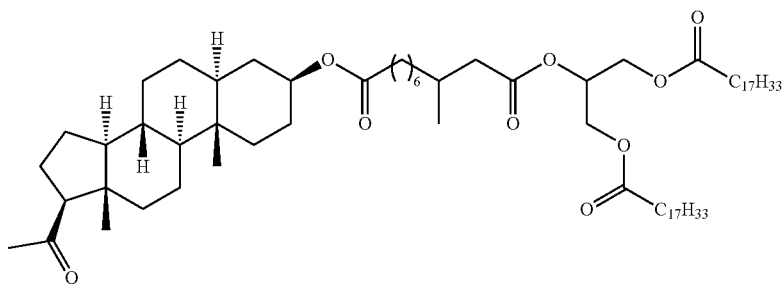

I-26

DMAP (57 mg, 0.47 mmol) and EDC·HCl (119 mg, 0.62 mmol) were added to a solution of iso-allopregnanolone (100 mg, 0.31 mmol) and Int-187 (257 mg, 0.31 mmol) in $CH_2Cl_2$ (7.0 mL) and the mixture stirred at room temperature for 2 days before being concentrated in vacuo. The residue was purified by normal phase flash column chromatography on silica gel (Biotage Isolera, 25 g, Siliasep cartridge) using n-heptane and EtOAc (gradient: 1:0 to 1:1). Fractions containing the desired product were concentrated in vacuo. The product was re-purified by normal phase flash column chromatography on silica gel (Biotage Isolera, 25 g, Siliasep cartridge) using n-heptane and EtOAc (gradient: 1:0 to 7:3) to give the desired compound (133 mg, 38%) as a colourless oil. UPLC3-MS: (XB BEH C4 Long Acidic 20 to 95): $R_t$=7.94 min., 100% (ELS). MS (ESIpos) m/z=1136.9, 1137.8 $(M+NH4^++H)^+$. 1H NMR (400 MHz, $CDCl_3$): δ (ppm)=5.38-5.22 (m, 5H), 4.73-4.62 (m, 1H), 4.27 (dd, J=4.2, 11.9 Hz, 2H), 4.12 (dd, J=6.0, 11.9 Hz, 2H), 2.49 (t, J=8.9 Hz, 1H), 2.34-2.20 (m, 8H), 2.17-2.05 (m, 5H), 2.05-1.85 (m, 10H), 1.83-1.07 (m, 79H), 1.01 (dt, J=3.7, 13.5 Hz, 1H), 0.92-0.83 (m, 11H), 0.80 (s, 3H), 0.68 (dt, J=3.6, 11.3 Hz, 1H), 0.58 (s, 3H). $^{13}$C NMR (100 MHz, $CDCl_3$): δ(ppm)=209.6, 173.4, 173.32, 173.29, 172.3, 130.1, 129.8, 73.4, 68.9, 63.9, 62.2, 56.7, 54.2, 44.7, 44.3, 41.7, 39.1, 36.9, 36.7, 35.6, 35.5, 34.8, 34.1, 32.0, 31.6, 30.4, 29.9, 29.79, 29.75, 29.7, 29.61, 29.56, 29.49, 29.45, 29.41, 29.35, 29.3, 29.19, 29.17, 28.6, 27.6, 27.30, 27.25, 26.8, 25.1, 24.9, 24.5, 22.9, 22.8, 21.3, 19.6, 14.2, 13.5, 12.3.

Synthesis of IAL-CMSI-C₅bMe-2-TG-oleate: 1-(1-(((((3S,5S,8R,9S,10S,13S,14S,17S)-17-acetyl-10,13-dimethylhexadecahydro-1H-cyclopenta[a]phenanthren-3-yl)oxy)carbonyl)oxy)ethyl) 5-(1,3-bis(oleoyloxy)propan-2-yl) 3-methylpentanedioate I-27

Cesium carbonate ($Cs_2CO_3$, 224 mg, 0.69 mmol) was added to a mixture of Int-210 (258 mg, 0.34 mmol) in toluene (5.0 mL) and the mixture stirred at room temperature for 15 min. Compound 2.1, described above in the synthesis of I-22, (127 mg, 0.30 mmol) and tetrabutylammonium iodide (TBAI, 55 mg, 0.15 mmol) were added and the mixture was stirred 80° C. for 1 h. The reaction mixture was cooled to room temperature. Water and ethyl acetate were added. The layers were separated. The aqueous layer was extracted with ethyl acetate. The combined organic layers were washed with brine, dried over magnesium sulfate, filtered and concentrated in vacuo. The residue was purified by normal phase flash column chromatography on silica gel (Biotage Isolera, 25 g, Siliasep cartridge) using n-heptane and EtOAc (gradient: 1:0 to 1:1) to give the desired compound (224 mg, 66%) as a colourless oil. UPLC3-MS: (XB BEH $C_4$ Long Acidic 20 to 95): $R_t$=7.53 min., 100% (ELS). MS (ESIpos) m/z=1154.83, 1155.69 $(M+NH_4++H)^+$. $^1$H NMR (400 MHz, $CDCl_3$): δ (ppm)=6.74 (q, J=5.4 Hz, 1H), 5.37-5.20 (m, 5H), 4.60-4.50 (m, 1H), 4.31-4.24 (m, 2H), 4.12 (dd, J=7.5, 4.4 Hz, 2H), 2.53-2.36 (m, 4H), 2.32-2.18 (m, 6H), 2.18-2.08 (m, 4H), 2.05-1.84 (m, 10H), 1.79-1.06 (m, 67H), 1.06-0.96 (m, 4H), 0.96-0.83 (m, 7H), 0.79 (s, 3H), 0.68 (dt, J=3.7, 11.2 Hz, 1H), 0.58 (s, 3H). $^{13}$C NMR (100 MHz, $CDCl_3$): δ(ppm)=209.6, 173.3, 171.3, 170.24, 170.21, 152.6, 130.1, 129.8, 91.2, 78.3, 69.2, 63.9, 62.2, 56.7, 54.1, 44.7, 44.6, 44.3, 40.63, 40.55, 40.5, 40.4, 39.1, 36.7, 35.53, 35.52, 34.1, 33.8, 33.7, 32.00, 31.97, 31.6, 29.9, 29.80, 29.76, 29.7, 29.62, 29.58, 29.5, 29.4, 29.3, 29.21, 29.18, 28.5, 27.31, 27.27, 27.2, 24.9, 24.5, 22.9, 22.8, 21.3, 19.7, 19.6, 19.5, 14.2, 13.5, 12.3.

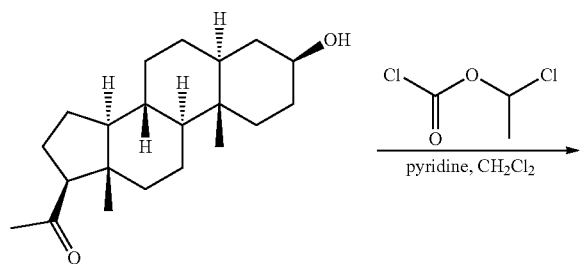

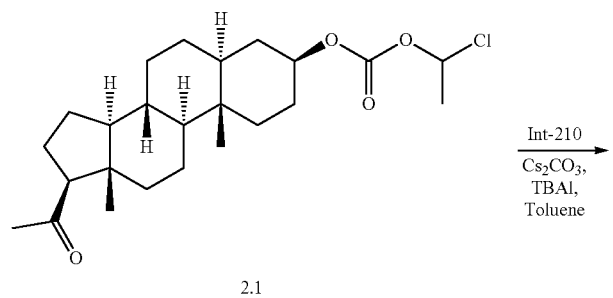

2.1

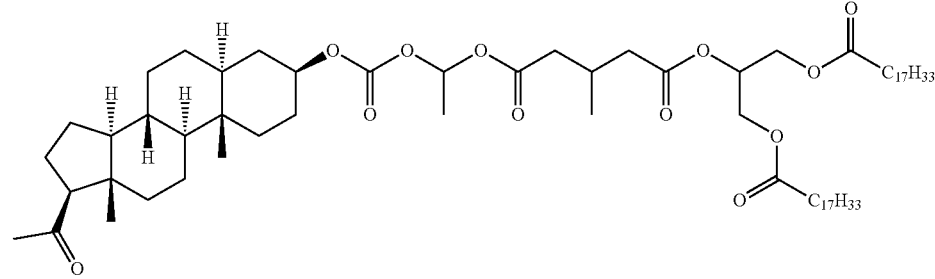

I-27

Synthesis of ALL-CMSI-C10b'bMe-2-TG-oleate: I-1

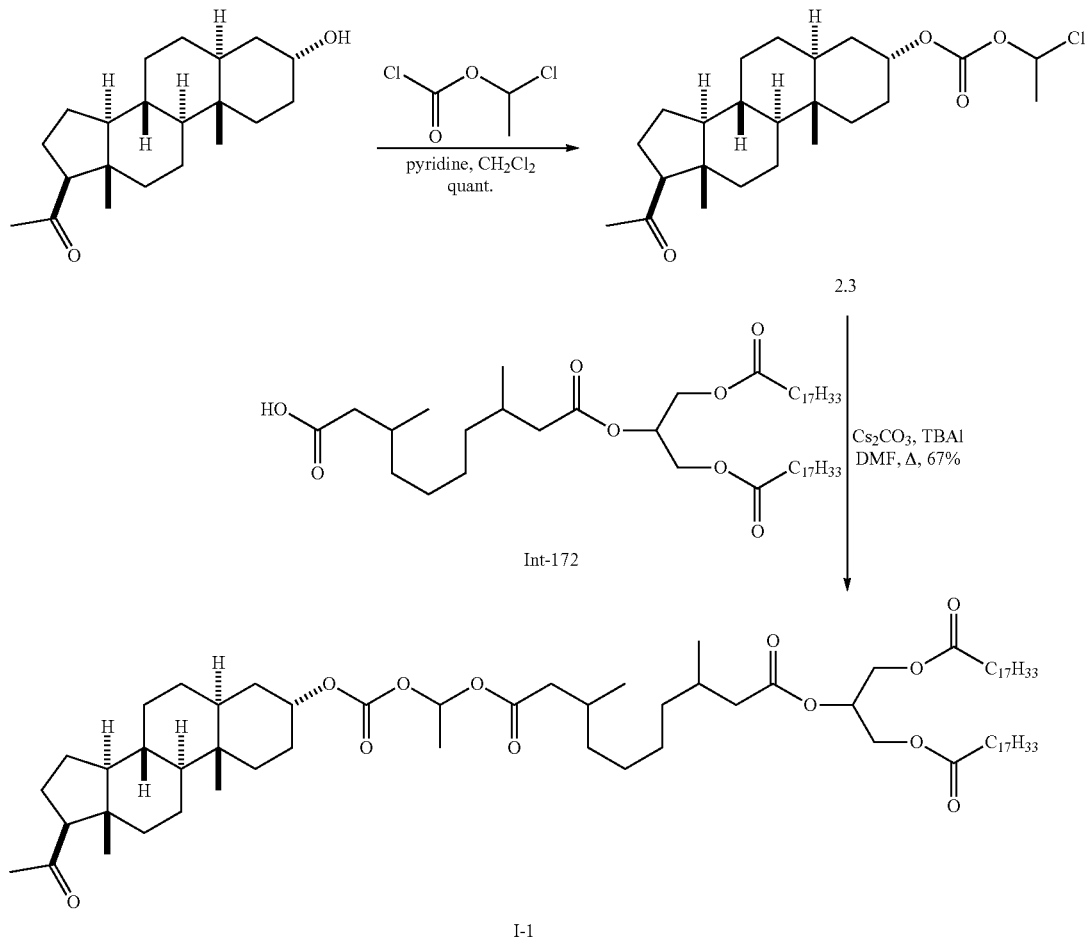

Step 1: Preparation of Compound 2.3

1-Chloroethyl chloroformate (67.8 µL, 0.628 mmol) and pyridine (95.2 µL, 1.18 mmol) were added to allopregnanolone (125 mg, 0.393 mmol) in $CH_2Cl_2$ (5 mL) at 0° C. and the mixture stirred at 0° C. for 30 minutes and then at rt for two hours. The reaction was diluted with $CH_2Cl_2$ (30 mL) and the organic phase washed with water and brine (30 mL each), dried ($MgSO_4$) and concentrated under reduced pressure to give crude compound 2.3 (167 mg, quant.) as a colourless solid that was used without purification; $^1$H NMR (400 MHz, $CDCl_3$) δ 6.447/6.444 (each q, J=5.8 Hz, 1H), 4.98 (m, 1H), 2.52 (t, J=8.4 Hz, 1H), 2.14 (m, 1H), 2.111/2.109 (each s, 3H), 2.01 (m, 1H), 1.86 (m, 1H), 1.849/1.846 (each d, J=5.8 Hz, 3H), 1.74-1.49 (m, 9H), 1.44-1.10 (m, 8H), 1.02-0.78 (m, 2H), 0.80 (s, 3H), 0.60 (s, 3H).

Step 2: ALL-CMSI-C10b'bMe-2-TG-oleate I-1

Cesium carbonate ($Cs_2CO_3$, 43.4 mg, 133 µmol) and tetra-n-butylammonium iodide (TBAI, 8.2 mg, 22.2 µmol) were added to a suspension of Int-172 (37.0 mg, 44.4 µmol) and compound 2.3 (18.9 mg, 44.4 µmol) in DMF (2 mL) and the mixture heated at 60° C. for 1.5 hours. The reaction was cooled to rt, diluted with ethyl acetate (30 mL) and the organic phase washed with water and brine (30 mL each), dried ($MgSO_4$) and concentrated under reduced pressure to give the crude product. Silica gel chromatography (8% to 10% ethyl acetate/hexanes) gave ALL-CMSI-$C_{10}$b'bMe-2-TG-oleate I-1 (36.5 mg, 67%) as a colourless oil. $^1$H NMR (401 MHz, $CDCl_3$) δ 6.776/6.770 (each q, J=5.4 Hz, 1H), 5.39-5.22 (m, 5H), 4.91 (m, 1H), 4.28 (dd, J=11.9, 4.2 Hz, 2H), 4.13 (dd, J=11.9, 6.0 Hz, 2H), 2.51 (t, J=8.9 Hz, 1H), 2.37-2.25 (m, 6H), 2.18-2.06 (m, 3H), 2.10 (s, 3H), 2.05-1.77 (m, 12H), 1.72-1.45 (m, 18H), 1.43-1.07 (m, 53H), 0.93 (d, J=6.6 Hz, 3H), 0.92 (d, J=6.6 Hz, 3H), 1.00-0.74 (m, 3H), 0.87 (t, J=6.4 Hz, 6H), 0.78 (s, 3H), 0.59 (s, 3H). $^{13}$C NMR (101 MHz, $CDCl_3$) δ 209.8 (C), 173.4 (2C; C), 172.4 (C), 171.2 (C), 152.8 (C), 130.2 (2C; CH), 129.8 (2C; CH), 91.2 (CH), 75.2 (CH), 69.0 (CH), 63.9 (CH), 62.3 (2C; $CH_2$), 56.9 (CH), 54.0 (CH), 44.4 (C), 41.8-41.6 (2C; $CH_2$), 39.8 (CH), 39.2 ($CH_2$), 36.8-36.6 (2C; $CH_2$), 35.9 (C), 35.5 (CH), 34.2 (2C; $CH_2$), 32.82/32.79 ($CH_2$), 32.7 ($CH_2$), 32.0 (2C; $CH_2$), 31.9 ($CH_2$), 31.7 ($CH_3$), 30.5 (CH), 30.3 (CH), 29.9 (2C; $CH_2$), 29.8 (2C; $CH_2$), 29.7 (2C; $CH_2$), 29.5 (4C; $CH_2$), 29.3 (2C; $CH_2$), 29.24 (2C; $CH_2$), 29.22 (2C; $CH_2$), 28.3 ($CH_2$), 27.4 (2C; $CH_2$), 27.3 (2C; $CH_2$), 27.20 ($CH_2$), 27.17 ($CH_2$), 26.1/26.0 ($CH_2$), 25.0 (2C; $CH_2$), 24.5 ($CH_2$), 22.9 ($CH_2$), 22.8 (2C; $CH_2$), 20.9 ($CH_2$), 19.8-19.6 (3C; $CH_3$), 14.3 (2C; $CH_3$), 13.6 ($CH_3$), 11.4 ($CH_3$). Note: Multiple peaks were observed for several $^{13}$C NMR signals of the C10b'bMe linker, these are reported as a range of peaks (eg: 34.1-33.8 ppm).

Synthesis of ALL-CMSI-C5bMe-2-TG-oleate: I-2

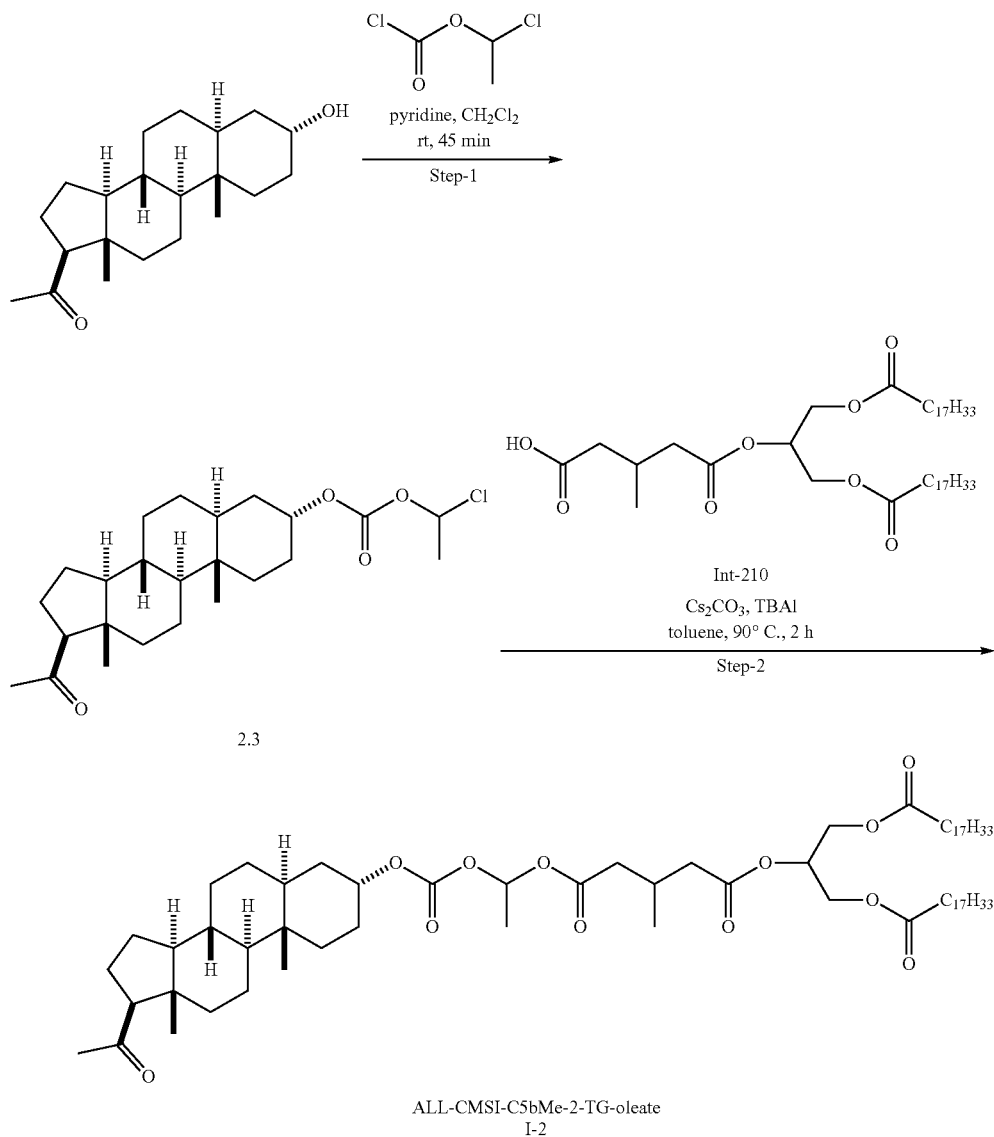

ALL-CMSI-C5bMe-2-TG-oleate
I-2

To a solution of Int-210 (11.6 g, 15.56 mmol) in toluene (100 mL) was added Cs$_2$CO$_3$ (10.1 g, 31.132 mmol) and the mixture was stirred at room temperature for 15 min, then compound 2.3 (6.6 g, 15.566 mmol, prepared as described in the synthesis of I-1) (pre dissolved in 100 mL toluene) and TBAI (2.87 g, 7.783 mmol) were added at room temperature. The reaction mixture was heated to 90° C. and stirred for 2 h. The reaction was monitored by TLC. After completion of the reaction, the reaction mixture was diluted with water (200 ml) and extracted with ethyl acetate (3×300 ml), then the combined organic layers were dried over Na$_2$SO$_4$. The mixture was filtered and the filtrate concentrated under vacuum to get the crude product, which was purified by column chromatography using silica gel (100-200 mesh). Pure compound was eluted at 20% ethyl acetate and hexane as a mobile phase. The pure fraction was concentrated under vacuum to obtain the desired ALL-CMSI-C5bMe-TG-Oleate I-2 (8.5 g, 48%) as a viscous oil. $^1$H NMR (400 MHz, Chloroform-d) δ 6.77 (q, J=5.5 Hz, 1H), 5.40-5.22 (m, 5H), 4.92 (q, J=2.4 Hz, 1H), 4.29 (dt, J=11.8, 4.2 Hz, 2H), 4.13 (dd, J=12.0, 6.0 Hz, 2H), 2.52 (t, J=8.9 Hz, 1H), 2.43 (ddd, J=16.6, 5.6, 3.2 Hz, 3H), 2.31 (t, J=7.6 Hz, 5H), 2.25 (dd, J=7.7, 2.2 Hz, 1H), 2.14 (s, 1H), 2.11 (s, 3H), 2.00 (q, J=6.5 Hz, 8H), 1.76-1.59 (m, 8H), 1.51 (dd, J=9.8, 5.5 Hz, 6H), 1.40 (dd, J=12.1, 3.6 Hz, 1H), 1.31 (d, J=9.8 Hz, 50H), 1.14 (ddt, J=18.8, 12.7, 7.3 Hz, 3H), 1.03 (d, J=6.0 Hz, 3H), 0.95 (dt, J=12.4, 6.2 Hz, 2H), 0.88 (t, J=6.6 Hz, 6H), 0.82 (d, J=4.1 Hz, 1H), 0.79 (s, 3H), 0.60 (s, 3H). $^{13}$C NMR (101 MHz, Chloroform-d) δ 209.74 (1C), 173.28 (2C), 171.30 (1C), 170.17 (1C), 152.67 (1C), 130.04 (1C), 129.73 (1C), 91.15 (1C), 75.23 (1C), 69.14 (1C), 63.83 (1C), 62.08 (1C), 56.76 (1C), 53.83 (1C), 44.26 (1C), 40.50 (1C), 40.37 (1C), 39.66 (1C), 39.08 (1C), 35.75 (1C), 35.43 (1C), 34.02 (1C), 32.69 (1C), 32.60 (1C), 31.94 (1C), 31.75 (1C), 31.59 (1C), 29.80-29.13 (28C), 28.18 (1C), 27.26 (1C), 27.22 (1C), 24.85 (1C), 24.40 (1C), 22.79 (1C), 22.73 (1C), 20.80 (1C), 19.67 (1C), 19.52 (1C), 14.17 (1C), 13.50 (1C), 11.33 (1C). ELSD: 17.08 min, 99.71% purity; LCMS: 10.13, 100% purity; MASS (ESI, +ve) m/z: 1155.26 (MH+18).

Alternative Synthesis of
ALL-CMSI-C5bMe-2-TG-oleate: I-2
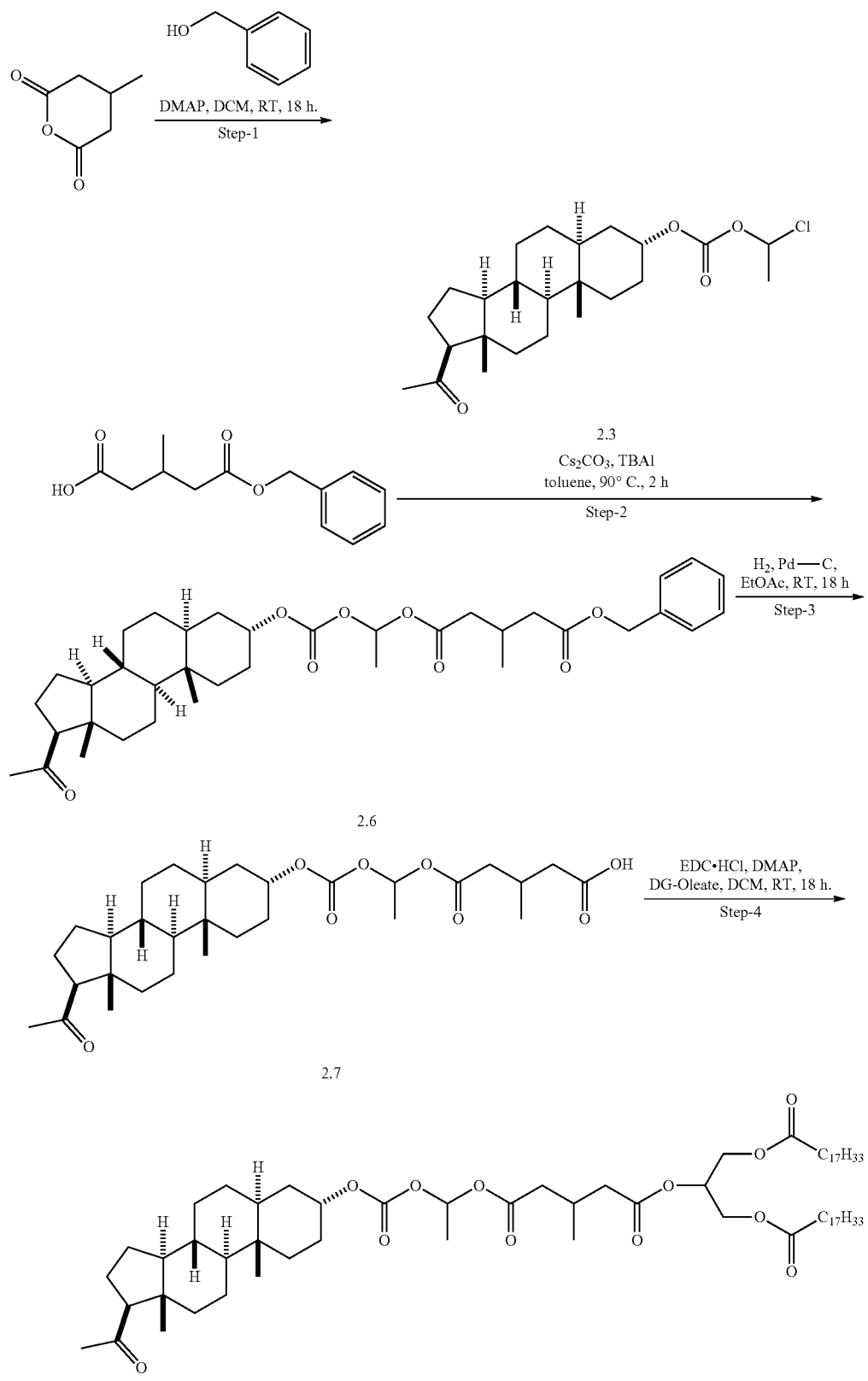

Step 1: Synthesis of 5-(benzyloxy)-3-methyl-5-oxopentanoic acid

To a solution of compound 4-methyldihydro-2H-pyran-2,6 (3H)-dione (3.0 g, 23.428 mmol) and DMAP (1.42 g, 11.71 mmol) in DCM (60 ml) was added benzyl alcohol (1.26 g, 11.71 mmol), then the reaction mixture was stirred at room temperature for 18 h at 0° C. The reaction was monitored by TLC, and after completion of reaction, the reaction mixture was concentrated under vacuum to get crude compound, which was purified by column chromatography using 12% Ethyl Acetate and n-Hexane as eluent to get pure 5-(benzyloxy)-3-methyl-5-oxopentanoic acid (2.5 g, 45.5%) as light yellow liquid. 1H NMR (400 MHz, Chloroform-d) δ 7.37 (s, 5H), 5.14 (s, 2H), 2.87 (dd, J=16.9, 4.1 Hz, 1H), 2.59-2.37 (m, 2H), 2.32 (m, 2H), 1.07 (d, J=6.1 Hz, 3H).

Step 2: Synthesis of Compound 2.6

To a solution of 5-(benzyloxy)-3-methyl-5-oxopentanoic acid (3.34 g, 78.58 mmol) in toluene (30 ml) was added $Cs_2CO_3$ (5.12 g, 157.17 mmol). The reaction was stirred at room temperature for 15 min and then compound 2.3 (1.85 g, 78.75 mmol) (pre dissolved in 30 ml Toluene) and TBAI (2.87 g, 7.783 mmol) were added at room temperature. The reaction mixture was stirred at 90° C. for 2 h. The reaction was monitored by TLC, and after completion of the reaction, the reaction mixture was diluted with water (200 ml) and extracted with ethyl acetate (3×200 ml), combined organic layer dried over $Na_2SO_4$, distilled under vacuum to get crude compound, which was purified by column chromatography using silica gel (100-200 mesh). Pure compound was eluted at 15% ethyl acetate and hexane as a mobile phase then pure fraction was conc. in the rota vapour to get pure compound 2.6 (3.0 g, 61.22%) as viscous oil. $^1$H NMR (400 MHz, Chloroform-d) δ 7.39 (m, 5H), 6.81 (s, 1H), 5.16 (s, 2H), 4.95 (m, 1H), 2.60-2.41 (m, 1H), 2.40-2.24 (m, 1H), 2.19-2.15 (m, 6H), 2.05-1.89 (d, J=15.3 Hz, 4H), 1.68-1.49 (m, 14H), 1.36 (dt, J=44.3, 5.7 Hz, 4H), 1.26-1.19 (dt, J=10.7, 4.8 Hz, 4H), 1.07-0.65 (m, 9H).

Step 3: Synthesis of Compound 2.7

To a solution of compound 2.6 (3.0 g, 4.80 mmol) in ethyl acetate (100 ml) was added palladium on carbon (10% w/w, 3.0 g) and the resulting suspension was evacuated and flushed with $N_2$ three times. The reaction mixture was then stirred at room temperature for 18 h under 20 kg $H_2$ pressure. After completion of the reaction, the reaction mixture was filtered through a celite bed, and washed with ethyl acetate (200 ml). The filtrate was concentrated under reduced pressure to afford crude compound 2.7 (1.6 g, 72%) as a colourless oil which was used in the next step without purification. $^1$H NMR (400 MHz, Chloroform-d) δ 6.82 (m, 1H), 4.97 (d, J=3.1 Hz, 1H), 2.62-2.43 (m, 3H), 2.37 (s, 1H), 2.42-2.28 (m, 2H), 2.21 (dd, J=11.0, 9.1 Hz, 4H), 2.16 (s, 2H), 2.12-1.99 (m, 6H), 1.70 (s, 1H), 1.63-1.51 (m, 4H), 1.49-1.38 (m, 8H), 1.41-1.26 (m, 2H), 1.31-1.14 (m, 3H), 1.11 (d, J=6.0 Hz, 2H), 1.07-0.64 (s, 6H).

Step 4: Synthesis of I-2

To a stirred solution of compound 2.7 (1.0 g, 1.87 mmol) and Int-112 (0.69 g 1.12 mmol) in DCM (20 ml) was added EDC·HCl (0.89 g, 4.67 mmol) and DMAP (0.28 g, 1.87 mmol) at room temperature. The reaction mixture was then stirred at room temperature for 18 h. The progress of the reaction was monitored by TLC. After completion of the reaction, the reaction mixture was concentrated under vacuum to get crude material which was purified by column chromatography purification using 5% ethyl acetate and n-Hexane as eluent to yield pure I-2 (1.05 g, 49.9%) as yellowish viscous liquid. $^1$H NMR (400 MHz, Chloroform-d) δ 6.82 (s, 1H), 5.38-5.31 (m, 5H), 4.96 (q, J=2.4 Hz, 1H), 4.19 (dt, J=11.8, 4.2 Hz, 2H), 4.15 (dd, J=12.0, 6.0 Hz, 2H), 2.52 (t, J=8.9 Hz, 1H), 2.49-2.45 (ddd, J=16.6, 5.6, 3.2 Hz, 3H), 2.34 (t, J=7.6 Hz, 5H), 2.28 (dd, J=7.7, 2.2 Hz, 1H), 2.15 (s, 3H), 2.05 (q, J=6.5 Hz, 8H), 1.70-1.56 (m, 8H), 1.45-1.30 (d, J=9.8 Hz, 50H), 1.08 (ddt, J=18.8, 12.7, 7.3 Hz, 3H), 1.00 (d, J=6.0 Hz, 2H), 0.97 (dt, J=12.4, 6.2 Hz, 2H), 0.88 (t, J=6.6 Hz, 6H), 0.82) d, J=4.1 Hz, 1H), 0.79 (s, 3H), 0.60 (s, 3H). $^{13}$C NMR (101 MHz, Chloroform-d) δ 209.74 (1C), 173.25 (2C), 171.28 (1C), 170.18 (1C), 152.68 (1C), 130.03 (2C), 129.73 (2C), 91.15 (1C), 75.23 (1C), 69.16 (1C), 63.83 (1C), 62.08 (2C), 56.77 (1C), 53.85 (1C), 44.25 (1C), 40.48 (1C), 39.67 (1C), 39.08 (1C), 35.75 (1C), 35.43 (1C), 34.01 (1C), 32.71 (1C), 32.60 (1C), 31.93-29.12 (21C), 28.18-27.20 (8C), 25.91 (1C), 24.85 (1C), 24.39 (1C), 22.81 (2C), 22.71 (1C), 20.80 (1C), 19.66 (1C), 19.46 (1C), 14.15 (1C), 13.48 (1C), 11.32 (2C). ELSD: 12.37 min, 98.44% purity. MASS (ESI, +ve) m/z: 1154.73 (MH+18).

Synthesis of ALL-CMSI-C$_8$b'bMe-2-TG-oleate I-4

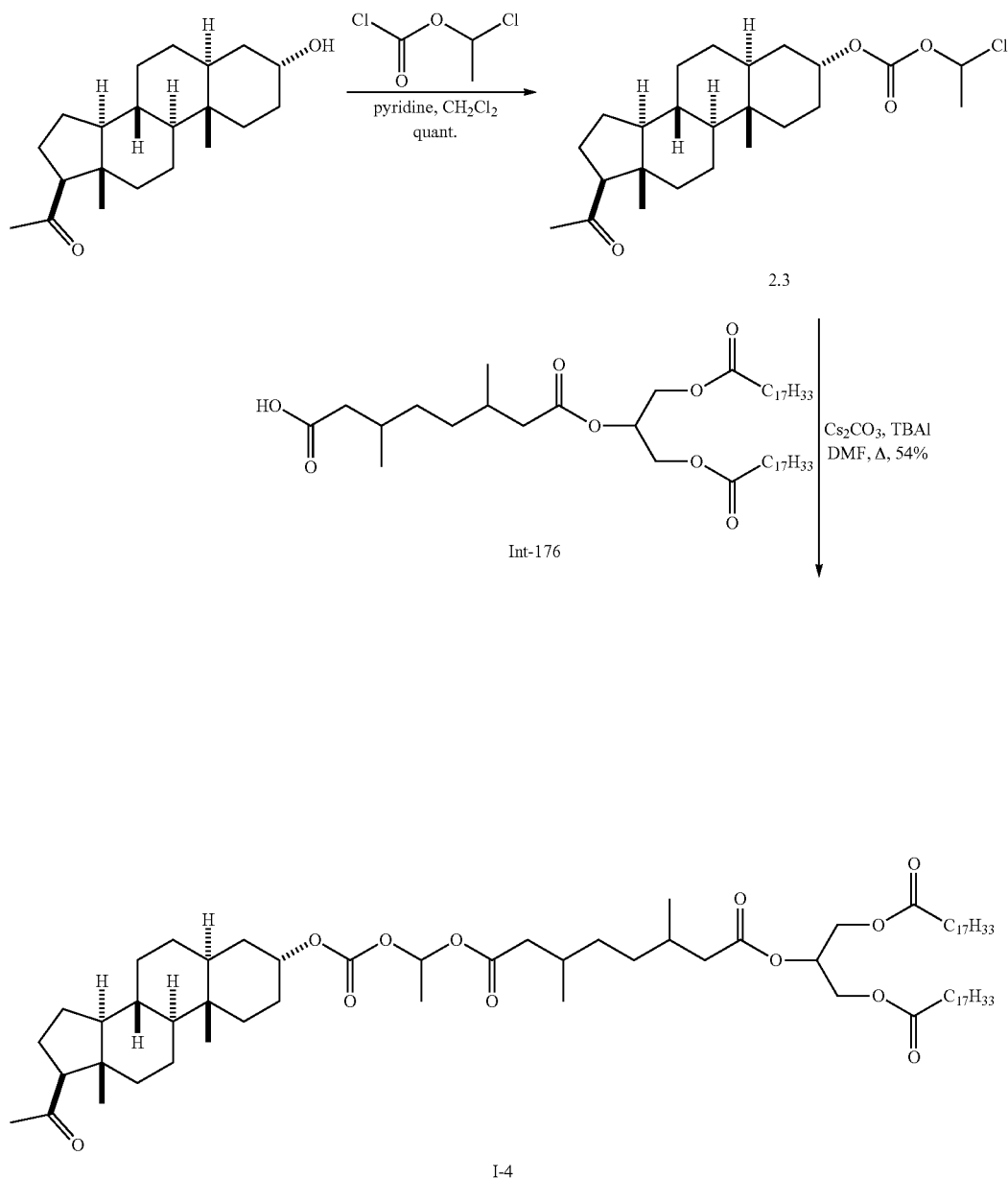

Cesium carbonate (Cs$_2$CO$_3$, 42.5 mg, 131 µmol) and tetra-n-butylammonium iodide (TBAI, 8.0 mg, 21.7 µmol) were added to a suspension of Int-176 (35.0 mg, 43.5 µmol) and compound 2.3 (18.5 mg, 43.5 µmol) in DMF (2 mL) and the mixture heated at 60° C. for 3.5 hours. The reaction was cooled to rt, diluted with ethyl acetate (30 mL) and the organic phase washed with water and brine (30 mL each), dried (MgSO$_4$) and concentrated under reduced pressure to give the crude product. Silica gel chromatography (8% to 12% ethyl acetate/hexanes) gave ALL-CMSI-C$_8$b'bMe-2-TG-oleate I-4 (28.2 mg, 54%) as a colourless oil. $^1$H NMR (401 MHz, CDCl$_3$) δ 6.779/6.775 (each q, J=5.4 Hz, 1H), 5.41-5.22 (m, 5H), 4.92 (m, 1H), 4.29 (dd, J=11.9, 4.3 Hz, 2H), 4.14 (dd, J=11.9, 6.0 Hz, 2H), 2.52 (t, J=8.9 Hz, 1H), 2.37-2.27 (m, 6H), 2.19-2.07 (m, 3H), 2.11 (s, 3H), 2.07-1.79 (m, 12H), 1.72-1.46 (m, 15H), 1.522/1.520 (each d, J=5.4 Hz, 3H), 1.43-1.09 (m, 50H), 1.00-0.75 (m, 8H), 0.88 (t, J=6.9 Hz, 6H), 0.79 (s, 3H), 0.60 (s, 3H); $^{13}$C NMR (101 MHz, CDCl$_3$) δ 209.8 (C), 173.4 (2C; C), 172.2 (C), 171.1 (C), 152.8 (C), 130.2 (2C; CH), 129.9 (2C; CH), 91.2 (CH), 75.3 (CH), 69.0 (CH), 64.0 (CH), 62.3 (2C; CH$_2$), 56.9 (CH), 54.0 (CH), 44.4 (C), 41.8-41.5 (2C; CH$_2$), 39.8 (CH), 39.2 (CH$_2$), 35.9 (C), 35.6 (CH), 34.2 (2C; CH$_2$), 34.1-33.8 (2C; CH$_2$), 32.84/32.79 (CH$_2$), 32.7 (CH$_2$), 32.0 (2C; CH$_2$), 31.9 (CH$_2$), 31.7 (CH$_3$), 30.7-30.3 (2C; CH), 29.9 (2C; CH$_2$), 29.8 (2C; CH$_2$), 29.7 (2C; CH$_2$), 29.46 (2C; CH$_2$), 29.45 (2C; CH$_2$), 29.31 (2C; CH$_2$), 29.25 (2C; CH$_2$), 29.23 (2C; CH$_2$), 28.3 (CH$_2$), 27.4 (2C; CH$_2$), 27.3 (2C; CH$_2$), 26.1/26.0 (CH$_2$), 25.0 (2C; CH$_2$), 24.5 (CH$_2$), 22.9 (CH$_2$), 22.8 (2C; CH$_2$), 20.9 (CH$_2$), 19.8-19.5 (3C; CH$_3$), 14.2 (2C; CH$_3$), 13.6 (CH$_3$), 11.4 (CH$_3$). Note: Multiple peaks were observed for most $^{13}$C NMR signals of the C$_8$b'bMe linker, these are reported as a range of peaks (eg: 34.1-33.8 ppm).

Synthesis of ALL-FSI5-C$_{12}$a'aMe-2-TG I-5

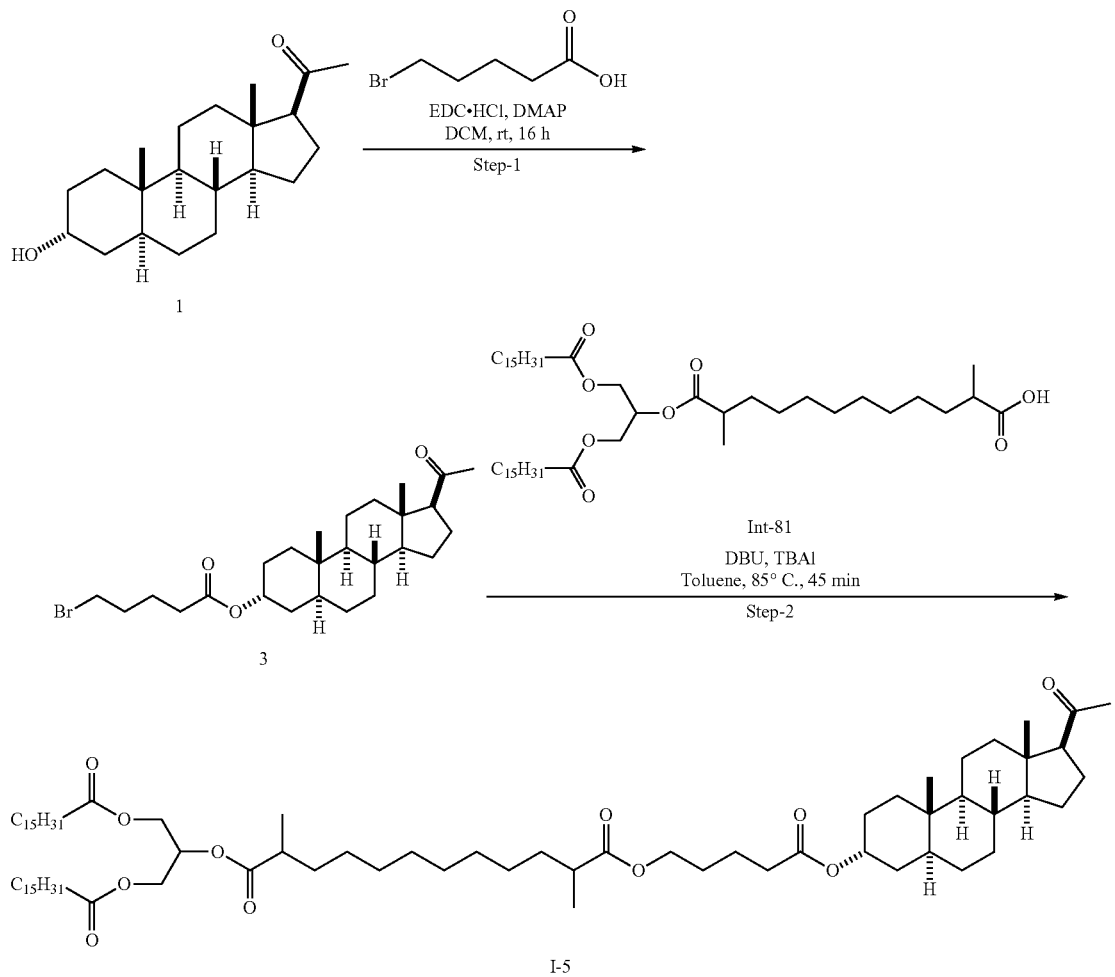

Step 1: Compound 3

To a solution of allopreganolone (200 mg, 0.62 mmol) in DCM (3 ml) was added EDC·HCl (300 mg, 1.57 mmol) and DMAP (38 mg, 0.31 μmmol) and stirred at rt for 15 min, then 5-bromopentanoic acid (220 mg, 1.13 mmol) was added at room temperature and stirred at rt for 16 h. The reaction was monitored by TLC, and after completion of reaction, the reaction mixture was diluted with water (10 ml) and extracted with DCM (3×10 ml). The combined organic layer was dried over Na$_2$SO$_4$, and concentrated to get crude material. The crude material was purified by column purification. The product was eluted at 4% ethyl acetate/hexane to afford 3 (270 mg, 89.30%) as a white solid. $^1$H NMR (400 MHz, CDCl3) δ 5.11-5.05 (m, 1H), 3.48 (t, 2H), 2.57 (t, 1H), 2.40 (t, 2H), 2.16 (s, 3H), 2.08-2.02 (m, 1H), 2.10-1.90 (m, 2H), 1.90-1.79 (m, 2H), 1.75-1.60 (m, 4H), 1.59-1.40 (m, 4H), 1.35-1.15 (m, 7H), 1.01 (m, 2H), 0.84 (s, 6H), 0.65 (s, 4H).

Step 2: ALL-FSI5-C12a'aMe-TG I-5

To a solution of Int-81 (0.20 g, 0.24 mmol) in toluene (3 ml) was added DBU (0.075 g, 0.49 mmol) and stirred at rt for 15 min then compound 3 (0.118 g, 0.24 mmol) and TBAI (0.045 g, 0.12 mmol) was added at room temperature. The reaction mixture was stirred at 85° C. for 45 min. The reaction was monitored by TLC, and after completion of reaction, reaction mixture was diluted with water (15 ml) and extracted with ethyl acetate (3×10 ml), combined organic layer dried over Na$_2$SO$_4$, then distilled under vacuum to get crude compound, which was purified by combi flash purification, compound was eluted at 5% ethyl acetate and hexane as a mobile phase then the pure fraction was concentrated to get pure compound ALL-FSI5-C12a'aMe-TG I-5 (65 mg, 21.74%) as viscous oil. $^1$H NMR (400 MHz, CDCl$_3$) δ 5.42-5.15 (m, 1H), 5.08 (s, 1H), 4.33 (dt, 2H), 4.23-4.05 (m, 4H), 2.59 (t, 1H), 2.54-2.43 (m, 2H), 2.41-2.30 (m, 5H), 2.24-2.19 (m, 2H), 2.16 (s, 3H), 2.09-2.03 (m, 2H), 1.74-1.61 (m, 18H), 1.54-1.42 (m, 8H), 1.29-1.22 (s, 61H), 1.18 (d, J=7.0 Hz, 4H), 0.92 (t, J=6.7 Hz, 12H), 0.84 (s, 3H), 0.65 (s, 3H). $^{13}$C NMR (101 MHz, CDCl3) δ 209.71 (1C), 176.95 (2C), 175.91 (2C), 173.30 (2C), 172.76 (1C), 69.98 (1C), 68.71 (1C), 63.88 (1C), 63.71 (1C), 62.16 (1C), 56.78 (1C), 54.16 (1C), 44.28 (1C), 40.16 (1C), 39.62 (1C), 39.55 (1C), 39.09 (1C), 35.86 (1C), 35.47 (1C), 34.30 (1C), 34.08 (3C), 33.80 (1C), 33.65 (1C), 32.99 (1C), 32.92 (1C), 31.96 (4C), 31.92 (1C), 31.57 (2C), 29.74-29.17 (14C), 28.29 (1C), 28.16 (1C), 27.32 (1C), 27.20 (1C), 26.15 (1C), 24.89 (3C), 24.40 (2C), 22.81 (1C), 22.73 (5C), 21.63 (1C), 20.84 (1C), 17.05 (1C), 14.17 (3C), 13.49 (1C), 11.37 (1C). CPLC (ELSD): 13.77 min, 100% purity; MASS (ESI, +ve) m/z: 1228 (MH$^+$+18). ELSD Method: PDS_HPLC_GEMINI_X-Bridge-GRD-4; Mobie Phase: (A) Water (B) Methanol; Column: C4 Jupitor, 100*4.6 mm, 5 μm; Column Flow: 1.0 ml/min; Column Temperature: Ambient; ELSD: SPRAY CHAMBER −50° C. The run took 13.77 min at 100% B.

Synthesis of ALL-CMSI-C12a'aMe-2-TG I-6

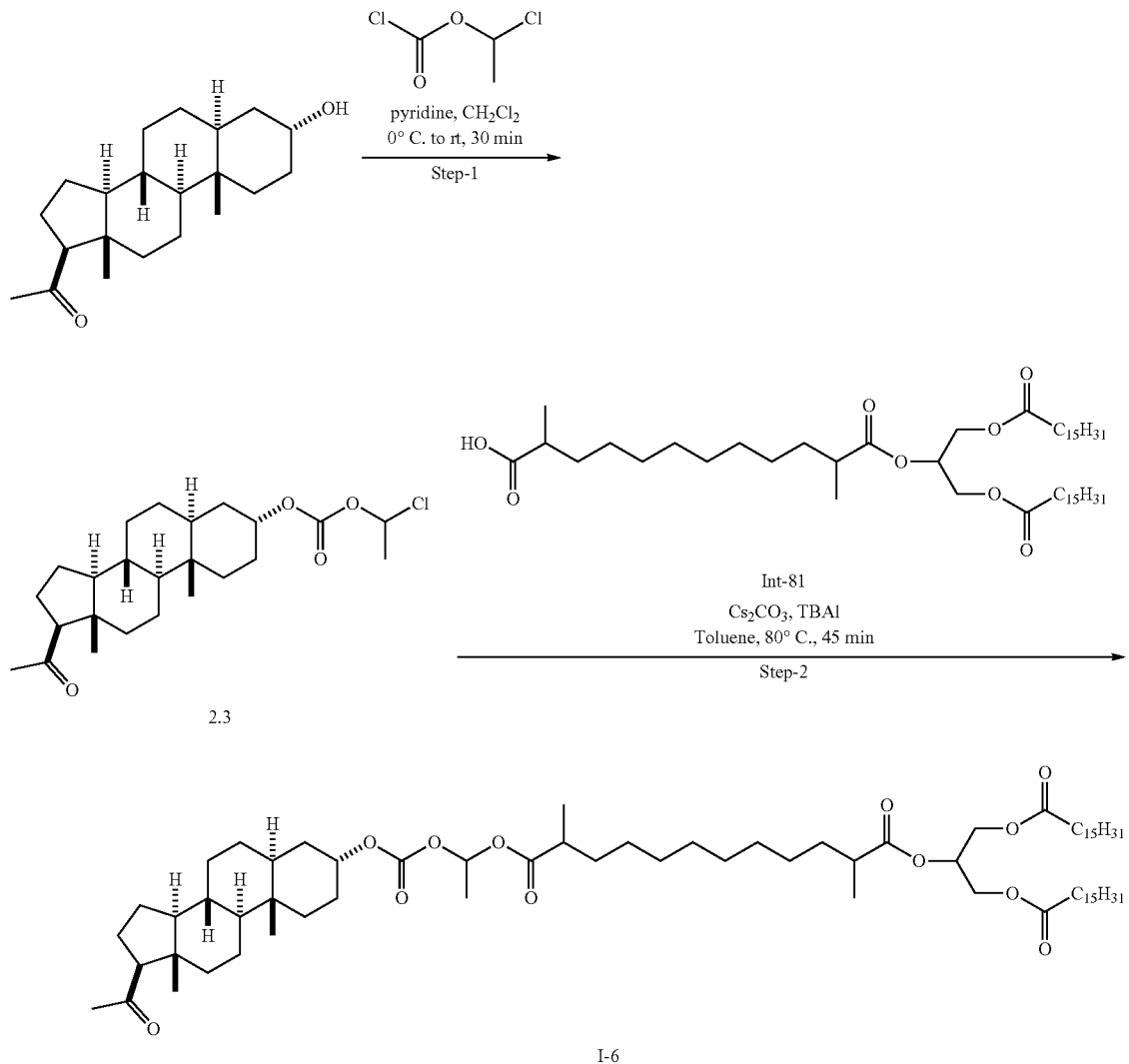

To a solution of Int-81 (0.20 g, 0.24 mmol) in toluene (3 ml) was added Cs$_2$CO$_3$ (0.160 g, 0.49 mmol) and the mixture stirred at rt for 15 min., then compound 2.3 (0.089 g, 0.21 mmol, prepared as described in the synthesis of I-1) and TBAI (0.045 g, 0.12 mmol) were added at room temperature. The reaction mixture was stirred at 80° C. for 45 min. The reaction was monitored by TLC, and after completion of the reaction, the reaction mixture was diluted with water (15 ml) and extracted with ethyl acetate (3×10 ml), combined organic layer dried over Na$_2$SO$_4$. The organic layer was concentrated to get crude compound, which was purified by combi flash purification, compound was eluted at 6% ethyl acetate and hexane as a mobile phase then pure fraction was concentrated to get pure compound ALL-CMSI-C12a'aMe-TG I-6 (52 mg, 18%) as viscous oil.

$^1$H NMR (400 MHz, CDCl3) δ 6.82 (q, 1H), 5.31 (m, 1H), 4.96 (s, 1H), 4.35-4.30 (m, 2H), 4.21-4.16 (m, 2H), 2.56 (t, 1H), 2.48 (q, 2H), 2.34 (t, 3H), 2.18 (m, 3H), 2.03 (d, 1H), 1.89 (d, 1H), 1.70-1.55 (m, 20H), 1.45-1.17 (m, 74H), 092 (t, 10H), 0.83 (s, 3H), 0.64 (s, 3H). $^{13}$C NMR (101 MHz, CDCl$_3$) δ 209.74 (1C), 175.91 (1C), 174.76 (1C), 173.31 (2C), 152.68 (1C), 91.13 (1C), 77.26 (1C), 68.72 (1C), 63.84 (1C), 62.15 (1C), 56.78 (1C), 53.83 (1C), 44.27 (1C), 39.65 (1C), 39.55 (1C), 39.40 (1C), 39.34 (1C), 39.09 (1C), 35.75 (1C), 35.43 (1C), 34.08 (2C), 33.66 (1C), 33.48 (1C), 33.39 (1C), 32.70 (1C), 32.60 (1C), 31.96 (2C), 31.76 (1C), 31.58 (1C), 29.74-29.16 (25C), 28.19 (1C), 27.21-27.04 (3C), 25.91 (1C), 24.89 (2C), 24.40 (1C), 22.79 (2C), 20.80 (1C), 19.67 (1C), 17.06 (1C), 16.80 (1C), 16.76 (1C), 16.69 (1C). HPLC (ELSD): 11.30 min, 100% purity; MASS (ESI, +ve) m/z: 1216 (MH++18). ELSD Method:—PDS_HPLC_GEMINI_X-Bridge-GRD-4; Mobie Phase: (A) Water (B) Methanol; Column: C4 Jupitor, 100*4.6 mm, 5 μm; Column Flow: 1.0 ml/min; Column Temperature: Ambient; ELSD: SPRAY CHAMBER −50° C. Time: 11.3 min at 100% B.

Synthesis of ALL-C10-2-TG I-7

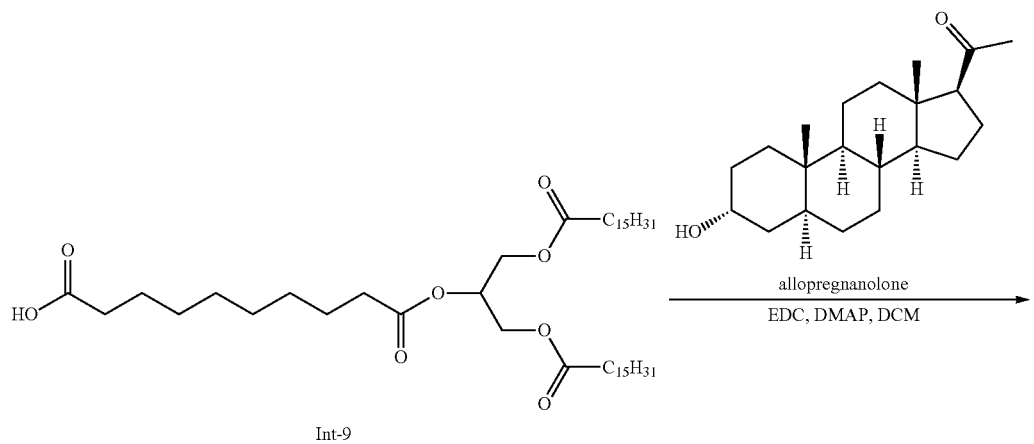

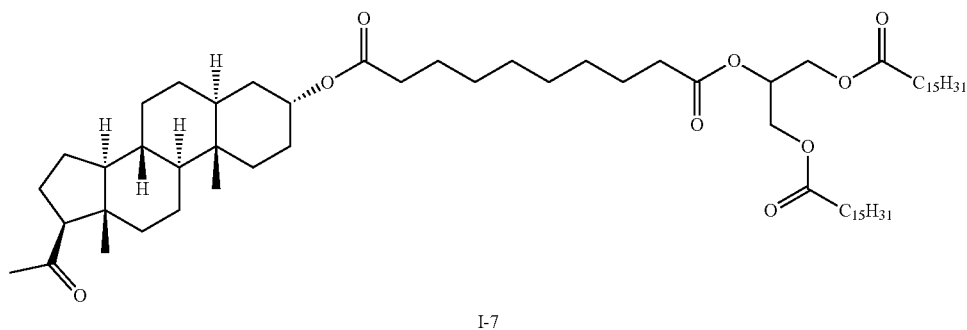

I-7

To a solution of allopreganolone (80 mg, 0.251 μmol) in DCM (20 vol) was added DMAP (30 mg, 0.251 μmol), EDC·HCl (120 mg, 0.628 μmol) followed by Int-9 (340 mg, 0.452 mol) at room temperature and stirred for 16 h. The reaction was monitored by TLC and after completion, the reaction mixture was diluted with DCM (20 Vol), washed with water (20 Vol), aqueous sodium bicarbonate (10 Vol) and brine (10 Vol). The collected organic layers were dried over $Na_2SO_4$, filtered and the solvent was removed under reduced pressure. The crude material was purified by column purification. The product was eluted at 10%-20% ethyl acetate/hexane to afford: ALL-C10-2-TG I-7 (30 mg, 11.3%) as viscous liquid. $^1$H NMR (400 MHz, $CDCl_3$) δ 5.31-5.30 (m, 1H), 5.28-5.00 (s, 1H), 4.35-4.31 (m, 2H), 4.20-4.16 (m, 2H), 2.59-2.54 (t, 1H), 2.37-2.31 (m, 7H), 2.21-2.18 (m, 1H), 2.15 (s, 3H), 2.06-2.03 (m, 2H), 1.74-1.61 (m, 8H), 1.56-1.24 (m, 73H), 0.97-0.90 (m, 12H), 0.64 (s, 3H). $^{13}$C NMR (101 MHz, $CDCl_3$) δ 209 (1C), 173.3 (2C), 172.9 (2C), 69.72 (1C), 68.88 (1C), 63.85 (1C), 62.06 (2C), 56.77 (1C), 54.13 (1C), 44.27 (1C), 40.10 (1C), 39.07 (1C) 35.82 (1C), 35.4 (1C), 34.80 (1C), 34.17-34.06 (2C), 32.9-32.89 (3C), 31.94-31.91 (4C), 31.5 (1C), 29.72-29.05 (29C), 28.2 (1C), 26.1 (1C), 25.1 (1C), 24.87 (2C), 24.38 (1C), 22.7-22.7 (2C), 20.81 (1C). HPLC (ELSD): 12.32 min, 100% purity; MASS (ESI, +ve) m/z: 1072 ($MH^+$+18). ELSD Method: PDS_HPLC_X-Bridge-150-1 ml-Min_100% methanol. Mobile Phase: 100% MEOH; System: Agilent Technologies 1260 Infinity with PDA Detector & ELSD Detector. Column: X-BRIDGE C18, 150*4.6 mm, 5p Column Flow: 1.0 ml/min; Column Temp: Ambient; ELSD: SPRAY CHAMBER −50° C.; the run consisted of an isocratic method at 100% A for 20 min.

Synthesis of ALL-CMSI-C5bMe-2-TG I-8

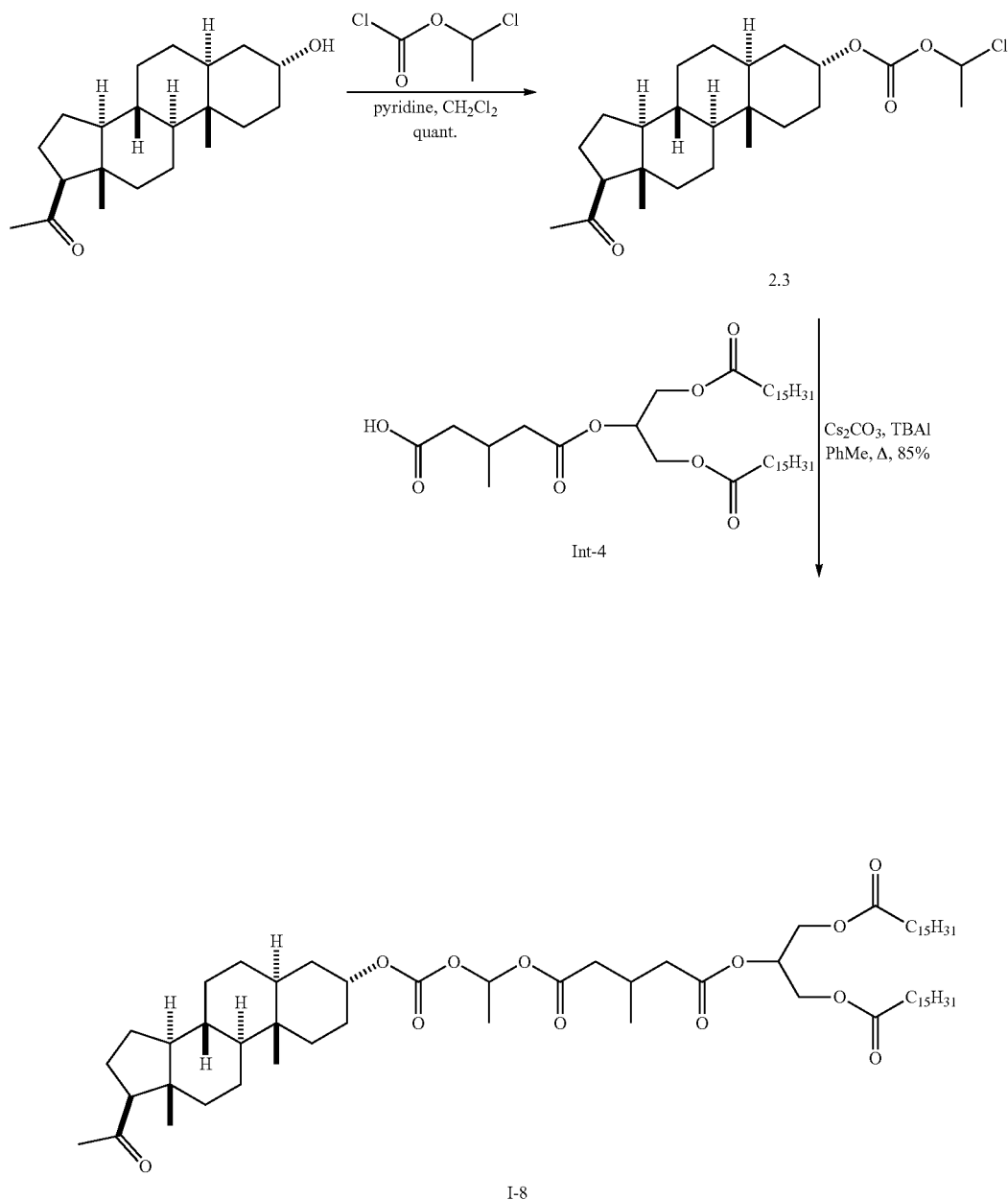

Cesium carbonate (Cs$_2$CO$_3$, 4.5 mg, 16.8 μmol) and tetra-n-butylammonium iodide (TBAI, 1.6 mg, 4.2 μmol) were added to a suspension of Int-4 (6.1 mg, 8.8 μmol) and compound 2.3 (3.6 mg, 8.4 μmol, prepared as described in the synthesis of I-1) in toluene (1 mL) and the mixture heated at reflux for two hours. The reaction was cooled to rt, diluted with ethyl acetate (40 mL) and the organic phase washed with water (30 mL) and brine (2×30 mL each), dried (MgSO$_4$) and concentrated under reduced pressure to give the crude product. Silica gel chromatography (15% to 30% ethyl acetate/hexanes) gave ALL-CMSI-C$_5$bMe-2-TG I-8 (7.8 mg, 85%) as a colourless oil. $^1$H NMR (401 MHz, CDCl$_3$) δ 6.77 (m, 1H), 5.27 (m, 1H), 4.92 (m, 1H), 4.34-4.25 (m, 2H), 4.13 (dd, J=11.9, 6.0 Hz, 2H), 2.55-2.38 (m, 4H), 2.34-2.22 (m, 6H), 2.14 (m, 1H), 2.11 (s, 3H), 2.00 (m, 1H), 1.85 (m, 1H), 1.71-1.47 (m, 13H), 1.52 (d, J=5.5 Hz, 3H), 1.43-1.08 (m, 56H), 1.03 (d, J=6.2 Hz, 3H), 0.99-0.80 (m, 2H), 0.88 (t, J=6.9 Hz, 6H), 0.79 (s, 3H), 0.60 (s, 3H); $^{13}$C NMR (101 MHz, CDCl$_3$) δ 209.9 (C), 173.4 (2C; C), 171.4 (C), 152.8 (C), 91.3 (CH), 75.4 (CH), 69.3 (CH), 64.0 (CH), 62.2 (2C; CH$_2$), 56.9 (CH), 54.0 (CH), 40.70/40.62 (CH$_2$), 40.59/40.56 (CH$_2$), 40.51/40.48 (CH$_2$), 39.8 (CH), 39.2 (CH$_2$), 35.9 (C), 35.6 (CH), 34.2 (CH$_2$), 32.84/32.80 (CH$_2$), 32.7 (CH$_2$), 32.1 (CH$_2$), 31.9 (CH$_2$), 31.7 (CH$_3$), 29.85 (2C; CH$_2$), 29.81 (2C; CH$_2$), 29.78 (2C; CH$_2$), 29.6 (2C; CH$_2$), 29.5 (2C; CH$_2$), 29.4 (2C; CH$_2$), 29.3 (2C; CH$_2$), 28.3 (CH$_2$), 26.1 (CH$_2$), 26.0 (CH$_2$), 25.0 (2C; CH$_2$), 24.5 (CH$_2$), 22.9 (CH$_2$), 22.8 (2C; CH$_2$), 20.9 (CH$_2$), 19.8 (CH$_3$), 19.63/19.58 (CH$_3$), 14.3 (2C; CH$_3$), 13.6 (CH$_3$), 11.4 (CH$_3$); HPLC (ELSD): 16.75 min, 100% purity; MASS (ESI, +ve) m/z: 1103.28 (MH++18).

Synthesis of ALL-ASI-C$_5$bMe-2-TG-oleate I-9

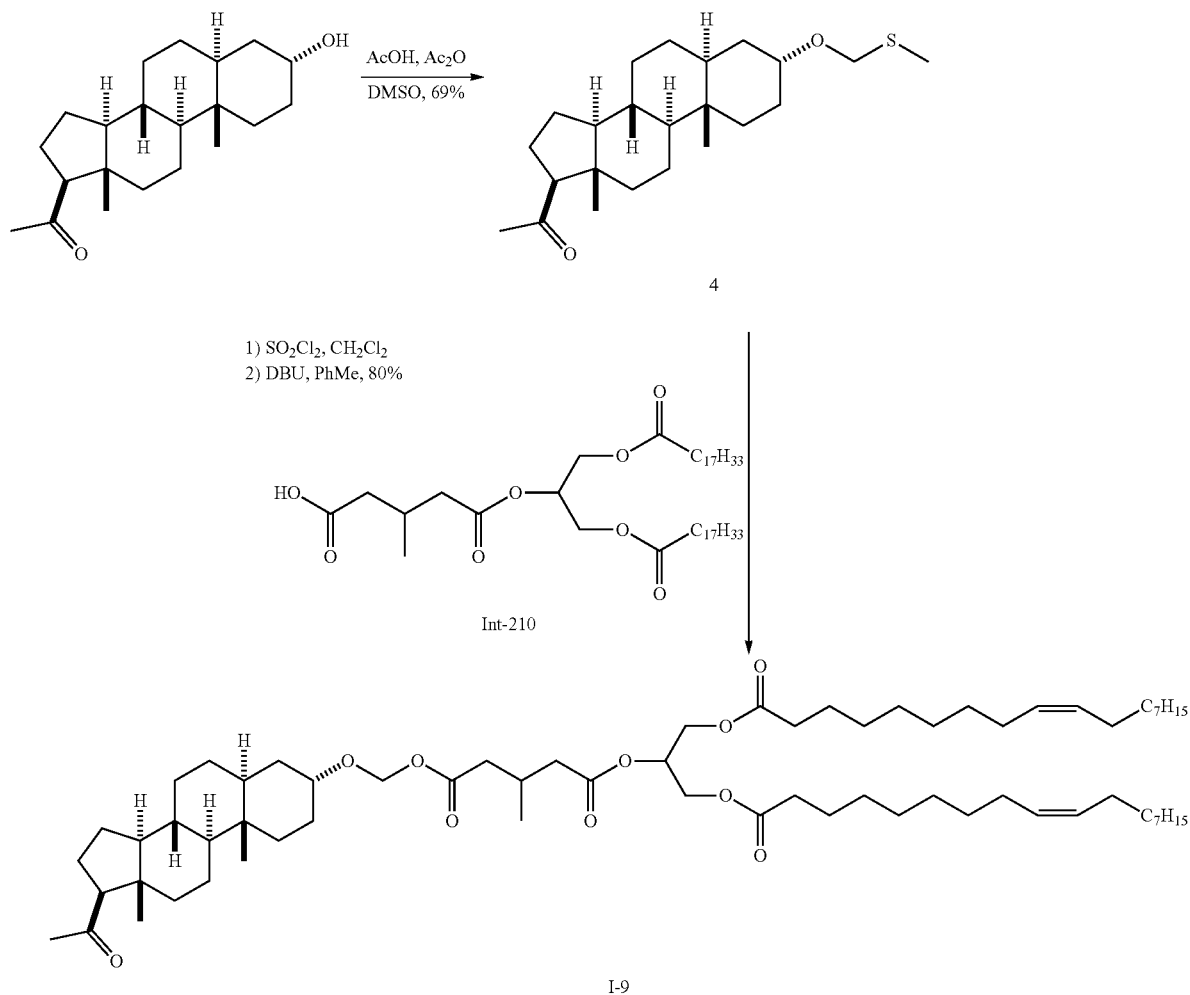

Step 1: Compound 4

A mixture of allopregnanolone (250 mg, 0.785 mmol), acetic acid (0.35 mL, 5.54 mmol), acetic anhydride (1.12 mL, 10.0 mmol) and DMSO (1.72 mL, 20.1 mmol) was stirred at rt for three days and 19 hours. The reaction was diluted with ethyl acetate (50 mL) and the organic layer washed with sat. aq. NaHCO$_3$ and brine (50 mL each), dried (MgSO$_4$) and concentrated under reduced pressure to give the crude product. Purification by silica gel chromatography (8% ethyl acetate/hexanes with 0.5% Et$_3$N) gave compound 4 (206 mg, 69%) as a colourless solid. $^1$H NMR (401 MHz, CDCl$_3$) δ 4.63 (s, 2H), 3.91 (m, 1H), 2.52 (t, J=9.0 Hz, 1H), 2.16 (s, 3H), 2.12 (m, 1H), 2.10 (s, 3H), 1.99 (dt, J=11.9, 3.3 Hz, 1H), 1.78-1.09 (m, 18H), 0.94 (m, 1H), 0.80 (m, 1H), 0.79 (s, 3H), 0.60 (s, 3H); $^{13}$C NMR (101 MHz, CDCl$_3$) δ 209.9 (C), 72.2 (CH$_2$), 71.1 (CH), 64.0 (CH), 57.0 (CH), 54.3 (CH), 44.4 (C), 39.9 (CH), 39.3 (CH$_2$), 36.0 (C), 35.6 (CH), 33.04 (CH$_2$), 33.02 (CH$_2$), 32.0 (CH$_2$), 31.7 (CH$_3$), 28.6 (CH$_2$), 25.6 (CH$_2$), 24.5 (CH$_2$), 22.9 (CH$_2$), 20.9 (CH$_2$), 13.9 (CH$_3$), 13.6 (CH$_3$), 11.6 (CH$_3$).

Step 2: ALL-ASI-C5bMe-2-TG-oleate I-9

Sulfuryl chloride (6.0 μL, 74.0 μmol) was added to a solution of compound 4 (20.0 mg, 52.8 μmol) in CH$_2$Cl$_2$ (2 mL) at 0° C. and the reaction was stirred at 0° C. for 30 minutes. The reaction was concentrated under reduced pressure, dissolved in toluene (3×5 mL) and re-concentrated under reduced pressure. This crude residue was then dissolved in toluene (1.5 mL) and added to a solution of Int-210 (47.5 mg, 63.4 μmol) and DBU (12.6 μL, 84.5 μmol) in toluene (1 mL) that had been pre-stirred for 1.5 hours, and the mixture was stirred at rt for one hour. The reaction was diluted with ethyl acetate (30 mL) and the organic phase washed with water and brine (25 mL each), dried (MgSO$_4$) and concentrated under reduced pressure to give the crude product. Purification by silica gel chromatography (8% to 9% ethyl acetate/hexanes) gave ALL-ASI-C$_5$bMe-2-TG-oleate I-9 (45.7 mg, 80%) as a colourless oil. $^1$H NMR (401 MHz, CDCl$_3$) δ 5.39-5.23 (m, 7H), 4.301/4.296 (each dd, J=11.9, 4.3 Hz, 2H), 4.13 (dd, J=11.9, 6.0 Hz, 2H), 3.86 (m, 1H), 2.56-2.38 (m, 4H), 2.34-2.21 (m, 6H), 2.16 (m, 1H), 2.11 (s, 3H), 2.06-1.93 (m, 9H), 1.75 (m, 1H), 1.71-1.08 (m, 60H), 1.04 (d, J=6.5 Hz, 3H), 0.88 (t, J=6.9 Hz, 6H), 0.99-0.75 (m, 3H), 0.78 (s, 3H), 0.60 (s, 3H). $^{13}$C NMR (101 MHz, CDCl$_3$) δ 209.8 (C), 173.4 (2C; C), 172.0 (C), 171.4 (C), 130.2 (2C; CH), 129.8 (2C; CH), 87.8 (CH$_2$), 74.7 (CH), 69.3 (CH), 64.0 (CH), 62.2 (2C; CH$_2$), 56.9 (CH), 54.2 (CH), 44.4 (C), 41.0 (CH$_2$), 40.8 (CH$_2$), 39.5 (CH), 39.2 (CH$_2$), 36.0 (C), 35.6 (CH), 34.1 (2C; CH$_2$), 33.6

($CH_2$), 32.7 ($CH_2$), 32.04 (2C; $CH_2$), 31.99 ($CH_2$), 31.7 ($CH_3$), 29.9 (2C; $CH_2$), 29.8 (2C; $CH_2$), 29.7 (2C; $CH_2$), 29.46 (2C; $CH_2$), 29.45 (2C; $CH_2$), 29.31 (2C; $CH_2$), 29.26 (2C; $CH_2$), 29.23 (2C; $CH_2$), 28.5 ($CH_2$), 27.39 (CH), 27.36 (2C; $CH_2$), 27.31 (2C; $CH_2$), 26.5 ($CH_2$), 25.0 (2C; $CH_2$), 24.5 ($CH_2$), 22.9 ($CH_2$), 22.8 (2C; $CH_2$), 20.9 ($CH_2$), 19.8 ($CH_3$), 14.2 (2C; $CH_3$), 13.6 ($CH_3$), 11.5 ($CH_3$).

Synthesis of ALL-ASI-$C_{10}$b'bMe-2-TG-oleate I-32

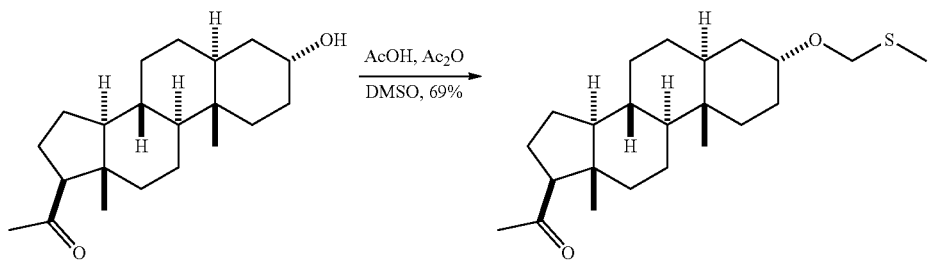

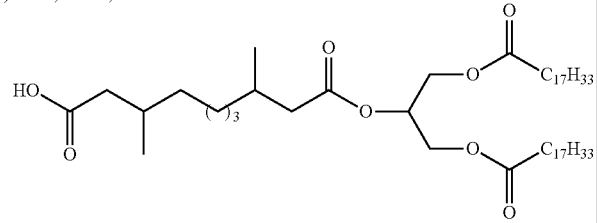

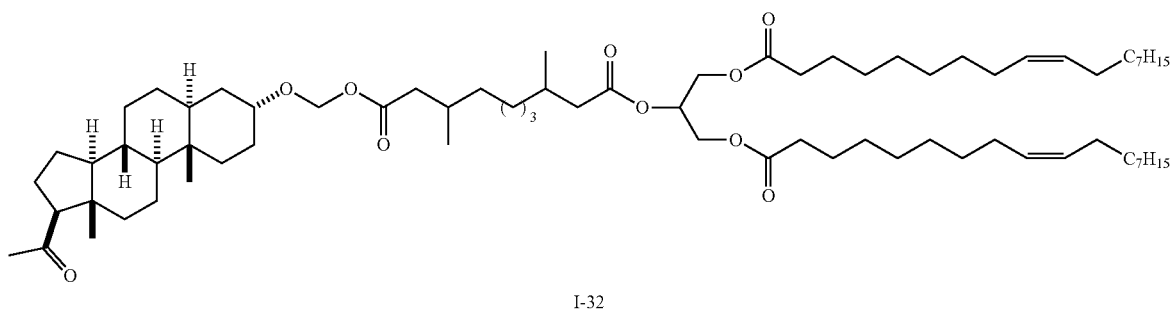

ALL-ASI-C10b'bMe-2-TG-oleate I-32 was synthesized using the procedure provided above for I-9, replacing Int-210 with Int-172. Purification by silica gel chromatography (3% ethyl acetate/toluene) gave ALL-ASI-C10b'bMe-2-TG-oleate I-32 (15.7 mg, 34%) as a colourless oil. $^1$H NMR (401 MHz, $CDCl_3$) δ 5.40-5.23 (m, 5H), 5.31 (s, 2H), 4.29 (dd, J=12.0, 4.0 Hz, 2H), 4.14 (dd, J=11.9, 6.0 Hz, 2H), 3.85 (m, 1H), 2.52 (t, J=9.0 Hz, 1H), 2.35-2.27 (m, 6H), 2.19-2.07 (m, 3H), 2.10 (s, 3H), 2.06-1.87 (m, 11H), 1.80-1.09 (m, 70H), 0.93 (d, J=6.6 Hz, 3H), 0.92 (d, J=6.9 Hz, 3H), 0.88 (t, J=6.9 Hz, 6H), 0.96-0.74 (m, 2H), 0.77 (s, 3H), 0.59 (s, 3H); $^{13}$C NMR (101 MHz, $CDCl_3$) δ 209.9 (C), 173.4 (C), 173.0 (C), 172.4 (C), 130.2 (CH), 129.9 (CH), 87.7 ($CH_2$), 74.7 (CH), 69.0 (CH), 64.0 (CH), 62.3 ($CH_2$), 56.9 (CH), 54.2 (CH), 44.4 (C), 42.15/42.14 ($CH_2$), 41.80/41.79 ($CH_2$), 39.5 (CH), 39.2 ($CH_2$), 36.85/36.83 ($CH_2$), 36.83/36.81 ($CH_2$), 36.0 (C), 35.6 (CH), 34.2 ($CH_2$), 33.59/33.58 ($CH_2$), 32.7 ($CH_2$), 32.1 ($CH_2$), 32.0 ($CH_2$), 31.7 ($CH_3$), 30.48/30.46 (CH), 30.3 (CH), 29.91 ($CH_2$), 29.85 ($CH_2$), 29.7 ($CH_2$), 29.5 ($CH_2$), 29.32 ($CH_2$), 29.26 ($CH_2$), 29.23 ($CH_2$), 28.5 ($CH_2$), 27.4 ($CH_2$), 27.3 ($CH_2$), 27.24/27.23 ($CH_2$), 27.21/27.20 ($CH_2$), 26.5 ($CH_2$), 25.0 ($CH_2$), 24.5 ($CH_2$), 22.9 ($CH_2$), 22.8 ($CH_2$), 20.9 ($CH_2$), 19.82/19.81 ($CH_3$), 19.67/19.65 ($CH_3$), 14.3 ($CH_3$), 13.6 ($CH_3$), 11.6 ($CH_3$); Note: Numerous signals were doubled due to the presence of diastereoisomers; ESI-HRMS: calcd. for $C_{73}H_{126}NaO_{10}$ [M+H$^+$] 1185.9243; found 1185.9223.

Synthesis of ALL-ASI-C12b'bMe-2-TG-oleate I-34

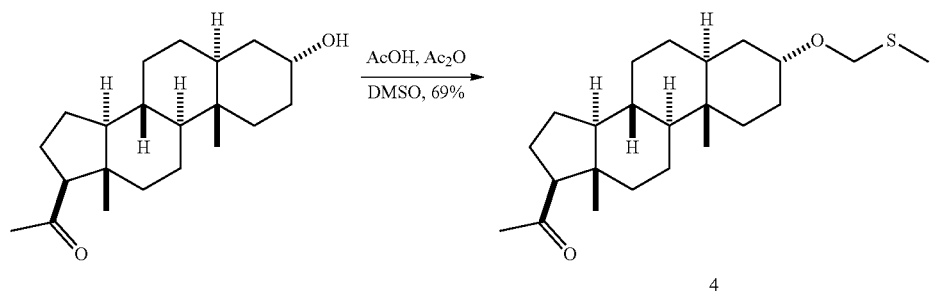

4

1) SO₂Cl₂, CH₂Cl₂
2) DBU, PhMe, 50%

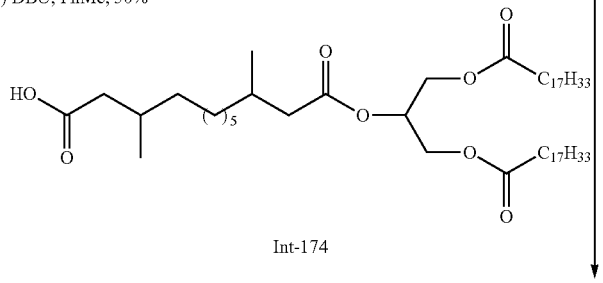

Int-174

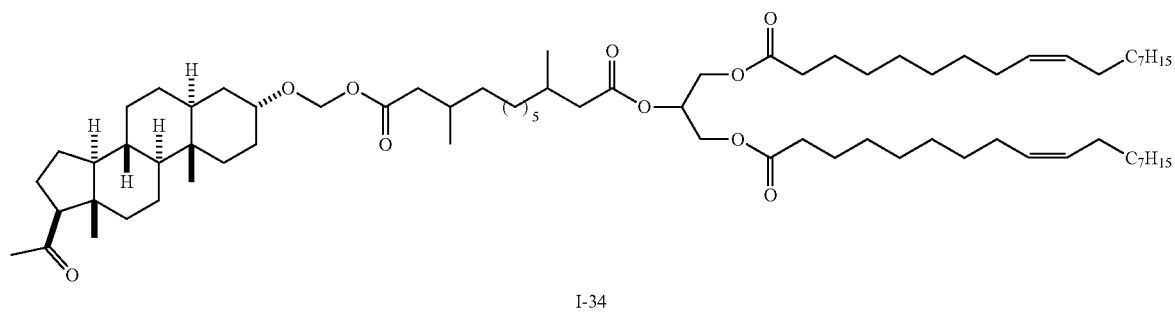

I-34

ALL-ASI-C12b'bMe-2-TG-oleate I-34 was synthesized using the procedure provided above for I-9, replacing Int-210 with Int-174. Purification by silica gel chromatography (3% ethyl acetate/toluene) gave ALL-ASI-$C_{12}$b'bMe-2-TG-oleate I-34 (23.5 mg, 50%) as a colourless oil.

$^1$H NMR (401 MHz, CDCl$_3$) δ 5.39-5.24 (m, 5H), 5.31 (s, 2H), 4.28 (dd, J=11.9, 3.7 Hz, 2H), 4.14 (dd, J=11.9, 6.0 Hz, 2H), 3.85 (m, 1H), 2.52 (t, J=9.0 Hz, 1H), 2.36-2.26 (m, 6H), 2.18-2.06 (m, 3H), 2.10 (s, 3H), 2.06-1.87 (m, 11H), 1.81-1.08 (m, 74H), 0.94 (d, J=6.6 Hz, 3H), 0.92 (d, J=6.6 Hz, 3H), 0.88 (t, J=6.9 Hz, 6H), 1.00-0.74 (m, 2H), 0.77 (s, 3H), 0.59 (s, 3H); $^{13}$C NMR (101 MHz, CDCl$_3$) δ 209.9 (C), 173.4 (2C; C), 173.1 (C), 172.4 (C), 130.2 (2C; CH), 129.8 (2C; CH), 87.7 (CH$_2$), 74.7 (CH), 69.0 (CH), 64.0 (CH), 62.3 (2C; CH$_2$), 56.9 (CH), 54.2 (CH), 44.4 (C), 42.2 (CH$_2$), 41.8 (CH$_2$), 39.5 (CH), 39.2 (CH$_2$), 36.9 (CH$_2$), 36.8 (CH$_2$), 36.0 (C), 35.6 (CH), 34.2 (2C; CH$_2$), 33.59/33.57 (CH$_2$), 32.7 (CH$_2$), 32.04 (2C; CH$_2$), 31.98 (CH$_2$), 31.7 (CH$_3$), 30.5 (CH), 30.4 (CH), 29.92 (2C; CH$_2$), 29.90 (2C; CH$_2$), 29.8 (2C; CH$_2$), 29.7 (2C; CH$_2$), 29.5 (4C; CH$_2$), 29.31 (2C; CH$_2$), 29.25 (2C; CH$_2$), 29.23 (2C; CH$_2$), 28.5 (CH$_2$), 27.4 (2C; CH$_2$), 27.3 (2C; CH$_2$), 27.1 (2C; CH$_2$), 26.5 (CH$_2$), 25.0 (2C; CH$_2$), 24.5 (CH$_2$), 22.9 (CH$_2$), 22.8 (2C; CH$_2$), 20.9 (CH$_2$), 19.8 (CH$_3$), 19.7 (CH$_3$), 14.3 (2C; CH$_3$), 13.6 (CH$_3$), 11.6 (CH$_3$).

Synthesis of ALL-ASI-C$_{6-2}$-TG-oleate I-40

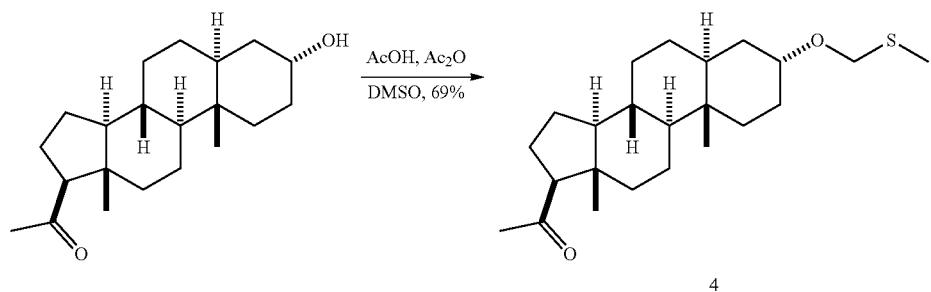

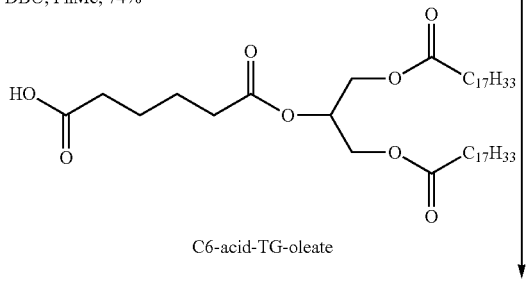

C6-acid-TG-oleate

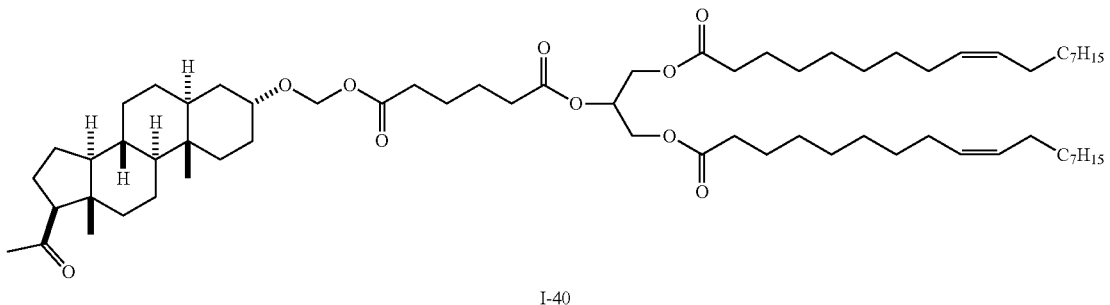

I-40

ALL-ASI-C6-2-TG-oleate I-40 was synthesized using the procedure provided above for I-9, replacing Int-210 with C6-acid-TG-oleate (Int-276). C6-acid-TG-oleate was prepared from Int-112 and adipoyl chloride using the procedures depicted in Scheme 10. Purification by silica gel chromatography (8% to 9% ethyl acetate/hexanes) gave ALL-ASI-C$_{6-2}$-TG-oleate I-40 (31.6 mg, 74%) as a colourless oil. $^1$H NMR (401 MHz, CDCl$_3$) δ 5.39-5.28 (m, 4H), 5.31 (s, 2H), 5.25 (m, 1H), 4.29 (dd, J=11.9, 4.3 Hz, 2H), 4.13 (dd, J=11.9, 5.9 Hz, 2H), 3.85 (m, 1H), 2.52 (t, J=8.9 Hz, 1H), 2.38-2.26 (m, 8H), 2.14 (m, 1H), 2.10 (s, 4H), 2.06-1.94 (m, 9H), 1.78-1.08 (m, 66H), 0.87 (t, J=6.8 Hz, 6H), 0.98-0.73 (m, 2H), 0.77 (s, 3H), 0.59 (s, 3H); $^{13}$C NMR (101 MHz, CDCl$_3$) δ 209.9 (C), 173.4 (2C; C), 173.0 (C), 172.4 (C), 130.2 (2C; CH), 129.8 (2C; CH), 87.9 (CH$_2$), 74.8 (CH), 69.2 (CH), 63.9 (CH), 62.1 (2C; CH$_2$), 56.9 (CH), 54.1 (CH), 44.4 (C), 39.5 (CH), 39.2 (CH$_2$), 36.0 (C), 35.6 (CH), 34.12 (2C; CH$_2$), 34.10 (CH$_2$), 33.9 (CH$_2$), 33.6 (CH$_2$), 32.6 (CH$_2$), 32.03 (2C; CH$_2$), 31.98 (CH$_2$), 31.7 (CH$_3$), 29.9 (2C; CH$_2$), 29.8 (2C; CH$_2$), 29.7 (2C; CH$_2$), 29.5 (4C; CH$_2$), 29.31 (2C; CH$_2$), 29.25 (2C; CH$_2$), 29.21 (2C; CH$_2$), 28.5 (CH$_2$), 27.4 (2C; CH$_2$), 27.3 (2C; CH$_2$), 26.5 (CH$_2$), 25.0 (2C; CH$_2$), 24.5 (CH$_2$), 24.3 (CH$_2$), 24.2 (CH$_2$), 22.9 (CH$_2$), 22.8 (2C; CH$_2$), 20.9 (CH$_2$), 14.3 (2C; CH$_3$), 13.6 (CH$_3$), 11.5 (CH$_3$); ESI-HRMS: calcd. for C$_{67}$H$_{114}$NaO$_{10}$ [M+Na$^+$] 1101.8304; found 1101.8299.

Synthesis of ALL-ASI-C$_{8-2}$-TG-oleate I-41

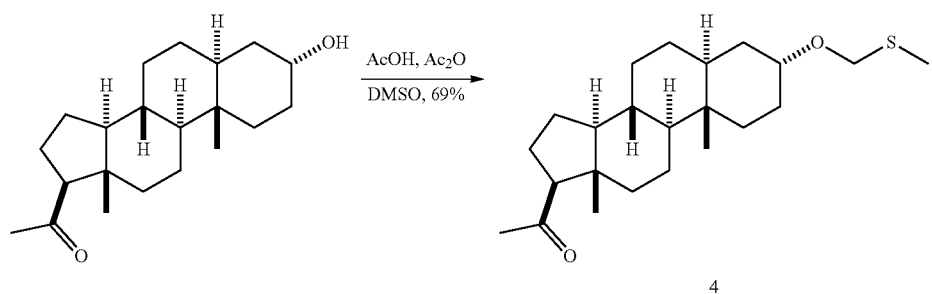

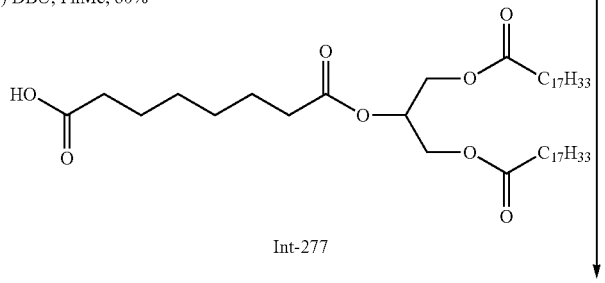

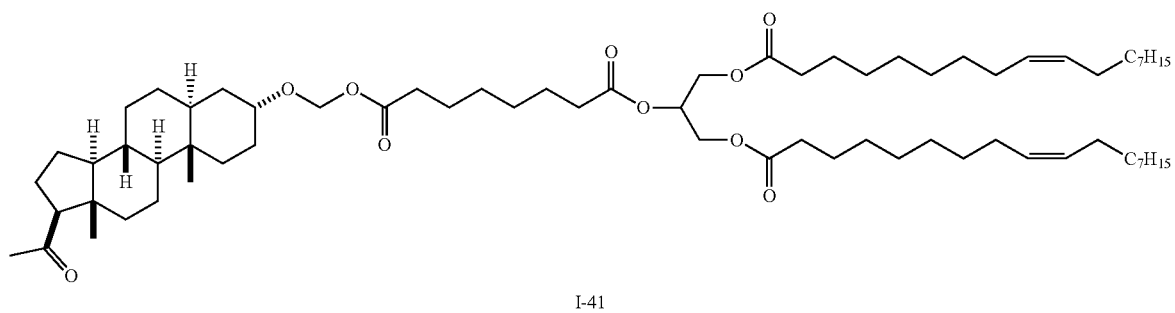

I-41

ALL-ASI-C8-2-TG-oleate I-41 was synthesized using the procedure provided above for I-9, replacing Int-210 with Int-277. Purification by silica gel chromatography (8% to 9% ethyl acetate/hexanes) gave ALL-ASI-C$_{8-2}$-TG-oleate I-41 (35.0 mg, 80%) as a colourless oil. $^1$H NMR (401 MHz, CDCl$_3$) δ 5.40-5.29 (m, 5H), 5.31 (s, 2H), 5.25 (m, 1H), 4.29 (dd, J=11.9, 4.4 Hz, 2H), 4.14 (dd, J=11.9, 5.9 Hz, 2H), 3.85 (m, 1H), 2.53 (t, J=8.9 Hz, 1H), 2.31 (t, J=7.6 Hz, 4H), 2.30 (t, J=7.6 Hz, 4H), 2.13 (m, 1H), 2.11 (s, 3H), 2.07-1.93 (m, 9H), 1.79-1.09 (m, 70H), 0.99-0.73 (m, 2H), 0.88 (t, J=6.8 Hz, 6H), 0.77 (s, 3H), 0.59 (s, 3H); $^{13}$C NMR (101 MHz, CDCl$_3$) δ 209.9 (C), 173.4 (3C; C), 172.8 (C), 130.2 (2C; CH), 129.8 (2C; CH), 87.8 (CH$_2$), 74.8 (CH), 69.1 (CH), 64.0 (CH), 62.2 (2C; CH$_2$), 56.9 (CH), 54.2 (CH), 44.4 (C), 39.5 (CH), 39.2 (CH$_2$), 36.0 (C), 35.6 (CH), 34.5 (CH$_2$), 34.17 (CH$_2$), 34.15 (2C; CH$_2$), 33.6 (CH$_2$), 32.7 (CH$_2$), 32.04 (2C; CH$_2$), 31.98 (CH$_2$), 31.7 (CH$_3$), 29.9 (2C; CH$_2$), 29.8 (2C; CH$_2$), 29.7 (2C; CH$_2$), 29.5 (4C; CH$_2$), 29.31 (2C; CH$_2$), 29.25 (2C; CH$_2$), 29.21 (2C; CH$_2$), 28.9 (CH$_2$), 28.8 (CH$_2$), 28.5 (CH$_2$), 27.4 (2C; CH$_2$), 27.3 (2C; CH$_2$), 26.5 (CH$_2$), 25.0 (2C; CH$_2$), 24.8 (CH$_2$), 24.7 (CH$_2$), 24.5 (CH$_2$), 22.9 (CH$_2$), 22.8 (2C; CH$_2$), 20.9 (CH$_2$), 14.3 (2C; CH$_3$), 13.6 (CH$_3$), 11.6 (CH$_3$); ESI-HRMS: calcd. for C$_{69}$H$_{118}$NaO$_{10}$ [M+Na$^+$] 1129.8617; found 1129.8599.

Synthesis of ALL-ASI-C8bMe-2-TG-oleate I-42

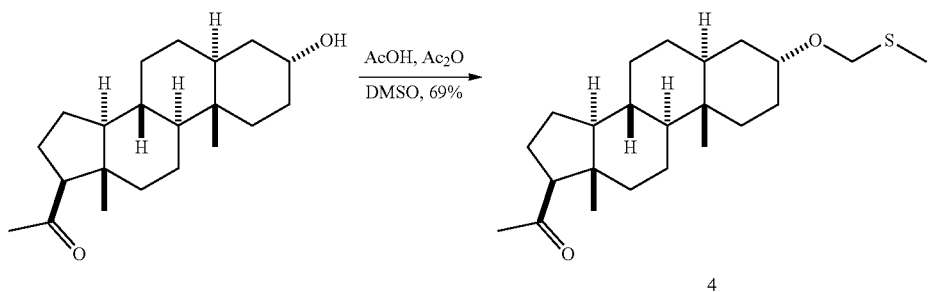

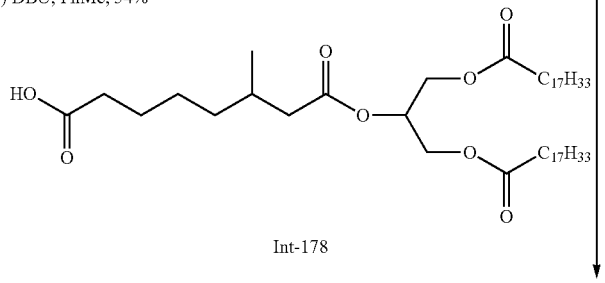

Int-178

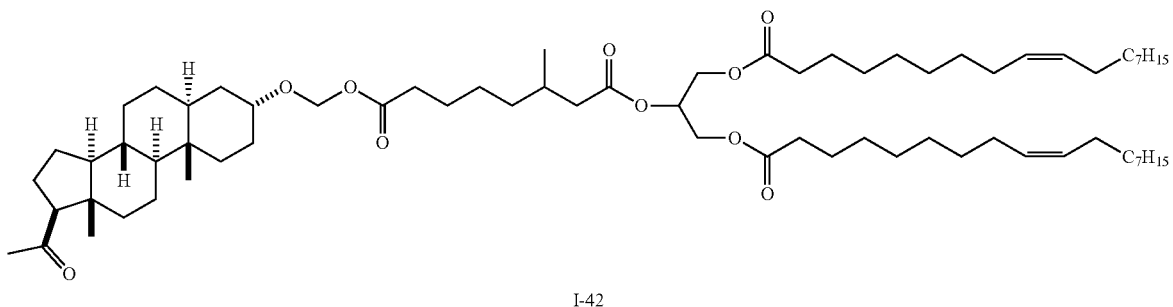

I-42

ALL-ASI-C8bMe-2-TG-oleate I-42 was synthesized using the procedure provided above for I-9, replacing Int-210 with Int-178. Purification by silica gel chromatography (8% to 9% ethyl acetate/hexanes) gave ALL-ASI-C8bMe-2-TG-oleate I-42 (24.0 mg, 54%) as a colourless oil. $^1$H NMR (401 MHz, CDCl$_3$) δ 5.39-5.23 (m, 5H), 5.31 (s, 2H), 4.28 (dd, J=11.9, 4.3 Hz, 2H), 4.13 (dd, J=11.9, 6.0 Hz, 2H), 3.85 (m, 1H), 2.52 (t, J=8.9 Hz, 1H), 2.36-2.25 (m, 7H), 2.19-2.07 (m, 2H), 2.10 (s, 3H), 2.06-1.87 (m, 10H), 1.75 (m, 1H), 1.69-1.08 (m, 67H), 0.93 (d, J=6.6 Hz, 3H), 0.87 (t, J=6.8 Hz, 6H), 1.00-0.74 (m, 2H), 0.77 (s, 3H), 0.59 (s, 3H); $^{13}$C NMR (101 MHz, CDCl$_3$) δ 209.9 (C), 173.40 (2C; C), 173.38 (C), 172.3 (C), 130.2 (2C; CH), 129.9 (2C; CH), 87.8 (CH$_2$), 74.7 (CH), 69.0 (CH), 64.0 (CH), 62.3 (2C; CH$_2$), 56.9 (CH), 54.2 (CH), 44.4 (C), 41.7 (CH$_2$), 39.5 (CH), 39.1 (CH$_2$), 36.4 (CH$_2$), 36.0 (C), 35.6 (CH), 34.5 (CH$_2$), 34.2 (2C; CH$_2$), 33.6 (CH$_2$), 32.7 (CH$_2$), 32.04 (2C; CH$_2$), 31.99 (CH$_2$), 31.7 (CH$_3$), 30.3 (CH), 29.90 (2C; CH$_2$), 29.85 (2C; CH$_2$), 29.7 (2C; CH$_2$), 29.5 (4C; CH$_2$), 29.32 (2C; CH$_2$), 29.26 (2C; CH$_2$), 29.23 (2C; CH$_2$), 28.5 (CH$_2$), 27.4 (2C; CH$_2$), 27.3 (2C; CH$_2$), 26.6 (CH$_2$), 26.5 (CH$_2$), 24.98 (CH$_2$), 24.96 (2C; CH$_2$), 24.5 (CH$_2$), 22.9 (CH$_2$), 22.8 (2C; CH$_2$), 20.9 (CH$_2$), 19.6 (CH$_3$), 14.3 (2C; CH$_3$), 13.6 (CH$_3$), 11.6 (CH$_3$); ESI-HRMS: calcd. for C$_{70}$H$_{121}$O$_{10}$ [M+H+] 1143.8774; found 1143.8762.

Synthesis of ALL-ASI-C8b'bMe-2-TG-oleate I-13

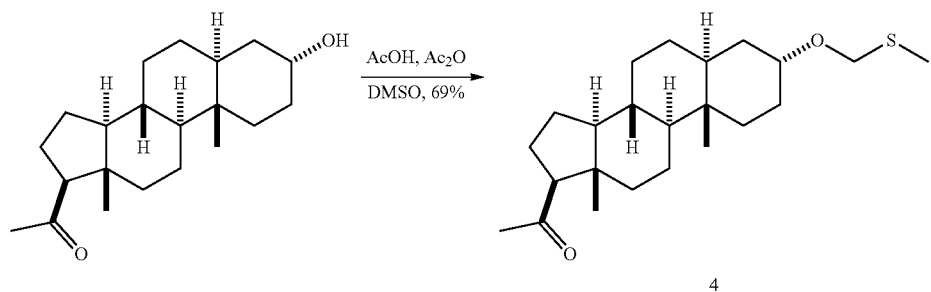

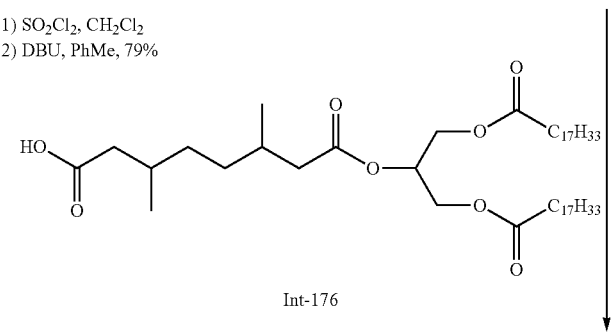

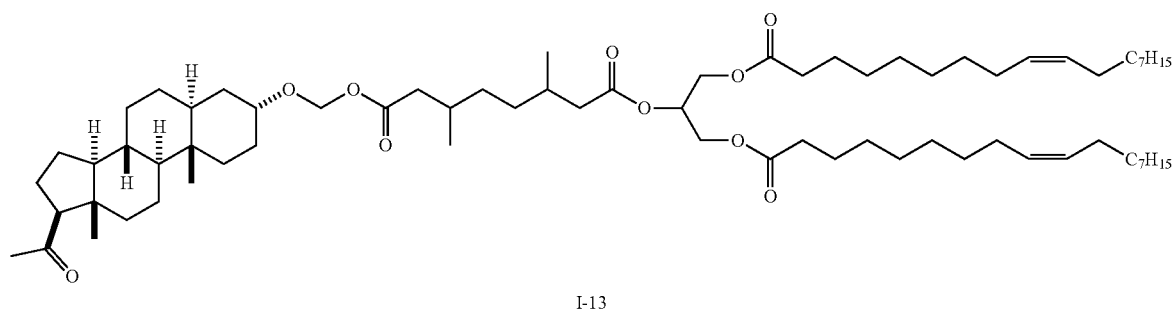

ALL-ASI-C8b'bMe-2-TG-oleate I-13 was synthesized using the procedure provided above for I-9, replacing Int-210 with Int-176. Purification by silica gel chromatography (8% to 9% ethyl acetate/hexanes) gave ALL-ASI-C8b'bMe-2-TG-oleate I-13 (47.5 mg, 79%) as a colourless oil. $^1$H NMR (401 MHz, CDCl$_3$) δ 5.42-5.19 (m, 5H), 5.30 (s, 2H), 4.28 (dd, J=11.9, 4.3 Hz, 2H), 4.13 (dd, J=11.9, 6.0 Hz, 2H), 3.85 (m, 1H), 2.52 (t, J=8.9 Hz, 1H), 2.37-2.26 (m, 6H), 2.17-2.07 (m, 3H), 2.10 (s, 3H), 2.05-1.86 (m, 11H), 1.80-1.08 (m, 65H), 0.96-0.91 (m, 6H), 0.87 (t, J=6.8 Hz, 6H), 0.98-0.74 (m, 3H), 0.77 (s, 3H), 0.59 (s, 3H); $^{13}$C NMR (101 MHz, CDCl$_3$) δ 209.8 (C), 173.4 (2C; C), 172.86/172.84 (C), 172.26/172.24 (C), 130.2 (2C; CH), 129.9 (2C; CH), 87.7 (CH$_2$), 74.7 (CH), 69.06 (CH), 64.0 (CH), 62.3 (2C; CH$_2$), 56.9 (CH), 54.2 (CH), 44.4 (C), 42.1/42.0 (CH$_2$), 41.8/41.6 (CH$_2$), 39.5 (CH), 39.2 (CH$_2$), 36.0 (C), 35.6 (CH), 34.2 (2C; CH$_2$), 34.1 (CH$_2$), 33.9 (CH$_2$), 33.59/33.58 (CH$_2$), 32.7 (CH$_2$), 32.04 (2C; CH$_2$), 32.00 (CH$_2$), 31.7 (CH$_3$), 30.7/30.5 (CH), 30.5/30.4 (CH), 29.91 (2C; CH$_2$), 29.85 (2C; CH$_2$), 29.66 (2C; CH$_2$), 29.46 (2C; CH$_2$), 29.45 (2C; CH$_2$), 29.32 (2C; CH$_2$), 29.26 (2C; CH$_2$), 29.23 (2C; CH$_2$), 28.6 (CH$_2$), 27.4 (2C; CH$_2$), 27.3 (2C; CH$_2$), 26.51/26.49 (CH$_2$), 25.0 (2C; CH$_2$), 24.5 (CH$_2$), 22.9 (CH$_2$), 22.8 (2C; CH$_2$), 20.9 (CH$_2$), 19.9/19.8 (CH$_3$), 19.7/19.6 (CH$_3$), 14.2 (2C; CH$_3$), 13.6 (CH$_3$), 11.6 (CH$_3$). Note: Doubled peaks were observed for a number of $^{13}$C NMR signals due to the presence of diastereomers; ESI-HRMS: calcd. for C$_{71}$H$_{122}$NaO$_{10}$ [M+Na$^+$] 1157.8930; found 1157.8911.

Synthesis of ALL-CASI-C8-2-TG-oleate I-29

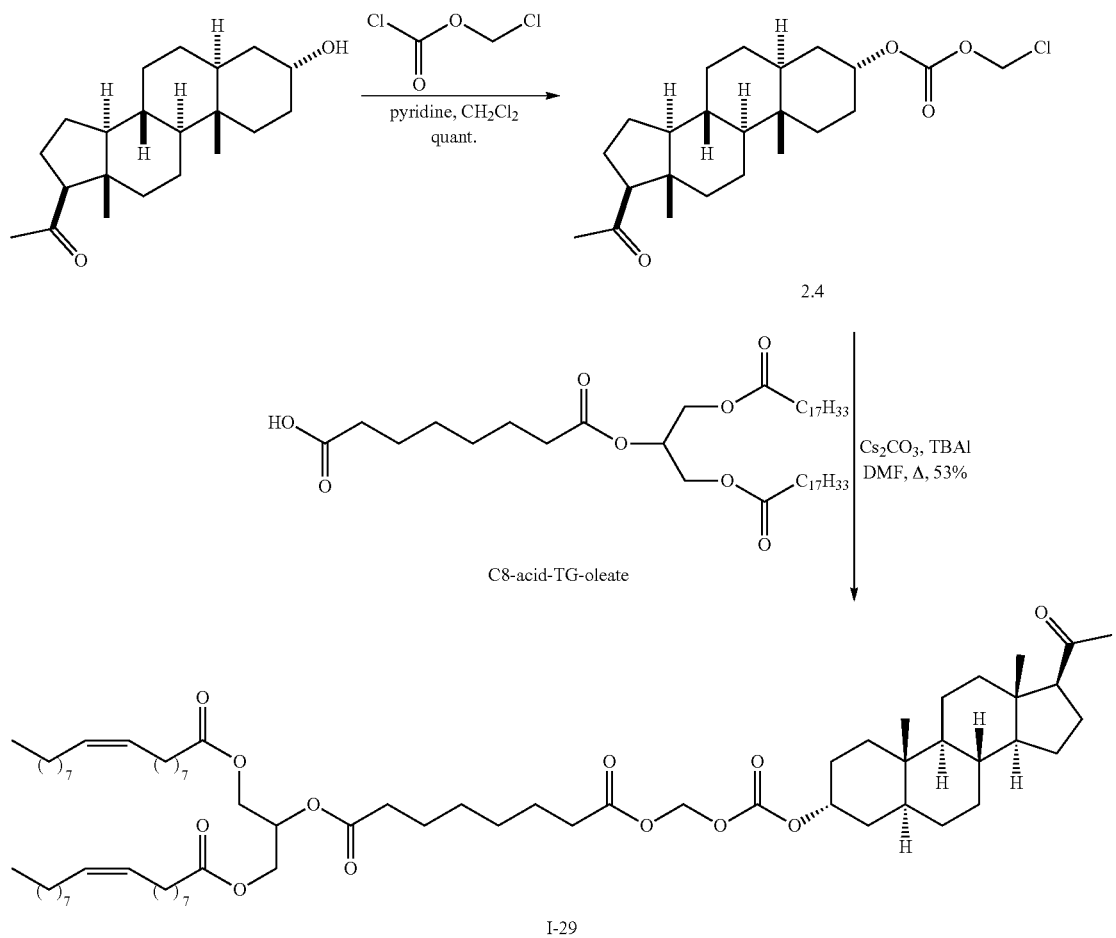

Step 1: Preparation of Compound 2.4

Chloromethyl chloroformate (22.3 μL, 0.251 mmol) and pyridine (38.1 μL, 0.471 mmol) were added to allopregnanolone (50.0 mg, 0.157 mmol) in CH$_2$Cl$_2$ (2 mL) at 0° C. and the mixture stirred at 0° C. for 30 minutes and then at rt for one hour. The reaction was diluted with CH$_2$Cl$_2$ (30 mL) and the organic phase washed with water and brine (30 mL each), dried (MgSO$_4$) and concentrated under reduced pressure to give crude compound 2.4 (64.5 mg, quant.) as a colourless solid that was used without purification; $^1$H NMR (400 MHz, CDCl$_3$) δ 5.74 (ABq, 2H), 4.99 (m, 1H), 2.52 (t, J=9.0 Hz, 1H), 2.16 (m, 1H), 2.11 (s, 3H), 2.00 (dt, J=11.8, 3.3 Hz, 1H), 1.88 (m, 1H), 1.75-1.47 (m, 9H), 1.44-1.12 (m, 8H), 1.01-0.77 (m, 2H), 0.80 (s, 3H), 0.61 (s, 3H).

Step 2: ALL-CASI-C8-2-TG-oleate I-29

Cs$_2$CO$_3$ (36.5 mg, 112 μmol) and TBAI (6.9 mg, 18.7 μmol) were added to a solution of C8-acid-TG-oleate (Int-277) (29.0 mg, 37.3 μmol, prepared from Int-112 and oxalyl chloride using the procedures depicted in Scheme 10) and compound 2.4 (15.3 mg, 39.4 μmol) in DMF (2 mL) and the mixture was heated at 70° C. for two hours. The reaction was cooled to rt, diluted with ethyl acetate (30 mL) and the organic phase washed with water and brine (30 mL each), dried (MgSO$_4$) and concentrated under reduced pressure to give the crude product. Silica gel chromatography (8% to 10% ethyl acetate/hexanes) gave ALL-CASI-C$_{8-2}$-TG-oleate I-29 (22.7 mg, 53%) as a colourless oil; $^1$H NMR (401 MHz, CDCl$_3$) δ 5.78-5.71 (m, 2H), 5.39-5.20 (m, 5H), 4.94 (m, 1H), 4.29 (dd, J=11.9, 4.3 Hz, 2H), 4.13 (dd, J=11.9, 5.9 Hz, 2H), 2.52 (t, J=8.9 Hz, 1H), 2.37 (t, J=7.5 Hz, 2H), 2.31 (t, J=7.6 Hz, 2H), 2.30 (t, J=7.6 Hz, 4H), 2.14 (m, 1H), 2.10 (s, 3H), 2.05-1.93 (m, 9H), 1.84 (m, 1H), 1.79-1.12 (m, 61H), 0.98-0.75 (m, 2H), 0.87 (t, J=6.7 Hz, 6H), 0.78 (s, 3H), 0.59 (s, 3H); $^{13}$C NMR (101 MHz, CDCl$_3$) δ 209.8 (C), 173.4 (2C; C), 172.8 (C), 172.3 (C), 153.6 (C), 130.2 (2C; CH), 129.9 (2C; CH), 81.9 (CH$_2$), 75.7 (CH), 69.1 (CH), 63.9 (CH), 62.2 (2C; CH$_2$), 56.9 (CH), 54.0 (CH), 44.4 (C), 39.8 (CH), 39.2 (CH$_2$), 35.9 (C), 35.6 (CH), 34.2 (3C; CH$_2$), 33.9 (CH$_2$), 32.8 (CH$_2$), 32.7 (CH$_2$), 32.0 (2C; CH$_2$), 31.9 (CH$_2$), 31.7 (CH$_3$), 29.9 (2C; CH$_2$), 29.8 (2C; CH$_2$), 29.7 (2C; CH$_2$), 29.5 (4C; CH$_2$), 29.31 (2C; CH$_2$), 29.25 (2C; CH$_2$), 29.22 (2C; CH$_2$), 28.77 (CH$_2$), 28.76 (CH$_2$), 28.3 (CH$_2$), 27.4 (2C; CH$_2$), 27.3 (2C; CH$_2$), 26.1 (CH$_2$), 25.0 (2C; CH$_2$), 24.7 (CH$_2$), 24.5 (CH$_2$), 24.4 (CH$_2$), 22.9 (CH$_2$), 22.8 (2C; CH$_2$), 20.9 (CH$_2$), 14.3 (2C; CH$_3$), 13.6 (CH$_3$), 11.4 (CH$_3$).

Synthesis of ALL-CASI-C8b'bMe-2-TG-oleate I-30

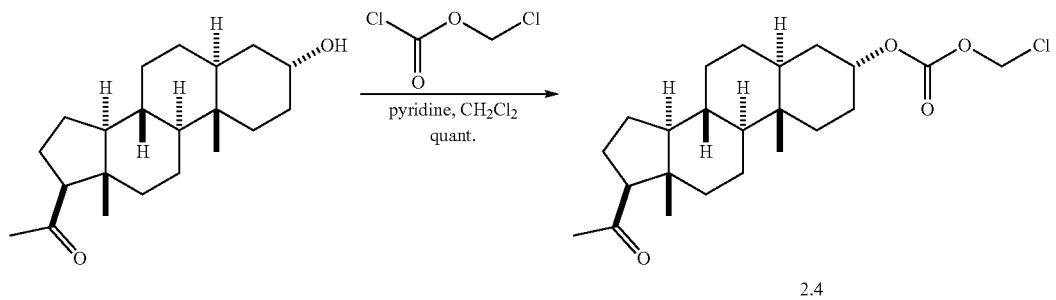

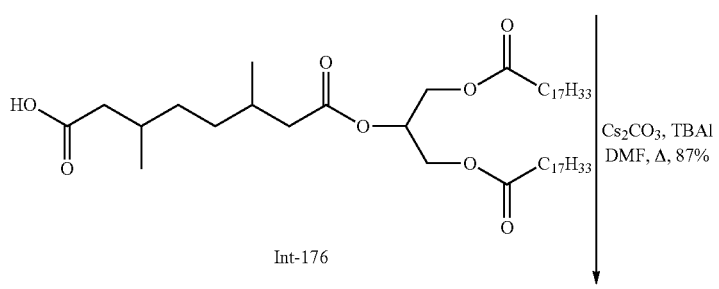

Int-176

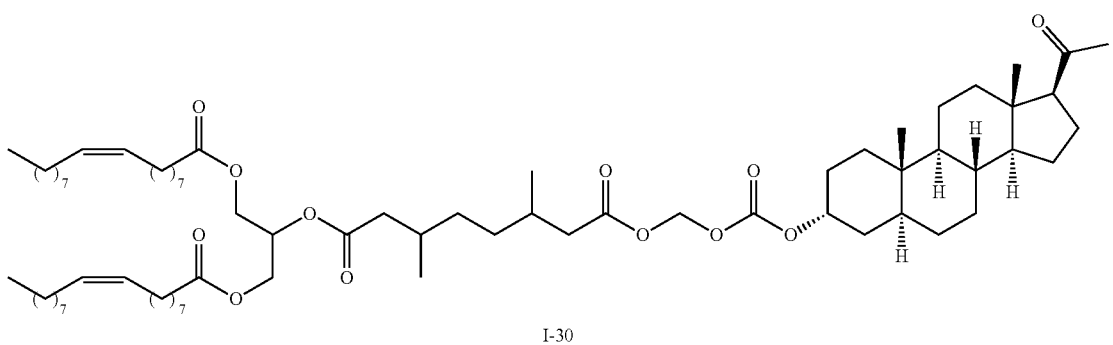

I-30

ALL-CASI-8b'bMe-2-TG-oleate I-30 was synthesized using the procedure provided above for I-29, replacing C$_8$-acid-TG-oleate with Int-176. The product was purified by silica gel chromatography (8% to 9% ethyl acetate/hexanes) to give ALL-CASI-C8b'bMe-2-TG-oleate I-30 (35.8 mg, 87%) as a colourless oil. $^1$H NMR (401 MHz, CDCl$_3$) δ 5.81-5.70 (m, 2H), 5.40-5.22 (m, 5H), 4.94 (m, 1H), 4.28 (dd, J=11.9, 4.3 Hz, 2H), 4.13 (dd, J=11.9, 6.0 Hz, 2H), 2.52 (t, J=8.9 Hz, 1H), 2.42-2.27 (m, 6H), 2.23-2.07 (m, 3H), 2.10 (s, 3H), 2.07-1.80 (m, 12H), 1.76-1.10 (m, 65H), 1.00-0.75 (m, 8H), 0.87 (t, J=6.7 Hz, 6H), 0.79 (s, 3H), 0.59 (s, 3H); $^{13}$C NMR (101 MHz, CDCl$_3$) δ 209.8 (C), 173.4 (2C; C), 172.2 (C), 171.7 (C), 153.6 (C), 130.1 (2C; CH), 129.8 (2C; CH), 81.8 (CH$_2$), 75.6 (CH), 69.0 (CH), 63.9 (CH), 62.2 (2C; CH$_2$), 56.8 (CH), 54.0 (CH), 44.4 (C), 41.8/41.6 (CH$_2$), 41.5/41.3 (CH$_2$), 39.7 (CH), 39.2 (CH$_2$), 35.9 (C), 35.5 (CH), 34.1 (2C; CH$_2$), 34.00/33.97 (CH$_2$), 33.85/33.83 (CH$_2$), 32.8 (CH$_2$), 32.7 (CH$_2$), 32.0 (2C; CH$_2$), 31.9 (CH$_2$), 31.7 (CH$_3$), 30.60/30.43 (CH), 30.43/30.25 (CH), 29.89 (2C; CH$_2$), 29.83 (2C; CH$_2$), 29.65 (2C; CH$_2$), 29.45 (4C; CH$_2$), 29.30 (2C; CH$_2$), 29.24 (2C; CH$_2$), 29.21 (2C; CH$_2$), 28.3 (CH$_2$), 27.34 (2C; CH$_2$), 27.30 (2C; CH$_2$), 26.1 (CH$_2$), 25.0 (2C; CH$_2$), 24.5 (CH$_2$), 22.9 (CH$_2$), 22.8 (2C; CH$_2$), 20.9 (CH$_2$), 19.76/19.71 (CH$_3$), 19.57/19.52 (CH$_3$), 14.3 (2C; CH$_3$), 13.6 (CH$_3$), 11.4 (CH$_3$); Note: A number of doubled signals were observed in the $^{13}$C NMR spectrum due to the presence of diastereoisomers.

Synthesis of ALL-CASI-C$_5$bMe-2-TG-oleate I-39

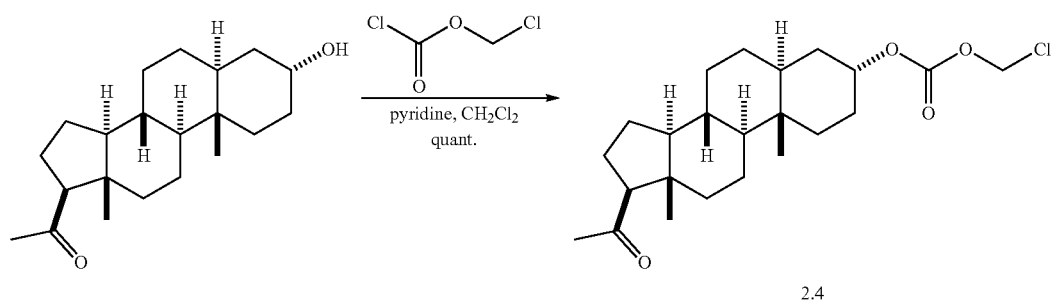

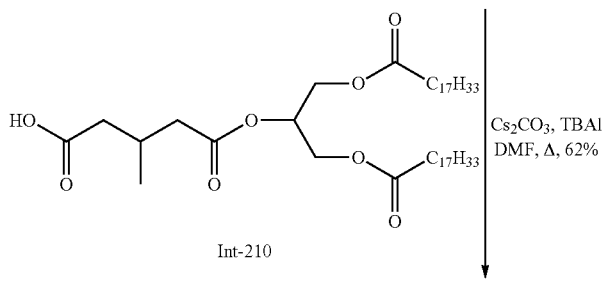

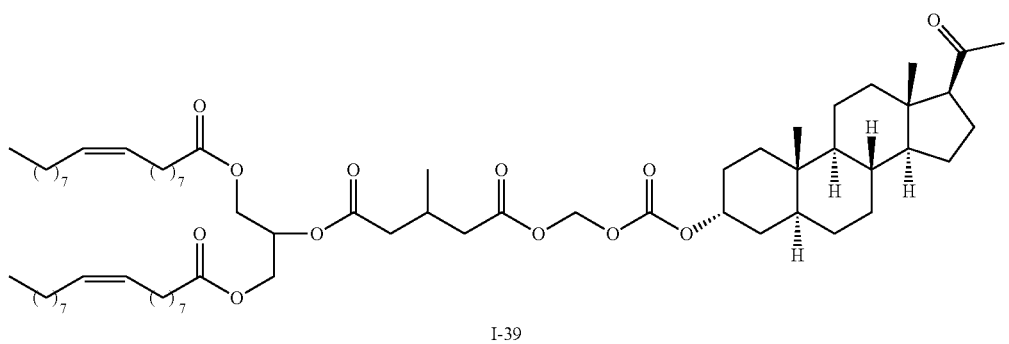

I-39

ALL-CASI-C5bMe-2-TG-oleate I-39 was synthesized using the procedure provided above for I-29, replacing C8-acid-TG-oleate with Int-210. The product was purified by silica gel chromatography (9% to 10% ethyl acetate/hexanes) to give ALL-CASI-C5bMe-2-TG-oleate I-39 (27.6 mg, 62%) as a colourless oil. $^1$H NMR (401 MHz, CDCl$_3$) δ 5.78-5.73 (m, 2H), 5.40-5.22 (m, 5H), 4.95 (m, 1H), 4.300/4.295 (each dd, J=11.9, 4.2 Hz, 2H), 4.13 (dd, J=11.9, 6.0 Hz, 2H), 2.56-2.38 (m, 4H), 2.30 (t, J=7.6 Hz, 4H), 2.36-2.25 (m, 2H), 2.14 (m, 1H), 2.11 (s, 3H), 2.08-1.93 (m, 9H), 1.84 (m, 1H), 1.74-1.08 (m, 61H), 1.03 (d, J=6.3 Hz, 3H), 0.87 (t, J=6.9 Hz, 6H), 0.99-0.76 (m, 2H), 0.79 (s, 3H), 0.59 (s, 3H); $^{13}$C NMR (101 MHz, CDCl$_3$) δ 209.8 (C), 173.4 (2C; C), 171.3 (C), 170.9 (C), 153.6 (C), 130.2 (2C; CH), 129.8 (2C; CH), 81.8 (CH$_2$), 75.7 (CH), 69.3 (CH), 63.9 (CH), 62.2 (2C; CH$_2$), 56.8 (CH), 54.0 (CH), 44.4 (C), 40.6 (CH$_2$), 40.3 (CH$_2$), 39.7 (CH), 39.2 (CH$_2$), 35.9 (C), 35.5 (CH), 34.1 (2C; CH$_2$), 32.8 (CH$_2$), 32.7 (CH$_2$), 32.0 (2C; CH$_2$), 31.9 (CH$_2$), 31.7 (CH$_3$), 29.9 (2C; CH$_2$), 29.8 (2C; CH$_2$), 29.7 (2C; CH$_2$), 29.5 (4C; CH$_2$), 29.31 (2C; CH$_2$), 29.25 (2C; CH$_2$), 29.22 (2C; CH$_2$), 28.3 (CH$_2$), 27.4 (2C; CH$_2$), 27.3 (2C; CH$_2$), 27.2 (CH), 26.1 (CH$_2$), 25.0 (2C; CH$_2$), 24.5 (CH$_2$), 22.9 (CH$_2$), 22.8 (2C; CH$_2$), 20.9 (CH$_2$), 19.7 (CH$_3$), 14.3 (2C; CH$_3$), 13.6 (CH$_3$), 11.4 (CH$_3$); ELSD: 6.42 min, 99.67% purity; MASS (ESI, +ve) m/z: 1123.65 (MH++18).

Synthesis of ALL-CDMPHB-C5bMe-2-TG-oleate
I-10

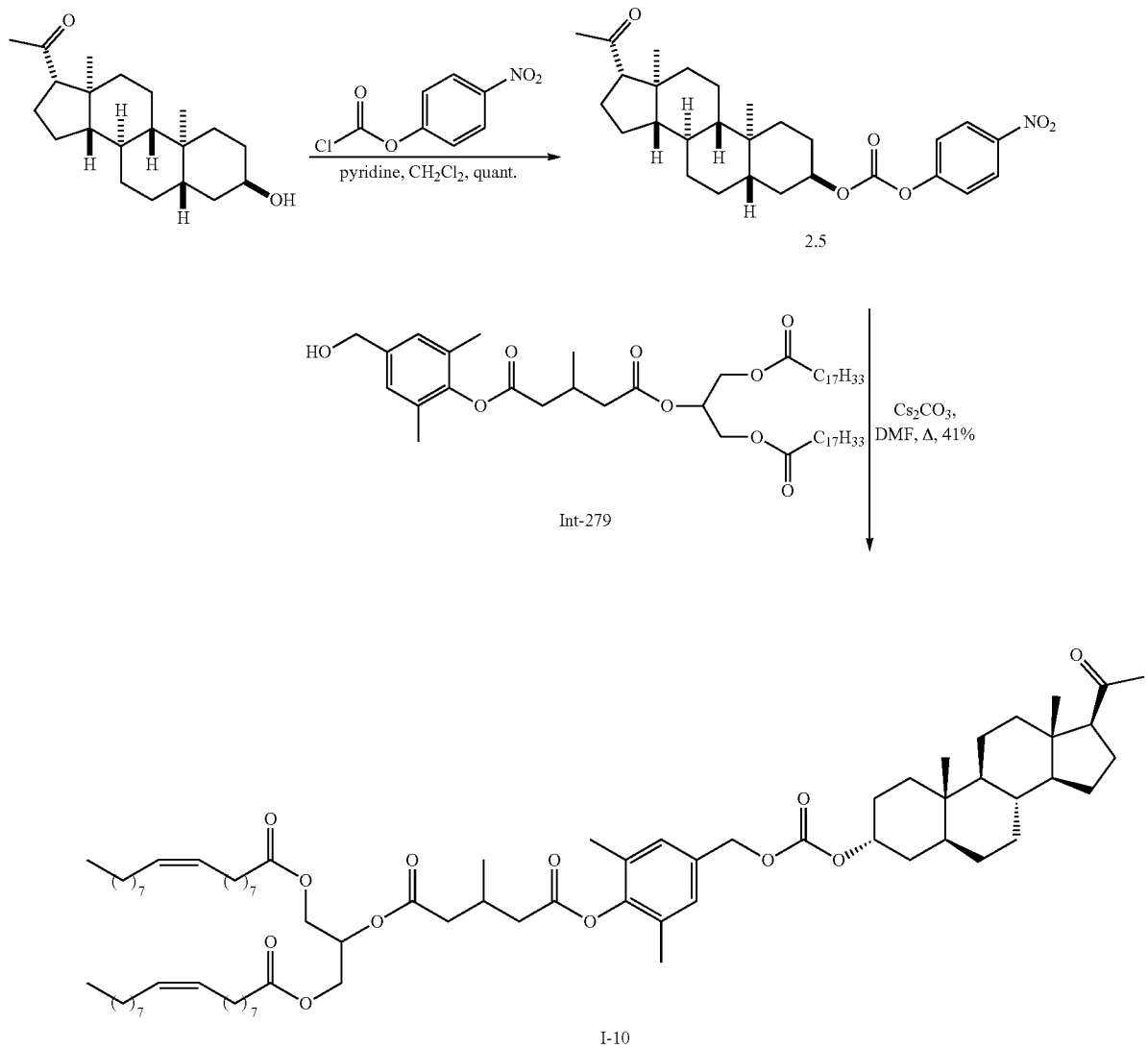

Step 1: Preparation of Compound 2.5

4-Nitrophenyl chloroformate (79.7 mg, 0.396 mmol) and pyridine (57.1 µL, 0.706 mmol) were added to allopregnanolone (90.0 mg, 0.283 mmol) in $CH_2Cl_2$ (10 mL) at 0° C. and the mixture was stirred at rt for 2.5 hours. The reaction was diluted with $CH_2Cl_2$ (30 mL) and the organic phase washed with sat. aq. $NaHCO_3$ (3×30 mL) and brine (30 mL), dried ($MgSO_4$) and concentrated under reduced pressure to compound 2.5 (137 mg, quant.) as a colourless solid containing a small amount of a closely-eluting PNP by-product (ca. 14% on mass basis). $^1H$ NMR (401 MHz, $CDCl_3$) δ 8.32-8.24 (m, 2H), 7.43-7.36 (m, 2H), 5.05 (m, 1H), 2.53 (t, J=9.0 Hz, 1H), 2.15 (m, 1H), 2.12 (s, 3H), 2.03 (m, 1H), 1.94 (m, 1H), 1.80-1.49 (m, 8H), 1.45-1.14 (m, 9H), 0.98 (m, 1H), 0.86 (m, 1H), 0.83 (s, 3H), 0.62 (s, 3H).

Step 2: ALL-CDMPHB-C5bMe-2-TG-oleate I-10

Potassium carbonate (13.7 mg, 99.3 µmol) was added to a solution of compound 2.5 (12.0 mg, 24.8 µmol) and Int-279 (24.1 mg, 27.3 µmol) in DMF (1.5 mL) and the mixture heated at 70° C. for two days and two hours. The reaction was cooled to rt, diluted with ethyl acetate (20 mL), washed with sat. aq. $NaHCO_3$ (3×20 mL) and brine (20 mL), dried ($MgSO_4$) and concentrated under reduced pressure to give the crude product. Purification by silica gel chromatography (20% to 25% diethyl ether/hexanes) gave ALL-CDMPHB-C5bMe-2-TG-oleate I-10 (12.4 mg, 41%) as a colourless oil. Note: The $^1H$ NMR spectrum suggested the presence of 5-10% of a $2^{nd}$ species containing DMPHB peaks but no allopregnanolone signals. $^1H$ NMR (401 MHz, $CDCl_3$) δ 7.10 (s, 2H), 5.39-5.24 (m, 5H), 5.05 (s, 2H), 4.91 (m, 1H), 4.32 (dd, J=11.9, 4.2 Hz, 2H), 4.147/4.145 (each dd, J=11.9, 6.0 Hz, 2H), 2.73 (dd, J=14.9, 5.1 Hz, 1H), 2.66-2.48 (m, 4H), 2.37 (dd, J=15.2, 7.3 Hz, 1H), 2.31 (t, J=7.6 Hz, 4H), 2.14 (s, 6H), 2.13 (m, 1H), 2.10 (s, 3H), 2.07-1.91 (m, 8H), 1.84 (m, 1H), 1.72-1.07 (m, 61H), 1.15 (d, J=6.4 Hz, 3H), 0.99-0.73 (m, 3H), 0.88 (t, J=6.9 Hz, 6H), 0.78 (s, 3H), 0.59 (s, 3H); ESI-HRMS: calcd. for $C_{76}H_{122}NaO_{12}$ [M+Na$^+$] 1249.8829; found 1249.8792.

Synthesis of ALL-TML-C8bMe-2-TG oleate I-12

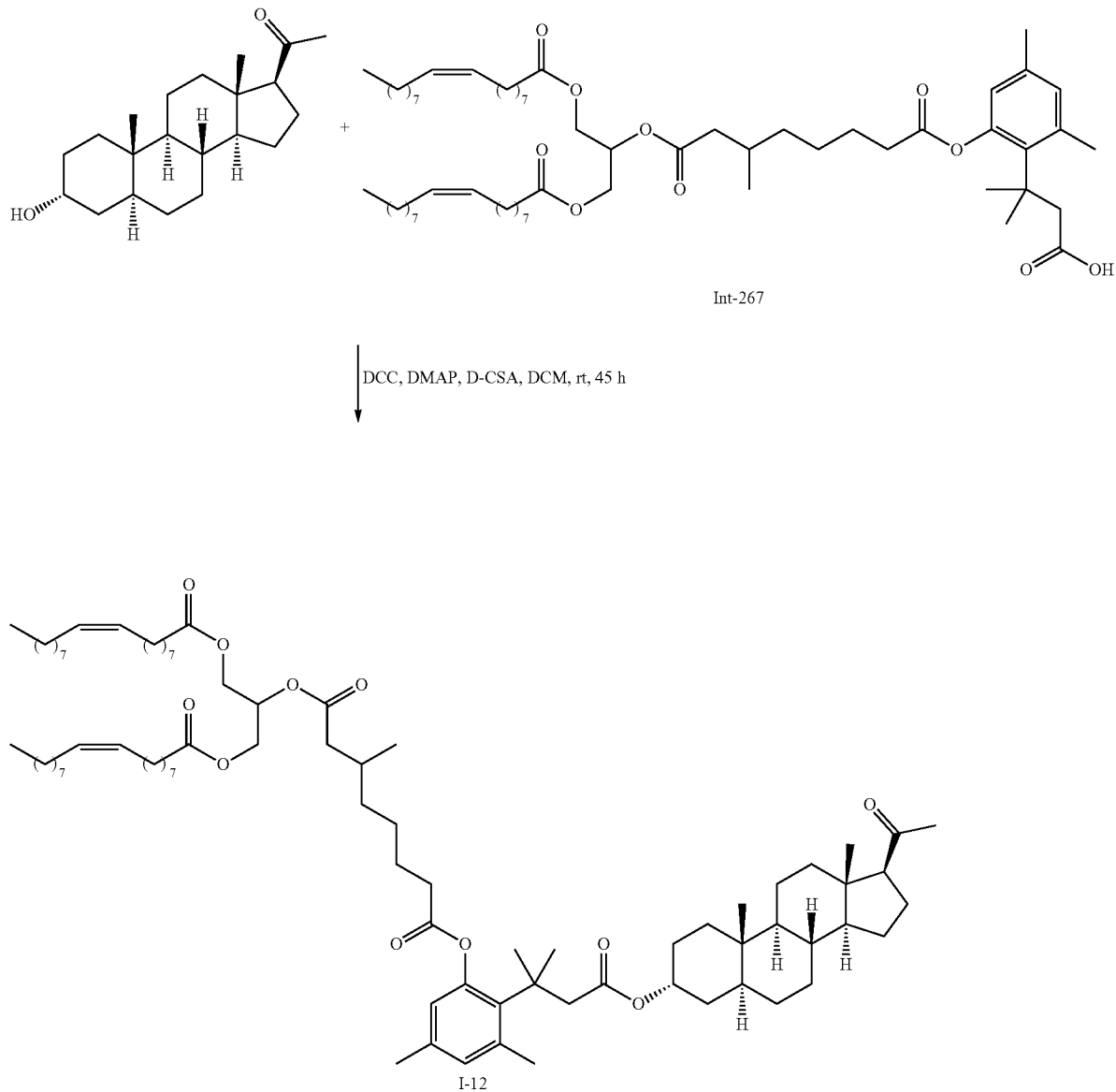

To a stirred solution of Int-267 (0.500 g, 0.502 mmol) in DCM (5 ml) was added DMAP (0.061 g, 0.502 mmol), DCC (0.310 g, 1.50 mmol) and D-camphorsulfonic acid (D-CSA) (0.030 g, 0.150 mmol). The reaction mixture was stirred at room temperature for 10 minutes. Allopregnanolone (0.159 g, 0.502 mmol) was added and the resulting reaction mixture was stirred at room temperature for 48 hours. The progress of the reaction was monitored by TLC. After 48 h, the reaction was completed. The reaction mixture was diluted with DM water (5 ml) and extracted with DCM (3×10 ml), and the combined organic layer was dried over sodium sulphate and concentrated under vacuum to get crude material. Purification was done by column chromatography using 100-200 mesh silica gel, and pure compound was eluted at 10% ethyl acetate/hexane to yield ALL-TML-C$_8$bMe-2-TG oleate I-12 (100 mg, 15.37%). $^1$H NMR (400 MHz, Chloroform-d) δ 6.84 (S, 1H), 6.59 (S, 1H), 5.42-5.30 (m, 4H), 4.96 (S, 1H), 4.35 (dd, J=12.0 Hz, 4.0 Hz, 2H), 4.20 (dd, J=11.6 Hz, 5.6 Hz, 2H)), 2.95 (m, 2H), 2.62 (m, 6H), 2.48-2.33 (m, 5H), 2.30 (S, 3H), 2.26-2.12 (m, 6H), 2.05 (d, J=5.6 Hz, 8H), 1.79-1.59 (m, 12H), 1.34-1.12 (m, 56H), 1.00 (d, J=4.8 Hz, 3H), 0.93 (m, 9H), 0.75 (s, 3H), 0.64 (s, 3H). NOTE: some peaks were obscured due to residual moisture at 1.6 ppm. $^{13}$C NMR (101 MHz, Chloroform-d) δ 209.65 (1C), 173.27 (2C), 172.46 (1C), 172.14 (1C), 171.35 (1C), 149.53 (1C), 137.93 (1C), 135.90 (1C), 133.62 (1C), 132.36 (1C), 130.02-129.72 (5C), 123.07 (2C), 69.72 (1C), 68.90 (1C), 63.89 (1C), 62.12 (1C), 56.91 (1C), 54.03 (1C), 48.95 (1C), 44.26 (2C), 41.58 (1C), 39.87 (1C), 39.15 (1C), 39.07 (1C), 36.35 (1C), 35.62 (1C), 35.38 (1C), 34.97 (1C), 34.02 (2C), 32.74 (1C), 31.92 (2C), 31.66 (2C), 31.55 (1C), 30.18-28.22 (22C), 27.23 (3C), 27.19 (2C), 25.46 (2C), 24.83 (1C), 24.41 (1C), 22.70 (1C), 20.76 (4C), 19.45 (1C), 14.14 (1C), 13.46 (1C), 11.26 (1C). ELSD: 17.95 min, 98.58% purity; LCMS (202 nm): 6.362 min, 100% purity; MASS (ESI, +ve) m/z: 1313.58 (MH+18).

Synthesis of ALL-TML-C8b'bMe-2-TG oleate I-14

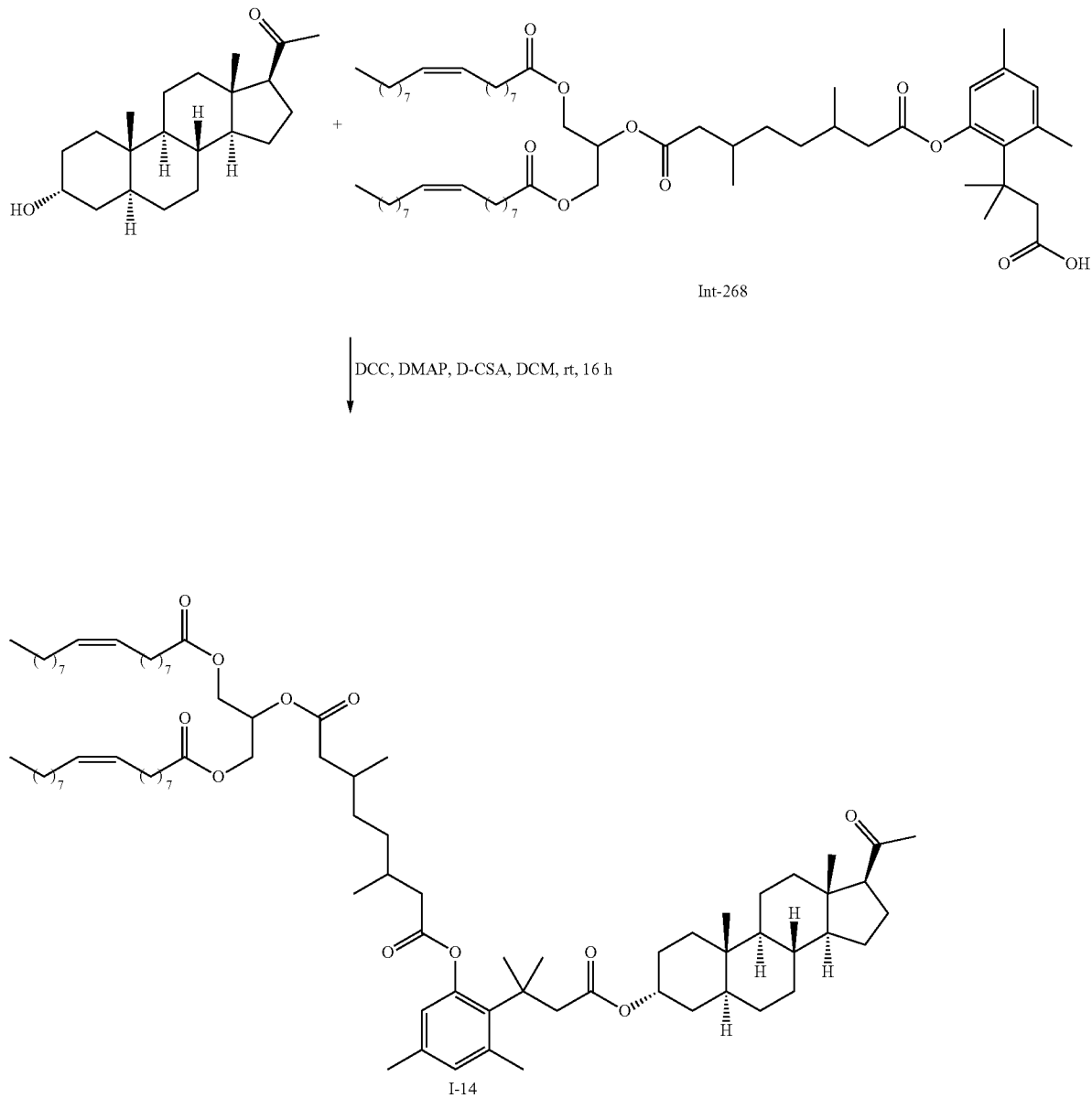

To a stirred solution of Int-268 (0.500 g, 0.495 mmol) in DCM (5 ml) was added DMAP (0.062 g, 0.495 mmol), DCC (0.306 g, 1.48 mmol) and D-CSA (0.0301 g, 0.148 mmol). The reaction mixture was stirred at room temperature for 10 Minutes. Allopregnanolone (0.157 g, 0.495 mmol) was added and the resulting reaction mixture was stirred at room temperature for 16 hours. The progress of reaction was monitored by TLC, and after 16 h the reaction was completed. The reaction mixture was diluted with DM water (30 ml) and extracted with DCM (3×25 ml), and the combined organic layer was dried over sodium sulphate and concentrated under vacuum to get crude material. Purification was done by column chromatography using 100-200 mesh silica gel, and pure compound was eluted at 8% ethyl acetate/ hexane to get ALL-TML-C8b'bMe-2-TG oleate I-14 (100 mg, 15.41%). $^1$H NMR (400 MHz, Chloroform-d) δ 7.28 (S, 1H), 6.82 (S, 1H), 5.40-5.28 (m, 4H), 4.94 (m, 1H), 4.33 (dd, J=12.0 Hz, 4.18 Hz, 2H) (dd, J=12.0 Hz, 6.0 Hz, 2H)), 2.84 (m, 4H), 2.58 (d, J=9.6 Hz, 4H), 2.42-2.28 (m, 10H), 2.24 (S, 3H), 2.19-2.14 (m, 6H), 2.07-2.02 (m, 14H), 1.70-1.58 (m, 6H), 1.31-1.23 (m, 56H), 1.08 (d, J=5.2 Hz, 3H), 0.98 (d, J=6.4 Hz, 3H), 0.91 (t, J=13.2 Hz, 10H), 0.73 (S, 3H), 0.69 (d, J=3.2 Hz, 3H). $^{13}$C NMR (101 MHz, Chloroform-d) δ 209.66 (1C), 173.28 (2C), 172.14 (1C), 171.94 (1C), 171.35 (1C), 149.51 (1C), 137.95 (1C), 135.87 (1C), 133.63 (1C), 132.34 (1C), 130.03-129.72 (5C), 123.03 (1C), 69.71 (1C), 68.91 (1C), 63.90 (1C), 62.12 (1C), 56.91 (1C), 54.02 (1C), 48.97 (1C), 42.47 (1C), 41.49 (1C), 39.87 (1C), 39.06 (1C), 37.10 (1C), 36.63 (1C), 35.62 (1C), 35.38 (1C), 33.84 (2C), 32.75 (1C), 31.92 (2C), 31.67 (2C), 31.55 (1C), 30.57-29.11 (24C), 27.23 (3C), 27.19 (2C), 25.47 (3C), 24.84 (1C), 24.41 (1C), 22.70 (1C), 19.78 (4C), 19.40 (1C), 14.14 (1C), 13.46 (1C), 11.43 (1C). ELSD: 19.22 min, 98.20% purity. LCMS (202 nm): 6.323 min, 91.23% purity. MASS (ESI, +ve) m/z: 1327.87 (MH+18).

Synthesis of ALL-TML-C5bMe-2-TG I-31

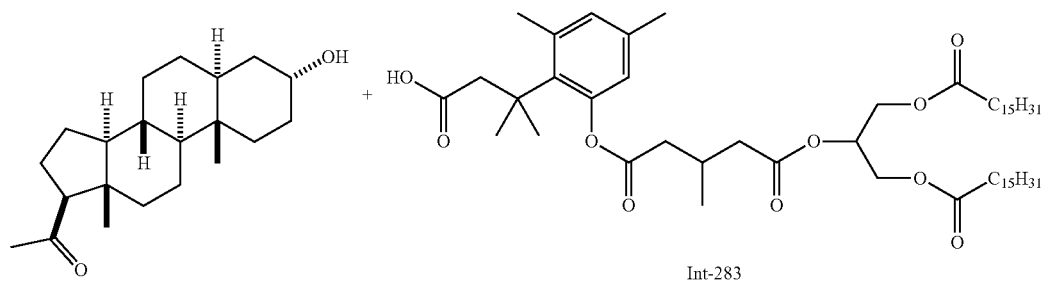

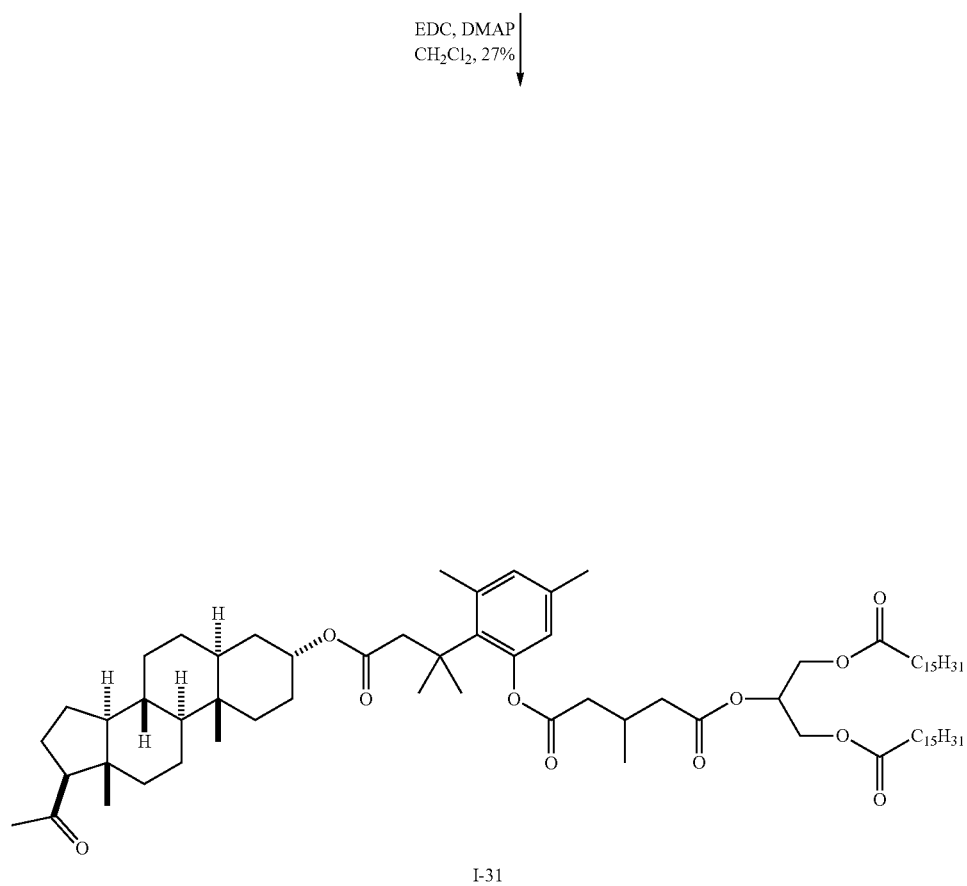

DMAP (4.7 mg, 38.8 μmol) and EDC·HCl (14.9 mg, 77.7 μmol) were added to a solution of allopregnanolone (14.8 mg, 46.6 μmol) and Int-154 (35.0 mg, 38.8 μmol) in $CH_2Cl_2$ (1.5 mL) and the mixture stirred at rt for one day and 22 hours. The reaction was diluted with $CH_2Cl_2$ (5 mL), silica gel was added and the mixture concentrated under reduced pressure. Purification by silica gel chromatography (8% to 12% ethyl acetate/hexanes) gave ALL-TML-C5bMe-2-TG I-31 (12.8 mg, 27%) as a colourless oil. $^1$H NMR (401 MHz, $CDCl_3$) δ 6.80 (d, J=1.9 Hz, 1H), 6.56 (d, J=1.7 Hz, 1H), 5.29 (m, 1H), 4.91 (m, 1H), 4.315/4.308 (each dd, J=11.9, 4.2 Hz, 2H), 4.15 (dd, J=11.9, 5.9 Hz, 2H), 2.834/2.829 (each ABq, $\Delta\delta_{AB}$=0.077, $J_{AB}$=14.8 Hz, 2H), 2.67 (dd, J=15.3, 5.5 Hz, 1H), 2.56 (s, 3H), 2.63-2.47 (m, 4H), 2.35 (dd, J=14.7, 8.4 Hz, 1H), 2.30 (t, J=7.5 Hz, 4H), 2.23 (s, 3H), 2.14 (m, 1H), 2.12 (s, 3H), 2.02 (m, 1H), 1.72-1.03 (m, 75H), 1.13 (d, J=6.3 Hz, 3H), 0.94-0.80 (m, 2H), 0.87 (t, J=6.9 Hz, 6H), 0.71 (s, 3H), 0.63 (m, 1H), 0.60 (s, 3H); $^{13}$C NMR (101 MHz, $CDCl_3$) δ 209.8 (C), 173.4 (2C; C), 171.43 (C), 171.40 (C), 171.2 (C), 149.5 (C), 138.1 (C), 136.1 (C), 133.7 (C), 132.6 (CH), 123.2 (CH), 69.9 (CH), 69.3 (CH), 64.0 (CH), 62.2 (2C; $CH_2$), 57.0 (CH), 54.2 (CH), 49.1 ($CH_2$), 44.4 (C), 41.4 ($CH_2$), 40.7 ($CH_2$), 40.0 (CH), 39.3 ($CH_2$), 39.2 (C), 35.8 (C), 35.5 (CH), 34.2 (2C; $CH_2$), 32.9 (2C; $CH_2$), 32.1 (2C; $CH_2$), 32.0 ($CH_2$), 31.83/31.81 ($CH_3$), 31.81/31.79 ($CH_3$), 31.7 ($CH_3$), 29.84 (6C; $CH_2$), 29.81 (4C; $CH_2$), 29.77 (2C; $CH_2$), 29.6 (2C; $CH_2$), 29.5 (2C; $CH_2$), 29.4 (2C; $CH_2$), 29.3 (2C; $CH_2$), 28.4 ($CH_2$), 27.3 (CH), 26.2 ($CH_2$), 25.6 ($CH_3$), 25.0 (2C; $CH_2$), 24.5 ($CH_2$), 23.0 ($CH_2$), 22.8 (2C; $CH_2$), 20.9 ($CH_2$), 20.5 ($CH_3$), 19.9 ($CH_3$), 14.3 (2C; $CH_3$), 13.6 ($CH_3$), 11.4 ($CH_3$); Note: Some doubled signals were observed due to the presence of diastereoisomers.

Synthesis of ALL-CMSI-C12b'bMe-2-TG oleate
I-35

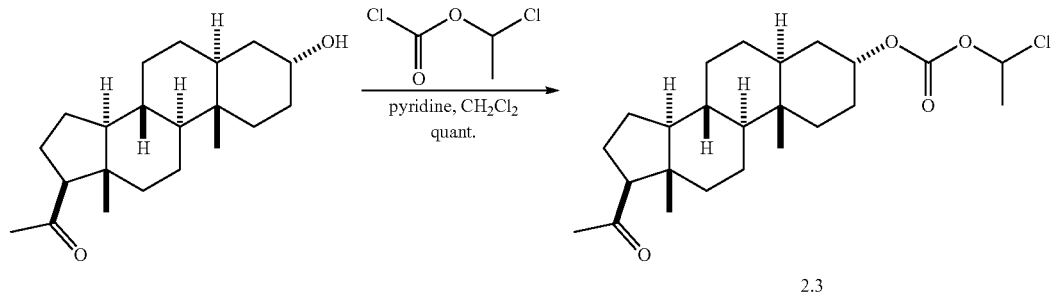

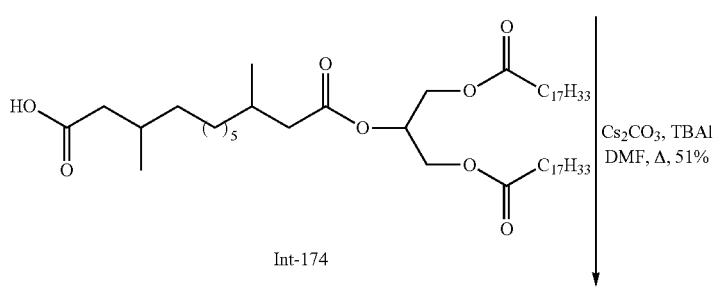

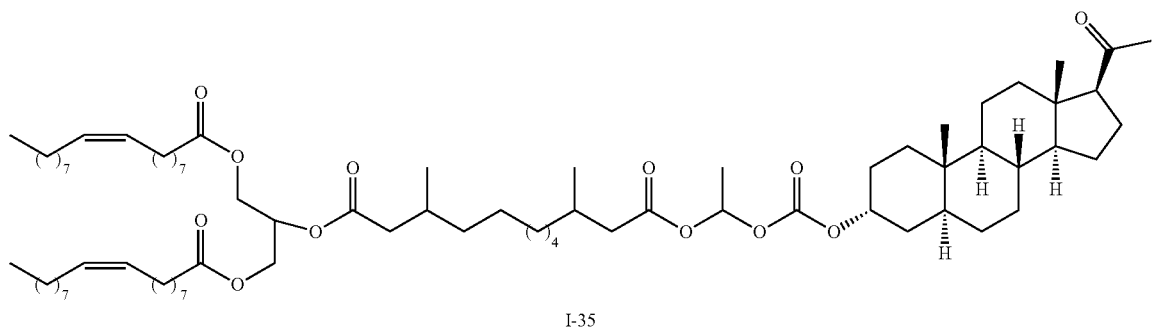

I-35

Cs$_2$CO$_3$ (36.5 mg, 112 µmol) and TBAI (6.9 mg, 18.7 µmol) were added to a solution of Int-174 (29.0 mg, 37.3 µmol) and compound 2.3 (15.3 mg, 39.4 µmol, prepared as shown in the synthesis of I-1) in DMF (2 mL) and the mixture was heated at 70° C. for two hours. The reaction was cooled to rt, diluted with ethyl acetate (30 mL) and the organic phase was washed with water and brine (30 mL each), dried (MgSO$_4$) and concentrated under reduced pressure to give the crude product. Silica gel chromatography (8% to 10% ethyl acetate/hexanes) gave ALL-CMSI-C$_{12}$b'bMe-2-TG oleate I-35 (22.7 mg, 53%) as a colourless oil. $^1$H NMR (401 MHz, CDCl$_3$) δ 5.78-5.71 (m, 2H), 5.39-5.20 (m, 5H), 4.94 (m, 1H), 4.29 (dd, J=11.9, 4.3 Hz, 2H), 4.13 (dd, J=11.9, 5.9 Hz, 2H), 2.52 (t, J=8.9 Hz, 1H), 2.37 (t, J=7.5 Hz, 2H), 2.31 (t, J=7.6 Hz, 2H), 2.30 (t, J=7.6 Hz, 4H), 2.14 (m, 1H), 2.10 (s, 3H), 2.05-1.93 (m, 9H), 1.84 (m, 1H), 1.79-1.12 (m, 61H), 0.98-0.75 (m, 2H), 0.87 (t, J=6.7 Hz, 6H), 0.78 (s, 3H), 0.59 (s, 3H); $^{13}$C NMR (101 MHz, CDCl$_3$) δ 209.8 (C), 173.4 (2C; C), 172.8 (C), 172.3 (C), 153.6 (C), 130.2 (2C; CH), 129.9 (2C; CH), 81.9 (CH$_2$), 75.7 (CH), 69.1 (CH), 63.9 (CH), 62.2 (2C; CH$_2$), 56.9 (CH), 54.0 (CH), 44.4 (C), 39.8 (CH), 39.2 (CH$_2$), 35.9 (C), 35.6 (CH), 34.2 (3C; CH$_2$), 33.9 (CH$_2$), 32.8 (CH$_2$), 32.7 (CH$_2$), 32.0 (2C; CH$_2$), 31.9 (CH$_2$), 31.7 (CH$_3$), 29.9 (2C; CH$_2$), 29.8 (2C; CH$_2$), 29.7 (2C; CH$_2$), 29.5 (4C; CH$_2$), 29.31 (2C; CH$_2$), 29.25 (2C; CH$_2$), 29.22 (2C; CH$_2$), 28.77 (CH$_2$), 28.76 (CH$_2$), 28.3 (CH$_2$), 27.4 (2C; CH$_2$), 27.3 (2C; CH$_2$), 26.1 (CH$_2$), 25.0 (2C; CH$_2$), 24.7 (CH$_2$), 24.5 (CH$_2$), 24.4 (CH$_2$), 22.9 (CH$_2$), 22.8 (2C; CH$_2$), 20.9 (CH$_2$), 14.3 (2C; CH$_3$), 13.6 (CH$_3$), 11.4 (CH$_3$).

Synthesis of ALL-CMSI-C6-2-TG oleate I-43

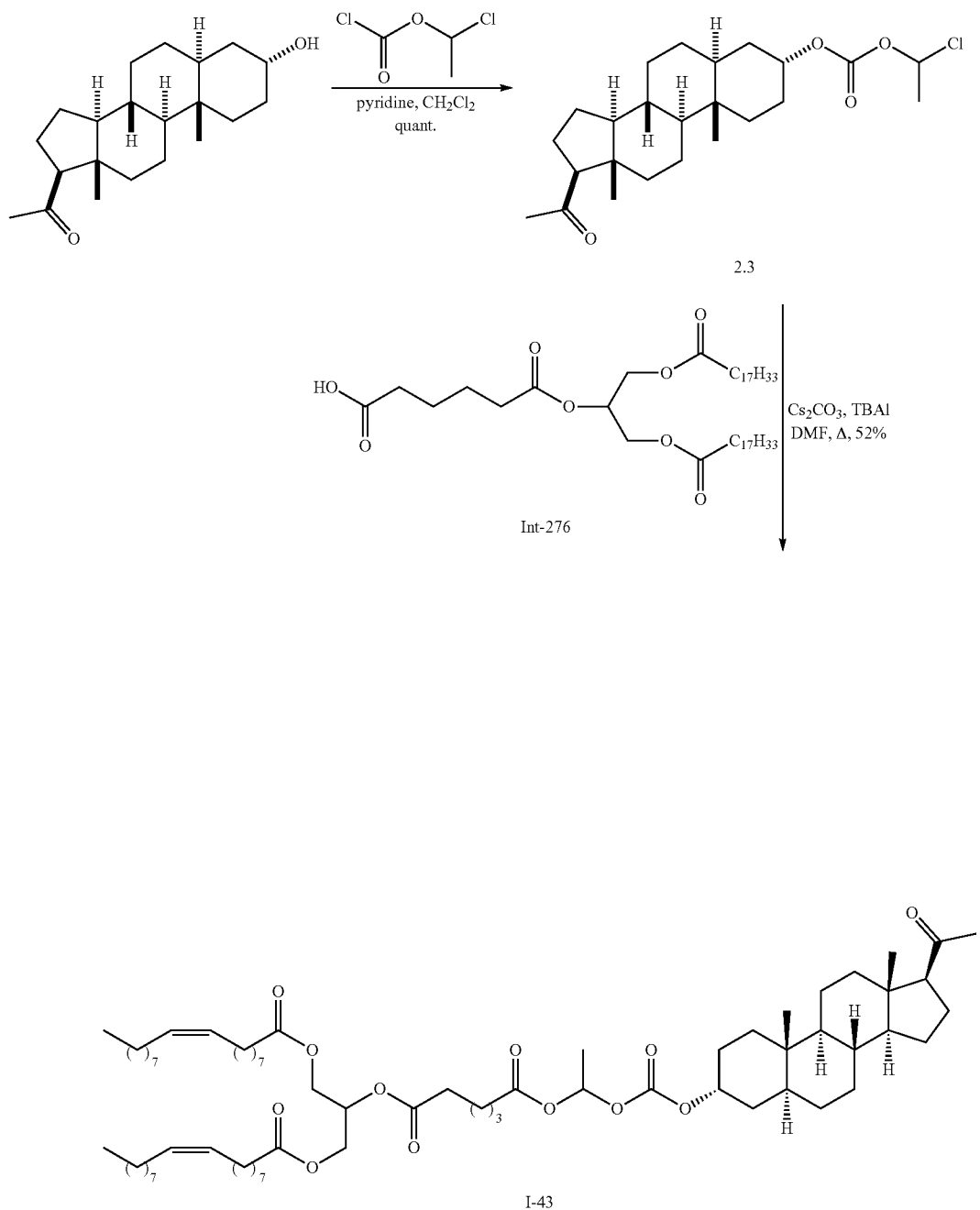

ALL-CMSI-C6-2-TG-oleate I-43 was synthesized using the procedure provided above for I-35, replacing Int-174 with Int-276. The product was purified by silica gel chromatography (9% to 10% ethyl acetate/hexanes) to give ALL-CMSI-C6-2-TG-oleate I-43 (24.6 mg, 52%) as a colourless oil. $^1$H NMR (401 MHz, CDCl$_3$) δ 6.765/6.762 (each q, J=5.4 Hz, 1H), 5.41-5.19 (m, 5H), 4.92 (m, 1H), 4.29 (dd, J=11.9, 4.3 Hz, 2H), 4.13 (dd, J=11.9, 5.9 Hz, 2H), 2.52 (t, J=8.9 Hz, 1H), 2.41-2.26 (m, 8H), 2.15 (m, 1H), 2.11 (s, 3H), 2.07-1.91 (m, 9H), 1.85 (m, 1H), 1.73-1.46 (m, 19H), 1.520/1.517 (each d, J=5.4 Hz, 3H), 1.43-1.08 (m, 45H), 0.99-0.76 (m, 3H), 0.87 (t, J=6.9 Hz, 6H), 0.78 (s, 3H), 0.60 (s, 3H); $^{13}$C NMR (101 MHz, CDCl$_3$) δ 209.9 (C), 173.4 (2C; C), 172.4 (C), 171.3 (C), 152.8 (C), 130.2 (2C; CH), 129.9 (2C; CH), 91.3 (CH), 75.3 (CH), 69.3 (CH), 64.0 (CH), 62.2 (2C; CH$_2$), 56.9 (CH), 54.0 (CH), 44.4 (C), 39.8 (CH), 39.2 (CH$_2$), 35.9 (C), 35.5 (CH), 34.1 (2C; CH$_2$), 33.8 (CH$_2$), 33.74/33.72 (CH$_2$), 32.84/32.78 (CH$_2$), 32.72/32.70 (CH$_2$), 32.1 (2C; CH$_2$), 31.9 (CH$_2$), 31.7 (CH$_3$), 29.91 (2C; CH$_2$), 29.85 (2C; CH$_2$), 29.7 (2C; CH$_2$), 29.5 (4C; CH$_2$), 29.33 (2C; CH$_2$), 29.26 (2C; CH$_2$), 29.23 (2C; CH$_2$), 28.3 (CH$_2$), 27.4 (2C; CH$_2$), 27.3 (2C; CH$_2$), 26.1/26.0 (CH$_2$), 25.0 (2C; CH$_2$), 24.5 (CH$_2$), 24.2 (CH$_2$), 24.02/24.00 (CH$_2$), 22.9 (CH$_2$), 22.8 (2C; CH$_2$), 20.9 (CH$_2$), 19.8 (CH$_3$), 14.3 (2C; CH$_3$), 13.6 (CH$_3$), 11.4 (CH$_3$).

Synthesis of ALL-CMSI-C8-2-TG oleate I-44

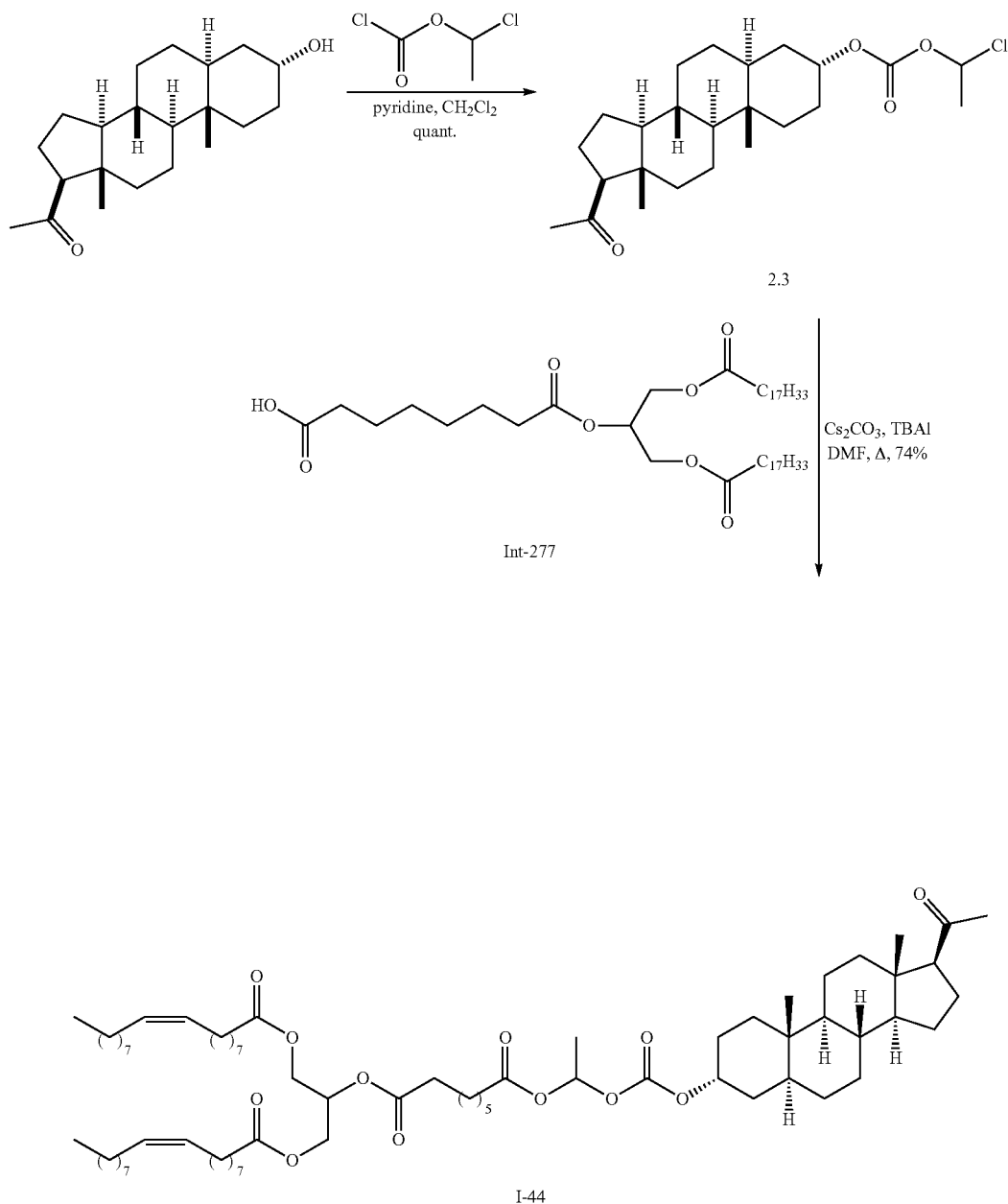

ALL-CMSI-C8-2-TG-oleate I-44 was synthesized using the procedure provided above for I-35, replacing Int-174 with Int-277. The product was purified by silica gel chromatography (9% to 10% ethyl acetate/hexanes) to give ALL-CMSI-C8-2-TG-oleate I-44 (34.5 mg, 74%) as a colourless oil. $^1$H NMR (401 MHz, CDCl$_3$) δ 6.765/6.761 (each q, J=5.4 Hz, 1H), 5.40-5.20 (m, 5H), 4.92 (m, 1H), 4.29 (dd, J=11.9, 4.3 Hz, 2H), 4.13 (dd, J=11.9, 5.9 Hz, 2H), 2.52 (t, J=8.9 Hz, 1H), 2.39-2.26 (m, 8H), 2.14 (m, 1H), 2.10 (s, 3H), 2.07-1.91 (m, 9H), 1.85 (m, 1H), 1.73-1.47 (m, 19H), 1.516/1.511 (each d, J=5.4 Hz, 3H), 1.42-1.08 (m, 49H), 1.00-0.73 (m, 3H), 0.87 (t, J=6.9 Hz, 6H), 0.78 (s, 3H), 0.59 (s, 3H); $^{13}$C NMR (101 MHz, CDCl$_3$) δ 209.9 (C), 173.4 (2C; C), 172.8 (C), 171.7 (C), 152.8 (C), 130.2 (2C; CH), 129.8 (2C; CH), 91.2 (CH), 75.3 (CH), 69.1 (CH), 63.9 (CH), 62.2 (2C; CH$_2$), 56.9 (CH), 53.9 (CH), 44.4 (C), 39.8 (CH), 39.2 (CH$_2$), 35.9 (C), 35.5 (CH), 34.16 (CH$_2$), 34.15 (2C; CH$_2$), 34.09/34.07 (CH$_2$), 32.82/32.78 (CH$_2$), 32.71/32.69 (CH$_2$), 32.0 (2C; CH$_2$), 31.9 (CH$_2$), 31.7 (CH$_3$), 29.9 (2C; CH$_2$), 29.8 (2C; CH$_2$), 29.7 (2C; CH$_2$), 29.5 (4C; CH$_2$), 29.32 (2C; CH$_2$), 29.25 (2C; CH$_2$), 29.22 (2C; CH$_2$), 28.80 (CH$_2$), 28.75 (CH$_2$), 28.3 (CH$_2$), 27.4 (2C; CH$_2$), 27.3 (2C; CH$_2$), 26.1/26.0 (CH$_2$), 25.0 (2C; CH$_2$), 24.7 (CH$_2$), 24.50 (CH$_2$), 24.48 (CH$_2$), 22.9 (CH$_2$), 22.8 (2C; CH$_2$), 20.9 (CH$_2$), 19.8 (CH$_3$), 14.3 (2C; CH$_3$), 13.6 (CH$_3$), 11.4 (CH$_3$); Note: Doubled peaks were observed in some cases due to the presence of diastereoisomers; ESI-HRMS: calcd. for C$_{75}$H$_{128}$NaO$_{12}$ [M+Na$^+$] 1201.8829; found 1201.8807.

Synthesis of ALL-CMSI-C8bMe-2-TG oleate I-45

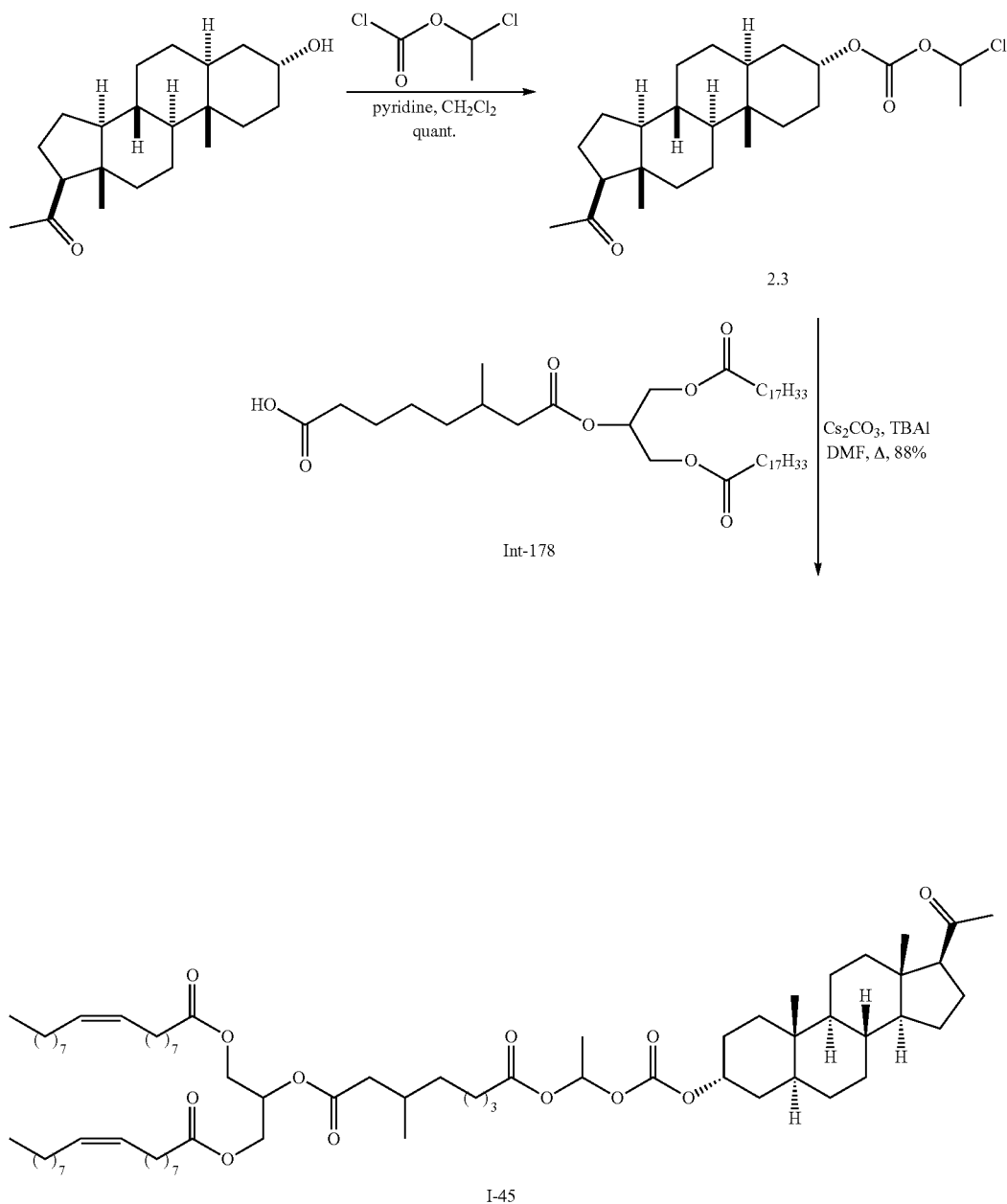

ALL-CMSI-C8bMe-2-TG-oleate I-45 was synthesized using the procedure provided above for I-35, replacing Int-174 with Int-178. The product was purified by silica gel chromatography (8% to 10% ethyl acetate/hexanes) to give ALL-CMSI-C8bMe-2-TG-oleate I-45 (48.5 mg, 88%) as a colourless oil. $^1$H NMR (401 MHz, CDCl$_3$) δ 6.770/6.767 (each q, J=5.4 Hz, 1H), 5.41-5.21 (m, 5H), 4.92 (m, 1H), 4.29 (dd, J=11.9, 4.3 Hz, 2H), 4.14 (dd, J=11.9, 5.9 Hz, 2H), 2.52 (t, J=8.9 Hz, 1H), 2.37-2.26 (m, 7H), 2.20-2.06 (m, 2H), 2.11 (s, 3H), 2.07-1.90 (m, 10H), 1.85 (m, 1H), 1.521/1.519 (each d, J=5.4 Hz, 3H), 1.72-1.08 (m, 66H), 0.93 (d, J=6.2 Hz, 3H), 1.00-0.76 (m, 3H), 0.88 (t, J=6.9 Hz, 6H), 0.79 (s, 3H), 0.60 (s, 3H); $^{13}$C NMR (101 MHz, CDCl$_3$) δ 209.8 (C), 173.4 (2C; C), 172.3 (C), 171.6 (C), 152.8 (C), 130.1 (2C; CH), 129.8 (2C; CH), 91.2 (CH), 75.2 (CH), 69.0 (CH), 63.9 (CH), 62.2 (2C; CH$_2$), 56.9 (CH), 53.9 (CH), 44.3 (C), 41.7 (CH$_2$), 39.7 (CH), 39.2 (CH$_2$), 36.4 (CH$_2$), 35.8 (C), 35.5 (CH), 34.12 (2C; CH$_2$), 34.09 (CH$_2$), 32.80/32.75 (CH$_2$), 32.69/32.67 (CH$_2$), 32.0 (2C; CH$_2$), 31.8 (CH$_2$), 31.7 (CH$_3$), 30.3 (CH), 29.9 (2C; CH$_2$), 29.8 (2C; CH$_2$), 29.6 (2C; CH$_2$), 29.4 (4C; CH$_2$), 29.3 (2C; CH$_2$), 29.23 (2C; CH$_2$), 29.20 (2C; CH$_2$), 28.3 (CH$_2$), 27.33 (2C; CH$_2$), 27.28 (2C; CH$_2$), 26.4 (CH$_2$), 26.1/26.0 (CH$_2$), 24.9 (2C; CH$_2$), 24.8 (CH$_2$), 24.5 (CH$_2$), 22.9 (CH$_2$), 22.8 (2C; CH$_2$), 20.9 (CH$_2$), 19.8 (CH$_3$), 19.6 (CH$_3$), 14.2 (2C; CH$_3$), 13.6 (CH$_3$), 11.4 (CH$_3$); Note: Doubled peaks were observed in some cases due to the presence of diastereoisomers; ESI-HRMS: calcd. for C$_{75}$H$_{128}$NaO$_{12}$ [M+Na$^+$] 1201.8829; found 1201.8807.

Synthesis of ALL-CMSI-C5bMe-acid
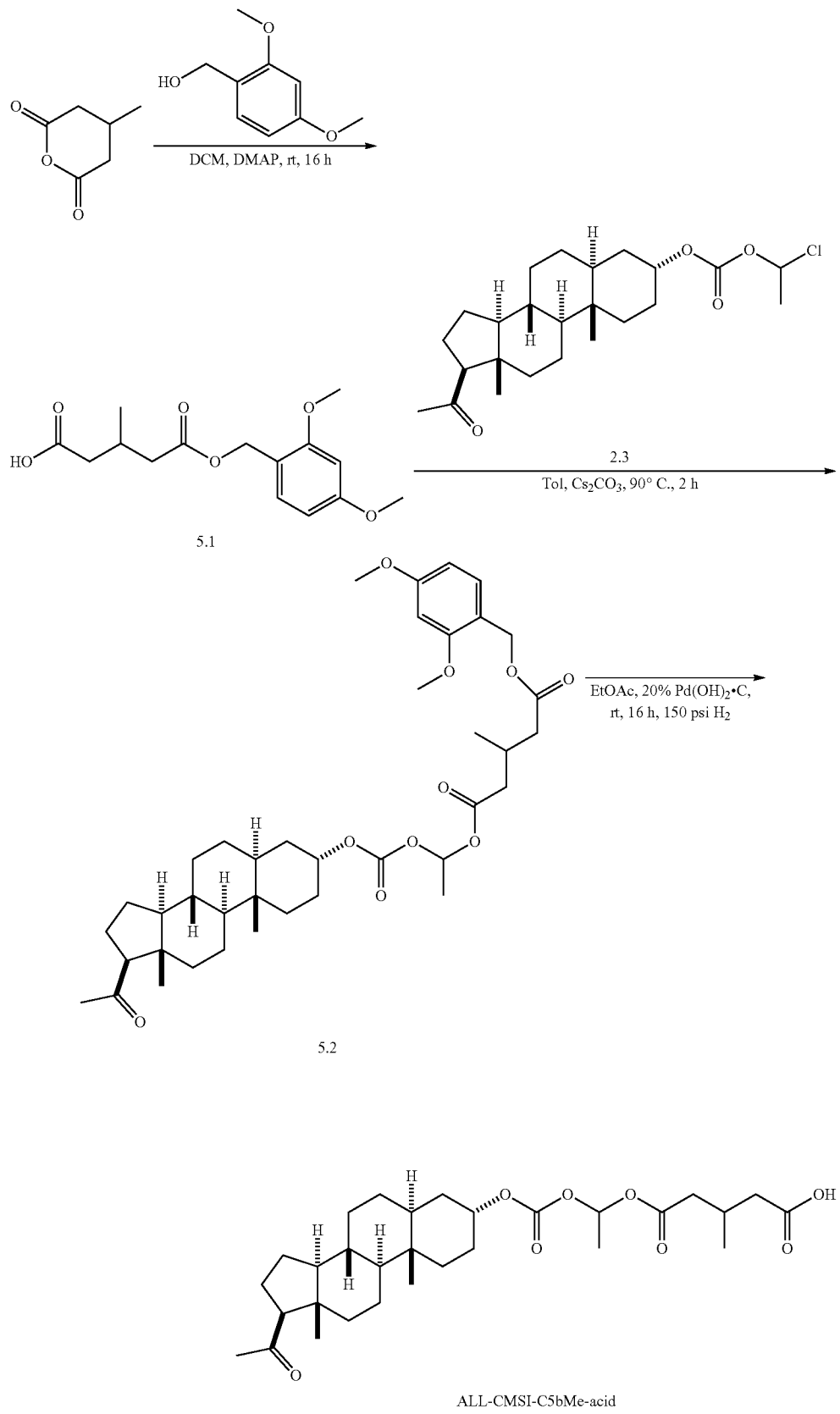

Step 1: Compound 5.1

To a solution of 4-methyldihydro-2H-pyran-2,6 (3H)-dione (1.5 g, 11.718 mmol) in DCM (20 ml) was added DMAP (1.42 g, 11.718 mmol). The reaction mixture was stirred at room temperature for 10 min, then (2,4-dimethoxyphenyl)methanol (0.98 g, 5.859 mmol) was added. The reaction mixture was stirred at room temperature for an additional 16 h. The reaction was monitored by TLC. After completion of the reaction, the reaction mixture was diluted with water (20 ml) and extracted with DCM (3×20 ml). The organic layer was washed with 1 N HCl (20 ml). The combined organic layer was dried over $Na_2SO_4$ and evaporated under vacuum to get crude compound 5.1 as a colorless liquid (1.9 g, quantitative yield), which was directly used in the next step. $^1$H NMR (400 MHz, $CDCl_3$) δ 7.30 (d, J=8.8 Hz, 1H), 6.50 (dd, J=2.0 Hz, 2H), 5.13 (s, 2H), 3.88 (s, 3H), 3.82 (s, 3H), 2.91 (m, 1H), 2.51 (d, J=5.2 Hz, 2H), 2.45 (d, J=6.4 Hz, 2H), 1.08 (s, 3H).

Step 2: Compound 5.2

To a solution of compound 2.3 (2.15 g, 5.067 mmol; produced as shown in the synthesis of I-1) in toluene (5 ml) was added $Cs_2CO_3$ (3.29 g, 10.134 mmol) and stirred at room temperature for 15 min then compound 5.1 (1.5 g, 5.067 mmol) (pre dissolved in 10 ml Toluene) and TBAI (0.934 g, 25.33 mmol) were added at room temperature. The reaction mixture was stirred at 90° C. for 2 h. The reaction was monitored by TLC. After completion of the reaction, the reaction mixture was diluted with water (10 ml) and extracted with ethyl acetate (3×10 ml), and the combined organic layer was dried over $Na_2SO_4$, The reaction mixture was reduced under vacuum to get crude compound 5.2, which was purified by column chromatography using silica gel (100-200 mesh). Pure compound was eluted at 12% ethyl acetate and hexane as a mobile phase then pure fraction was under vacuum to get pure compound 5.2 (1.9 g, 55.96%). $^1$H NMR (400 MHz, Chloroform-d) δ 7.28 (q, J=9.6 Hz, 1H), 6.79 (d, J=5.6 Hz, 1H), 6.48 (dd, J=5.6 Hz, 2H), 5.32 (m, 1H), 5.10 (s, 2H), 3.83 (s, 6H), 2.56-2.31 (s, 6H), 2.18 (s, 3H), 1.67-1.50 (m, 10H), 1.43 (d, J=10.0 Hz, 2H), 1.04-0.93 (m, 6H), 1.32-1.18 (m, 10H), 0.82 (s, 3H), 0.61 (s, 3H).

Step 3: ALL-CMSI-C5bMe-acid

To a solution of compound 5.2 (1.65 g, 2.42 mmol) in ethyl acetate (20 ml) was added 20% Palladium hydroxide on carbon (0.900 g, (50% moisture)) and the resulting suspension was flushed with $N_2$ three times. The reaction mixture was stirred at rt for 16 h under 150 psi $H_2$ pressure (in an autoclave). After completion of the reaction, the reaction mixture was filtered through a pad of celite, and washed with ethyl acetate (30 ml). The filtrate was concentrated under reduced pressure to afford crude material which was purified by column chromatography using silica gel (60-120 mesh). Pure compound was eluted at 15% ethyl acetate and hexane as a mobile phase and pure fractions were concentrated under vacuum to get pure ALL-CMSI-C5bMe-acid (0.500 g). $^1$H NMR (400 MHz, Chloroform-d) δ 6.80 (q, J=5.2 Hz, 1H), 4.94 (m, 1H), 4.13 (m, 2H), 2.52 (dd, J=17.6, 8.8 Hz, 5H), 2.36 (t, J=7.6 Hz, 1H), 2.13 (s, 3H), 2.03 (t, J=14.4 Hz, 2H), 1.89 (m, 2H), 1.55 (d, J=5.2 Hz, 6H), 1.48-1.23 (m, 9H), 1.11 (s, 3H), 1.01-0.89 (m, 4H), 0.84 (d, J=14.4 Hz, 3H), 0.61 (s, 3H); $^{13}$C NMR (101 MHz, Chloroform-d) δ 209.91 (1C), 177.69 (1C), 177.64 (1C), 170.23 (1C), 152.67 (1C), 91.18 (1C), 75.25 (1C), 63.82 (1C), 56.74 (1C), 53.81 (1C), 44.26 (1C), 40.29 (1C), 40.20 (1C), 39.63 (1C), 39.04 (1C), 35.72 (1C), 34.40 (1C), 32.57 (1C), 31.51 (1C), 29.68 (1C), 28.14 (1C), 25.89 (1C), 24.36 (1C), 22.78 (1C), 21.04 (1C), 20.76 (1C), 19.61 (2C), 13.45 (1C), 11.25 (1C); ELSD: 3.88 min, 100% purity; LCMS (202 nm): 4.66 min., 82.18% purity; MASS (ESI, +ve) m/z: 552.36 (MH+18).

Synthesis of ALL-CMSI-C5bMe-2-TG-octanoate
I-36

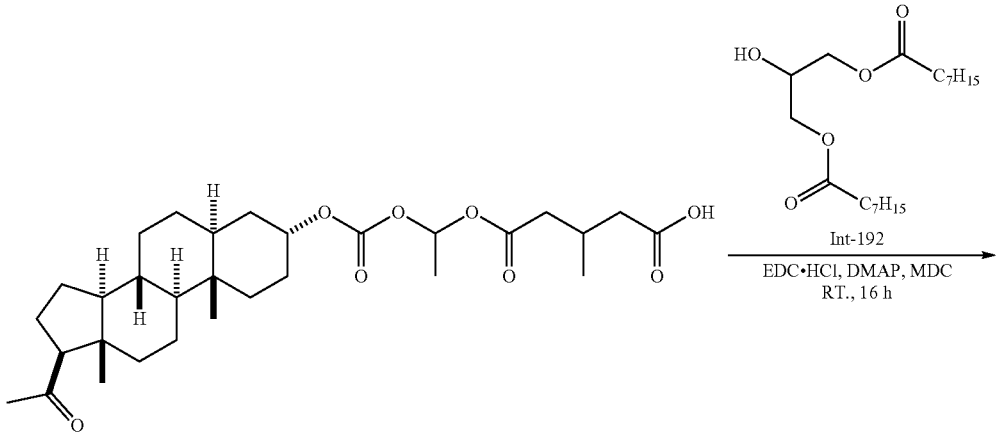

ALL-CMSI-C5bMe-acid

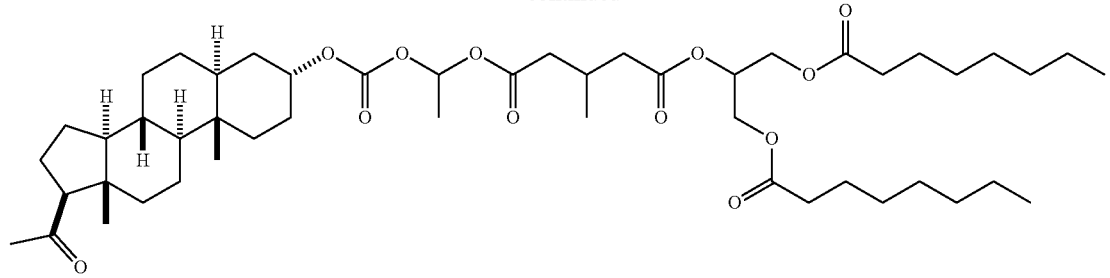

I-36

To a stirred solution of ALL-CMSI-C5bMe-acid (0.250 g, 0.468 mmol) in DCM (3 ml) was added DMAP (0.057 g, 0.468 mmol), and EDC·HCl (0.223 g, 1.17 mmol). The reaction mixture was stirred at room temperature for 10 minutes. Int-192 (0.161 g, 0.468 mmol) was added and the resulting reaction mixture was stirred at room temperature for an additional 16 hours. After completion of the reaction, the reaction mixture was diluted with DM water (3 ml) and extracted with DCM (3×3 ml), and the combined organic layer was dried over sodium sulphate and concentrated under vacuum to get crude material. Purification was done by column chromatography using 100-200 mesh silica gel. Pure compound was eluted at 4% Ethyl acetate/DCM to get 1.29 (m, 27H), 1.08 (d, J=5.6 Hz, 3H), 1.00-0.99 (m, 8H), 0.64 (S, 3H). $^{13}$CNMR (101 MHz, Chloroform d) δ 209.65 (1C), 173.27 (2C), 171.26 (1C), 170.14 (1C), 152.65 (1C), 91.14 (1C), 75.20 (1C), 69.14 (1C), 65.00 (1C), 63.81 (1C), 62.05 (1C), 56.75 (1C), 53.83 (1C), 44.23 (1C), 39.65 (1C), 39.06 (1C), 35.73 (1C), 35.41 (3C), 31.65 (2C), 29.70 (1C), 29.05 (3C), 28.90 (3C), 28.15 (1C), 27.13 (1C), 25.89 (1C). 24.83 (3C), 24.37 (1C), 22.59 (1C), 22.79 (2C), 20.77 (1C), 19.63 (1C), 19.47 (1C), 14.06 (4C), 13.45 (1C), 11.29 (1C). ELSD: 5.13 min, 100% purity; LCMS (230 nm): 17.037 min, 100% purity; MASS (ESI, +ve) m/z: 878.46 (MH+18).

Synthesis of ALL-CMSI-C$_5$bMe-2-TG-butyrate I-37

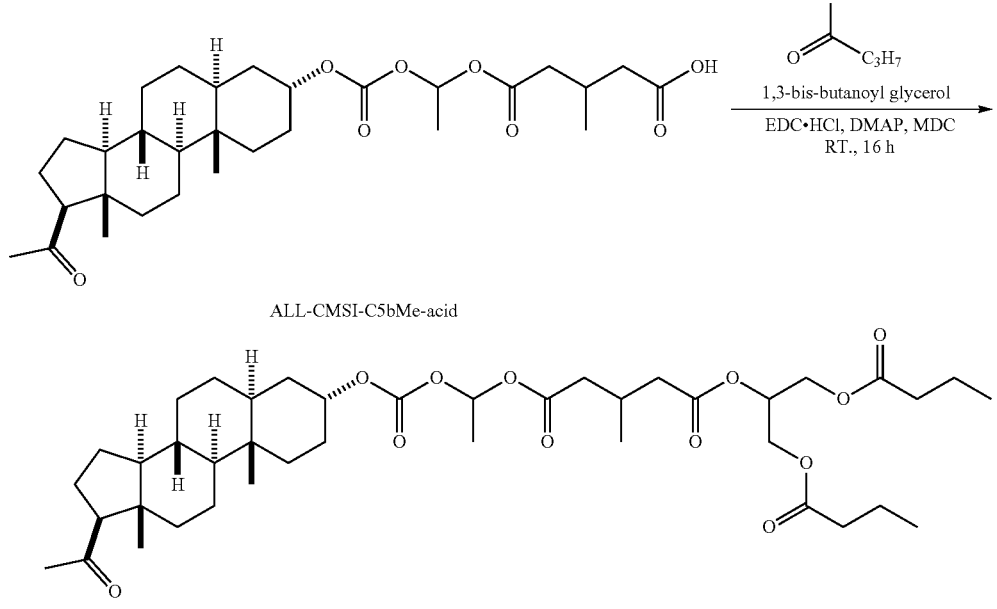

I-37

ALL-CMSI-C5bMe-2-TG-octanoate I-36 (90 mg, 22.35%). $^1$H NMR (400 MHz, Chloroform-d) δ 6.82 (q, J=5.2 Hz, 1H), 5.34 (m, 1H), 4.96 (m, 1H), 4.35 (d, J=11.6 Hz, 2H), 4.20 (dd, J=11.6, 5.6 Hz, 2H), 2.58 (d, J=8.8 Hz, 4H), 2.37-2.29 (m, 6H), 2.20 (S, 3H), 1.70-1.56 (m, 19H), 1.32-

ALL-CMSI-C5bMe-2-TG-butyrate 1-37 was synthesized using the procedure provided above for I-36, replacing Int-192 with Int-115. Purification was done by column chromatography using 100-200 mesh silica gel, and pure compound was eluted at 3% Ethyl acetate/DCM to get ALL-CMSI-C5bMe-2-TG-butyrate I-37 (100 mg, 28.56%). $^1$H NMR (400 MHz, Chloroform-d) δ 6.80 (q, J=5.2 Hz, 1H), 5.32 (m, 1H), 4.94 (m, 1H), 4.34 (d, J=11.2 Hz, 2H), 4.18 (dd, J=11.2, 5.6 Hz, 2H), 2.57 (m, 1H), 2.47 (d, J=10.8 Hz, 4H), 2.34-2.27 (m, 6H), 2.15 (S, 3H), 1.71-1.54 (m, 14H), 1.43-1.35 (m, 2H), 1.27-1.17 (m, 8H), 1.12 (S, 3H), 1.06 (t, J=5.6 Hz, 3H), 0.99-0.80 (m, 10H), 0.61 (S, 3H). $^{13}$CNMR (101 MHz, Chloroform d) δ 209.91 (1C), 173.73 (1C), 173.10 (3C), 171.29 (1C), 170.19 (1C), 152.65 (1C), 91.13 (1C), 75.21 (1C), 69.13 (1C), 65.00 (1C), 63.81 (1C), 62.25 (1C), 56.74 (1C), 53.81 (1C), 44.24 (1C), 40.55 (1C), 40.36 (1C), 39.05 (1C), 35.96 (3C), 35.40 (1C), 32.67 (1C), 31.93 (1C), 29.70 (1C), 28.15 (1C), 27.13 (1C), 25.93 (1C), 24.36 (1C), 22.77 (1C), 20.77 (1C), 19.63 (2C), 14.13 (4C), 11.29 (2C). ELSD: 4.07 min, 100% purity; LCMS (202 nm): 4.919 min, 100% purity; MASS (ESI, +ve) m/z: 766.38 (MH$^+$+18).

Synthesis of ALL-CMSI-C5bMe-2-TG-acetate I-38

ALL-CMSI-C5bMe-2-TG-acetate I-38 was synthesized using the procedure provided above for I-36, replacing Int-192 with Int-284. Purification was done by column chromatography using 100-200 mesh silica gel, and pure compound was eluted at 10-11% ethyl acetate/hexane to get ALL-CMSI-C5bMe-2-TG-acetate I-38 (100 mg, 30.87%). $^1$H NMR (400 MHz, Chloroform-d) δ 6.80 (q, J=5.2 Hz, 1H), 5.32 (m, 1H), 4.93 (m, 1H), 4.33 (d, J=12 Hz, 2H), 4.18 (d, J=5.6 Hz, 2H), 3.51 (m, 1H), 2.52 (d, J=8 Hz, 4H), 2.31 (m, 2H), 2.18-2.00 (S, 8H), 1.88 (d, J=13.6 Hz, 1H), 1.68-1.54 (m, 6H), 1.40 (d, J=8 Hz, 3H), 1.27-1.18 (S, 10H), 1.06-1.05 (m, 3H), 0.99-0.81 (m, 8H), 0.62 (S, 3H). $^{13}$C NMR (101 MHz, Chloroform-d) δ 209.67 (1C), 171.32 (1C), 170.46 (2C), 170.20 (1C), 152.66 (1C), 91.15 (1C), 75.22 (1C), 69.00 (1C), 63.81 (1C), 62.29 (3C), 56.74 (1C), 53.84 (1C), 44.23 (1C), 40.58 (1C), 40.51 (1C), 40.39 (1C), 39.05 (1C), 35.73 (1C), 35.44 (1C), 32.66 (1C), 31.73 (1C), 28.15 (1C), 27.17 (1C), 25.89 (1C), 24.36 (1C), 22.79 (1C), 20.77 (2C), 20.67 (1C), 19.62 (2C), 19.44 (1C), 13.46 (1C), 11.29 (1C). ELSD: 3.70 min, 100% purity; LCMS (202 nm): 4.787 min, 100% purity; MASS (ESI, +ve) m/z: 710.32 (MH+18).

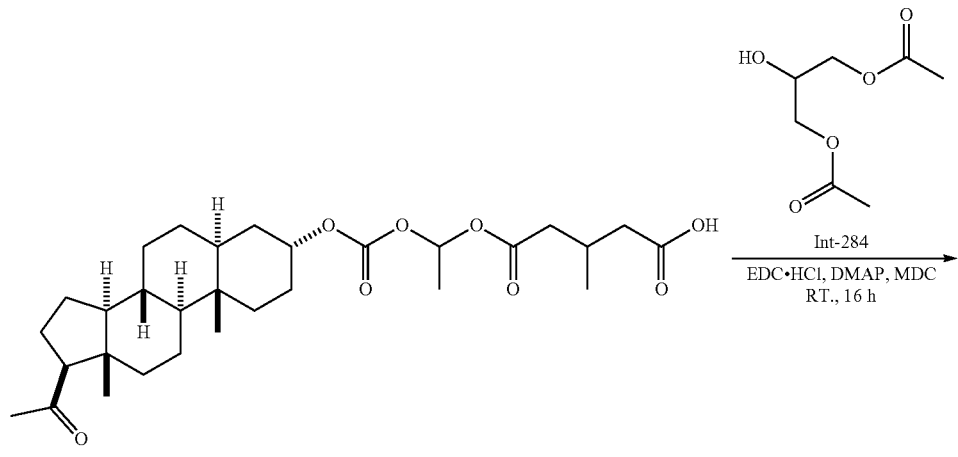

ALL-CMSI-C5bMe-acid

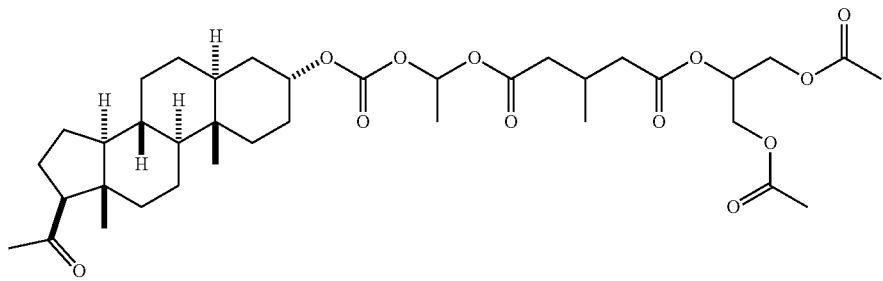

I-38

Synthesis of ALL-CASI-C8b'Me-2-TG-oleate I-49

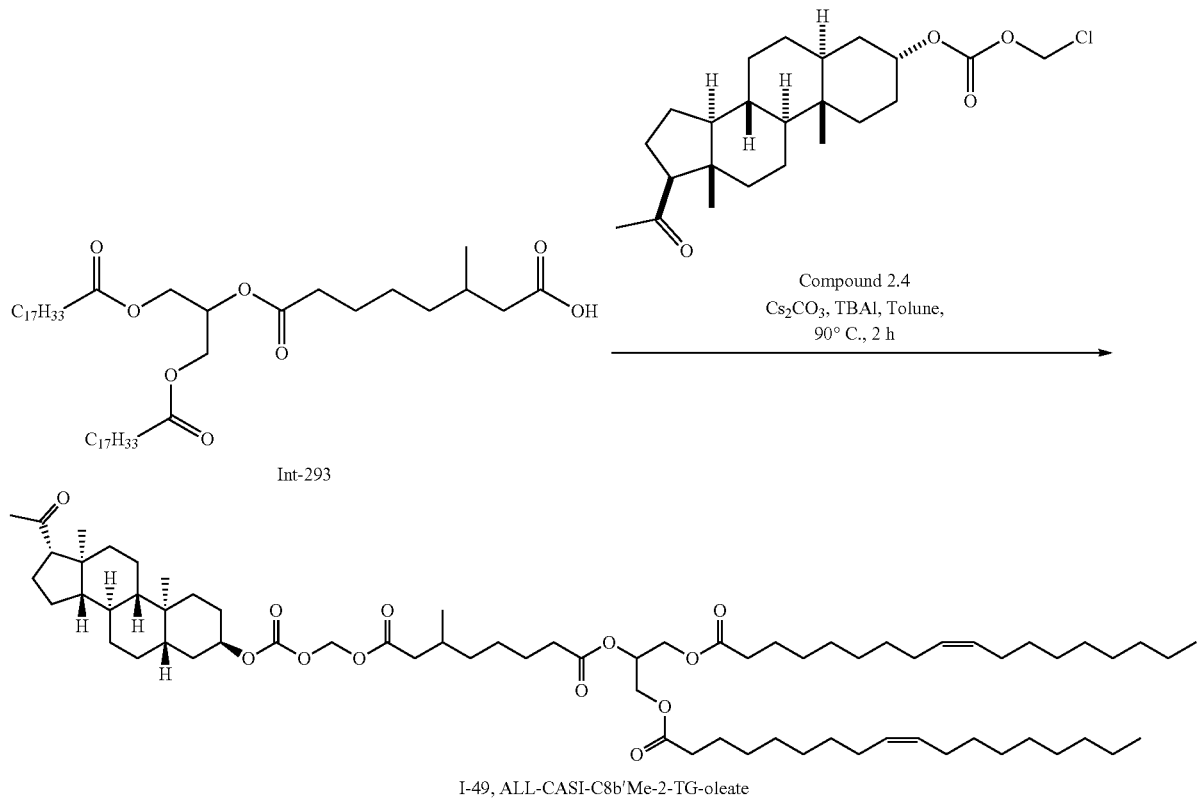

Int-293

Compound 2.4
Cs$_2$CO$_3$, TBAI, Tolune,
90° C., 2 h

I-49, ALL-CASI-C8b'Me-2-TG-oleate

To a solution of Int-293 (0.240 g, 0.303 mmol) in toluene (100 ml) was added Cs$_2$CO$_3$ (0.197 g, 0.607 mmol) and stirred it at room temperature for 15 min then Compound 2.4 (0.124 g, 0.303 mmol) (pre dissolved in 2 ml Toluene) and TBAI (0.056 g, 0.151 mmol) was added at room temperature. Reaction mixture was stirred at 90° C. for 2 h. The reaction was monitored by TLC. After completion of reaction, reaction mixture was diluted with water (50 ml) and extracted with ethyl acetate (2×50 ml), combined organic layer dried over sodium sulphate and distilled under vacuum to get crude compound, which was purified by column chromatography using silica gel (100-200 mesh). Pure compound was eluted at 3-5% ethyl acetate and hexane as a mobile phase then pure fraction was conc. in the rota vapour to get pure compound as ALL-CASI-C8b'Me-2-TG-oleate I-49 (100 mg, 28.3%) as viscous oil: 1H NMR (400 MHz, Chloroform-d) δ 5.78 (s, 1H), 5.41-5.25 (m, 1H), 4.97 (m, 1H), 4.32 (dd, J=11.9, 4.4 Hz, 2H), 4.16 (dd, J=11.9, 5.9 Hz, 2H), 2.57-2.29 (m, 8H), 2.26-2.13 (m, 6H), 2.13 (s, 3H), 2.03-1.85 (m, 10H), 1.76-1.51 (m, 10H), 1.47-1.15 (m, 61H), 0.99-0.81 (m, 12H), 0.62 (s, 3H); 13C NMR (101 MHz, Chloroform-d) δ 209.68 (1C), 173.25 (2C), 172.63 (1C), 153.49 (1C), 130.01 (2C), 129.70 (2C), 81.62 (1C), 75.51 (1C), 68.97 (1C), 63.78 (1C), 62.05 (2C), 56.70 (1C), 53.84 (1C), 44.23 (1C), 41.26 (1C), 39.61 (1C), 39.03 (1C), 36.19 (1C), 35.73 (1C), 35.41 (1C), 34.02 (2C), 32.67 (1C), 32.55 (1C), 31.91 (1C), 31.73 (1C), 31.54 (1C), 29.94-29.08 (21C), 28.15 (1C), 27.22 (2C), 27.17 (2C), 26.33 (1C), 25.95 (1C), 24.84 (2C), 24.36 (1C), 22.77 (1C), 22.69 (2C), 20.77 (1C), 19.48 (1C), 14.12 (2C), 13.46 (1C), 11.31 (1C); ELSD: 6.57 min, 98.03% purity; MASS (ESI, +ve) m/z: 1184.87 (MH+18).

Synthesis of ALL-CASI-C5bMe-2-TG-octanoate
I-47

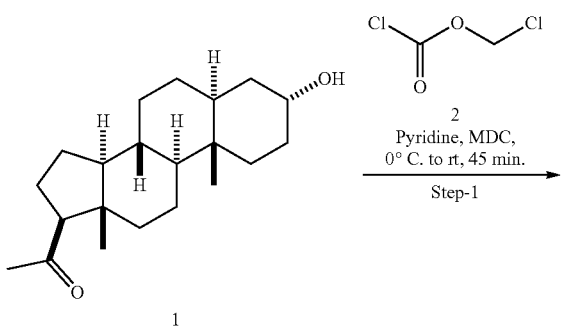

Pyridine, MDC,
0° C. to rt, 45 min.
Step-1

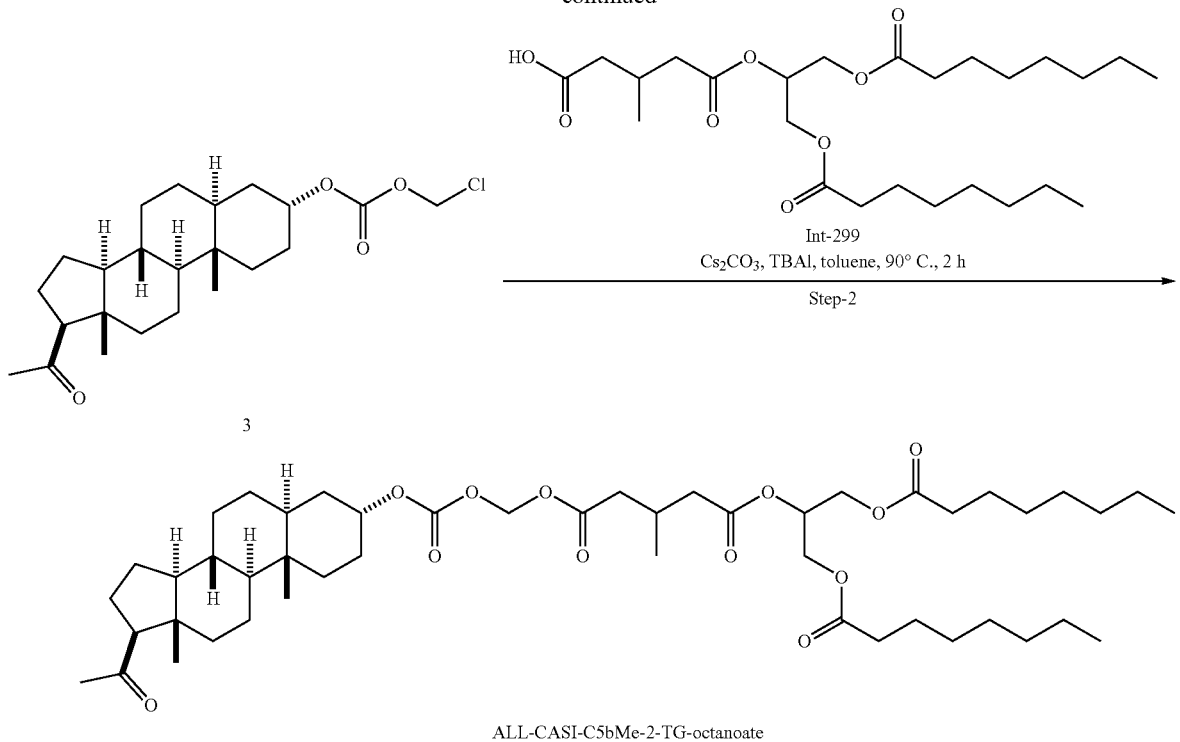

Int-299
Cs₂CO₃, TBAI, toluene, 90° C., 2 h
Step-2

ALL-CASI-C5bMe-2-TG-octanoate

ALL-CASI-C5bMe-2-TG-octanoate I-47 was synthesized using the procedure provided above for I-29, replacing C8-acid-TG-oleate with Int-299. Purification by flash column chromatography using silica gel (230-400 mesh) with 8% ethyl acetate in hexane as the mobile phase produced ALL-CASI-C5bMe-2-TG-octanoate I-47 (108 g, 53.3%) as viscous oil: 1H NMR (400 MHz, Chloroform-d) δ 5.81 (s, 2H), 5.29 (m, 1H), 4.99 (s, 1H), 4.33-4.36 (ddd, J=11.9, 4.2, 1.9 Hz, 2H), 4.15-4.20 (dd, J=11.9, 6.0 Hz, 2H), 2.59-2.44 (m, 4H), 2.36 (m, 6H), 2.15 (s, 3H), 2.02-2.04 (m, 1H), 1.87-1.91 (m, 1H), 1.53-1.72 (m, 17H), 1.399-1.47 (m, 3H), 1.14-1.38 (m, 21H), 1.07-1.09 (d, J=6.0 Hz, 3H), 1.05-0.80 (m, 8H), 0.64 (s, 3H); 13C NMR (101 MHz, Chloroform-d) δ 209.64 (1C), 173.23 (1C), 171.21 (1C), 170.74 (1C), 153.45 (1C), 130.03 (1C), 129.72 (1C), 81.74 (1C), 75.60 (1C), 69.24 (1C), 63.81 (1C), 62.07 (1C), 56.74 (1C), 53.88 (1C), 44.23 (1C), 40.51 (1C), 40.18 (1C), 39.66 (1C), 39.06 (1C), 35.76 (1C), 35.45 (1C), 34.01 (1C), 32.70 (1C), 32.59 (1C), 31.92 (1C), 31.75 (1C), 31.53 (1C), 29.79 (1C), 29.73 (1C), 29.54 (1C), 29.33 (1C), 29.19 (1C), 29.14 (1C), 29.11 (1C), 28.17 (1C), 27.24 (1C), 27.20 (1C), 27.11 (1C), 25.98 (1C), 24.85 (1C), 24.38 (1C), 22.82 (1C), 22.69 (1C), 20.80 (1C), 19.56 (1C), 14.12 (1C), 13.47 (1C), 11.32 (1C); ELSD: 5.78 min, 99.04% purity; qNMR: 97.37% purity; MASS (ESI, +ve) m/z: 865.89 (MH+18).

Synthesis of ALL-CASI-C5-2-TG-oleate I-50

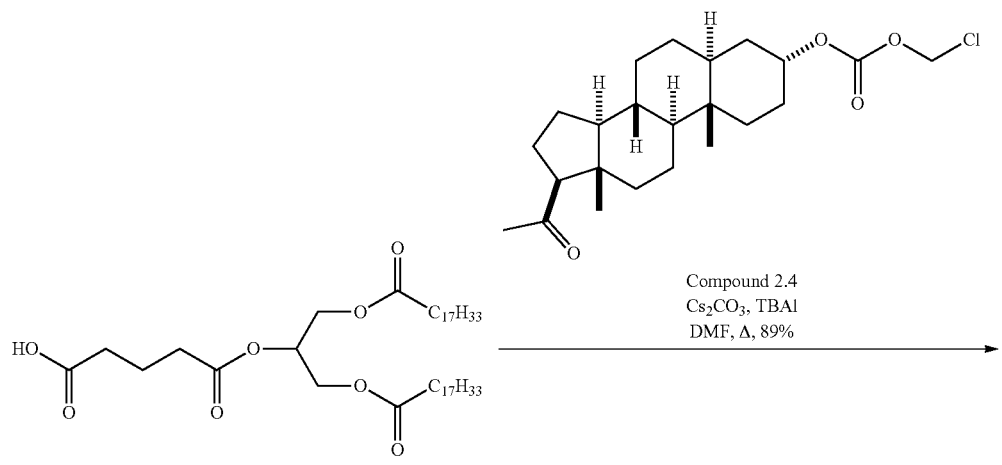

Compound 2.4
Cs₂CO₃, TBAI
DMF, Δ, 89%

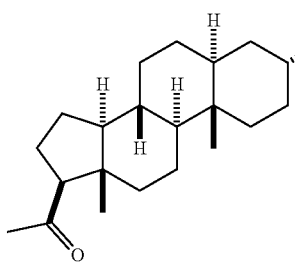

I-50, ALL-CASI-C5-2-TG-oleate

ALL-CASI-C5-2-TG-oleate I-50 was synthesized using the procedure provided above for I-29, replacing C8-acid-TG-oleate with Int-300. Silica gel chromatography (8% to 10% ethyl acetate/hexanes) gave ALL-CASI prodrug I-50 (44.5 mg, 89%) as a colourless oil: $^1$H NMR (401 MHz, CDCl$_3$) δ 5.78-5.73 (m, 2H), 5.38-5.21 (m, 5H), 4.94 (m, 1H), 4.30 (dd, J=11.9, 4.3 Hz, 2H), 4.12 (dd, J=11.9, 5.9 Hz, 2H), 2.52 (t, J=8.9 Hz, 1H), 2.46 (t, J=7.4 Hz, 2H), 2.41 (t, J=7.3 Hz, 2H), 2.30 (t, J=7.6 Hz, 4H), 2.14 (m, 1H), 2.10 (s, 3H), 2.05-1.91 (m, 11H), 1.84 (m, 1H), 1.73-1.08 (m, 61H), 0.87 (t, J=6.9 Hz, 6H), 0.99-0.76 (m, 2H), 0.78 (s, 3H), 0.59 (s, 3H); $^{13}$C NMR (101 MHz, CDCl$_3$) δ 209.8 (C), 173.4 (2C; C), 172.0 (C), 171.5 (C), 153.6 (C), 130.2 (2C; CH), 129.8 (2C; CH), 81.9 (CH$_2$), 75.7 (CH), 69.4 (CH), 63.9 (CH), 62.1 (2C; CH$_2$), 56.8 (CH), 54.0 (CH), 44.4 (C), 39.8 (CH), 39.2 (CH$_2$), 35.9 (C), 35.5 (CH), 34.1 (2C; CH$_2$), 33.1 (CH$_2$), 32.9 (CH$_2$), 32.8 (CH$_2$), 32.7 (CH$_2$), 32.0 (2C; CH$_2$), 31.9 (CH$_2$), 31.7 (CH$_3$), 29.9 (2C; CH$_2$), 29.8 (2C; CH$_2$), 29.7 (2C; CH$_2$), 29.5 (4C; CH$_2$), 29.30 (2C; CH$_2$), 29.24 (2C; CH$_2$), 29.21 (2C; CH$_2$), 28.3 (CH$_2$), 27.4 (2C; CH$_2$), 27.3 (2C; CH$_2$), 26.1 (CH$_2$), 25.0 (2C; CH$_2$), 24.5 (CH$_2$), 22.9 (CH$_2$), 22.8 (2C; CH$_2$), 20.9 (CH$_2$), 19.7 (CH$_2$), 14.2 (2C; CH$_3$), 13.6 (CH$_3$), 11.4 (CH$_3$).

Synthesis of ALL-CASI-C6-2-TG-oleate I-51

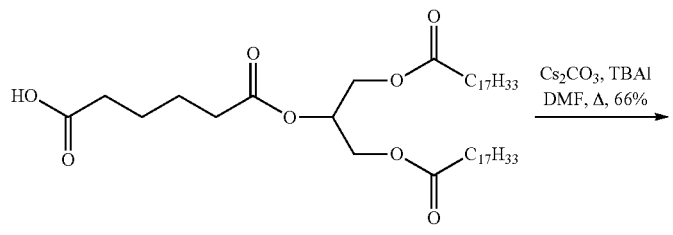

Int-276

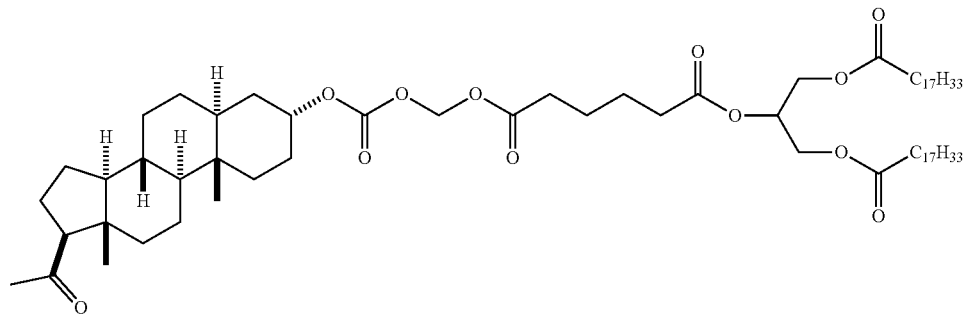

ALL-CASI-C6-2-TG-oleate

Cesium carbonate (Cs$_2$CO$_3$, 39.1 mg, 120 μmol) and tetra-n-butylammonium iodide (TBAI, 7.4 mg, 20.0 μmol) were added to a solution of acid-TG Int-276 (30.0 mg, 40.0 μmol) and chloromethyl carbonate 2.4 (16.5 mg, 40.0 μmol) in DMF (2 mL) and the mixture heated at 70° C. for 2.5 hours. The reaction was cooled to rt, diluted with ethyl acetate (30 mL) and the organic phase washed with water and brine (30 mL each), dried (MgSO$_4$) and concentrated under reduced pressure to give the crude product. Silica gel chromatography (4% ethyl acetate/toluene) gave ALL-CASI prodrug I-51 (29.5 mg, 66%) as a colourless oil: $^1$H NMR (401 MHz, CDCl$_3$) δ 5.78-5.72 (m, 2H), 5.40-5.20 (m, 5H), 4.95 (m, 1H), 4.30 (dd, J=11.9, 4.3 Hz, 2H), 4.13 (dd, J=11.9, 5.9 Hz, 2H), 2.52 (t, J=8.9 Hz, 1H), 2.40 (t, J=7.0 Hz, 2H), 2.34 (t, J=7.0 Hz, 2H), 2.30 (t, J=7.6 Hz, 4H), 2.14 (m, 1H), 2.10 (s, 3H), 2.07-1.90 (m, 9H), 1.85 (m, 1H), 1.73-1.06 (m, 65H), 0.99-0.75 (m, 2H), 0.87 (t, J=6.8 Hz, 6H), 0.79 (s, 3H), 0.59 (s, 3H); $^{13}$C NMR (101 MHz, CDCl$_3$) δ 209.8 (C), 173.4 (2C; C), 172.4 (C), 171.9 (C), 153.6 (C), 130.2 (2C; CH), 129.9 (2C; CH), 81.9 (CH$_2$), 75.7 (CH), 69.3 (CH), 63.9 (CH), 62.2 (2C; CH$_2$), 56.9 (CH), 54.0 (CH), 44.4 (C), 39.8 (CH), 39.2 (CH$_2$), 35.9 (C), 3565 (CH), 34.1 (2C; CH$_2$), 33.8 (CH$_2$), 33.6 (CH$_2$), 32.8 (CH$_2$), 32.7 (CH$_2$), 32.0 (2C; CH$_2$), 31.9 (CH$_2$), 31.7 (CH$_3$), 29.9 (2C; CH$_2$), 29.8 (2C; CH$_2$), 29.7 (2C; CH$_2$), 29.5 (4C; CH$_2$), 29.31 (2C; CH$_2$), 29.25 (2C; CH$_2$), 29.22 (2C; CH$_2$), 28.3 (CH$_2$), 27.4 (2C; CH$_2$), 27.3 (2C; CH$_2$), 26.1 (CH$_2$), 25.0 (2C; CH$_2$), 24.5 (CH$_2$), 24.2 (CH$_2$), 23.9 (CH$_2$), 22.9 (CH$_2$), 22.8 (2C; CH$_2$), 20.9 (CH$_2$), 14.3 (2C; CH$_3$), 13.6 (CH$_3$), 11.4 (CH$_3$).

Synthesis of ALL-CASI-C8bMe-2-TG-oleate I-52

Cesium carbonate (Cs$_2$CO$_3$, 39.5 mg, 121 μmol) and tetra-n-butylammonium iodide (TBAI, 7.5 mg, 20.2 μmol) were added to a solution of acid-TG Int-178 (32.0 mg, 40.4 μmol) and chloromethyl carbonate 2.4 (16.6 mg, 40.4 μmol) in DMF (2 mL) and the mixture heated at 70° C. for two hours. The reaction was cooled to rt, diluted with ethyl acetate (30 mL) and the organic phase washed with water and brine (30 mL each), dried (MgSO$_4$) and concentrated under reduced pressure to give the crude product. Silica gel chromatography (8% to 90% ethyl acetate/hexanes) gave ALL-CASI prodrug I-52 (29.0 mg, 62%) as a colourless oil: $^1$H NMR (401 MHz, CDCl$_3$) δ 5.79-5.72 (m, 2H), 5.40-5.23 (m, 5H), 4.95 (m, 1H), 4.29 (dd, J=11.9, 4.3 Hz, 2H), 4.14 (dd, J=11.9, 5.9 Hz, 2H), 2.53 (t, J=8.9 Hz, 1H), 2.38 (t, J=7.5 Hz, 2H), 2.35-2.27 (m, 5H), 2.19-2.08 (m, 2H), 2.11 (s, 3H), 2.07-1.89 (m, 10H), 1.85 (m, 1H), 1.73-1.09 (m, 67H), 0.93 (d, J=6.6 Hz, 3H), 1.00-0.76 (m, 2H), 0.88 (t, J=6.9 Hz, 6H), 0.79 (s, 3H), 0.60 (s, 3H); $^{13}$C NMR (101 MHz, CDCl$_3$) δ 209.8 (C), 173.4 (2C; C), 172.2 (2C; C), 153.6 (C), 130.2 (2C; CH), 129.8 (2C; CH), 81.9 (CH$_2$), 75.7 (CH), 69.0 (CH), 63.9 (CH), 62.3 (2C; CH$_2$), 56.8 (CH), 54.0 (CH), 44.4 (C), 41.7 (CH$_2$), 39.8 (CH), 39.2 (CH$_2$), 36.3 (CH$_2$), 35.9 (C), 35.5 (CH$_2$), 34.2 (2C; CH$_2$), 34.0 (CH$_2$), 32.8 (CH$_2$), 32.7 (CH$_2$), 32.0 (2C; CH$_2$), 31.9 (CH$_2$), 31.7 (CH$_3$), 30.3 (CH), 29.9 (2C; CH$_2$), 29.8 (2C; CH$_2$), 29.7 (2C; CH$_2$), 29.5 (4C; CH$_2$), 29.3 (2C; CH$_2$), 29.24 (2C; CH$_2$), 29.22 (2C; CH$_2$), 28.3 (CH$_2$), 27.4 (2C; CH$_2$), 27.3 (2C; CH$_2$), 26.4 (CH$_2$), 26.1 (CH$_2$), 25.0 (2C; CH$_2$), 24.7 (CH$_2$), 24.5 (CH$_2$), 22.9 (CH$_2$), 22.8 (2C; CH$_2$), 20.9 (CH$_3$), 19.6 (CH$_3$), 14.3 (2C; CH$_3$), 13.6 (CH$_3$), 11.4 (CH$_3$); Note: The presence of only two carbonyl signals in the 170 to 175 ppm range of the $^{13}$C NMR spectrum suggests that the peak at 172.2 ppm could be attributable to both of the carbonyl carbon atoms of the C8bMe linker.

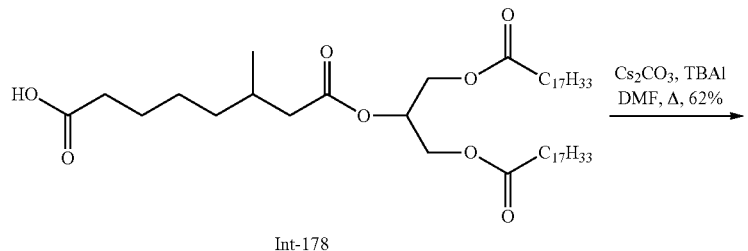

Int-178

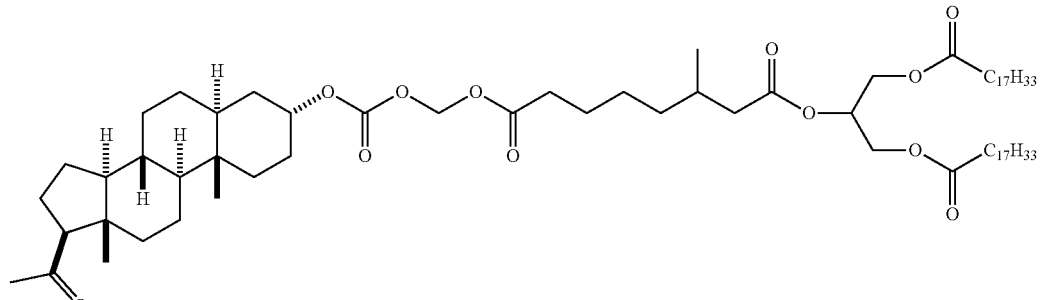

ALL-CASI-C8bMe-2-TG-oleate

Synthesis of ALL-CDMPHB-C8b'bMe-2-TG-oleate 1-16

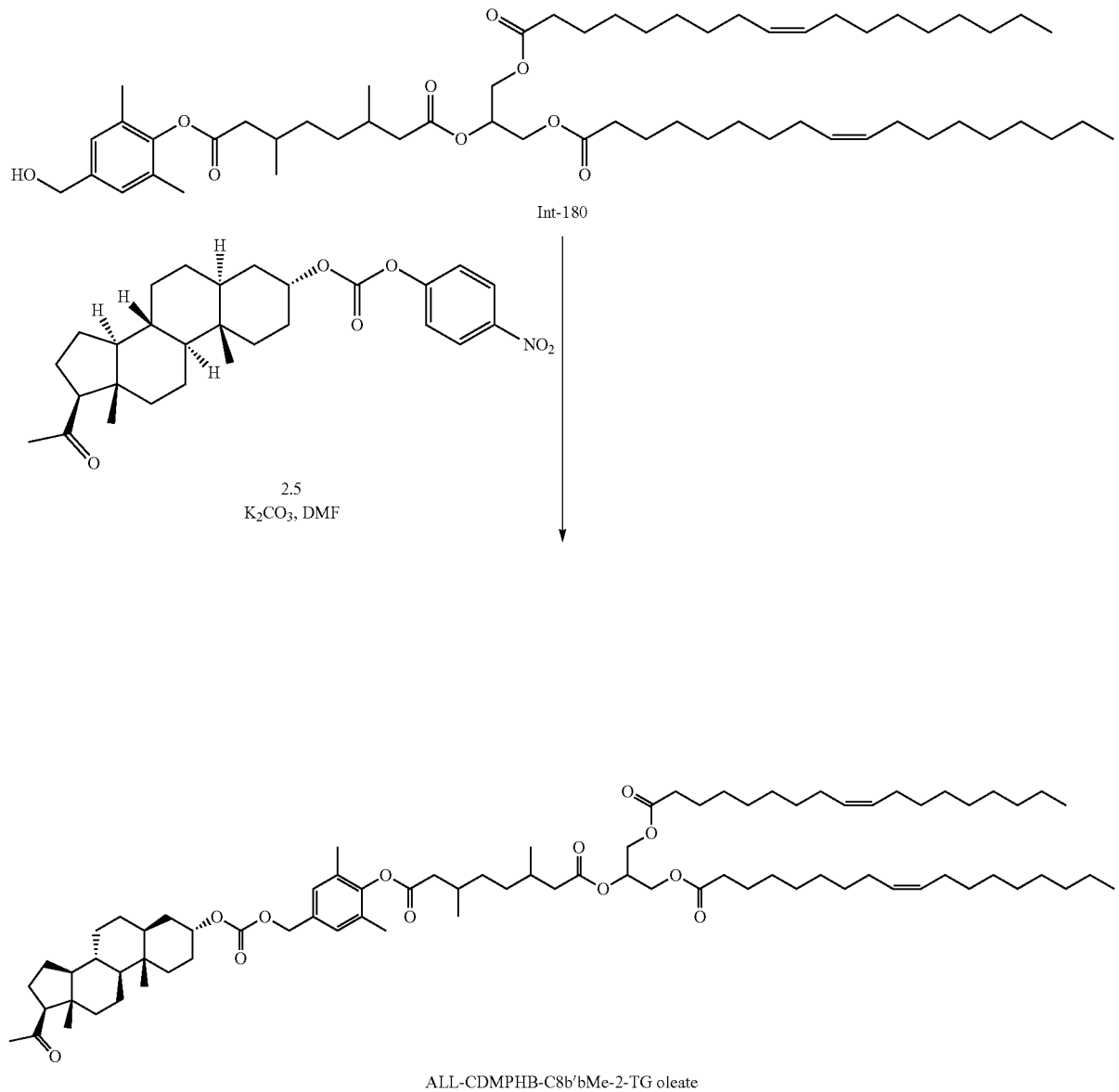

To a stirring solution of compound 2.5 (0.9 g, 0.186 mmol) in DMF (10 ml) was added $K_2CO_3$ (0.77 g, 0.558 mmol) and stirred reaction mixture at 0° for 30 min. Then Int-180 (0.400 g, 0.186 mmol) in 3 ml DMF was added, then reaction mixture was stirred at r.t for 48 h. The progress of reaction was monitored by TLC, After completion of the reaction, it was diluted with water (50 ml) and extracted with ethyl acetate (3×50 ml). The combined organic layer was dried over $Na_2SO_4$ and evaporated under vacuum to get crude material, which was purified by combi flash purification. Pure compound was eluted at 8% ethyl acetate/hexane as a mobile phase; the pure fractions were conc. in the rota vapour to get ALL-CDMPHB-C8b'bMe-2-TG-oleate I-16 (0.09 g, 11%) as viscous liquid: $^1H$ NMR (400 MHz, $CDCl_3$) δ 7.12 (s, 2H), 5.36 (m, 5H), 5.07 (m, 2H), 4.93 (s, 1H), 4.33 (dd, J=12.0, 4.4 Hz, 2H), 4.18 (dd, J=11.6, 5.6 Hz, 2H), 2.64-2.54 (m, 5H), 2.34 (t, J=14.8 Hz, 2H), 2.16 (d, J=15.2 Hz, 10H), 1.88 (d, J=15.2 Hz, 8H), 1.62 (m, 10H), 1.31 (m, 50H), 1.18 (s, 1H), 1.09 (d, J=6.4, 4H), 0.98 (d, J=6.4 Hz, 4H), 0.90-0.807 (m, 14H), 0.61 (s, 3H); $^{13}C$ NMR (101 MHz, $CDCl_3$) δ 173.26 (2C), 172.12 (1C), 170.68 (1C), 153.72 (2C), 148.37 (2C), 132.79 (1C), 130.44 (2C), 130.03 (2C), 129.71 (1C), 128.95 (1C), 74.60 (1C), 68.93 (1C), 63.82 (1C), 62.13 (2C), 56.74 (1C), 53.82 (1C), 44.25 (2C), 41.65 (1C), 41.51 (1C), 41.41 (1C), 41.26 (1C), 39.60 (1C), 39.07 (1C), 35.74 (1C), 35.42 (1C), 34.02 (1C), 33.86 (2C), 33.79 (1C), 32.79 (1C), 32.61 (1C), 31.91 (1C), 31.73 (1C), 31.55 (1C), 30.56 (1C), 30.51 (1C), 30.36 (1C), 30.31 (1C), 30.06 (1C), 29.77-29.12 (15C), 27.23 (1C), 27.18 (1C), 26.04 (1C), 24.84 (2C), 24.37 (1C), 22.77 (2C), 22.69 (1C), 20.77 (1C), 19.90 (1C), 19.70 (1C), 19.61 (1C), 19.43 (1C), 16.51 (1C), 14.13 (2C), 13.47 (1C), 11.31 (1C); ELSD: 17.22 min, 97.95% purity; MASS (ESI, +ve) m/z: 1300.86 (M+18).

Synthesis of IAL-ASI-C8b'bMe-2-TG-oleate I-19

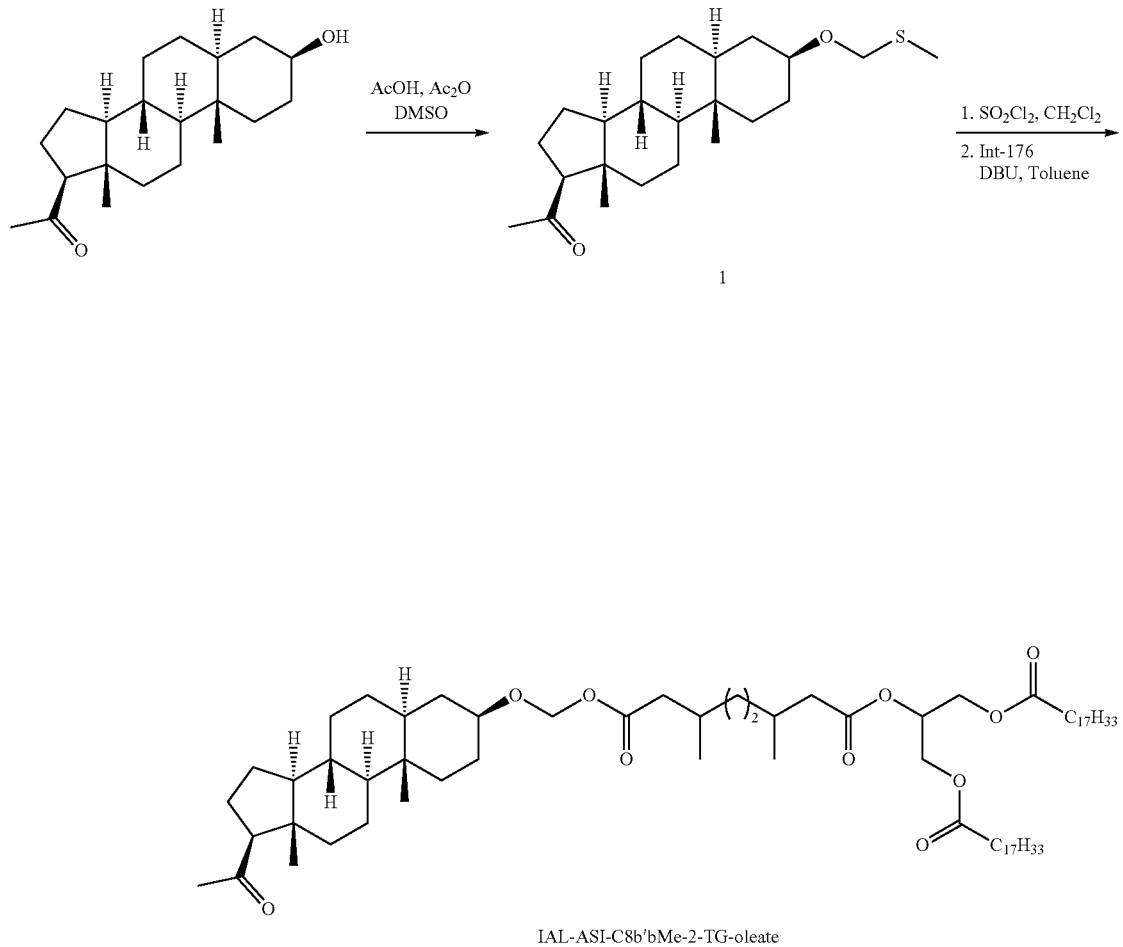

IAL-ASI-C8b'bMe-2-TG-oleate

A mixture of iso-allopregnanolone (310 mg, 0.97 mmol), acetic anhydride (0.92 mL, 9.73 mmol) and acetic acid (0.31 mL, 5.35 mmol) in DMSO (1.38 mL) was stirred at 40° C. for 3 hours and then at room temperature overnight. The reaction mixture was quenched with a saturated aqueous solution of NaHCO$_3$ and extracted with EtOAc. The combined organic layer was washed with brine, dried over magnesium sulfate, filtered and concentrated in vacuo. The residue was purified by normal phase flash column chromatography on silica gel (Biotage Isolera, 25 g, Siliasep cartridge) using n-heptane and EtOAc (gradient: 1:0 to 1:1) to give thioether 1 (232 mg, 63%) as a white solid: $^1$H NMR (400 MHz, CDCl$_3$): δ(ppm)=4.63 (s, 2H), 3.60-3.51 (m, 1H), 2.49 (t, J=9.0 Hz, 1H), 2.17-2.04 (m, 7H), 1.97 (td, J=3.1, 11.7 Hz, 1H), 1.82-1.75 (m, 1H), 1.75-1.53 (m, 6H), 1.45-1.02 (m, 11H), 1.00-0.81 (m, 2H), 0.77 (s, 3H), 0.66 (dt, J=4.3, 11.3 Hz, 1H), 0.57 (s, 3H); $^{13}$C NMR (100 MHz, CDCl$_3$): δ(ppm)=209.6, 75.3, 72.0, 63.9, 56.7, 54.3, 44.9, 44.3, 39.1, 37.0, 35.8, 35.5, 34.5, 32.1, 31.6, 28.8, 28.0, 24.5, 22.9, 21.3, 13.8, 13.5, 12.3.

Sulfuryl chloride (85 µL, 0.85 mmol) was added to a mixture of 1 (230 mg, 0.61 mmol) in CH$_2$Cl$_2$ (5.0 mL) at 0° C. The mixture was stirred at 0° C. for 10 min and then at room temperature for 30 min. The reaction was concentrated under a stream of N$_2$, dissolved in toluene (3×3 mL) and concentrated in vacuo. The residue was diluted with toluene (2.0 mL) and added to a pre-stirred solution of Int-176 (586 mg, 0.73 mmol) and DBU (145 µL, 0.97 mmol) in toluene (3.0 mL). The resulting mixture was stirred at room temperature overnight. Water and ethyl acetate were added. The layers were separated. The aqueous layer was extracted with ethyl acetate. The combined organic layers were washed with brine, dried over magnesium sulfate, filtered and concentrated in vacuo. The residue was purified by normal phase flash column chromatography on silica gel (Biotage Isolera, 40 g, Silicycle Siliasep cartridge) using n-heptane and EtOAc (gradient: 1:0 to 3:2) to give I-19 (455 mg, 66%) as a colourless oil: UPLC3-MS: (XB BEH C4 Long Acidic 20 to 95): R$_t$=7.10 min., 100% (ELS). MS (ESIpos) m/z=1152.8, 1153.8 (M+NH$_4$+H)$^+$; $^1$H NMR (400 MHz, CDCl$_3$): δ(ppm)=5.39-5.23 (m, 7H), 4.28 (dd, J=4.3, 11.9 Hz, 2H), 4.13 (dd, J=6.0, 11.9 Hz, 2H), 3.57-3.47 (m, 1H), 2.50 (t, J=8.9 Hz, 1H), 2.37-2.25 (m, 6H), 2.20-1.79 (m, 18H), 1.75-1.54 (m, 11H), 1.51-1.03 (m, 61H), 1.00-0.85 (m, 17H), 0.79 (s, 3H), 0.66 (dt, J=3.8, 11.4 Hz, 1H), 0.59 (s, 3H); $^{13}$C NMR (100 MHz, CDCl$_3$): δ(ppm)=209.7, 173.4, 172.82, 172.80, 172.3, 172.2, 130.1, 129.8, 87.5, 79.1, 69.0, 64.0, 62.2, 56.8, 54.3, 44.9, 44.4, 42.1, 42.0, 41.8, 41.6, 39.2, 37.0, 35.7, 35.6, 35.2, 34.14, 34.06, 33.9, 32.1, 32.03, 32.01, 31.6, 30.7, 30.51, 30.47, 30.3, 29.9, 29.8, 29.7, 29.4, 29.3, 29.24, 29.22, 29.15, 28.8, 28.7, 27.35, 27.3, 25.0, 24.5, 22.9, 22.8, 21.3, 19.9, 19.75, 19.68, 19.5, 14.2, 13.6, 12.3.

Synthesis of ALL-CDMOPHB-C10b'bMe-2-TG-oleate I-53

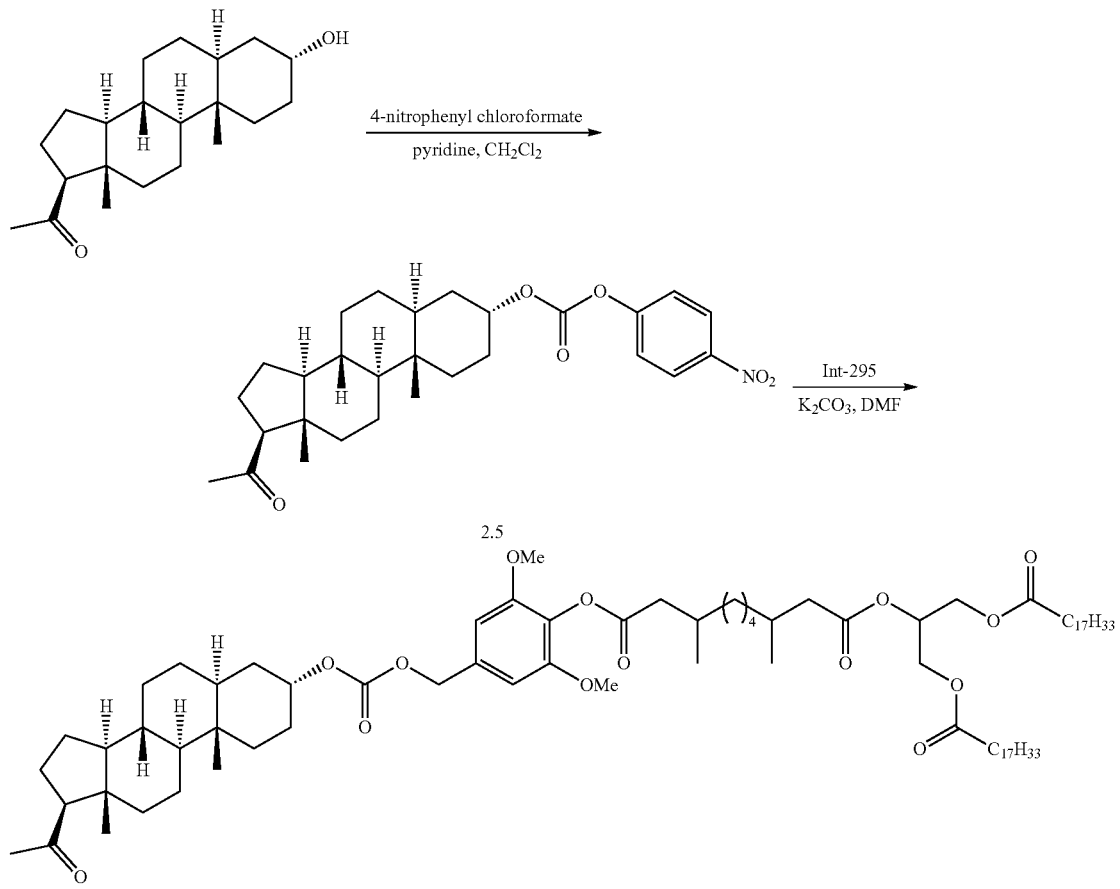

ALL-CDMOPHB-C10b'bMe-2-TG-oleate

4-Nitrophenyl chloroformate (237 mg, 1.18 mmol) was added to a mixture of pyridine (159 µL, 1.95 mmol) and allopregnanolone (250 mg, 0.78 mmol) in $CH_2Cl_2$ (7.0 mL). The resulting mixture was stirred at room temperature for 2 h before being concentrated in vacuo. The residue was purified by normal phase flash column chromatography (Biotage Isolera, 40 g, Silicycle siliasep cartridge) using n-heptane and EtOAc (gradient: 1:0 to 4:1) to give the desired compound (336 mg, 88%) as a white solid: UPLC4_AP-MS: (BEH C8 Long Acidic 2 to 95): $R_t$=3.26 min., 100% (ELS). MS (ESIpos) m/z=506.3 $(M+Na+H)^+$; $^1H$ NMR (400 MHz, $CDCl_3$): δ (ppm)=8.23 (d, J=9.1 Hz, 2H), 7.37 (d, J=9.1 Hz, 2H), 5.00 (s, 1H), 2.49 (t, J=8.8 Hz, 1H), 2.17-2.02 (m, 4H), 1.98 (d, J=13.2 Hz, 1H), 1.90 (d, J=14.8 Hz, 1H), 1.78-1.48 (m, 9H), 1.43-1.09 (m, 9H), 0.94 (qd, J=5.7, 24.6 Hz, 1H), 0.87-0.73 (m, 4H), 0.57 (s, 3H); $^{13}C$ NMR (100 MHz, $CDCl_3$): δ(ppm)=209.6, 155.7, 151.9, 145.2, 125.2, 121.9, 76.6, 63.8, 56.7, 53.9, 44.2, 39.8, 39.0, 35.8, 35.4, 32.7, 32.6, 31.8, 31.5, 28.2, 26.0, 24.4, 22.8, 20.8, 13.5, 11.3.

Potassium carbonate ($K_2CO_3$, 172 mg, 1.24 mmol) was added to a mixture of 1-(1,3-bis(oleoyloxy)propan-2-yl) 10-(4-(hydroxymethyl)-2,6-dimethoxyphenyl) 3,8-dimethyldecanedioate (Int-295, 207 mg, 0.21 mmol) in N,N-dimethylformamide (3.0 mL) at 0° C. The mixture was stirred at 0° C. for 30 min. (3R,5S,8R,9S,10S,13S,14S,17S)-17-acetyl-10,13-dimethylhexadecahydro-1H-cyclopenta[a]phenanthren-3-yl) (4-nitrophenyl) carbonate (100 mg, 0.21 mmol) was added and the mixture was warmed to 70° C. and stirred for 20 h. The reaction mixture was cooled to room temperature and concentrated in vacuo. Water and ethyl acetate were added. The layers were separated. The aqueous layer was extracted with ethyl acetate. The combined organic layers were washed with brine, dried over sodium sulfate, filtered and concentrated in vacuo. The residue was purified twice by normal phase flash column chromatography on silica gel (Biotage Isolera, 25 g, Silicycle Siliasep cartridge) using n-heptane and EtOAc (gradient: 1:0 to 3:2) to give the desired compound (159 mg, 57%) as a colourless gum: UPLC3-MS: (XB BEH C4 Long Acidic 20 to 95): $R_t$=7.06 min., 95% (UV), 100% (ELS). MS (ESIpos) m/z=1360.9, 1361.8 $(M+NH_4+H)^+$; $^1H$ NMR (400 MHz, $CDCl_3$): δ(ppm)=6.63 (s, 2H), 5.37-5.22 (m, 5H), 5.07 (s, 2H), 4.89 (s, 1H), 4.27 (dd, J=4.1, 11.9 Hz, 2H), 4.12 (dd, J=6.0, 11.9 Hz, 2H), 3.79 (s, 6H), 2.57 (dd, J=5.9, 14.6 Hz, 1H), 2.49 (t, J=8.9 Hz, 1H), 2.40-2.26 (m, 6H), 2.17-1.87 (m, 16H), 1.84 (d, J=13.8 Hz, 1H), 1.72-1.06 (m, 74H), 1.03 (d, J=6.6 Hz, 3H), 0.98-0.89 (m, 4H), 0.89-0.76 (m, 12H), 0.57 (s, 3H); $^{13}C$ NMR (100 MHz, $CDCl_3$): δ(ppm)=209.6, 173.3, 172.3, 170.8, 154.7, 152.3, 133.8, 130.0, 129.8, 128.8, 105.2, 74.8, 69.4, 68.9, 63.8, 62.2, 56.8, 56.2, 53.9, 44.3, 41.72, 41.70, 41.5, 41.4, 39.7, 39.1, 36.77, 36.75, 36.7, 35.8, 35.5, 34.1, 32.8, 32.7, 32.0, 31.9, 31.8, 31.6, 30.7, 30.4, 29.82, 29.76, 29.72, 29.68, 29.6, 29.42, 29.37, 29.3, 29.22, 29.16, 29.14, 29.08, 28.2, 27.3, 27.22, 27.18, 27.16, 26.1, 24.9, 24.4, 22.8, 22.7, 20.8, 19.60, 19.57, 19.55, 19.5, 14.2, 13.5, 11.4.

Synthesis of ALL-CDMOPHB-C10bMe-2-TG-oleate I-54

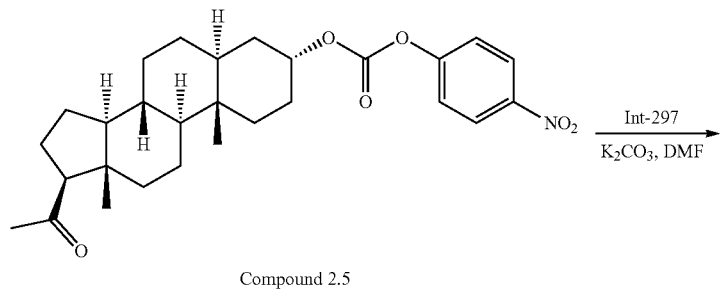

Compound 2.5

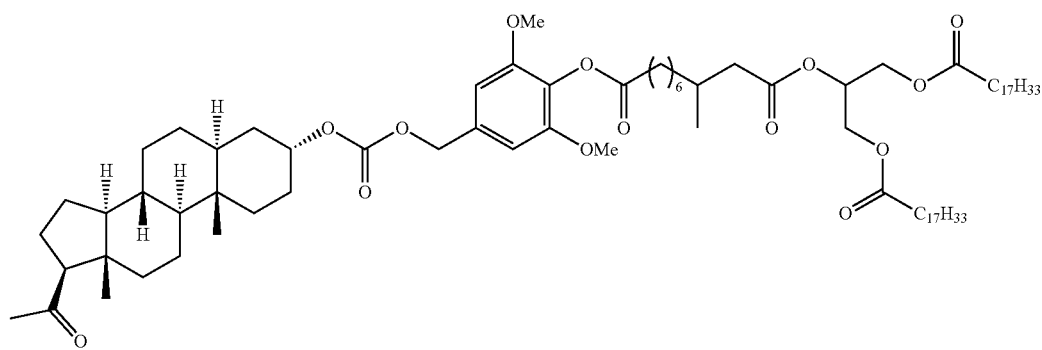

ALL-CDMOPHB-C10bMe-2-TG-oleate
I-54

Potassium carbonate (K$_2$CO$_3$, 172 mg, 1.24 mmol) was added to a mixture of 1-(1,3-bis(oleoyloxy)propan-2-yl) 10-(4-(hydroxymethyl)-2,6-dimethoxyphenyl) 3-methyldecanedioate (Int-297, 204 mg, 0.21 mmol) in N,N-dimethylformamide (3.0 mL) at 0° C. The mixture was stirred at 0° C. for 30 min. (3R,5S,8R,9S,10S,13S,14S,17S)-17-acetyl-10,13-dimethylhexadecahydro-1H-cyclopenta[a]phenanthren-3-yl (4-nitrophenyl) carbonate (100 mg, 0.21 mmol) was added and the mixture was warmed to 70° C. and stirred for 20 h. The reaction mixture was cooled to room temperature and concentrated in vacuo. Water and ethyl acetate were added. The layers were separated. The aqueous layer was extracted with ethyl acetate. The combined organic layers were washed with brine, dried over sodium sulfate, filtered and concentrated in vacuo. The residue was purified twice by normal phase flash column chromatography on silica gel (Biotage Isolera, 25 g, Silicycle Siliasep cartridge) using n-heptane and EtOAc (gradient: 1:0 to 3:2) to give ALL-CDMOPHB-C10bMe-2-TG-oleate I-54 (166 mg, 60%) as a colourless gum: UPLC3-MS: (XB BEH C4 Long Acidic 20 to 95): R$_t$=7.03 min., 98% (UV), 100% (ELS). MS (ESIpos) m/z=1346.9, 1347.8 (M+NH$_4$+H)$^+$; $^1$H NMR (400 MHz, CDCl$_3$): δ(ppm)=6.63 (s, 2H), 5.37-5.22 (m, 5H), 5.07 (s, 2H), 4.90 (s, 1H), 4.27 (dd, J=4.2, 11.8 Hz, 2H), 4.12 (dd, J=6.0, 11.9 Hz, 2H), 3.80 (s, 6H), 2.58 (t, J=7.4 Hz, 2H), 2.49 (t, J=8.9 Hz, 1H), 2.35-2.26 (m, 5H), 2.18-2.06 (m, 5H), 2.03-1.87 (m, 10H), 1.83 (d, J=14.0 Hz, 1H), 1.79-1.05 (m, 76H), 0.92 (d, J=6.6 Hz, 4H), 0.86 (t, J=6.8 Hz, 6H), 0.83-0.76 (m, 4H), 0.58 (s, 3H); $^{13}$C NMR (100 MHz, CDCl$_3$): δ(ppm)=209.6, 173.3, 172.3, 171.4, 154.7, 152.3, 133.7, 130.1, 129.8, 128.9, 105.3, 74.8, 69.4, 68.9, 63.9, 62.2, 56.8, 56.2, 53.9, 44.3, 41.7, 39.7, 39.1, 36.7, 35.8, 35.5, 34.1, 33.9, 32.9, 32.7, 32.0, 31.8, 31.6, 30.4, 29.83, 29.76, 29.72, 29.68, 29.6, 29.54, 29.50, 29.43, 29.38, 29.3, 29.23, 29.17, 29.15, 29.1, 28.2, 27.3, 27.2, 26.9, 26.1, 25.1, 24.9, 24.4, 22.83, 22.75, 20.8, 19.6, 14.2, 13.5, 11.4.

Synthesis of IAL-ASI-C5bMe-2-TG-oleate I-21

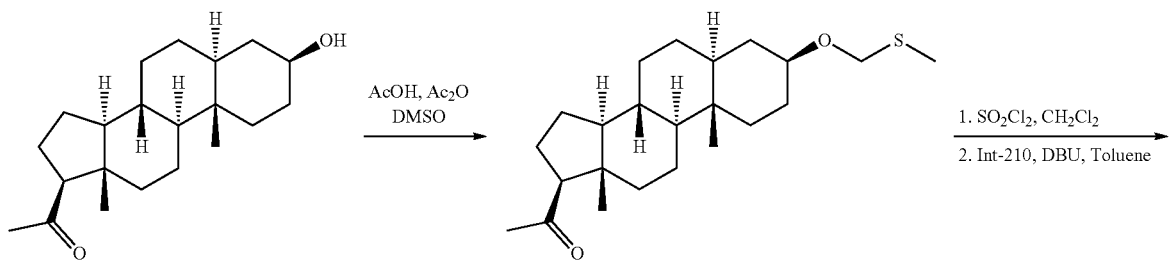

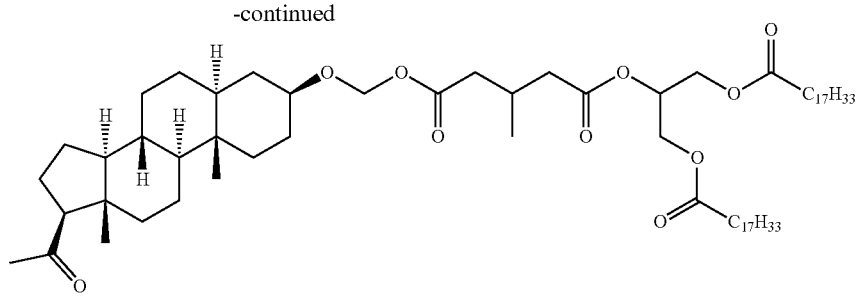

IAL-ASI-C5bMe-2-TG-oleate

A mixture of iso-allopregnanolone (110 mg, 0.35 mmol), acetic anhydride (0.33 mL, 3.45 mmol) and acetic acid (0.11 mL, 1.90 mmol) in DMSO (0.49 mL) was stirred at 40° C. for 3 hours and then at room temperature overnight. The reaction mixture was quenched with a saturated aqueous solution of NaHCO$_3$ and extracted with EtOAc. The combined organic layer was washed with brine, dried over magnesium sulfate, filtered and concentrated in vacuo. The residue was purified by normal phase flash column chromatography on silica gel (Biotage Isolera, 25 g, Siliasep cartridge) using n-heptane and EtOAc (gradient: 1:0 to 1:1) to give the desired thioether (128 mg, 49%) as a white solid: $^1$H NMR (400 MHz, CDCl$_3$): δ(ppm)=4.64 (s, 2H), 3.62-3.52 (m, 1H), 2.50 (t, J=9.0 Hz, 1H), 2.18-2.12 (m, 4H), 2.09 (s, 3H), 2.01-1.95 (m, 1H), 1.86-1.77 (m, 1H), 1.76-1.54 (m, 6H), 1.46-1.03 (m, 11H), 1.02-0.86 (m, 2H), 0.79 (s, 3H), 0.67 (dt, J=4.2, 11.3 Hz, 1H), 0.58 (s, 3H); $^{13}$C NMR (100 MHz, CDCl$_3$): δ(ppm)=209.7, 75.3, 72.0, 64.0, 56.8, 54.4, 44.9, 44.4, 39.2, 37.1, 35.9, 35.6, 34.6, 32.1, 31.6, 28.8, 28.1, 24.5, 22.9, 21.3, 13.9, 13.6, 12.4.

Sulfuryl chloride (47 µL, 0.47 mmol) was added to a mixture of 1-((3S,5S,8R,9S,10S,13S,14S,17S)-10,13-dimethyl-3-((methylthio)methoxy)hexadecahydro-1H-cyclopenta[a]phenanthren-17-yl)ethan-1-one (128 mg, 0.34 mmol) in CH$_2$Cl$_2$ (2.0 mL) at 0° C. The mixture was stirred at room temperature for 40 min under a nitrogen atmosphere. The reaction was concentrated in vacuo, dissolved in toluene (3×3 mL) and concentrated in vacuo. The residue was diluted with toluene (1.0 mL) and added to a pre-stirred solution of Int-210 (304 mg, 0.41 mmol) and DBU (81 µL, 0.54 mmol) in toluene (1.5 mL). The resulting mixture was stirred at room temperature overnight. Water and ethyl acetate were added. The layers were separated. The aqueous layer was extracted with ethyl acetate. The combined organic layers were washed with brine, dried over magnesium sulfate, filtered and concentrated in vacuo. The residue was purified by normal phase flash column chromatography on silica gel (Biotage Isolera, 12 g, Silicycle Siliasep cartridge) using n-heptane and EtOAc (gradient: 1:0 to 1:1). Fractions containing the desired product were concentrated in vacuo. The residue was purified a further three times by normal phase flash column chromatography on silica gel (Biotage Isolera, 25 g, Silicycle Siliasep cartridge) using n-heptane and EtOAc (gradient: 1:0 to 7:3) to give IAL-ASI-C$_5$bMe-2-TG-oleate I-21 (65 mg, 16%) as a colourless oil: UPLC3-MS: (XB BEH C4 Long Acidic 20 to 95): R$_t$=7.50 min., 99.9% (ELS). MS (ESIpos) m/z=1096.9, 1097.8 (M+NH$_4$+H)$^+$; 1H NMR (400 MHz, CDCl$_3$): δ(ppm)= 5.39-5.22 (m, 7H), 4.29 (ddd, J=2.5, 4.2, 11.9 Hz, 2H), 4.15-4.07 (m, 3H), 3.56-3.46 (m, 1H), 2.53-2.37 (m, 4H), 2.32-2.20 (m, 6H), 2.18-2.09 (m, 4H), 2.05-1.93 (m, 10H), 1.83 (d, J=12.7 Hz, 1H), 1.76-1.53 (m, 11H), 1.50-0.82 (m, 66H), 0.78 (s, 3H), 0.66 (dt, J=3.7, 11.3 Hz, 1H), 0.58 (s, 3H); $^{13}$C NMR (100 MHz, CDCl$_3$): δ(ppm)=209.7, 173.3, 171.9, 171.4, 171.2, 130.1, 129.8, 87.6, 79.2, 69.2, 63.9, 62.2, 60.5, 56.8, 54.3, 44.9, 44.3, 40.9, 40.7, 39.2, 37.0, 35.7, 35.6, 35.1, 34.1, 32.1, 32.0, 31.6, 29.9, 29.82, 29.77, 29.7, 29.6, 29.5, 29.4, 29.3, 29.23, 29.20, 28.7, 28.6, 27.33, 27.28, 24.9, 24.5, 22.9, 22.8, 21.3, 21.1, 19.7, 14.3, 14.2, 13.6, 12.3.

Synthesis of ALL-ASI-C8b'Me-2-TG-oleate I-48

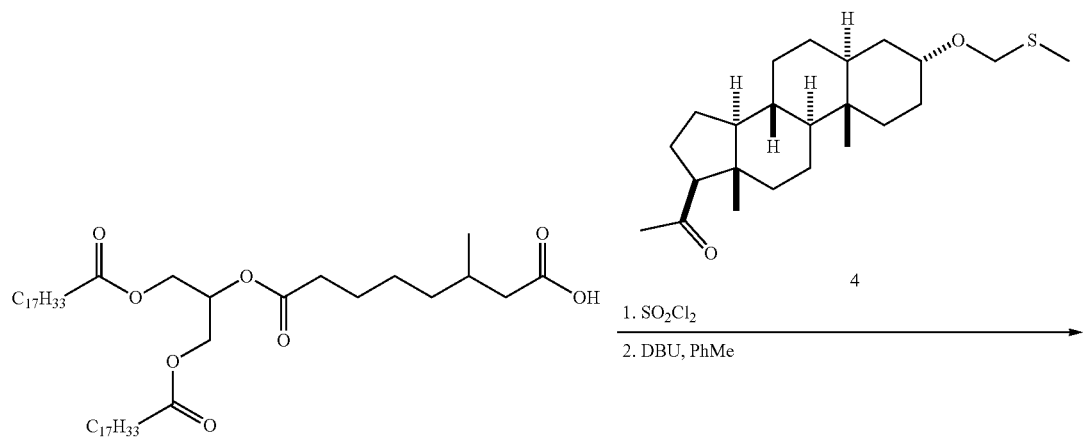

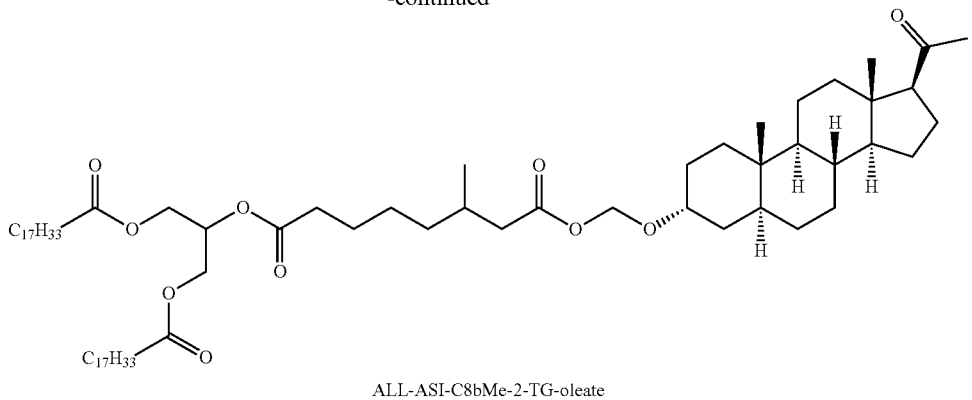

ALL-ASI-C8b'Me-2-TG-oleate

ALL-ASI-C8b'Me-2-TG-oleate I-48 was synthesized using the procedure provided above for I-9, replacing Int-210 with compound 1. Purification by flash chromatography, using 3-4% EtOAc/hexane as the eluent, afforded ALL-ASI-C8b'Me-2-TG-oleate I-48 (90 mg) as viscous liquid: $^1$H NMR (400 MHz, Chloroform-d) δ 5.34-5.39 (m, 4H), 5.33 (s, 2H), 5.26-5.28 (m, 1H), 4.29-4.33 (dd, 2H), 4.14-4.18 (m, 2H), 3.87 (s, 1H), 2.52-5.57 (t, 1H), 2.31-2.36 (m, 6H), 2.11-2.20 (m, 4H), 2.00-2.03 (m, 8H), 1.59-1.79 (m, 10H), 1.41-1.52 (m, 4H), 1.28-1.32 (m, 54H), 1.15-1.22 (m, 6H), 0.97-0.99 (d, 3H), 0.88-0.91 (t, 6H), 0.79 (s, 3H), 0.61 (s, 3H); $^{13}$C NMR (101 MHz, Chloroform-d) δ 209.75 (1C), 173.26 (2C), 172.63 (1C), 130.03 (2C), 129.71 (2C), 87.55 (1C), 74.55 (1C), 68.97 (1C), 63.83 (1C), 62.06 (2C), 56.76 (1C), 54.04 (1C), 44.27 (1C), 41.92 (1C), 41.90 (1C), 39.35 (1C), 39.09 (1C), 36.28 (1C), 35.86 (1C), 35.47 (1C), 34.03 (2C), 33.44 (1C), 32.53 (1C), 31.91 (1C), 31.55 (1C), 30.05 (1C), 29.12-29.77 (24C), 28.41 (1C), 27.23 (1C), 27.19 (1C), 26.39 (1C), 24.85 (2C), 24.38 (1C), 22.77 (1C), 22.69 (2C), 20.79 (1C), 19.61 (1C), 14.12 (1C), 13.46 (1C), 11.42 (1C); ELSD: 6.52 min, 98.17% purity; MASS (ESI, +ve) m/z: 1139.22 (MH+18)

Synthesis of ALL-C5bMe-2-TG-oleate I-55

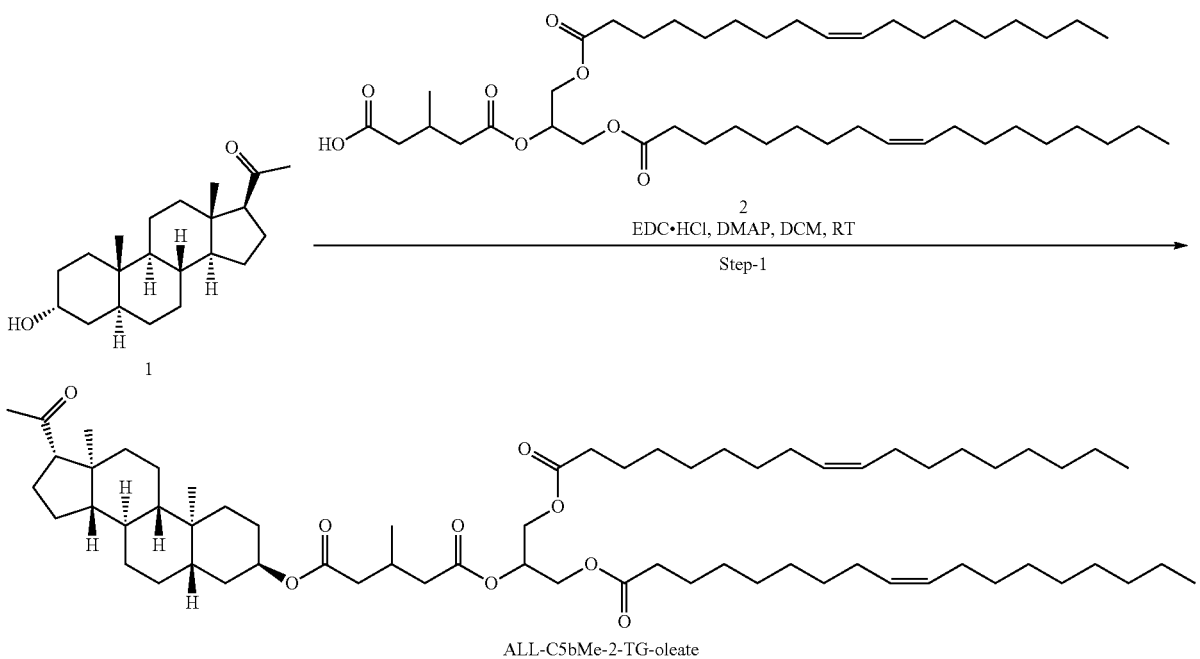

ALL-C5bMe-2-TG-oleate 4-(Dimethyl amino) pyridine (DMAP, 0.076 g, 0.627 mmol), N—(3-dimethylaminopropyl)-N'-ethylcarbodiimide hydrochloride (EDC·HCl, 0.240 g, 1.25 mmol), and 2 (0.540 g, 0.627 mmol) were added to a solution of allopregnanolone (0.200 g, 0.627 mmol) in DCM (5.0 mL) and the mixture stirred at room temperature for 16 hours. The reaction was diluted with DCM (10 mL), silica gel was added and the mixture concentrated under reduced pressure. Purification by Flash column chromatography (2% to 5% ethyl acetate/hexanes) gave ALL-C5bMe-2-TG-oleate I-55 (0.090 g, 14%) as colorless oil: $^1$H NMR (400 MHz, Chloroform-d) δ 5.33-5.30 (m, 5H), 5.08 (m, 1H), 4.35 (m, 2H), 4.19 (m, 2H), 2.59-2.29 (m, 3H), 2.15 (s, 6H), 2.06-2.00 (m, 8H), 1.73-1.57 (m, 18H), 1.50-1.20 (m, 52H), 1.22 (d, J=6.8 Hz, 4H), 1.00-0.83 (m, 8H), 0.64 (s, 3H); $^{13}$C NMR (101 MHz, Chloroform-d) δ 209.66 (1C), 173.24 (2C), 171.63 (1C), 171.44 (1C), 130.02 (1C), 129.70 (1C), 91.26 (1C), 70.06 (1C), 69.06 (1C), 63.84 (1C), 62.07 (1C), 56.73 (2C), 54.08 (1C), 44.24 (1C), 41.21 (1C), 40.74 (1C), 40.12 (1C), 39.05 (1C), 35.82 (1C), 35.44 (1C), 33.99 (1C), 32.96 (1C), 32.90 (1C), 31.90 (1C), 31.52 (1C), 29.76-29.11 (25C), 28.27 (1C), 27.54 (1C), 27.22 (1C), 27.18 (1C), 26.14 (1C), 24.83 (1C), 24.37 (1C), 22.78 (1C), 22.69 (1C), 20.80 (1C), 19.57 (1C), 14.12 (1C), 13.45 (1C), 11.33 (1C); ELSD: 6.45 min, 98.37% purity; MASS (ESI, +ve) m/z: 1066.27 (M+18).

Synthesis of ALL-CASI-C5bMe-2-MG I-58 eluent to get pure 1 (90 mg) as viscus yellowish liquid: $^1$H NMR (400 MHz, Chloroform-d) δ 7.28-7.40 (m, 10H), 5.76 (s, 2H), 5.25-5.28 (t, J=4.8 Hz, 1H), 4.95 (m, 1H), 4.54-4.55 (d, J=5.6 Hz, 4H), 3.64-3.66 (d, J=5.2 Hz, 4H), 2.44-2.57 (m, 4H), 2.27-2.35 (m, 3H), 2.15 (m, 1H), 2.13 (s, 3H), 2.01-2.04 (m, 2H), 1.86-1.90 (m, 2H), 1.69-1.71 (m, 4H), 1.55 (m, 8H), 1.38-1.44 (m, 4H), 1.14-1.43 (m, 3H), 1.03-1.05 (d, J=6.0 Hz, 2H), 0.80 (s, 2H), 0.61 (s, 2H).

A solution of 1 (90 mg, 0.116 mmol) in ethyl acetate (25 ml) was added palladium on carbon (0.09 g) and the resulting suspension re-evacuated and flushed with N$_2$ three times. The reaction mixture was then stirred at room temperature for 24 hours under 20 kg/cm$^2$H2 pressure (in

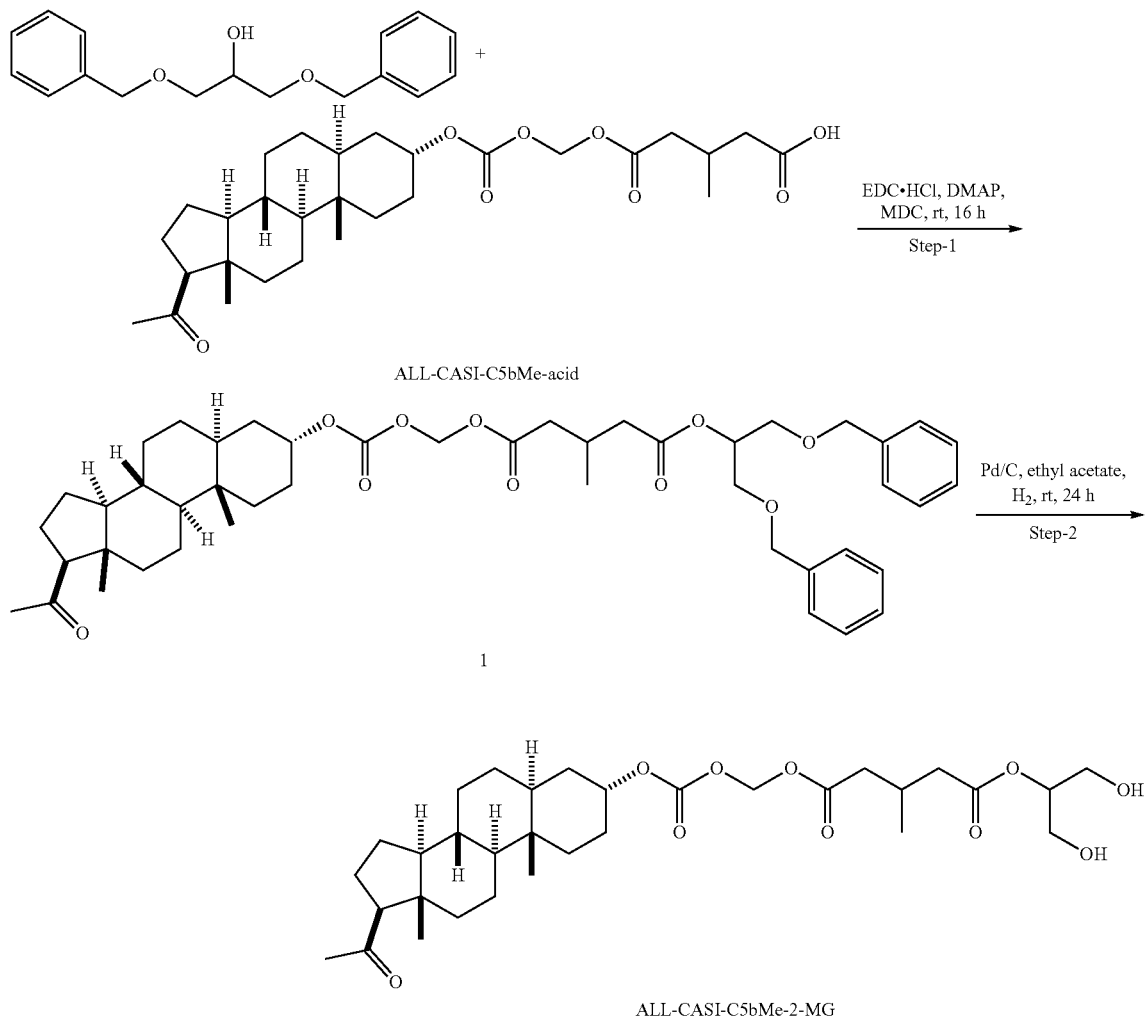

To a solution of ALL-CASI-C5bMe-acid (200.0 mg, 0.384 mmol) and 1,3-bis(benzyloxy)propan-2-ol (104 mg, 0.384 mmol) in DCM (10 ml) was added DMAP (46 mg, 0.384 mmol) at room temperature. EDC·HCl (73 mg, 0.384 mmol) was added into the reaction mixture after 15 minutes. The reaction was then stirred at room temperature for 16 hours. After completion of the reaction, the reaction mixture was diluted with DCM (50 ml) and washed with water (50 ml) and brine (50 ml). The organic layer was dried over sodium sulphate and concentrated under vacuum to get crude residue. Purification was performed by column chromatography using 7% to 9% ethyl acetate in hexanes as autoclaves), after completion of reaction, the reaction mixture was filtered through a celite bed, washing with ethyl acetate (50 ml). The filtrate was concentrated under reduced pressure to afford crude ALL-CASI-C5bMe-2-MG I-58 (0.065 g). The crude mixture was purified by distillation under vacuum: $^1$H NMR (400 MHz, Chloroform-d) δ 5.80 (s, 2H), 4.98-4.99 (m, 2H), 3.87-3.89 (m, 4H), 2.40-2.59 (m, 6H), 2.023-2.20 (m, 6H), 1.87 (m, 2H), 1.53-1.75 (m, 6H), 1.40-1.43 (m, 2H), 1.17-1.35 (m, 8H), 1.10-1.12 (d, 3H), 0.83 (m, 4H), 0.64 (s, 3H); ELSD purity: 99.76% (5.22 min); MASS (ESI, +ve) m/z: 612.32 (MH+18).

Synthesis of ALL-CASI-C6b'Me-2-TG-oleate I-59

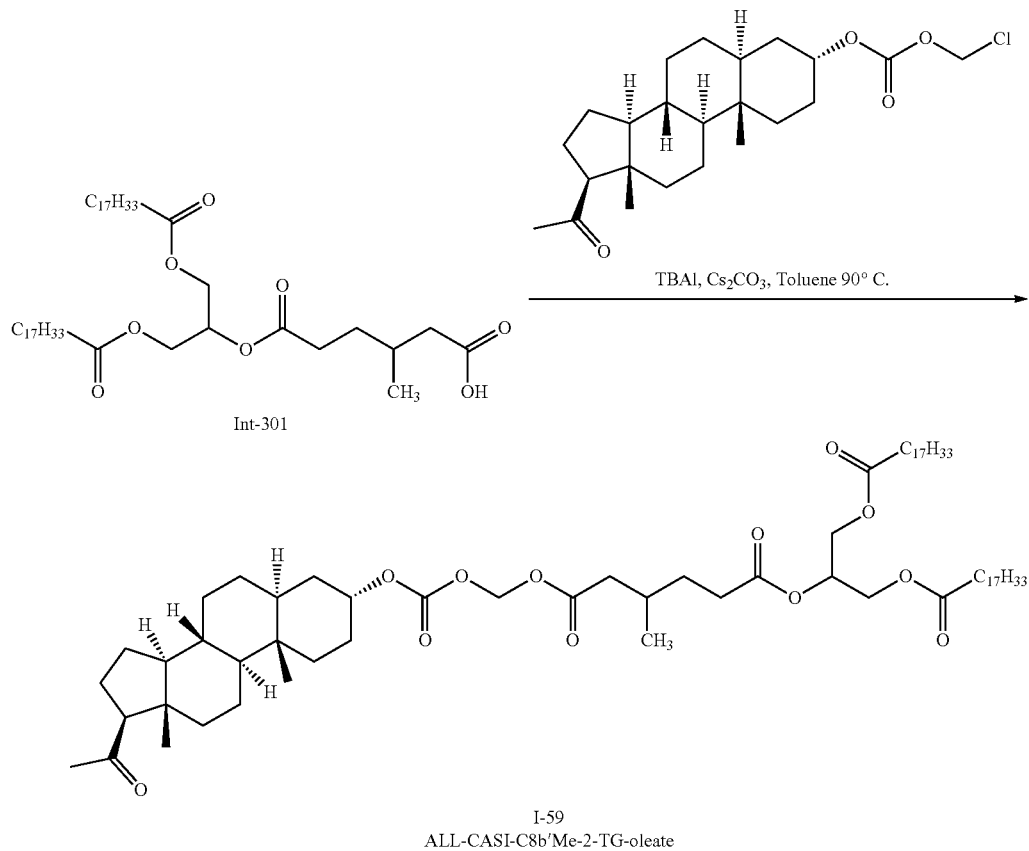

I-59
ALL-CASI-C8b'Me-2-TG-oleate

ALL-CASI-C6b'Me-2-TG-oleate I-59 was synthesized using the procedure provided above for I-29, replacing $C_8$-acid-TG-oleate with Int-301. Purification by flash column chromatography with 2-8% ethyl acetate in hexane as the mobile phase produced pure ALL-CASI-C6b'Me-2-TG-oleate (0.100 g, 36%) as a viscous oil: $^1$H NMR (400 MHz, CDCl$_3$) δ 5.78 (s, 2H), 5.36-5.32 (m, 4H), 5.28-5.27 (m, 1H), 4.97 (m, 1H), 4.33 (dd, J=4.4, 4.0 Hz, 2H), 4.18 (dd, J=6.0, 6.0 Hz, 2H), 2.55 (t, J=7.6 Hz, 1H), 2.39-2.31 (m, 8H), 2.25 (m, 2H), 2.13 (s, 3H), 2.02-2.01 (bs, 8H), 1.85 (m, 2H), 1.80-1.42 (m, 10H), 1.40-1.75 (m, 54H), 1.00 (d, J=6.4 Hz, 3H), 0.91 (t, J=5.6 Hz, 7H), 0.81 (s, 3H), 0.62 (s, 3H); $^{13}$C NMR (101 MHz, CDCl$_3$) δ 209.64 (1C), 173.2 (2C), 172.4 (1C), 171.1 (1C), 153.4 (1C), 130.02 (2C), 129.70 (2C), 81.69 (1C), 75.55 (1C), 69.21 (1C), 63.80 (1C), 62.02 (2C), 56.73 (1C), 53.86 (1C), 44.22 (1C), 40.91 (1C), 39.64 (1C), 39.06 (1C), 35.74 (1C), 35.43 (1C), 34.01 (2C), 32.68 (1C), 32.58 (1C), 31.90 (2C), 31.73 (2C), 31.51 (1C), 31.27 (2C), 29.7 (5C), 29.53 (4C), 29.31 (4C), 29.11 (2C), 28.15 (2C), 27.20 (2C), 25.96 (1C), 24.84 (2C), 24.36 (1C), 22.80 (2C), 19.5 (1C), 22.67 (2C), 20.78 (1C), 19.15 (1C), 14.10 (2C), 13.45 (1C), 11.30 (1C); MASS (ESI, +ve) m/z: 1154.53 (MH+18); ELSD: 6.30 min, 99.35% purity.

Example 3: Lymphatic Transport Assay in Rats

In order to assess the lymphatic transport of disclosed lipid prodrugs in rats, the mesenteric lymph ducts of rats used in this study were cannulated to allow continual collection of mesenteric lymph. Lipid formulations containing the compound of interest were then administered to the animals. The lymph was collected and drug concentrations in the lymph subsequently quantified.

Lipid-based formulations of the compounds of the invention or control compounds were prepared similarly to previous methods (Trevaskis, N. L. et al., Pharmaceutical Research, 2005, 22(11), 1863-1870, WO 2016/023082, and WO 2017/041139, hereby incorporated by reference). Briefly, approximately 2 mg of the compound, 40 mg oleic acid and 25 mg Tween 80 were mixed in a glass vial until equilibrated (gentle heat, i.e., below 50° C., was applied for a short period if needed). An aqueous phase consisting of 5.6 mL phosphate buffered saline (PBS, pH 7.4) was subsequently added to the lipid phase and the formulation was emulsified by ultrasonication with an ultrasonic processor equipped with a 3.2-mm microprobe tip running at 30% of the maximum amplitude of 240 m and a frequency of 20 kHz for 2 min at room temperature. The preparation can be scaled up for dosing 3-4 animals. The aqueous phase can be modified with 50 mM sulfobutyl ether7 β-cyclodextrin (SBE7 β-CD).

Male Sprague-Dawley (SD) rats were selected for the lymphatic transport studies. Rats (240-320 g) were maintained on a standard diet and fasted overnight with free access to water prior to experiments. Anesthetized rats were placed on a heated pad at 37° C. and cannulas were inserted into the duodenum (for formulation administration and rehydration), mesenteric lymph duct (for lymph collection) and carotid artery (in cases where blood collection is conducted). Post-surgery, rats were re-hydrated for 0.5 h via intraduodenal infusion of normal saline at 2.8 mL/h. The lipid formulations were infused into the duodenum at 2.8 mL/h for 2 h after which, normal saline was infused at 2.8 mL/h for the remainder of the experiment. Lymph was continuously collected for up to 8 h into pre-weighed Eppendorf tubes containing 10 μL of 1,000 IU/mL heparin. The collection tubes were changed hourly and lymph flow was measured gravimetrically. Aliquots of hourly lymph samples were stored at −20° C. prior to assay.

Drug concentration in lymph was expressed as total drug, which included free drug and drug associated with different glycerides. To assay for total drug, lymph samples were treated with a lipase or other appropriate conditions to liberate free active agent prior to measurement of active agent levels in the lymph. Treatment with a lipase or other hydrolysis conditions liberates free active agent from any corresponding re-esterified glycerides. Porcine pancreatic lipase is appropriate for this purpose. Alternatively, hydrolysis with 0.5 M NaOH may be used. Drug concentration in lymph was also expressed as intact prodrug, in which lymph samples were directly assayed for the administered prodrug by LC-MS without any prior hydrolysis.

Transport of compounds into lymph during each hourly collection period will be calculated from the product of the volume of lymph collected and the measured concentrations in lymph.

Table A shows the percentage of dosed compound recovered from the collected lymph. Compounds having a lymphatic transport designated as "A" demonstrated ≥50% and <75% transport into the lymph; compounds having a lymphatic transport designated as "B" demonstrated ≥25% and <50% transport into the lymph; compounds having a lymphatic transport designated as "C" demonstrated ≥10% and <25% transport into the lymph; compounds having a lymphatic transport designated as "D" demonstrated ≥1% and <10% transport into the lymph; compounds having a lymphatic transport designated as "E" demonstrated <1% transport into the lymph.

TABLE A

Lymphatic Transport Assay Results in Rats for Selected Compounds

| Cmpd ID | Compound | Rat - cumulative lymphatic transport: Mean, total lymphatic transport over 6 or 8 hours (%) | N |
|---|---|---|---|
|  | Allopregnanalone | 0.1% | 2 |
| I-1 | ALL-CMSI-C10b'bMe-2-TG-oleate | B | 3 |
| I-4 | ALL-CMSI-C8b'bMe-2-TG-oleate | B | 3 |
| I-5 | ALL-FSI5-C12a'aMe-2-TG | D | 3 |
| I-6 | ALL-CMSI-C12a'aMe-2-TG | D | 3 |
| I-7 | ALL-C10-2-TG | A | 3 |
| I-8 | ALL-CMSI-C5bMe-2-TG | B | 3 |
| I-1 | ALL-CMSI-C10b'bMe-2-TG-oleate | B | 3 |
| I-3 | ALL-ASI-C12a'bMe-2-TG-oleate | C | 3 |

TABLE A-continued

Lymphatic Transport Assay Results in Rats for Selected Compounds

| Cmpd ID | Compound | Rat - cumulative lymphatic transport: Mean, total lymphatic transport over 6 or 8 hours (%) | N |
|---|---|---|---|
| I-4 | ALL-CMSI-C8b'bMe-2-TG-oleate | B | 3 |
| I-9 | ALL-ASI-C5bMe-2-TG-oleate | A | 3 |
| I-12 | ALL-TML-C8b'bMe-2-TG oleate | D | 3 |
| I-13 | ALL-ASI-C8b'bMe-2-TG-oleate | B | 3 |
| I-14 | ALL-TML-C8b'bMe-2-TG oleate | D | 3 |
| I-16 | ALL-CDMPHB-C8b'bMe-2-TG-oleate | D | 3 |
| I-29 | ALL-CASI-C8-2-TG-oleate | C | 3 |
| I-30 | ALL-CASI-C8b'bMe-2-TG-oleate | B | 2 |
| I-32 | ALL-ASI-C10b'bMe-2-TG-oleate | B | 3 |
| I-35 | ALL-CMSI-C12b'bMe-2-TG-oleate | D | 3 |
| I-39 | ALL-CASI-C5bMe-2-TG-oleate | B | 3 |
| I-40 | ALL-ASI-C6-2-TG-oleate | B | 4 |
| I-41 | ALL-ASI-C8-2-TG-oleate | B | 3 |
| I-42 | ALL-ASI-C8bMe-2-TG-oleate | C | 2 |
| I-43 | ALL-CMSI-C6-2-TG-oleate | B | 3 |
| I-44 | ALL-CMSI-C8-2-TG-oleate | B | 3 |
| I-45 | ALL-CMSI-C8bMe-2-TG-oleate | B | 3 |
| I-48 | ALL-ASI-C8b'Me-2-TG-oleate | B | 3 |
| I-49 | ALL-CASI-C8b'Me-2-TG-oleate | B | 3 |
| I-50 | ALL-CASI-C5-2-TG-oleate | C | 3 |
| I-51 | ALL-CASI-C6-2-TG-oleate | B | 3 |
| I-52 | ALL-CASI-C8bMe-2-TG-oleate | C | 2 |
| I-53 | ALL-CDMOPHB-C10b'bMe-2-TG-oleate | D | 3 |
| I-54 | ALL-CDMOPHB-C10bMe-2-TG-oleate | B | 2 |

Example 4: Pharmacokinetic (PK) Studies in Rats, Dogs, and Non-Human Primates

Rat Pharmacokinetic Studies

In order to assess the oral bioavailability of test compounds, pharmacokinetic studies were conducted using the following procedure.

For rats: The day before drug administration, male Sprague-Dawley rats (240-320 g) were anesthetized and the carotid artery was cannulated. The rats were then allowed to regain consciousness and fasted overnight prior to the commencement of experiments with free access to water. The next morning, formulations containing parent compounds or prodrugs were administered via oral gavage or via the jugular vein cannula, and blood samples were collected from the carotid artery cannula at −5 min (pre-dose), 0.25, 0.5, 1, 1.5, 2, 4, 6, 8, and 24 hours post-dose. $K_2$ EDTA or heparin was used as an anticoagulant. During the blood sample collection period, the rats had free access to water but remained fasted for a further 8 h following drug administration. In these allopregnanolone (ALLO) related studies, the blood samples were centrifuged at 3500×g for 5 min to separate plasma. Plasma samples were stored at −20° C. prior to assay by HPLC-MS-MS. The plasma samples were assayed for free drug (i.e. non-glyceride associated drug) and not hydrolized prior to assay. Small quantities of EDTA or heparin were added to the formulation to maintain the patency of the cannulae.

In some cases, the prodrug formulations for each rat contained 2 mg of the ALLO prodrug dispersed in 40 mg oleic acid, 25 mg Tween 80 and 2 ml PBS. Doses were normalized to a 2 mg/kg equivalent dose of ALLO (i.e., allopregnanolone). This formulation is referred to herein as the "Discovery Formulation."

In some cases, the following formulation was used ("SEDDS-CremEL"): prodrug is dissolved in 1:1:1 mixture of soybean oil, cremophor EL and maisine-CC at a concentration of 100 mg/g. Before dosing, the formulation is dispersed in water (10x) to a final prodrug concentration of 10 mg/mL and dosed in mL/kg by oral gavage. Sample preparation procedure is provided below using compound I-2 as an example:

1. Test article (~262 mg in the case of compound I-2) provided pre-weighed in a –30 mL vial.
2. Pre-mix SEDDS formulation (1:1:1 soybean oil, maisine CC, kolliphor EL (1.5 g each)), mix and equilibrate 30 mins at 37° C. with periodic gentle mixing.
3. Add SEDDS formulation to test article in provided vial (9:1 by weight) (100 mg/g, for 262.5 mg prodrug add SEDDS weight 2.36 g), transferring by weight, equilibrate at 37° C. for 30 minutes and then agitate gently at room temperature overnight (upright). Do not vortex.
4. Immediately before dosing, pre-disperse formulation in water (add water to provided vial and mix rapidly to form a homogenous emulsion) in a 1:9 SEDDS (g): water (mL) ratio (for 262.5 mg prodrug+2.36 g SEDDS, add 23.6 g water), and dose by volume/weight.

Alternatively, in other cases the following formulation was used ("SEDDS-Peceol"): prodrug is dissolved in mixture (w/w) of sesame oil (25%), cremophor RH40 (48%) and peceol (27%) at a concentration of either 50 mg/g or 150 mg/g. Before dosing, the formulation is dispersed in water (5x) to a final prodrug concentration of 10 mg/mL and 30 mg/mL and dosed in mL/kg by oral gavage.

Table B shows the Mean Plasma AUC, Tmax and Cmax values for exemplary compounds. Compounds were formulated in a lipid-based formulation similar to that described in Example 3, using a smaller volume of water to disperse the mixture.

TABLE B

Rat Pharmacokinetic Results for Exemplary Compounds

| Cmpd # | Formulation | Mean Plasma AUC, 0-24 h (nmol · h/L) (SD) | Tmax (h) (SD) | Cmax (nmol/L) (SD) |
|---|---|---|---|---|
| I-1 | Discovery Formulation | 592 (98) | 1.5 (—) | 387 (79) |
| I-5 | Discovery Formulation | 83.9 (53.1) | 1.8 (0.6) | 62.8 (41.8) |
| I-6 | Discovery Formulation | 320.9 (34.2) | 1 (—) | 239.2 (1.2) |
| I-7 | Discovery Formulation | 504.8 (64.5) | 1.38 (0.2) | 393.8 (131) |
| I-8 | Discovery Formulation | 368.1 (25.7) | 2.3 (1.4) | 241.2 (43.9) |
| I-9 | Discovery Formulation | 192.1 (53.3) | 1.3 (0.3) | 126 (48) |
| I-10 | Discovery Formulation | 117.3 (19.8) | 1.5 (0.5) | 68.9 (11.8) |
| I-12 | Discovery Formulation | 249 (21) | 1.5 (—) | 178 (41) |
| I-14 | Discovery Formulation | 132 (58) | 1.5 (—) | 96 (46) |
| I-16 | Discovery Formulation | 29 (6) | 1.7 (0.3) | 14 (5) |
| I-29 | Discovery Formulation | 107.9 (47.7) | 1.7 (0.3) | 61 (26.7) |
| I-30 | Discovery Formulation | 293 (81.7) | 1.67 (0.3) | 202.7 (50.9) |
| I-35 | Discovery Formulation | 163.4 (49.3) | 1.17 (0.3) | 120.6 (19) |
| I-36 | SEDDS-CremEL | 312 (57) | 1.2 (0.3) | 242 (62) |
| I-37 | SEDDS-CremEL | 191 (36) | 0.8 (0.3) | 138 (49) |
| I-38 | SEDDS-CremEL | 450 (64) | 1 (—) | 335 (60) |
| I-39 | Discovery Formulation | 509 (201) | 1.3 (0.6) | 314 (133) |
| I-40 | Discovery Formulation | 265 (97) | 1.7 (0.3) | 165 (73) |
| I-41 | Discovery Formulation | 211 (72) | 1.7 (0.6) | 129 (26) |
| I-42 | Discovery Formulation | 470 (75) | 1.5 (—) | 334 (183) |
| I-43 | Discovery Formulation | 307 (62) | 1.5 (—) | 208 (27) |
| I-44 | Discovery Formulation | 220 (28) | 1.5 (—) | 150 (32) |
| I-45 | Discovery Formulation | 347.3 (67.6) | 1.5 (—) | 282 (38) |
| I-49 | Discovery Formulatoin | 513 (41) | 1.7 (0.3) | 370.5 (37.3) |
| I-50 | Discovery Formulatoin | 270 (130) | 1.5 (—) | |
| I-51 | Discovery Formulation | 357.5 (48.9) | 1.7 (0.3) | 193.3 (5.3) |
| I-52 | Discovery Formulation | 268.2 (61.1) | 1.7 (0.3) | 150.1 (24.7) |
| I-53 | Discovery Formulation | 409.7 (82.6) | 1.5 (—) | 208.9 (19.5) |
| I-54 | Discovery Formulatoin | 352.4 (94.8) | 1.5 (—) | 187.5 (12.7) |

Table C below shows PK results for compound I-2 in rats.

TABLE C

Pharmacokinetic Results for Compound I-2

| Dose mg/kg | Formulation | N | $C_{max}$ µM | $T_{max}$ h | $T_{1/2}$ h | AUCinf_ob µM*h | AUC_D_Inf µM*kg*h/mg |
|---|---|---|---|---|---|---|---|
| 10 | SEDDS-CremEL | 5 | 1.15 | 0.8 | 1.4 | 1.75 ± 0.16 | 0.175 |
| 30 | SEDDS-CremEL | 5 | 2.76 | 1.0 | 1.3 | 5.43 ± 1.1 | 0.181 |
| 100 | SEDDS-CremEL | 5 | 6.51 | 1.6 | 0.9 | 21.7 ± 2.8 | 0.217 |

Table D below shows PK results for compound I-2 in rats.

TABLE D

Pharmacokinetic Results for Compound I-2 in rats

| Dose mg/kg | Formulation | N | $C_{max}$ nM | $T_{max}$ h | $T_{1/2}$ h | AUCINF_obs nM*h | AUCINF_D_obs nM*kg*h/mg |
|---|---|---|---|---|---|---|---|
| 100 | SEDDS-CremEL | 5 | 4127 | 1.3 | 2.2 | 16159 | 161.6 |
| 100 | SEDDS-Peceol | 5 | 3905 | 2 | 2.3 | 16281 | 162.8 |
| 300 | SEDDS-Peceol | 5 | 7250 | 2.8 | 2.3 | 40793 | 136.0 |

Blood samples were collected via jugular vein cannula (JVC) in accordance with test facility standard operating procedures. If the sample could not be collected from the primary collection site an alternate approved collection site was used in accordance with test facility standard operating procedures. All blood collection sites were documented.

Blood samples were collected into tubes with appropriate anticoagulant as outlined above. Sample tubes were prefilled with 5 µL of lipase inhibitor (Orlistat, at 2 mg/mL in DMSO) and 10 µL Complete™ protease inhibitor solution (See preparation protocol) and kept chilled on wet ice.

Tubes were stored on wet ice until processed to plasma by centrifugation (3500 rpm at 5° C. for 10 minutes) within 30 minutes of collection. Samples were split into two equal aliquots (2×50 µL) and transferred into individual uniquely labeled matrix tubes and stored at nominal −70° C. until transferred as listed below.

The results are shown in Tables E1 and E2 below.

TABLE E1

Free allopregnanolone in rats

| Cmpd ID | Dose (umoL/kg) | Tmax (h) | Cmax (uM) | AUCinf (nmol · h/L) |
|---|---|---|---|---|
| I-2 | 8.8 | 1.5 | 0.45 | 1.19 |
| I-39 | 8.8 | 1.5 | 0.53 | 1.34 |
| I-36 | 8.8 | 1.5 | 0.54 | 1.12 |
| I-47 | 8.8 | 1.5 | 0.52 | 1.15 |

TABLE E2

Total allopregnanolone in rats

| Cmpd ID | Dose (umoL/kg) | Tmax (h) | Cmax (uM) | AUCinf (nmol · h/L) |
|---|---|---|---|---|
| I-2 | 8.8 | | | |
| I-39 | 8.8 | 1.07 | 3.4 | 2.50 |
| I-36 | 8.8 | 1.76 | 0.8 | 3.86 |
| I-47 | 8.8 | 1.49 | 0.9 | 3.03 |

Dog Pharmacokinetic Studies

For the dog studies, male beagle dogs (body weights between 9.1-11.7 kg) were held in a large-animal research facility prior to the commencement of studies. The dogs were fasted for 12 h up to 30 min prior to drug administration. At 30 minutes prior to drug dosing, each animal received ~20 g of high fat food (Teklad, TD.07096), then each animal were offered 100 g of beef-flavored canned food. Food was removed immediately prior to dosing. Following the 4 hour sample collection, food was returned (any remaining canned food and 200 g of regular diet). Water was available ad libitum throughout the study for all dogs.

For oral administration, test compounds were prepared in the following formulation ("SEDDS-Peceol"): prodrug is dissolved in mixture (w/w) of sesame oil (25%), cremophor RH40 (48%) and peceol (27%) at a concentration of 10, 30, or 300 mg/g. Before dosing, the formulation is dispersed in water (5×) to a final prodrug concentration of 2, 6, 20, or 30 mg/mL and dosed in mL/kg by oral gavage.

If an oral capsule group is included in a study as described here, compound dissolved in the formulation may be administrated to the fed dog by placing the capsules as far posterior to the pharynx as possible, closing the mouth and rubbing the throat to stimulate swallowing. Subsequently 10 mL of water may be administered orally via a syringe.

If an IV group is included in a study as described here, parent ALLO (0.5 mg/kg dose) may be administered as an intravenous bolus (formulation contained ALLO at concentration of 1.5 mg/mL) by way of a percutaneous catheter placed in a peripheral vein, followed by a 2 mL flush with normal saline.

Blood samples (approx. 1.5 mL each) were taken via venepuncture of the cephalic vein 5 min prior to administration up to 48 hours post-dosing. During the blood sample collection period, the animals had free access to water but remained fasted for a further 4 hours following drug administration.

Plasma was separated by centrifugation and aliquots of each plasma sample transferred into eppendorf tubes and stored at −80° C. prior to analysis by LC-MS.

Table E below shows PK results for compound I-2.

TABLE F

Pharmacokinetic Results for Compound I-2 in Dogs

| Dose mg/kg | Formulation | N | $C_{max}$ nM | $T_{max}$ h | $T_{1/2}$ h | AUCINF_obs nM*h | AUCINF_D_obs nM*kg*h/mg |
|---|---|---|---|---|---|---|---|
| 10 | SEDDS-Peceol | 5 | 86 ± 9 | 1.9 ± 0.2 | 6.2 ± 1.9 | 477 ± 60 | 47.7 ± 6.0 |
| 30 | SEDDS-Peceol | 5 | 319 ± 51 | 2 ± 0 | 3.9 ± 0.4 | 1591 ± 327 | 53 ± 10.9 |
| 100 | SEDDS-Peceol | 5 | 919 ± 99 | 1.9 ± 0.2 | 4.6 ± 0.8 | 6143 ± 481 | 61 ± 4.8 |

Non-Human Primate Pharmacokinetic Studies

For the non-human primate studies, male cynomolgus monkeys will be held in a large-animal research facility prior to the commencement of studies. The monkeys will be fasted overnight up to 30 min prior to drug administration. Thirty minutes prior to drug administration, each monkey will receive 30 mL of Ensure Milkshake via oral gavage and will be allowed access to a normal ration of primate chow. The primate chow will be removed at the time of drug administration and will be then returned 4 hours after drug administration. Water will be available ad libitum throughout the study for all monkeys.

Test compounds will be prepared in the SEDDS-CremEL or SEDDS-Peceol formulations described above. Parent ALLO (i.e., non-prodrug allopregnanolone) will be prepared in a formulation of 20% aqueous hydroxypropyl-β-cyclodextrin. Formulations may be filled into hard gelatin capsules without any water added for pre-dispersion. Test compounds will be dosed at 5 mg/kg, and parent ALLO will be dosed at 1.5 mg/kg (dosages may be modified as needed). Drug will be administered in a single capsule followed by 10 mL of water by oral gavage. Alternately, formulations may be pre-dispersed as described above and dosed via oral gavage. For the IV group, parent ALLO (0.5 mg/kg dose) will be administered as an intravenous bolus (formulation contained ALLO at a concentration of 1.5 mg/mL) by way of a percutaneous catheter placed in a peripheral vein followed by a 2 mL flush with normal saline prior to removal of the catheter.

After oral administration, blood samples (approx. 1 mL each) will be taken via venipuncture of a peripheral vein 5 min prior to administration up to 48 hours post-dosing. Blood samples will be transferred into tubes containing dipotassium EDTA anticoagulant, and the tubes will be placed on crushed ice until processing. Within 30 minutes of collection, the blood samples will be processed to isolate plasma by centrifuging at 2200×g for 10 minutes at 5° C.±3° C. The plasma samples will be stored in polypropylene tubes at −80° C. prior to analysis by LC-MS.

Non-Human Primate

This study evaluated the pharmacokinetic profile of parent API (allopregnanolone, ALLO) plasma exposure resulting from oral administration of four different prodrugs in self-Emulsifying Drug Delivery Systems (SEDDS) administered orally to fed male monkeys over four sessions (every three days) at 10 mg/kg (Session 1, ALL-CMSI-C5bMe-2-TG-oleate (I-2)), 9.88 mg/kg (Session 2, ALL-CASI-C5bMe-2-TG-oleate (I-39)), 7.57 mg/kg (Session 3, ALL-CMSI-C5bMe-2-TG-octanoate (I-36)) and 7.45 mg/kg (Session 4, ALL-CASI-C5bMe-2-TG-octanoate (I-47)). The study design is presented in Table F3. Following overnight fasting, animals received 30 mL of Ensure Milkshake by oral gavage and normal ration of food 30 minutes before dosing. The drug exposures were quantified over 24 hours after dosing.

TABLE F3

Study design

| Dose Session/Day | No. of Males | Cmpd IDs (SEDDS Formulation)* | Dose Level (mg/kg) | Dose Conc. (mg/m) | Dose Volume | Dose Vehicle* | Dose Route | Post-Dose Flush |
|---|---|---|---|---|---|---|---|---|
| 1/Day 1 | 5 | ALL-CMSI-C5bMe-2-TG-oleate (I-2) | 10 | 2 | 5 | 27% Peceol, 48% Cremophor RH40, 25% Sesame Oil. (to be dispersed 1:4 in water as per protocol) | PO | 10 |
| 2/Day 4 | 5 | ALL-CASI-C5bMe-2-TG-oleate (I-39) | 9.88 | 1.98 | 5 | | PO | 10 |
| 3/Day 7 | 5 | ALL-CMSI-C5bMe-2-TG-octanoate (I-36) | 7.57 | 1.51 | 5 | | PO | 10 |
| 4/Day 10 | 5 | ALL-CASI-C5bMe-2-TG-octanoate (I-47) | 7.45 | 1.49 | 5 | | PO | 10 |

*SEDDS Formulation = TA dissolved in 27% Peceol, 48% Cremophor RH40, 25% Sesame Oil. (to be dispersed 1:4 in water as per Sponsor's DF preparation protocol).

For all 4 dose sessions, the prodrugs were pre-formulated with SEDDS (27% Peceol, 48% Cremophor RH40, 25% Sesame Oil and diluted with water) prior to oral dosing to five fed cynomolgus monkeys.

The oral administration of the prodrugs over four sessions were well-tolerated in non-naïve male cynomolgus monkeys. The prodrugs, (1-2, 1-39, 1-36 and 1-47) were detectable in plasma samples after dose administration at all time-points (from 0.5 to 24 hours post-dose). While Total ALLO was also detectable in all post-dose time points (up to 24 hr post-dose), Free ALLO was mainly detectable between 1 hr and 8 hr post-dose.

NCA was performed using software Phoenix 64, WinNonlin 6.3 (Pharsight, A Certara™ Company) to estimate exposure of Free ALLO and Total ALLO API. Major NCA parameters are presented below. The results are shown in Tables F4 and F5.

TABLE F4

Free allopregnanolone in NHP

| Cmpd ID | Dose umoL/kg | Tmax hr | Cmax uM | AUCinf nmol · h/L |
|---|---|---|---|---|
| I-2 | 8.8 | 4.0 | 0.10 | 0.70 |
| I-39 | 8.8 | 4.0 | 0.14 | 0.77 |
| I-36 | 8.8 | 4.0 | 0.10 | 0.62 |
| I-47 | 8.8 | 4.0 | 0.12 | 0.78 |

TABLE F5

Total allopregnanolone in NHP

| Cmpd ID | Dose umoL/kg | Tmax hr | Cmax uM | AUCinf nmol · h/L |
|---|---|---|---|---|
| I-2 | 8.8 | 3.2 | 1.8 | 13.4 |
| I-39 | 8.8 | 4.4 | 1.07 | 7.04 |
| I-36 | 8.8 | 4.0 | 2.72 | 16.2 |
| I-47 | 8.8 | 4.0 | 1.17 | 7.4 |

Example 5: In Vitro Hydrolysis of Compounds by Rat Digestive Fluid or Porcine Pancreatic Lipase In vitro hydrolysis of test compounds may be performed via incubation with rat digestive fluid. Rat digestive fluid will be collected from anesthetized rats via cannulation of the common bile-pancreatic duct immediately prior to the entry of the duct into the duodenum (i.e., below the point of entry of pancreatic secretions). This allows simultaneous collection of bile and pancreatic fluid. The digestive fluid will be collected continuously for 2 h, during which time a blank lipid formulation (prepared as described in the rat lymphatic transport studies but without the addition of drug) will be infused into the duodenum at a rate of 2.8 mL/h to mimic conditions following drug administration. Bile and pancreatic fluid will be maintained at 37° C. and used within 0.5 h of collection for in vitro prodrug hydrolysis experiments. The hydrolysis experiments will be conducted via incubation (at 37° C.) of -0.375 mL of rat digestive fluid with -0.625 mL of the drug-loaded lipid formulations (as described in the rat lymphatic transport studies). The volume ratio of digestive fluid to formulation will mimic the flow rate of bile and pancreatic fluid (-1.5 mL/h) and the infusion rate of the intraduodenal formulations (2.8 mL/h) during the in vivo lymphatic transport studies. Aliquots of 10 µL (samples taken at 0, 2, 5, 10, 15, 30, 60, 90, 120, 180 min) will be added to 990 µL of acetonitrile/water (4:1, v/v) to stop lipolysis, vortexed for 1 min and centrifuged at 4500 g for 5 min to precipitate proteins prior to analysis. The supernatant will be analysed by HPLC-MS for residual compound concentrations, and the potential products of compound hydrolysis analyzed.

To provide for higher throughput of experiments, unless otherwise stated, in vitro hydrolysis of compounds will generally be performed via incubation with porcine pancreatic lipase. This provides a more reproducible source of pancreatic enzymes, facilitates enhanced experimental throughput, and is also a greater challenge than collected rat enzymes (since enzyme activity in rat intestinal fluid is low). Briefly, pancreatic lipase solution will be prepared prior to the hydrolysis experiment by dispersion of 1 g porcine pancreatin in 5 ml of lipolysis buffer and 16.9 µL of 0.5 M NaOH. The suspension will be mixed well and centrifuged at 3500 rpm for 15 minutes at 5° C. to provide a supernatant. An amount of 1000 mL of lipolysis buffer will be prepared with 0.474 g of tris-maleate (2 mM), 0.206 g of $CaCl_2 \cdot H_2O$ (1.4 mM) and 8.775 g of NaCl (150 mM) adjusted with NaOH to pH 6.5. To assess the potential for prodrug hydrolysis in the intestine, 20 µL of prodrug solution (1 mg/mL dissolved in acetonitrile), 900 µL of simulated intestinal micellar solution [prepared with 0.783 g of NaTDC (3 mM) and 0.291 g of phosphatidylcholine (0.75 mM) in 500 mL lipolysis buffer] and 100 µL of enzyme solution will be incubated at 37° C. 20 µL samples of the incubation solution will be taken at 0, 5, 10, 15, 30, 60, 90, 120, and 180 minutes post incubation and added to 180 µL of MeCN to stop lipolysis. The mixture will be vortexed and centrifuged at 5000 rpm for 5 minutes to precipitate proteins prior to analysis. The supernatant will be analyzed by HPLC-MS for residual compound concentrations, and the potential products of compound hydrolysis analyzed.

On incubation with digestive enzymes, the monoglyceride forms of the prodrugs are formed very rapidly. The stability in simulated intestinal conditions is therefore better assessed by the stability of the monoglyceride form that is generated by the initial digestion process. The monoglyceride form must remain intact to be absorbed and re-esterified in the enterocyte prior to entry into the lymphatics. A comparison of the stability profiles of the monoglyceride forms of test compounds during in vitro incubation with freshly collected rat bile and pancreatic fluid (BPF) or porcine pancreatic lipase will be used to evaluate the influence of linker structure on the stability of the monoglyceride intermediates.

Example 6: In Vitro Release of Therapeutic Agent from Prodrugs in Lymph Supplemented with Lipoprotein Lipase In order to probe the release of free therapeutic agent from lipid prodrugs in the lymphatics, prodrugs will be incubated with rat lymph supplemented with lipoprotein lipase (LPL, 200 unit/mL). LPL is a key enzyme required for the hydrolysis of lipoprotein associated TG in normal physiological conditions and is therefore expected to be a key contributor to lipolysis of the re-esterified drug-TG construct in plasma, largely via liberation of fatty acids in the sn-1 and the sn-3 position of the TG-mimetic, prior to drug release from the 2' positon via esterase hydrolysis. LPL is tethered to lymphocytes or lymphatic/vascular endothelial cells under physiological conditions. In these in vitro studies, rat lymph will therefore be supplemented with LPL to better reflect the in vivo situation. To start hydrolysis, 10 µL of LPL solution (10,000 unit/mL) will be added to a mixture of 10 µL of prodrug solution (1 mg/mL dissolved in acetonitrile) and 500 µL of blank Sprague Dawley rat lymph. The solution will be incubated at 37° C. Samples (20 µL) of the incubation solution will be taken at 0, 5, 10, 15, 30, 60, 90, 120, and 180 minutes post incubation and added to 980 µL of 9:1 (v/v) MeCN/water to stop lipolysis. The mixture will be vortexed and centrifuged at 4500 g for 5 minutes to precipitate proteins prior to analysis. The supernatant will be analyzed by HPLC-MS/MS for concentrations of the released therapeutic agent.

Example 7: In Vitro Release of Therapeutic Agent From Prodrugs in Plasma Supplemented with Lipoprotein Lipase In order to probe the release of free drug from TG prodrugs in the systemic circulation, prodrugs are incubated with plasma (rat, dog, monkey, or human) supplemented with lipoprotein lipase (LPL, 200 IU/ml). LPL is a key enzyme required for the hydrolysis of lipoprotein associated TG in the systemic circulation and is therefore expected to be a key contributor to lipolysis of the re-esterified drug-TG construct in plasma, largely via liberation of fatty acids in the sn-1 and the sn-3 position of the TG-mimetic, prior to drug release from the 2' position via esterase hydrolysis. LPL is active in plasma but is tethered to the luminal surface of vascular endothelial cells under physiological conditions. In the current in vitro studies, plasma is therefore supplemented with LPL to better reflect the in vivo situation.

To start hydrolysis, 10 μl of LPL solution (10,000 IU/ml) will be added to a mixture of 10 μl of prodrug solution (1 mg/ml dissolved in organic solvent, e.g., THF, DMSO, or acetonitrile) and 500 μl of blank plasma. The mixture will be incubated at 37° C. Samples (20 μl) of the incubation solution will be taken at 0, 5, 15, 30, 60, 90, 120, and 180 minutes post-incubation and added to 180 μl of acetonitrile to stop lipolysis. The mixture will be vortexed and centrifuged at 4500×g for 5 minutes to precipitate proteins prior to analysis. The supernatant will be analyzed by HPLC-MS/MS for the potential products (MG form, acid form, and free drug) of prodrug hydrolysis.

The in vitro hydrolysis profile of selected prodrug compounds will be determined in rat, dog, monkey and/or human plasma supplemented with LPL.

Tables G1-G4 shows the percentage of parent API (i.e., free allopreganolone) recovered from rat, dog, monkey and/or human plasma. Compounds having an in vitro release designated as "A" demonstrated ≥60% release into plasma; compounds having an in vitro release designated as "B" demonstrated ≥20% and <60% release into plasma; compounds having an in vitro release designated as "C" demonstrated <20% release into plasma.

TABLE G1

Percent of free allopregnanolone (parent API) present in rat plasma

| Cmpd ID | Parent API present at end of experiment (%) |
|---|---|
| I-1 | C |
| I-3 | A |
| I-4 | A |
| I-6 | A |
| I-7 | B |
| I-8 | A |
| I-9 | B |
| I-12 | A |
| I-13 | A |
| I-14 | B |
| I-16 | A |
| I-29 | A |
| I-30 | B |
| I-31 | B |
| I-34 | B |
| I-35 | A |
| I-39 | A |
| I-40 | A |
| I-41 | A |
| I-42 | A |
| I-43 | A |
| I-44 | B |
| I-45 | A |
| I-51 | B |
| I-52 | A |
| I-53 | A |
| I-54 | B |

TABLE G2

Percent of free allopregnanolone (parent API) present in dog plasma

| Cmpd ID | Parent API present at end of experiment (%) |
|---|---|
| I-8 | B |

TABLE G3

Percent of free allopregnanolone (parent API) present in monkey plasma

| Cmpd ID | Parent API present at end of experiment (%) |
|---|---|
| I-1 | C |
| I-2 | B |
| I-4 | C |
| I-9 | B |
| I-10 | C |
| I-12 | C |
| I-13 | C |
| I-14 | C |
| I-29 | B |
| I-30 | B |
| I-31 | C |
| I-32 | C |
| I-34 | C |
| I-35 | C |
| I-39 | B |
| I-40 | A |
| I-41 | B |
| I-42 | B |
| I-43 | B |
| I-44 | B |
| I-50 | A |
| I-51 | A |
| I-52 | A |
| I-53 | C |

TABLE G4

Percent of free allopregnanolone (parent API) present in human plasma

| Compound ID | Parent API present at end of experiment (%) |
|---|---|
| I-2 | C |
| I-8 | C |
| I-9 | C |
| I-10 | C |
| I-12 | C |
| I-29 | B |
| I-30 | C |
| I-32 | C |
| I-39 | B |
| I-40 | B |
| I-41 | C |
| I-42 | C |
| I-43 | C |
| I-44 | C |
| I-45 | C |
| I-48 | C |
| I-49 | B |
| I-50 | A |
| I-51 | A |
| I-52 | B |
| I-53 | C |
| I-54 | C |

We claim:
1. A compound of formula I-47:

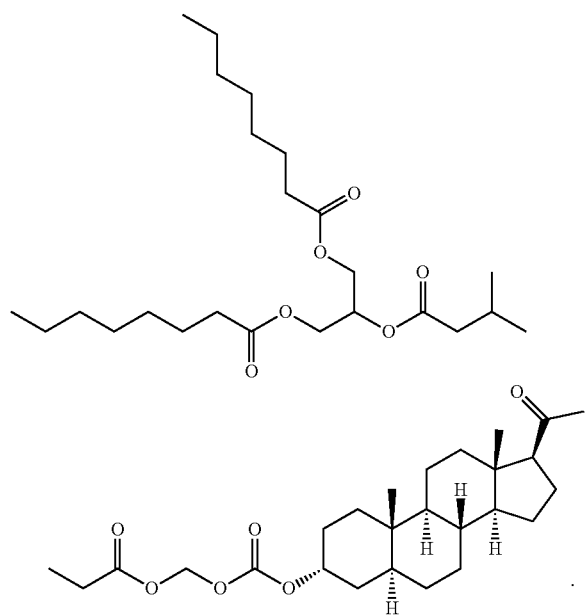

(I-47)

2. A pharmaceutically acceptable composition comprising the compound according to claim 1, and a pharmaceutically acceptable excipient.

3. The pharmaceutically acceptable composition according to claim 2, wherein the composition is formulated for oral administration.

4. An oral dosage form comprising the compound according to claim 1.

5. The oral dosage form of claim 4, further comprising a lipid-based vehicle.

6. The oral dosage form of claim 5, wherein the lipid-based vehicle comprises sesame oil.

7. The oral dosage form of claim 6, wherein the lipid-based vehicle is a substantially non-aqueous vehicle.

8. The oral dosage form of claim 7, wherein the oral dosage form is a capsule.

9. The oral dosage form of claim 4, wherein the oral dosage form comprises a self-emulsifying drug delivery system (SEDDS).

10. The oral dosage form of claim 9, wherein the SEDDS comprises sesame oil and a water-soluble surfactant.

11. The oral dosage form of claim 10, wherein the water-soluble surfactant comprises a polyoxyethylene castor oil.

12. The oral dosage form of claim 11, wherein the polyoxyethylene castor oil comprises polyoxyl 40 hydrogenated castor oil.

13. The oral dosage form of claim 12, wherein the SEDDS further comprises glycerol mono- and diesters having fatty acid chains from 8 to 40 carbon atoms.

14. The oral dosage form of claim 13, wherein the SEDDS is substantially non-aqueous.

15. The oral dosage form of claim 14, wherein the oral dosage form is a capsule.

* * * * *

UNITED STATES PATENT AND TRADEMARK OFFICE
CERTIFICATE OF CORRECTION

PATENT NO. : 11,975,073 B2  
APPLICATION NO. : 18/341519  
DATED : May 7, 2024  
INVENTOR(S) : Daniel Kenneth Bonner et al.

Page 1 of 2

It is certified that error appears in the above-identified patent and that said Letters Patent is hereby corrected as shown below:

In the Claims

The structure of I-47 at Column 427, Lines 5-30 depicted as:

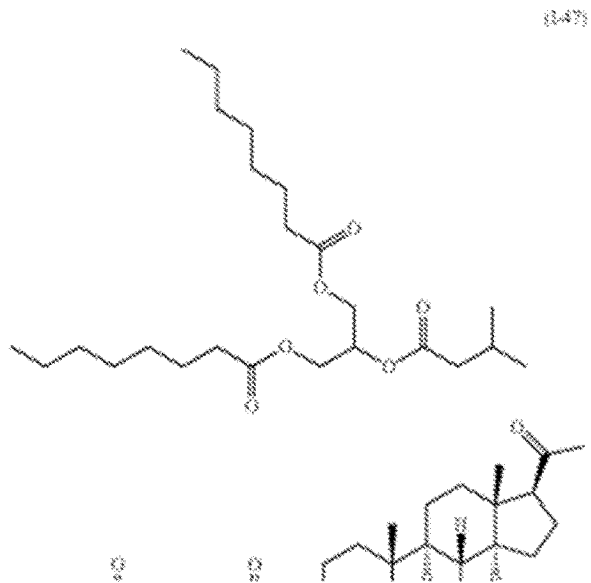

Should be replaced with:

Signed and Sealed this  
Eighteenth Day of February, 2025

Coke Morgan Stewart  
*Acting Director of the United States Patent and Trademark Office*

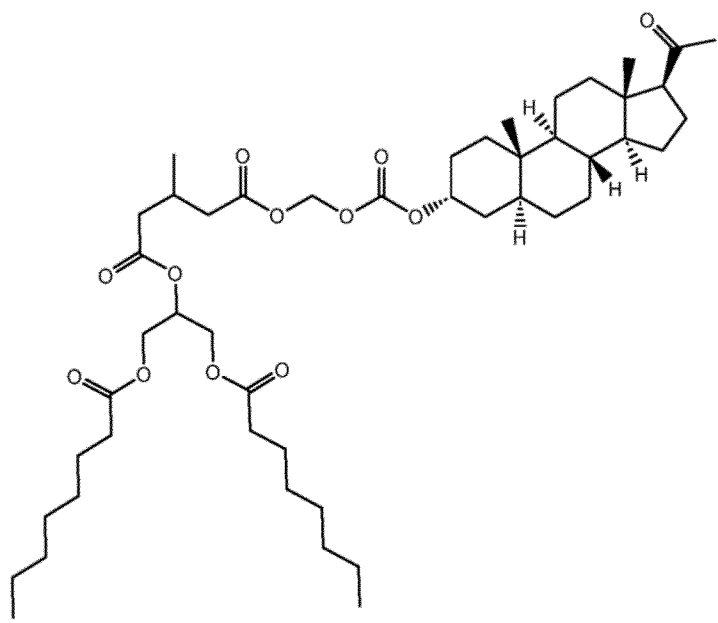

CERTIFICATE OF CORRECTION (continued)
U.S. Pat. No. 11,975,073 B2